US012691242B2

(12) United States Patent
Huddart et al.

(10) Patent No.: US 12,691,242 B2
(45) Date of Patent: Jul. 28, 2026

(54) HEADGEAR ASSEMBLIES AND INTERFACE ASSEMBLIES WITH HEADGEAR

(71) Applicant: Fisher & Paykel Healthcare Limited, Auckland (NZ)

(72) Inventors: Brett John Huddart, Auckland (NZ); Jeroen Hammer, Auckland (NZ); Matthew Robert Geoff Slight, Auckland (NZ); Vitaly Kapelevich, Auckland (NZ); David Monroy Felix, Auckland (NZ); Callum Ross Gordon, Auckland (NZ); Bruce Michael Walls, Auckland (NZ); Melissa Catherine Bornholdt, Auckland (NZ); Matthew Roger Stephenson, Auckland (NZ); Paul Mathew Freestone, Auckland (NZ); Ryan Anthony Graham, Auckland (NZ); Mark Arvind McLaren, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/630,935

(22) Filed: Apr. 9, 2024

(65) Prior Publication Data

US 2024/0358958 A1 Oct. 31, 2024

Related U.S. Application Data

(63) Continuation of application No. 17/061,544, filed on Oct. 1, 2020, now Pat. No. 12,102,765, which is a (Continued)

(51) Int. Cl.
*A61M 16/00* (2006.01)
*A61M 16/06* (2006.01)
(Continued)

(52) U.S. Cl.
CPC .... *A61M 16/0683* (2013.01); *A61M 16/0666* (2013.01); *A61M 16/0825* (2014.02);
(Continued)

(58) Field of Classification Search
CPC .......... A61M 16/0683; A61M 16/0825; A61M 16/0666; A61M 16/06; A61M 2205/0216; A61M 16/00
See application file for complete search history.

(56) References Cited

U.S. PATENT DOCUMENTS

| | | | |
|---|---|---|---|
| 301,111 | A | 7/1884 | Genese |
| 472,238 | A | 4/1892 | Orden |

(Continued)

FOREIGN PATENT DOCUMENTS

| | | |
|---|---|---|
| CA | 996301 | 9/1976 |
| CA | 1311662 | 12/1992 |

(Continued)

OTHER PUBLICATIONS

Langnau, Jan. 2, 2012, Tips on Clips Part 2: Make it Snappy, https://www.makepartsfast. com/tips-on-clips-part-2-make-it-snappy/, 9 pp.

(Continued)

*Primary Examiner* — Margaret M Luarca
*Assistant Examiner* — Sarah B Lederer
(74) *Attorney, Agent, or Firm* — VIA LLP

(57) ABSTRACT

A headgear system and/or an interface assembly incorporating a headgear system that, in some configurations, is configured to transform from elasticated or "stretchy" behavior to "inelastic" behavior at least in response to normal or expected forces encountered during the intended therapy. In some configurations, upon fitment to the head of a user, the system automatically adjusts toward or to an appropriate size. A headgear portion or assembly for use in (Continued)

combination with a breathing apparatus in some configurations is at least substantially inelastic and is three dimensional in shape. The headgear portion or assembly can comprise a plastic core and a textile casing. The headgear, or part thereof, may also have integrally moulded labels, connectors, adjustment mechanisms and/or grips.

22 Claims, 157 Drawing Sheets

Related U.S. Application Data continuation of application No. 15/511,192, filed as application No. PCT/NZ2015/050149 on Sep. 16, 2015, now Pat. No. 10,874,814.

(60) Provisional application No. 62/198,104, filed on Jul. 28, 2015, provisional application No. 62/196,672, filed on Jul. 24, 2015, provisional application No. 62/159,857, filed on May 11, 2015, provisional application No. 62/138,304, filed on Mar. 25, 2015, provisional application No. 62/062,720, filed on Oct. 10, 2014, provisional application No. 62/053,026, filed on Sep. 19, 2014, provisional application No. 62/050,925, filed on Sep. 16, 2014.

(51) Int. Cl.
*A61M 16/08* (2006.01)
*A61M 16/20* (2006.01)

(52) U.S. Cl.
CPC .... *A61M 16/0866* (2014.02); *A61M 16/0875* (2013.01); *A61M 16/208* (2013.01); *A61M 16/06* (2013.01); *A61M 2205/0216* (2013.01); *A61M 2210/0618* (2013.01)

(56) References Cited

U.S. PATENT DOCUMENTS

| | | | |
|---|---|---|---|
| 577,926 A | 3/1897 | Miller |
| 718,470 A | 1/1903 | Jones |
| 751,091 A | 2/1904 | Moran |
| 770,013 A | 9/1904 | Linn |
| 1,364,104 A | 1/1921 | Geer |
| 1,635,545 A | 7/1927 | Drager |
| 1,942,442 A | 1/1934 | Motsinger |
| 2,199,690 A | 5/1940 | Bullard |
| 2,296,150 A | 9/1942 | Dockson et al. |
| 2,353,643 A | 7/1944 | Bulbulian |
| 2,359,506 A | 10/1944 | Battley et al. |
| 2,388,604 A | 11/1945 | Eisenbud |
| 2,390,233 A | 12/1945 | Akerman et al. |
| 2,508,050 A | 5/1950 | Valente |
| 2,586,851 A | 2/1952 | Monro et al. |
| 2,611,897 A | 9/1952 | Adams |
| 2,661,514 A | 12/1953 | Ada |
| 2,693,800 A | 11/1954 | Caldwell |
| 2,738,788 A | 3/1956 | Matheson et al. |
| 2,843,121 A | 7/1958 | Hudson |
| 2,859,748 A | 11/1958 | Hudson |
| 3,045,672 A | 7/1962 | Croasdaile |
| 3,156,922 A | 11/1964 | Anderson |
| 3,295,529 A | 1/1967 | Corrigall et al. |
| 3,416,521 A | 12/1968 | Humphrey |
| 3,457,564 A | 7/1969 | Holloway |
| 3,490,452 A | 1/1970 | Greenfield |
| 3,500,474 A | 3/1970 | Austin |
| 3,530,031 A | 9/1970 | Loew |
| 3,792,702 A | 2/1974 | Delest |
| 3,834,682 A | 9/1974 | McPhee |
| 3,850,171 A | 11/1974 | Ball et al. |
| 3,887,968 A | 6/1975 | Lynam |
| 3,972,321 A | 8/1976 | Proctor |
| 3,990,757 A | 11/1976 | Gill |
| 3,992,720 A | 11/1976 | Nicolinas |
| 3,994,022 A | 11/1976 | Villari et al. |
| 3,994,521 A | 11/1976 | Van Gompel |
| 4,051,556 A | 10/1977 | Davenport et al. |
| 4,062,068 A | 12/1977 | Davenport et al. |
| 4,090,510 A | 5/1978 | Segersten |
| 4,106,165 A | 8/1978 | Clowers et al. |
| D250,047 S | 10/1978 | Lewis et al. |
| D250,131 S | 10/1978 | Lewis et al. |
| 4,127,130 A | 11/1978 | Naysmith |
| D252,322 S | 7/1979 | Johnson |
| 4,167,185 A | 9/1979 | Lewis |
| 4,201,205 A | 5/1980 | Bartholomew |
| 4,266,540 A | 5/1981 | Panzik et al. |
| 4,278,082 A | 7/1981 | Blackmer |
| 4,288,891 A | 9/1981 | Boden |
| 4,313,437 A | 2/1982 | Martin |
| 4,328,605 A | 5/1982 | Hutchinson, V. et al. |
| 4,354,488 A | 10/1982 | Bartos |
| 4,367,735 A | 1/1983 | Dali |
| 4,402,316 A | 9/1983 | Gadberry |
| 4,413,382 A | 11/1983 | Siegmann |
| 4,437,462 A | 3/1984 | Piljay |
| 4,450,603 A | 5/1984 | Hirsch |
| 4,453,292 A | 6/1984 | Bakker |
| 4,458,373 A | 7/1984 | Maslow |
| 4,477,928 A | 10/1984 | Graff |
| 4,606,077 A | 8/1986 | Phillips |
| D293,613 S | 1/1988 | Wingler |
| 4,734,940 A | 4/1988 | Galet et al. |
| 4,753,233 A | 6/1988 | Grimes |
| 4,782,832 A | 11/1988 | Trimble et al. |
| 4,817,596 A | 4/1989 | Gallet |
| 4,848,334 A | 7/1989 | Bellm |
| 4,853,275 A | 8/1989 | Tracy et al. |
| 4,856,508 A | 8/1989 | Tayebi |
| 4,915,105 A | 4/1990 | Lee |
| 4,941,467 A | 7/1990 | Takata |
| 4,944,310 A | 7/1990 | Sullivan |
| 4,947,488 A | 8/1990 | Ashinoff |
| D310,431 S | 9/1990 | Bellm |
| 4,971,051 A | 11/1990 | Toffolon |
| 4,986,269 A | 1/1991 | Hakkinen |
| 5,010,925 A | 4/1991 | Atkinson et al. |
| 5,016,625 A | 5/1991 | Hsu et al. |
| 5,042,478 A | 8/1991 | Kopala et al. |
| D320,677 S | 10/1991 | Kumagai et al. |
| 5,052,084 A | 10/1991 | Braun |
| D321,419 S | 11/1991 | Wallace |
| 5,065,756 A | 11/1991 | Rapoport |
| 5,074,297 A | 12/1991 | Venegas |
| 5,094,236 A | 3/1992 | Tayebi |
| 5,113,857 A | 5/1992 | Dickerman et al. |
| 5,148,578 A | 9/1992 | Clarke et al. |
| 5,148,802 A | 9/1992 | Sanders et al. |
| 5,191,882 A | 3/1993 | Vogliano |
| 5,231,979 A | 8/1993 | Rose |
| 5,245,995 A | 9/1993 | Sullivan et al. |
| D340,317 S | 10/1993 | Cole |
| 5,269,296 A | 12/1993 | Landis et al. |
| 5,279,020 A | 1/1994 | Coe |
| D354,128 S | 1/1995 | Rinehart |
| D355,484 S | 2/1995 | Rinehart |
| 5,388,743 A | 2/1995 | Silagy |
| 5,438,979 A | 8/1995 | Johnson et al. |
| 5,477,852 A | 12/1995 | Landis et al. |
| 5,488,948 A | 2/1996 | Dubruille |
| 5,513,634 A | 5/1996 | Jackson |
| 5,529,062 A | 6/1996 | Byrd |
| 5,533,506 A | 7/1996 | Wood |
| 5,546,605 A | 8/1996 | Mallardi |
| 5,551,419 A | 9/1996 | Froehlich et al. |
| 5,566,395 A | 10/1996 | Nebeker |
| 5,595,174 A | 1/1997 | Gwaltney |
| 5,601,078 A | 2/1997 | Schaller et al. |
| D378,610 S | 3/1997 | Reischel et al. |
| 5,657,752 A | 8/1997 | Landis et al. |

(56) References Cited

U.S. PATENT DOCUMENTS

| | | | |
|---|---|---|---|
| 5,724,965 | A | 3/1998 | Handke et al. |
| 5,752,510 | A | 5/1998 | Goldstein |
| 5,755,578 | A | 5/1998 | Contant et al. |
| 5,774,901 | A | 7/1998 | Minami |
| 5,823,020 | A | 10/1998 | Benda |
| 5,884,624 | A | 3/1999 | Barnett et al. |
| 5,921,239 | A | 7/1999 | McCall et al. |
| 5,941,245 | A | 8/1999 | Hannah et al. |
| 5,941,856 | A | 8/1999 | Kovacs et al. |
| 6,017,315 | A | 1/2000 | Starr et al. |
| 6,019,101 | A | 2/2000 | Cotner et al. |
| 6,044,844 | A | 4/2000 | Kwok et al. |
| 6,050,260 | A | 4/2000 | Daniell et al. |
| 6,119,694 | A | 9/2000 | Correa et al. |
| 6,192,886 | B1 | 2/2001 | Rudolph |
| D440,302 | S | 4/2001 | Wolfe |
| 6,256,798 | B1 | 7/2001 | Egolf et al. |
| 6,272,690 | B1 | 8/2001 | Carey et al. |
| 6,282,725 | B1 | 9/2001 | Vanidestine, Jr. |
| 6,298,850 | B1 | 10/2001 | Argraves |
| 6,338,342 | B1 | 1/2002 | Fecteau et al. |
| 6,347,631 | B1 | 2/2002 | Hansen et al. |
| D455,891 | S | 4/2002 | Biedrzycki |
| 6,418,928 | B1 | 7/2002 | Bordewick et al. |
| 6,422,238 | B1 | 7/2002 | Lithgow |
| 6,431,172 | B1 | 8/2002 | Bordewick |
| 6,435,181 | B1 | 8/2002 | Jones, Jr. et al. |
| 6,439,234 | B1 | 8/2002 | Curti et al. |
| 6,470,886 | B1 | 10/2002 | Jestrabek-Hart |
| 6,478,026 | B1 | 11/2002 | Wood |
| 6,491,034 | B1 | 12/2002 | Gunaratnam et al. |
| 6,536,435 | B1 | 3/2003 | Fecteau et al. |
| 6,561,188 | B1 | 5/2003 | Ellis |
| 6,561,191 | B1 | 5/2003 | Kwok |
| 6,571,854 | B1 | 6/2003 | Palmer |
| 6,581,594 | B1 | 6/2003 | Drew et al. |
| 6,581,601 | B2 | 6/2003 | Ziaee |
| 6,588,424 | B2 | 7/2003 | Bardel |
| 6,631,718 | B1 | 10/2003 | Lovell |
| 6,637,434 | B2 | 10/2003 | Noble |
| 6,644,315 | B2 | 11/2003 | Ziaee |
| 6,651,658 | B1 | 11/2003 | Hill et al. |
| 6,659,102 | B1 | 12/2003 | Sico |
| 6,662,803 | B2 | 12/2003 | Gradon et al. |
| 6,679,257 | B1 | 1/2004 | Robertson et al. |
| 6,679,265 | B2 | 1/2004 | Strickland et al. |
| 6,772,761 | B1 | 8/2004 | Rucker, Jr. |
| 6,851,425 | B2 | 2/2005 | Jaffre et al. |
| 6,883,519 | B2 | 4/2005 | Schmidtke et al. |
| 6,886,564 | B2 | 5/2005 | Sullivan et al. |
| 6,892,729 | B2 | 5/2005 | Smith et al. |
| 6,907,882 | B2 | 6/2005 | Ging et al. |
| 6,951,218 | B2 | 10/2005 | Gradon et al. |
| 7,004,165 | B1 | 2/2006 | Salcido |
| D520,140 | S | 5/2006 | Chaggares |
| 7,036,508 | B2 | 5/2006 | Kwok |
| 7,062,795 | B2 | 6/2006 | Skiba et al. |
| 7,066,179 | B2 | 6/2006 | Eaton et al. |
| D526,094 | S | 8/2006 | Chen |
| 7,096,864 | B1 | 8/2006 | Mayer et al. |
| 7,096,867 | B2 | 8/2006 | Smith et al. |
| 7,201,169 | B2 | 4/2007 | Wilkie et al. |
| 7,207,333 | B2 | 4/2007 | Tohara |
| 7,210,481 | B1 | 5/2007 | Lovell et al. |
| 7,219,669 | B1 | 5/2007 | Lovell et al. |
| 7,225,811 | B2 | 6/2007 | Ruiz et al. |
| 7,318,437 | B2 | 1/2008 | Gunaratnam et al. |
| 7,353,826 | B2 | 4/2008 | Sleeper et al. |
| 7,353,827 | B2 | 4/2008 | Geist |
| 7,814,911 | B2 | 10/2010 | Bordewick et al. |
| 7,845,352 | B2 | 12/2010 | Sleeper et al. |
| 7,856,982 | B2 * | 12/2010 | Matula, Jr. ........ A61M 16/0683 128/206.28 |
| 7,861,715 | B2 | 1/2011 | Jones et al. |
| 7,870,860 | B2 | 1/2011 | McCormick et al. |
| 7,896,003 | B2 | 3/2011 | Matula et al. |
| 7,913,692 | B2 | 3/2011 | Kwok |
| 7,967,014 | B2 | 6/2011 | Heidmann |
| 8,042,539 | B2 | 10/2011 | Chandran et al. |
| 8,047,893 | B2 | 11/2011 | Fenske |
| 8,074,651 | B2 | 12/2011 | Bierman et al. |
| 8,104,473 | B2 | 1/2012 | Woodard et al. |
| 8,132,270 | B2 | 3/2012 | Lang et al. |
| 8,136,524 | B2 | 3/2012 | Ging et al. |
| 8,209,995 | B2 | 7/2012 | Kieling et al. |
| 8,297,285 | B2 | 10/2012 | Henry et al. |
| 8,371,302 | B2 | 2/2013 | Ging et al. |
| 8,443,807 | B2 | 5/2013 | McAuley et al. |
| D686,313 | S | 7/2013 | Matula et al. |
| 8,479,741 | B2 | 7/2013 | McAuley et al. |
| 8,505,538 | B2 | 8/2013 | Amarasinghe |
| 8,517,025 | B2 | 8/2013 | Ho et al. |
| 8,522,785 | B2 | 9/2013 | Berthon-Jones et al. |
| 8,573,201 | B2 | 11/2013 | Rummery et al. |
| 8,596,271 | B2 | 12/2013 | Matula, Jr. et al. |
| 8,596,274 | B2 | 12/2013 | Hieber et al. |
| 8,631,793 | B2 | 1/2014 | Omura et al. |
| 8,636,005 | B2 | 1/2014 | Gradon et al. |
| 8,636,007 | B2 | 1/2014 | Rummery et al. |
| 8,636,008 | B2 | 1/2014 | Flory et al. |
| 8,757,157 | B2 | 6/2014 | Price et al. |
| 8,783,257 | B2 | 7/2014 | McAuley et al. |
| 8,794,239 | B2 | 8/2014 | Gunaratnam |
| 8,839,789 | B2 | 9/2014 | Guney et al. |
| 8,856,975 | B2 | 10/2014 | Lang et al. |
| 8,857,435 | B2 | 10/2014 | Matula, Jr. et al. |
| 8,915,251 | B2 | 12/2014 | Lubke et al. |
| 8,950,404 | B2 | 2/2015 | Formica et al. |
| 8,997,742 | B2 | 4/2015 | Moore et al. |
| 9,032,955 | B2 | 5/2015 | Lubke et al. |
| 9,044,564 | B2 | 6/2015 | Dravitzki et al. |
| 9,103,161 | B2 | 8/2015 | Mader |
| 9,138,555 | B2 | 9/2015 | McAuley et al. |
| 9,149,596 | B2 | 10/2015 | Valcic et al. |
| 9,265,909 | B2 | 2/2016 | Ho et al. |
| 9,302,065 | B2 | 4/2016 | Smith et al. |
| 9,320,866 | B2 | 4/2016 | McAuley et al. |
| 9,333,315 | B2 | 5/2016 | McAuley et al. |
| 9,339,622 | B2 | 5/2016 | McAuley et al. |
| 9,480,809 | B2 | 11/2016 | Guney et al. |
| 9,517,320 | B2 | 12/2016 | Barlow et al. |
| 9,550,038 | B2 | 1/2017 | McAuley et al. |
| 9,555,943 | B2 | 1/2017 | Breen, IV et al. |
| 9,592,336 | B2 | 3/2017 | Nielsen et al. |
| 9,629,974 | B2 | 4/2017 | Gibson |
| 9,656,038 | B2 | 5/2017 | Rummery et al. |
| 9,744,385 | B2 | 8/2017 | Henry |
| 9,782,554 | B2 | 10/2017 | Mazzone et al. |
| 9,878,118 | B2 | 1/2018 | Formica |
| D810,277 | S | 2/2018 | Amarasinghe |
| 9,884,160 | B2 | 2/2018 | Mcauley |
| 9,901,700 | B2 | 2/2018 | McAuley et al. |
| 9,925,349 | B2 | 3/2018 | Jablonski |
| 9,974,914 | B2 | 5/2018 | McAuley |
| 9,993,606 | B2 | 6/2018 | Gibson et al. |
| 10,039,665 | B2 | 8/2018 | Blaszczykiewicz et al. |
| 10,065,010 | B2 | 9/2018 | Smith et al. |
| 10,071,217 | B2 | 9/2018 | Grashow |
| 10,080,856 | B2 | 9/2018 | McLaren |
| 10,137,319 | B2 | 11/2018 | Carr et al. |
| 10,207,072 | B2 | 2/2019 | Dunn et al. |
| 10,279,138 | B2 | 5/2019 | Ovzinsky |
| 10,456,546 | B2 | 10/2019 | McLaren et al. |
| 10,646,680 | B2 | 5/2020 | Huddart et al. |
| 10,668,242 | B2 | 6/2020 | Bearne |
| 10,675,428 | B2 | 6/2020 | Guney et al. |
| 10,792,451 | B2 | 10/2020 | Allan et al. |
| 10,828,449 | B2 | 11/2020 | Higgins et al. |
| 10,828,452 | B2 | 11/2020 | Huddart et al. |
| 10,874,814 | B2 | 12/2020 | Huddart et al. |
| 11,000,663 | B2 | 5/2021 | Felix et al. |
| 11,253,668 | B2 | 2/2022 | Freestone |
| 11,331,449 | B2 | 5/2022 | McLaren et al. |
| 11,419,999 | B2 | 8/2022 | Patel et al. |

(56) References Cited

U.S. PATENT DOCUMENTS

| | | |
|---|---|---|
| 11,607,518 B2 | 3/2023 | Hammer et al. |
| 11,648,365 B2 | 5/2023 | Huddart et al. |
| 11,701,486 B2 | 7/2023 | Mashal et al. |
| 11,752,292 B2 | 9/2023 | McLaren et al. |
| 11,806,452 B2 | 11/2023 | McLaren et al. |
| 11,813,384 B2 | 11/2023 | Huddart et al. |
| 11,819,618 B2 | 11/2023 | Felix et al. |
| 11,819,620 B2 | 11/2023 | Hammer |
| 11,850,365 B2 | 12/2023 | Freestone et al. |
| 11,865,263 B2 | 1/2024 | Smith et al. |
| 11,878,119 B2 | 1/2024 | McLaren et al. |
| 2002/0005198 A1 | 1/2002 | Kwok et al. |
| 2002/0020416 A1 | 2/2002 | Namey |
| 2002/0046755 A1 | 4/2002 | Voss |
| 2002/0052568 A1 | 5/2002 | Houser et al. |
| 2002/0053347 A1 | 5/2002 | Ziaee |
| 2002/0059935 A1 | 5/2002 | Wood |
| 2002/0096178 A1 | 7/2002 | Ziaee |
| 2002/0157668 A1 | 10/2002 | Bardel |
| 2003/0005933 A1 | 1/2003 | Izuchukwu |
| 2003/0051732 A1 | 3/2003 | Smith et al. |
| 2003/0079749 A1 | 5/2003 | Strickland et al. |
| 2003/0084903 A1 | 5/2003 | Fecteau et al. |
| 2003/0111080 A1 | 6/2003 | Olsen et al. |
| 2003/0121519 A1 | 7/2003 | Estes et al. |
| 2003/0164170 A1 | 9/2003 | Drew et al. |
| 2003/0172936 A1 | 9/2003 | Wilkie et al. |
| 2003/0196656 A1 | 10/2003 | Moore |
| 2003/0196658 A1 | 10/2003 | Ging et al. |
| 2003/0196659 A1 | 10/2003 | Gradon et al. |
| 2003/0196664 A1 | 10/2003 | Jacobson |
| 2003/0200970 A1 | 10/2003 | Stenzler et al. |
| 2004/0067333 A1 | 4/2004 | Amarasinghe |
| 2004/0211427 A1 | 10/2004 | Jones et al. |
| 2004/0226566 A1 | 11/2004 | Gunaratnam et al. |
| 2005/0011524 A1 | 1/2005 | Thomlinson et al. |
| 2005/0016067 A1 | 1/2005 | Pettit |
| 2005/0028822 A1 | 2/2005 | Sleeper et al. |
| 2005/0033247 A1 | 2/2005 | Thompson |
| 2005/0066976 A1 | 3/2005 | Wondka |
| 2005/0076913 A1 | 4/2005 | Ho et al. |
| 2005/0098183 A1 | 5/2005 | Nash et al. |
| 2005/0150497 A1 | 7/2005 | Eifler et al. |
| 2005/0161049 A1 | 7/2005 | Wright |
| 2005/0199239 A1 | 9/2005 | Lang et al. |
| 2005/0199242 A1 | 9/2005 | Matula et al. |
| 2005/0205096 A1 | 9/2005 | Matula |
| 2005/0235999 A1 | 10/2005 | Wood et al. |
| 2005/0262619 A1 | 12/2005 | Musal et al. |
| 2006/0060200 A1 | 3/2006 | Ho et al. |
| 2006/0081250 A1 | 4/2006 | Bordewick et al. |
| 2006/0096596 A1 | 5/2006 | Occhialini et al. |
| 2006/0107958 A1 | 5/2006 | Sleeper |
| 2006/0113147 A1 | 6/2006 | Harris |
| 2006/0118117 A1 | 6/2006 | Berthon-Jones et al. |
| 2006/0124131 A1 | 6/2006 | Chandran |
| 2006/0137690 A1 | 6/2006 | Gunaratnam et al. |
| 2006/0174887 A1 | 8/2006 | Chandran et al. |
| 2006/0174892 A1 | 8/2006 | Leksutin et al. |
| 2006/0196510 A1 | 9/2006 | McDonald et al. |
| 2006/0196511 A1 | 9/2006 | Lau et al. |
| 2006/0237018 A1 | 10/2006 | McAuley et al. |
| 2007/0000492 A1 | 1/2007 | Hansel et al. |
| 2007/0010786 A1 | 1/2007 | Casey et al. |
| 2007/0089749 A1 | 4/2007 | Ho et al. |
| 2007/0125385 A1 | 6/2007 | Ho et al. |
| 2007/0125387 A1 | 6/2007 | Zollinger et al. |
| 2007/0130663 A1 | 6/2007 | Lang et al. |
| 2007/0137653 A1 | 6/2007 | Wood |
| 2007/0163600 A1 | 7/2007 | Hoffman |
| 2007/0169777 A1 | 7/2007 | Amarasinghe et al. |
| 2007/0175480 A1 | 8/2007 | Gradon et al. |
| 2007/0209663 A1 | 9/2007 | Marque et al. |
| 2007/0215161 A1 | 9/2007 | Frater et al. |
| 2007/0235033 A1 | 10/2007 | Reier et al. |
| 2007/0295335 A1 | 12/2007 | Nashed |
| 2008/0041388 A1 | 2/2008 | McAuley et al. |
| 2008/0041393 A1 | 2/2008 | Bracken |
| 2008/0047560 A1 | 2/2008 | Veliss et al. |
| 2008/0052806 A1 | 3/2008 | McDaniel |
| 2008/0053450 A1 | 3/2008 | Van Kerkwyk et al. |
| 2008/0060648 A1 | 3/2008 | Thornton et al. |
| 2008/0060653 A1 | 3/2008 | Hallet et al. |
| 2008/0060657 A1 | 3/2008 | McAuley et al. |
| 2008/0065015 A1 | 3/2008 | Fiser |
| 2008/0083412 A1 | 4/2008 | Henry et al. |
| 2008/0092906 A1 | 4/2008 | Gunaratnam et al. |
| 2008/0099024 A1 | 5/2008 | Gunaratnam et al. |
| 2008/0110464 A1 | 5/2008 | Davidson et al. |
| 2008/0134480 A1 | 6/2008 | Shiue |
| 2008/0196728 A1 | 8/2008 | Ho |
| 2008/0230068 A1 | 9/2008 | Rudolph |
| 2008/0230069 A1 | 9/2008 | Valcic et al. |
| 2008/0264422 A1 | 10/2008 | Fishman |
| 2008/0302366 A1 | 12/2008 | McGinnis et al. |
| 2008/0314388 A1 | 12/2008 | Brambilla et al. |
| 2009/0000624 A1 | 1/2009 | Lee et al. |
| 2009/0014007 A1 | 1/2009 | Brambilla et al. |
| 2009/0032026 A1 | 2/2009 | Price et al. |
| 2009/0044808 A1 | 2/2009 | Guney et al. |
| 2009/0044809 A1 | 2/2009 | Welchel et al. |
| 2009/0120442 A1 | 5/2009 | Ho |
| 2009/0133697 A1 | 5/2009 | Kwok et al. |
| 2009/0145429 A1 | 6/2009 | Ging et al. |
| 2009/0173349 A1 | 7/2009 | Hernandez et al. |
| 2009/0178680 A1 | 7/2009 | Chang |
| 2009/0183739 A1 | 7/2009 | Wondka |
| 2009/0211583 A1 | 8/2009 | Carroll |
| 2009/0250060 A1 | 10/2009 | Hacke et al. |
| 2009/0320187 A1 | 12/2009 | Petzl et al. |
| 2010/0000538 A1 | 1/2010 | Edwards et al. |
| 2010/0000544 A1 | 1/2010 | Blaszczykiewicz et al. |
| 2010/0018534 A1 | 1/2010 | Veliss et al. |
| 2010/0037897 A1 | 2/2010 | Wood |
| 2010/0154798 A1 | 6/2010 | Henry et al. |
| 2010/0224199 A1 | 9/2010 | Smith et al. |
| 2010/0258132 A1 | 10/2010 | Moore |
| 2010/0258136 A1 | 10/2010 | Doherty et al. |
| 2010/0282265 A1 | 11/2010 | Melidis et al. |
| 2010/0307502 A1 | 12/2010 | Rummery et al. |
| 2010/0313532 A1 | 12/2010 | Stjernfelt et al. |
| 2010/0313891 A1 | 12/2010 | Veliss et al. |
| 2010/0319700 A1 | 12/2010 | Ng et al. |
| 2011/0048425 A1 | 3/2011 | Chang |
| 2011/0191938 A1 | 8/2011 | Elliott |
| 2011/0197341 A1 | 8/2011 | Formica |
| 2011/0197431 A1 | 8/2011 | Tang |
| 2011/0220113 A1 | 9/2011 | Newman |
| 2011/0247628 A1 | 10/2011 | Ho |
| 2011/0259335 A1 | 10/2011 | Sullivan |
| 2011/0265791 A1 | 11/2011 | Ging et al. |
| 2011/0265796 A1 | 11/2011 | Amarasinghe et al. |
| 2012/0067349 A1 | 3/2012 | Barlow et al. |
| 2012/0125339 A1 | 5/2012 | Ho et al. |
| 2012/0132209 A1 | 5/2012 | Rummery |
| 2012/0138063 A1 | 6/2012 | Eves et al. |
| 2012/0174355 A1 | 7/2012 | Fraze |
| 2012/0222680 A1 | 9/2012 | Eves et al. |
| 2012/0247490 A1 | 10/2012 | Matthews |
| 2012/0285464 A1 | 11/2012 | Birch et al. |
| 2012/0304999 A1 | 12/2012 | Swift et al. |
| 2013/0000648 A1 | 1/2013 | Madaus et al. |
| 2013/0008449 A1 | 1/2013 | Busch et al. |
| 2013/0139822 A1 | 6/2013 | Gibson |
| 2013/0152918 A1 | 6/2013 | Rummery et al. |
| 2013/0152937 A1 | 6/2013 | Jablonski |
| 2013/0160769 A1 | 6/2013 | Ng et al. |
| 2013/0220327 A1 | 8/2013 | Barlow et al. |
| 2013/0228173 A1 | 9/2013 | Busch |
| 2013/0247916 A1 | 9/2013 | Symons |
| 2013/0319421 A1 | 12/2013 | Hitchcock et al. |
| 2014/0026888 A1 | 1/2014 | Matula |
| 2014/0026890 A1 | 1/2014 | Haskard et al. |
| 2014/0083428 A1 | 3/2014 | Rothermel et al. |

(56)        References Cited

U.S. PATENT DOCUMENTS

| | | | |
|---|---|---|---|
| 2014/0102456 A1 | 4/2014 | Ovizinsky |
| 2014/0137870 A1 | 5/2014 | Barlow |
| 2014/0158726 A1 | 6/2014 | Malara |
| 2014/0166019 A1 | 6/2014 | Ho et al. |
| 2014/0190486 A1 | 7/2014 | Dunn et al. |
| 2014/0209098 A1 | 7/2014 | Dunn |
| 2014/0209298 A1 | 7/2014 | Baldasaro |
| 2014/0216452 A1 | 8/2014 | Miller et al. |
| 2014/0305439 A1 | 10/2014 | Chodkowski |
| 2014/0358054 A1 | 12/2014 | Capra |
| 2015/0000615 A1 | 1/2015 | Imran et al. |
| 2015/0005685 A1 | 1/2015 | Chetlapalli et al. |
| 2015/0028519 A1 | 1/2015 | Lang et al. |
| 2015/0033457 A1 | 2/2015 | Tryner et al. |
| 2015/0051000 A1 | 2/2015 | Henn |
| 2015/0090268 A1 | 4/2015 | Madaus et al. |
| 2015/0128953 A1 | 5/2015 | Formica et al. |
| 2015/0151070 A1 | 6/2015 | Capra et al. |
| 2015/0190262 A1 | 7/2015 | Capra et al. |
| 2015/0202397 A1 | 7/2015 | Pastoor |
| 2015/0217150 A1 | 8/2015 | Harris |
| 2015/0285337 A1 | 10/2015 | Dingley et al. |
| 2015/0290415 A1 | 10/2015 | Dunn |
| 2016/0022944 A1 | 1/2016 | Chodkowski et al. |
| 2016/0038707 A1 | 2/2016 | Allan et al. |
| 2016/0045700 A1 | 2/2016 | Amarasinghe |
| 2016/0082214 A1 | 3/2016 | Barlow et al. |
| 2016/0166793 A1 | 6/2016 | McLaren et al. |
| 2016/0178027 A1 | 6/2016 | Wetzel |
| 2016/0256655 A1 | 9/2016 | Mah |
| 2016/0278463 A1 | 9/2016 | Stevenson |
| 2016/0375214 A1 | 12/2016 | Chodkowski et al. |
| 2017/0136269 A1 | 5/2017 | Jacotey et al. |
| 2017/0182276 A1 | 6/2017 | Hammer |
| 2017/0189636 A1 | 7/2017 | Gibson et al. |
| 2017/0216548 A1 | 8/2017 | Gerhardt |
| 2017/0319808 A1 | 11/2017 | Answine |
| 2018/0209618 A1 | 7/2018 | Pontano |
| 2018/0214655 A1 | 8/2018 | Kooij et al. |
| 2018/0264218 A1 | 9/2018 | Chodkowski |
| 2019/0111227 A1 | 4/2019 | Veliss et al. |
| 2019/0117026 A1 | 4/2019 | Guerra |
| 2019/0118009 A1 | 4/2019 | Vogus |
| 2019/0151592 A1 | 5/2019 | Bornholdt |
| 2019/0220327 A1 | 7/2019 | Otenko |
| 2020/0230343 A1 | 7/2020 | Sims et al. |
| 2020/0338294 A1 | 10/2020 | McLaren et al. |
| 2022/0126049 A1 | 4/2022 | Amarasinghe |
| 2023/0347090 A1 | 11/2023 | Huddart et al. |
| 2024/0024606 A1 | 1/2024 | McLaren et al. |
| 2024/0033461 A1 | 2/2024 | Felix et al. |
| 2024/0077763 A1 | 3/2024 | Yoon et al. |
| 2024/0139456 A1 | 5/2024 | Freestone |
| 2024/0165360 A1 | 5/2024 | Smith et al. |
| 2024/0181194 A1 | 6/2024 | Hammer |

FOREIGN PATENT DOCUMENTS

| | | |
|---|---|---|
| CA | 2995960 | 2/2017 |
| CN | 2172538 | 7/1994 |
| CN | 2504493 Y | 8/2002 |
| CN | 2562067 Y | 7/2003 |
| CN | 1784250 | 6/2006 |
| CN | 1901963 A | 1/2007 |
| CN | 201033204 | 3/2008 |
| CN | 201171846 | 12/2008 |
| CN | 101432039 A | 5/2009 |
| CN | 100502972 C | 6/2009 |
| CN | 101516427 | 8/2009 |
| CN | 202822396 U | 3/2013 |
| CN | 103536996 | 1/2014 |
| DE | 895692 | 11/1953 |
| DE | 2706284 | 8/1978 |
| DE | 3122034 | 12/1982 |
| DE | 3907428 | 9/1990 |
| DE | 10254399 | 6/2004 |
| DE | 10341550 A1 | 3/2005 |
| DE | 102006011151 | 9/2007 |
| DE | 102012010775 | 12/2013 |
| EP | 0 350 322 | 1/1990 |
| EP | 0352948 A2 | 1/1990 |
| EP | 0 401 307 | 8/1995 |
| EP | 0 879 565 | 11/1998 |
| EP | 0 982 049 | 3/2000 |
| EP | 1 187 650 | 12/2005 |
| EP | 2 060 294 | 5/2009 |
| EP | 2 130 563 | 12/2009 |
| EP | 2 517 757 | 10/2012 |
| EP | 2 022 528 | 3/2016 |
| FR | 2390116 | 3/1938 |
| FR | 2618340 | 11/1970 |
| FR | 825960 | 1/1989 |
| FR | 2658725 | 8/1991 |
| FR | 2749176 | 12/1997 |
| FR | 2804421 | 8/2001 |
| GB | 190224431 | 12/1902 |
| GB | 339522 | 12/1930 |
| GB | 826198 | 12/1959 |
| GB | 880824 | 10/1961 |
| GB | 1467828 | 3/1977 |
| GB | 2133275 | 7/1984 |
| GB | 2188236 | 9/1987 |
| GB | 1211268 | 4/2000 |
| GB | 2478305 | 9/2011 |
| GB | 2491227 | 11/2012 |
| GB | 2553475 | 3/2018 |
| JP | S46-12114 | 4/1971 |
| JP | 46-016719 | 6/1971 |
| JP | S55-89072 | 7/1980 |
| JP | S56120849 | 9/1981 |
| JP | 368861 U | 5/2000 |
| JP | 2004-016488 | 1/2004 |
| JP | 2003-053874 | 9/2004 |
| JP | 2009-125306 | 6/2009 |
| JP | 2010-090973 | 4/2010 |
| JP | 2000-102624 | 5/2013 |
| JP | 2018-127729 | 8/2018 |
| KR | 10-2011-0028950 | 3/2011 |
| NZ | 585295 | 12/2011 |
| TW | 201340900 | 1/2013 |
| WO | WO 95/12432 | 5/1995 |
| WO | WO 97/32494 | 9/1997 |
| WO | WO 98/003225 | 1/1998 |
| WO | WO 98/018514 | 5/1998 |
| WO | WO 99/04842 | 2/1999 |
| WO | WO 99/058181 | 11/1999 |
| WO | WO 00/50122 | 8/2000 |
| WO | WO 00/069497 | 11/2000 |
| WO | WO 00/074758 | 12/2000 |
| WO | WO 01/041854 | 6/2001 |
| WO | WO 01/097892 | 12/2001 |
| WO | WO 02/44749 | 6/2002 |
| WO | WO 02/047749 | 6/2002 |
| WO | WO 02/074372 | 9/2002 |
| WO | WO 04/039185 | 5/2004 |
| WO | WO 04/041341 | 5/2004 |
| WO | WO 04/073778 | 9/2004 |
| WO | WO 05/021075 | 3/2005 |
| WO | WO 05/032634 | 4/2005 |
| WO | WO 05/046776 | 5/2005 |
| WO | WO 05/051468 | 6/2005 |
| WO | WO 05/063328 | 7/2005 |
| WO | WO 05/118042 | 12/2005 |
| WO | WO 05/123166 | 12/2005 |
| WO | WO 06/130903 | 12/2006 |
| WO | WO 06/138416 | 12/2006 |
| WO | WO 07/022562 | 3/2007 |
| WO | WO 07/041786 | 4/2007 |
| WO | WO 07/068044 | 6/2007 |
| WO | WO 07/125487 | 11/2007 |
| WO | WO 07/147088 | 12/2007 |
| WO | WO 08/007985 | 1/2008 |
| WO | WO 08/060295 | 5/2008 |
| WO | WO 08/070929 | 6/2008 |

(56) References Cited

FOREIGN PATENT DOCUMENTS

| | | | | |
|---|---|---|---|---|
| WO | WO 08/106716 | 9/2008 | | |
| WO | WO 08/148086 | 12/2008 | | |
| WO | WO 09/026627 | 3/2009 | | |
| WO | WO 09/038918 | 3/2009 | | |
| WO | WO 09/052560 | 4/2009 | | |
| WO | WO 09/059353 | 5/2009 | | |
| WO | WO 09/092057 | 7/2009 | | |
| WO | WO 09/108995 | 9/2009 | | |
| WO | WO 09/139647 | 11/2009 | | |
| WO | WO 09/148956 | 12/2009 | | |
| WO | WO 10/066004 | 6/2010 | | |
| WO | WO 10/081295 | 7/2010 | | |
| WO | WO 10/131189 | 11/2010 | | |
| WO | WO 10/139014 | 12/2010 | | |
| WO | WO 11/072739 | 6/2011 | | |
| WO | WO 11/077254 | 6/2011 | | |
| WO | WO-2011077254 A2 * | 6/2011 | ............ | A61M 16/00 |
| WO | WO 11/112401 | 9/2011 | | |
| WO | WO 12/07300 | 1/2012 | | |
| WO | WO 12/045127 | 4/2012 | | |
| WO | WO 12/069951 | 5/2012 | | |
| WO | WO 12/071300 | 5/2012 | | |
| WO | WO 12/143822 | 10/2012 | | |
| WO | WO 12/154883 | 11/2012 | | |
| WO | WO 12/177152 | 12/2012 | | |
| WO | WO 13/006913 | 1/2013 | | |
| WO | WO 13/026091 | 2/2013 | | |
| WO | WO 13/026092 | 2/2013 | | |
| WO | WO 13/064930 | 5/2013 | | |
| WO | WO 14/020469 | 2/2014 | | |
| WO | WO 14/025267 | 2/2014 | | |
| WO | WO 14/031673 | 2/2014 | | |
| WO | WO-2014025267 A1 * | 2/2014 | ............ | A61M 16/06 |
| WO | WO 14/075141 | 5/2014 | | |
| WO | WO 14/077708 | 5/2014 | | |
| WO | WO 14/110622 | 7/2014 | | |
| WO | WO 14/110626 | 7/2014 | | |
| WO | WO 14/129913 | 8/2014 | | |
| WO | WO 14/175752 | 10/2014 | | |
| WO | WO 14/175753 | 10/2014 | | |
| WO | WO 15/033287 | 3/2015 | | |
| WO | WO 15/043229 | 4/2015 | | |
| WO | WO 15/070289 | 5/2015 | | |
| WO | WO 15/079396 | 6/2015 | | |
| WO | WO 15/083060 | 6/2015 | | |
| WO | WO 15/151019 | 10/2015 | | |
| WO | WO 15/187986 | 12/2015 | | |
| WO | WO 16/043603 | 3/2016 | | |
| WO | WO 17/030447 | 2/2017 | | |
| WO | WO 17/059476 | 4/2017 | | |
| WO | WO 17/150990 | 9/2017 | | |
| WO | WO 17/158474 | 9/2017 | | |
| WO | WO 17/158544 | 9/2017 | | |
| WO | WO 17/160166 | 9/2017 | | |
| WO | WO 17/216708 | 12/2017 | | |
| WO | WO 19/003094 | 1/2019 | | |

OTHER PUBLICATIONS cpap.com, InnoMed/Resp Care Bravo Nasal Pillow CPAP Mask with Headgear, (http://web.archive.org/web/*/https://www.cpap.com/productpage/bravo-nasal-interface/), downloaded Feb. 24, 2020, 5 pp.

Pad A Cheek, LLC, Sleep apnea can make beautiful sleep elusive, (http://web.archive.org/web/20070701000000*/http://www.padacheek.com/;Wayback Machine), downloaded Feb. 24, 2020, 3 pp.

Philips Respironics 'System One Heated Humidifier—User Manual', 2011, pp. 1-16, [retrieved on Nov. 25, 2013] from the internet: URL: http://www.cpapxchange.com/cpap-machines-biap-machines/system-one-60-series-cpap-humidifier-manual.pdf.

* cited by examiner

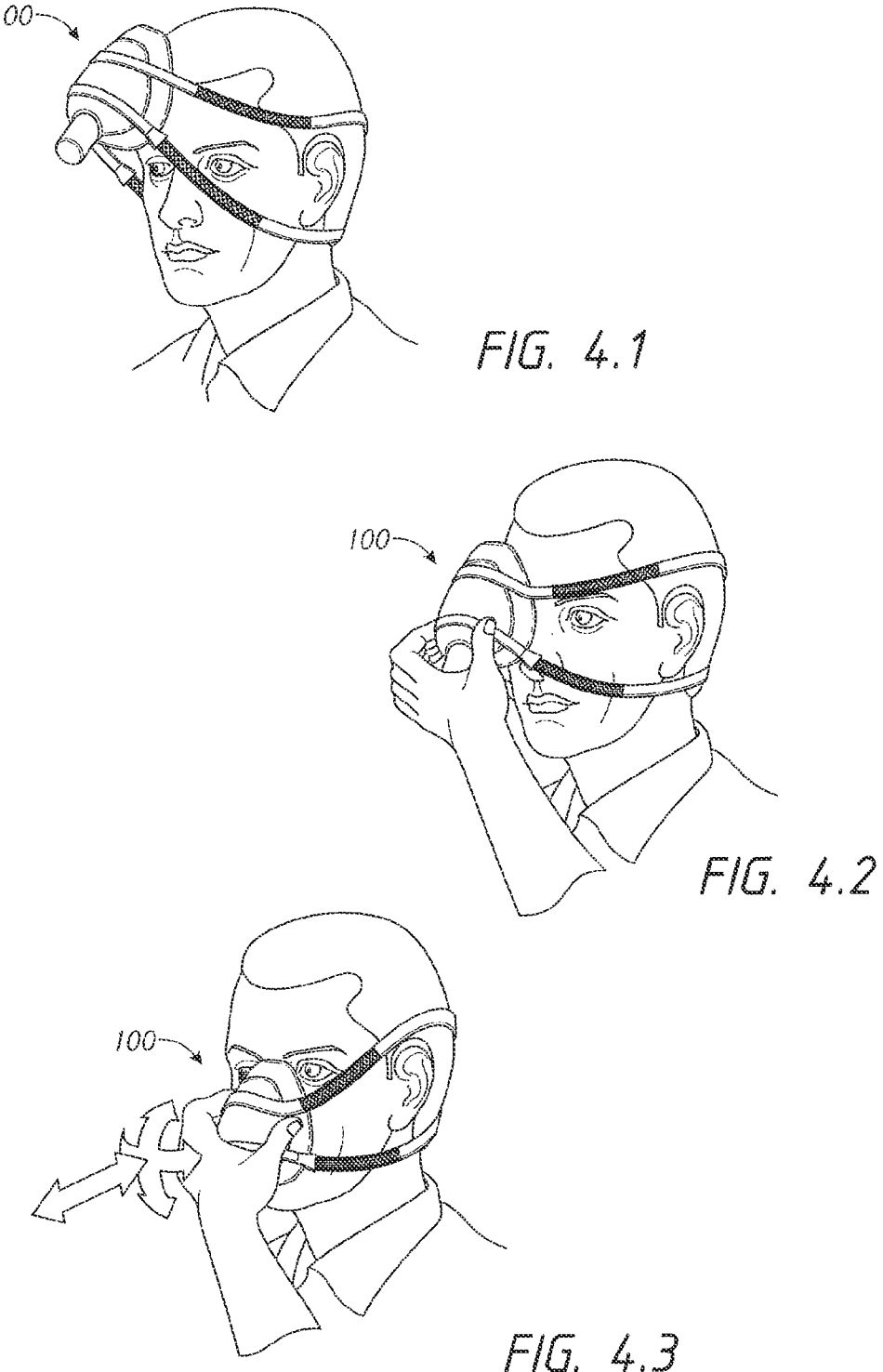
FIG. 4.1
FIG. 4.2
FIG. 4.3

Upper Retention Plane

Lower Retention Plane

Upper Retention Plane

Lower Retention Plane

Upper Retention Plane

Lower Retention Plane

Multi-interface Configurations

| | | Full Face | Nasal | Pillows / Prongs | Cannula |
|---|---|---|---|---|---|
| 1-plane | | Not practical | Yes | Yes | Yes |
| 2-plane (fwd converge) | [M] | Somewhat practical | Yes | Yes | Yes |
| 2-plane (rear converge) | | Yes | Yes | Yes, less practical | Yes, not practical |
| 2-plane (separated/ angled) | [M] | Yes | Yes | Yes, less practical | Yes, not practical |
| 2-plane (horizontal/ parallel) | | Yes | Yes | Yes, not practical | Yes, not practical |

Less Stability ————————————————→ More Stability

*FIG. 13.1*

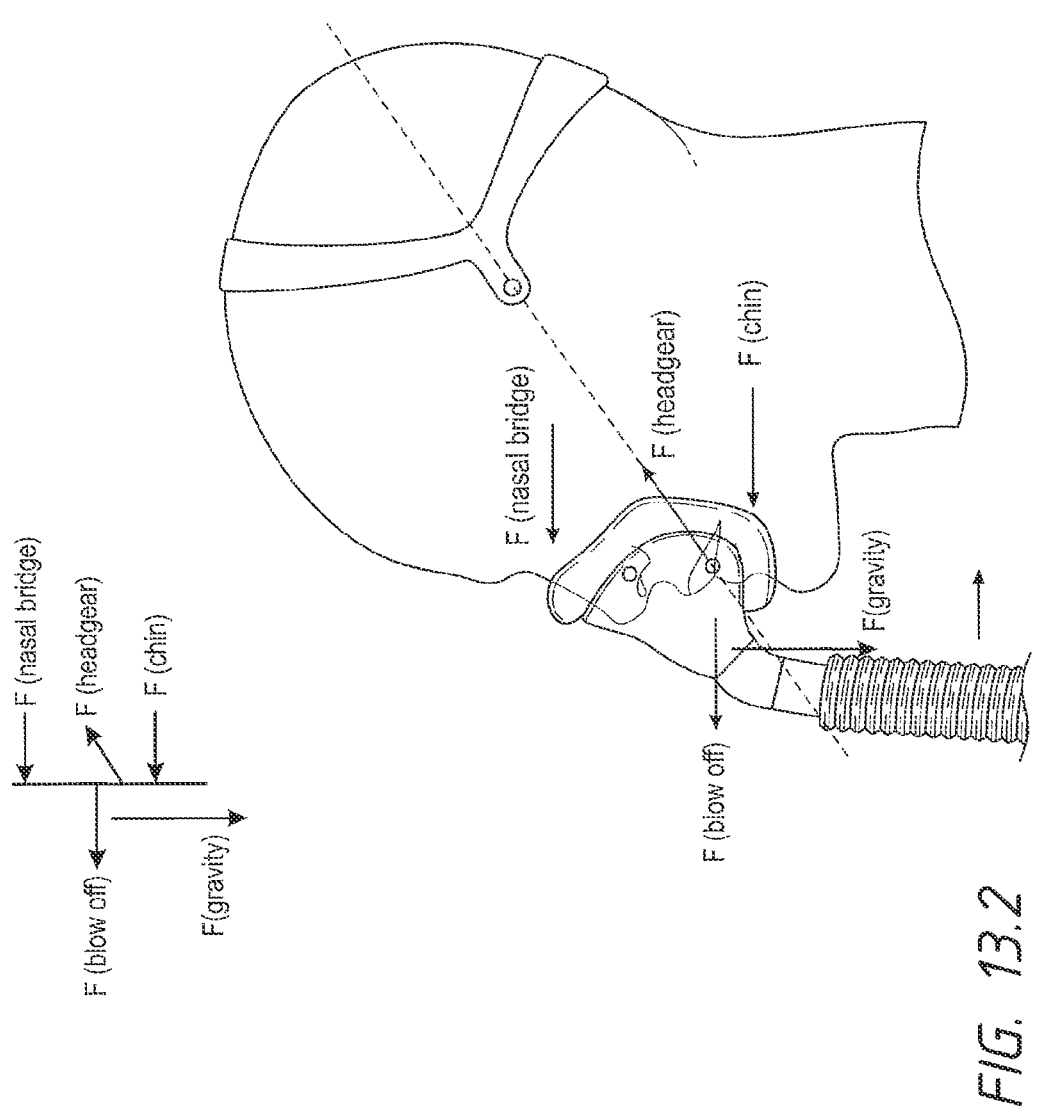
FIG. 13.2

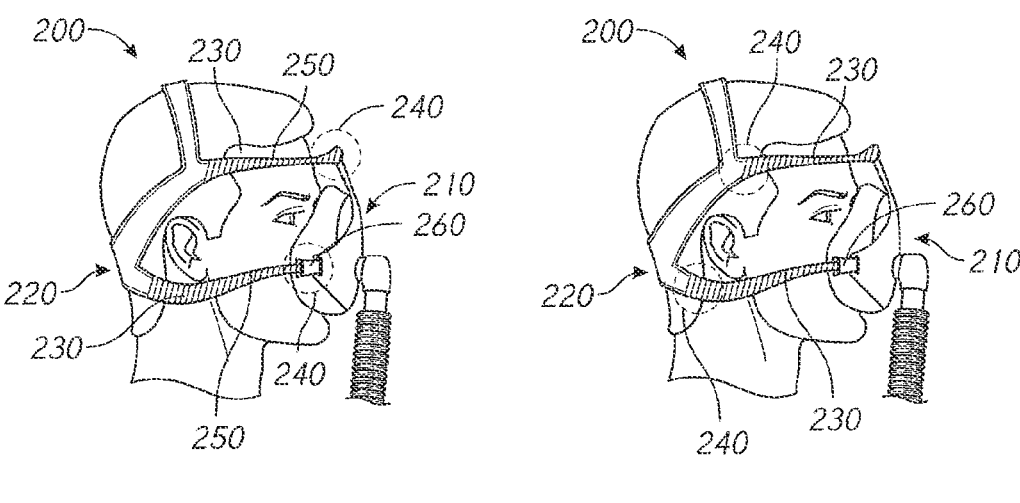
FIG. 14                    FIG. 15
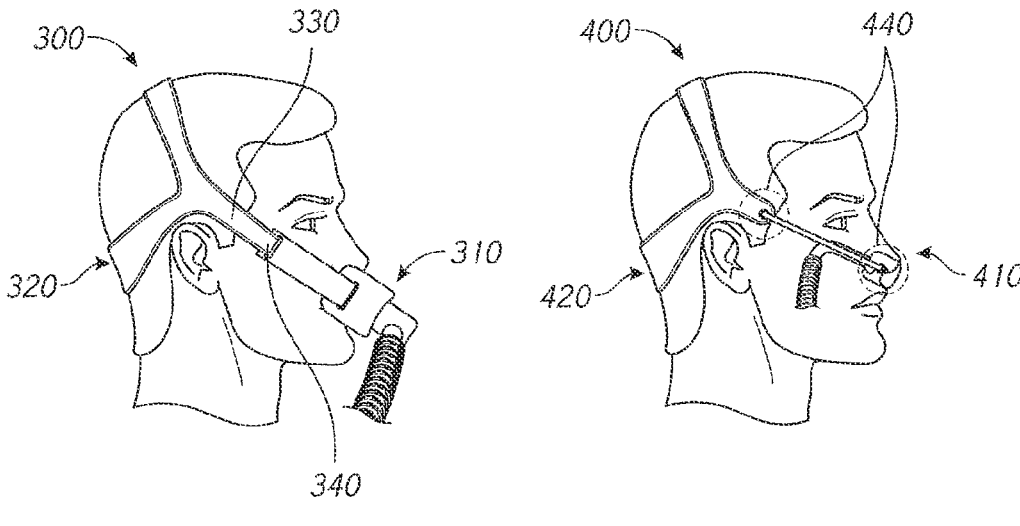
FIG. 16                    FIG. 17

27 ←
26 ←
28 ←
1010
1030
26 ←
27 ←
28 ←
1000

Section 2
Section 1
Section 3
1110
1130
1100

Section 1　~ Polypropylene

Section 2　~ TPU / TPE
　　　　　　70 shore A

Section 3　~ TPE
　　　　　　40 shore D

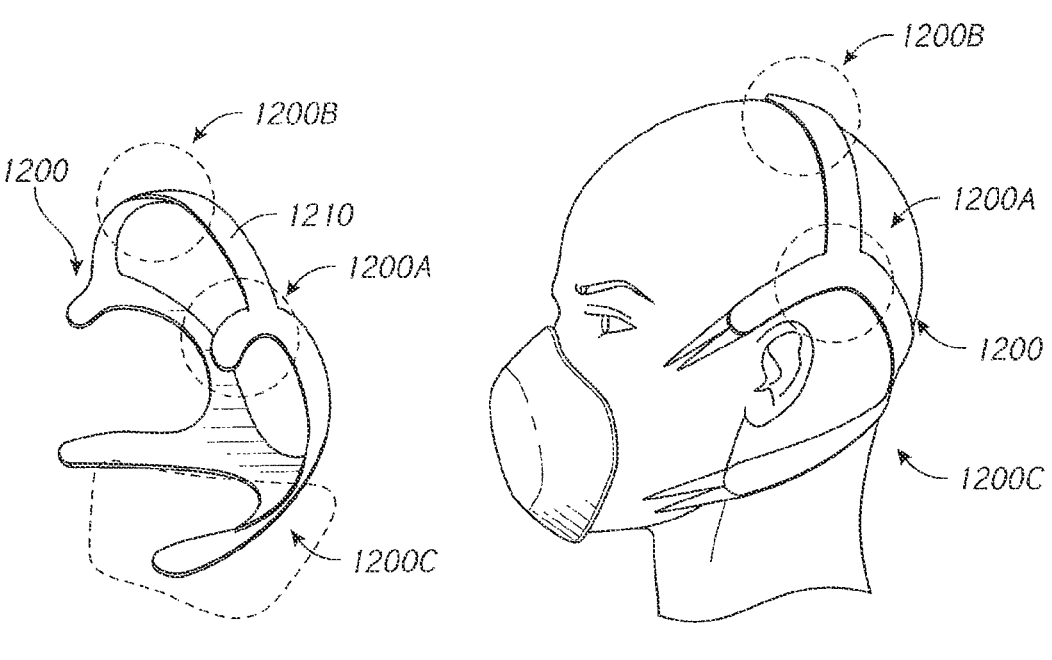
*FIG. 30* *FIG. 31*
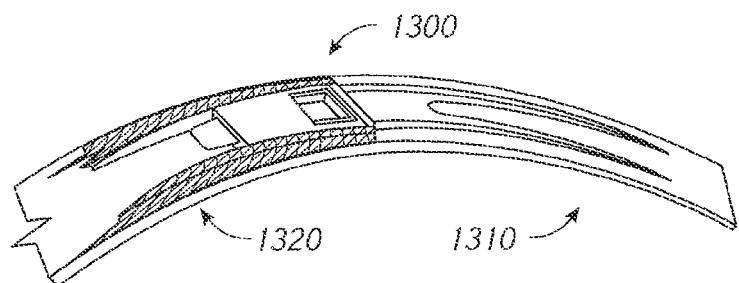
*FIG. 32*
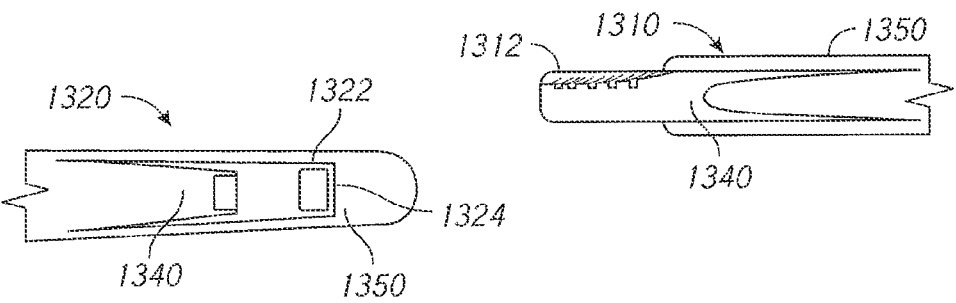
*FIG. 33*

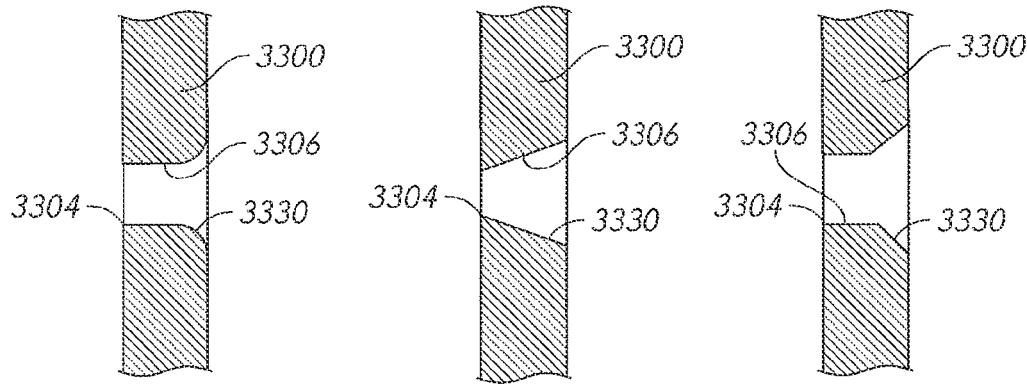
*FIG. 109A*     *FIG. 109B*     *FIG. 109C*
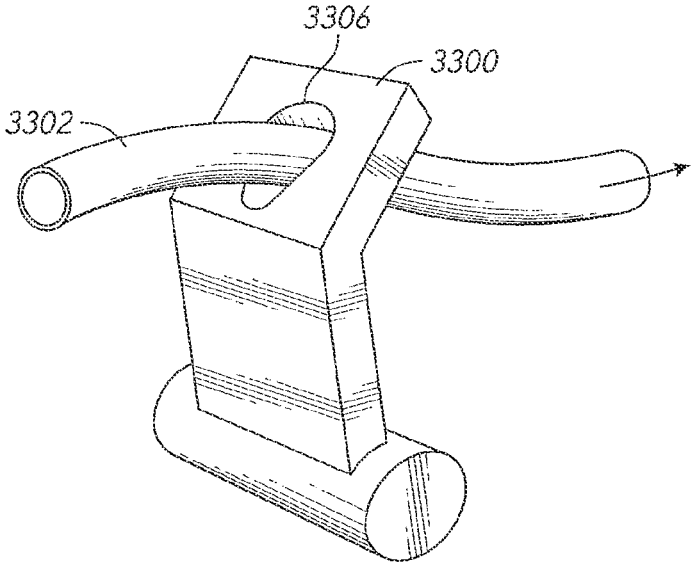
*FIG. 110*

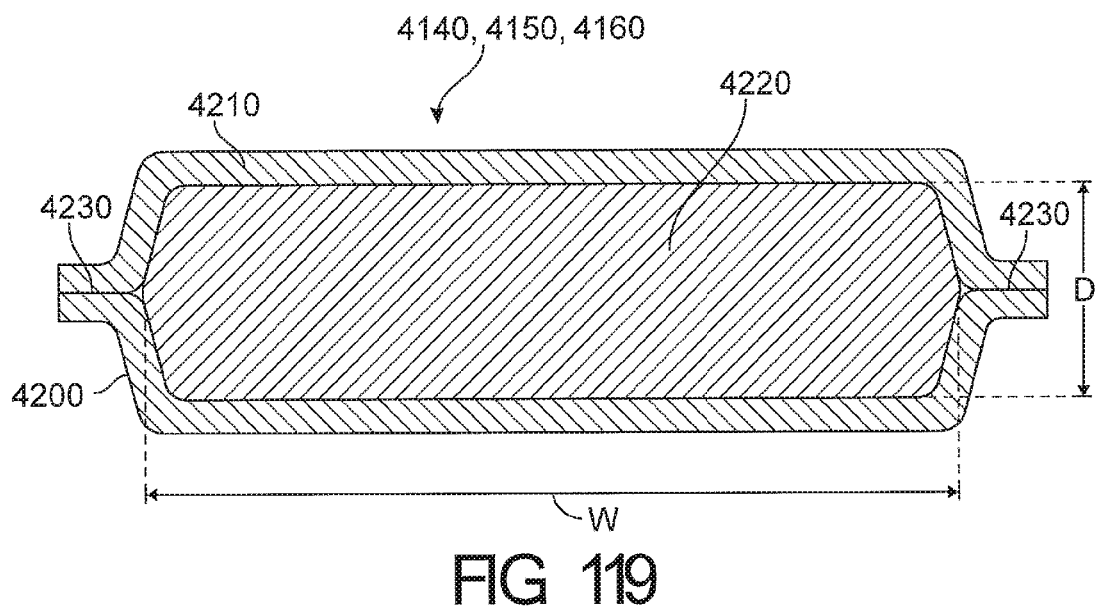
FIG 119
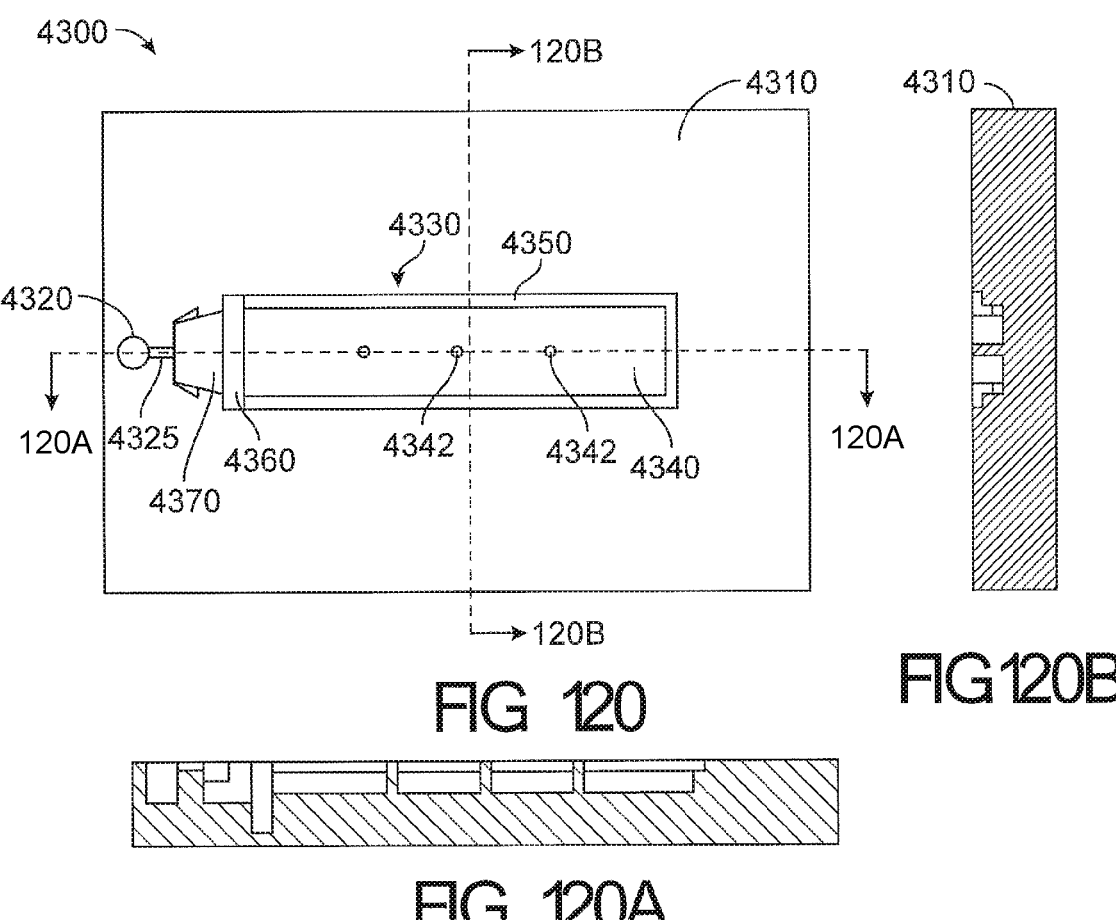
FIG 120
FIG 120B
FIG 120A

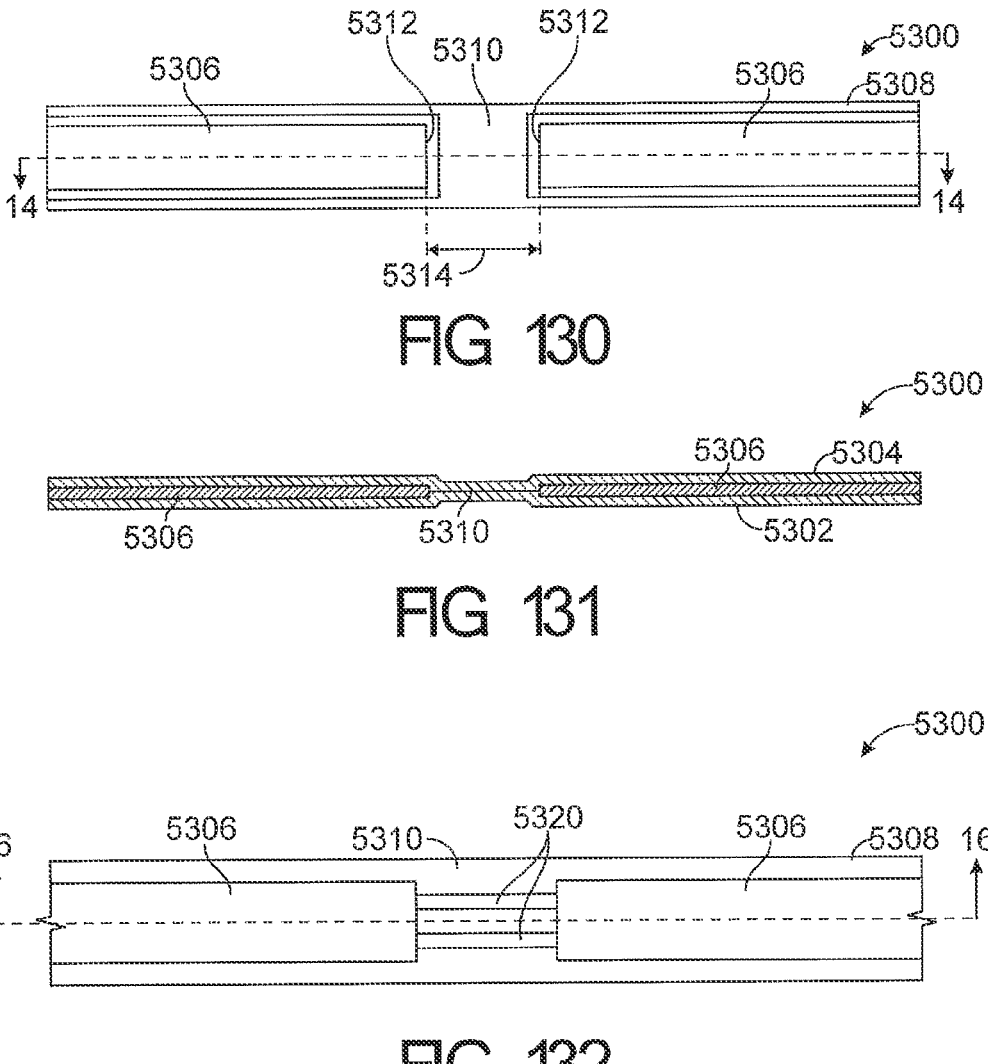
FIG 130
FIG 131
FIG 132
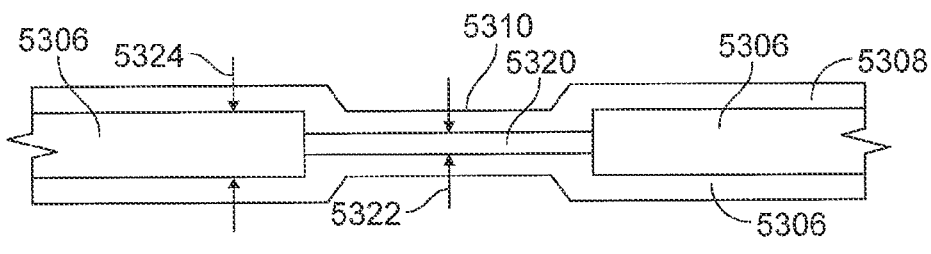
FIG 133

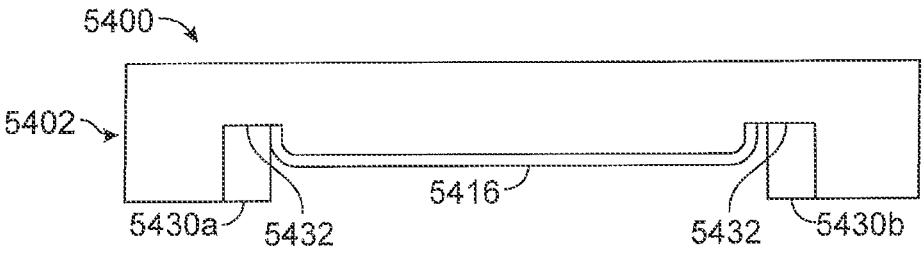
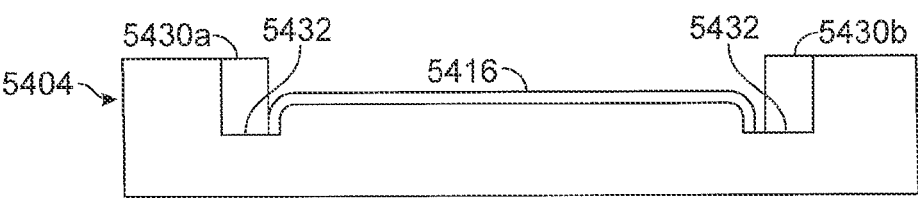
FIG 136
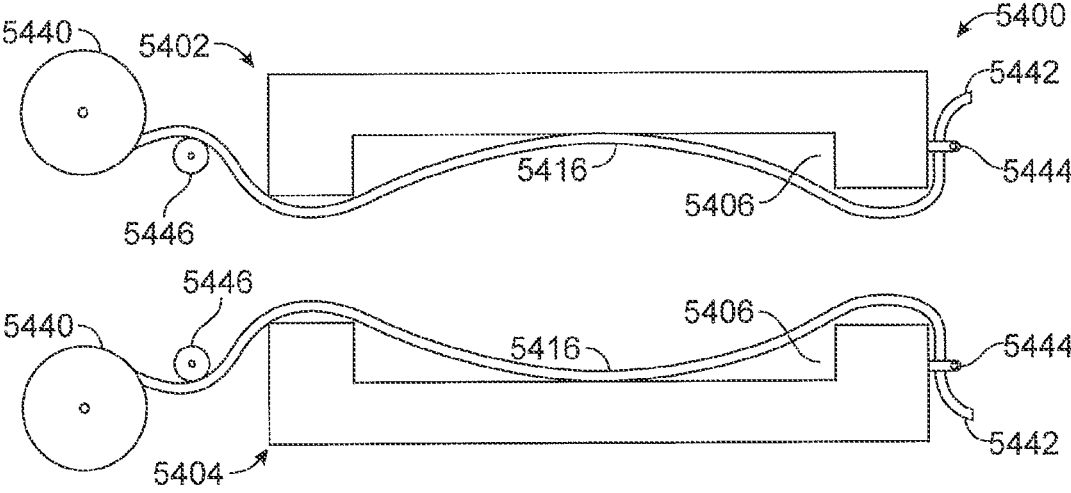
FIG 137

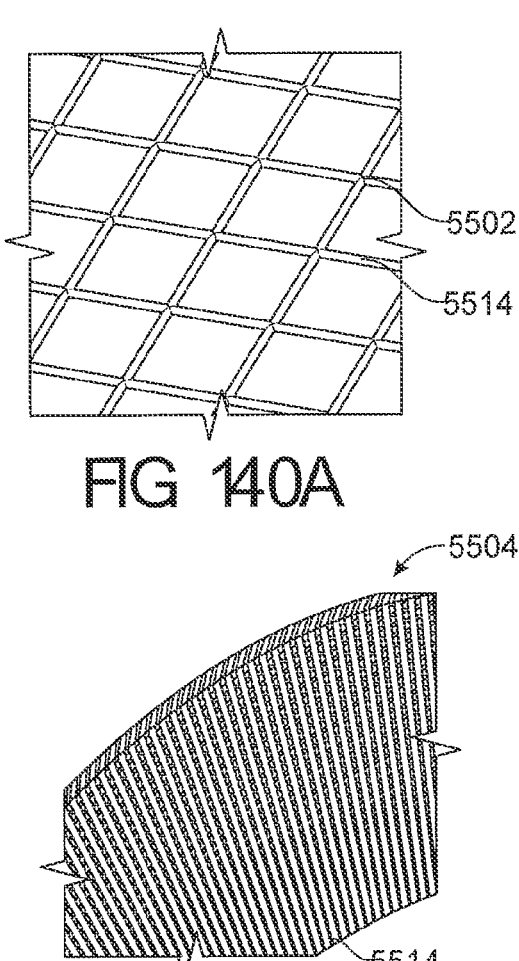
5502
5514
FIG 140A
5504
5514
FIG 140B
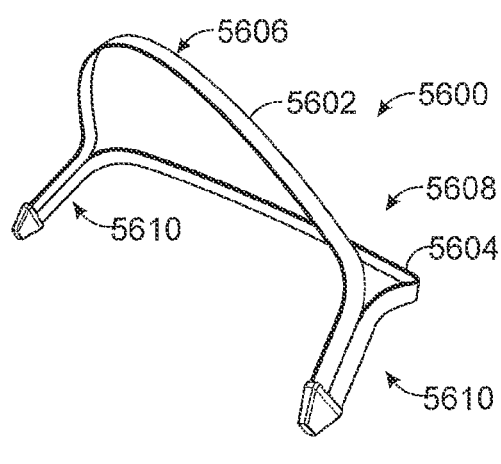
5606
5602    5600
5608
5610    5604
5610
FIG 141

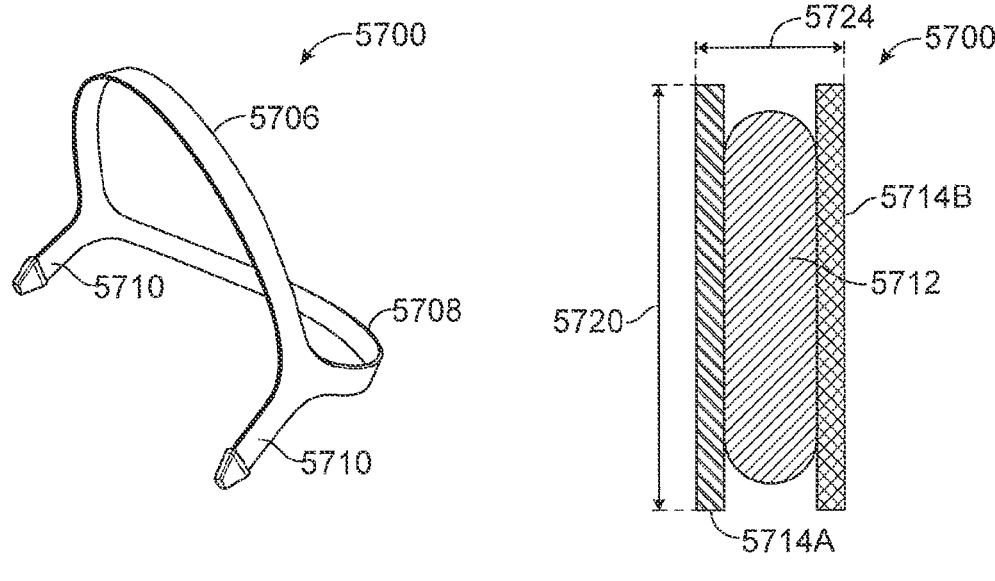
FIG 144      FIG 145
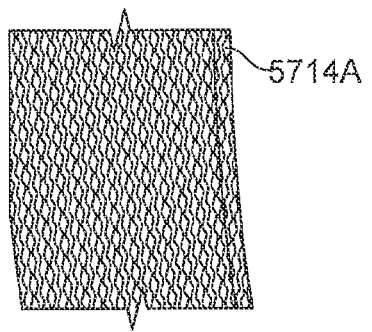
FIG 146A
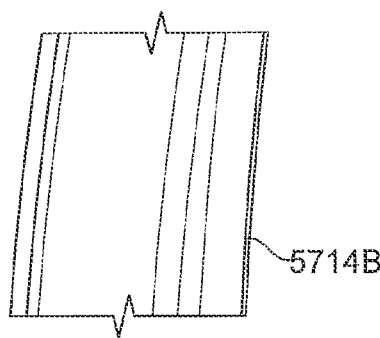
FIG 146B

—5914A

—5914B

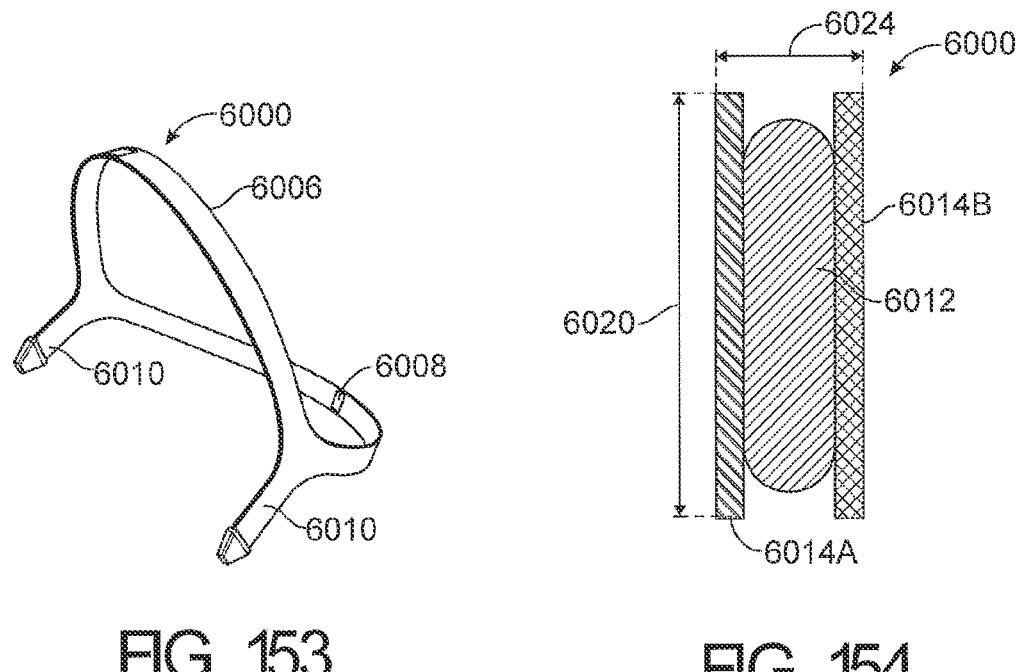
FIG 153
FIG 154
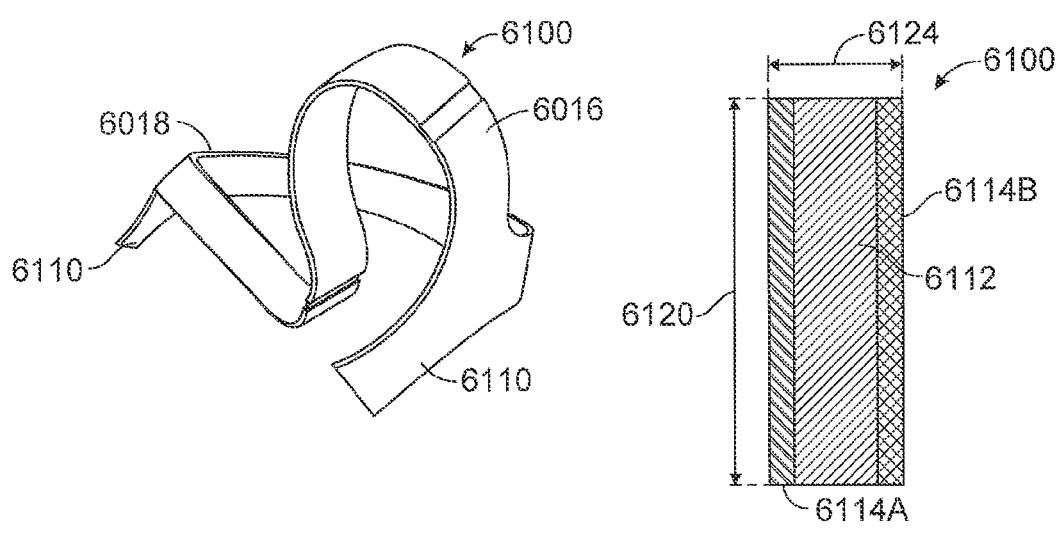
FIG 155
FIG 156

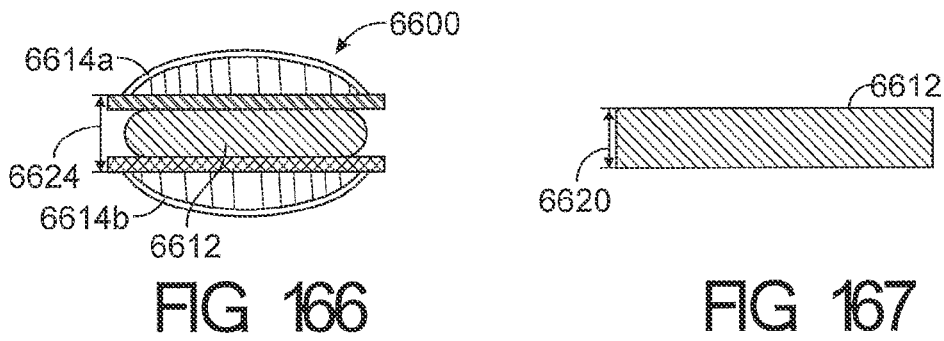
FIG 166
FIG 167
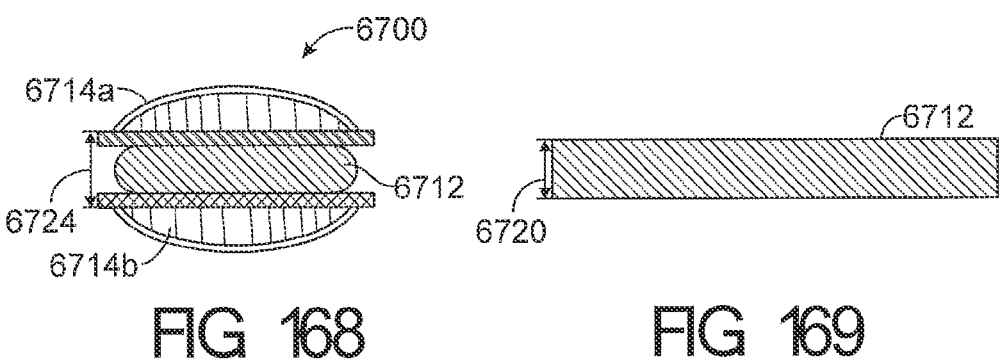
FIG 168
FIG 169

6800

6824

6812

6814b

6814a

6812

6820

6924

6912

6914

6800

6912

6920

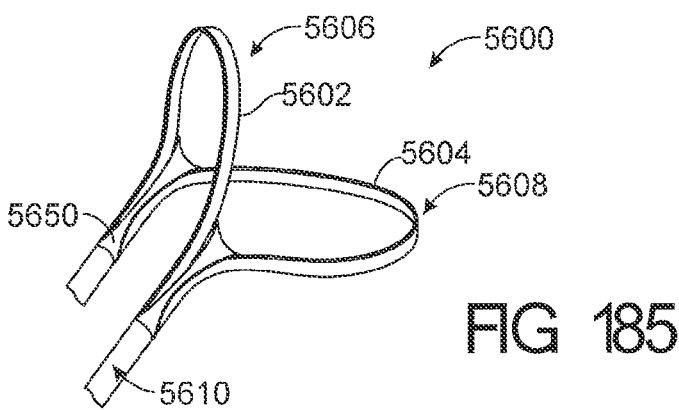
FIG 185
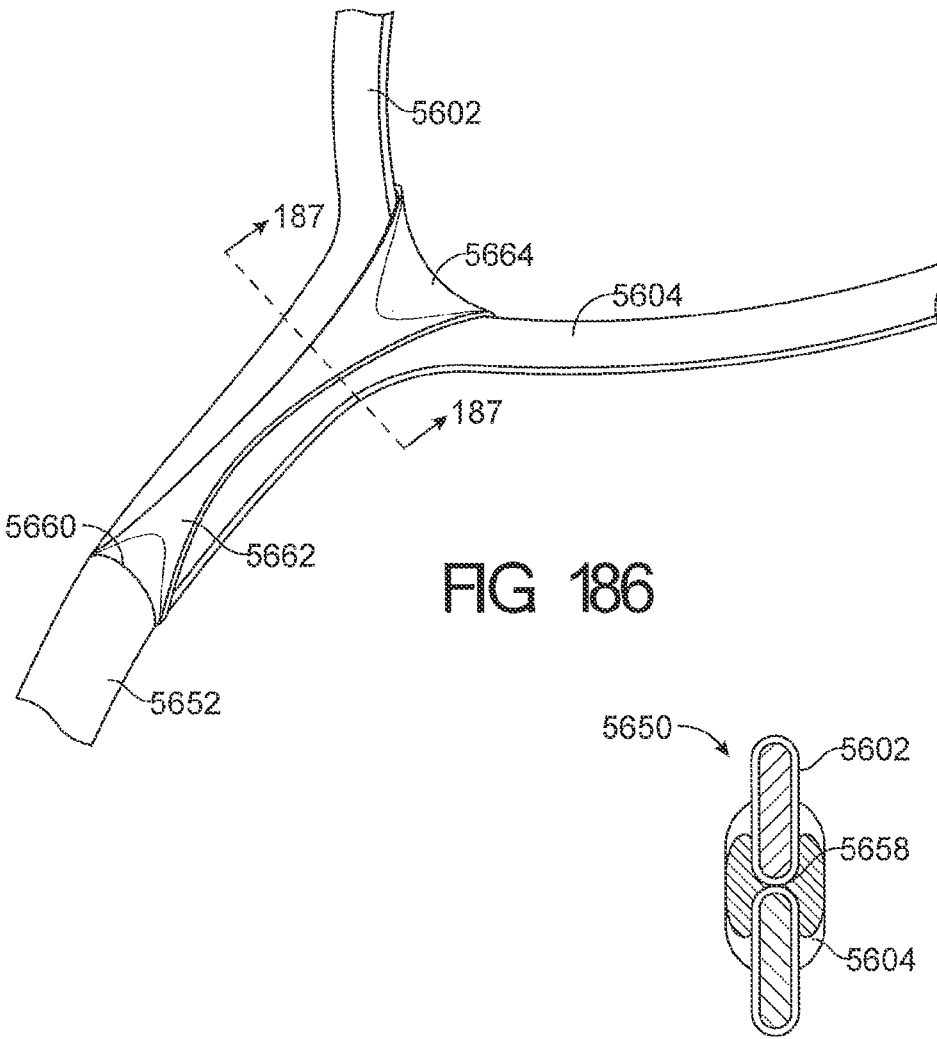
FIG 186
FIG 187

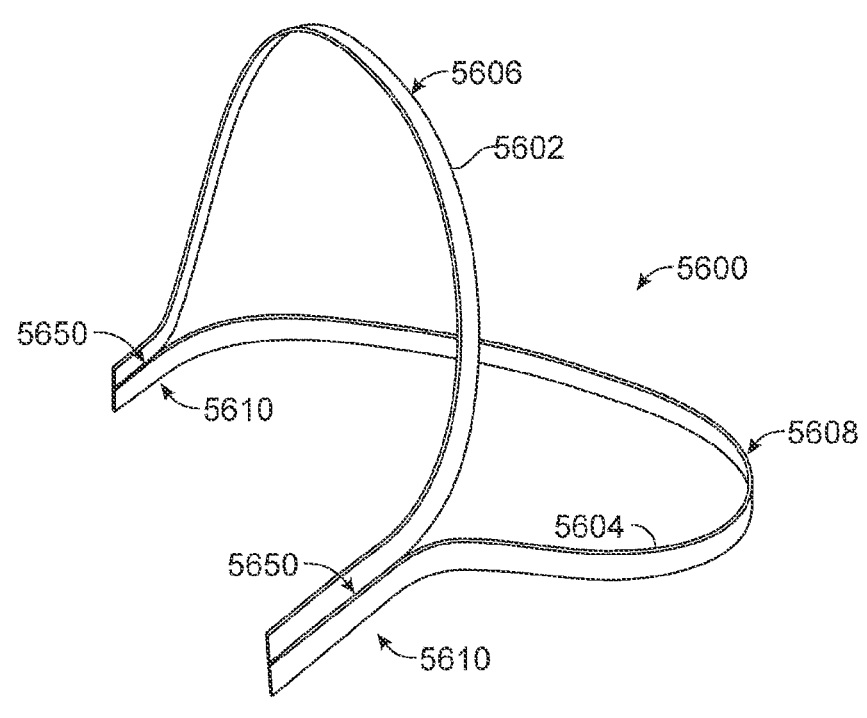
FIG 188
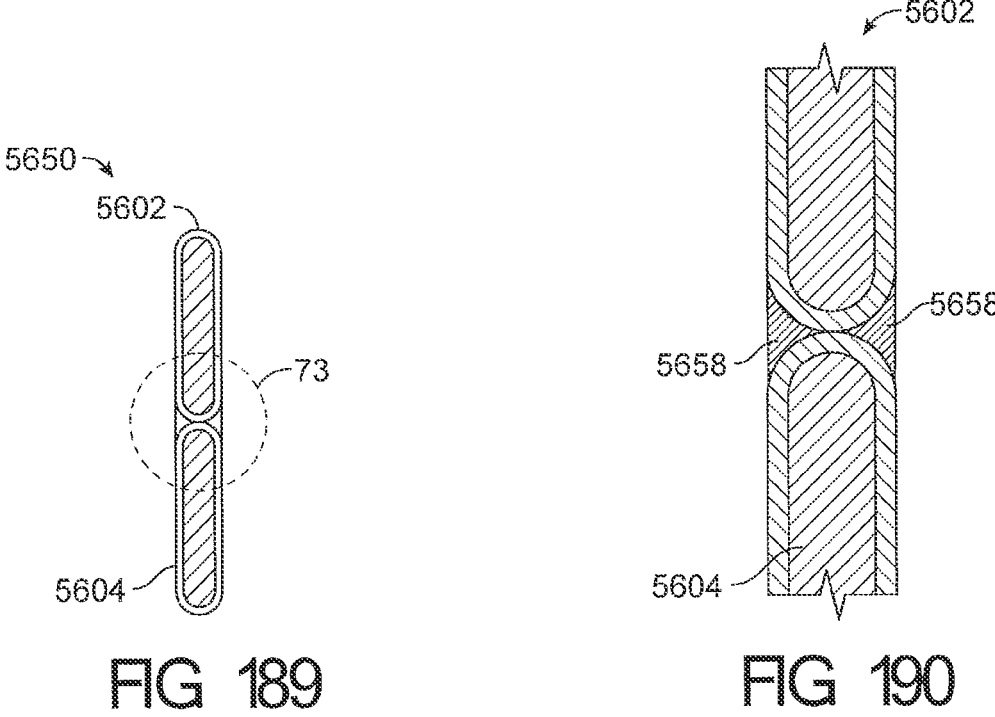
FIG 189                       FIG 190

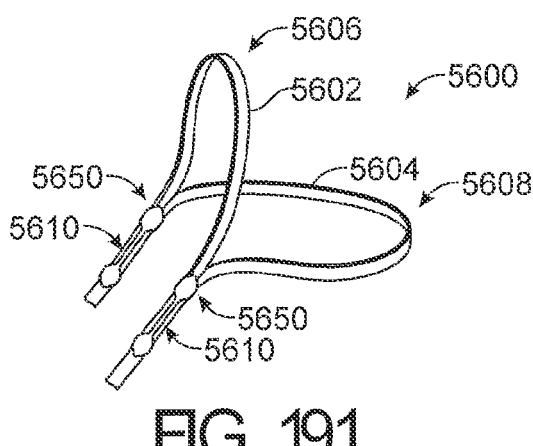
FIG 191
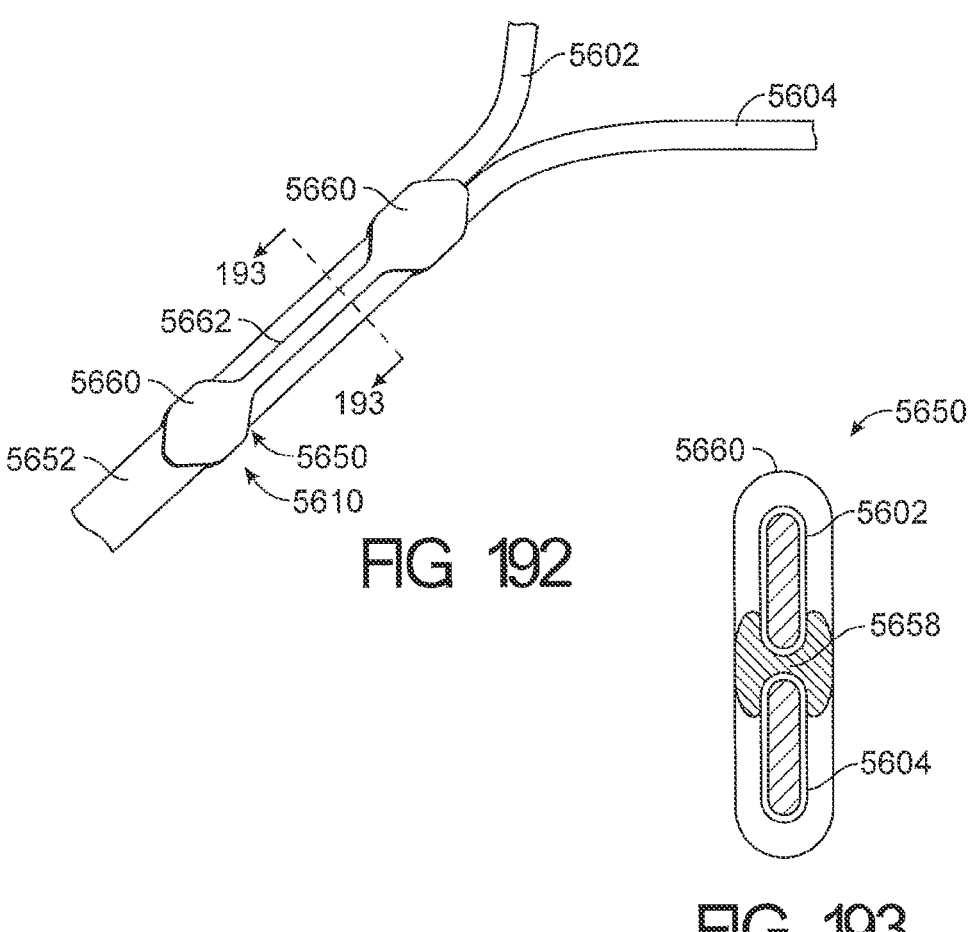
FIG 192
FIG 193

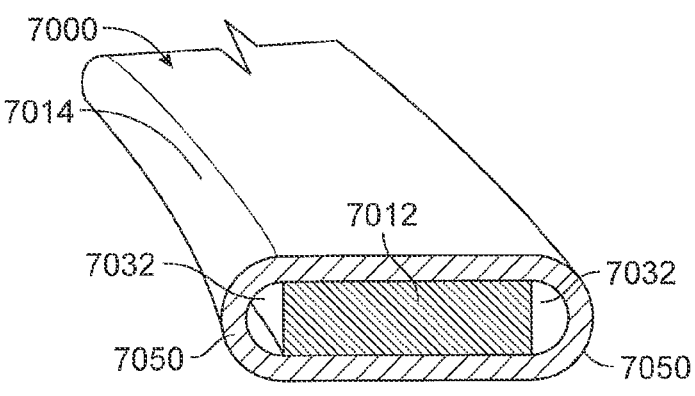
FIG 194
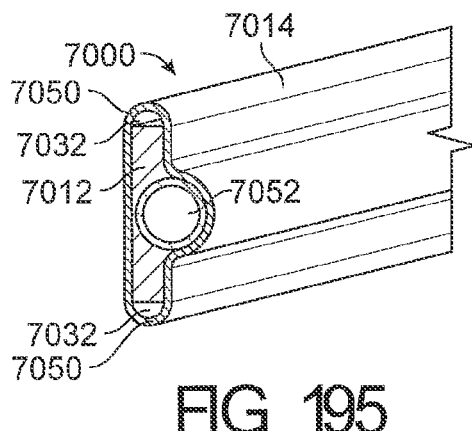
FIG 195
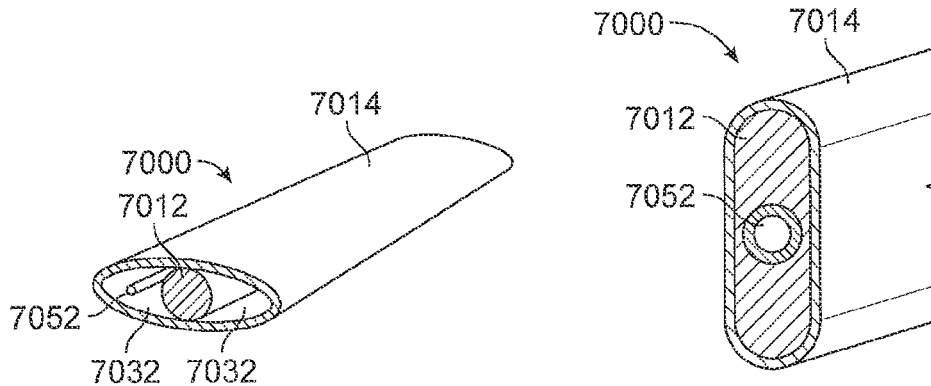
FIG 196                    FIG 197

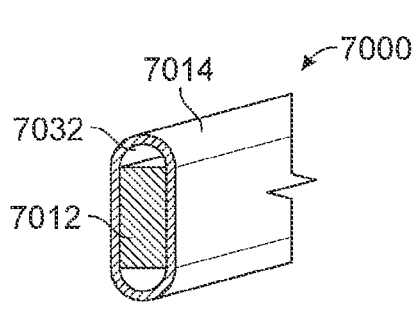
FIG 212
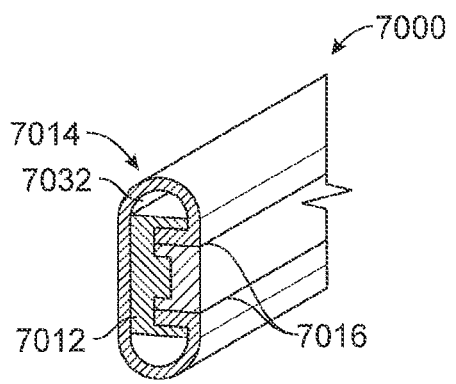
FIG 213
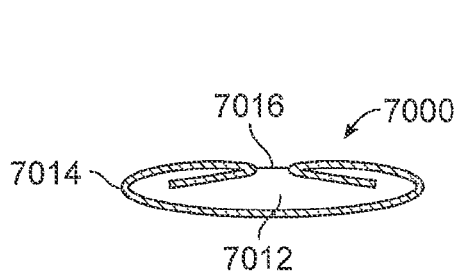
FIG 214
FIG 215
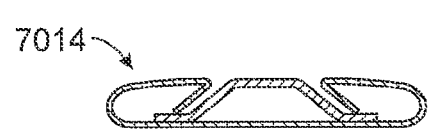
FIG 216A
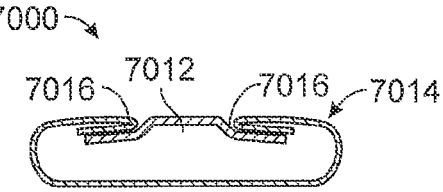
FIG 216B

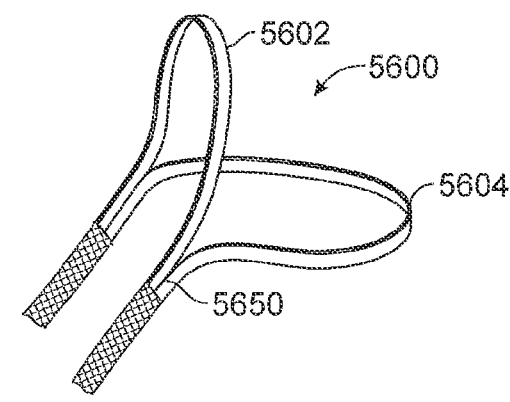
FIG 228
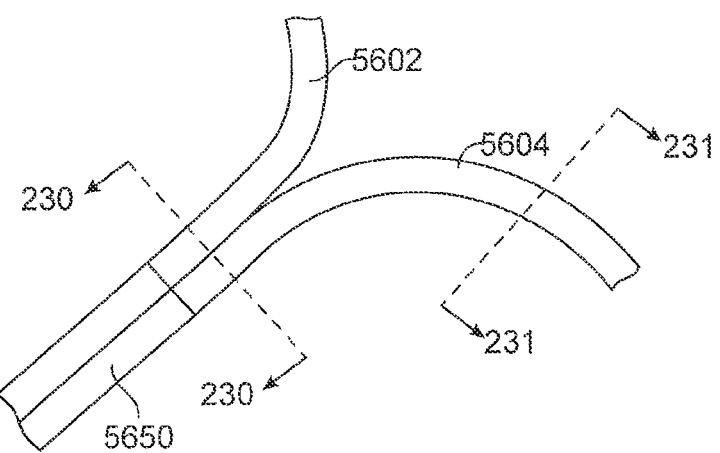
FIG 229
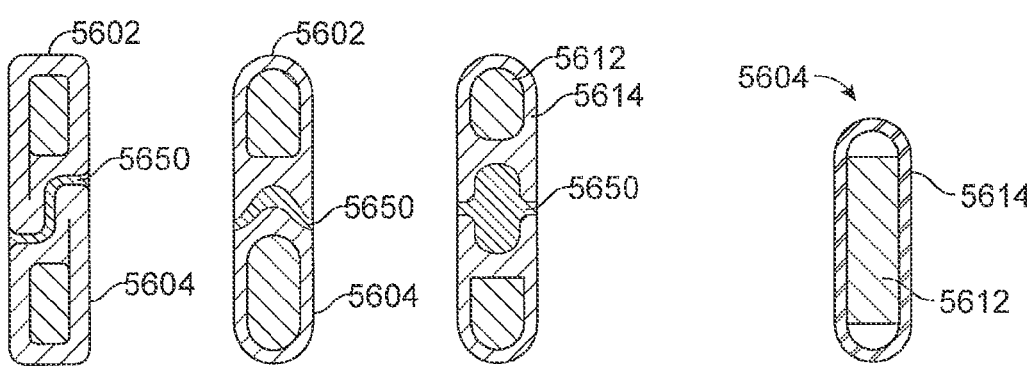
FIG 230                    FIG 231

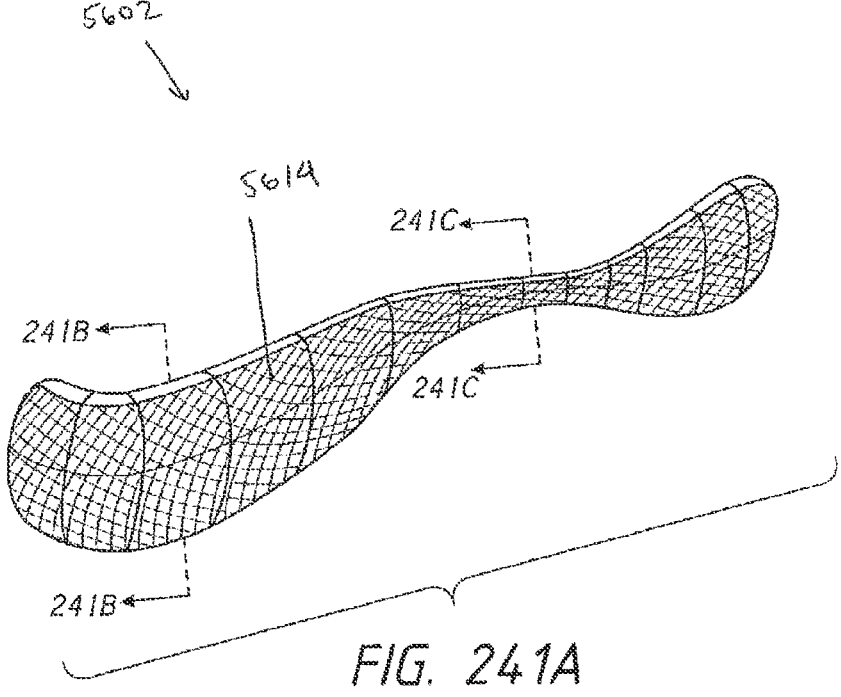
FIG. 241A
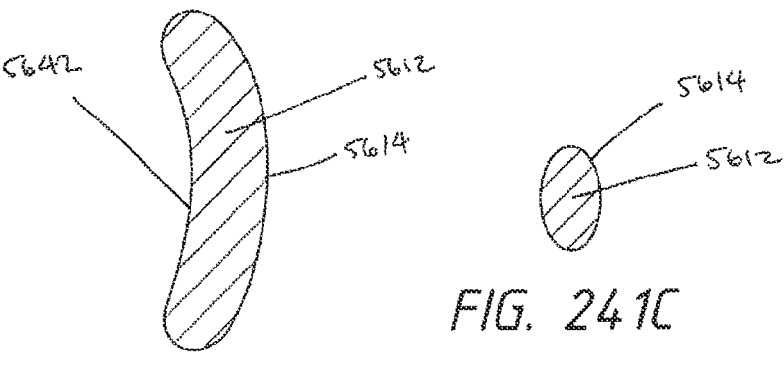
FIG. 241B
FIG. 241C

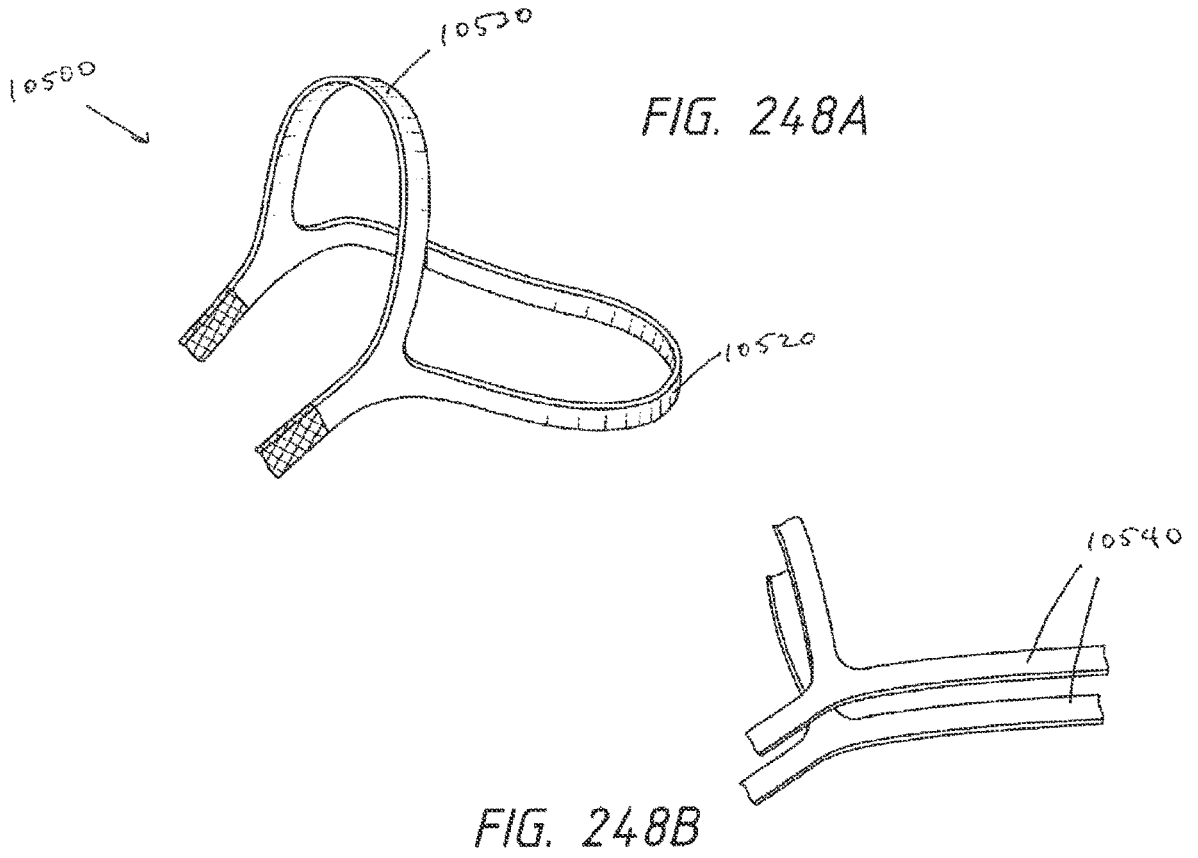
FIG. 248A
FIG. 248B
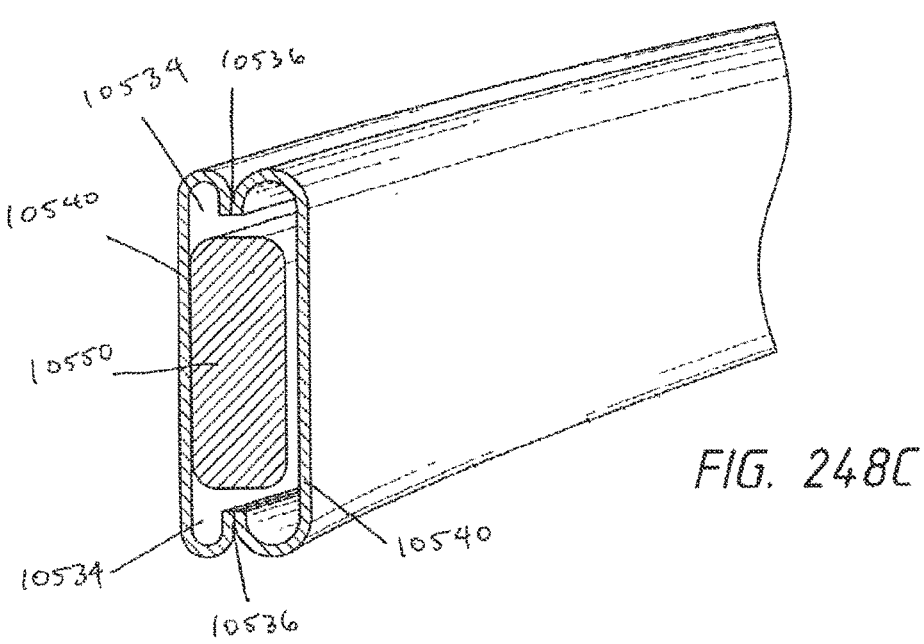
FIG. 248C

HEADGEAR ASSEMBLIES AND INTERFACE ASSEMBLIES WITH HEADGEAR

INCORPORATION BY REFERENCE TO ANY PRIORITY APPLICATIONS

Any and all applications for which a foreign or domestic priority claim is made in connection with the present application are hereby incorporated by reference and made a part of the disclosure.

BACKGROUND

Field

The present disclosure relates to headgear and interface assemblies for use in respiratory therapy. More particularly, the present disclosure relates to a substantially inelastic three dimensional headgear, portions thereof and a process for moulding such headgear. Further applications of the moulding process are also disclosed.

Description of Related Art

The treatment of respiratory ailments or conditions with therapies, such as NIV, Bi-level or CPAP, involves the delivery of pressurized air to the airways of a human via a conduit and a breathing apparatus (e.g., a mask or cannula). Typically, a mask creates at least a substantial "seal" on or around the nose and/or the mouth of a user while a cannula does not provide a seal but provides a delivery pathway for supplemental respiratory gas delivery.

A result of creating this "seal" is that the combination of the enclosure area of the breathing apparatus and its internal pressure creates a resulting force that attempts to push the breathing apparatus off of the face. To counteract this force, it is normal to use a headgear comprising a series of straps that pass around the back and/or top of a user's head. Headgear such as this are typically made from a compliant material, such as Breath-o-prene™. The use of such a material results in the headgear having relatively little structure when not being worn. This lack of structure can give rise to the straps of the headgear becoming tangled, which in turn can make it difficult for a user to don the headgear and breathing apparatus.

The strap(s) require some form of adjustment to account for variation in head size, this adjustment mechanism is typically provided via an adjustment loop between the mask body and the head gear. The adjustment loop can have a hook-and-loop or similar fastener that permits an end of the strap to be passed through a mounting location on the mask or through a clip that attaches to the mask and then attached to another section of the strap. Such an arrangement permits adjustment of the headgear by positioning the end of the strap at a desired location on the other section of the strap to vary a size of the adjustment loop.

These types of mechanism are one solution to providing an adjustment mechanism for the headgear and, thus, the interface assembly. Such systems also require a reasonable level of user interaction and, as a result, is prone to misuse or mis-adjustment (e.g., over-tightening). As a practical matter, micro-adjustment of such systems is difficult and time-consuming to accomplish. The creation of practical and not so practical solutions to this has been the subject of considerable development effort from a number of organisations, which has resulted in numerous patents.

Further, these traditional headgear are usually configured to have some elasticity. This can result in the headgear stretching over, and applying pinching forces to, the user's head, which can be uncomfortable. It is desirable to make headgear and breathing apparatus that are easy to use and comfortable to wear because this may improve a user's compliance with the therapy being provided.

SUMMARY

The systems, methods and devices described herein have innovative aspects, no single one of which is indispensable or solely responsible for their desirable attributes. Without limiting the scope of the claims, some of the advantageous features will now be summarized.

A headgear system and/or an interface assembly incorporating a headgear system that upon fitment to the head of a user automatically adjusts to the correct size and, once in use, transforms in properties from an elasticated "stretchy" strap/strapping to an "inelastic" strap/strapping.

In some configurations, a headgear assembly for supporting a respiratory interface on a user comprises a rear headgear portion configured to contact the rearward and/or upper portions of a head of the user. The rear headgear portion comprises a plastic core and a textile casing. The plastic core and the textile casing are formed as an integral structure by the application of a molten plastic material into the textile casing. Each side of the rear headgear portion comprises a mounting portion configured to be located forwardly of an ear of the user in use. An interface connection arrangement is provided to the mounting portion on each side of the headgear assembly. Each interface connection arrangement is configured to be directly or indirectly coupled to the respiratory interface. Each interface connection arrangement includes at least one length adjusting arrangement. Each length adjusting arrangement comprises an elastic element, a core member and a restriction arrangement. The core member is associated with the elastic element and is fixed relative to one end of the elastic element. The core member passes through the restriction arrangement. The restriction arrangement is configured to selectively engage the core member to resist movement of the core member relative to the restriction arrangement.

In some configurations, the rear headgear portion has no structure passing below the ear of the user that would inhibit removal of the rear headgear portion in an upward direction.

In some configurations, each of the interface connection arrangements comprises at least a first length adjusting arrangement and a second length adjusting arrangement.

In some configurations, a location of at least one of the first length adjusting arrangement and the second length adjusting arrangement on the mounting portion is adjustable.

In some configurations, each of the mounting portions comprises a plurality of mounting locations for the first length adjusting arrangement and the second length adjusting arrangement, wherein the mounting locations are unitarily formed with the plastic core.

In some configurations, at least one connector is configured to connect the interface connection arrangements to the respiratory interface.

In some configurations, the at least one connector comprises at least one collection passage configured to receive a portion of the core members.

In some configurations, the restriction arrangements are located on the rear headgear portion.

In some configurations, the rear headgear portion defines at least one collection passage configured to receive a portion of the core members.

In some configurations, the at least one collection passage is defined by the plastic core or between the plastic core and the textile casing.

In some configurations, the restriction arrangements are located remotely from an end of the elastic element.

In some configurations, a guide for a portion of the core member is provided between the end of the elastic element and the restriction arrangement.

In some configurations, the elastic element comprises an inelastic portion that restricts the elastic element to a maximum length.

In some configurations, a headgear assembly for supporting a respiratory interface on a user comprises a rear headgear portion configured to contact the rearward and/or upper portions of a head of the user. The rear headgear portion comprises a plastic core and a textile casing. The plastic core and the textile casing are formed as an integral structure by the application of a molten plastic material into the textile casing. An interface connection arrangement is provided to each side of the headgear assembly. Each interface connection arrangement is configured to be directly or indirectly coupled to the respiratory interface. Each interface connection arrangement includes at least one length adjusting arrangement. Each length adjusting arrangement comprises an elastic element, a core member and a restriction arrangement. The core member is associated with the elastic element and is fixed relative to one end of the elastic element. The core member passes through the restriction arrangement. The restriction arrangement is configured to selectively engage the core member to resist movement of the core member relative to the restriction arrangement. The at least one restriction arrangement is located on the rear headgear portion.

In some configurations, the rear headgear portion has no structure passing below the ear of the user that would inhibit removal of the rear headgear portion in an upward direction.

In some configurations, the rear headgear portion defines at least one collection passage configured to receive a portion of the core members.

In some configurations, the at least one collection passage is defined by the plastic core or between the plastic core and the textile casing.

In some configurations, the restriction arrangement is located remotely from the other end of the elastic element.

In some configurations, a guide for a portion of the core member is provided between the end of the elastic element and the restriction arrangement.

In some configurations, the elastic element comprises an inelastic portion that restricts the elastic element to a maximum length.

A headgear system and/or an interface assembly incorporating a headgear system that upon fitment to the head of a user automatically adjusts to the correct size and, once in use, transforms in properties from an elasticated "stretchy" strap/strapping to an "inelastic" strap/strapping.

In some configurations, a headgear assembly for supporting a respiratory interface on a user includes a substantially inelastic rear portion, a substantially inelastic front portion, a first elastic side portion on a first side of the headgear assembly, and a second elastic side portion of a second side of the headgear assembly. At least one filament extends through or along the first and second elastic side portions. The at least one filament coupled to one of the inelastic rear portion and the inelastic front portion, and at least one restriction arrangement. The at least one filament passes through the at least one restriction arrangement. The at least one restriction arrangement is configured to selectively engage the at least one filament to resist movement of the at least one filament relative to the at least one restriction arrangement.

In some configurations, the at least one restriction arrangement is configured to provide a first resistance force to movement or attempted movement of the at least one filament in a direction that allows the inelastic rear portion and the inelastic front portion to move away from one another.

In some configurations, the at least one restriction arrangement is configured to provide a second resistance force to movement or attempted movement of the at least one filament in a direction that allows the inelastic rear portion and the inelastic front portion to move toward one another, wherein the second resistance force is less than the first resistance force.

In some configurations, the inelastic front portion is rigid.

In some configurations, the inelastic front portion is configured to be connected to a respiratory interface.

In some configurations, the inelastic front portion defines at least one collection passage that accommodates a portion of the at least one filament.

In some configurations, each of the first and second elastic side portions comprises an end cap having an opening through which the at least one filament passes. The end cap can be overmolded onto the respective one of the first and second elastic side portions. The end cap can be coupled to the inelastic front portion.

In some configurations, the inelastic rear portion, the inelastic front portion, the first elastic side portion and the second elastic side portion define a closed loop perimeter.

In some configurations, the at least one filament comprises a first filament associated with the first elastic side portion and a second filament associated with the second elastic side portion. The at least one restriction arrangement can comprise a first restriction arrangement associated with the first elastic side portion and a second restriction arrangement associated with the second elastic side portion.

In some configurations, the at least one collection passage comprises a first collection passage that accommodates a portion of the first filament and a second collection passage that accommodates a portion of the second filament.

In some configurations, the restriction arrangement comprises a pair of lock jaws that define a space therebetween through which the filament passes. The lock jaws have a first relative position engaging the filament to provide the first resistance force and a second relative position that provides the second resistance force.

In some configurations, the interface includes a forehead support and the at least one collection passage is located on the forehead support.

In some configurations, the headgear comprises upper and lower elastic side portions on each side, upper and lower filaments and upper and lower restriction arrangements. In some such configurations, the there is an upper collection passage and lower collection passage. These upper and lower collection passages on each side of the headgear can be separate from one another.

In some configurations, inelastic front portion defines an opening configured to receive a portion of the respiratory interface, wherein the at least one collection passage comprises a first collection passage and a second collection passage, wherein at least a portion of the first collection passage is located above the opening and at least a portion of the second collection passage is located below the opening.

In some configurations, the inelastic front portion is configured to connect to a plurality of different interfaces.

In some configurations, the inelastic front portion comprises separate portions on each side of the headgear assembly.

In some configurations, a headgear assembly for supporting a respiratory interface on a user defines a perimeter that surrounds a head of the user. The headgear assembly can include a first portion having a fixed length along the perimeter and a second portion having a fixed length along the perimeter. At least one elastic portion has a variable length along the perimeter, wherein the at least one elastic portion has a first length and a second length that is greater than the first length. At least one filament is secured to one of the first portion and the second portion and extends through the at least one elastic portion and into at least one collection passage of the other of the first portion and the second portion. The at least one filament has a filament length that is greater than the second length of the at least one elastic portion. At least one restriction arrangement is configured to selectively engage the at least one filament to resist movement of the at least one filament relative to the at least one restriction arrangement. The at least one restriction arrangement is located at an entrance to the at least one collection passage.

In some configurations, the first portion is a front portion of the headgear assembly.

In some configurations, the second portion is a rear portion of the headgear assembly.

In some configurations, the first portion defines the at least one collection passage.

In some configurations, the at least one elastic portion is restricted to a maximum length.

In some configurations, the at least one elastic portion comprises an inelastic element that defines the maximum length.

In some configurations, the at least one elastic portion comprises a first elastic portion and a second elastic portion, wherein each of the first elastic portion and the second elastic portion extend between the first portion and the second portion.

In some configurations, the at least one filament comprises a first filament associated with the first elastic portion and a second filament associated with the second elastic portion. The at least one restriction arrangement comprises a first restriction arrangement associated with the first elastic side portion and a second restriction arrangement associated with the second clastic side portion.

In some configurations, the at least one collection passage comprises a first collection passage that accommodates a portion of the first filament and a second collection passage that accommodates a portion of the second filament.

In some configurations, the restriction arrangement comprises a pair of lock jaws that define a space therebetween through which the filament passes. The lock jaws have a first relative position engaging the filament to provide a first level of resistance and a second relative position that provides a second level or resistance that is lower that the first level.

In some configurations, a directional lock includes a housing defining an interior space, a first opening and a second opening. Each of the first and second openings communicates with the interior space. At least one lock element is pivotally coupled to the housing for rotation about a fixed pivot axis. The lock element has an aperture configured to receive a core element. The lock element is movable between a first position, in which the aperture is aligned with the first opening and the second opening, and a second position, in which the aperture is not aligned with the first opening and the second opening.

In some configurations, the lock element is a lock washer.

In some configurations, at least one of the first opening and the second opening is elongate in a direction perpendicular to the pivot axis such that the at least one of the first opening and the second opening can accommodate a core element that passes through the aperture of the at least one lock element in both the first position and the second position.

In some configurations, the at least one lock element comprises a first lock element and a second lock element.

In some configurations, the housing comprises and internal wall positioned between the first lock element and the second lock element.

In some configurations, a headgear assembly for supporting a respiratory interface on a user includes a rear headgear portion configured to contact the rearward and/or upper portions of a head of the user. Each side of the rear headgear portion comprises a mounting portion configured to be located forwardly of an ear of the user in use. The rear headgear portion has no structure passing below the ear of the user that would inhibit removal of the rear headgear portion in an upward direction. An interface connection arrangement is provided to the mounting portion on each side of the headgear assembly. Each interface connection arrangement is configured to be directly or indirectly coupled to the respiratory interface. Each interface connection arrangement comprises at least one length adjusting arrangement. Each length adjusting arrangement comprises an elastic element, a core member and a restriction arrangement. The core member is associated with the elastic element and is fixed relative to one end of the elastic element. The core member passes through the restriction arrangement. The restriction arrangement is configured to selectively engage the core member to resist movement of the core member relative to the restriction arrangement.

In some configurations, each of the interface connection arrangements comprises at least a first length adjusting arrangement and a second length adjusting arrangement.

In some configurations, the first length adjusting arrangement and the second length adjusting arrangement are spaced apart from one another on the mounting portion.

In some configurations, a location of at least one of the first length adjusting arrangement and the second length adjusting arrangement on the mounting portion is adjustable.

In some configurations, at least one connector is configured to connect the interface connection arrangements to the respiratory interface.

In some configurations, the at least one connector comprises at least one collection passage configured to receive a portion of the core members.

In some configurations, a single connector is configured to connect both of the interface connection arrangements to the respiratory interface.

In some configurations, the connector defines an opening configured to receive a portion of the respiratory interface, wherein the at least one collection passage comprises a first collection passage and a second collection passage, wherein at least a portion of the first collection passage is located above the opening and at least a portion of the second collection passage is located below the opening.

In some configurations, the connector is configured to connect to a plurality of different interfaces.

In some configurations, the at least one connector comprises a connector on each side of the headgear assembly.

In some configurations, the restriction arrangement comprises a pair of lock jaws that define a space therebetween through which the core member passes. The lock jaws have a first relative position engaging the core member to provide a first level of resistance and a second relative position that provides a second level or resistance that is lower that the first level.

In some configurations, a headgear assembly for supporting a respiratory interface on a user comprises at least one inelastic portion and at least one elastic portion having a first end and a second end. At least one filament extends through or along the at least one elastic portion. The first end of the at least one elastic portion is fixed relative to the at least one inelastic portion and the at least one filament. The second end of the at least one elastic portion is movable relative to the at least one inelastic portion and the at least one filament. The headgear assembly also comprises at least one restriction arrangement. The at least one filament passes through the at least one restriction arrangement. The at least one restriction arrangement is configured to selectively engage the at least one filament to resist movement of the at least one filament relative to the at least one restriction arrangement. The at least one restriction arrangement is located remotely from each of the first end and the second end of the at least one elastic portion.

In some configurations, the inelastic portion is a rear headgear portion configured to contact a rearward and/or upper portion of the user's head in use, wherein the at least one restriction arrangement is located on the rear headgear portion.

In some configurations, the rear headgear portion comprises a top strap and the at least one restriction arrangement is located on the top strap.

In some configurations, the headgear assembly is configured such that the at least one restriction arrangement is located on the top of the user's head in use.

In some configurations, the rear headgear portion comprises a rear strap and the at least one restriction arrangement is located on the rear strap.

In some configurations, the headgear assembly is configured such that the at least one restriction arrangement is located behind the user's ear in use.

In some configurations, a guide for the at least one filament is provided between the restriction arrangement and one of the first and second ends of the at least one elastic portion.

In some configurations, the restriction arrangement comprises a pair of lock jaws that define a space therebetween through which the filament passes. The lock jaws have a first relative position engaging the filament to provide a first level of resistance and a second relative position that provides a second level or resistance that is lower that the first level.

In some configurations, a patient interface system comprises a body portion sized and shaped to surround the nose and/or mouth of a user and adapted to create at least a substantial seal with the user's face. A coupling permits the patient interface to be coupled to a gas delivery system. A headgear system allows the body portion to be positioned and retained on an users head, with the head-gear system providing the ability to transform from an elastic type elongation behaviour to a non-elongating type behaviour when the interface system is in use.

In some configurations, the transformational locking behaviour is provided by a group of directional locking features.

In some configurations, the transformational locking behaviour is provided by a group of directional locking features which are located on retention planes.

In some configurations, the transformational locking behaviour is provided by a group of directional locking features which enable independent relative movement to each other.

In some configurations, the transformational locking behaviour is provided by a group of directional locking features which have dependent movement to each other.

In some configurations, the interface system contains a combination of independent and dependent movement.

In some configurations, the transformational locking behaviour is provided by a directional locking feature/s which are located on the mask body.

In some configurations, the transformational locking behaviour is provided by a directional locking feature/s which are located on or within the headgear system.

In some configurations, a combination of directional locking feature/s located on the mask body and located on or within the headgear system are used.

In some configurations, the directional lock is positioned in a location that is proximal with the connection point to the headgear.

In some configurations, the directional lock is positioned in a location that is distal with the connection point to the headgear.

In some configurations, the directional lock module incorporates a mechanism which enables user attachment/detachment between it and the mask body.

In some configurations, the directional lock module incorporates a mechanism which enables user attachment/detachment between it and the remainder of the headgear system.

In some configurations, the non-stretch behaviour of the headgear system is such that there is less than 4 mm of mask movement when the patient interface system is subjected to variable pressure waveform.

In some configurations, a patient interface system comprises a body portion sized and shaped to provide a cannulated gas delivery system into the nasal passages. A coupling permits the patient interface to be coupled to a gas delivery system. A headgear system allows the body portion to be positioned and retained on an users head, with the head-gear system providing the ability to transform from an elastic type elongation behaviour to a non-elongating type behaviour when the interface system is in use.

In some configurations, a patient interface system includes a body portion sized and shaped to surround the nose and/or mouth of a user and adapted to create at least a substantial seal with the user's face. A coupling permits the patient interface to be coupled to a gas delivery system. A headgear system allows the body portion to be positioned and retained on an users head, with the head-gear system providing the ability to transform from an elastic type elongation behaviour to a non-elongating type behaviour when the interface system is in use.

In some configurations, the positional stability of the headgear system is achieved via two principal portions, one that passes on or below the occipital protruberance, the other passing over the top of the head in loosely the position of the crown of the head. The relative position of these two is maintained by the material of the headgear being shape sustaining.

In some configurations, the positional stability of the headgear system is achieved via two principal portions, one that passes on or below the occipital protuberance, the other passing over the top of the head in loosely the position of the crown of the head. The relative position of these two is maintained by the gusset or connecting member/s.

In some configurations, the non-stretch behaviour of the body portion of the headgear is achieved through constructing it from a single inelastic material and variable cross sectional geometry.

In some configurations, the non-stretch behaviour of the body portion of the headgear is achieved through constructing it from a single thermoplastic material and variable cross sectional geometry.

In some configurations, the non-stretch behaviour of the body portion of the headgear is achieved through constructing it from a single thermoset material and variable cross sectional geometry.

In some configurations, the non-stretch behaviour of the body portion of the headgear is achieved through constructing it from multiple thermoplastic materials.

In some configurations, the non-stretch behaviour of the body portion of the headgear is achieved through constructing it from multiple thermoset materials.

In some configurations, the non-stretch behaviour of the body portion of the headgear is achieved through constructing it from multiple thermoplastic materials & variable cross sectional geometry.

In some configurations, the non-stretch behaviour of the body portion of the headgear is achieved through constructing it from thermoplastic material/s and an incorporated lining or padding.

In some configurations, the non-stretch behaviour of the body portion of the headgear is achieved through constructing it from thermoset material/s and an incorporated lining or padding.

In some configurations, a headgear assembly for a respiratory interface includes a rear headgear portion, an interface coupling portion, and a length adjusting portion that adjusts a length of the headgear assembly or a perimeter length of the interface assembly when coupled to a respiratory interface. The headgear assembly exhibits an elastic force tending to contract the headgear length or the perimeter length and a non-elastic lock force tending to inhibit elongation of the headgear length or the perimeter length.

In some configurations, the headgear assembly comprises at least one retention plane.

In some configurations, the headgear assembly comprises two retention planes.

In some configurations, the retention planes converge in a direction moving from rearward to forward.

In some configurations, the retention planes converge in a direction moving from forward to rearward.

In some configurations, one of the retention planes is angled relative to the other retention plane.

In some configurations, the retention planes are separated from one another at the interface attachment locations.

In some configurations, the retention planes are generally parallel with one another.

In some configurations, the retention planes are generally horizontal.

In some configurations, the headgear assembly further comprises a manually-adjustable length adjusting portion In some configurations, the interface coupling portion can be connected to a plurality of types of interfaces.

In some configurations, the length adjusting portion comprises at least a first portion and a second portion.

In some configurations, the first portion and the second portion are on opposite sides of the headgear assembly.

In some configurations, the interface coupling portion extends between the first portion and the second portion.

In some configurations, the first portion and the second portion are on the same side of the headgear assembly.

In some configurations, the interface coupling portion extends between the first portion and the second portion.

In some configurations, at least one core member forms a portion of the headgear length or perimeter length and can be locked relative to another portion of the headgear assembly or interface assembly to inhibit elongation of the headgear length or perimeter length.

In some configurations, a length of the core member is greater than a maximum extended length of the length adjusting portion.

In some configurations, a length of the rear headgear portion is greater than or equal to a length of the core member.

In some configurations, a length of the rear headgear portion is greater than or equal to a length of the core member.

In some configurations, at least one core collector accommodates an excess portion of the core that, at any particular headgear length or perimeter length, does not form a portion of the headgear length or perimeter length.

In some configurations, a length of the core member is less than a combined length of the core collector and a maximum extended length of the length adjusting portion.

In some configurations, a length of the rear headgear portion and a length of the core collector is fixed, and adjustment of a length of the length adjusting member provides substantially all of a length adjustment of the headgear length or the perimeter length.

In some configurations, a nasal cannula system comprises a nasal cannula and a headgear. At least one adjustment arrangement allows adjustment of a perimeter length of the nasal cannula system. The at least one adjustment arrangement includes a core member coupled to one of the headgear and the nasal cannula and a lock coupled to the other of the headgear and the nasal cannula. The lock can engage the core member to retain the nasal cannula system in a desired adjusted perimeter length.

In some configurations, the lock can retain the desired adjusted perimeter length in response to normal or expected forces in use, such as the weight of the nasal cannula and hose pull forces, for example.

In some configurations, the lock allows slippage of the core member at forces above a threshold such that the perimeter length can be increased beyond the desired adjusted perimeter length.

In some configurations, the lock is a directional lock and allows movement of the core member in a direction that reduces the perimeter length at a relatively low force, which is lower than the normal or expected forces in use.

In some configurations, the directional lock is of any structure or arrangement disclosed herein.

In some configurations, at least one biasing element applies a force to the nasal cannula system tending to reduce the perimeter length.

In some configurations, the biasing element allows the nasal cannula system to be self-fitting or automatically adjustable.

In some configurations, the nasal cannula system comprises at least one quick release arrangement that allows the perimeter loop to be quickly and easily broken, such as for removal or application of the nasal cannula system from or to a user.

In some configurations, the headgear is a single strap or a bifurcated strap arrangement.

In some configurations, the nasal cannula comprises a body having a rigid frame portion and a softer user-contacting portion.

In some configurations, an excess portion of the at least one core member that is not actively defining a portion of the perimeter length is accommodated in either the nasal cannula or the headgear. In some such configurations, the excess portion is internal to the nasal cannula or the headgear. In some such configurations, the excess portion is accommodated in a circular accumulator.

In some configurations, multiple adjustment arrangements are provided. In some such configurations, an adjustment arrangement is provided on each side of the nasal cannula system. In some such configurations, the excess portions of the core members of each side are positioned above and below one another on or within the nasal cannula.

In some configurations, a nasal cannula system comprises a nasal cannula and a headgear. At least one adjustment arrangement allows adjustment of a perimeter length of the nasal cannula system. The at least one adjustment arrangement includes a core member coupled to one portion of the headgear and a lock coupled to another portion of the headgear that is movable relative to the first portion. The lock can engage the core member to retain the nasal cannula system in a desired adjusted perimeter length.

In some configurations, the lock can retain the desired adjusted perimeter length in response to normal or expected forces in use, such as the weight of the nasal cannula and hose pull forces, for example.

In some configurations, the lock allows slippage of the core member at forces above a threshold such that the perimeter length can be increased beyond the desired adjusted perimeter length.

In some configurations, the lock is a directional lock and allows movement of the core member in a direction that reduces the perimeter length at a relatively low force, which is lower than the normal or expected forces in use.

In some configurations, the directional lock is of any structure or arrangement disclosed herein.

In some configurations, at least one biasing element applies a force to the nasal cannula system tending to reduce the perimeter length.

In some configurations, the biasing element allows the nasal cannula system to be self-fitting or automatically adjustable.

In some configurations, the nasal cannula system comprises at least one quick release arrangement that allows the perimeter loop to be quickly and easily broken, such as for removal or application of the nasal cannula system from or to a user.

In some configurations, the headgear is a single strap or a bifurcated strap arrangement.

In some configurations, the nasal cannula comprises a body having a rigid frame portion and a softer user-contacting portion.

In some configurations, an excess portion of the at least one core member that is not actively defining a portion of the perimeter length is accommodated in the headgear. In some such configurations, the excess portion is internal to the headgear. In some such configurations, the excess portion is accommodated in a circular accumulator.

In some configurations, multiple adjustment arrangements are provided. In some such configurations, an adjustment arrangement is provided on each side of the nasal cannula system.

In some configurations, a directional lock includes a lock member having an aperture or opening and is configured to engage a core member or filament that passes through the opening. The opening can change cross-sectional dimensions between one side of the lock member and the other side of the lock member and/or the profile of the opening can be tapered.

In some configurations, the side of the opening that defines a working edge of the lock member that engages the core member in a locked position is smaller than the opposite side of the opening.

In some configurations, the profile of the opening tapers towards a pivot axis of the lock member.

In some configurations, a directional lock includes a first lock member and a second lock member, each having an aperture or opening and is configured to engage a core member or filament that passes through the opening. A motion transfer element causes movement of the second lock member in response to movement of the first lock member.

In some configurations, the motion transfer element pushes the second lock member in response to movement of the first lock member, but allows the second lock member to move away from the first lock member.

In some configurations, the motion transfer element is a link, which deflects to allow the second lock member to move away from the first lock member.

In accordance with at least one of the embodiments disclosed herein, a headgear is provided comprising a top strap, a rear strap, a front strap, a yoke and a connector. The headgear is configured to be substantially inelastic and three dimensional in structure.

According to a further aspect, the headgear is constructed from a composite material, wherein a textile casing is integrally formed about a plastic core.

According to a further aspect, the headgear comprises integrally moulded labels, connections, and/or adjustment features.

According to a further aspect, a headgear component comprises a grip that is moulded to a textile strap.

According to a further aspect, the textile casing comprises a first portion that covers an inwardly-facing surface of the headgear.

According to a further aspect, the textile casing comprises a second portion that covers an outwardly-facing surface of the headgear.

According to a further aspect, the first portion and the second portion of the textile casing meet at first and second edges.

According to a further aspect, the first portion and the second portion are not connected to one another at the first and second edges.

According to a further aspect, the textile casing comprises one or more retainer holes configured to engage a retaining pin of a moulding tool.

According to a further aspect, the headgear comprises at least one flexible joint that permits the strap to bend.

According to a further aspect, the at least one flexible joint comprises a gap between portions of the plastic core and wherein the textile casing extends within the gap to connect the portion of the plastic core.

According to a further aspect, the headgear comprises at least one bridge portion extending within the flexible joint between the portions of the plastic core.

According to a further aspect, the at least one bridge portion is unitarily formed with the portions of the plastic core.

According to a further aspect, the headgear assembly comprises a top strap, a rear strap connected to the top strap at an upper connection point located on a side of a user's forehead, and a lower side strap connected to the top and rear straps at the upper connection point. The headgear assembly also comprises a first length adjusting portion adjusting the distance between the upper connection point and a frame of the respiratory interface, and a second length adjusting portion connected to the lower side strap at a lower connection point located forward of the user's ear and approximately in line with the user's mouth, wherein the second adjustment mechanism adjusts the distance between the lower connection point and the frame of the respiratory interface.

According to a further aspect, the top strap and the rear strap are formed unitarily as an integral structure.

According to a further aspect, the top strap, the rear strap and the lower side strap are formed unitarily as an integral structure.

According to a further aspect, the first length adjusting portion includes a fabric strap having a hook and loop fastener mechanism.

According to a further aspect, the second length adjusting portion includes a plurality of length adjusting mechanisms.

According to a further aspect, the headgear assembly comprises a top strap and a rear strap connected to the top strap at an upper connection point located on a side of a user's forehead. The headgear assembly also comprises an upper side strap connected to the top and rear straps at the upper connection point and connected to a frame of the respiratory interface. The upper side strap extends between the user's ear and eye and across the user's cheek towards the frame of the respiratory interface. The headgear assembly further comprises a lower side strap connected to the rear strap at a rear connection point located behind the user's ear. The lower side strap extends below the user's ear and across the user's cheek towards the frame of the respiratory interface. The headgear assembly additionally comprises a first length adjusting portion connected to the lower side strap and the frame of the respiratory interface. The first length adjusting portion adjusts the distance between the lower side strap and the frame of the respiratory interface.

According to a further aspect, the top strap and the rear strap are formed unitarily as an integral structure.

According to a further aspect, the top strap, the rear strap, the upper side strap and the lower side strap are formed unitarily as an integral structure.

According to a further aspect, the first length adjusting portion includes a one-way adjusting mechanism.

According to a further aspect, the headgear assembly further comprises a second length adjusting portion connected between the upper side strap and the frame of the respiratory interface, wherein the second length adjusting portion adjusts the distance between the upper side strap and the frame of the respiratory interface.

According to a further aspect, the headgear assembly comprises a top strap, a rear strap connected to the top strap at an upper connection point located on a side of a user's forehead, and a front strap connected to the top and rear straps at the upper connection point and connected to the respiratory interface. The front strap extends between the user's ear and eye and towards a bottom of the user's nose.

According to a further aspect, the top strap and the rear strap are formed unitarily as an integral structure.

According to a further aspect, the top strap, the rear strap and the front strap are formed unitarily as an integral structure.

According to a further aspect, the front strap extends across the front of the respiratory interface and forms a portion of a frame of the respiratory interface.

According to a further aspect, the headgear assembly further comprises a length adjusting portion connected between the front strap and the respiratory interface, wherein the length adjusting portion adjusts the distance between the front strap and the respiratory interface.

According to a further aspect, the headgear assembly comprises a top strap, a rear strap connected to the top strap at an upper connection point located on a side of a user's forehead, and a lower side strap connected to the top and rear straps at the upper connection point and extends away from the upper connection point in a substantially vertical direction. The lower strap is positioned in front of the user's ear. The headgear assembly also comprises a first length adjusting portion connected to the lower strap at a first lower connection point, the first length adjusting portion adjusting the distance between the first lower connection point and a frame of the respiratory interface. The first lower connection point is positioned in line with the user's eye and the first length adjusting portion extends across the user's cheeks just below the eyes. The headgear assembly further comprises a second length adjusting portion connected to the lower strap at a second lower connection point, the second length adjusting portion adjusting the distance between the second lower connection point and the frame of the respiratory interface. The second lower connection point is positioned approximately in line with a bottom of the user's nose and the second length adjusting portion extends substantially horizontally across the users cheek.

According to a further aspect, the top strap and the rear strap are formed unitarily as an integral structure.

According to a further aspect, the top strap, the rear strap and the lower side strap are formed unitarily as an integral structure.

According to a further aspect, at least one of the first or second length adjusting portions include a one-way adjusting mechanism.

In accordance with at least one of the embodiments disclosed herein, a headgear comprises a plastic core and a textile casing. The plastic core and the textile casing are formed as an integral structure by the application of a molten plastic material onto the textile casing.

According to a further aspect, the textile casing comprises a first portion that covers an inwardly-facing surface of the headgear.

According to a further aspect, the textile casing comprises a second portion that covers an outwardly-facing surface of the headgear.

According to a further aspect, the first portion and the second portion of the textile casing meet at first and second edges.

According to a further aspect, the first portion and the second portion are not connected to one another at the first and second edges.

According to a further aspect, the textile casing comprises one or more retainer holes configured to engage a retaining pin of a moulding tool.

According to a further aspect, the headgear comprises at least one flexible joint that permits the headgear to bend.

According to a further aspect, the at least one flexible joint comprises a gap between portions of the plastic core and the textile casing extends within the gap to connect the portion of the plastic core.

According to a further aspect, the headgear comprises at least one bridge portion extending within the flexible joint between the portions of the plastic core.

According to a further aspect, the at least one bridge portion is unitarily formed with the portions of the plastic core.

In accordance with at least one of the embodiments disclosed herein, a method of making a headgear comprises placing a textile casing within a moulding tool, introducing a molten plastic material into the moulding tool and into contact with the textile casing, and allowing the molten plastic material to solidify on the textile casing to form a plastic core.

According to a further aspect, the placing of the textile casing into the moulding tool comprises placing a first textile portion and a second textile portion into the moulding tool, and the introducing the molten plastic material into the moulding tool comprises introducing the molten plastic material between the first and second textile portions.

According to a further aspect, the method further comprises retaining an end of each of the first and second textile portions at which the molten plastic material is introduced within a retaining feature of the moulding tool.

According to a further aspect, the method further comprises capturing at least one edge of the textile casing between first and second separable portions of a moulding tool.

According to a further aspect, the method further comprises engaging an opening of the textile casing with a retention pin of the moulding tool.

According to a further aspect, the method further comprises securing the textile casing within the moulding tool prior to the introduction of the molten plastic material.

According to a further aspect, the securing of the textile casing comprises securing the textile casing by one or more of a static electrical charge, air pressure, retaining the textile casing with another component inserted into the moulding tool, or supporting a strip of material that forms the textile casing extending through the moulding tool on each side of the moulding tool.

According to a further aspect, the supporting the strip of material comprises supporting one end on a roll and securing a free end relative to the moulding tool.

According to a further aspect, the method further comprises forming a flexible joint by providing a gap in plastic core along a length of the headgear, and extending the textile casing along the gap.

According to a further aspect, the method further comprises extending a flexible bridge portion of plastic material through the flexible joint from a portion of the plastic core on one side of the gap to a portion of the plastic core on the opposite side of the gap.

In accordance with at least one embodiment disclosed herein, a headgear comprises a first strap and a second strap, wherein the first strap and the second strap cooperate to form at least one of a top strap, a rear strap and a front strap of the headgear.

In accordance with at least one of the embodiments disclosed herein, a method of making a headgear comprises placing a textile casing within a moulding tool, introducing a molten plastic material into the moulding tool and into contact with an inside of the textile casing, and allowing the molten plastic material to solidify in the textile casing to form a plastic core.

According to a further aspect, the first strap and the second strap cooperate to form the rear strap, wherein the first strap and the second strap overlap one another within the rear strap, and wherein only one of the first strap and the second strap defines the top strap.

According to a further aspect, the first strap and the second strap cooperate to form the front strap, wherein the first strap and the second strap are stacked within the front strap, and wherein the first strap and the second strap alone defines a respective one of the top strap and the rear strap.

According to a further aspect, one or both of the straps are constructed from a plastic core and a textile casing formed as an integral structure by the application of a molten plastic material onto the textile casing.

In accordance with at least one embodiment disclosed herein, a headgear includes an inner core, a first outer layer defining an inner surface of the headgear that faces the user in use, and a second outer layer defining an outer surface of the headgear that faces away from the user in use. The first layer and the second layer have different colors, textures or other indicia that permit tactile or visual differentiation of the inner surface and the outer surface.

According to a further aspect, the first outer layer or the second outer layer comprises one of a polyurethane (imitation leather), patterned polyester, wool with mesh knit, unbroken loop, nylon, a composite of spacer fabric and unbroken loop or a composite of foam an unbroken loop.

According to a further aspect, edges of one or both of the first and second outer layers extend beyond the inner core.

According to a further aspect, the inner core comprises an interior cut-out.

In accordance with at least one embodiment disclosed herein, a headgear comprises a first strap, a second strap, and a connector that couples the first strap to the second strap, wherein the connector is formed by over-moulding onto the first strap and the second strap.

According to a further aspect, the first strap and the second strap are stacked in a vertical direction within the connector.

According to a further aspect, the connector includes a portion extending between and separating the first strap from the second strap.

According to a further aspect, the connector includes a front band portion and a rear band portion separated by a bridge portion, wherein the bridge portion does not surround an entirety of both the first strap and the second strap.

According to a further aspect, the connector includes a front band portion and a rear gusset.

According to a further aspect, the front band portion and the rear gusset are separated by a bridge portion, wherein the bridge portion does not surround an entirety of both the first strap and the second strap.

In accordance with at least one embodiment disclosed herein, a strap of a headgear comprises an inner core, at least one outer layer that at least partially surrounds the inner core, and at least one air gap within the outer layer.

According to a further aspect, the at least one air gap comprises a first air gap at one lateral edge of the strap and a second air gap at the opposite lateral edge of the strap.

According to a further aspect, a portion of the inner core is externally exposed.

According to a further aspect, a conduit is positioned within the air gap.

According to a further aspect, the air gap is defined by the inner core.

In accordance with at least one embodiment disclosed herein, a strap of a headgear comprises an inner core, at least one outer layer, and at least one conduit extending lengthwise along the strap and within the outer layer.

According to a further aspect, the conduit is at least partially received within a recess of the inner core.

According to a further aspect, the conduit is completely encapsulated within the inner core.

According to a further aspect, the at least one conduit comprises a first conduit and a second conduit.

According to a further aspect, the at least one conduit is defined by the core.

In accordance with at least one embodiment disclosed herein, a strap of a headgear includes an inner core, at least one outer layer, and at least one reinforcement member.

According to a further aspect, the reinforcement member is embedded within the core.

According to a further aspect, the reinforcement member is configured to hold opposing outer layers or opposing sides of an outer layer apart from one another prior to the formation of the inner core.

In accordance with at least one embodiment disclosed herein, a strap of a headgear comprises an inner core, at least one outer layer, and at least one cushioning layer.

According to a further aspect, the cushioning layer surrounds the inner core.

According to a further aspect, a portion of the cushioning layer is externally exposed.

In accordance with at least one embodiment disclosed herein, a strap of a headgear comprises an inner core and an outer layer that at least partially surrounds the inner core, the outer layer comprising edges. The edges are embedded in the inner core.

According to a further aspect, the outer layer comprises more than one piece or more than two pieces.

According to a further aspect, a first piece of outer layer is located on one side of the strap and a second piece of the outer layer is located on an opposite side of the strap.

According to a further aspect, a third piece of the outer layer is located on one edge of the strap and a fourth piece of the outer layer is located on an opposite edge of the strap.

According to a further aspect, at least two pieces of the outer layer are located on one side of the strap.

In accordance with at least one embodiment disclosed herein, a strap of a headgear comprises an inner core and an outer layer, wherein the outer layer is textured.

According to a further aspect, the outer layer is ribbed or quilted.

According to a further aspect, the core is textured such that it imparts a texture to the outer layer.

In accordance with at least one embodiment disclosed herein, a headgear, strap or other portion thereof has one or more features as described herein or a method of making such a headgear, strap or other portion thereof.

BRIEF DESCRIPTION OF THE DRAWINGS

Preferred embodiments of the present invention will be described with reference to the accompanying drawings.

FIG. 4.1 illustrates a position of the exemplary headgear arrangement at a start of donning onto a user;

FIG. 4.2 illustrates a position of the exemplary headgear arrangement at a start of retraction;

FIG. 4.3 illustrates a position of the exemplary headgear arrangement at an end of donning;

FIG. 13.1 is a stability chart of various headgear types;

FIG. 13.2 illustrates a single retention plane interface assembly;

FIG. 14 is a side view of a full face mask with forehead support having a directional locking mechanism positioned at a connection between the headgear and the mask;

FIG. 15 is a side view of a full face mask with forehead support having a directional locking mechanism positioned within the headgear;

FIG. 16 is a side view of a nasal mask having a directional locking mechanism on a flat strap;

FIG. 17 is a side view of a nasal mask having directional locking mechanisms with a flexible core design;

FIG. 30 illustrates locations where an automatic adjuster can be positioned within an exemplary headgear assembly;

FIG. 31 illustrates locations where an automatic adjuster can be positioned within an exemplary headgear assembly worn by a user;

FIG. 32 illustrates an exemplary strap adjustment mechanism in assembled form;

FIG. 33 is a plan view of the exemplary strap adjustment mechanism in FIG. 32 separated into first and second portions;

FIGS. 109a-109c illustrate several lock members with different possible cross-sectional opening shapes.

FIG. 110 is a perspective view of a lock member having a tapered hole geometry.

FIGS. 111a and 111b illustrate lock members having alternative tapered hole geometries.

FIG. 112 is a graph of force versus distance illustrating the progressive holding force profile of the tapered hole geometries in comparison with a linear holding force profile.

FIGS. 113a and 113b illustrate a directional lock arrangement comprising a pair of lock members and a motion transfer element for transferring motion between the lock members. FIG. 113a illustrates the directional lock arrangement in an unlocked position and FIG. 113b illustrates the directional lock arrangement in a locked position.

FIGS. 114a and 114b illustrate another directional lock arrangement comprising a pair of lock members and an alternative motion transfer element for transferring motion between the lock members. FIG. 114a illustrates the directional lock arrangement in an unlocked position and FIG. 114b illustrates the directional lock arrangement in a locked position.

FIG. 115 illustrates a respiratory mask system comprising a headgear arrangement incorporating at least one directional lock arrangement. The directional lock arrangement is located behind the ear of the user.

FIG. 116 illustrates possible locations for placement of a directional lock arrangement on a user.

FIG. 117 illustrates a possible location for placement of a directional lock behind an ear of the user, with the placement area shown relative to bones of the skull.

FIG. 118A is a side view of the headgear of the present disclosure being worn by a user.

FIG. 118B is a perspective view of the headgear of the present disclosure.

FIG. 119 is a cross-sectional view of a strap that forms part of the presently disclosed headgear.

FIGS. 120, 120a, and 120c are a third angle orthographic view of one half of an injection moulding tool configured to mould a strap component similar to the headgear of the present disclosure.

Figure 121:
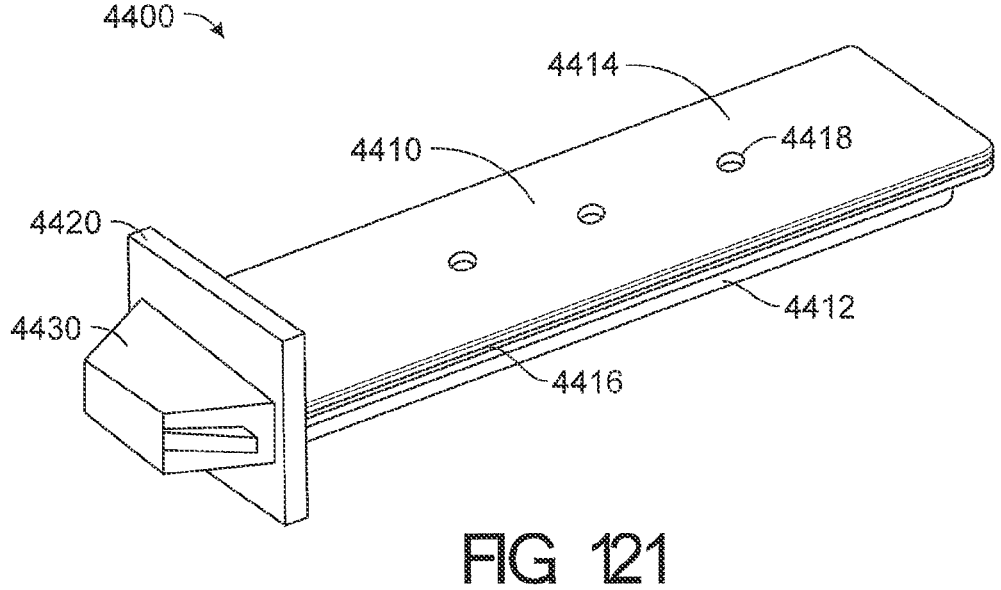

FIG. 121 is an isometric view of the strap component produced by the injection moulding tool of FIG. 120.

Figure 122:
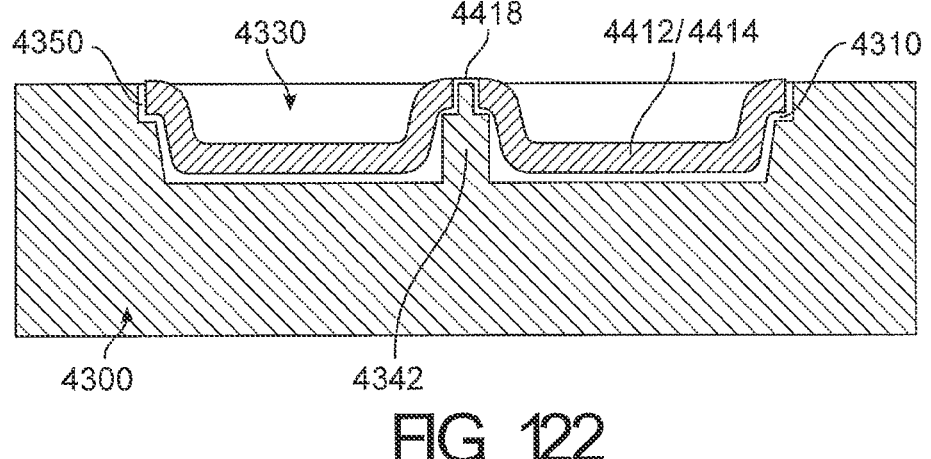

FIG. 122 is a cross-sectional view BB of the injection moulding tool of FIG. 120 with a textile casing placed inside.

Figure 123:
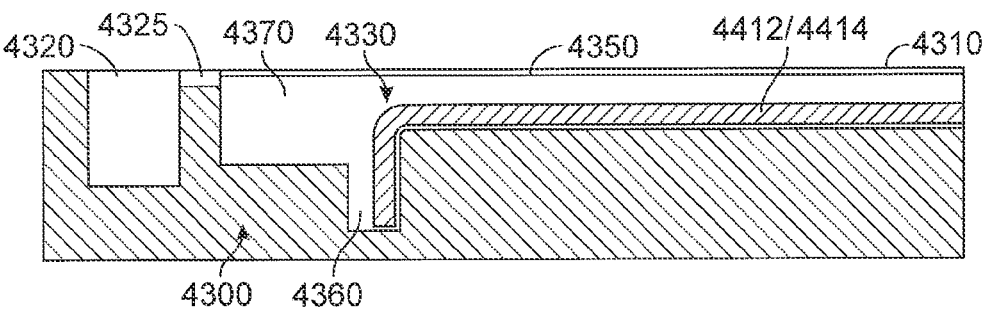

FIG. 123 is an enlarged view of the cross-section AA of the injection moulding tool of FIG. 120 with a textile casing placed inside.

Figure 124A:
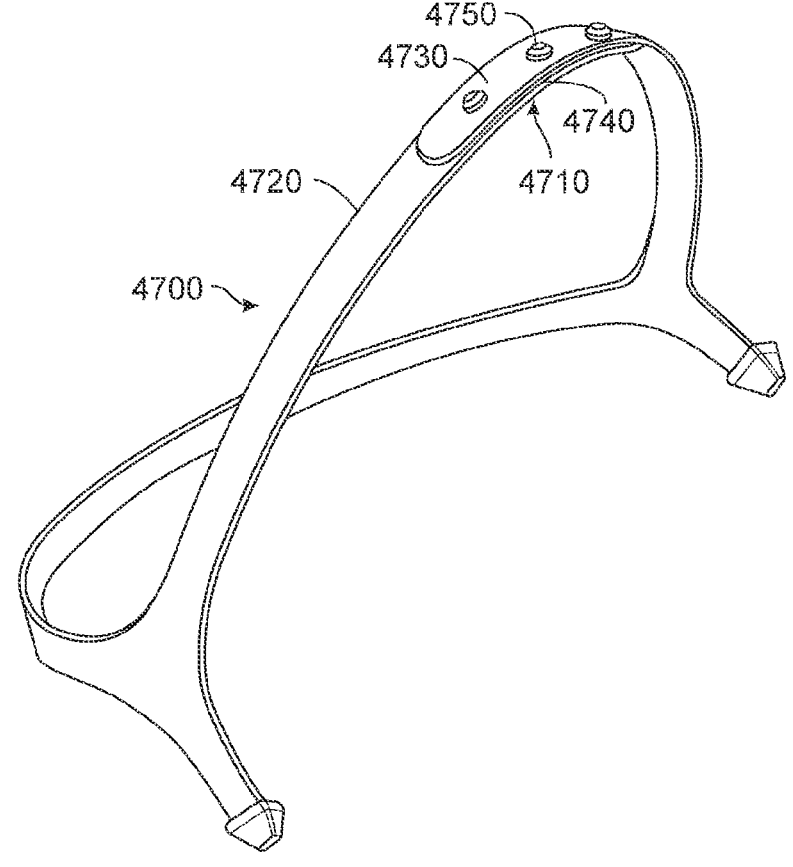

FIG. 124A is a perspective view of a second embodiment of the headgear of the present disclosure.

Figure 124B:
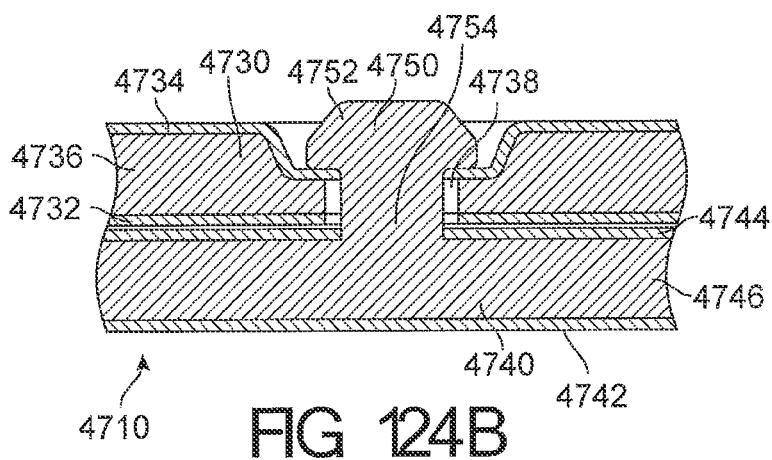

FIG. 124B is an enlarged cross-sectional view of a size adjustment system of the second embodiment of the headgear of the present disclosure.

Figure 125A:
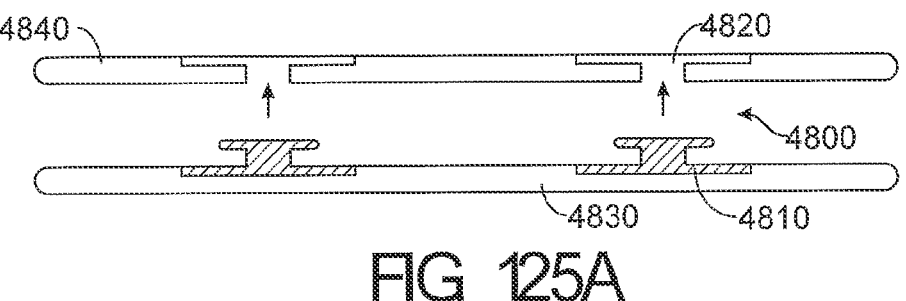

FIG. 125A is a cross-sectional view of a second embodiment of the size adjustment system of FIGS. 124A and 124B.

Figure 8A:
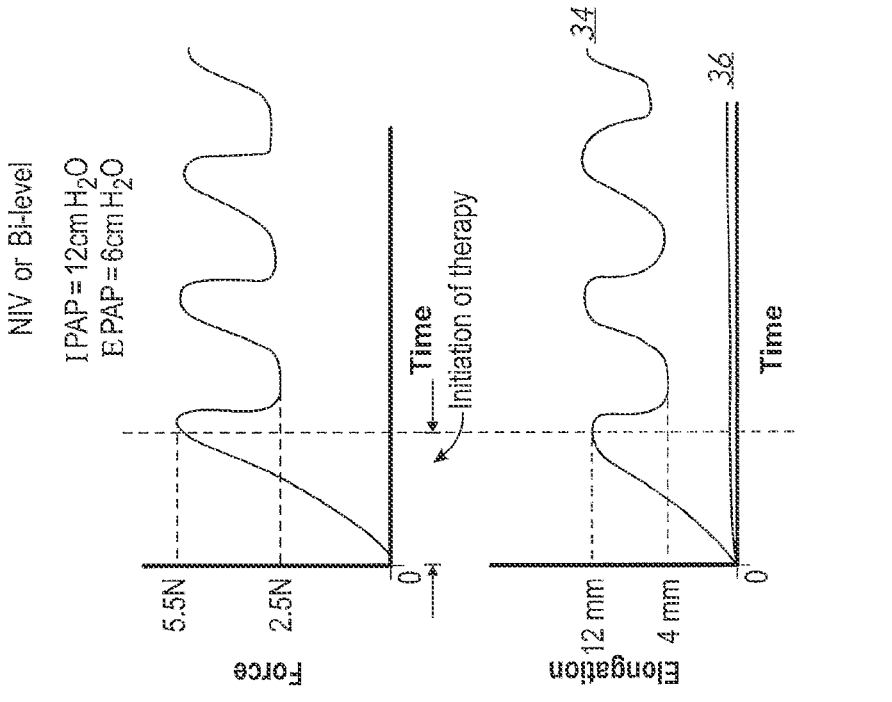
FIG. 8A shows a force profile and elongation profile of a constant pressure therapy for elastic and inelastic headgear systems.
Figure 125B:
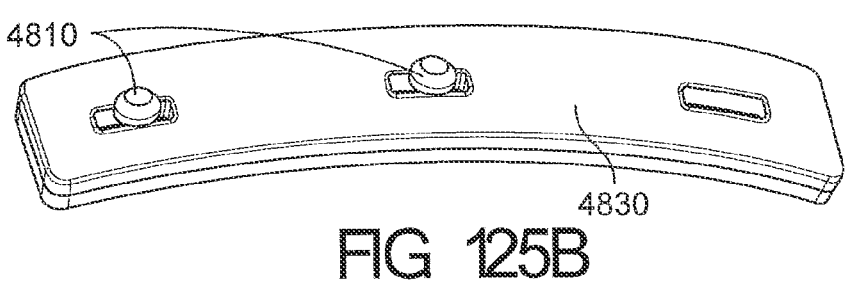

FIG. 125B is a plan view of the first strap of the size adjustment system of FIG. 8A.

Figures 125C, 125D, 125E, 125F, 125G, 125H, 125I:
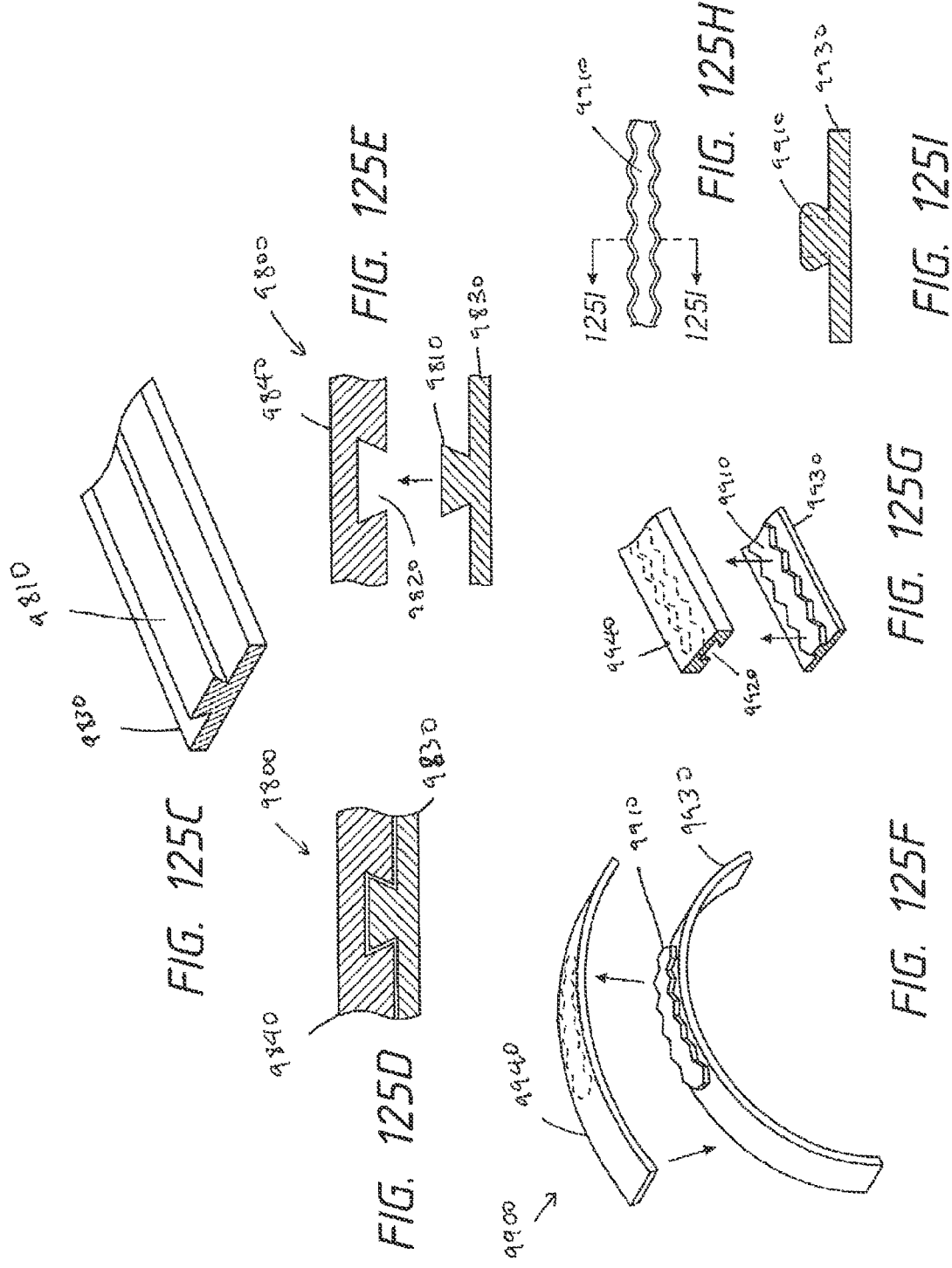

FIG. 125C is a perspective view of a first strap of an alternative size adjustment system.

FIG. 125D is a cross-sectional view of connected first and second straps of the size adjustment system of FIG. 125C.

FIG. 125E is a cross-sectional view of unconnected first and second straps of the size adjustment system of FIG. 125C.

FIG. 125F is a perspective exploded view of another alternative size adjustment system.

FIG. 125G is a close-up perspective exploded view of the size adjustment system of FIG. 125F.

FIG. 125H is a top-down view of the first strap of the size adjustment system of FIG. 125F.

FIG. 125I is a cross-sectional view of the second strap of the size adjustment system of FIG. 125F.

Figures 126, 127A, 127B:
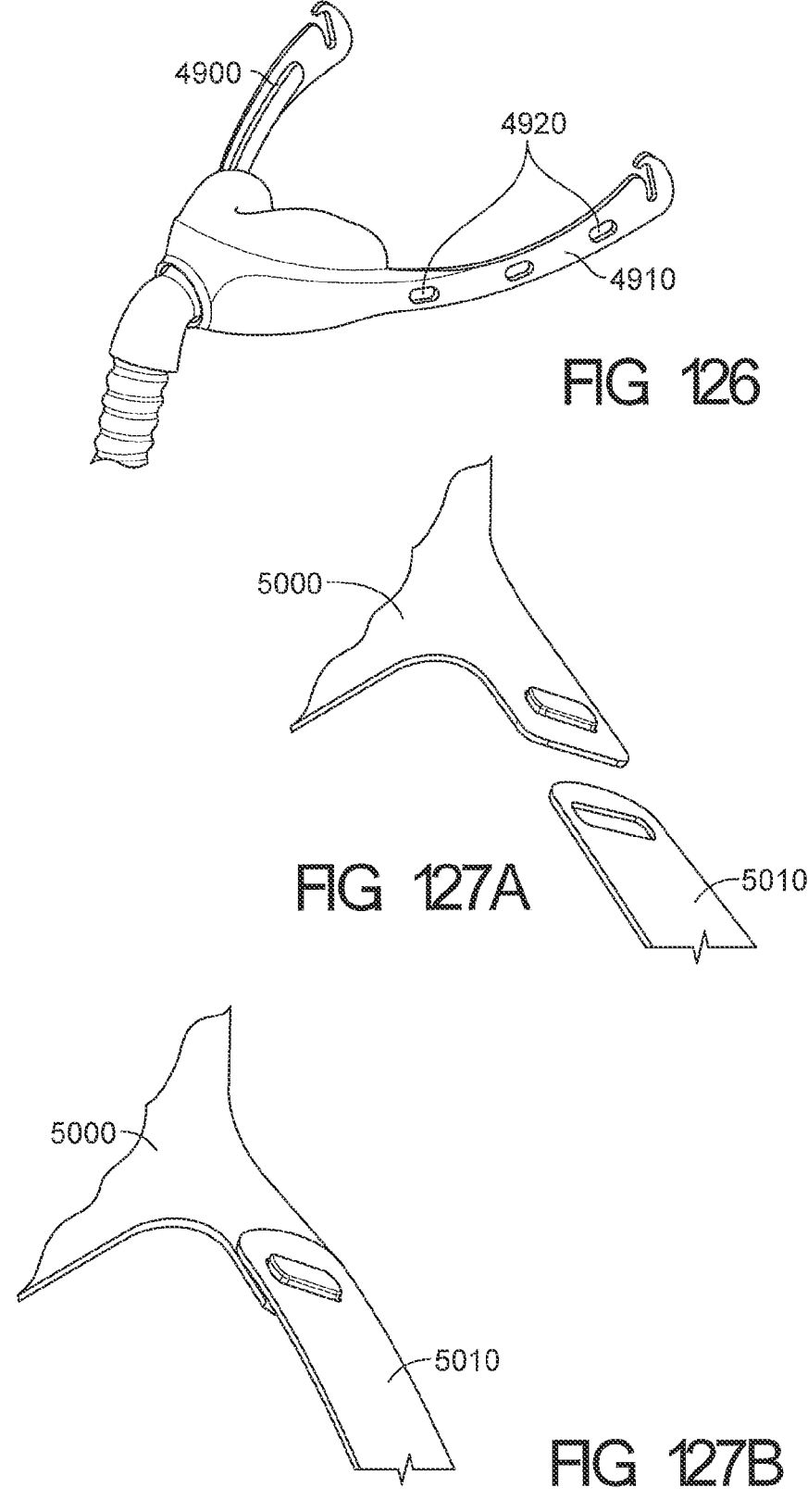

FIG. 126 is a perspective view of a breathing apparatus with cushion pads that are connected using the size adjustment systems of FIGS. 124A and 124B.

FIGS. 127A and 127B are plan views of a connection between breathing apparatus components.

Figure 128:
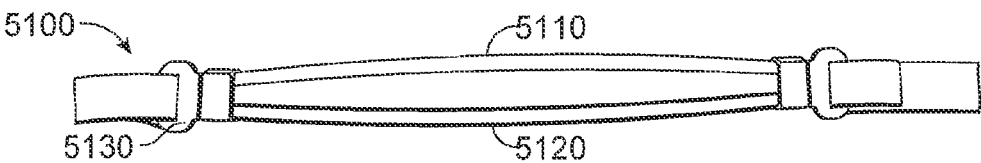

FIG. 128 is a plan view of a headgear component with a moulded grip.

Figure 129:
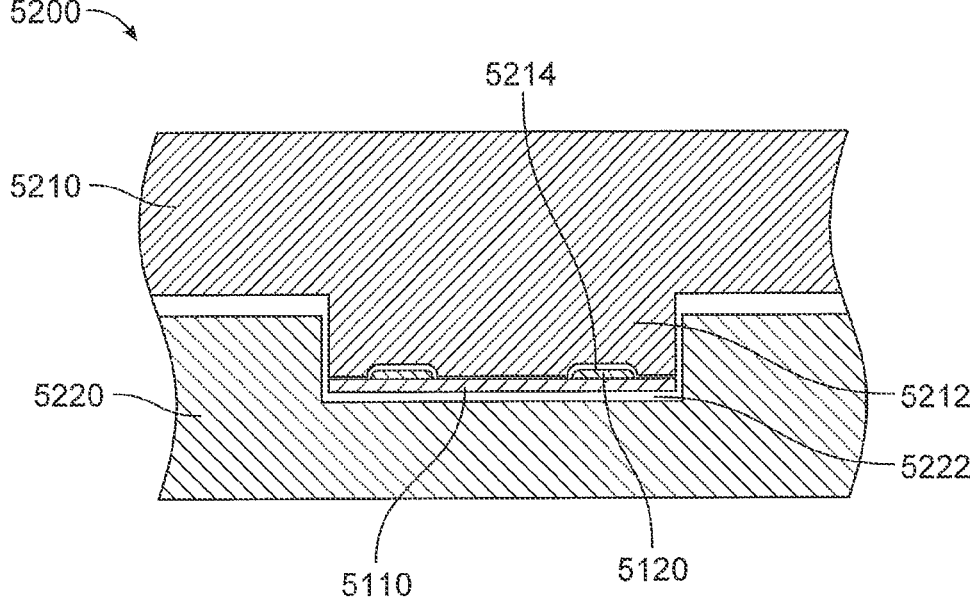

FIG. 129 is a cross-sectional view of a mould tool configured to form the headgear component of FIG. 128.

FIG. 130 is a side view of a headgear strap portion having a relatively inelastic core, a fabric casing on at least one surface of the core and a flexible joint between portions of the core.

FIG. 131 is a sectional view of the headgear strap portion of FIG. 130 taken along line 14-14 of FIG. 130.

FIG. 132 is a side view of a headgear strap portion having a relatively inelastic core, a fabric casing on at least one surface of the core and a flexible joint between portions of the core, wherein the flexible joint comprises flexible bridge portions extending between the portion of the core.

FIG. 133 is a cross sectional view of the headgear strap portion of FIG. 132 taken along line 16-16 of FIG. 132.

Figure 134:
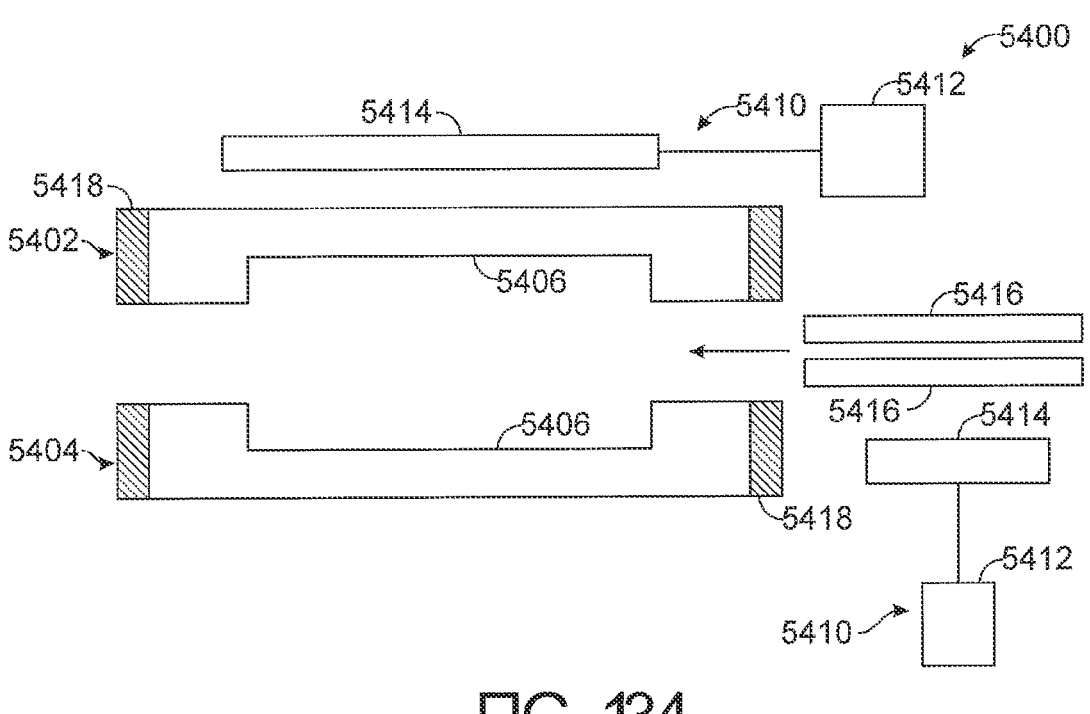

FIG. 134 illustrates a system for forming a headgear strap portion utilizing a static electrical charge to hold the fabric casing in place within a forming mould.

Figure 135:
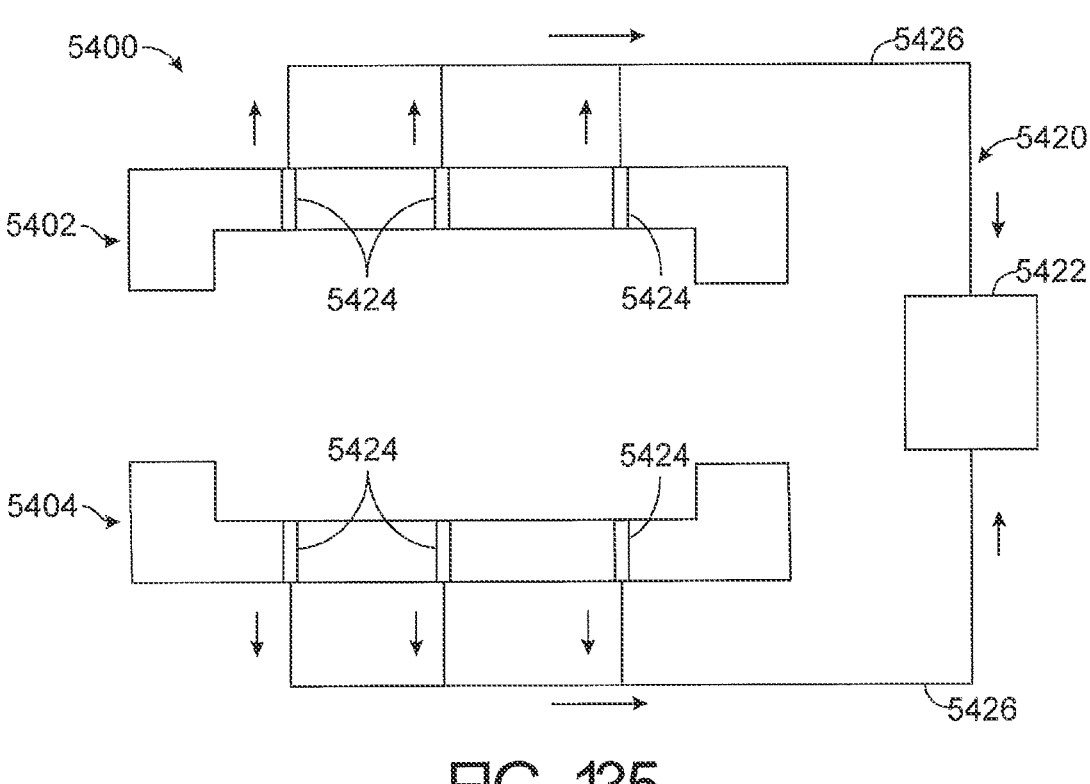

FIG. 135 illustrates a system for forming a headgear strap portion utilizing air pressure to hold the fabric casing in place within a forming mould.

FIG. 136 illustrates a system for forming a headgear strap portion utilizing one or more components for holding the fabric casing in place within a forming mould.

FIG. 137 illustrates a system for forming a headgear strap portion utilizing a roll of material for feeding the fabric casing into a forming mould.

Figure 138:
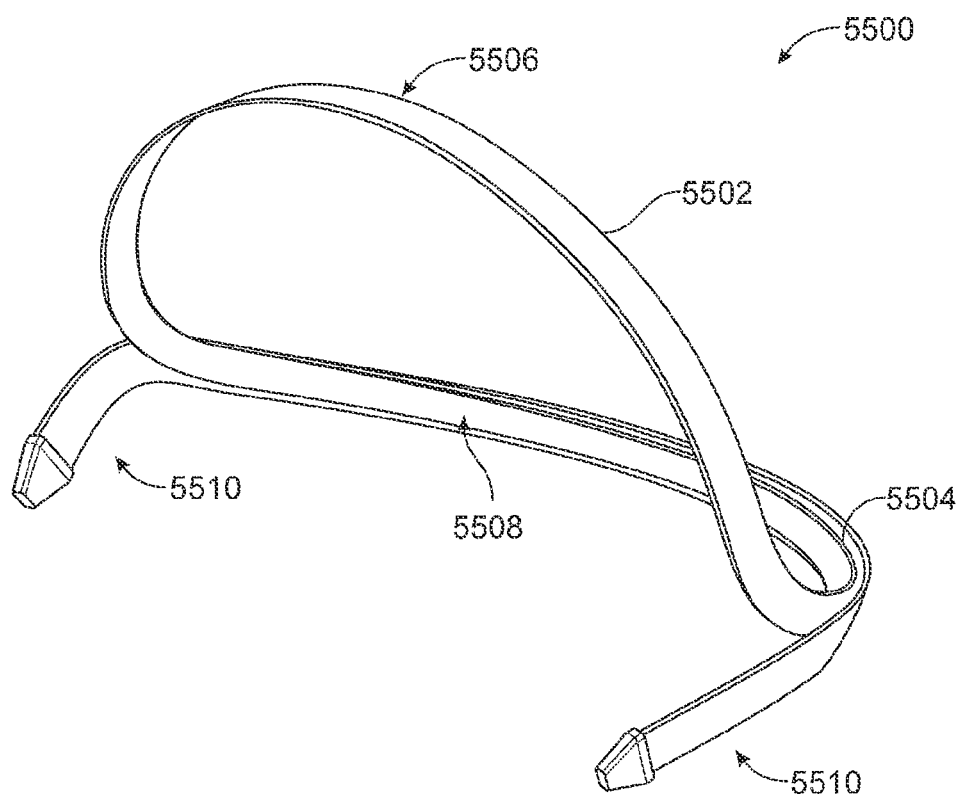

FIG. 138 illustrates a headgear having a first strap and a second strap.

Figures 139A, 139B, 139C, 139D:
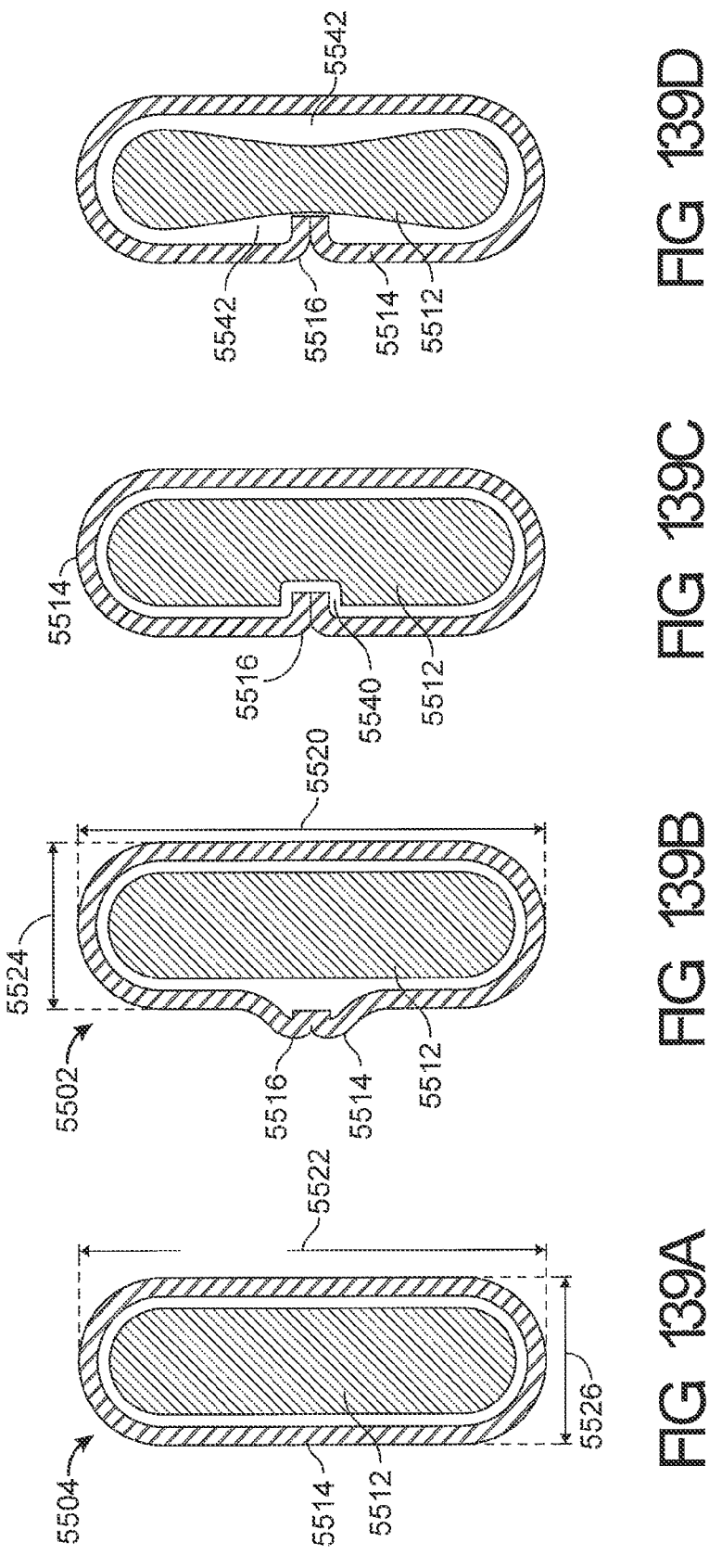

FIG. 139A is a sectional view of the second strap and FIG. 139B is a sectional view of the first strap.

FIG. 139C is a sectional view of an alternative strap in which a core of the strap includes a recess configured to receive a seam of a cover layer of the strap.

FIG. 139D is a sectional view of another alternative strap in which the core has one or more recesses occupying a substantial portion of a width direction of the core and the seam of the cover layer is located within the recess.

Figure 139E:
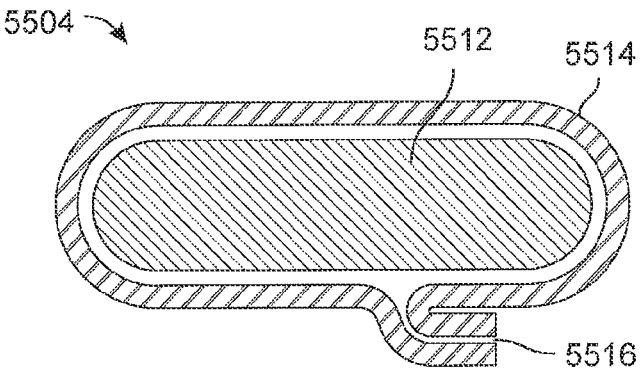

FIG. 139E is a sectional view of yet another alternative strap illustrating an alternative seam arrangement in which the seam of the cover layer is folded over onto the surface of the cover layer.

FIG. 140A is a view of an outer layer of the first strap and FIG. 140B is a view of an outer layer of the second strap.

FIG. 141 illustrates a headgear having a first strap and a second strap.

Figure 142A:
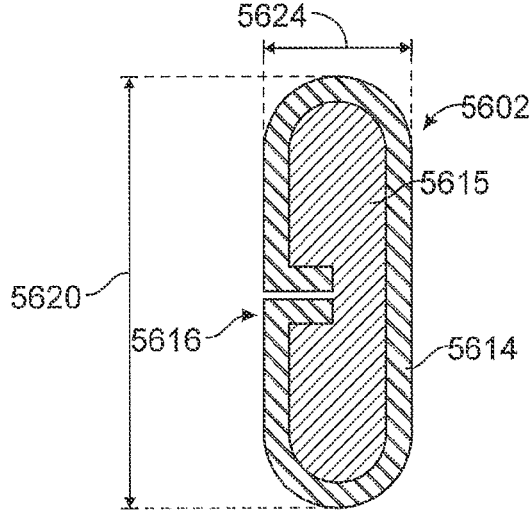
Figure 142B:
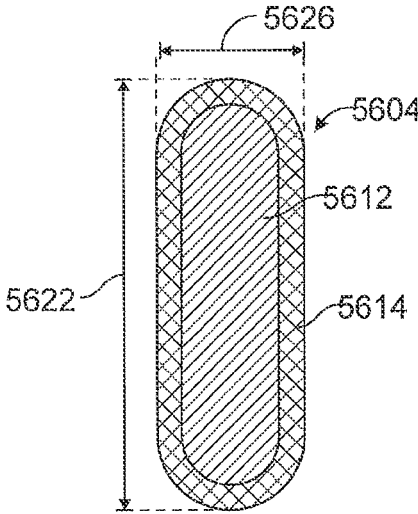

FIG. 142A is a sectional view of the first strap and FIG. 142B is a sectional view of the second strap.

Figure 143A:
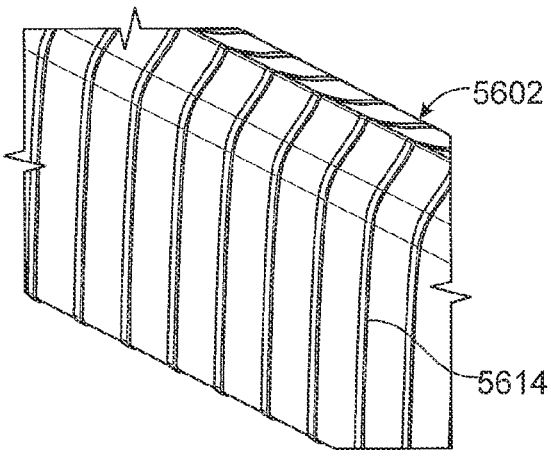
Figure 143B:
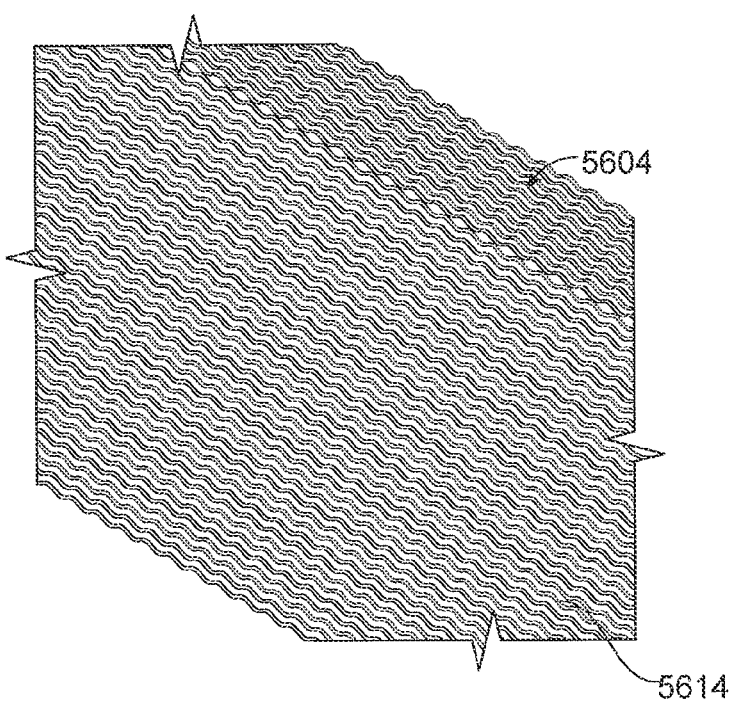

FIG. 143A is a view of an outer layer of the first strap and FIG. 143B is a view of an outer layer of the second strap.

FIG. 144 illustrates a headgear having an inner core, a first outer layer and a second outer layer.

FIG. 145 is a sectional view of a portion of the headgear of FIG. 144.

FIG. 146A is a view of the first outer layer and FIG. 146B is a view of the second outer layer of the headgear of FIG. 144.

Figures 147, 148, 149A, 149B:
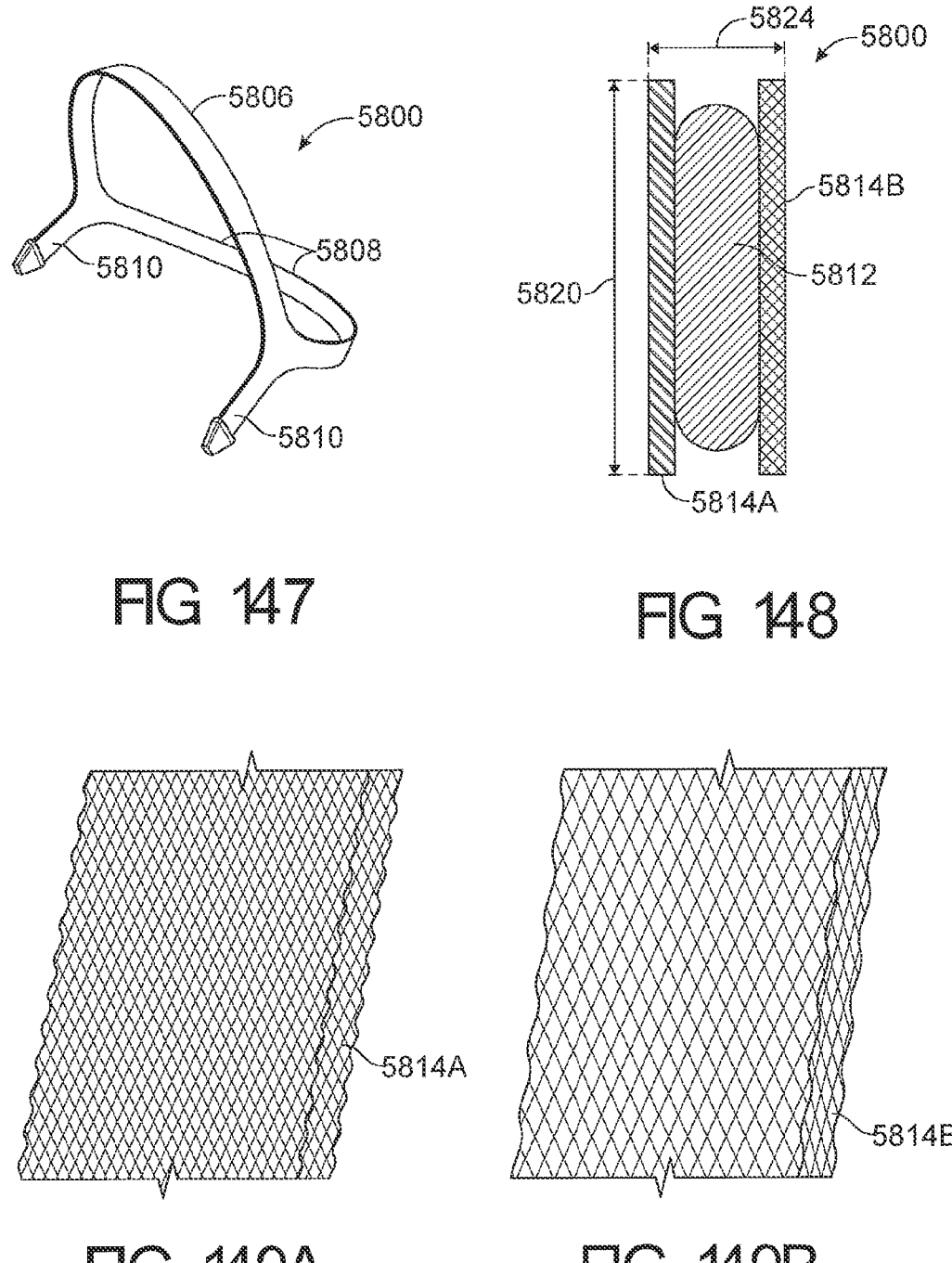

FIG. 147 illustrates a headgear having an inner core, a first outer layer and a second outer layer.

FIG. 148 is a sectional view of a portion of the headgear of FIG. 147.

FIG. 149A is a view of the first outer layer and FIG. 148B is a view of the second outer layer of the headgear of FIG. 147.

Figure 150:
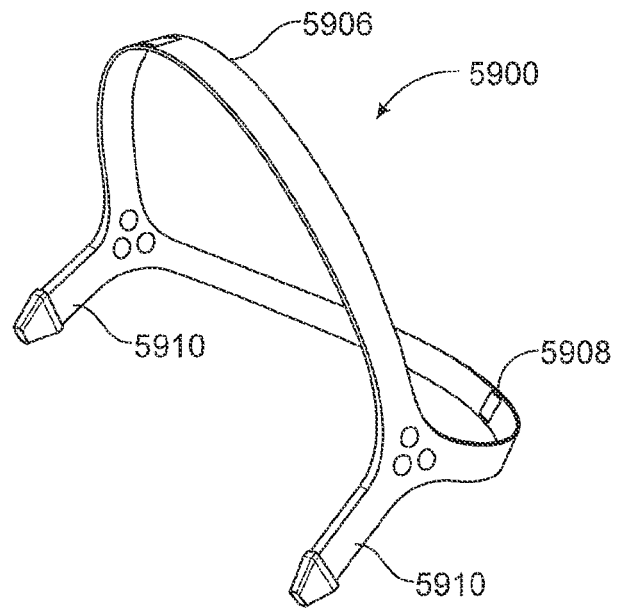

FIG. 150 illustrates a headgear having an inner core, a first outer layer and a second outer layer.

Figure 151:
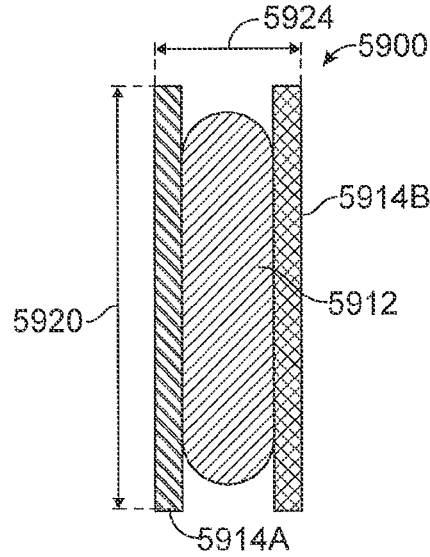

FIG. 151 is a sectional view of a portion of the headgear of FIG. 150.

Figures 152A, 152B:
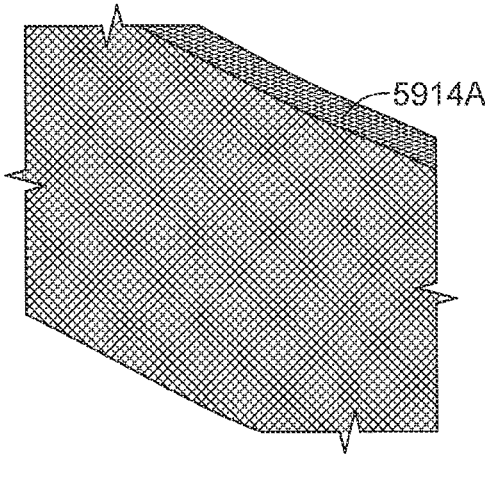

FIG. 152A is a view of the first outer layer and FIG. 152B is a view of the second outer layer of the headgear of FIG. 150.

FIG. 153 illustrates a headgear having an inner core, a first outer layer and
a second outer layer.

FIG. 154 is a sectional view of a portion of the headgear of FIG. 153.

FIG. 155 illustrates a headgear having an inner core, a first outer layer and
a second outer layer.

FIG. 156 is a sectional view of a portion of the headgear of FIG. 155.

Figure 157A:
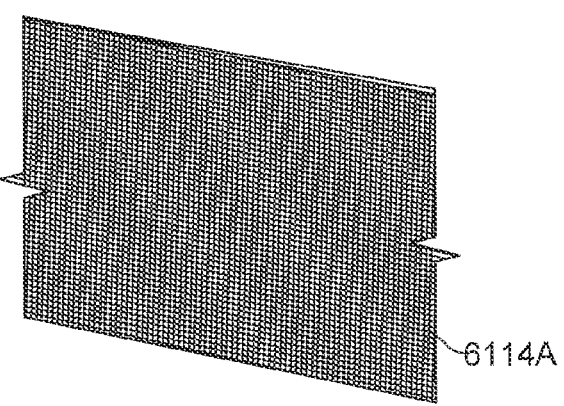
Figure 157B:
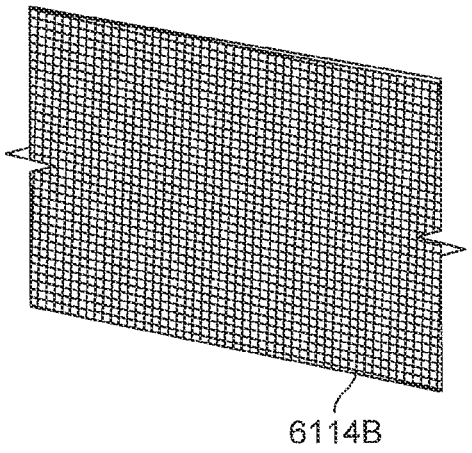

FIG. 157A is a view of the first outer layer and FIG. 157B is a view of the second outer layer of the headgear of FIG. 155.

Figure 158:
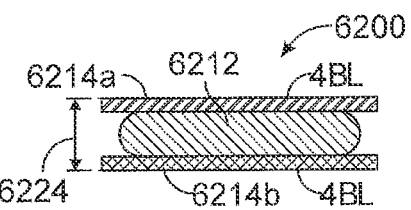

FIG. 158 is a sectional view of a headgear strap arrangement having a core and one or more outer layers.

Figure 159:
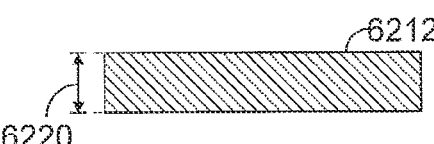

FIG. 159 is a side view of the core of the headgear strap arrangement of FIG. 158.

Figure 160:
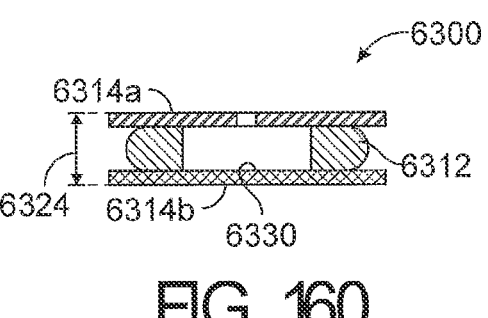

FIG. 160 is a sectional view of a headgear strap arrangement having a core and one or more outer layers.

Figure 161:
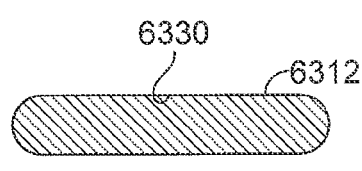

FIG. 161 is a side view of the core of the headgear strap arrangement of FIG. 160.

Figure 162:
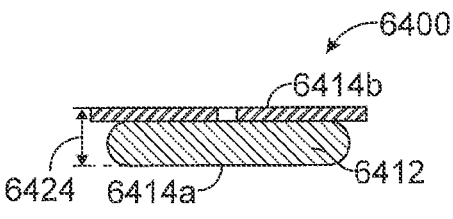

FIG. 162 is a sectional view of a headgear strap arrangement having a core and one or more outer layers.

Figure 163:
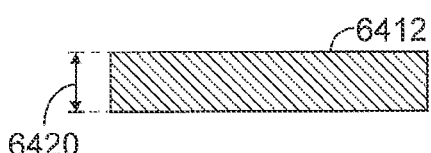

FIG. 163 is a side view of the core of the headgear strap arrangement of FIG. 162.

Figure 164:
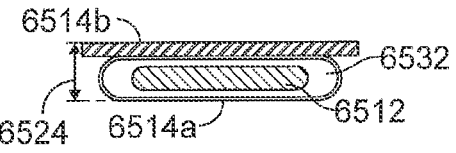

FIG. 164 is a sectional view of a headgear strap arrangement having a core and one or more outer layers.

Figure 165:
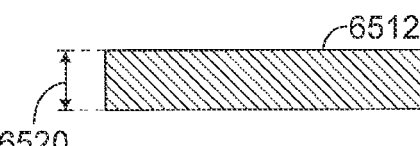

FIG. 165 is a side view of the core of the headgear strap arrangement of FIG. 164.

FIG. 166 is a sectional view of a headgear strap arrangement having a core and one or more outer layers.

FIG. 167 is a side view of the core of the headgear strap arrangement of FIG. 166.

FIG. 168 is a sectional view of a headgear strap arrangement having a core and one or more outer layers.

FIG. 169 is a side view of the core of the headgear strap arrangement of FIG. 168.

Figure 170:
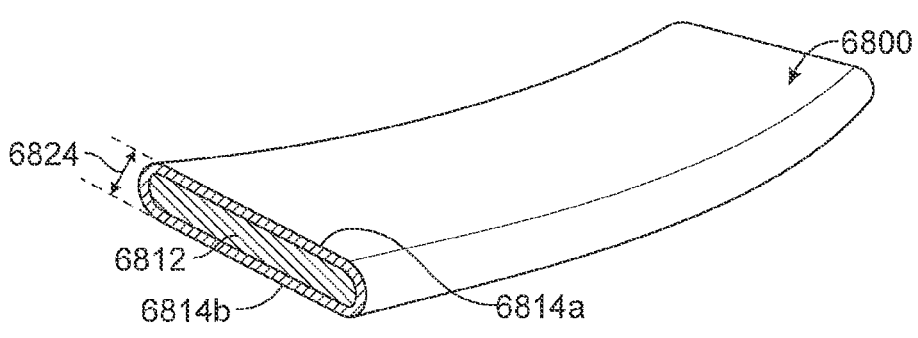

FIG. 170 is a sectional view of a headgear strap arrangement having a core and one or more outer layers.

Figure 171:
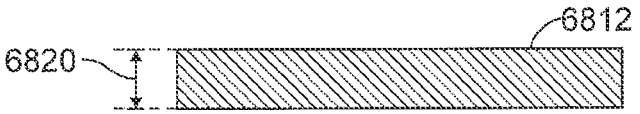

FIG. 171 is a side view of the core of the headgear strap arrangement of FIG. 170.

Figure 172:
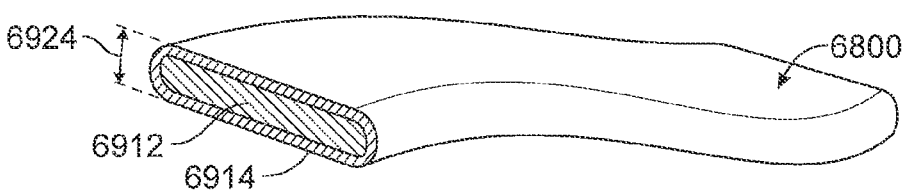

FIG. 172 is a sectional view of a headgear strap arrangement having a core and one or more outer layers.

Figure 173:
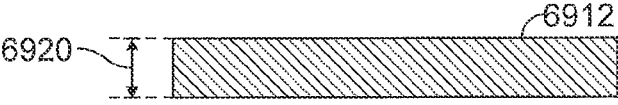

FIG. 173 is a side view of the core of the headgear strap arrangement of FIG. 172.

Figure 174:
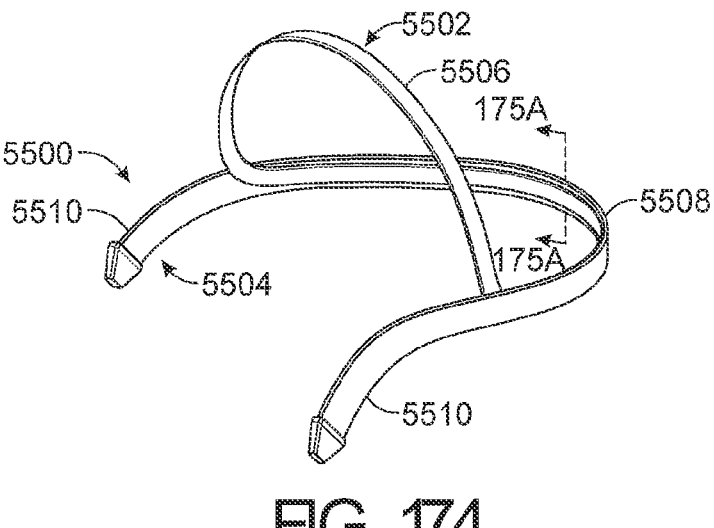

FIG. 174 is a perspective view of a headgear having a first strap and a second strap.

Figure 175A:
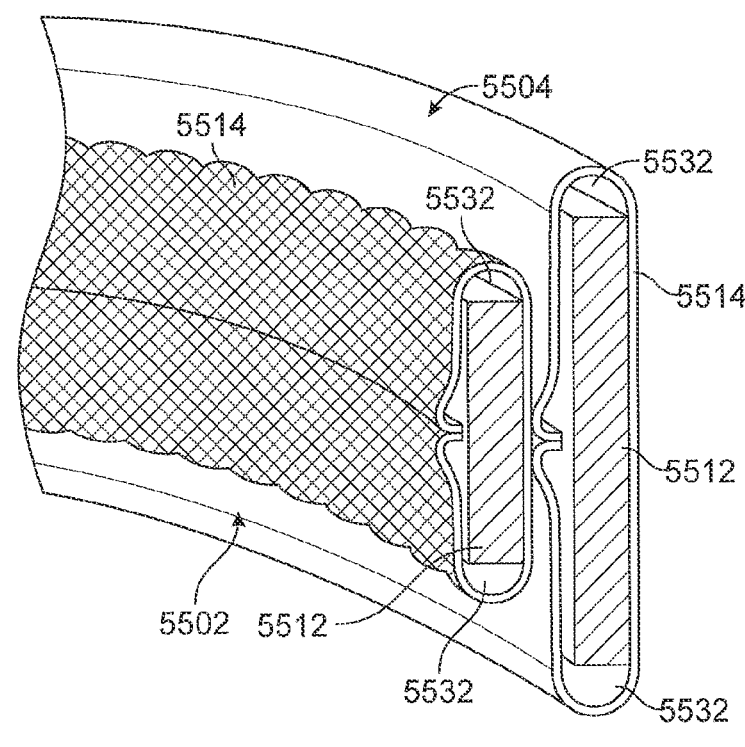

FIG. 175A is a sectional view of a portion of the headgear of FIG. 174.

Figure 175C:
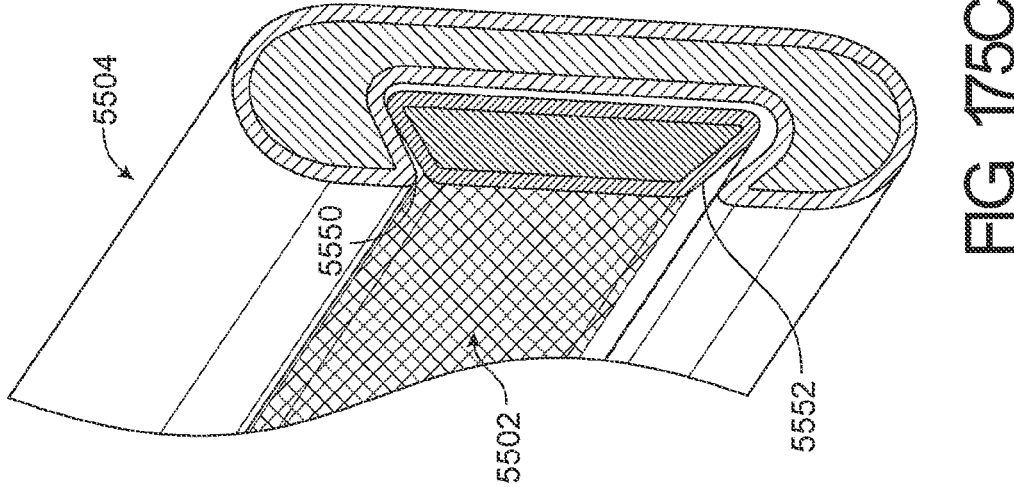
Figure 175B:
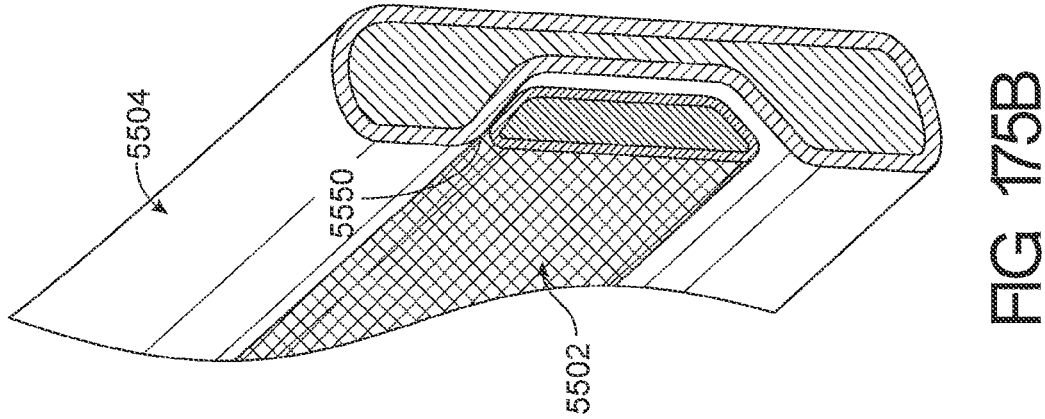

FIG. 175B is a sectional view of an alternative arrangement of the straps of the headgear of FIG. 174.

FIG. 175C is a sectional view of another alternative arrangement of the straps of the headgear of FIG. 174.

Figures 176, 177, 178:
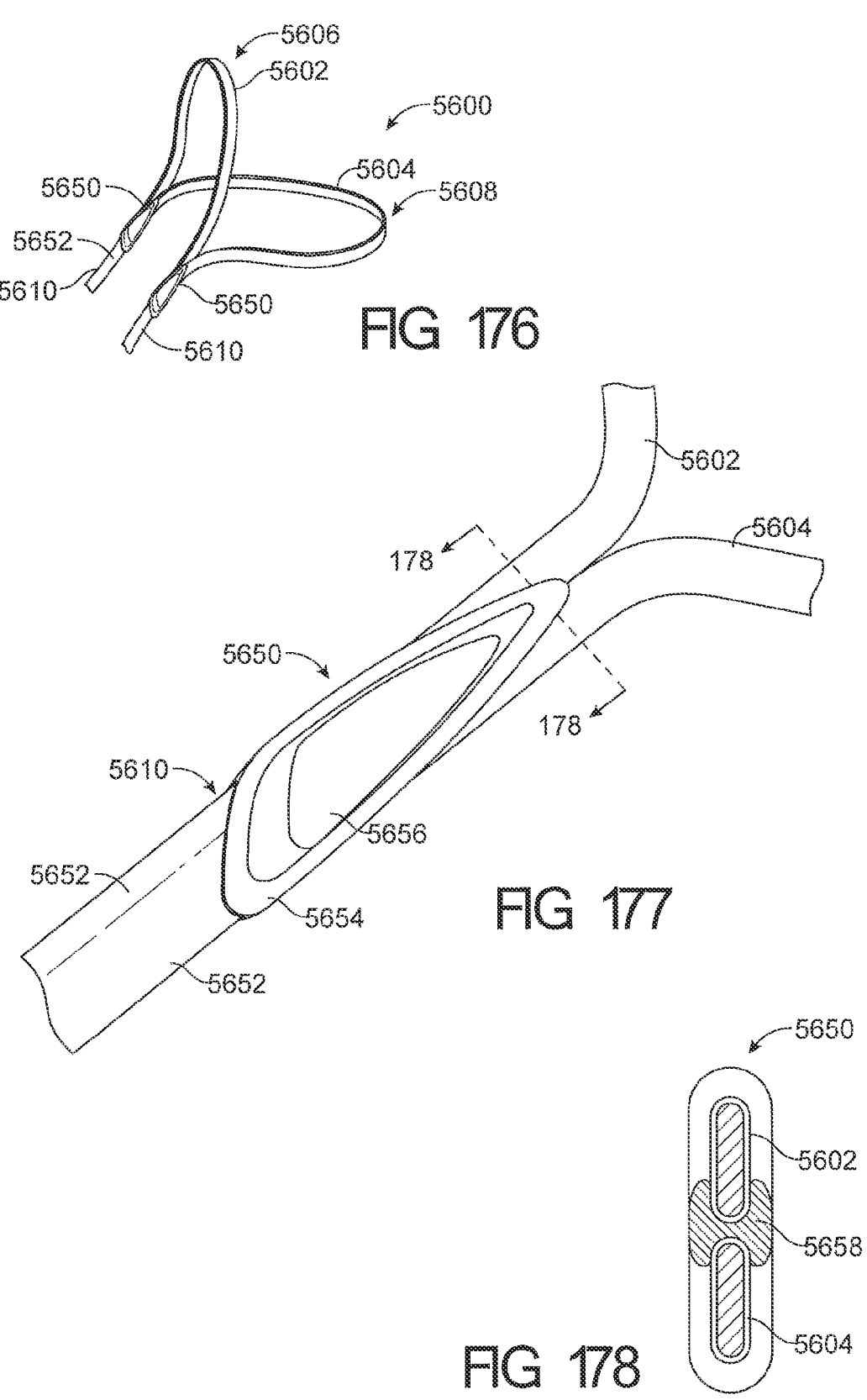

FIG. 176 is a perspective view of a headgear having at least a first strap and a second strap.

FIG. 177 is an enlarged view of the headgear of FIG. 176 including a coupling arrangement that couples at least the first strap and the second strap.

FIG. 178 is a sectional view of a portion of the headgear of FIG. 176 taken through the coupling arrangement of FIG. 177.

Figures 179, 180, 181:
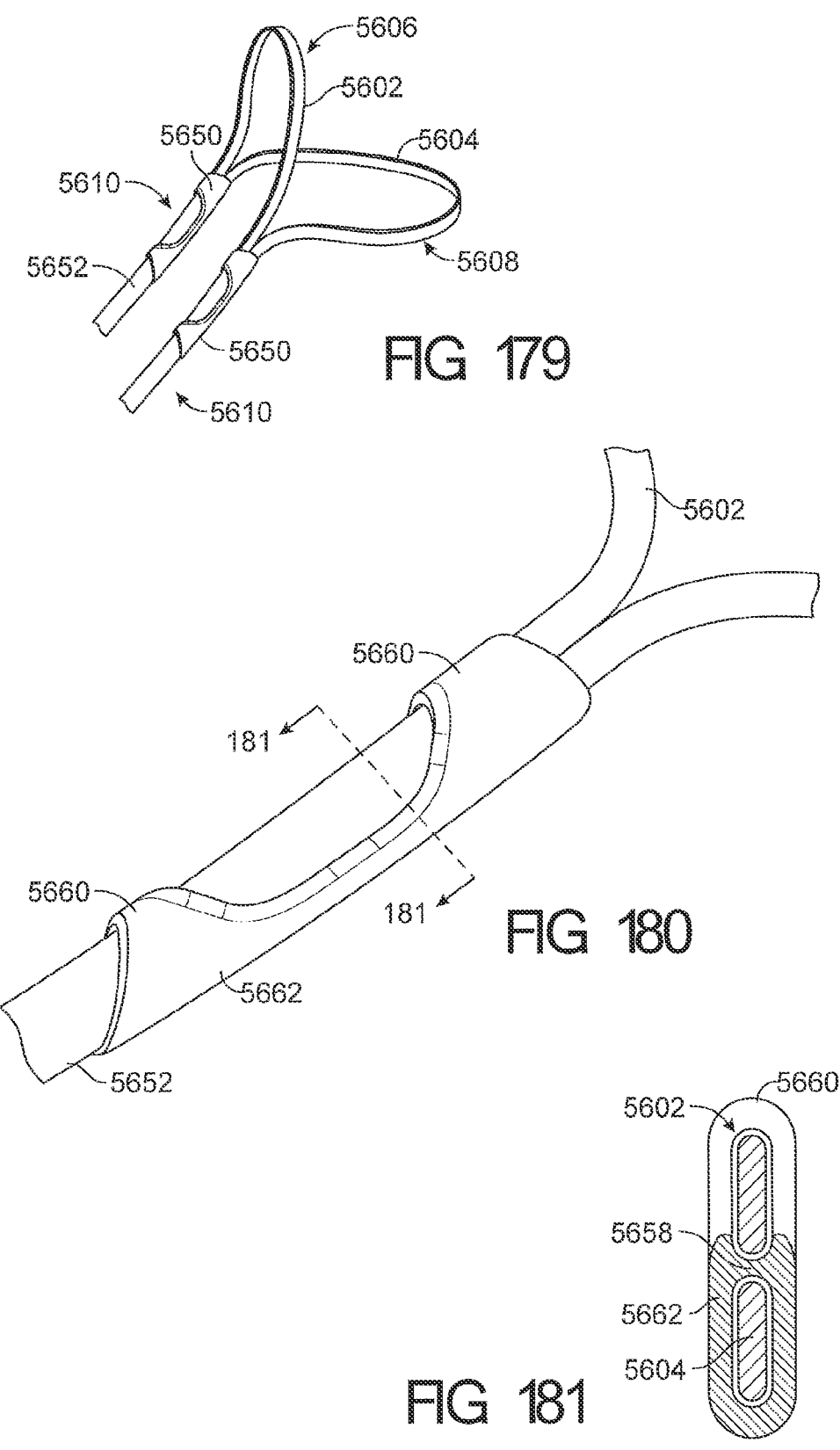

FIG. 179 is a perspective view of a headgear having at least a first strap and a second strap.

FIG. 180 is an enlarged view of the headgear of FIG. 179 including a coupling arrangement that couples at least the first strap and the second strap.

FIG. 181 is a sectional view of a portion of the headgear of FIG. 179 taken through the coupling arrangement of FIG. 180.

Figure 182:
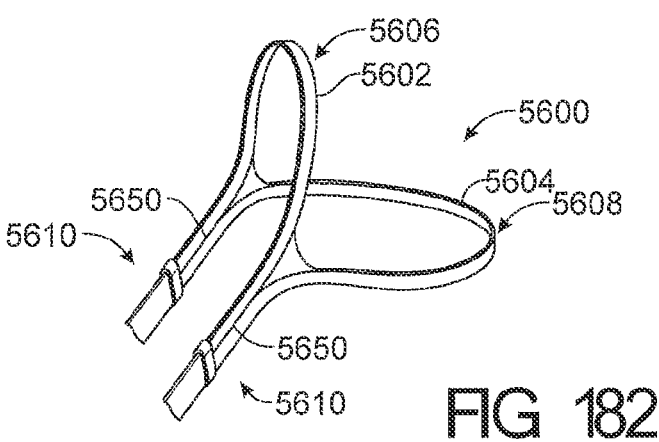

FIG. 182 is a perspective view of a headgear having at least a first strap and a second strap.

Figure 183:
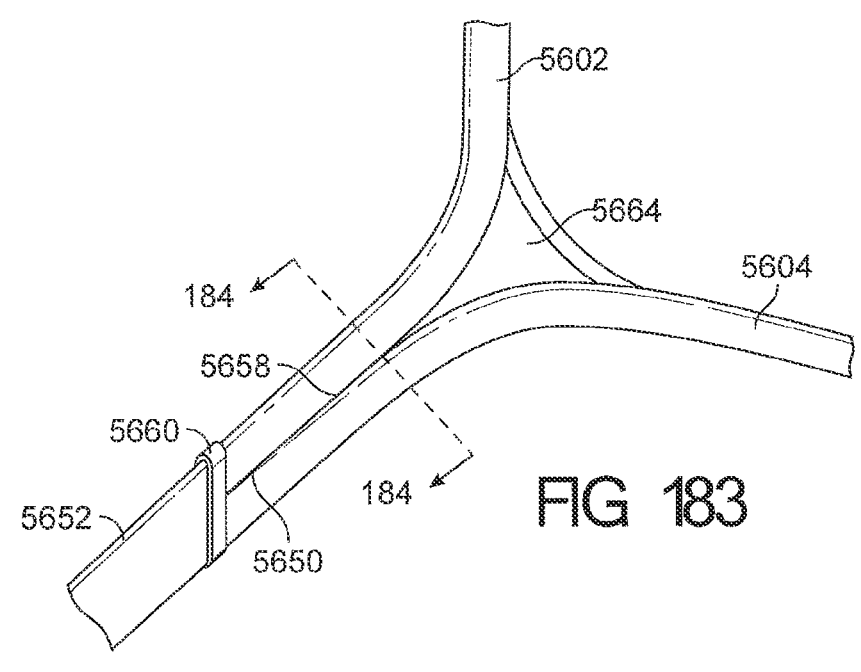

FIG. 183 is an enlarged view of the headgear of FIG. 182 including a coupling arrangement that couples at least the first strap and the second strap.

FIG. 187 is a sectional view of a portion of the headgear of FIG. 182 taken through the coupling arrangement of FIG. 183.

FIG. 185 is a perspective view of a headgear having at least a first strap and a second strap.

FIG. 186 is an enlarged view of the headgear of FIG. 185 including a coupling arrangement that couples at least the first strap and the second strap.

FIG. 187 is a sectional view of a portion of the headgear of FIG. 185 taken through the coupling arrangement of FIG. 186.

FIG. 188 is a perspective view of a headgear having at least a first strap and a second strap.

FIG. 189 is an enlarged view of the headgear of FIG. 188 including a coupling arrangement that couples at least the first strap and the second strap.

FIG. 190 is a sectional view of a portion of the headgear of FIG. 188 taken through the coupling arrangement of FIG. 189.

FIG. 191 is a perspective view of a headgear having at least a first strap and a second strap.

FIG. 192 is an enlarged view of the headgear of FIG. 191 including a coupling arrangement that couples at least the first strap and the second strap.

FIG. 193 is a sectional view of a portion of the headgear of FIG. 191 taken through the coupling arrangement of FIG. 192.

FIG. 194 is a sectional view of a headgear strap having a core and an outer layer with one or more air gaps or voids between the outer layer and the core.

FIG. 195 is a sectional view of a headgear strap having a core and an outer layer with one or more conduits between the outer layer and the core.

FIG. 196 is a sectional view of another headgear strap having a core and an outer layer with one or more conduits between the outer layer and the core.

FIG. 197 is a sectional view of a headgear strap having a core and an outer layer with one or more conduits at least partially surrounded by the core.

Figure 198:
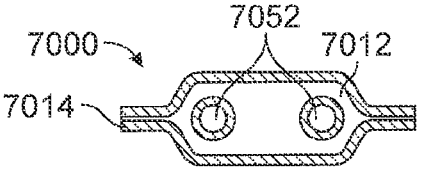

FIG. 198 is a sectional view of another headgear strap having a core and an outer layer with one or more conduits at least partially surrounded by the core.

Figure 199:
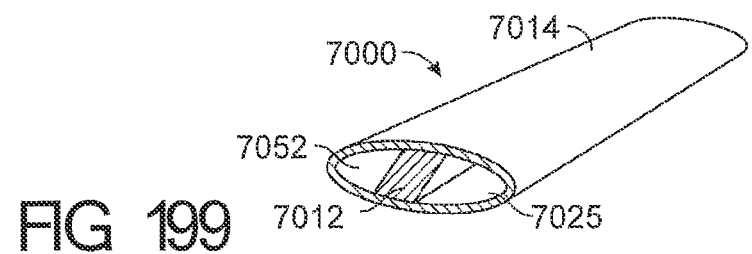

FIG. 199 a sectional view of a headgear strap having a core and an outer layer with a pair of conduits defined by the core.

Figure 200:
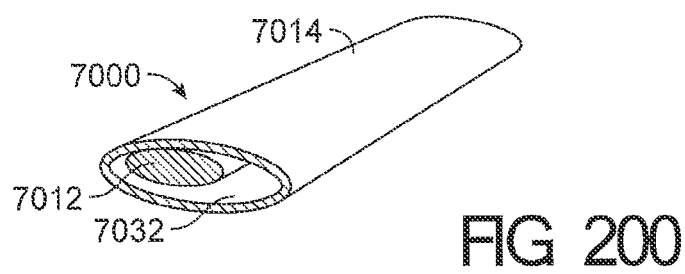

FIG. 200 is a sectional view of a headgear strap having a core and an outer layer with an air gap between the outer layer and the core.

Figure 201A:
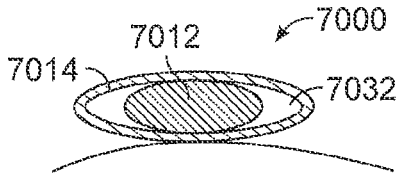

FIG. 201A is a sectional view of the headgear strap of FIG. 200 in a first position against a surface.

Figure 201B:
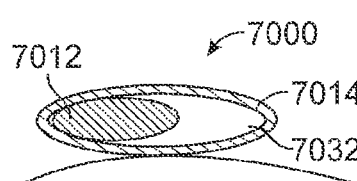

FIG. 201B is a sectional view of the headgear strap of FIG. 200 in a second position against the surface.

Figure 202:
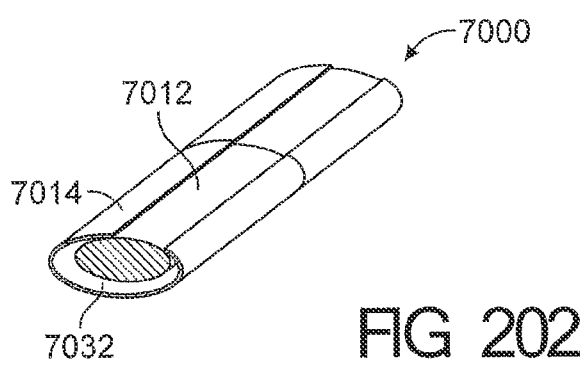

FIG. 202 is a sectional view of a headgear strap having a core and an outer layer with an air gap between the outer layer and the core, wherein a portion of the core is externally exposed.

Figure 203:
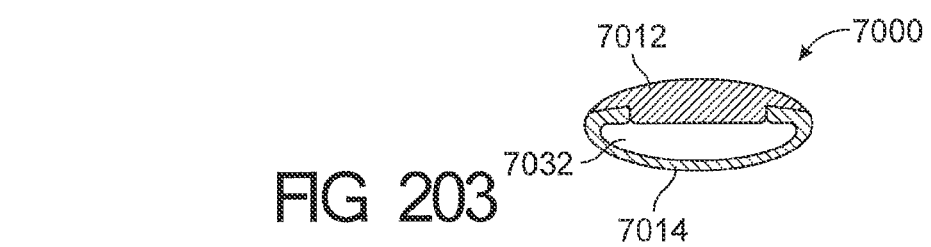

FIG. 203 is a sectional view of another headgear strap having a core and an outer layer with an air gap between the outer layer and the core, wherein a portion of the core is externally exposed.

Figure 204:
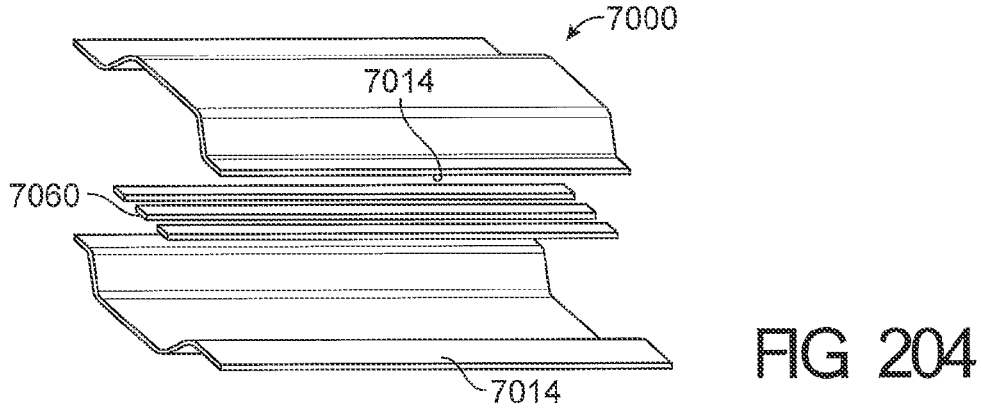

FIG. 204 is an exploded view of an outer layer and reinforcement members of a headgear strap.

Figure 205:
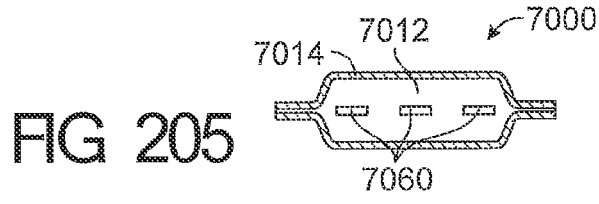

FIG. 205 is a sectional view of a headgear strap incorporating the outer layer and reinforcement members of FIG. 204.

Figures 206, 207, 208, 209, 210, 211:
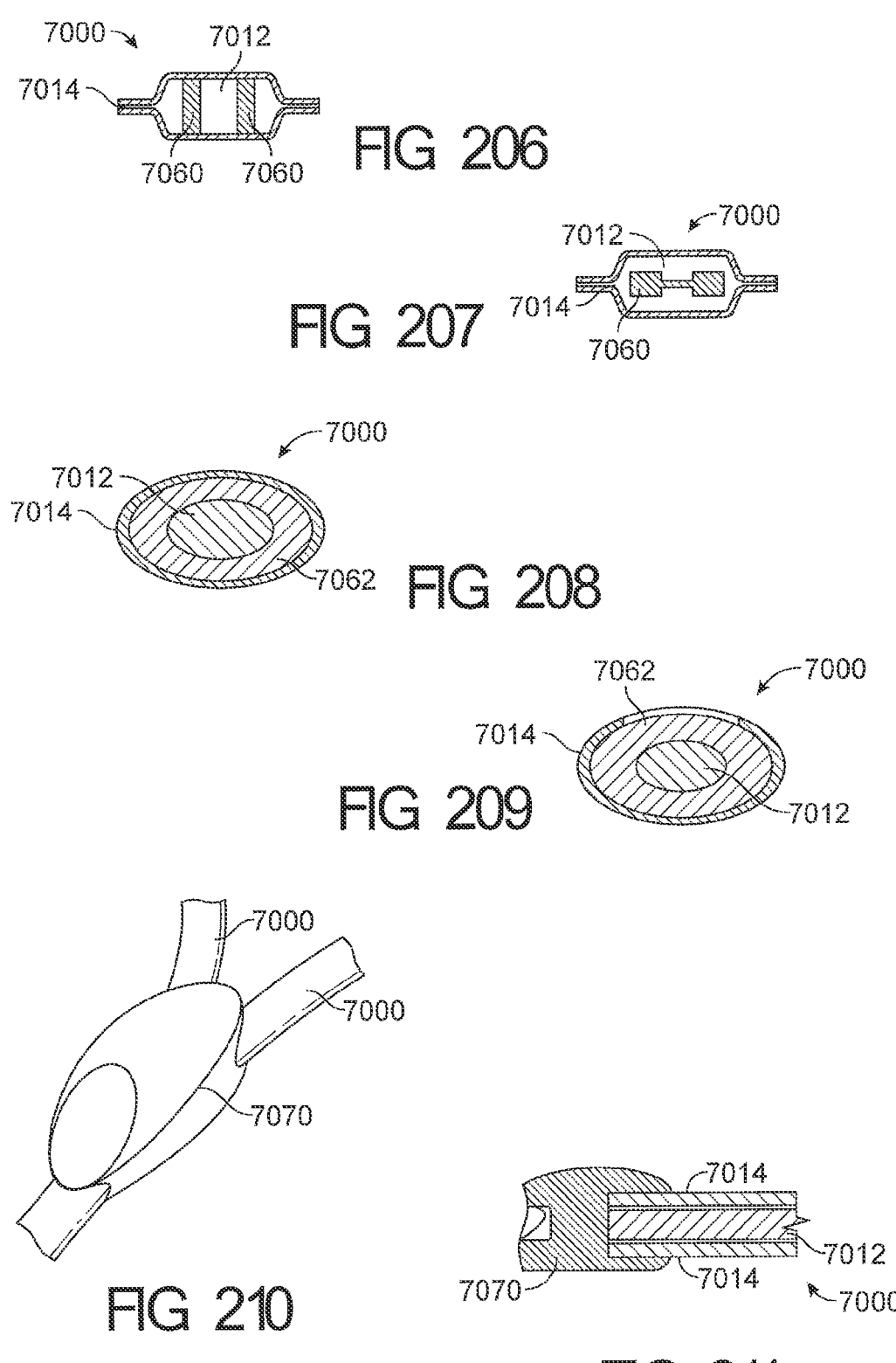

FIG. 206 is a sectional view of a headgear strap having a core, a first outer layer, a second outer layer and one or more reinforcement or separating members that separate the outer layers prior to the introduction of the core material.

FIG. 207 is a sectional view of a headgear strap having a core, a first outer layer, a second outer layer and a reinforcement member encapsulated in the core.

FIG. 208 is a sectional view of a headgear strap having a core, a cushioning layer and an outer layer.

FIG. 209 is a sectional view of another headgear strap having a core, a cushioning layer and an outer layer, wherein a portion of the cushioning layer is externally exposed.

FIG. 210 is a side view of a portion of a headgear having several straps and a connector that connects two or more of the straps.

FIG. 211 is a sectional view of the connector and one of the straps of FIG. 210.

FIG. 212 is a sectional view of a headgear strap having a core and a single piece, seamless outer layer.

FIG. 213 is a sectional view of a headgear strap having a core and a single piece outer layer having a seam, with edges of the outer layer embedded within the core.

FIG. 214 is a sectional view of another headgear strap having a core and a single piece outer layer having a seam, with edges of the outer layer embedded within the core.

FIG. 215 is a sectional view of a headgear strap having a core and a two piece outer layer having a pair of seams, with edges of the outer layer pieces embedded within the core.

FIG. 216A is a sectional view of a two piece outer layer without the core and FIG. 216B is a sectional view of the two piece outer layer after the core has been formed.

Figures 217, 218:
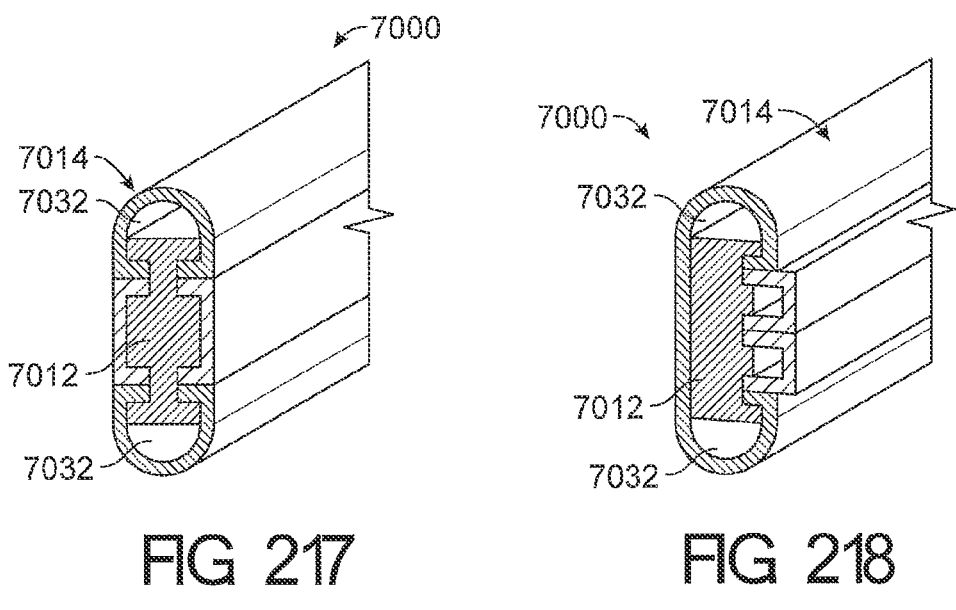

FIG. 217 is a sectional view of a headgear strap having a core and a four piece outer layer having four seams, with edges of the outer layer pieces embedded within the core.

FIG. 218 is a sectional view of another headgear strap having a core and a three piece outer layer having three seams, with edges of the outer layer pieces embedded within the core.

Figure 219:
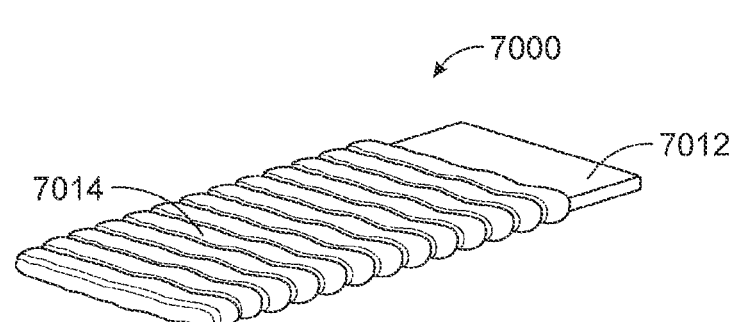

FIG. 219 is a perspective view of a headgear strap having a core and a textured outer layer, with a portion of the outer layer cut away to expose the core.

Figure 220:
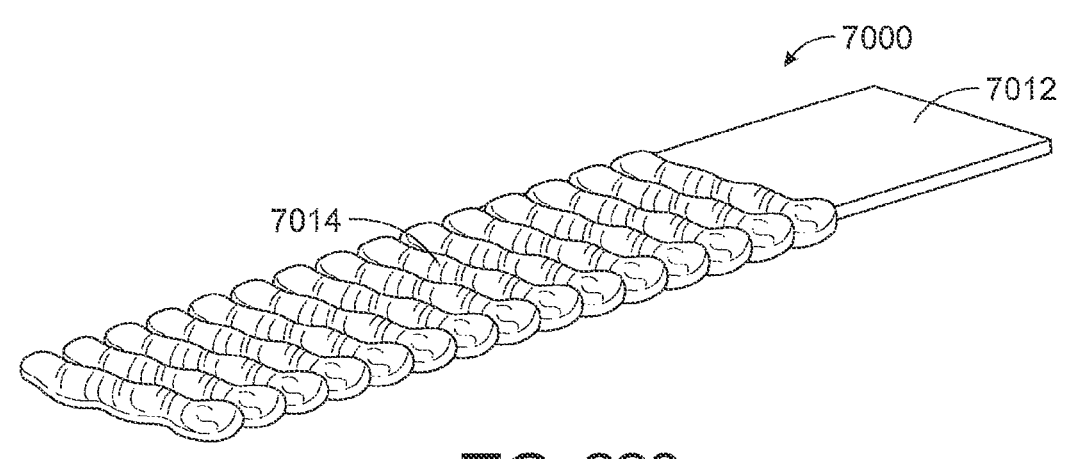

FIG. 220 is a perspective view of a headgear strap having a core and a quilted outer layer, with a portion of the outer layer cut away to expose the core.

Figures 221, 222, 223, 224:
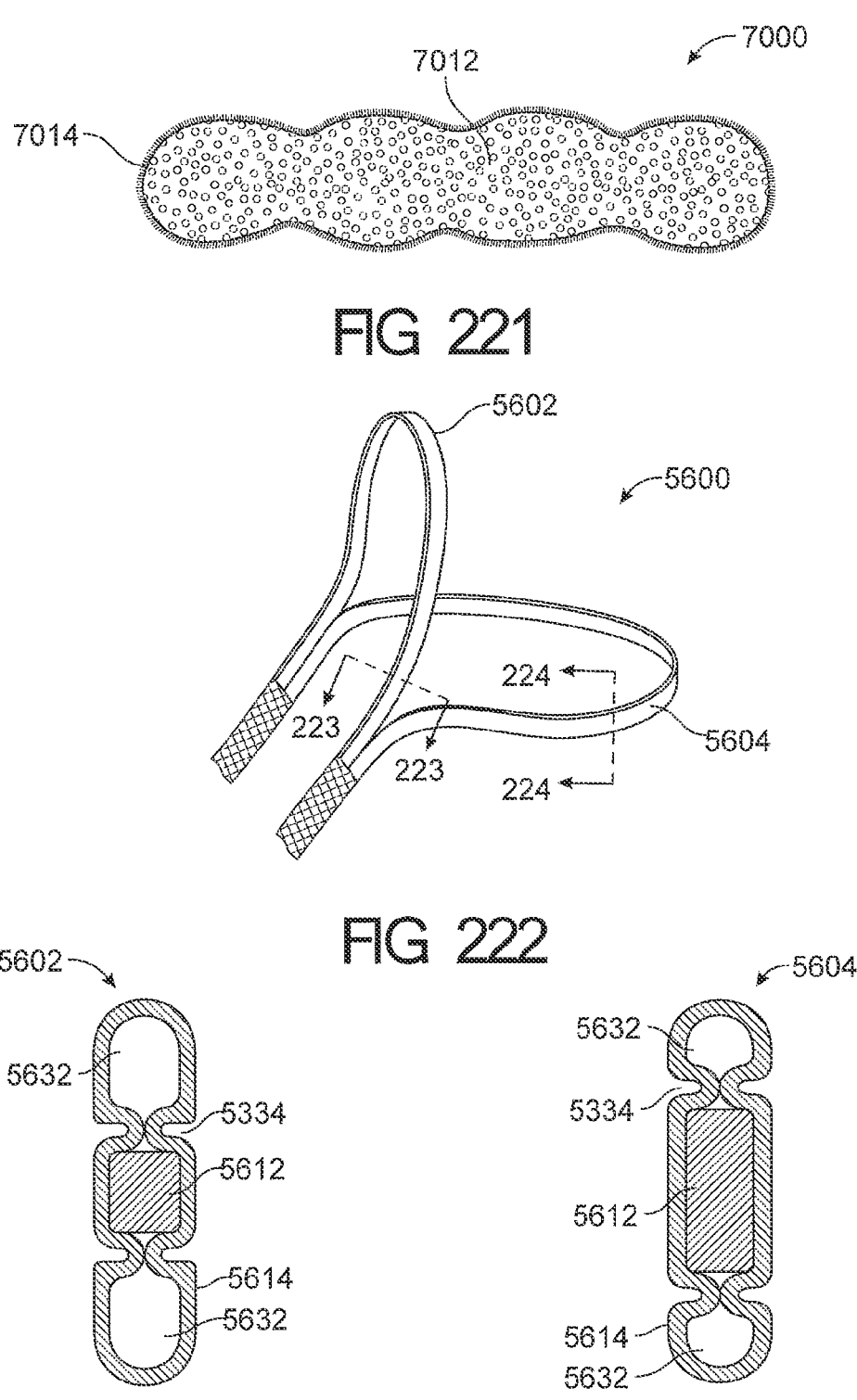

FIG. 221 is a sectional view of a headgear layer having a core and an outer layer, wherein the core imparts a textured shape to the outer layer.

FIG. 222 is a perspective view of a headgear having a first strap and a second strap.

FIG. 223 is a sectional view of the first strap of the headgear of Figure FIG. 224 is a sectional view of the second strap of the headgear of FIG. 222.

222.

Figure 225:
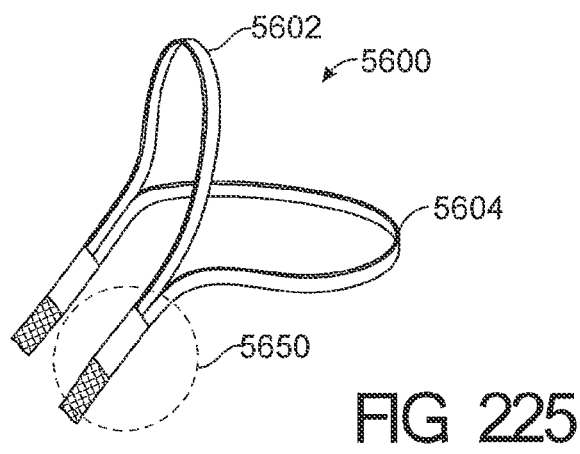

FIG. 225 is a perspective view of a headgear having a first strap, a second strap and a connection between the first strap and the second strap.

Figure 226:
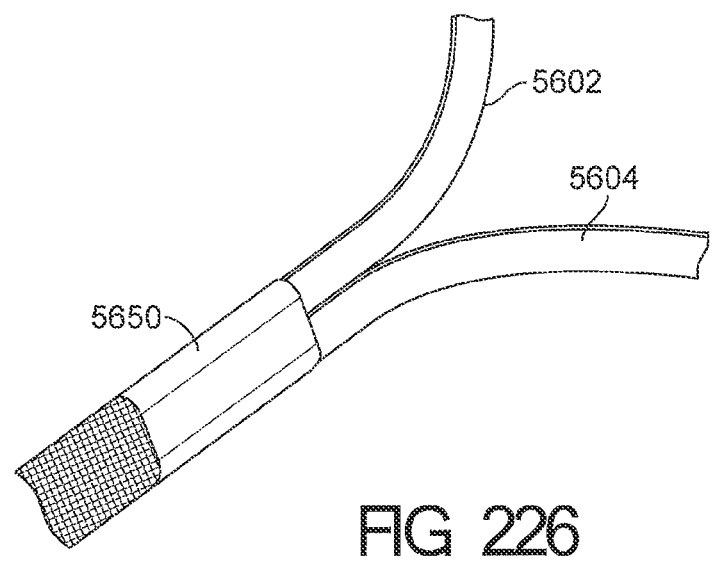

FIG. 226 is an enlarged view of a portion of the headgear of FIG. 225 including the connection.

Figure 227:
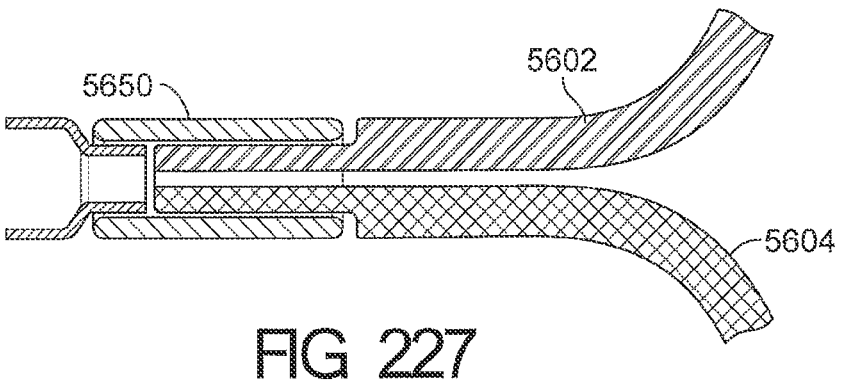

FIG. 227 is a sectional view of the connection of FIG. 226.

FIG. 228 is a perspective view of a headgear having a first strap, a second strap and a connection between the first strap and the second strap.

FIG. 229 is an enlarged view of the portion of the headgear of FIG. 228 including the connection.

FIG. 230 illustrated several possible sectional views of the straps within the connection.

FIG. 231 is a sectional view of the second strap of the headgear of FIG. 228.

Figure 232A:
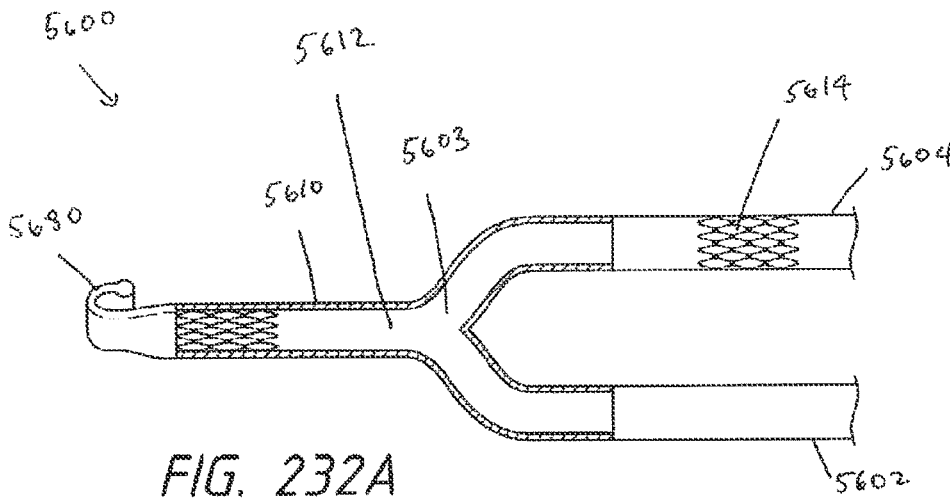

FIG. 232A is a top-down view of a front strap and bifurcated straps of an intra-moulded bifurcated headgear.

Figure 232B:
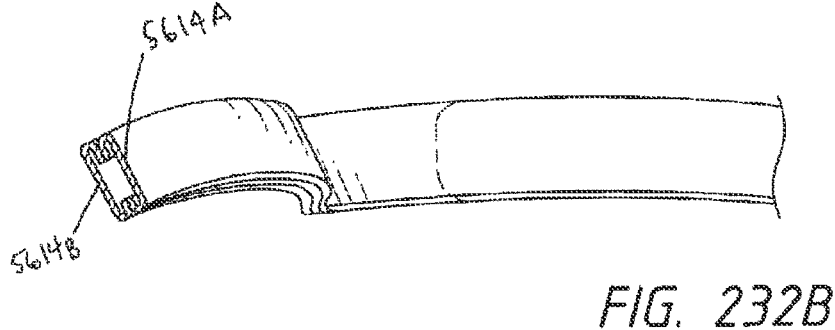

FIG. 232B is a perspective view of first and second cover layers joined together to form a strap of the intra-moulded bifurcated headgear of FIG. 232A.

Figure 232C:
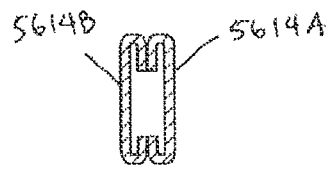

FIG. 232C is a cross-sectional view of first and second cover layers joined together to form a strap of the intra-moulded bifurcated headgear of FIG. 232A.

Figure 233:
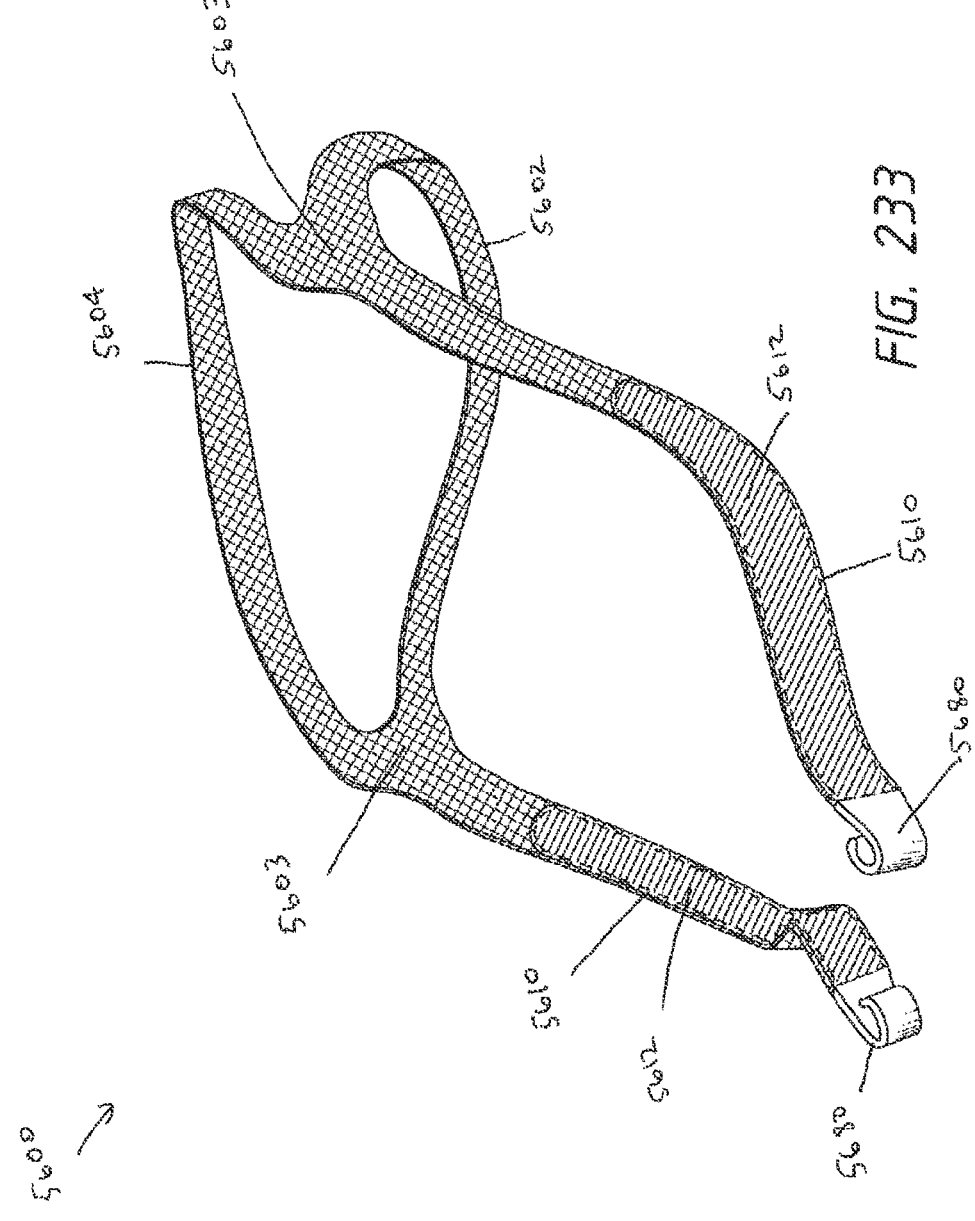

FIG. 233 is a perspective view of the intra-moulded bifurcated headgear of FIG. 232A having front straps that are partially rigid.

Figure 234:
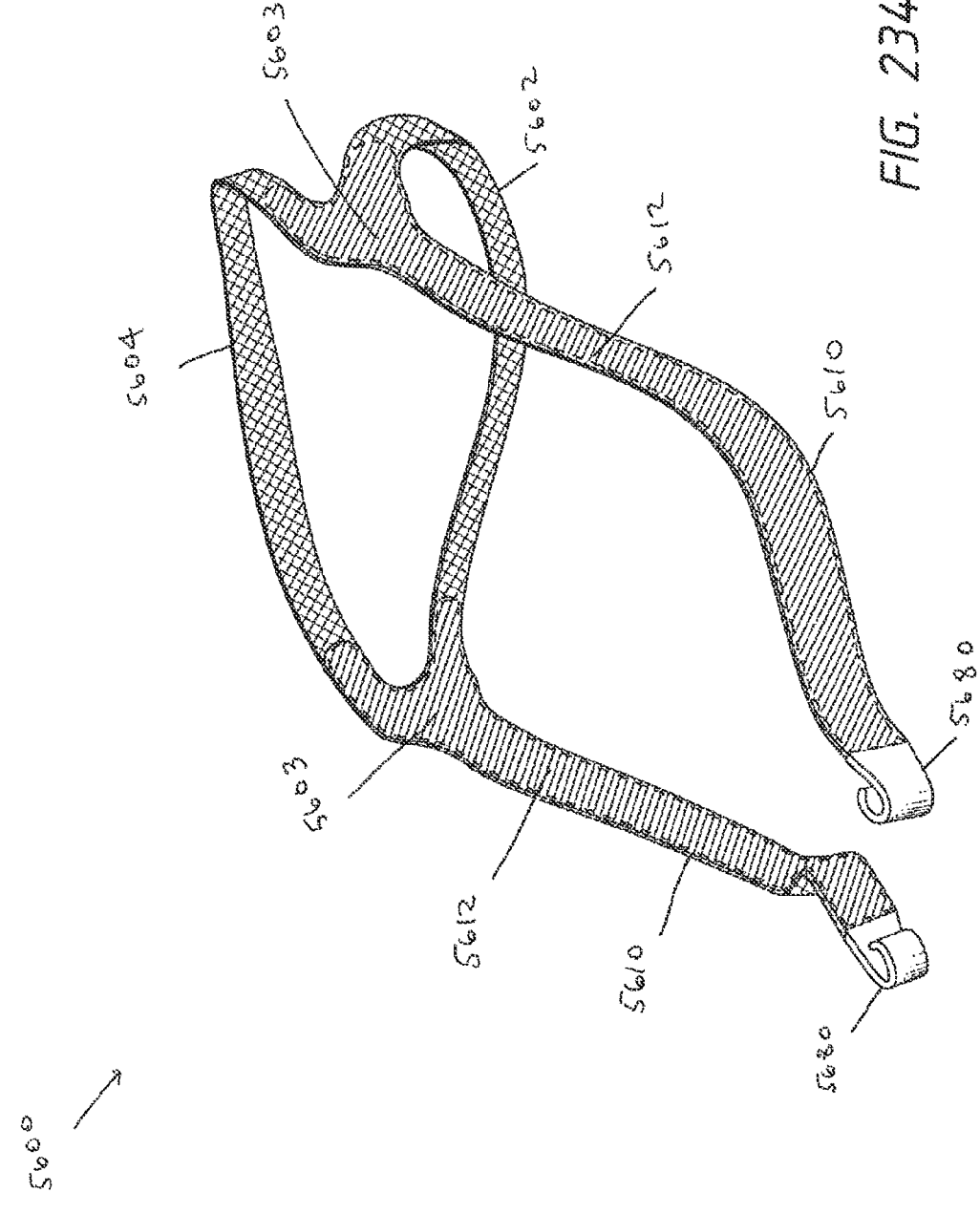

FIG. 234 is a perspective view of the intra-moulded bifurcated headgear of FIG. 232A having rigid front straps and partially rigid bifurcated straps.

Figure 235:
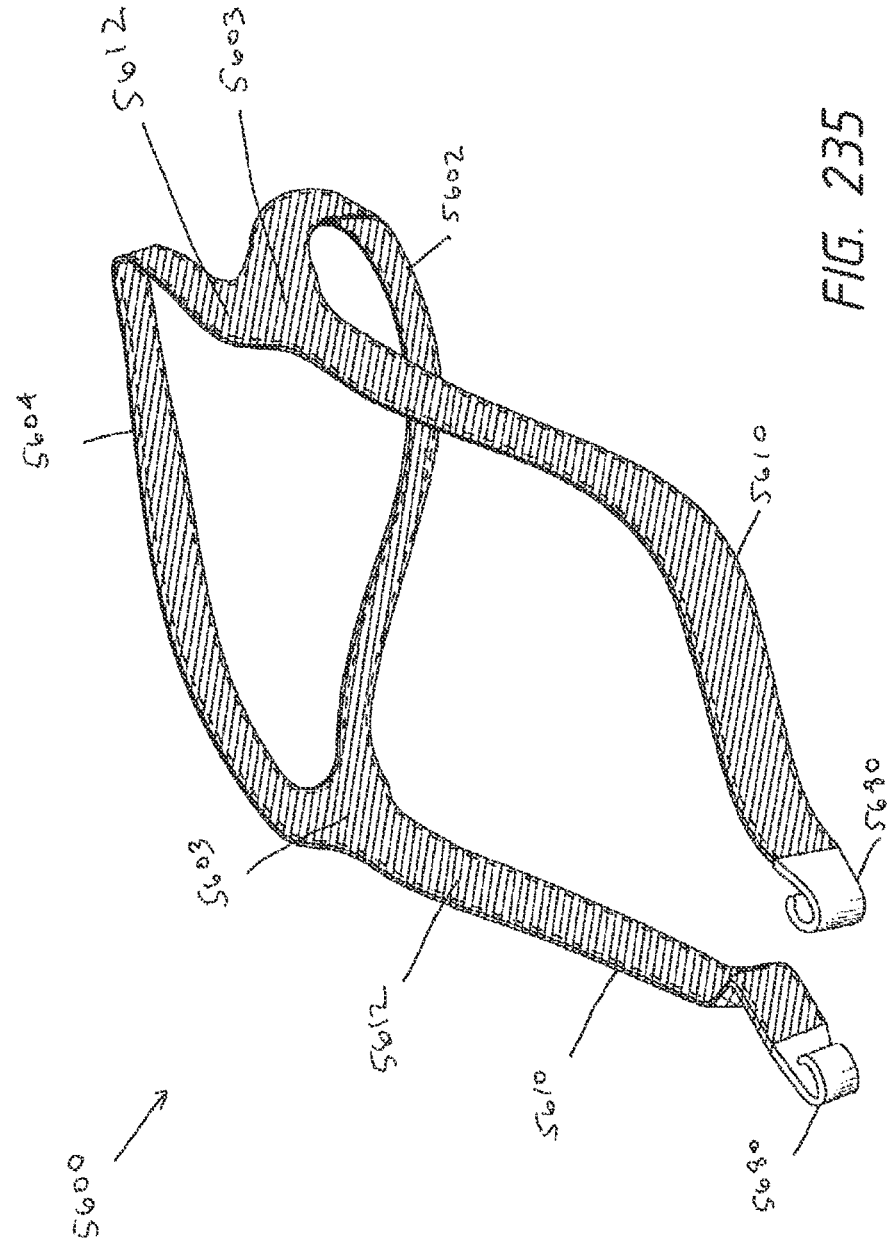

FIG. 235 is a perspective view of the intra-moulded bifurcated headgear of FIG. 232A having rigid front and bifurcated straps.

Figures 236A, 236B:
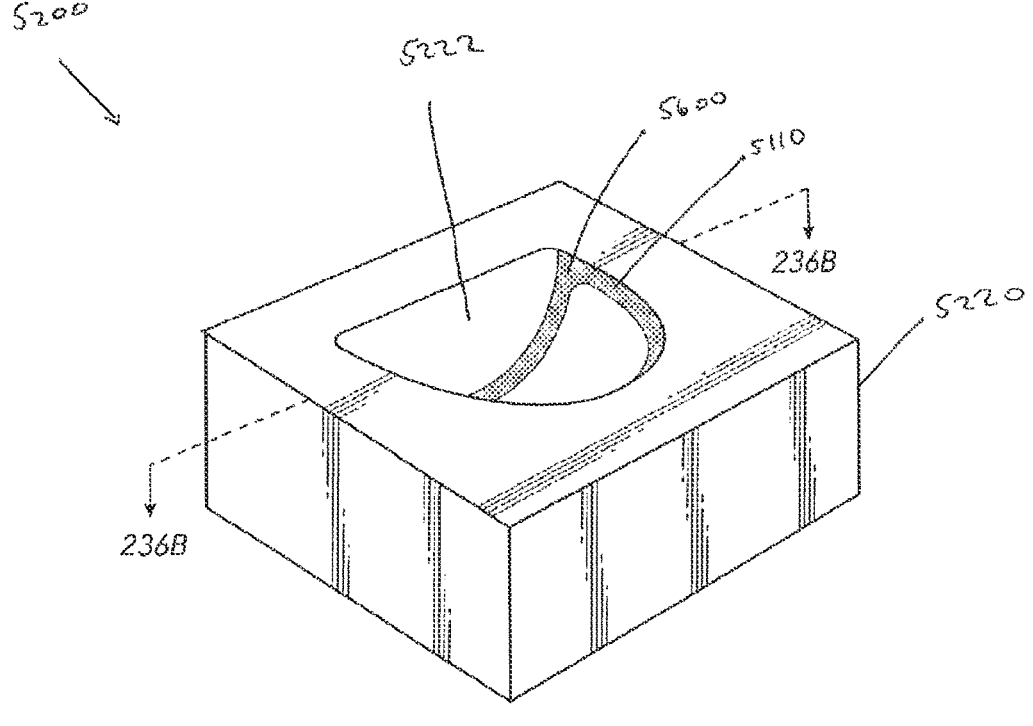

FIG. 236A is a perspective view of a mould tool configured to form the intra-moulded bifurcated headgear configuration of FIGS. 232A to 235.

FIG. 236B is a cross-sectional view of the mould tool of FIG. 236A along a line A-A.

Figure 236C:
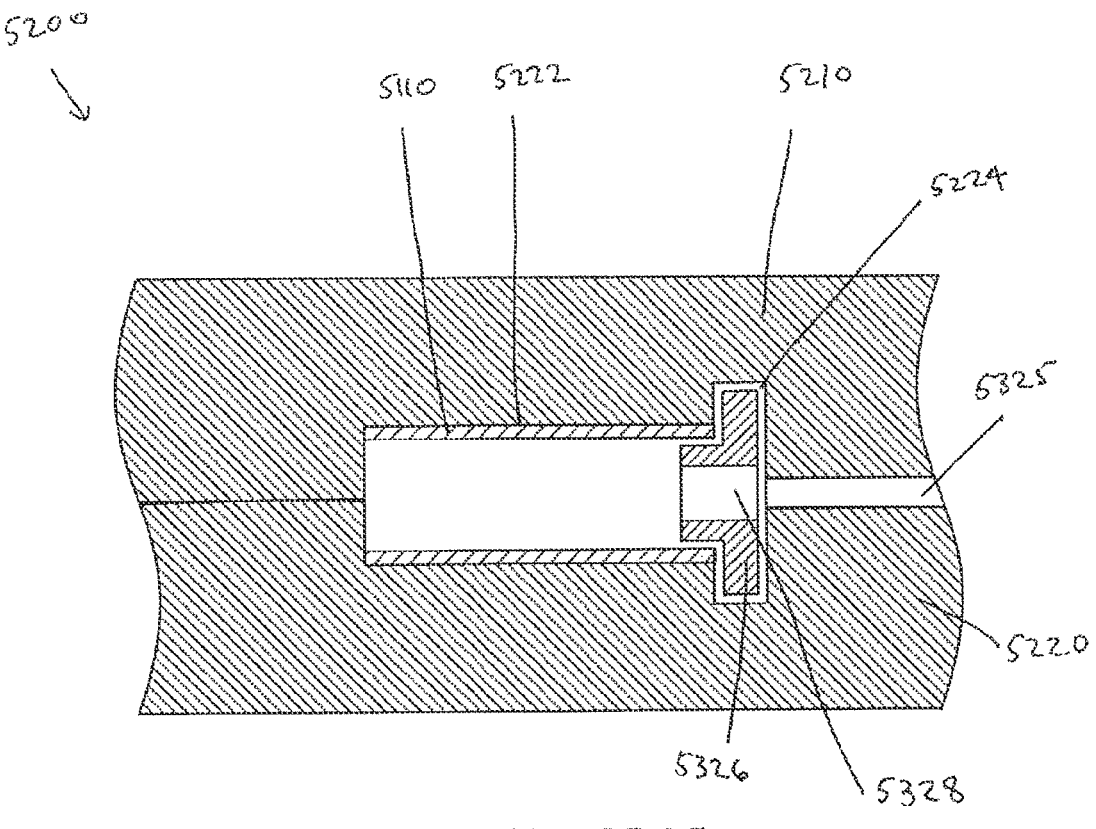

FIG. 236C is a cross-sectional view of a mould tool configured to secure in place a fabric casing within the mould tool.

Figures 236D, 236E, 236F, 236G:
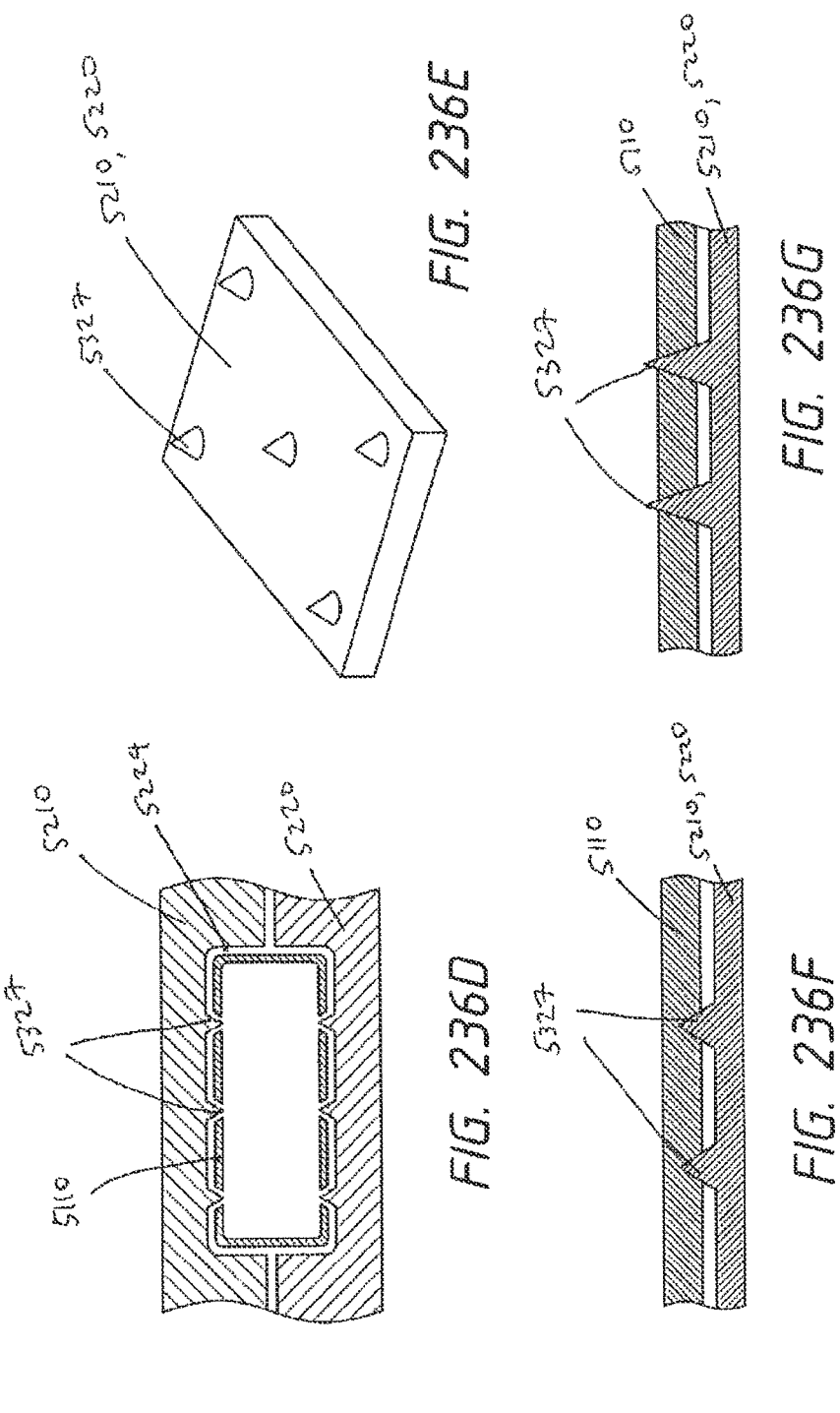

FIG. 236D is a cross-sectional view of a mould tool having retention spikes to secure in place a fabric casing within the mould tool.

FIG. 236E is a partial perspective view of the mould tool of FIG. 236D showing retention spikes to secure in place a fabric casing within the mould tool.

FIG. 236F is a cross-sectional view of the mould tool of FIG. 236D showing retention spikes piercing but not extending through the fabric casing.

FIG. 236G is a cross-sectional view of the mould tool of FIG. 236D showing retention spikes piercing through the fabric casing.

Figure 237A:
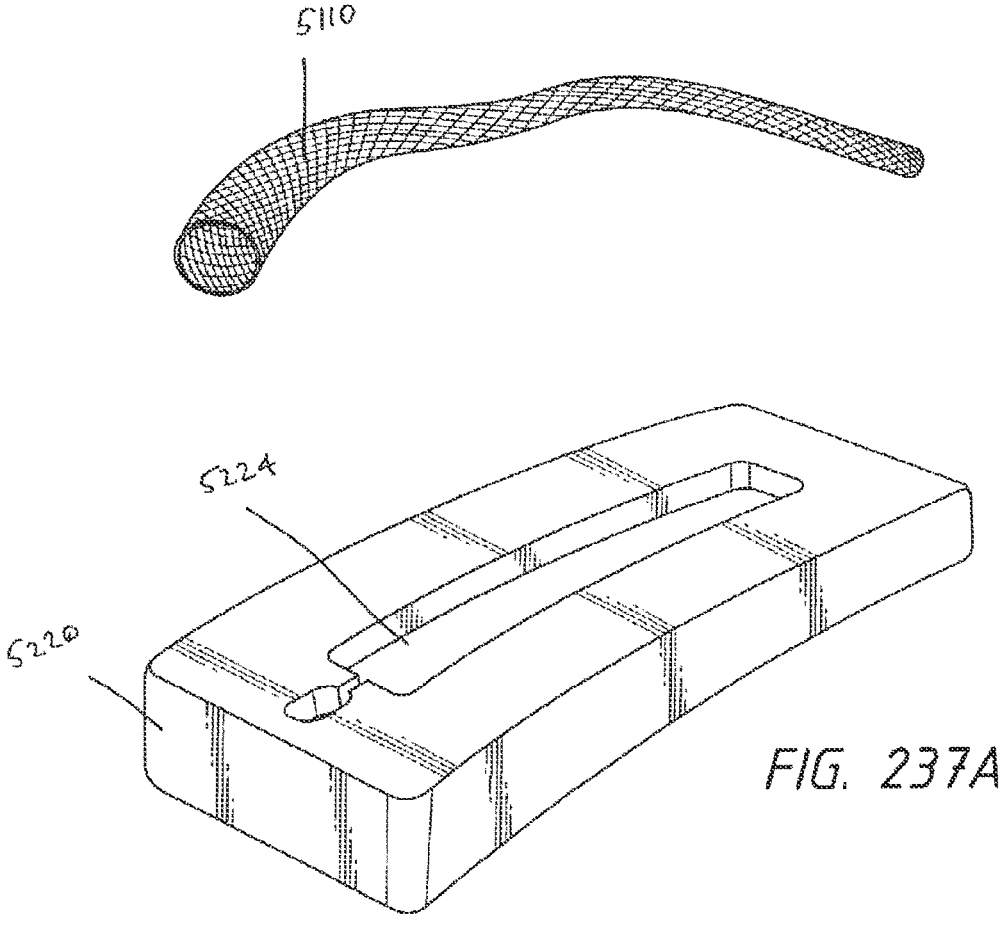

FIG. 237A is a perspective view of a mould tool for forming a headgear using a woven fabric casing.

Figure 237B:
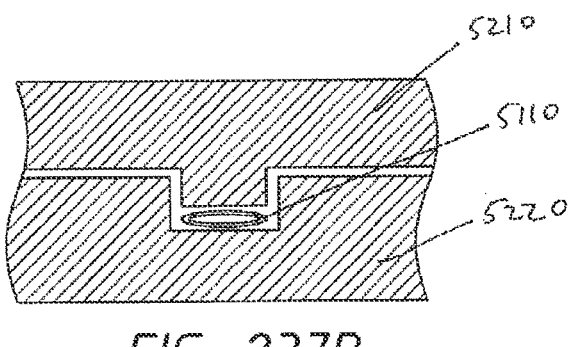

FIG. 237B is a cross-sectional view of the mould tool of FIG. 237A.

Figure 238:
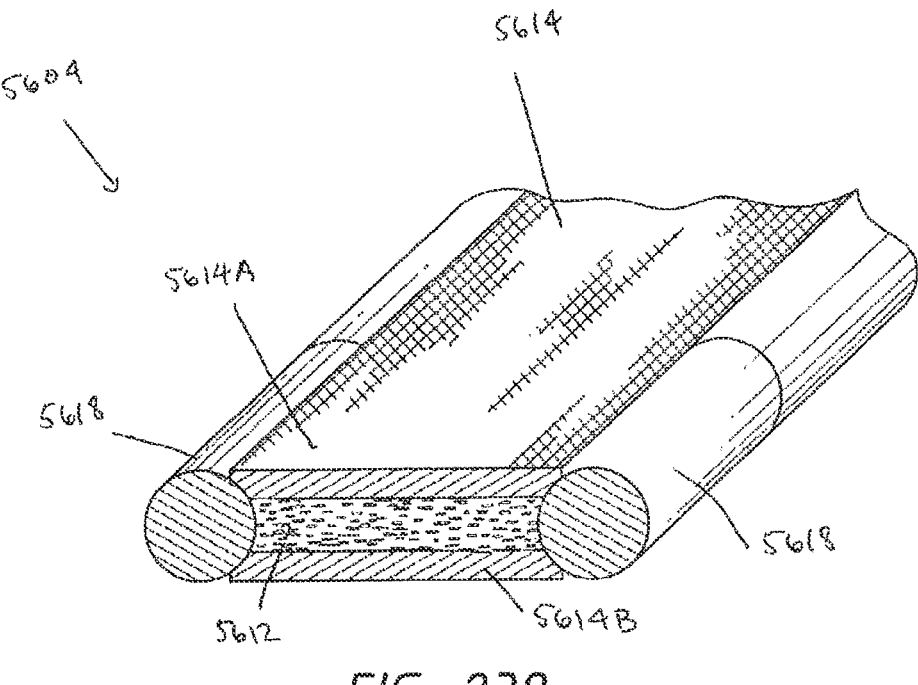

FIG. 238 is a perspective cross-sectional view of an alternative construction of an intra-moulded strap having a core, cover layers and rails.

Figures 239A, 239B, 239C:
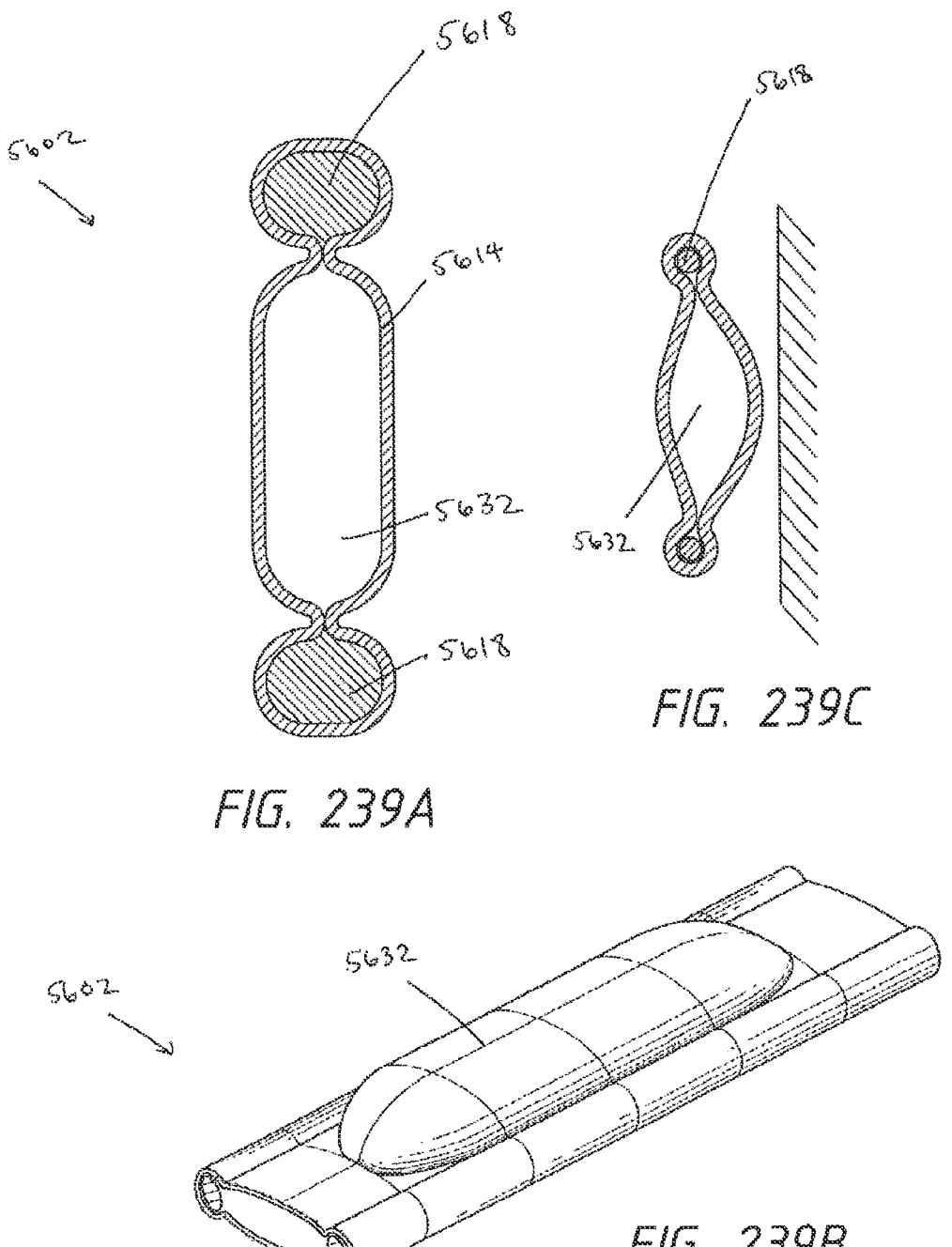

FIG. 239A is a cross-sectional view of an alternative construction of an intra-moulded strap having an airpocket core, a cover layer and intra-moulded rails.

FIG. 239B is a perspective view of the intra-moulded strap of FIG. 239A.

FIG. 239C is a cross-sectional view of the intra-moulded strap of FIG. 239A when donned by the user.

Figure 240A:
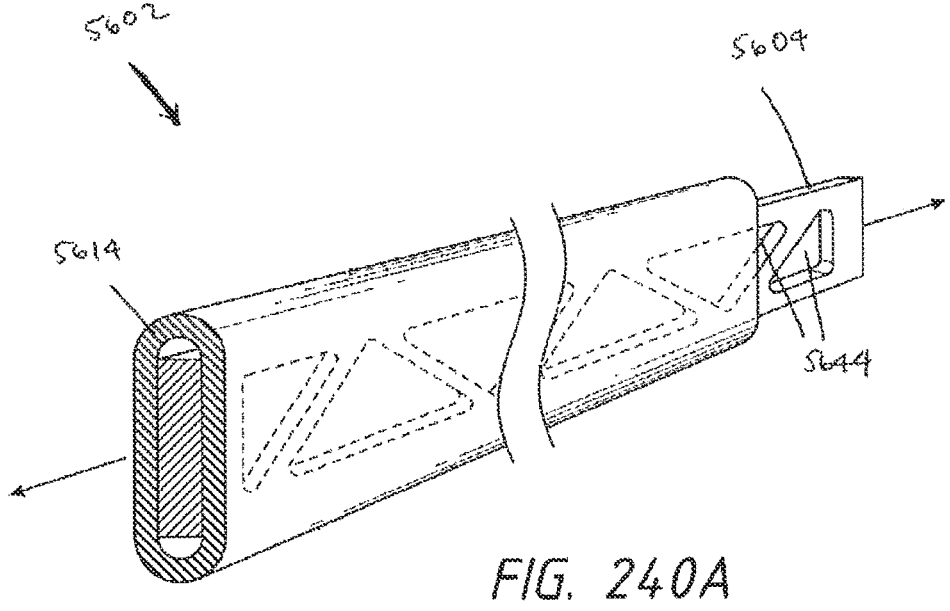

FIG. 240A is a perspective cross-sectional view of an alternative construction of an intra-moulded strap having a structured core.

Figure 240B:
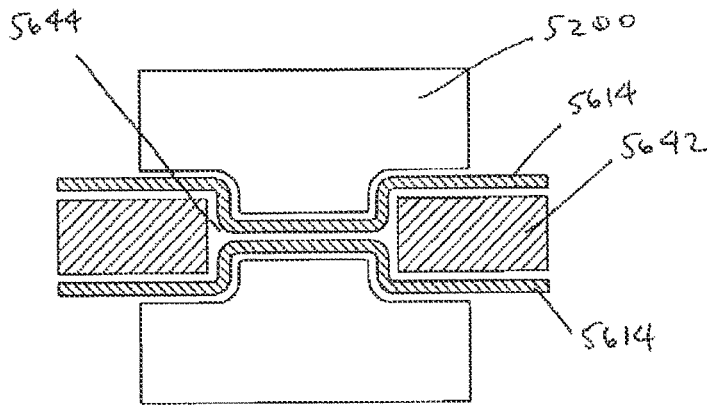

FIG. 240B is a cross-sectional view of a mould tool for constructing the structured core of the intra-moulded strap in FIG. 240A.

FIG. 241A is a perspective view of an alternative construction of an intra-moulded strap having a complex 3D shape with continuously variable geometry and cross-section along its length.

FIG. 241B is a cross-sectional view of the intra-moulded strap of FIG. 241A along a line A-A.

FIG. 241C is a cross-sectional view of the intra-moulded strap of FIG. 241A along a line B-B.

Figures 242A, 242B, 242C, 242D:
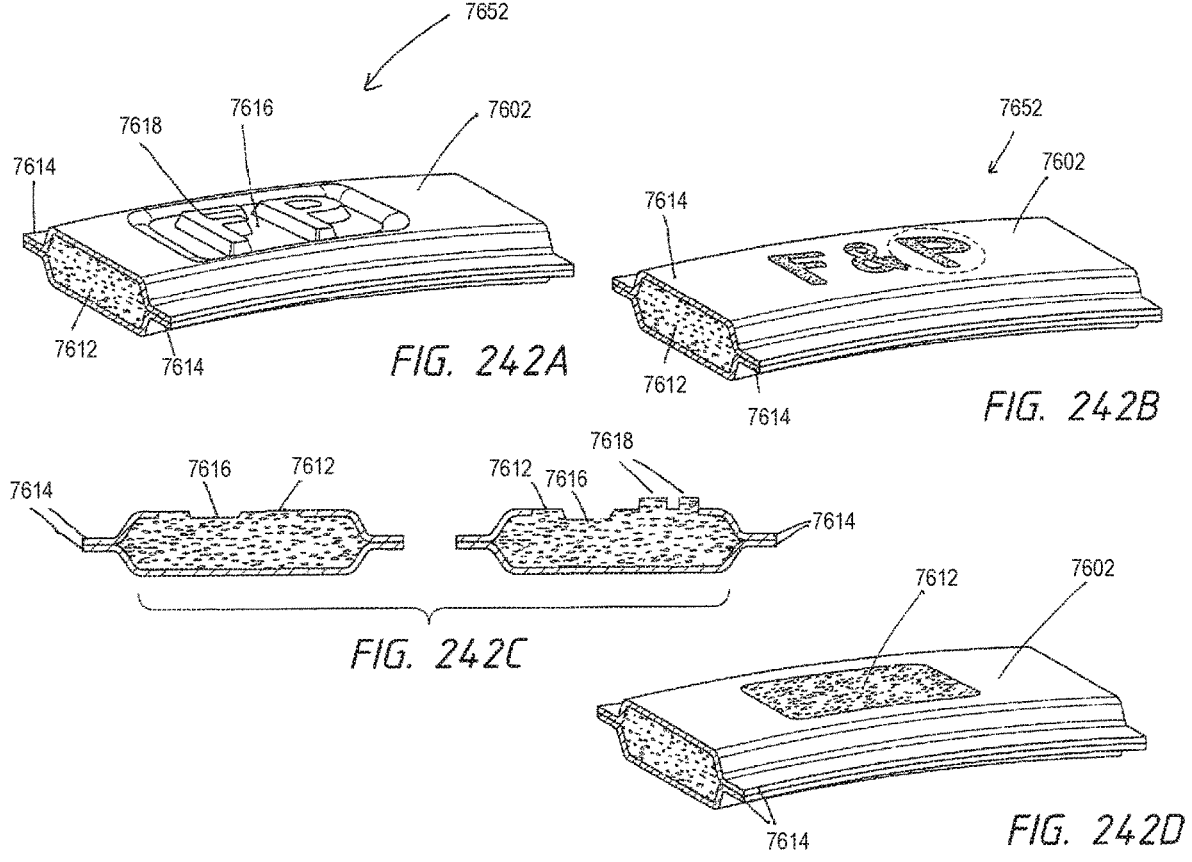

FIG. 242A is a perspective cross-sectional view of an alternative intra-moulded strap having embossed branding logos.

FIG. 242B is a perspective cross-sectional view of an alternative intra-moulded strap having laser cut branding logos.

FIG. 242C is a perspective cross-sectional view of the alternative intra-moulded strap of FIG. 242B.

FIG. 242D is a perspective cross-sectional view of an alternative intra-moulded strap having laser cut portion removed to expose core material.

Figure 242E:
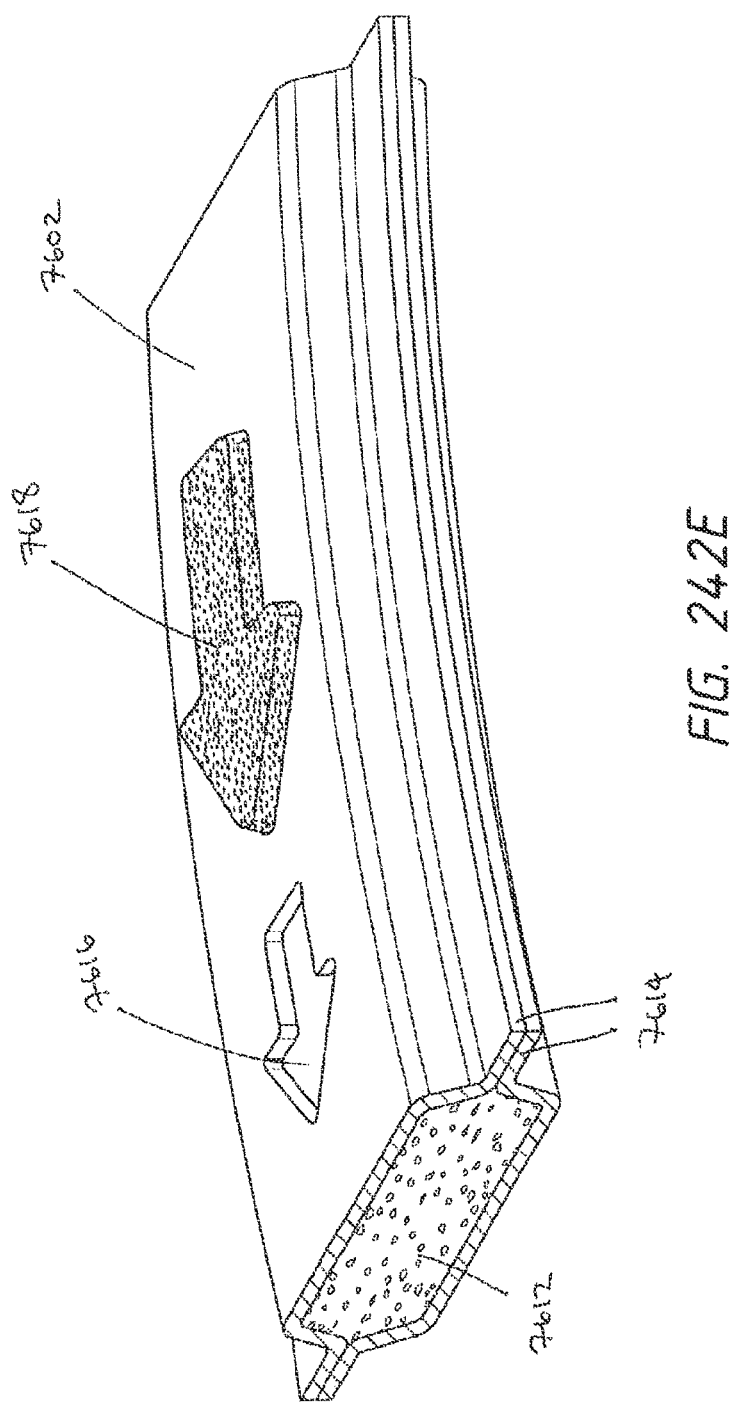

FIG. 242E is a perspective cross-sectional view of an alternative intra-moulded strap having an embossed indicator and a protruding indicator formed from protruding exposed core material.

Figures 242F, 242G:
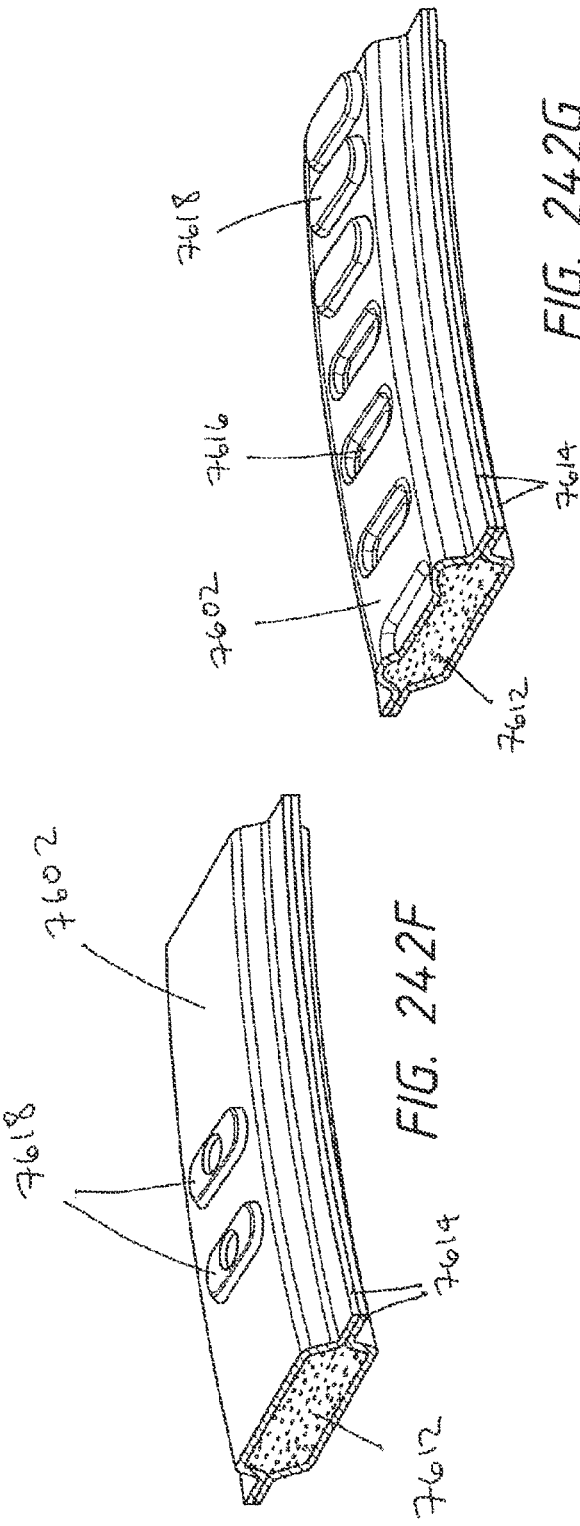

FIG. 242F is a perspective cross-sectional view of an alternative intra-moulded strap having protruding grip bumps with embossed features.

FIG. 242G is a perspective cross-sectional view of an alternative intra-moulded strap having embossed and protruding grip bumps.

Figures 243A, 243B, 243C:
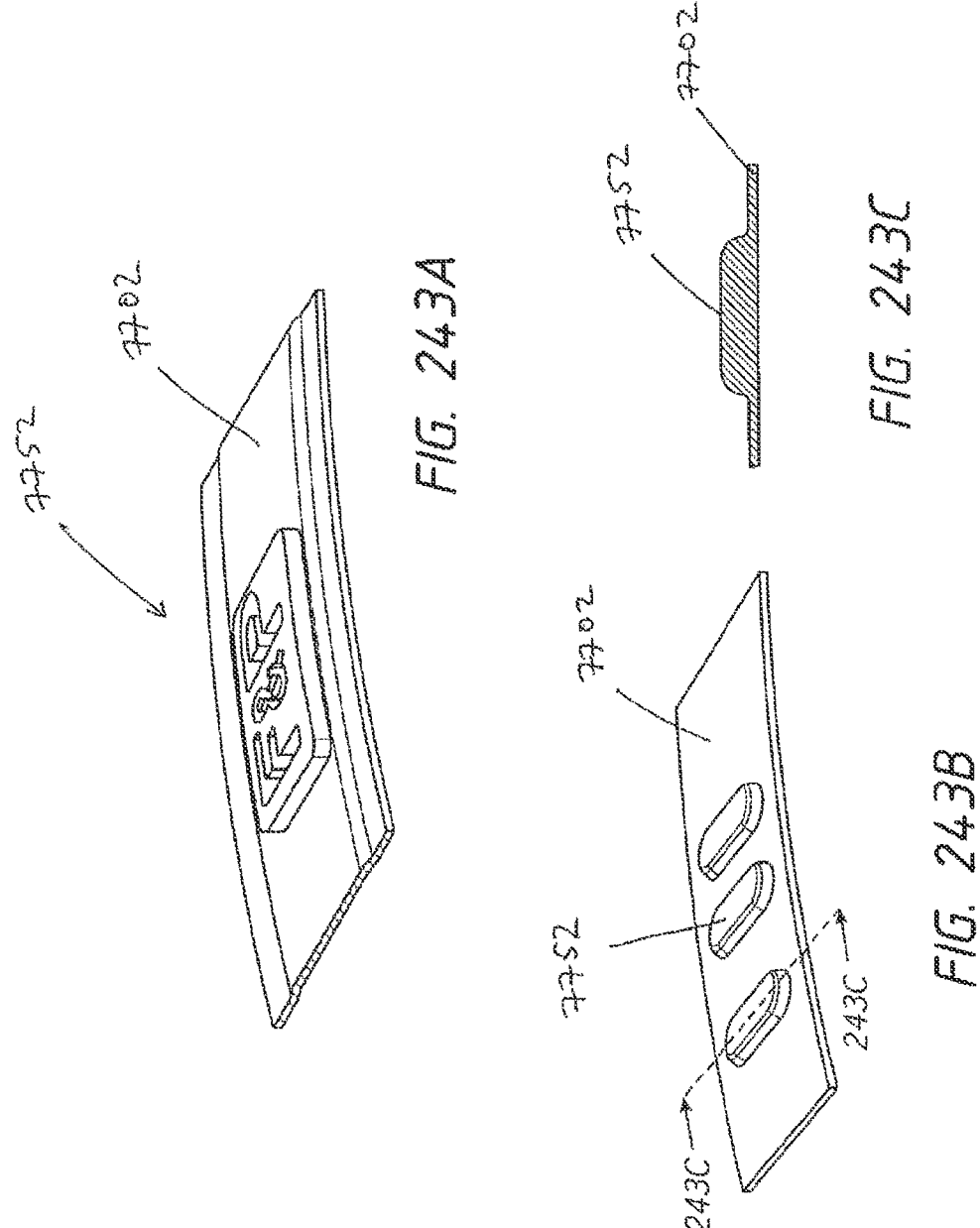

FIG. 243A is a perspective cross-sectional view of an alternative intra-moulded strap having over-moulded branding logos.

FIG. 243B is a perspective cross-sectional view of an alternative intra-moulded strap having over-moulded grip bumps.

FIG. 243C is a cross-sectional view of the alternative intra-moulded strap having over-moulded grip bumps of FIG. 243B along a line A-A.

Figures 244A, 244B:
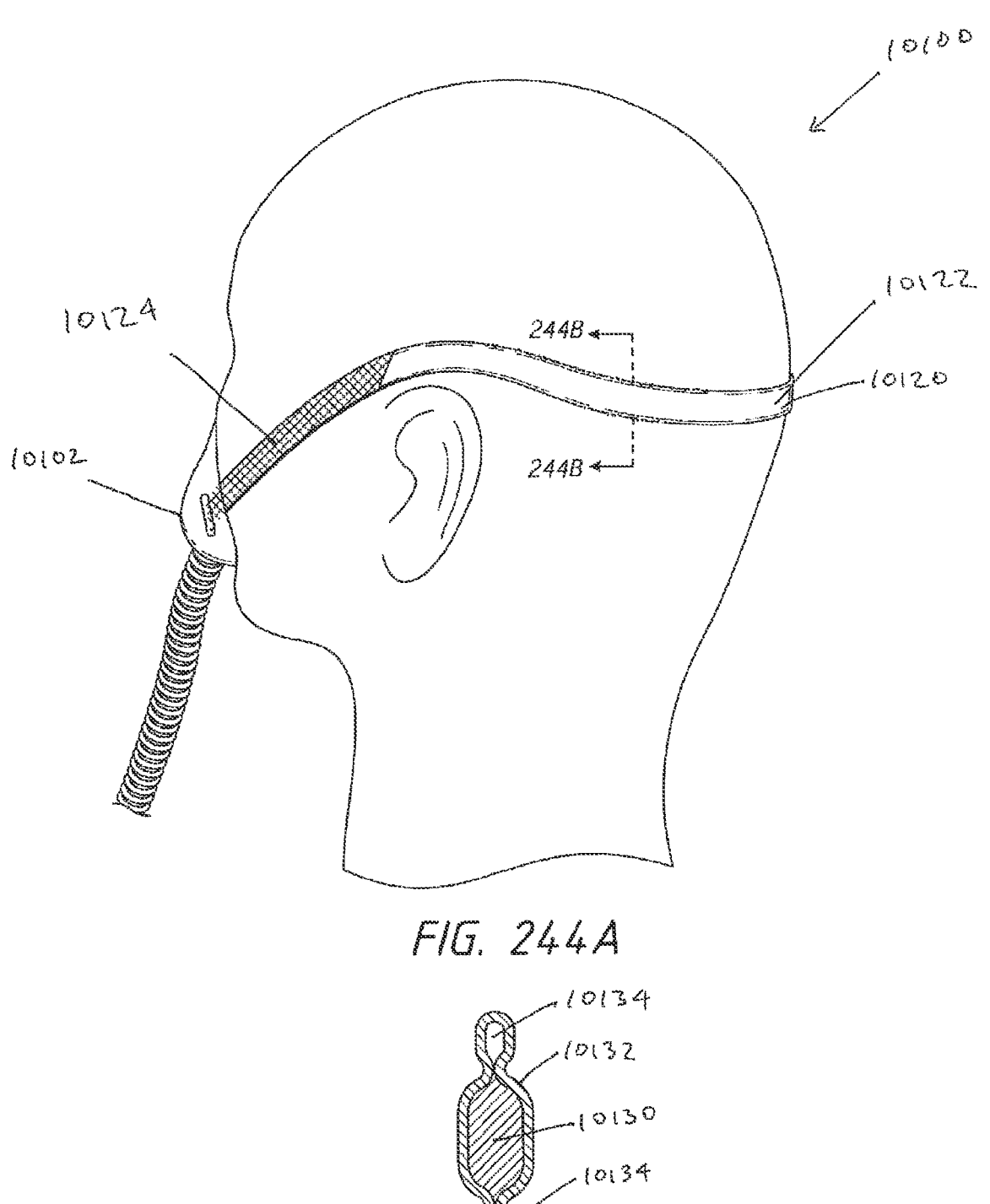

FIG. 244A is a rear perspective view of a moulded headgear configuration having a single back strap.

FIG. 244B is a cross-sectional view of the moulded headgear configuration of FIG. 244A along a line A-A.

Figures 245A, 245B, 245C:
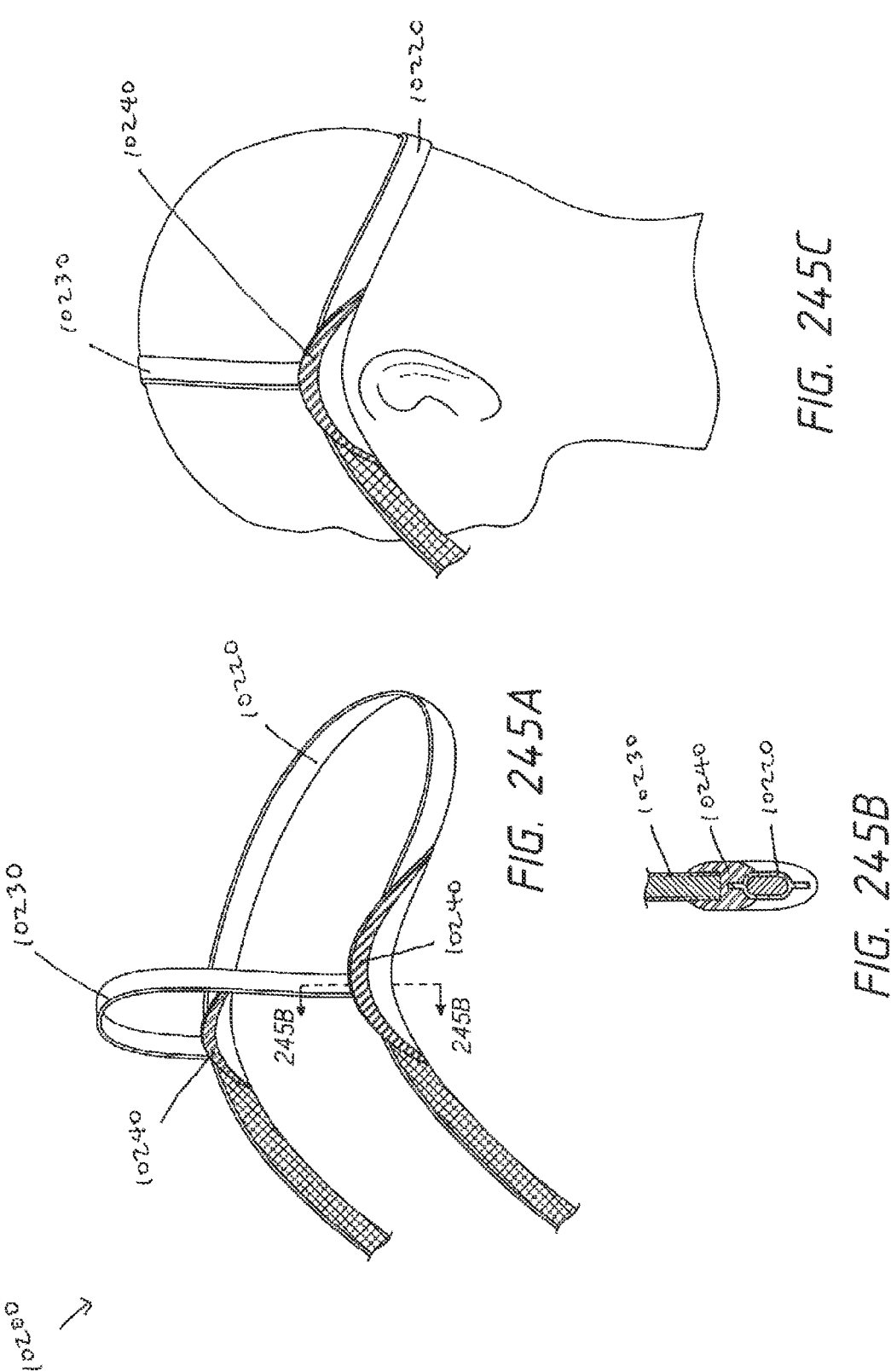

FIG. 245A is a side perspective view of a moulded headgear configuration having a lower strap connected to a crown strap by an arched connector.

FIG. 245B is a cross-sectional view of the moulded headgear configuration of FIG. 245A along a line A-A.

FIG. 245C is a side view of the moulded headgear configuration of FIG. 245A.

Figure 246:
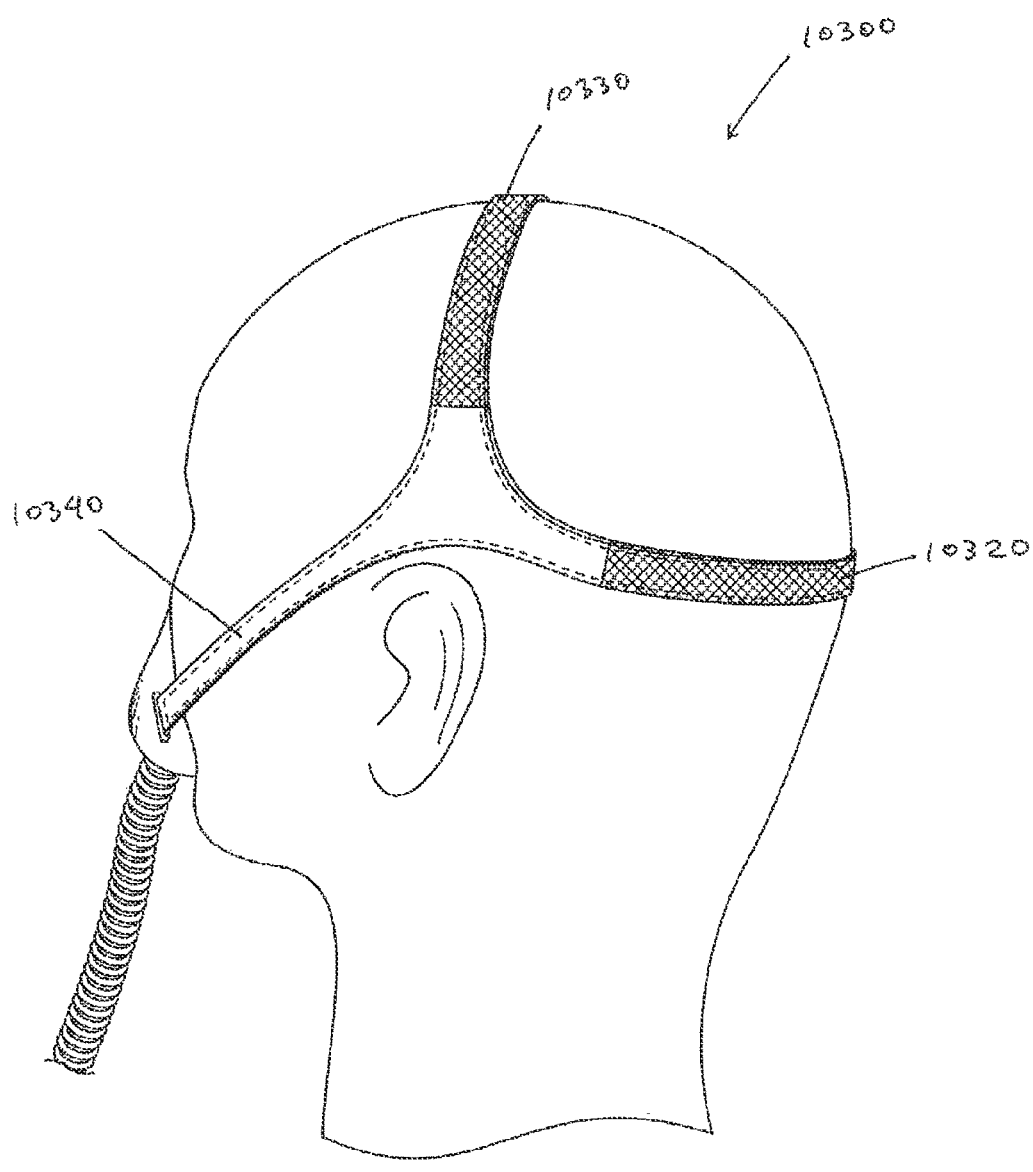

FIG. 246 is a rear perspective view of a moulded headgear configuration having a rigid front strap and elastic rear and crown straps.

Figures 247A, 247B, 247C, 247D:
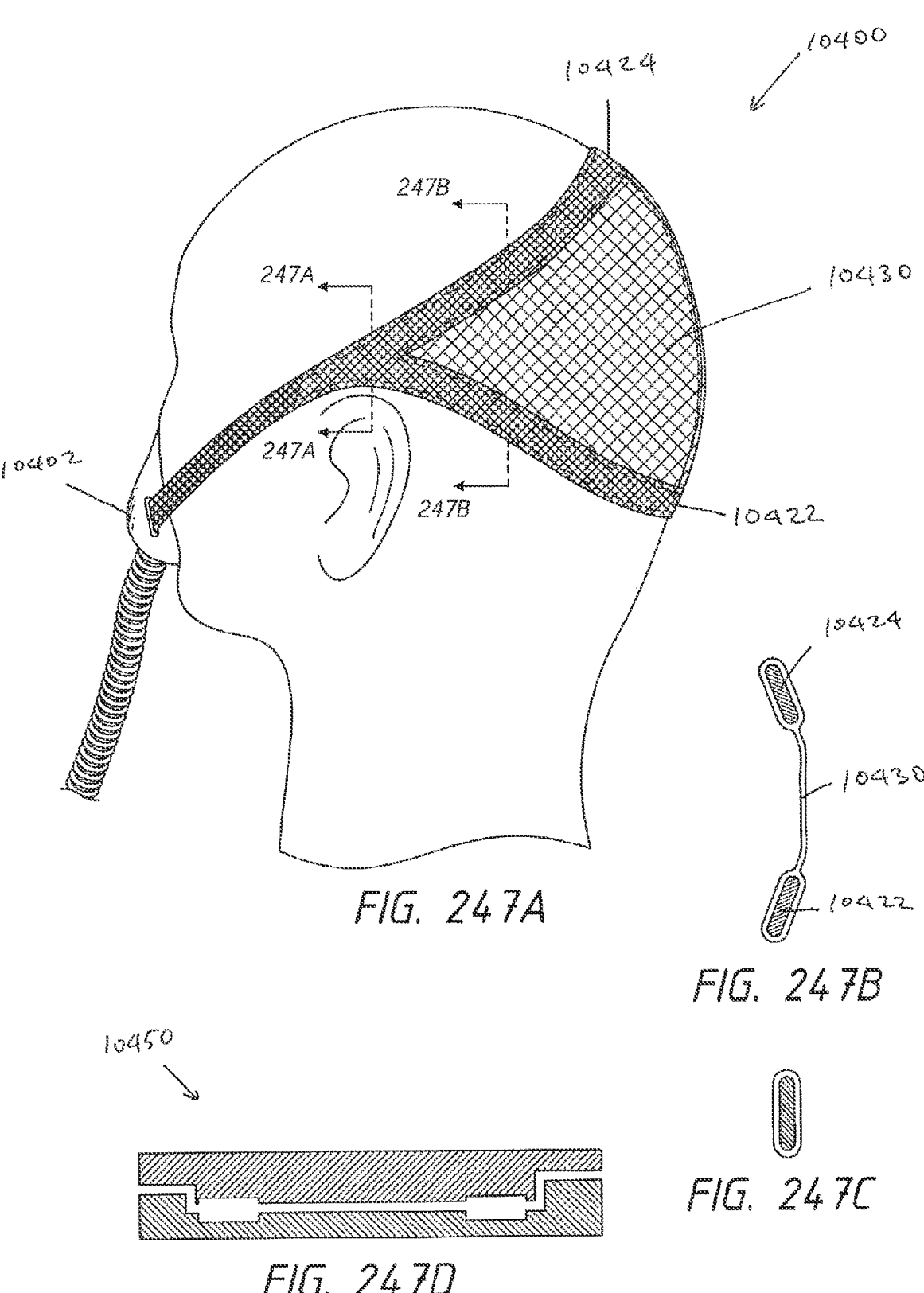

FIG. 247A is a rear perspective view of a moulded bifurcating headgear configuration having a having a variable knit intra-mould.

FIG. 247B is a cross-sectional view of the moulded headgear configuration of FIG. 247A along a line A-A.

FIG. 247C is a cross-sectional view of the moulded headgear configuration of FIG. 247A along a line B-B.

FIG. 247D is a moulding tool for forming the moulded headgear configuration of FIG. 247A.

FIG. 248A is a side perspective view of a moulded headgear configuration having a fully integrated bifurcated rear strap and crown strap.

FIG. 248B is a partial exploded perspective view of the moulded headgear configuration of FIG. 248A.

FIG. 248C is a cross-sectional perspective view of the moulded headgear configuration of FIG. 248A along a line A-A.

Figure 249A:
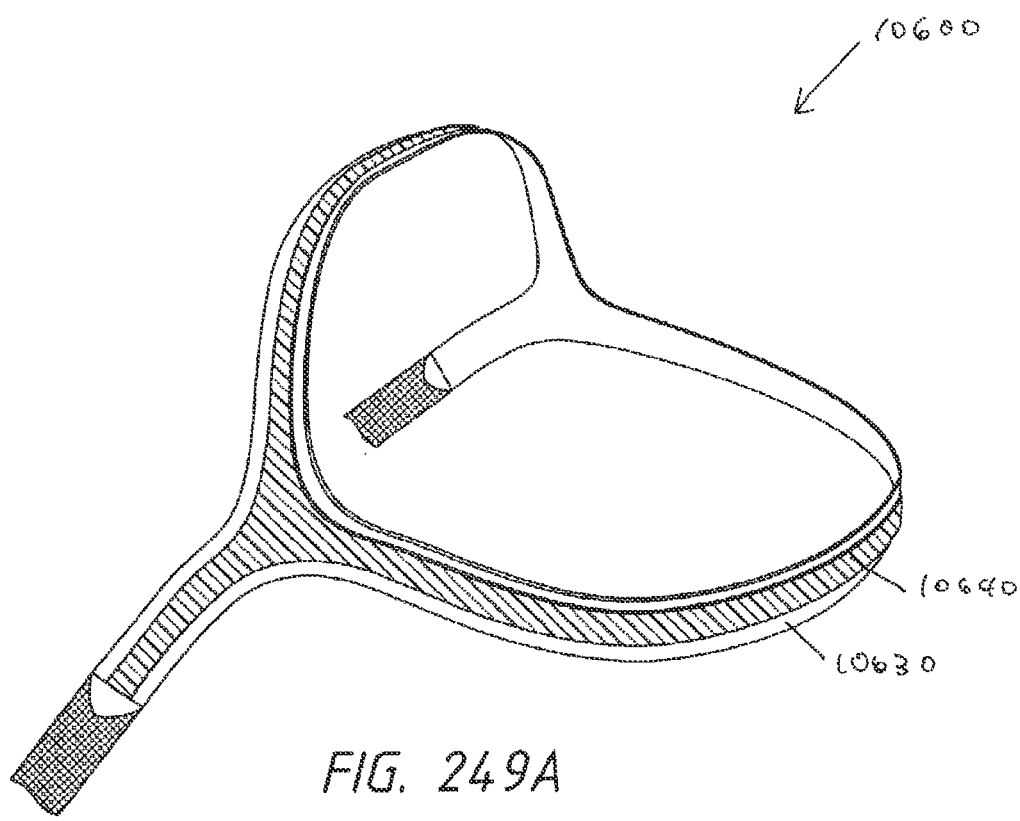

FIG. 249A is a side perspective view of a moulded headgear configuration having core material exposed and formed on the outside surface of the outer cover.

Figure 249B:
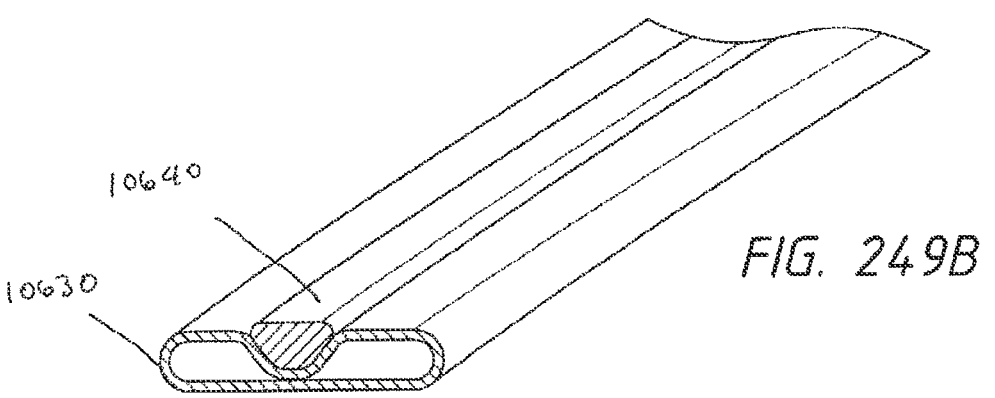

FIG. 249B is cross-sectional perspective view of the moulded headgear configuration of FIG. 248A having the core material recessed within the outer cover.

Figure 249C:
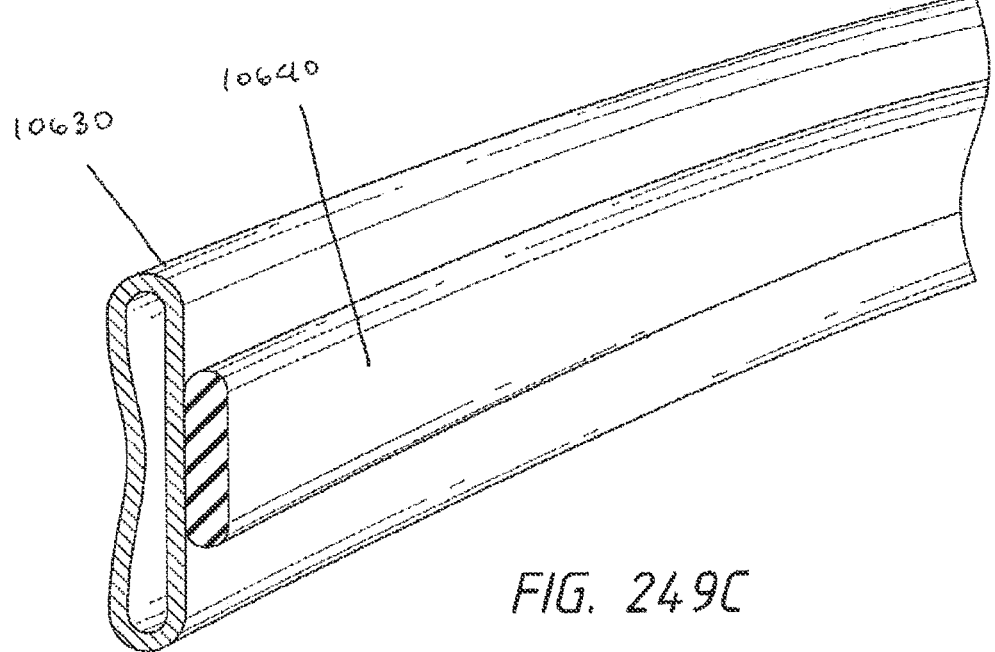

FIG. 249C is a cross-sectional perspective view illustrating an alternative construction of the moulded headgear configuration of FIG. 248A having core material positioned over the outer cover without recessing into the outer cover.

Figure 250:
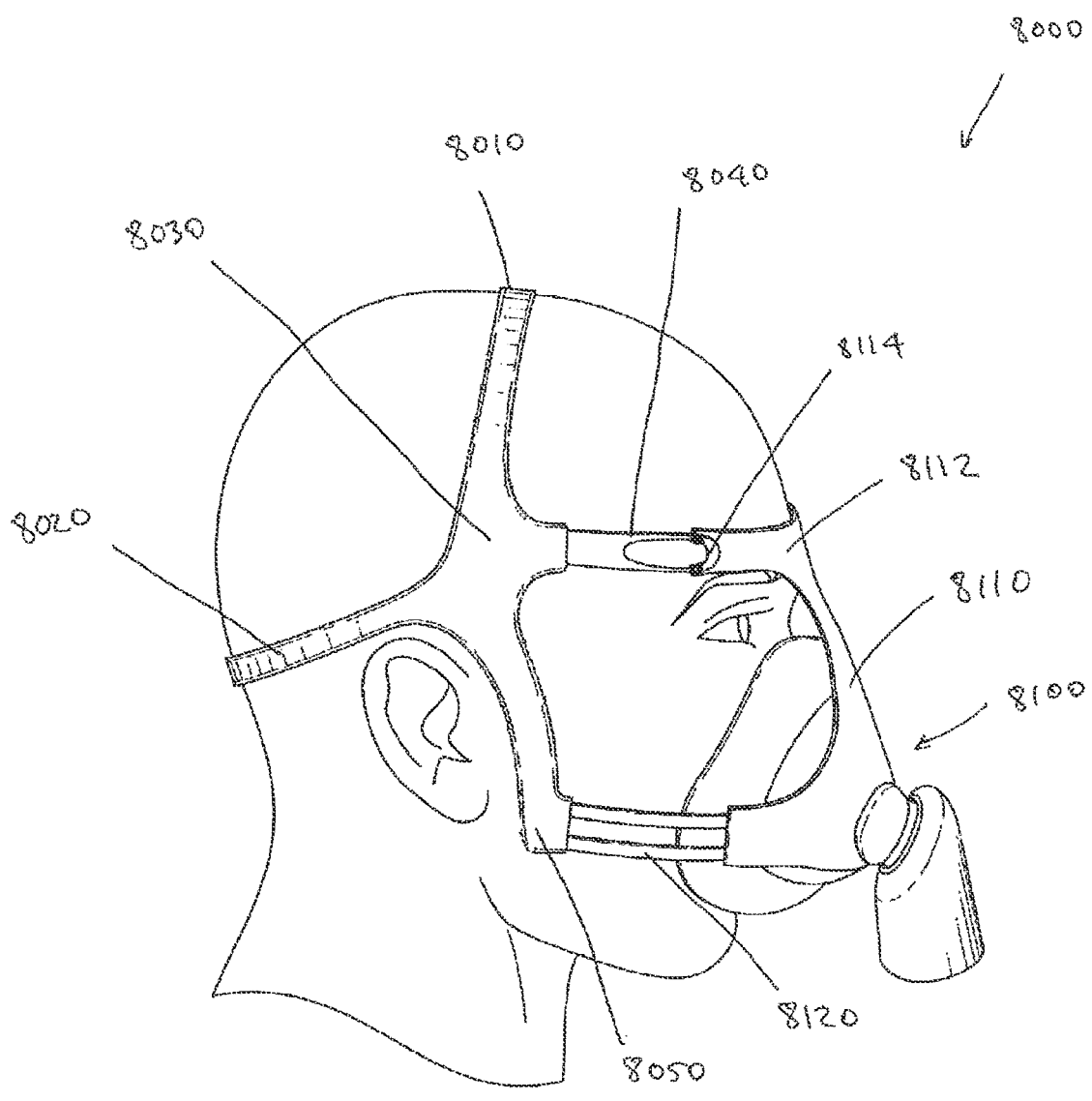

FIG. 250 is a side view of an exemplary intra-moulded headgear configuration for use in combination with a full-face mask.

Figure 251:
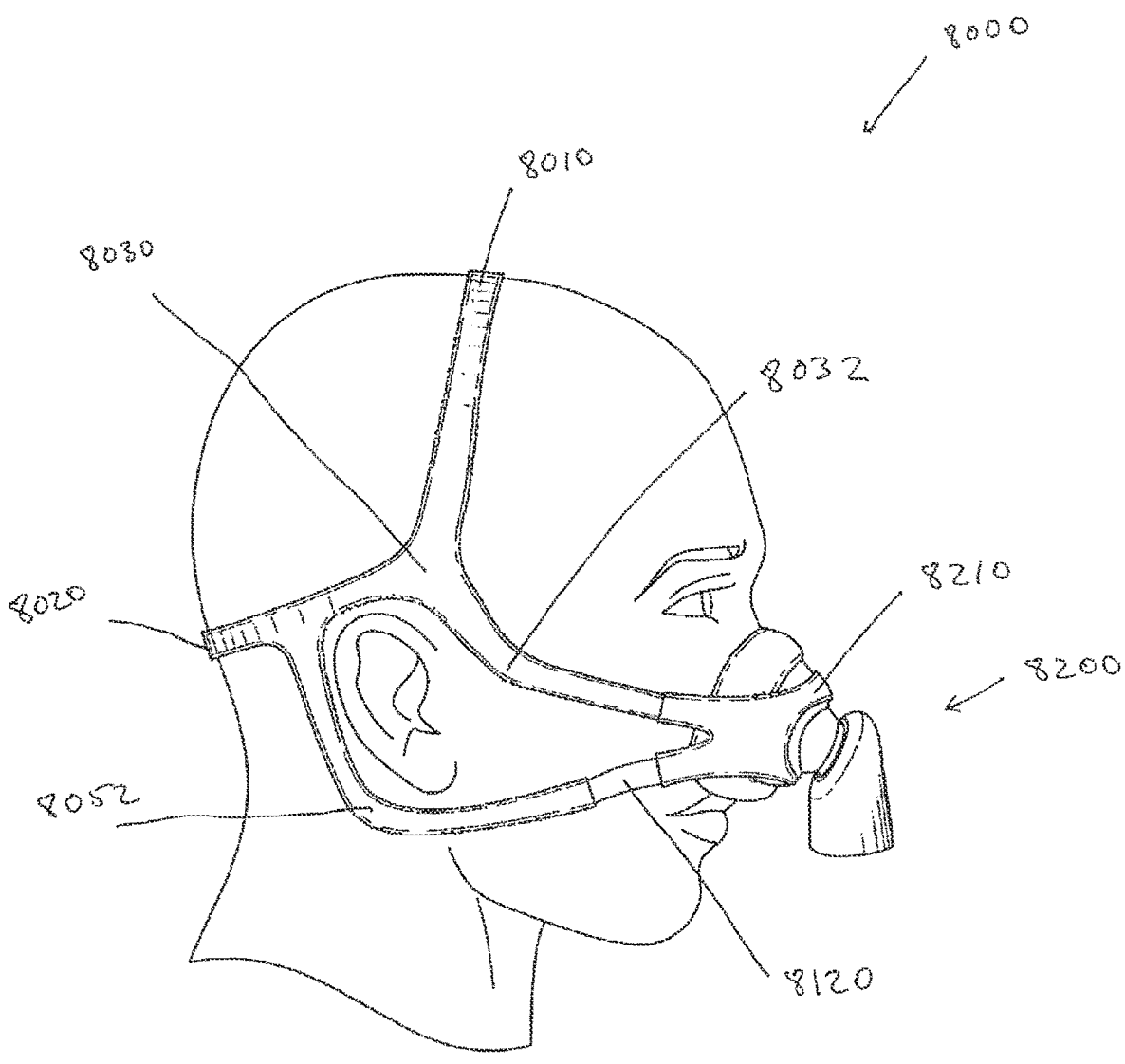

FIG. 251 is a side view of an exemplary intra-moulded headgear configuration having a below the ear lower strap for use in combination with a nasal mask.

Figure 252:
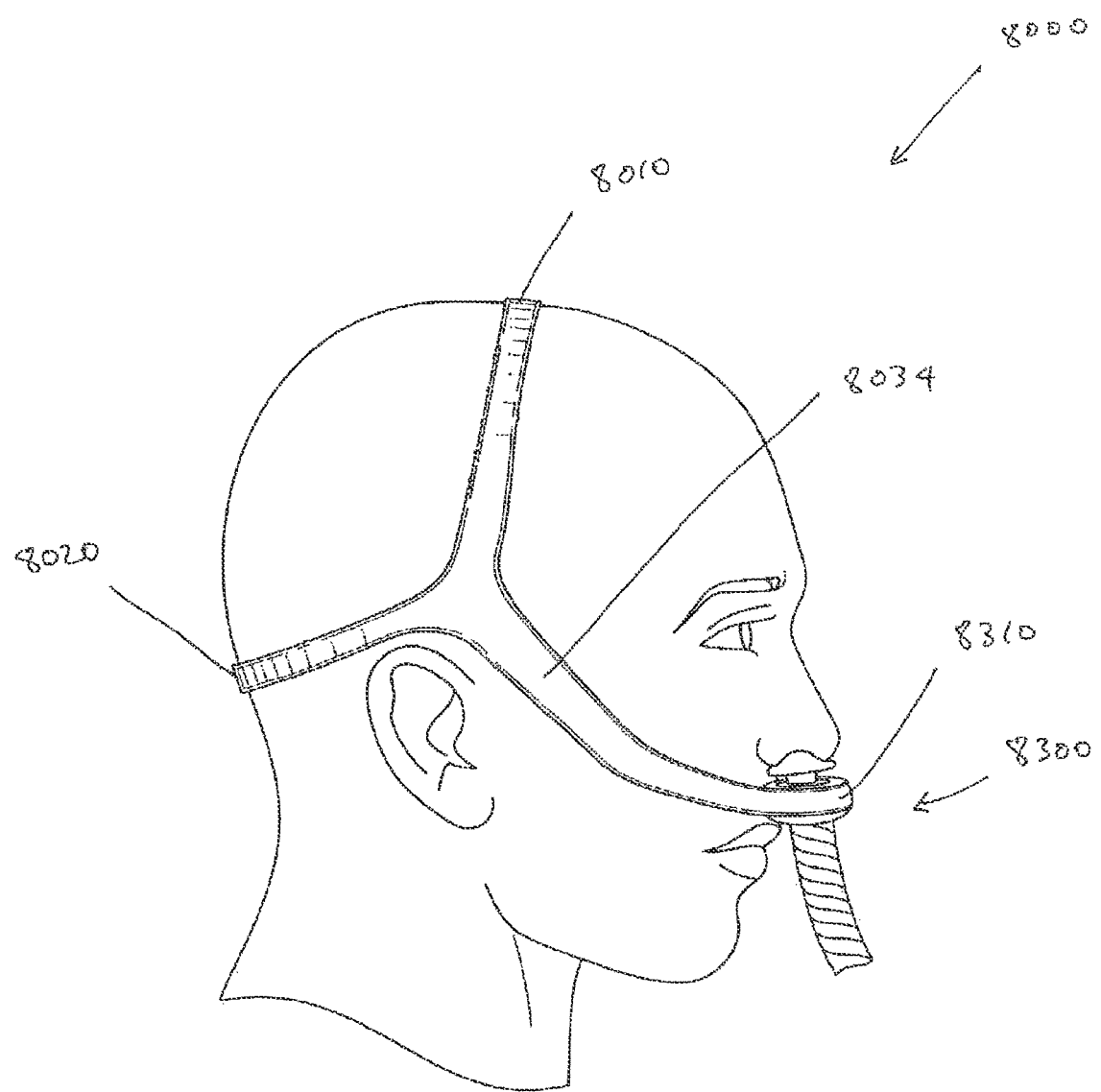

FIG. 252 is a side view of an exemplary intra-moulded headgear configuration for use in combination with a nasal pillows mask.

Figure 253:
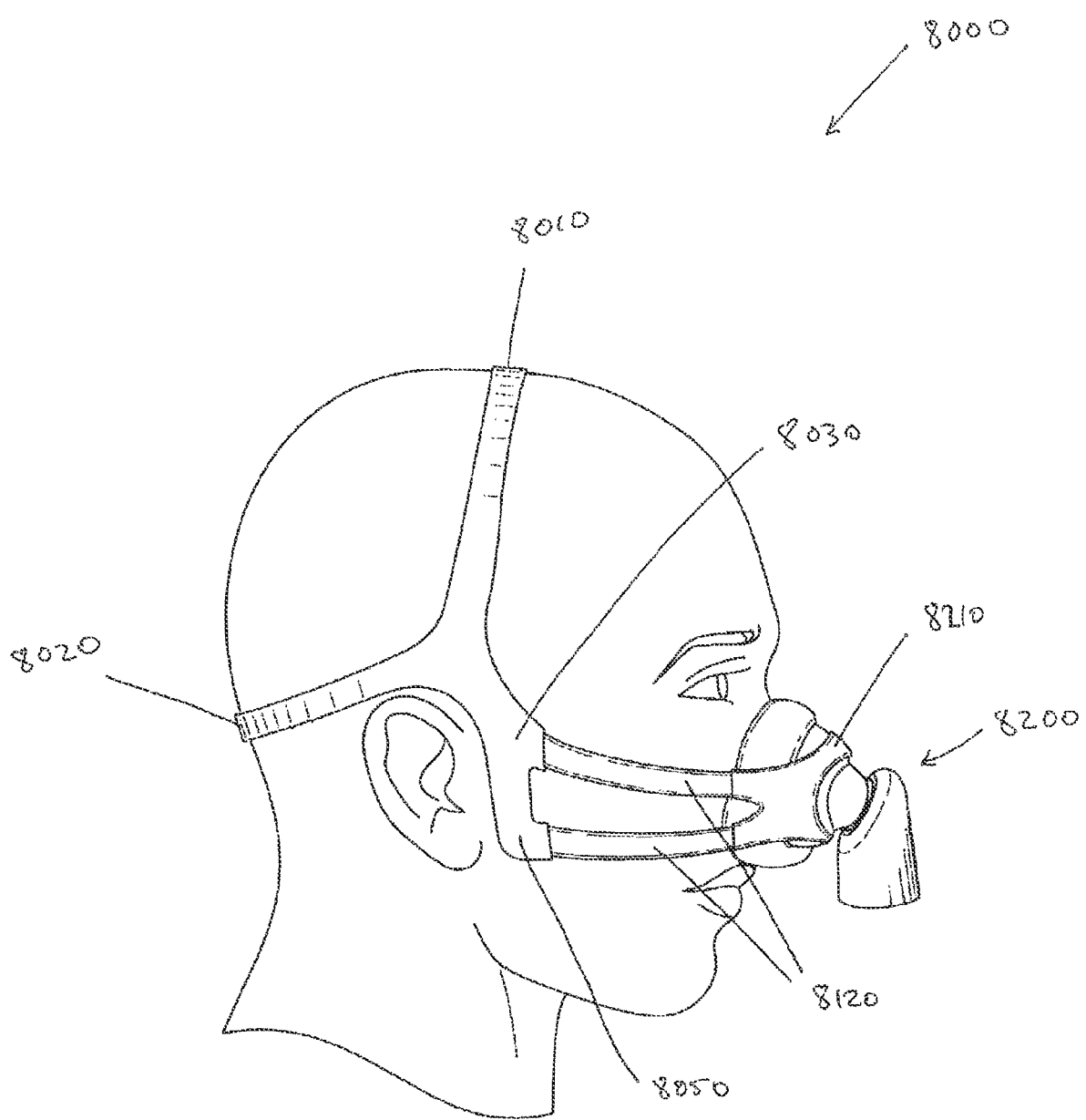

FIG. 253 is a side view of an exemplary intra-moulded headgear configuration for use in combination with a nasal mask.

Throughout the drawings, reference numbers can be reused to indicate general correspondence between reference elements. The drawings are provided to illustrate example embodiments described herein and are not intended to limit the scope of the disclosure.

DETAILED DESCRIPTION

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

As used herein the term 'substantially inelastic' shall refer to the ability of a headgear or material to resist stretching relative to the loads to which it may be subjected. Thus, a headgear or material may be substantially inelastic in one direction and may be somewhat elastic in another direction. In some configurations, the headgear or material is configured to be substantially inelastic in a direction in which loads are applied by the therapy with which the headgear or material is intended for use. A substantially inelastic headgear or material, for example, can resist stretching that would compromise a seal of a respiratory mask in a sealed system under normal or expected conditions. In an unsealed system, a substantially inelastic headgear or material, for example, can resist stretching that would compromise the appropriate placement of the respiratory interface in response to normal or expected conditions, such as hose pull forces or movement of the user. When the expected loading forces are relatively low, the headgear or material may have greater elasticity because the load will not be sufficient to cause stretching. Conversely, if it is expected that the headgear and/or material will be subjected to high loading forces, then greater inelasticity will be required to resist stretching.

Some embodiments disclosed herein involve a headgear system and/or an interface assembly incorporating a headgear system that upon fitment to the head of a user automatically adjusts to the correct size and, once in use, transforms in properties from an elasticated "stretchy" strap/strapping to an "inelastic" strap/strapping. In some configurations, the headgear (alone or as integrated in an interface assembly) exhibits a relatively small contraction force that tends to shorten the headgear. When coupled to a mask, the headgear and mask cooperate to define a perimeter of the interface assembly, which is reduced in length as a result of the contraction force toward a minimum perimeter length. Although not likely to be perfectly circular, the perimeter length is often referred to as a "circumference." Thus, with such an arrangement, the interface assembly can be positioned on the user's head and will automatically contract to or very near a proper head size, in a manner similar to an elasticated or "stretchy" headgear. The contraction force preferably is sufficient to support the weight of the interface assembly and at least substantially keep the interface assembly in place on the user's head at the smallest head size or minimum useful perimeter length of the interface assembly, which may or may not coincide with the minimum perimeter length. In some configurations, the retraction force can be sufficient to support the weight of a nasal cannula or other small interface, which can have a weight of about 50 grams, for example. In other configurations, the retraction force can be between about 0.5 Newtons and about 5.2 Newtons, or between about 1 Newton and about 2.6 Newtons, or between about 1 Newton and about 1.5 Newtons, including any value and sub-range within these ranges. In other configurations, the retraction force may be insufficient to support the weight of the interface and may require manual assistance to move the interface to a sealed position on the user's face. However, preferably, once the headgear is sufficiently retracted, it is then held in place by, for example, the directional lock(s). In some configurations, the contraction force is only sufficient or is configured to support the weight of the headgear.

However, in at least some configurations, the contraction force is less than is necessary to maintain the mask in sealed contact with the user's face during treatment/use. That is, the contraction force, alone, cannot resist the blow-off force. In some configurations, the contraction force is insufficient to resist the blow-off force throughout a range of usable perimeter lengths or headgear sizes. Therefore, the headgear and/or interface assembly also exhibits an inelastic behavior in response to forces tending to elongate the headgear or increase the perimeter length of the interface assembly. The headgear and/or interface assembly can have a locked mode that can produce a locking force tending to resist expansion, elongation or lengthening of the perimeter length. The locking force can be sufficient to resist elongation, or at least any significant elongation, of the perimeter length in response to blow-off forces. In some configurations, the locking force is sufficient to resist elongation in response to the highest blow-off forces expected with a variety of uses or treatments (e.g., Bi-Level or CPAP, NIV, etc.). In some configurations, the locking force may be selected for one or more particular uses/therapies, but may not be suitable for all uses/therapies. In some configurations, the locking force may be selected to resist elongation in response to forces in addition to blow-off forces, such as hose pull forces, for example. Such additional forces can be referred to collectively herein as "hose pull forces" and such additional resistance to elongation can be referred to herein as a "reserve."

In some configurations, the headgear and/or interface assembly also exhibits a yield force, above which expansion or elongation of the perimeter length is permitted. Preferably, the yield force is greater than the expected blow-off force. In some configurations, the yield force is greater than the expected blow-off force and the hose pull force. Thus, such a headgear and/or interface assembly has a reserve. Preferably, the yield force is set low enough that a user can at least relatively conveniently apply an elongation force to the headgear and/or interface assembly sufficient to exceed the yield force in order to permit the interface assembly to lengthen and to be applied to the user's head. As described above, the contraction force reduces the perimeter length toward a proper head size.

In some configurations, the headgear and/or interface assembly automatically transitions between a contraction mode, a locked mode and a yield mode in response to the presence or absence of external forces. For example, the headgear and/or interface assembly moves toward or to the minimum perimeter length in the absence of external lengthening or expanding forces. A lengthening or expansion force that is greater than the yield force can be applied to increase the perimeter length of the headgear and/or interface assembly to a length sufficient to permit the interface assembly to be positioned on the user's head. Once the lengthening or expansion force is removed (or reduced to below the contraction force), the contraction force acts to automatically reduce the perimeter length to or substantially to the proper head size such that the interface assembly is supported on the user's head. Upon the start of treatment (application of blow-off force) and/or application of hose pull force, the headgear and/or interface assembly automatically transforms to the locked mode to resist elongation, or at least resist any significant elongation, or increase of the perimeter length. At the end of treatment, or at any time as desired, a force above the yield force can be applied to the headgear and/or interface assembly to increase the perimeter length and permit removal of the interface assembly from the user's head.

Advantageously, with such an arrangement, micro-adjustments of the perimeter length of the headgear and/or interface assembly can be accomplished quickly and conveniently. For example, during treatment or use, the mask can be manipulated to effect micro-adjustment of the perimeter length. For instance, in the event of a leak between the mask and the user's face, the mask can be wiggled or otherwise moved to effect a micro-adjustment of the perimeter length to address the leak. In some cases, the seal of the mask may be compressed against the user's face, which can allow the contraction force to automatically reduce the perimeter length. Upon release of the mask, the headgear and/or interface assembly locks at, or very near, the reduced perimeter length. Thus, such configurations permit the headgear and/or interface assembly to micro-adjust, or move to an adjusted perimeter length, as a result of small manipulations (e.g., wiggling) of the mask. Manipulation of other portions of the interface assembly (e.g., headgear or breathing tube/gases conduit) can similarly result in micro-adjustment. Because of the nature of the human head and/or the conditions under which interface assemblies are used, quick and convenient micro-adjustment can dramatically improve performance and user satisfaction of an interface assembly. Treatment often occurs at night and/or under other situations when the user is lying down. Thus, the headgear can be in contact with surface, such as a pillow or bed. Movement of the user's head relative to such surfaces can cause movement of the headgear, which can alter the fit of the headgear. For example, hair can move or "compress" beneath the headgear, which can alter the fit. The headgear straps may move up, down or rotationally on the head, which can alter the fit. Such alterations in fit can result in leaks between the mask and the user's face. The above-described adjustment technology can permit such changes in fit to be addressed automatically or with small manipulations of the mask or other portions of the interface assembly. Moreover, the interface assembly can be removed and reapplied and automatically adjust to at or very near a proper headgear size. In contrast, if conventional non-stretch headgear is moved from its desired adjustment position, such as by mistake or as a result of cleaning, it can be difficult and time-consuming to reestablish the desired adjustment position. Conventional elasticated headgear addresses the adjustment issue, but because the contraction force must resist the highest expected blow-off and hose pull forces at the smallest useable headgear size, elasticated headgear applies a relatively large pressure to the user's head that is only partially relieved by the application of blow-off force. Such pressure may be substantial for a user with a relatively large head size and low treatment pressure.

As is described below with reference to specific directional lock arrangements, in some configurations, some amount of movement occurs in the headgear and/or interface assembly during transition from the elastic mode to the locked mode. For example, with some directional lock arrangements, the perimeter length may increase slightly during the transition from elastic mode to locked mode. In some cases, there exists a compromise between increased yield force and reduced perimeter length change during transition. Thus, references to any particular positions of the headgear and/or interface assembly or perimeter lengths can include such slight length changes during transition, if present.

The following example of the above-described adjustment technology is based on the delivery of CPAP. The series of graphs describe a typical operating envelope that a headgear system must be designed to operate over and how various current embodiments operate relative to that envelope. The envelope may comprise an entire CPAP treatment universe, that is, an entire range of typical, probable or possible CPAP pressures and an entire range of typical, probable or possible head sizes. Or, the envelope may comprise a subset of the CPAP treatment universe, such as a subset of pressures (e.g., low pressure or high pressure CPAP) or head (headgear or interface assembly) sizes (e.g., small, medium or large). The principles discussed in connection with CPAP treatment may apply to other treatments, as well.

Figure 1:
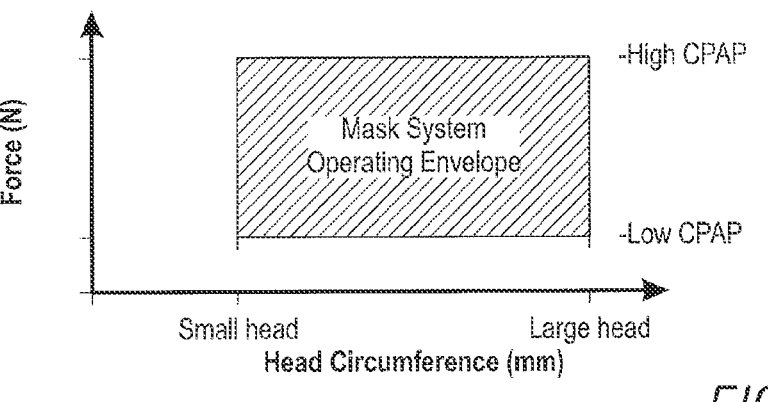
FIG. 1 is a graph illustrating an operating envelope representing a relationship between a force created when a mask enclosure is pressurised and a headgear sizing range of potential patients.

FIG. 1 is a graph that illustrates a relationship between the force that is created when a mask enclosure is pressurised and the headgear sizing range that is likely to be encountered across the range of potential patients. The operating envelope is illustrated as a rectangular area defined between minimum and maximum forces and minimum and maximum head sizes (circumferences).

Figure 2:
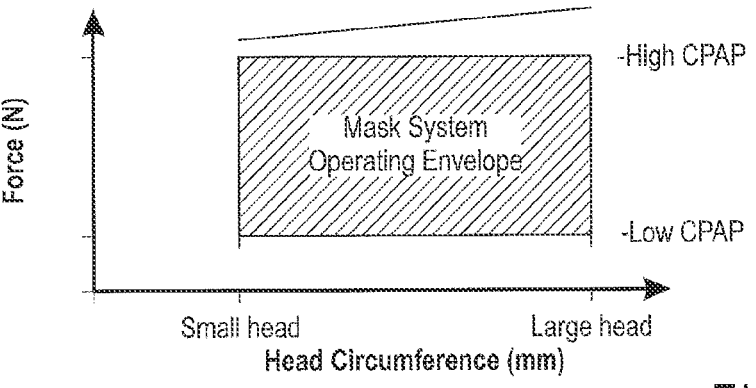
FIG. 2 illustrates the operating envelope of FIG. 1 with a force curve of an elasticated headgear system superimposed.

FIG. 2 illustrates the operating envelope of FIG. 1 with the performance characteristics (force curve) of an elasticated headgear system superimposed. It is apparent that for the elasticated system to offer sufficient performance across the mask system operating envelope, it must provide a greater force than the mask system can generate. Thus, at low CPAP pressures, the headgear provides a much greater force than is necessary to counteract the blow-off force. The additional force is applied a pressure to the user over an area defined by the mask and headgear, which is concentrated primarily at the mask and at the back of the head. The area of the headgear can be increased to apply the force over a larger area, thereby reducing the applied pressure. However, large headgear can be annoying or uncomfortable. For example, such large headgear can retain heat over a larger area than desirable.

Figure 3:
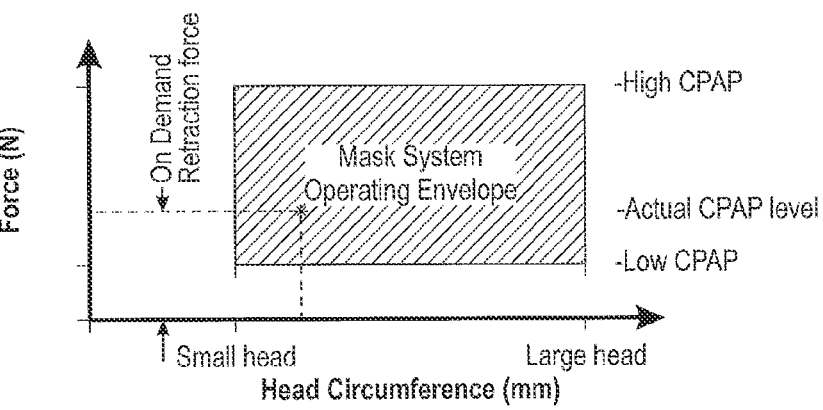
FIG. 3 illustrates the operating envelope of FIG. 1 with a force curve of an exemplary embodiment superimposed.

FIG. 3 illustrates the operating envelope of FIG. 1 with the performance of an example of a headgear system having the above-described automatic adjustment technology superimposed. In the illustrated example, the force generated by the headgear and/or interface assembly is sufficient to balance the forces generated by the pressurization of the enclosed area of the mask. In essence, the example headgear system automatically adjusts to the appropriate head size (circumference or perimeter length) with a relatively low contraction force and then provides a retention force "on-demand" that is matched to the actual CPAP pressure. Thus, the example headgear system can automatically adjust to meet the needs of any potential point within the CPAP envelope.

Figure 4:
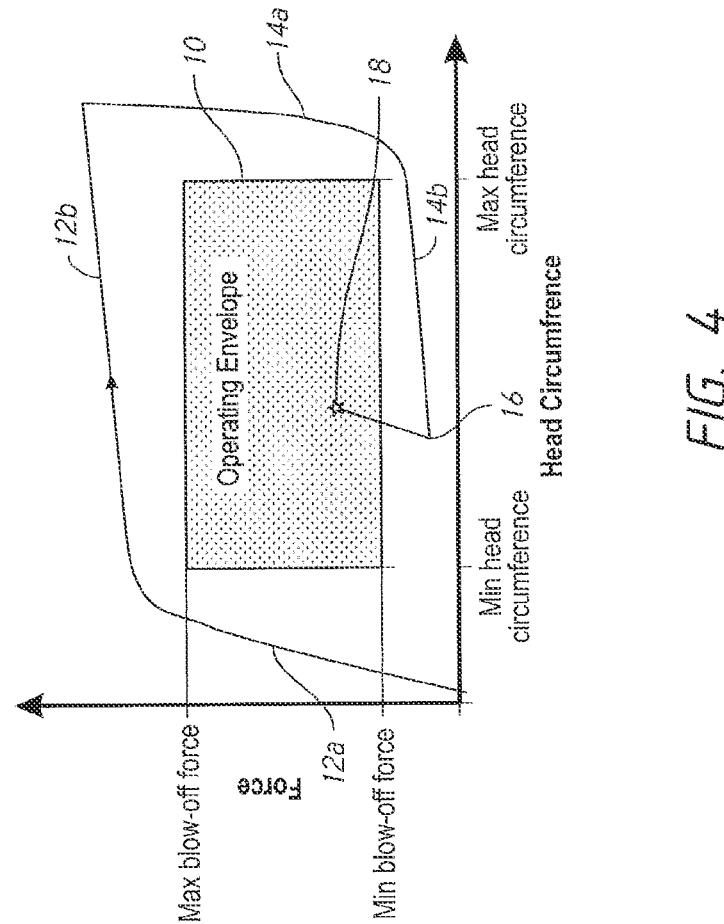
FIG. 4 is a graph of a force-deflection curve of an exemplary headgear arrangement.

FIG. 4 illustrates a graph of a force-deflection curve of an example of a headgear arrangement or interface assembly comprising a headgear arrangement. The deflection axis of the graph may represent the circumference or perimeter length of the headgear arrangement or interface assembly. The circumference or perimeter length, in turn, can represent the head circumference of a particular user when the headgear arrangement or interface assembly is fitted to the user. FIGS. 4.1-4.3 illustrate several discrete positions of a user putting on ("donning") and micro-adjusting an example interface assembly comprising a headgear arrangement. The graph of FIG. 4 is described below with additional reference to the donning positions of FIGS. 4.1-4.3.

The graph of FIG. 4 also illustrates an operating envelope 10 relevant to the headgear arrangement or interface assembly, which may be the same operating envelope as shown and described above with respect to FIGS. 1-3. The operating envelope 10 is illustrated as a rectangular area defined between minimum and maximum forces applied to the headgear arrangement or interface assembly as a result of the therapy and minimum and maximum head sizes or circumferences/perimeter lengths of the headgear arrangement. The operating envelope 10 can be specific to a therapy (e.g., CPAP or bi-level PAP) or can cover multiple therapies. Similarly, the head size or circumference/perimeter length can be specific to a size of headgear arrangement or can cover multiple sizes. The operating envelope 10 can be used to establish functional or behavioral criteria of a particular headgear arrangement and is utilized herein to illustrate features or behaviors of certain disclosed embodiments.

A graph containing an example force-deflection curve of an example headgear arrangement or interface assembly (referred to as "headgear" for convenience in the discussion of the graph) is illustrated relative to the example operating envelope 10. The curve originates at or near the origin of the graph, which may represent approximately zero force and a minimum circumference or perimeter length (referred to as "circumference" for convenience in the discussion of the graph) of the headgear. The minimum circumference is greater than zero, but typically at a value below a minimum head circumference (taking into consideration the interface, if any) of the intended user or range of users.

As illustrated in FIG. 4.1, to place the headgear 100 onto the user, typically, the headgear 100 will be elongated to a circumference greater than the actual head circumference of the user. Typically, a rear portion of the headgear 100 will be placed on the rear of the user's head and the user will grasp the front of the headgear 100 (e.g., the mask or other interface) and apply a pulling force to elongate the headgear 100 and move the mask or other interface over the crown of the head and toward the face.

As illustrated in the graph of FIG. 4, the example force-deflection curve initially rises with a steep pitch, in which the force increases a substantial amount with a relatively small increase in the circumference. In some configurations, the force-deflection curve rises above the maximum force level of the operating envelope 10 before reaching the minimum circumference of the operating envelope 10. This portion of the curve can be referred to as an initial elongation portion 12*a*.

At some location above the maximum force of the operating envelope 10, the force-deflection curve transitions to a shallower pitch, in which the circumference increases a substantial amount with a relatively small increase in the force. This shallow pitch portion of the force-deflection curve can relate to a yield force of the retention arrangement of the headgear 100. Preferably, the shallow pitch portion, which can be referred to as an elongation portion 12*b*, of the force-deflection curve extends at or above the maximum force level of the operating envelope 10 along a portion or an entirety of the circumference range of the operating envelope 10. In some configurations, the elongation portion 12*b* extends beyond the maximum circumference level of the operating envelope 10. That is, the headgear 100 can be configured to achieve a greater circumference than the intended maximum head circumference to allow the headgear 100 to be conveniently placed onto a user having the maximum head circumference of the operating envelope 10 of the headgear 100. In use, especially with users having head sizes on the smaller end of the operating envelope 10, the headgear 100 may not be elongated to a maximum circumference during donning and, in some cases, may not be elongated beyond the maximum circumference level of the operating envelope 10.

After the headgear 100 has been elongated to the maximum circumference, to a circumference greater than the operating envelope 10 or, in use, to some other circumference sufficient to allow donning onto the user, the illustrated force-deflection curve drops steeply (initial retraction portion 14*a*) and then transitions to a relatively shallow portion, in which the circumference reduces substantially with a relatively small change in force. This shallow portion of the curve can be referred to as a retraction portion 14*b* and is partially illustrated by FIG. 4.2. Preferably, in the retraction portion 14*b*, the headgear 100 reduces in circumference at a relatively low force level until the headgear 100 reaches an appropriate circumference to fit the user's head. The headgear 100 can be positioned on the user's head at this low force level (the left end of the retraction portion 14*b* or "fit point 16") until therapy is initiated or until another force attempting to elongate the headgear 100 is applied.

Advantageously, this relatively low force level allows the headgear 100 to be comfortable for the user. In some configurations, the retraction portion 14*b* of the force-deflection curve is at or below the minimum force level of the operating envelope 10. Thus, in such an arrangement, the retraction force of the headgear 100 can be lower than that necessary or desirable to resist minimum forces induced in the headgear 100 by the therapy (e.g., a low CPAP level). Accordingly, even at low therapy levels, the headgear 100 can be configured to produce only enough retention force to resist the therapy-induced forces because the minimum force level of the operating envelope 10 is above the retraction portion 14*b* of the force-deflection curve. In some configurations, as described below, the retraction portion 14*b* of the force deflection curve could fall within the operating envelope 10. Such an arrangement can be referred to as exhibiting "composite" behavior. However, preferably, the retraction portion 14*b* of a composite-behavior headgear force-deflection curve remains below the maximum force level of the operating envelope 10.

When therapy is commenced, or another elongating force is applied to the headgear 100, the force deflection curve rises relatively steeply from the fit point 16 to a point within the operating envelope 10 at which the retention force of the headgear 100 balances with the force induced by the therapy and/or other forces (e.g., hose pull forces) attempting to elongate the headgear 100. Such a point can be referred to as a balanced fit point 18. The force-deflection curve between the fit point 16 and the balanced fit point 18 can have substantially the same slope as the initial elongation portion 12*a*. The actual location of the balanced fit point 18 can be anywhere within the operating envelope 10 depending on the actual force induced by the therapy and the actual head size of the user. In any particular case, the force in the headgear 100, which is applied over an area related to headgear size as a pressure to the user, is substantially only the force necessary to counteract the forces induced by the therapy. Thus, in at least some configurations, the pressure applied to the user can be minimized for any particular headgear size and shape for the particular level of therapy utilized. The elongation portion 12*b* of the force-deflection curve can be spaced above the maximum force level of the operating envelope 10 to provide a reserve in which additional forces (e.g., hose pull forces) can be applied without elongation of the headgear 100. Once sufficient force is applied to the headgear 100 to reach the elongation portion 12*b* of the force-deflection curve, elongation of the headgear 100 can occur. However, the headgear 100 can be designed or configured to have a force-deflection curve that accommodates expected or usual therapy forces and hose pull forces or any combination thereof.

As described above, in at least some configurations, the user can manipulate the headgear 100 to cause a microadjustment of the perimeter length. Advantageously, such an arrangement allows the user to, for example, address leaks or tighten or loosen the headgear 100 (reduce the perimeter length) to a desired level by simply grasping the mask or other interface and moving (e.g., wiggling) the mask or other interface relative to the user's face and a rear portion of the headgear 100, as illustrated in FIG. 4.3. As indicated by the arrows in FIG. 4.3, the mask or other interface can be moved or adjusted in a plurality of directions, including toward and away from the user's face or in a rotational manner (e.g., about a vertical or horizontal/lateral axis). Movement toward the face can result in a reduction of the perimeter length or tightening of the headgear 100 to, for example, achieve a fit that is toward the tight end of the spectrum of an acceptable or desirable fit, which can be referred to as a "tight fit." Movement away from the face can result in elongation of the perimeter length or loosening of the headgear 100 to, for example, achieve a fit that is toward the loose end of the spectrum of an acceptable or desirable fit, which can be referred to as a "loose fit." Rotational movement about a vertical axis can cause one side of the headgear 100 to tighten and the other side to remain the same or loosen. Rotation about a horizontal or lateral axis can cause one of an upper or lower portion of the headgear 100 to tighten and the other of the upper or lower portion to loosen.

As described above, it is not necessary in all configurations that the retraction portion 14*b* of the force-deflection curve be located below a minimum force level of the operating envelope 10. The headgear 100 can be designed or configured to position the retraction portion 14*b* of the force-deflection curve within the operating envelope 10 and at a level that provides a sufficient degree of comfort to the user. In some cases, the user may desire that the headgear 100 apply some degree of force in order to provide the user with some tactile feedback that provides a feeling of comfort that the headgear 100 is securely holding the interface in place. Such force applied by the headgear 100 may, for some users, fall within the operating envelope 10 of the particular therapy. Thus, with such an arrangement, under at least some conditions, the retraction force of the headgear 100 may be sufficient to resist therapy forces at least as some lower therapy levels and/or certain larger head sizes.

Figure 5:
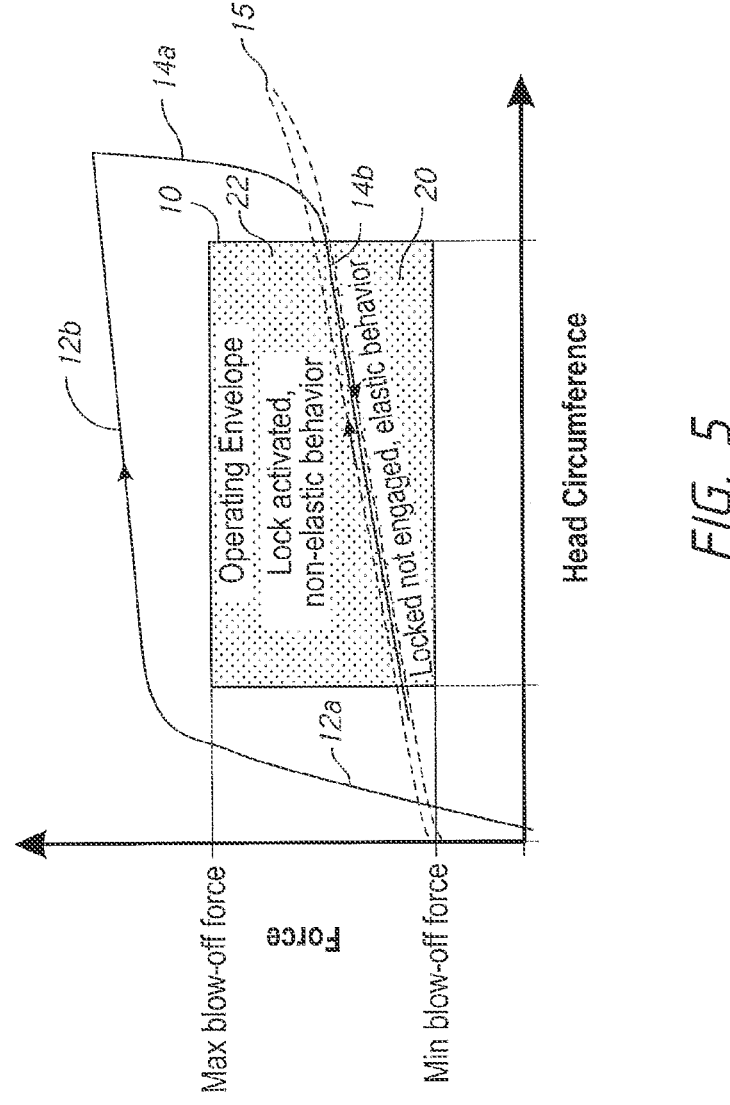
FIG. 5 is a graph containing an exemplary "composite" force-deflection curve.

FIG. 5 illustrates a graph containing an example "composite" force-deflection curve. For the sake of illustration, an example of an elastic headgear force-deflection curve is illustrated in the graph in addition to the composite force-deflection curve. The composite force-deflection curve can be substantially similar or identical to the force-deflection curve described above in connection with FIG. 4 except the composite force-deflection curve positions the retraction portion 14*b* within the operating envelope. The retraction portion 14*b* of the force-deflection curve divides the operating envelope into a lower portion 20 and an upper portion 22. The headgear can absorb forces in the lower portion 20 below the retraction portion 14*b* of the force-deflection curve utilizing the retraction force of the headgear, which can be provided by one or more elastic elements. Forces in the upper portion 22 above the retraction portion 14*b* of the force-deflection curve can be absorbed by the retention force of the headgear, which can be provided by one or more retention elements (e.g., locks), in a manner similar to that described above in connection with FIG. 4.

An example of an elastic headgear force curve 15 is illustrated overlying the retraction portion 14 of the force-deflection curve. The elastic headgear force curve 15 includes upper and lower curve portions separated by a relatively small vertical distance representing the internal frictional losses or hysteresis within the headgear. The force necessary to elongate the headgear is slightly greater than the retraction force of the headgear. An elastic headgear exhibiting the illustrated elastic force-deflection curve 15 can only accommodate applied therapy or other forces below the force-deflection curve 15. Applied forces above the force-deflection curve 15 will result in elongation of the elastic headgear. Thus, the force-deflection curve 15 of an elastic headgear must be positioned above the maximum force level of the operating envelope to avoid undesired elongation under at least some conditions (e.g., high therapy forces or small head size). The level of pressure applied to a user as a result of such a force-deflection curve 15 is likely to be uncomfortable under at least some conditions (e.g., low therapy forces or large head size).

In contrast, the composite force-deflection curve (or the balanced fit force-deflection curve shown and described in connection with FIG. 4) exhibits a relatively large vertical distance between the upper portion 12*b* of the curve and the lower portion 14*b* of the curve. At least a portion of the operating envelope falls within the vertical space between the upper portion 12*b* of the curve and the lower portion 14*b* of the curve. Accordingly, a headgear exhibiting such a force-deflection curve can resist relatively high forces while applying a relatively low force or pressure to the user in the absence of therapy or other elongation forces. In addition, once therapy is commenced, the force or pressure applied to the user remains the same (if below the retraction portion 14*b* of the force-deflection curve in a composite arrangement) or increases only to substantially the level needed to resist the applied force.

Figure 6:
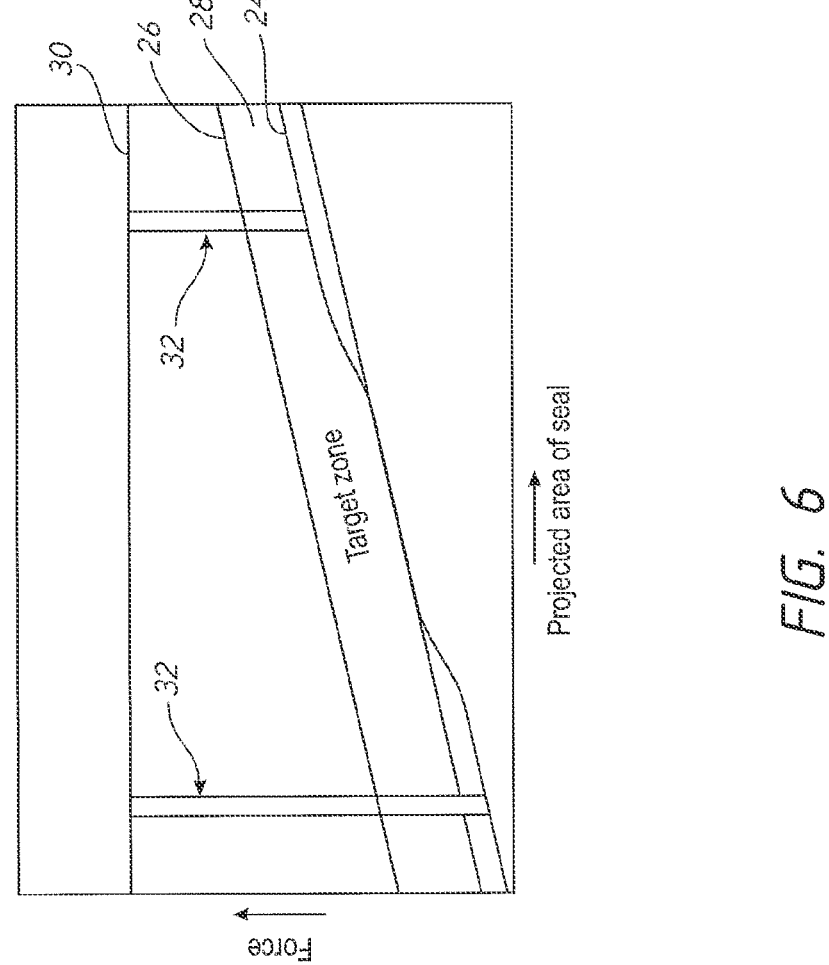
FIG. 6 is a force-area graph for maintaining an interface in sealed contact.

The forces applied to the headgear by the interface typically relate to a projected area of the seal of the interface. Smaller interfaces, such as nasal pillows or nasal masks, seal around a smaller area and, thus, produce a smaller force relative to larger interfaces, such as full face masks. Some interfaces (e.g., nasal cannula) may not create a seal with the face of the user and, thus, the forces applied to the headgear may relate primarily to the weight of the interface. FIG. 6 illustrates a graph of the force required to keep the interface in sealed contact with the user's face as it relates to the projected area of the seal. In general, the greater the projected area of the seal, the greater the force required to keep the interface in sealed contact with the user's face and, thus, the greater force that need to be resisted by the headgear. Such force can be referred to as a retention force of the headgear.

The graph of FIG. 6 includes two lines 24, 26 defining upper and lower limits of a range of acceptable retention forces for interfaces having different projected seal areas. The two lines 24, 26 are vertically spaced from one another and extend upwardly from left to right with a moderate slope. The lower line 24 can represent a minimum force necessary or desirable to maintain a seal with the user's face. The upper line 26 can represent a maximum desirable force, which can be greater than necessary to maintain a seal, but preferably is low enough to maintain user comfort or avoid excessive seal collapse. The space between the lower line 24 and the upper line 26 can represent a usable or target range 28 of adjustment to accommodate user preference, with the lower line 24 representing a usable or acceptable loose fit and the upper line 26 representing a usable or acceptable tight fit. The lower line 24 can include one or more relatively short, steep upward pitched sections that represent a transition between types of interfaces, such as nasal pillows to nasal mask and nasal mask to full face mask. The upper line 26 is illustrated as straight, but could include steep pitched sections corresponding to those of the lower line 24 to maintain a constant target adjustment range.

The graph of FIG. 6 also includes a flat or horizontal line 30 at a force level above the target range or target zone 28. This line 30 represents a force that will or is likely to cause skin damage to a user over a relatively short period of continued use of a particular headgear. This line 30 can be referred to as the maximum force line 30. The actual force value may vary depending on characteristics of the particular headgear, such as contact area or type of material. A vertical distance between the target zone 28 and the maximum force line 30 represents a margin of error 32 for adjustment of a headgear force. As illustrated, the margin for error 32 is reduced for an interface having a larger projected seal area, such as a full face mask, in comparison with an interface having a smaller projected seal area, such as nasal pillows or a nasal mask. Accordingly, especially with larger projected seal area interfaces, it is desirable that a headgear be easily or conveniently capable of adjustment to within or close to the target zone 28. Conventional inelastic headgear incorporates relatively coarse adjustments, such as one or more adjustable loops that are secured with hook-and-loop fasteners. Such headgear can be difficult to adjust to within the target zone 28, especially in environments in which the wearer of the headgear is not the person making the adjustments, which often occurs in hospital settings, for example.

Figure 7:
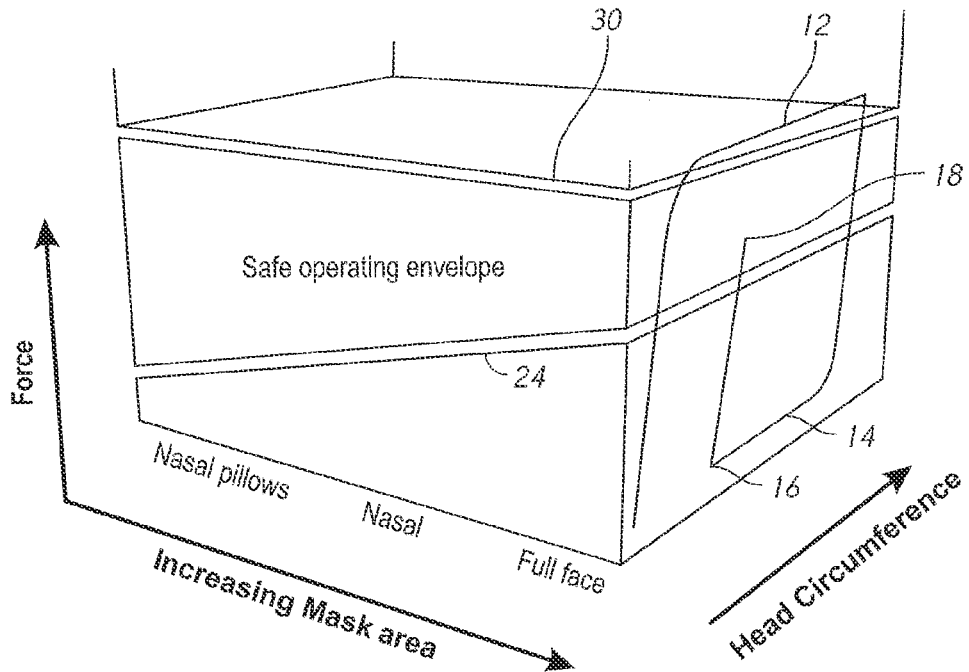
FIG. 7 is a three-dimensional graph of a relationship between headgear force, projected seal area and head circumference.

FIG. 7 illustrates a three-dimensional graph of a relationship between headgear force, projected seal area and circumference. The graph of FIG. 7 is a combination of the graph of FIG. 6 and the graph of FIG. 4. The graph of FIG. 7 illustrates the minimum force 24 for creating a seal between the interface and the user's face (the lower line 24 of the target zone 28 of FIG. 6). Below the minimum force line 24, the headgear force can be insufficient to create or maintain a seal. The graph of FIG. 7 also illustrates the maximum force line 30 above which skin damage is likely to occur. In between the minimum force line 24 and the maximum force line 30 is a safe operating envelope for the headgear force. The upper line of the target range is omitted for clarity.

The graph of FIG. 7 also illustrates a force-deflection curve of an example headgear. The force-deflection curve can be located within any plane along the projected seal area axis to illustrate design criteria for a headgear intended for use with a particular type of interface having a particular projected seal area. A headgear could also be designed taking into consideration the headgear forces and circumferences along a segment or an entirety of the projected seal area axis to design a headgear that will operate with multiple types of interfaces or that is universal for all types of interfaces (at least with respect to a particular therapy). In some configurations, as illustrated by the force-deflection curve in FIG. 7, the elongation portion 12 of the force-deflection curve can be located above the maximum force line 30.

In at least some configurations, headgear exhibiting a balanced fit or composite force-deflection curve, as described above, advantageously provides a retention force that falls within the safe operating envelope and, preferably, within the target zone. In at least some configurations, such headgear automatically adjusts to a suitable retention force within the safe operating envelope and, preferably, within the target zone. Thus, under-tightening or over-tightening by the user or by another can be reduced or eliminated.

As described above, the example headgear system performs several functions in the process of fitting, using and removing an interface or mask system. For fitment, the headgear system extends in length to enable it to be placed over a user's head. The headgear system retracts in length during the "fitment" process and provides sufficient force to the mask system such that the user feels that the mask system is secure. Once airway pressure is applied, the headgear system "transforms" in performance from an elastic or stretchy behaviour to one of inelastic behaviour. The headgear system also provides for micro-adjustment to tighten or loosen the mask based on the user's preference during use. For removal, the headgear system extends in length to enable it to be removed over a user's head. The combination of one or more, including all, of these features provides a mask system that requires minimal user interaction to fit and remove. This removes the potential for misuse and may help with improved usability of the mask system. The example headgear system can also mitigate the effects of excess pressure on the skin by reducing the probability, or even the possibility, of over-tightening of the head gear. The example headgear system can improve the overall compliance with the therapy. An additional feature to this is one which has a high degree of positional location and stability. This is both in terms of the activities of removal and refitting of the mask and during its use. Disclosed herein are one or more concepts for achieving a repeatable and stable positioning of the headgear and associated interface assembly on a patient or user's head. Also disclosed herein are one or more concepts for achieving a headgear system that supports transformational behaviour by providing portions that can selectively be made either elastic or inelastic and portions that provide an inelastic behaviour.

Figure 8B:
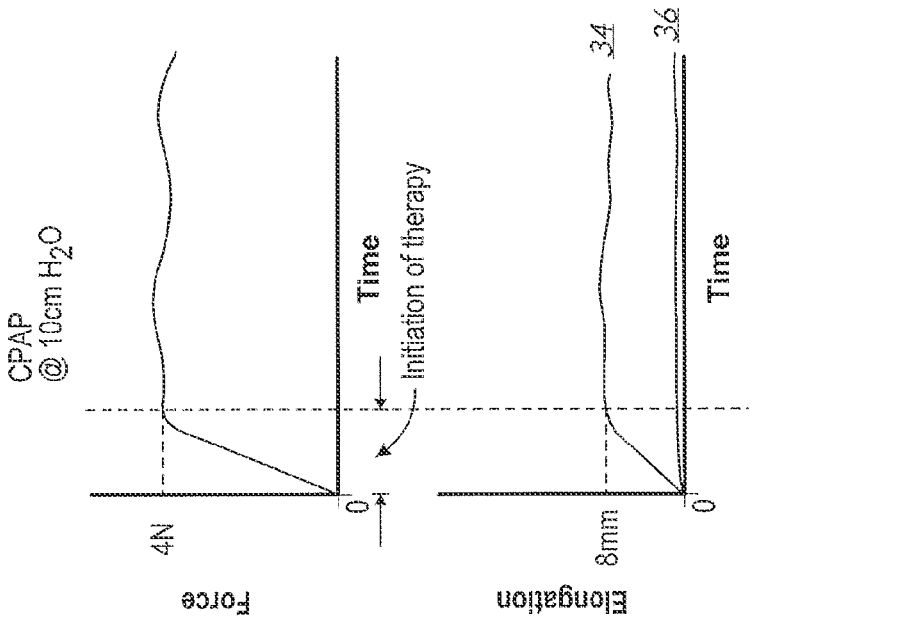
FIG. 8B shows a force profile and elongation profile of a variable pressure therapy for elastic and inelastic headgear systems.

FIGS. 8A and 8B illustrate the force profiles of constant pressure therapy and variable pressure therapy, respectively, along with associated elongation behaviour of elastic and inelastic headgear systems in graphical form for a full face mask. FIG. 8A includes two graphs of force and elongation, respectively, induced in the headgear over time with application of constant pressure therapy, such as CPAP at 10 cm of H2O. The upper graph illustrates the force that is induced in the headgear by the combination of the applied gas pressure and the mask enclosure area or, simply, the mask area. Despite the constant delivery pressure of the therapy, the force curve includes small oscillations that result from the user breathing and causing pressure changes within the mask. The lower graph illustrates the resulting elongation or movement in the headgear system and, thus, the mask body as the result of the forces applied. There are two elongation lines 34, 36 shown in the lower, elongation graph. The first line 34 illustrates the elongation behavior of a state-of-the-art elastic headgear, which elongates in response to the application of force. In the illustrated example, the elastic headgear elongates about 8 mm at the CPAP pressure compared to the length without CPAP pressure. The second line 36 illustrates the elongation behavior of the state-of-the-art inelastic headgear. As illustrated, the inelastic headgear exhibits very little elongation in response to applied force.

FIG. 8B similarly includes a graph of force and elongation, respectively, induced in the headgear over time with the application of oscillatory or variable pressure therapy, such as NIV or Bi-level PAP. For example, the illustrated therapy varies between a pressure of about 5 cm of H2O (e.g., expiratory positive airway pressure—EPAP) and about 12 cm of H2O (e.g., inspiratory positive airway pressure—IPAP). The upper graph illustrates the force that is induced in the headgear by the combination of the applied gas pressure and the mask enclosure area or, simply, the mask area. The lower graph illustrates the resulting elongation or movement in the headgear system and, thus, the mask body as the result of the forces applied. There are two elongation lines 34, 36 shown in the elongation graph. The first line 34, illustrates the elongation behavior of a state-of-the-art elastic headgear, which elongates and contracts along with increases and reductions in applied force. In the illustrated example, the elastic headgear elongates moves between about 4 mm and about 12 mm (at low pressure and high pressure, respectively) in response to the variable force curve compared to the length without CPAP pressure. Typical practice to reduce or prevent this movement is to over tighten the headgear system such that the force required elongate the headgear is greater than which is being produced by the combination of mask area and ventilation pressure. The application of this practice frequently leads to skin damage and the resulting wound care practices. The second line 36 illustrates the elongation behavior of the state-of-the-art inelastic headgear, which, as in FIG. 8A, exhibits very little elongation, but has the above-described limitations and drawbacks.

As shown in the example, state-of-the-art headgear systems when used with a full face mask, and which have not been over tightened, will elongate in length such that the mask body would move about 8 mm to about 12 mm during the change from peak inspiratory pressure to end expiratory pressure for NIV or IPAP to EPAP for bi-level ventilation. In at least some configurations, the present directional locking headgear systems exhibit behavior similar to the inelastic headgear in response to application of force in a direction tending to elongate the headgear. However, such configurations of the directional locking headgear systems exhibit one or more benefits of elastic headgear (e.g., automatic size adjustment or automatic fit) without the drawbacks associated with inelastic headgear (e.g., time-consuming and difficult adjustment). In at least some configurations, a headgear system incorporating a directional locking arrangement provides headgear elongation or mask movement of less than about 4 mm in response to applied force during therapy compared to a condition as applied to the user but without system pressure. In some configurations, a headgear system incorporating a directional locking arrangement provides headgear elongation or mask movement of less than about 4 mm between a high or maximum therapy pressure condition and a low or minimum therapy pressure condition (e.g., peak inspiratory pressure and end expiratory pressure for NIV).

The functional behaviour of the example headgear system involves the various headgear elements having elongation properties in design-specific locations, so that the elasticated or stretching behaviour can be switched on and off on demand, preferably with one or more of the directional locks and/or directional friction mechanisms disclosed herein. This can involve various features of the headgear being configured to deliver specific performance attributes in specific locations. With patient interfaces used in respiratory applications, the location of these features can depend on the interface type and the number of retention planes that are desired. A retention plane can be defined as a plane or planes through which forces that are generated in the interface assembly are resolved.

Figures 9, 10:
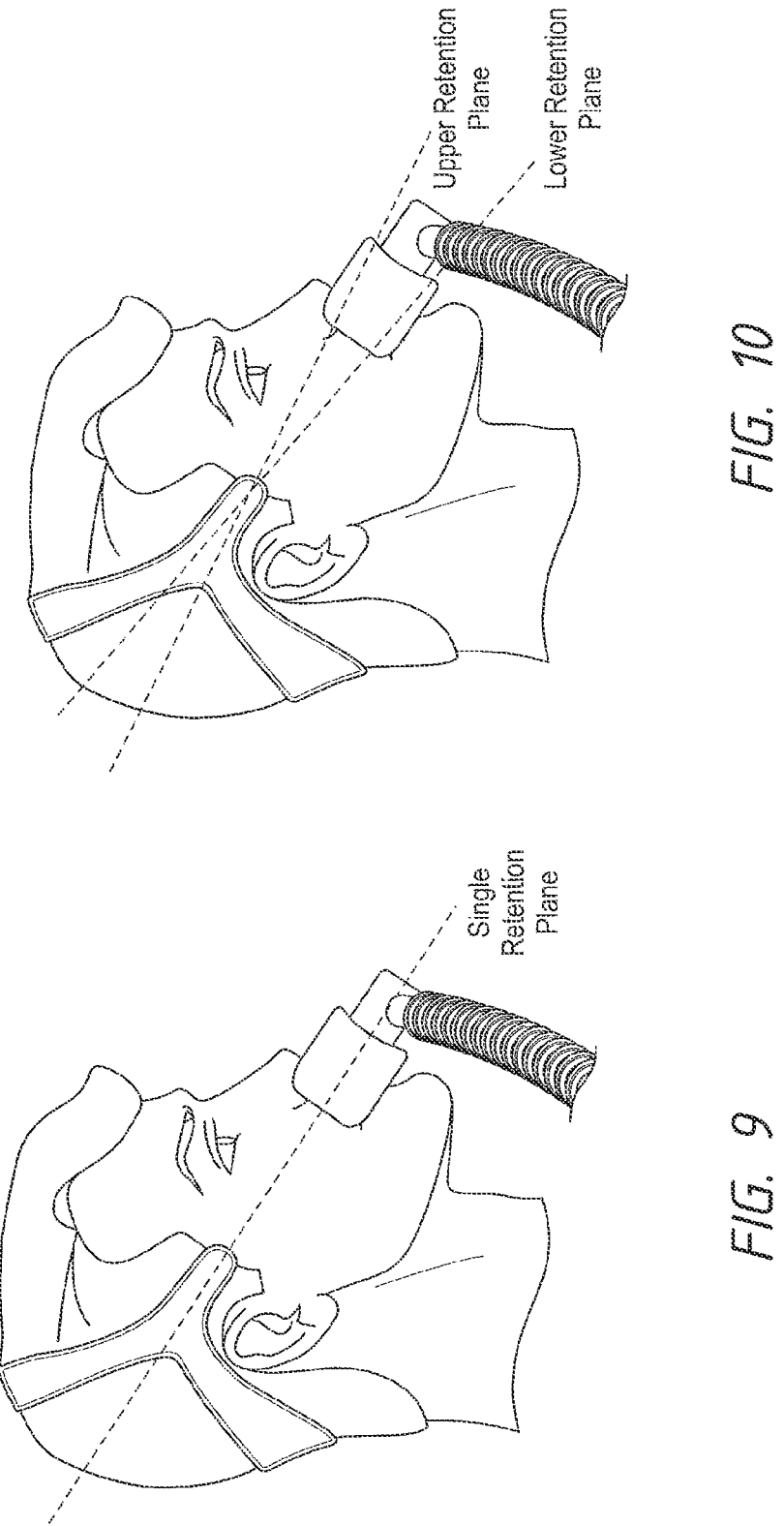
FIG. 9 is a side view of a nasal interface having a single retention plane.
FIG. 10 is a side view of a nasal interface having two retention planes.

For example, FIG. 9 illustrates a nasal interface, such as a nasal pillows mask, nasal mask or nasal cannula having a single retention plane. A first line extends between a mounting point on a first side of the nasal interface and a mounting point on the first side of a rear portion of the headgear. A second line extends between a mounting point on a second side of the nasal interface and a mounting point on the second side of the rear portion of the headgear. The first line and the second line cooperate to define the single retention plane. The retention plane can extend through or near a center of the nasal interface, which can be a geometric center or vertical center, for example. In some configurations, the retention plane can be off-center, such as in configurations in which it may be desirable to apply a bias force (e.g., upper or lower bias) to the nasal interface. The retention plane can extend generally from a location at or near (e.g., somewhat below) the underside of the user's nose to a location close to but somewhat above the user's ear. Such an arrangement may cause the retention plane to have an upward tilt in a front-to-back direction.

FIG. 10 illustrates a nasal interface, such as a nasal pillows mask, nasal mask or nasal cannula having multiple (e.g., two) retention planes. As described with respect to FIG. 9, each retention plane is defined by lines on each side of the interface assembly, which lines extend between points on the nasal interface and a rear portion of the headgear. In the arrangement of FIG. 10, the retention planes are offset from one another to define an angle in a front-to-back direction or from a side view. In the illustrated arrangement, a first retention plane extends through a relatively upper point on the nasal interface and a second retention plane extends through a relatively lower point on the nasal interface. The first and second retention planes can extend through a single point on the rear portion of the headgear (or very near one another) or can be spaced apart on the rear portion of the headgear, with the planes intersecting one another (crossing one another) between the nasal interface and the rear portion of the headgear or can be spaced apart between the nasal interface and the rear portion of the headgear. In the illustrated arrangement, the first retention plane is positioned at or near an upper edge of the inlet, breathing tube connector or gases conduit connector and the second retention plane is positioned at or near a lower edge of the inlet, breathing tube or gases conduit. In some configurations, the retention plane(s) can extend along a physical portion of the headgear or interface assembly. However, in other configurations, the retention plane(s) may not extend along a physical portion of the headgear or interface assembly. That is, for example, the retention plane(s) may not be aligned with a strap of the headgear.

Figure 11:
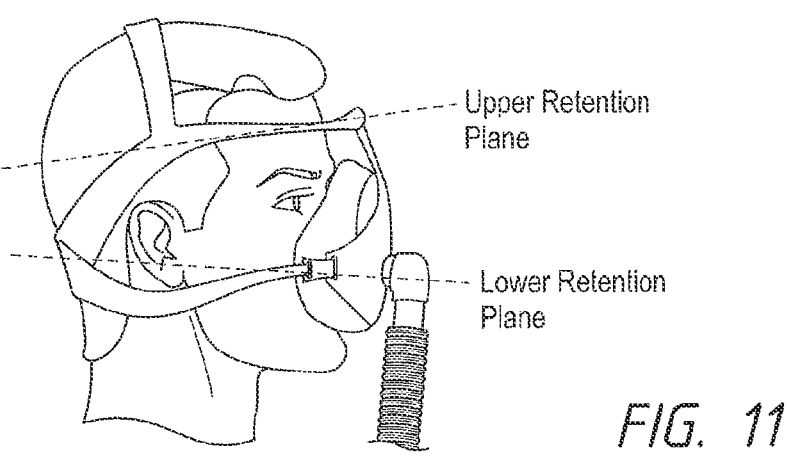
FIG. 11 is a side view of a full face mask having two retention planes.

Other types of interface assemblies can similarly utilize retention planes between the interface and a rear portion of the headgear. For example, FIG. 11 illustrates a full face mask having two retention planes. The illustrated full face mask includes an upwardly-extending frame portion or T-piece, which extends from a lower portion of the mask toward or to the user's forehead. In the illustrated arrangement, a first or upper retention plane extends between the T-piece and an upper location on a rear portion of the headgear. The upper retention plane can extend above the user's eyes and cars. The upper retention plane can be generally horizontal, but can be tilted somewhat in a front-to-back direction. For example, the upper retention plane can be tilted somewhat downward in a front-to-back direction to pass between the user's forehead and a center or rearward-most point on the back of the user's head. A second or lower retention plane extends between a base portion of the mask and a lower location on the rear portion of the headgear. The lower retention plane can extend between a point at about the user's mouth to a point below the user's ear. The lower retention plane can be generally horizontal, but can be tilted somewhat in a front-to-back direction. For example, the lower retention plane can be tilted somewhat upward in a front-to-back direction. The upper retention plane can extend along an upper strap of the headgear. The lower retention plane can extend generally along a lower strap of the headgear; however, the lower strap can be curved to accommodate the user's ear such that the lower retention plane overlies end portions of the lower strap, but does not overlie at least an intermediate portion of the lower strap. In other configurations, one or both of the upper and lower retention planes can partially or fully overlie an associated strap, can be partially or fully spaced from an associated strap or any combination of the two.

Figure 12:
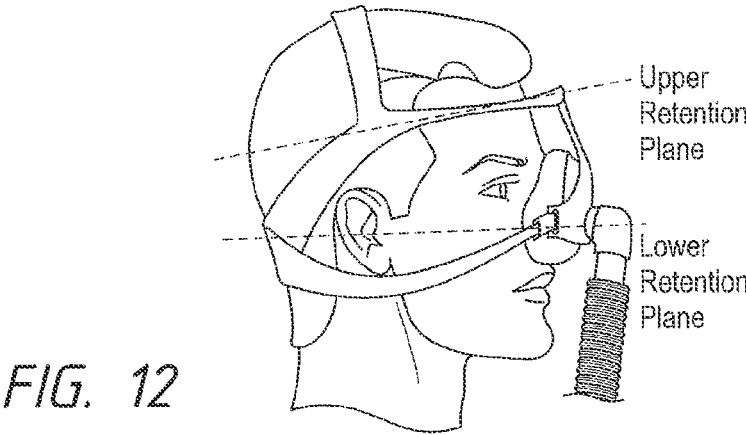
FIG. 12 is a side view of a nasal mask having two retention planes.

FIG. 12 illustrates a nasal mask having two retention planes. Similar to the full face mask of FIG. 11, the illustrated nasal mask includes an upwardly-extending frame portion or T-piece, which extends from a lower portion of the mask toward or to the user's forehead. In the illustrated arrangement, a first or upper retention plane extends between the T-piece and an upper location on a rear portion of the headgear. The upper retention plane can extend above the user's eyes and cars. The upper retention plane can be generally horizontal, but can be tilted somewhat in a front-to-back direction. For example, the upper retention plane can be tilted somewhat downward in a front-to-back direction to pass between the user's forehead and a center or rearward-most point on the back of the user's head. A second or lower retention plane extends between a base portion of the mask and a lower location on the rear portion of the headgear. The lower retention plane can extend between a point at about the user's nose to a point aligned with or below the user's ear. The lower retention plane can be generally horizontal, but can be tilted somewhat in a front-to-back direction. For example, the lower retention plane can be tilted somewhat downward in a front-to-back direction. The upper retention plane can extend along an upper strap of the headgear. The lower retention plane can extend between forward and rearward end portions of a lower strap of the headgear. The illustrated lower strap can be curved to accommodate the user's ear such that the lower retention plane does not overlie an intermediate portion of the lower strap. In either of the interface assemblies of FIGS. 11 and 12, the lower retention plane can pass through an inlet, breathing tube connector or gases conduit connector of the interface, such as through or near a center of the inlet or connector.

Figure 13:
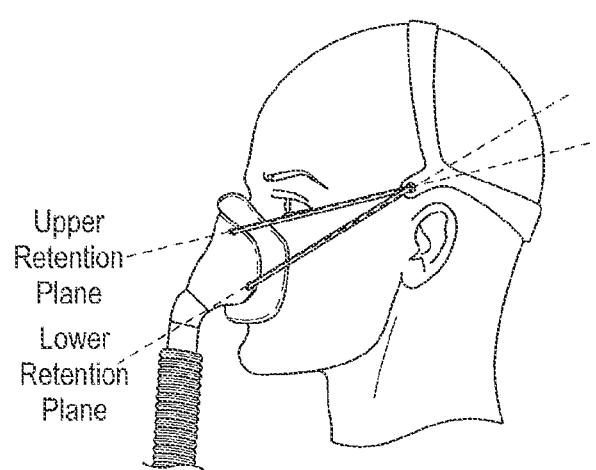
FIG. 13 is a side view of a mask having two retention planes that converge to a single point.

FIG. 13 illustrates an alternate arrangement that is applicable to a either a full face mask or a nasal mask in which there are two retention planes that converge to a single point within the head gear system. The retention planes can be vertically spaced from one another on the interface to provide some degree of stability to the interface. For example, in a full face mask, an upper retention plane can pass through or above the underside of the nose of the user and a lower retention plane can pass near or below the mouth of the user. In a nasal mask, the upper retention plane can pass above the underside of the nose of the user and the lower retention plane can pass below the underside of the nose of the user. The retention planes can intersect at a point generally above and/or forward of the ear of the user. The portions of the interface assembly coupling the mask to a rear portion of the headgear can be separate or interconnected, such that a single adjustment can at least potentially alter a length of both upper and lower portions. The length ratio of the upper and lower portions can be easily adjusted by moving the point of the interconnected portions that is located at the headgear connection point. The illustrated full face mask does not include a forehead rest or "T-piece." However, in some configurations, a T-piece could be provided. If desired, additional headgear element(s) or strap(s) could couple a rear portion of the headgear to the T-piece of the mask.

FIG. 13.1 is a chart that identifies a number of general categories of headgear types on the basis of the number and/or relative positioning of retention planes. The chart also identifies a number of interface types and provides an indication of the desirability or practicality of the resulting combinations of headgear type and interface type. Because of the automatic fit of at least some of the headgear assemblies disclosed herein, it is possible that a single headgear type can be utilized with multiple types of interfaces. Examples of possible combinations are described with reference to FIG. 13.1. The headgear types are listed from top to bottom in order of those that provide relatively less stability to those that provide relatively more stability, at least in certain configurations, such as those in which little to no external source of resistance to rotation of the interface is provided. The headgear types listed in the chart of FIG. 13.1 is not exclusive. Other headgear types may be used with the concepts disclosed herein, including modifications and hybrids of the illustrated headgear types.

In general, more stable headgear configurations can be universal or can provide at least an acceptable level of support to many or all interface types, or at least those interface types illustrated. In contrast, less stable headgear configurations may not be capable of providing a desirable or acceptable level of support to all interface types, at least without specific provisions to increase the stability of such inherently less stable configurations. In general, larger interfaces require or benefit from headgear that provides greater stability. It is often desirable or sometimes necessary to provide at least two retention planes for larger interfaces, such as full face masks. It can be advantageous for the two retention planes to be separated from one another in a vertical or height direction of the interface at the interface (e.g., at the points of attachment to the interface). In general, for a given headgear arrangement, the further the separation of the retention planes at the interface, the more stable the configuration. In some configurations, it can be advantageous for at least one of the retention planes to include an upward vector component.

One example headgear type provides a single retention plane. An example of such an arrangement is discussed herein with reference to FIG. 9. In general, single retention plane headgear can be impractical for use with full face interface types because the single retention plane headgear does not provide a desirable level of stability to the mask. Thus, the headgear may be able to secure the mask in place and maintain a seal, but the mask may be permitted to move and break the seal with relative ease or the interface assembly, although operable, may not provide a secure feeling to the user. In some cases, single retention plane headgear may not provide an acceptable level of stability to the mask. However, it is possible that some configurations of a single retention plane headgear could be suitable for use with a full face mask. For example, a single retention plane headgear utilizing rigid materials and/or configurations (e.g., shapes) could be suitable for use with a full face mask by providing resistance to rotation of the mask about a lateral axis. In addition, a single retention plane headgear can be suitable for use with a full face mask with careful location of the single retention plane relative to the full face mask, as illustrated in and described below with respect to FIG. 13.2. A single retention plane interface may be suitable or practical for use with nasal interfaces, such as nasal masks, nasal pillows or prongs and cannula.

FIG. 13.2 illustrated a single retention plane interface assembly comprising a headgear assembly and an interface, which is in the form of a full face mask. The illustrated mask omits a forehead rest or T-piece; however, in other configurations a T-piece could be provided. The headgear assembly includes a headgear rear portion and a headgear length or perimeter adjusting portion that allows adjustment of a position of the mask relative to the headgear rear portion. The single retention plane can extend from the mask to the headgear rear portion at a location above the user's ear, for example.

Forces acting on the mask can be summarized as a blow-off force created by pressure within the mask acting on the sealed area of the user's face and attempting to move the mask away from the user's face, a headgear force acting on the mask to resist the blow-off force, a force applied by the user's face along the contact area between the mask and the user's face, and a gravity force that acts on the mass of the mask and CPAP hose. The force applied by the user's face can be summarized by an upper force and a lower force. The upper force can be a force located at or near the nasal bridge of the user's nose ("nasal bridge force"), which can be generally the highest point or region of contact in a vertical direction. The lower force can be a force located at or near the chin of the user ("chin force"), which can be generally the lowest point or region of contact in a vertical direction.

The distributed gravity force can be summarized as a single point force ("gravity force") acting on the mask and CPAP hose at a center of gravity, which may be determined by the particular size and shape of the mask. In some configurations, the single retention plane extends between or passes through a point between the chin force and the blow-off force in a vertical direction.

The distributed blow-off force can be summarized as a single point force ("blow-off force") acting on the mask at a particular location, which may be determined by the particular size and shape of the mask and/or the specific shape of the user's face. The blow-off force can be located generally in a lower half of the mask height, such as at or near a geometric center of the mask. Assuming a generally triangular mask, the blow-off force can be located at approximately ⅓ of the height from the bottom of the mask. In some configurations, the single retention plane extends between or passes through a point between the chin force and the blow-off force in a vertical direction. Advantageously, such an arrangement can provide a desirable level of stability for a full face mask with a single retention plane. However, this arrangement can be applied to a multi-retention plane arrangement, as well, with the additional retention plane(s) providing additional stability.

The nasal bridge area can be a sensitive anatomical area and it can be desirable to avoid excessive force or pressure in this area. Thus, if the nasal bridge force is zero or minimal, the headgear force can be the only force countering the blow-off force. If the headgear force passes through a point vertically higher than the blow-off force, the nasal bridge force will be increased, which is generally undesirable. If the headgear force is too low, or too close to the chin force, the headgear force may not be able to counter the blow-off force or may provide an undesirably low level of counteraction of the blow-off force such that the scaling performance of the interface assembly is compromised. As described herein, preferably the retention plane comprises directional lock arrangement that provides an appropriate resistance to elongation of the headgear in response to the blow-off force. In combination with positioning of the retention plane as described herein, the resultant interface or headgear assembly can provide a suitable level of stability for a full face mask with a single retention plane type headgear. As with other headgear assemblies described herein, proper stability can be achieved without over-tightening of the headgear, which often occurs with prior art headgear arrangements.

Another example headgear type provides two retention planes that converge at a forward location (i.e., toward or at the interface). As used in herein in connection with FIG. 13.1, the term "converge" is intended to describe retention planes that lack substantial separation from one another at the interface or attachment locations. It is possible that the retention planes may meet at a single attachment point; however, convergent headgear types may also include those in which the retention planes are attached next to or close to one another. A two retention plane, forward converge headgear type can be suitable or at least somewhat practical for use with a full face headgear, because the additional retention plane may provide sufficient additional stability relative to a single retention plane headgear. As described with respect to single retention plane headgear types, the two retention plane, forward converge headgear type can employ rotation-resisting materials and/or configurations to provide improved performance with full face masks. A two retention plane, forward converge headgear type may be suitable or practical for use with nasal interfaces, such as nasal masks, nasal pillows or prongs and cannula.

Yet another example headgear type provides two retention planes that converge at a rearward location (i.e., away from the interface, such as at a rear portion of the headgear). A two retention plane, rearward converge headgear type can provide a sufficient level of stability to be suitable or practical for use with full face masks and with nasal masks. Examples of such a headgear type are shown and described herein in connection with FIGS. 10 and 13 with a nasal interface and a full face interface, respectively. A two retention plane, rearward converge headgear type may be less practical for use with pillows or prongs interface types because such interface types typically have a relatively small vertical or height dimension. The small height of pillows and prongs interface types can limit the ability to space the attachment locations of the retention planes on the interface and provide triangulation of the retention planes, at least without increasing the height dimension above what is required, which can be undesirable because pillows and prongs are often elected by users precisely due to their relatively small height dimension. A two retention plane, rearward converge headgear type may be impractical for use with cannula because it is not necessary to create a scaling force for a cannula. Thus, a two retention plane headgear type can be excessive for use with cannula. In addition, a two retention, rearward converge headgear type can be impractical for use with cannula for the same reasons as pillows and prongs. Cannula generally have an even smaller height dimension than pillows and prongs. However, in at least some configurations or under some circumstances, it may be practical or even desirable to use a two retention plane, rearward converge headgear type with pillows, prongs or cannula.

Still another example headgear type provides two retention planes that are separated and angled relative to one another or are non-parallel. In some configurations, the upper retention plane can be angled upward in a forward to rearward direction. The lower retention plane can be generally horizontal or angled. In other configurations, the lower retention plane can be angled in either direction. The upper retention plane can be generally horizontal or angled. A two retention plane, separated/angled headgear type can provide a sufficient level of stability to be suitable or practical for use with full face masks and with nasal masks. A two retention plane, separated/angled headgear type may be less practical for use with pillows or prongs interface types because such interface types typically have a relatively small vertical or height dimension for the reasons described above with respect to two retention plane, rearward converge headgear types. Similarly, a two retention plane, separated/angled headgear type may be impractical for use with cannula for the same reasons as pillows and prongs, as described above.

Another example headgear type provides two retention planes that are relatively, generally or substantially horizontal or parallel with one another. Examples of such two retention plane, parallel headgear types are shown and described in connection with FIGS. 11 and 12. A two retention plane, parallel headgear type can provide a sufficient level of stability to be suitable or practical for use with full face masks and with nasal masks. A two retention plane, parallel headgear type may be less practical for use with pillows or prongs interface types because such interface types typically have a relatively small vertical or height dimension for the reasons described above with respect to two retention plane, rearward converge headgear types. A two retention plane, parallel headgear type may be impractical for use with cannula for the same reasons as pillows and prongs, for the reasons described with respect to two retention plane, rearward converge headgear types.

Positioned or otherwise configured to act along at least one of the retention planes or lines is at least one mechanism or feature ("locking mechanism") that provides the ability to transform the function of the head gear from an elongating behaviour to a non-elongating behaviour. Along this plane, the directional locking functionality may be configured to operate as a single mechanism for the given retention plane or, preferably, to provide two independent locking mechanisms. The single mechanism arrangement is capable of varying the circumference or perimeter length of the headgear or interface assembly. The two locking mechanism arrangement (e.g., one mechanism on each side of the headgear or interface assembly) provides independent left and right control for fine adjustment for the fitting of the mask or other interface. In other arrangements, more than two locking mechanisms can be provided. In such arrangements, multiple locking mechanisms can be provided on each side of the headgear or interface assembly. Alternatively, the locking mechanisms can be otherwise located (e.g., one on each side and additional mechanism(s) on the top and/or rear) and can cooperate to allow for adjustment of the circumference or perimeter length of the headgear or interface assembly.

In some configurations, at least one locking mechanism is provided on each side of the interface assembly between the mask (or other interface) and a rear portion of the headgear. In some configurations, such as a full face mask 210 with forehead support or T-piece as illustrated in FIGS. 14 and 15, the mask 210 is connected to a rear portion of the headgear 220 by upper and lower connecting portions in the form of straps 230, for example, on each side of the interface assembly 200. The arrangements of FIGS. 14 and 15 illustrate a number of example locations where the locking feature or mechanism 240 can be located. In the illustrated arrangements, the interface assembly 200 includes an elasticated retraction feature or mechanism 250 in combination with or which acts in cooperation with the directional locking mechanism 240. The elasticated retraction mechanism 250 and the directional locking mechanism 240 can be integrated into a module, which can be referred to herein as a directional lock module or, simply, a module. In the arrangements shown, the directional locking mechanism 240 can be positioned at a connection between the headgear 220 and the mask 210, such as incorporated into an attachment fixture 260 (e.g., clip) to the mask body as illustrated in FIG. 14. Alternatively, as illustrated in FIG. 15, the directional locking mechanism can be positioned at a suitable location within the headgear 220, such as between a rear portion of the headgear 220 and the strap portions 230 connecting the rear portion of the headgear 220 with the mask 210, as illustrated in FIG. 15. Similar arrangements can be utilized in other configurations that use multiple retention planes.

In some arrangements, the directional locking mechanism or module utilizes a lock coupled to or otherwise movable with one portion of the interface assembly and an adjustment member coupled to or otherwise movable with a second portion of the interface assembly. The adjustment member can move relative to the lock to allow adjustment of the circumference or perimeter length of the headgear or interface assembly. The adjustment member can be in form of a core member, which can be a wire or filament or can be a strap, for example. A portion of the adjustment member is utilized to define a portion of the circumference or perimeter length at any given size adjustment of the interface assembly and another portion may be excess or surplus length that is not utilized at the given adjustment size. The surplus length will change along with changes in the circumference or perimeter length of the headgear or interface assembly. The accumulation of the surplus length can be accommodated by any suitable arrangement, such as accommodated within the mask frame or within an integral component within the headgear system.

FIGS. 16 and 17 illustrate arrangements that are applicable to nasal interfaces 300, such as nasal masks 310, (with or without a forehead rest or T-Piece, but often without a forehead rest or T-piece) or nasal cannula. In these arrangements, the directional locking mechanism 340 can incorporate or operate on a flat strap 330 or web, as discussed above.

The use of the flat strap 330 is especially beneficial in applications in which the force vectors between the pressurised mask seal and the headgear are not aligned. This results in a situation where moments are generated which preferably are sufficiently resolved through rigidity within the headgear system. This is achievable by the selection of the torsional rigidity and bending rigidity characteristics of the headgear straps, the combination of which significantly increases the level of rotational stability for the mask system.

In situations in which a straight line between the mounting point on the headgear and the mounting point on the mask 410 provides an acceptable location for a headgear component or a component that provides a connection between the mask and a rear portion of the headgear 420, the use of a flexible core design 430 may be desirable, as illustrated in FIG. 17. That is, unless constrained into a modified shape, the flexible core will assume a straight line between mounting points. Thus, flexible core designs are well-suited for use in arrangements in which a straight line path for the directional locking mechanism 440 (e.g., between the rear portion of the headgear 420 and the mask 430) is a desirable or acceptable location for the mechanism 440.

In some arrangements, the flat strap arrangement and the flexible core arrangement may be used in combination, such as in applications in which two or more retention planes are desirable or required. For example, the arrangements of FIGS. 11 and 12 or the arrangements of FIGS. 14 and 15 could utilize a flat strap arrangement along one of the upper or lower retention planes and a flexible core arrangement along the other of the upper or lower retention planes. In some configurations, the lower strap may be configured to use the flat strap arrangement and the top strap may be configured to use the flexible core arrangement. For instance, as illustrated, the lower strap may have a curved shape along its length to pass below and provide space to accommodate the user's ear. The upper strap, however, can be generally straight along its length. In some configurations, the upper strap can utilize a flat strap arrangement and the lower strap can utilize a flexible core arrangement. For example, the rear portion of the headgear can be configured to locate the mounting point such that a straight line between the headgear mounting point and the mounting point on the mask is appropriately located. Furthermore, as shown in FIG. 18 and FIG. 20, the use of a flat or relatively rigid headgear portion to aid in torsional or bending stability along the sides of the user's head, when connected in series with a flexible core arrangement, enables flexibility with the positioning of the directional locking mechanism.

A significant performance benefit of the directional locking-type of headgear system or interface assembly occurs when used in connection with respiratory ventilation patterns in which there is either a high constant pressure or a variable pressure waveform, such as non-invasive ventilation or bi-level ventilation, because the headgear system does not elongate during use or the circumference or perimeter length of the interface assembly remains constant. As described above, current state-of-the-art headgear arrangements can be generally categorized into elastic or inelastic systems. As described, inelastic systems can accommodate high constant pressure or variable pressure; however, such systems are prone to over-tightening and are difficult and time-consuming to adjust. Current state-of-the-art elastic headgear systems tend to elongate in response to high constant pressure or elongate and retract in response to pressure waves in a variable pressure waveform. Such elongation and retraction results in cyclic movement of the mask on the user's face, which can result in leaks. Leaks, in turn, can lead to loss of therapy and/or false triggering of breaths due the resulting volume and related pressure change within the mask. Furthermore, cyclic movement of the mask can result in abrasions and, potentially, skin damage due to movement or migration of the mask on the user's face.

Figures 18, 19, 20:
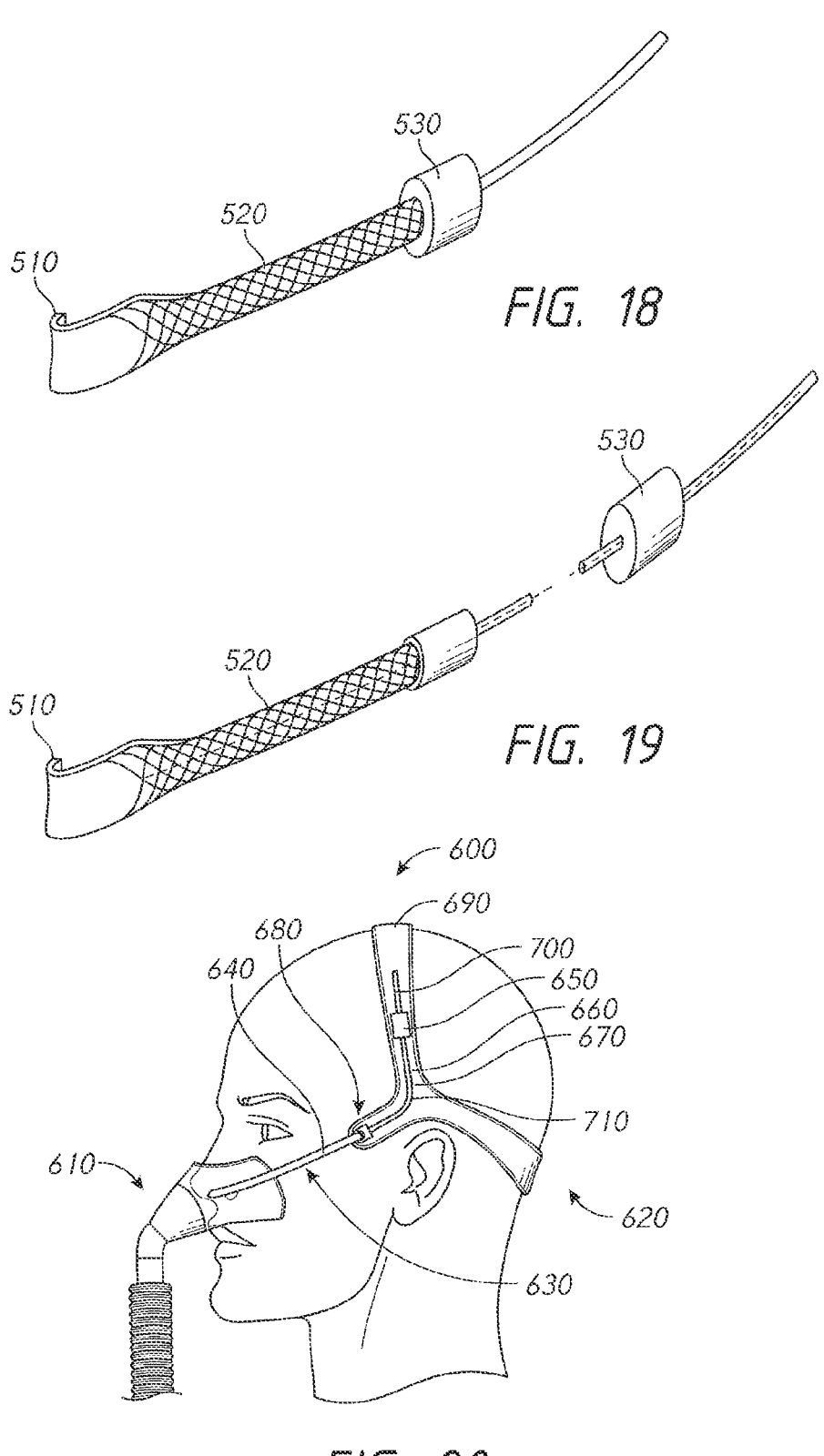
FIG. 18 illustrates a module of an interface assembly configured to extend between a mask or other interface and a rear portion of headgear that incorporates a directional lock arrangement.
FIG. 19 illustrates an alternate module of an interface assembly configured to extend between a mask or other interface and a rear portion of headgear that incorporates a directional lock arrangement that is spaced from a biasing arrangement.
FIG. 20 is a side view of an exemplary interface assembly.

FIGS. 18 and 19 illustrate examples of a portion or module of an interface assembly configured to extend between a mask or other interface and a rear portion of the headgear that incorporates a directional lock arrangement. Each of the illustrated module arrangements comprise a detachable clip 510 that defines a coupling between the mask body and the overall headgear system, which includes the module. The module includes an elastic section 520 extending between the detachable clip 510 and the directional lock 530, which produces a contraction force tending to move the clip 510 and the directional lock 530 toward one another. The elastic section 520 can be of any suitable arrangement, such as a braided member with one or more elastic elements, for example. FIG. 18 illustrates a variant that has the directional lock 530 located at the rearward end of the elastic section 520 and/or at a connection point between the module and a rearward portion of the headgear, which would position the directional lock 530 spaced from the mask, such as in the locations shown in FIG. 15 and FIG. 17, for example.

FIG. 19 illustrates an alternative variant that locates the directional lock 530 at a spaced location from the module and/or the connection point between the module and a rear portion of the headgear. Such an arrangement can be referred to herein as a "remote" lock arrangement. In some configurations, the lock can be positioned elsewhere within the headgear system, such as within a rear portion of the headgear, with a hollow conduit bridging the distance between the connection point between the module and the rear portion of the headgear and the location of the directional lock. Such an arrangement offers the ability to position the directional lock at a more suitable or desirable location with the headgear system, such as the location shown in FIG. 20, for example.

With reference to FIG. 20, the interface assembly 600 includes a mask 610 or interface (such as a nasal interface in the illustrated arrangement) and a headgear arrangement comprising a rear headgear portion 620 that engages a rear and/or upper portion of the user's head. The interface assembly 600 also includes an adjustment portion 630 that permits adjustment of a distance between the mask 610 and the rear portion of the headgear 620. The adjustment portion 630 can be a portion of the headgear arrangement, a portion of the interface or can be a separate component of the interface assembly.

In the illustrated arrangement, the adjustment portion 630 comprises a stretchable material 640, which can be configured to return toward its un-stretched position. Thus, the stretchable material 640 can exhibit a contraction force tending to reduce a circumference or perimeter length of the interface assembly. In some configurations, the stretchable material 640 is a braided material incorporating non-stretch and stretch elements. The non-stretch elements can provide a hard stop or maximum extension and the stretch elements can provide the contraction force. In other configurations, the stretch elements 640 or other biasing arrangement can be located remotely from the stretchable material of the adjustment portion 630.

The illustrated interface assembly also comprises a transformational lock arrangement, such as a directional lock arrangement. The illustrated directional lock arrangement comprises a directional lock 650, a filament core 660 and a filament guide 670 or housing (e.g., conduit or tube). Such an arrangement allows the directional lock 650 to be spaced from or remote from an attachment location 680 between the adjustment portion 630 and the rear headgear portion 620. In addition, the filament arrangement allows the directional lock 650 to be located in a non-linear arrangement with the adjustment portion 630. In other words, a functional axis of the directional lock 650 can be offset or angled relative to an axis of the adjustment portion 630 and/or a retention plane of the interface assembly 600.

The filament housing 670 can extend between the directional lock 650 and the attachment location 680 between the adjustment portion 630 and the rear headgear portion 620. In the illustrated arrangement, the filament housing 670 follows a curved path between the directional lock 650 and the attachment location 680 between the adjustment portion 630 and the rear headgear portion 620. For example, the directional lock 650 can be located on a crown strap 690 of the rear headgear portion 620 and the filament housing 670 can curve upwardly at a point rearward of the attachment location 680 onto the crown strap 690. The directional lock 650 can be located at any desired point on the crown strap 690, including a side portion or an upper or top portion, for example. In other configurations, the directional lock 650 can be located on other portions or at other locations on the rear headgear portion 620, such on a side or back of a rear strap of the rear headgear portion 620. Such arrangements can allow the directional lock 650 to be provided in a location that is more desirable than the attachment point between the adjustment portion 630 and the rear headgear portion 620 (referred to as "remote" mounting herein). For example, positioning the directional lock 650 on the top of the crown strap 690 may avoid contact with other objects (e.g., pillow) under many circumstances (e.g., the user lying face up or on his or her side). The particular location of the directional lock 650 can be selected based on a variety of relevant factors, such as comfort, clearance (e.g., for eyeglasses), filament length, among others.

In some configurations, the filament housing 670 extends past the directional lock 650 to accommodate excess filament 660 that is not being utilized to carry a load within the interface assembly 600. A portion of the filament housing 670 beyond the directional lock 650 can be referred to as an accumulation portion 700 or accumulation conduit. A portion of the filament housing 670 between the directional lock 650 and the attachment location 680 between the adjustment portion 630 and the rear headgear portion 620 can be referred to as a connecting portion 710 or connecting conduit. Although illustrated as a tube herein, the filament housing 670 can be provided in other forms, as well, such as a filament guide, for example. A filament guide arrangement may not entirely enclose the filament, but may simply provide guide surfaces at particular, discrete locations to direct the filament along a desired path.

One or more adjustment portions and/or transformational lock arrangements can be provided on each side of the interface assembly. Portions of the transformational lock arrangements on opposing sides of the interface assembly can be integrated with one another or share components. For example, the accumulation portion of the filament housing can connect a directional lock on one side of the interface assembly with a directional lock on the other side of the interface assembly. In some configurations, a single housing can be provided on the top or back of the interface assembly and can contain two separate lock mechanisms, which interact with elements (e.g., filaments) associated with transformational lock arrangements on opposite sides of the interface assembly. Alternatively, separate transformational or directional lock housings associated with lock arrangements on opposite sides of the interface assembly could be positioned near one another (longitudinally or laterally adjacent) on a top or rear portion of the rear headgear portion, for example.

A headgear system that incorporates a transformational mechanism as disclosed enables a portion of the headgear to be selectively switched from inelastic-type behaviour to an elastic-type behaviour to provide for convenient fitting and removal has a number of user advantages. Example mechanisms to achieve this behavior are disclosed herein and in Applicant's Application No. PCT/NZ2014/000074, the entirety of which is incorporated by reference herein. In some configurations, one or more of the advantages relate to the ability to provide an auto-adjusting, self-sizing or more intuitive adjustment interaction for the user. In addition, in at least some configurations, the headgear systems incorporating a transformational mechanism as disclosed enables undesirable movement of the mask body to be reduced or minimized in comparison with state-of-the-art headgear systems, which are typically constructed from either laminations of elasticated materials with the addition of stitching or stitched components or from an elasticated knitted construction. With these prior designs, movement of the mask caused by either hose pull or the interaction of applied respiratory pressure with the mask is likely to occur. Such movement may result in conditions ranging from leaks, loss of therapy, false triggering of breath patterns due to the resulting volume and pressure changes to skin abrasion or potential skin damage. To counteract this movement, a common practice is to over-tighten the headgear (either by providing a high elastic force in elastic systems or manual over-tightening in adjustable inelastic systems), such that the force required to elongate the headgear is greater than that which is produced by either hose pull or that generated via the pressurization of the mask. The application of additional pressure to the user as a result of this excess tightening can result in user discomfort, skin irritation or skin damage.

Due to the functionality of one or more of the auto-fit or transformational headgear systems disclosed herein, the elasticated behavior can be constrained to specific areas of a headgear system, where it is selectively switched on or off depending on usability conditions, rather than being a generic property of the headgear. This creates the opportunity to "engineer" the remaining portions of the headgear system to deliver specific performance attributes. In at least some configurations, a principal result of the combination of an engineered, transformational headgear system is to provide a behavior in which there is little to no movement in the mask body when in use.

Figures 21, 22:
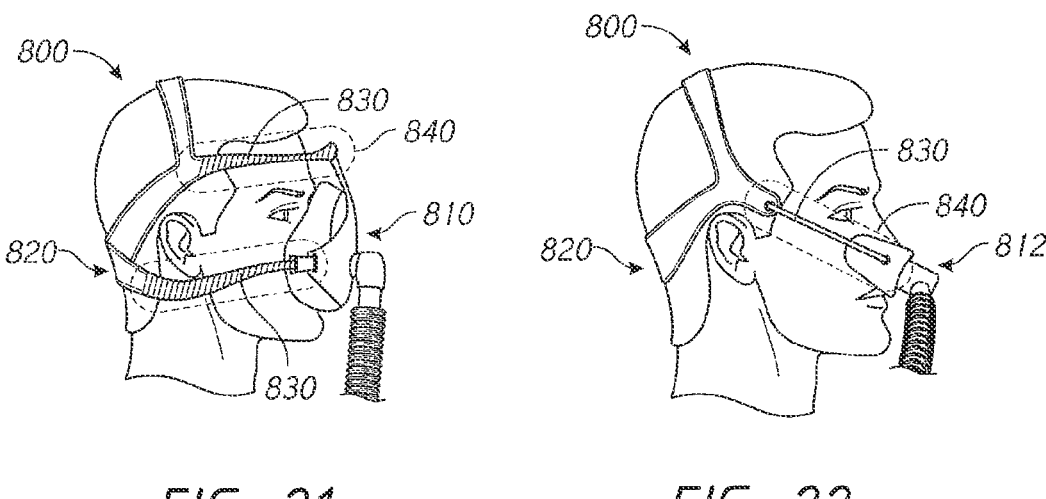
FIG. 21 is a side view of an exemplary full face mask.
FIG. 22 is a side view of an exemplary nasal pillows mask.

FIGS. 21 and 22 illustrate example headgear systems 800 for a full face mask 810 (FIG. 21) and a nasal pillows mask 812 (FIG. 22). The indicated areas 840 illustrate presently preferred locations for the portions where the selectable elastic/inelastic functionality exists. In each application, the selectable elastic/inelastic portion 830 is positioned between the mask 800 and a rear portion of the headgear system 820 and extends along the sides of the user's head. The remaining rear portion of the headgear system ideally is a relatively rigid three-dimensional (3D) structure, which has very little elastic behaviour in the force ranges encountered during normal or anticipated use. To achieve such behavior, in some configurations, both the form of the headgear and the material construction have a significant impact.

Form

Figures 23, 24:
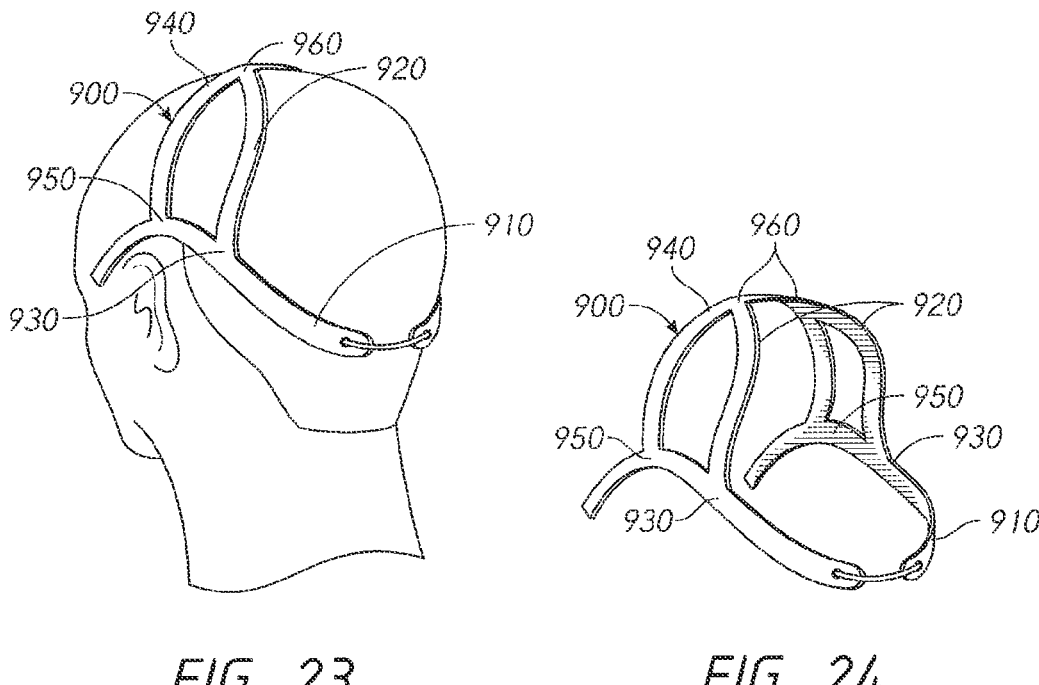
FIG. 23 is a rear perspective view of an exemplary headgear assembly positioned on a user.
FIG. 24 is a rear perspective view of the exemplary headgear assembly in FIG. 23.

Referring to FIGS. 23 and 24, the use of a top or crown strap 940 and a strap passing around the back of the user's head (rear strap 910) as disclosed herein utilizes the geometry of the human head to provide repeatability with fitment location and to provide stability of the headgear 900 when in use. Additional design features can be added to this basic crown strap 940 and rear strap 910 arrangement to further enhance these desirable properties, namely, the addition of a gusset 920 or web that links the rear or lower strap 910 to the crown strap 940, as illustrated in FIGS. 23 and 24. The addition of the gusset 920 or web member(s) reduce the relative movement between the rear and crown straps 910, 940, resulting in a more laterally stable design.

The gussets 920 can be attached to the rear strap 910 and the crown strap 940 at any suitable location. The attachment points 930, 960 of the gusset 930 on the rear strap 910 and the crown strap 940 can be can be substantially equidistant or equidistant from a junction 950 between the rear strap 910 and the crown strap 940 or can be spaced at different distances from the junction 950. In the illustrated arrangement, the gusset 920 attaches to the crown strap 940 at a distance further from the junction 950 than a distance from the junction 950 at which the gusset 920 is attached to the rear strap 910. The distance from the junction 950 to the gusset 920 on the crown strap 940 can be approximately twice or more than the distance from the junction 950 to the gusset 920 on the rear strap 910. In the illustrated arrangement, a distance between the attachment points 960 of the gussets 920 on each side of the headgear 900 can be less than a distance between the junction 950 and the attachment point 960 of one of the gussets 920 on the crown strap 940. That is, the length of the distance between gussets 920 on the crown strap 940 is less than one-third of the overall length of the crown strap 940. The rear strap 910 and/or crown strap 940 can be continuous or can be interrupted. Sections of an interrupted rear or crown strap 910, 940 can be connected by a suitable coupling, which can be a fixed length, elastic or adjustable.

Construction/Fabrication

Figures 25, 26, 27, 28, 29:
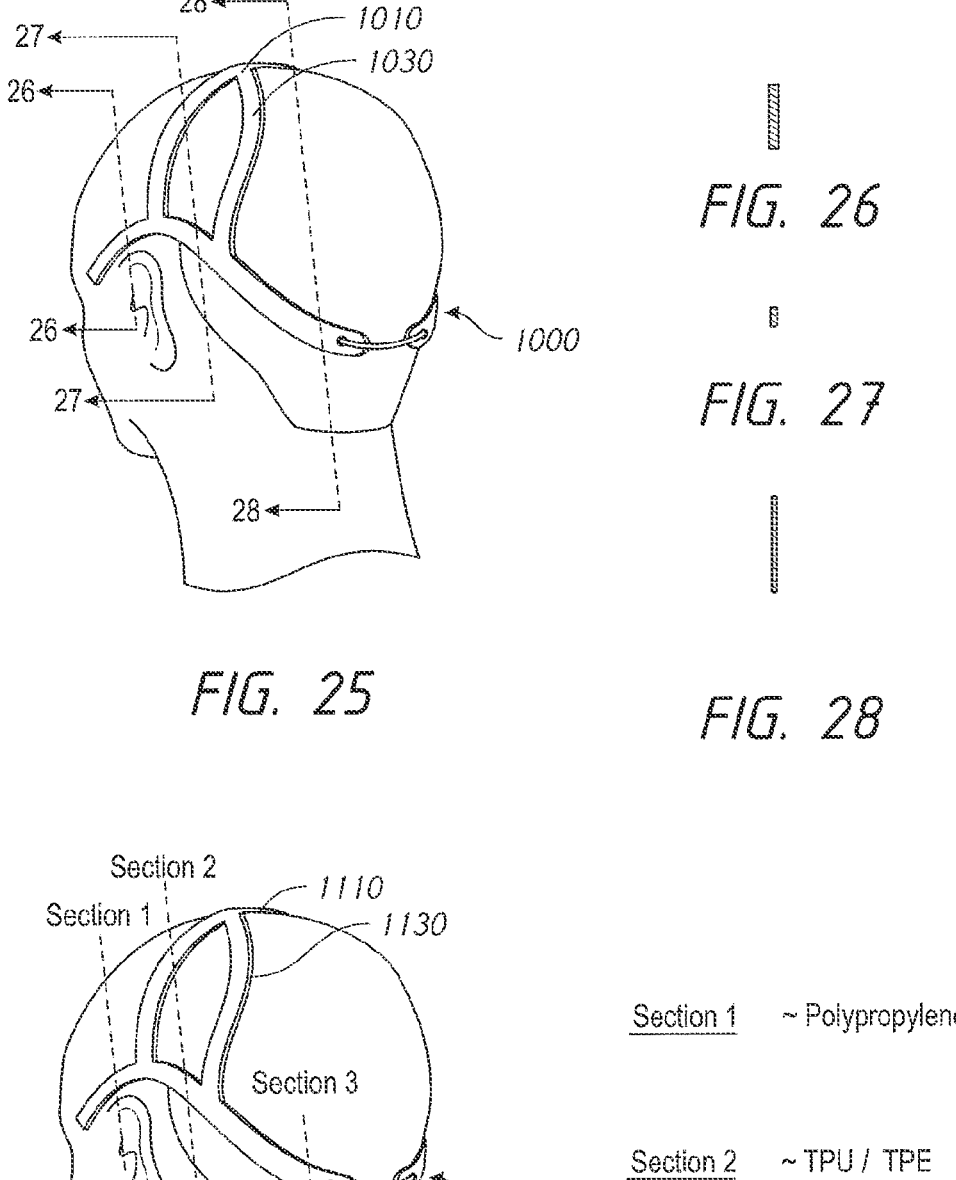
FIG. 25 is a rear perspective view of an exemplary headgear assembly on a user.
FIG. 26 is a sectional view of the exemplary headgear assembly along a line 26-26 in FIG. 25.
FIG. 27 is a sectional view of the exemplary headgear assembly along a line 27-27 in FIG. 25.
FIG. 28 is a sectional view of the exemplary headgear assembly along a line 28-28 in FIG. 25.
FIG. 29 is a rear perspective view of an exemplary headgear assembly illustrating portions of the exemplary headgear constructed from various material types.

The overall form of the headgear can be produced by a number of different techniques. For example, the headgear can be cut from a single sheet of at least relatively or substantially inelastic material. In other configurations, the headgear can be injection molded from a single or multiple thermoplastic or thermoset materials. In some configurations, the headgear or head frame is constructed from a single material with variations in cross sectional geometry providing portions of increased or decreased torsional and/or bending stiffness to enable the headgear to smoothly contour to the human head form, as illustrated in FIGS. 25-28. In other configurations, the headgear can be constructed by co-molding or multi-molding different materials in various portions to achieve the same or similar behaviour, as illustrated in FIG. 29.

The various portions of the headgear can be constructed to have desirable properties in desirable portions or areas of the headgear. For example, for the portion extending over the user's ear (section 1), it can be desirable to provide limited flexibility such that bending movement about a lateral axis or torsional movement about a longitudinal axis is limited. The portions rearward of section 1 (sections 2 and 3) desirably conform closely to the shape of the human head. Desirably, each of the sections 1, 2 and 3 exhibit relatively inelastic behaviour in force ranges normally encountered or expected in use. To achieve such behavior, various combinations of materials can be used. In the illustrated example, thermoplastic elastomers or thermoplastic urethanes of various shore hardness's are used to achieve the desired behaviours.

As described above, the headgear can comprise various portions having various cross-sectional dimensions such that the properties of the headgear can be varied in different areas of the headgear. With reference to FIGS. 25-28, a rear headgear portion, which ends generally forward and above the user's ears is shown and referred to simply as the headgear 1000. Three vertical sections of the headgear 1000 are illustrated. Section 1 is taken in a portion of the headgear 1000 that extends above and forward of the user's ear. Section 2 is taken in a portion of the headgear 1000 that is rearward of section 1 and can be generally positioned rearward of the user's ear. In the illustrated arrangement, section 2 is located between the crown strap 1010 and the gusset 1030. Section 3 is taken in a location of the headgear rearward of section 1 and section 2. In the illustrated arrangement, section 3 is taken in a location on the back portion of the headgear 1000, which can contact the back of the user's head.

Preferably, the portion containing section 1 is relatively tall to provide resistance to vertical bending loads, which would attempt to move a forward end of the headgear 1000 in a vertical direction. In the illustrated arrangement, the portion containing section 1 has a greater height than the portion containing section 2. In some configurations, the portion containing section 3 has a greater height than the portion containing section 2. In some configurations, the portion containing section 3 has a greater height than the portion containing section 1. A portion of the headgear 1000 at the rear of the user's head (e.g., the portion containing section 3) typically applies a greater force to the user's head as a result of directly opposing the blow-off force of the interface. As a result, it can be preferable to enlarge the area of the rear portion by providing the rear portion with a relatively large height to improve user comfort. In the illustrated configuration, the height at section 1 is about 10 mm, the height at section 2 is about 3 mm and the height at section 3 is about 15 mm. In other configurations, other dimensions can be used. For example, the dimensions may be different, but the headgear 1000 can retain the same height ratio between any or all of sections 1, 2 and 3. In other configurations, the dimensions may vary by a specific number (e.g., 1 mm, 2 mm or 3 mm) or by a percentage either taller or shorter than the illustrated dimensions. In some configurations, the height of the headgear 1000 changes gradually between the sections 1, 2 and 3. The actual height at any point on the headgear 1000 can be selected to address appropriate performance parameters, such as resistance to bending, force distribution and fit or clearance considerations.

In some configurations, the headgear 1000 can decrease in thickness in a direction from a forward end toward a rearward end. For example, the portion containing section 1 can have a thicker cross-section relative to the portion containing sections 2 and 3 such that the portion containing section 1 (a forward end portion) has a greater resistance to torsional loads. In addition, the portion containing section 2 can have a thicker cross-section relative to the portion containing section 3. Thus, the portion containing section 2 has a greater resistance to torsional loads than the portion containing section 3. In some configurations, the difference in thickness between the portion containing section 1 and the portion containing section 2 is greater than the difference in thickness between the portion containing section 2 and the portion containing section 3. The reduced thickness of the portions containing sections 2 and 3 allow those portions to bend in a transverse direction to better conform to the particular shape of the user's head. In the illustrated arrangement, the thickness at section 1 is about 1.5 mm, the thickness at section 2 is about 1 mm and the thickness at section 3 is about 0.8 mm. In other configurations, other dimensions can be used. For example, the dimensions may be different, but the headgear 1000 can retain the same thickness ratio between any or all of sections 1, 2 and 3. In other configurations, the dimensions may vary by a specific number (e.g., 0.1 mm, 0.2 mm or 0.3 mm) or by a percentage either thicker or thinner than the illustrated dimensions. In some configurations, the thickness of the headgear 1000 changes gradually between the sections 1, 2 and 3. The actual thickness at any point on the headgear 1000 can be selected to address appropriate performance parameters, such as resistance to torsional loads and lateral flexibility to improve fit.

With reference to FIG. 29, as discussed above, the headgear 1100 could alternatively or additionally vary in material type throughout the headgear 1100 to provide different properties in different portions of the headgear 1100. The headgear 1100 of FIG. 29 illustrates three sections taken at three different locations within the headgear 1100, which can be the same as or substantially the same as the locations of the headgear 1100 of FIGS. 25-28. The portion containing section 1 can be constructed of a first material or combination of materials, such as polypropylene, for example. Similar to the headgear 1000 of FIG. 25-28, the material selection for the portion containing section 1 can take into consideration a desire to provide resistance to bending in a vertical direction. The material or combination of materials of the portion containing section 2 can be different than the material(s) of one or both of the portions containing sections 1 and 3. For example, the portion containing section 2 can be constructed of a second material or combination of materials, such as a combination of thermoplastic polyurethane (TPU) and thermoplastic elastomer (TPE). The material or combination of materials of the portion containing section 3 can be different than the material(s) of one or both of the portions containing sections 1 and 2. For example, the portion containing section 3 can be constructed of a third material or combination of materials, such as TPE. Considerations in material selection for the different portions of the headgear 1100 can be the same as or similar to the considerations described with respect to dimensional selection in FIGS. 25-28.

In some configurations, the material selection results in the headgear 1100 having a different durometer or hardness in different portions. For example, the portion containing section 1 can have the highest durometer. In some configurations, the portion containing section 1 can have a durometer of about 65-70 shore D. The portion containing section 2 can have a durometer that is less than the durometer of the portion containing section 1. In some configurations, the portion containing section 2 has the lowest durometer of the portions containing sections 1, 2 and 3. For example, the portion containing section 2 can have a durometer of about 70 shore A. The portion containing section 3 can have a durometer that is between the durometers of the portions containing sections 1 and 2. For example, the portion containing section 3 can have a durometer of about 40 shore D. Considerations in hardness selection for the different portions of the headgear 1100 can be the same as or similar to the considerations described with respect to dimensional selection in FIGS. 25-28. Variations in hardness can be achieved by material selection or other methods, such as manipulation of the material, for example.

Combinations of these techniques are also possible. For example, two or more of the dimensions, material and hardness can be selected to provide varying properties throughout the headgear. In some cases, the headgear is in a 3D form that contours to the human head, behaves in a substantially non-elasticated manner and provides a stable connection point for the transformational lock arrangement.

The material selection for one or more portions of the headgear can involve other considerations, as well. For example, in some configurations, a portion or the entire headgear can comprise a material that exhibits little or no tendency to absorb moisture. In some configurations, a portion or the entire headgear can comprise a material that exhibits water vapor permeability. Advantageously, with such configurations, the headgear can avoid or prevent the absorption of moisture, such as sweat, or can allow moisture to move through the headgear material. Either configuration can improve comfort for the user.

The headgear can be further enhanced by the integration of textile-based lining or padding to either or both of the interior or exterior surfaces to engineer the textural and/or tactical properties of the headgear. In some configurations, hair pull and/or the detectable edge of the headgear by the wearer is reduced or minimized. When lining or padding is provided on only one side of the headgear (interior or exterior), or is otherwise distinguishable between sides (e.g., different color on the interior than on the exterior), the feature assists with usability of the overall device as it provides visual clues to the user regarding orientation of the headgear for fitment.

In some configurations, the headgear can comprise one or more adjusters that permit the headgear to be adjusted in size. For example, an adjuster can be provided in a strap portion of the headgear to allow a length of the strap portion to be adjusted. An adjuster could also be provided between strap portions to allow a relative position of the strap portions to be adjusted. In some configurations, the adjusters are self-adjusting or permit self-adjusting of the headgear. As used herein, self-adjusting refers to adjusters that allow adjustment of the headgear from a first position (e.g., a first length or relative position) to a second position (e.g., a second length or relative position) and retains the headgear in the second position without manipulation (e.g., manual locking) by a user. In some configurations, the adjusters can comprise biasing elements or arrangements. For example, the adjuster can comprise a biasing arrangement that tends to bias the strap portions in a first direction (e.g., toward a reduced length). Thus, the adjusters can simply allow a user to manipulate the headgear and then automatically secure the headgear in the desired position or the adjusters can assist in moving the headgear toward an appropriate fit position and then automatically secure the headgear in the appropriate fit position. Such adjusters can comprise any of the transformational locking arrangements disclosed in Applicant's Application No. PCT/NZ2014/000074.

FIGS. 30 and 31 illustrate examples of locations in which an automatic adjuster can be positioned within the headgear 1200. For example, an automatic adjuster can be positioned at location 1200A, which is at or near a junction between a top or crown strap portion and a circumferential portion or upper portion that is located above the user's ear. An automatic adjuster can be positioned at location 1200A on each side of the headgear 1200. An automatic adjuster at location 1200A can allow a relative position of the upper portion of the headgear 1200 to be adjusted relative to the crown strap 1210, such as in a forward-rearward direction. Alternatively, an automatic adjuster at location 1200A can allow a circumferential length of a portion of the headgear 1200 to be adjusted. In other words, a length of the upper portion of the headgear 1200 can be adjusted by an automatic adjuster at location 1200A. An automatic adjuster can be positioned at location 1200B, which is within the top or crown strap 1210. An automatic adjuster at location 1200B can allow a length of the crown strap 1210 to be adjusted. An automatic adjuster can be positioned at location 1200C, which is within a rear or lower portion of the headgear 1200. A single automatic adjuster can be positioned within the rear portion or an automatic adjuster can be provided within each side of the lower portion of the headgear 1200. An automatic adjuster at location 1200C can permit a circumferential length of the lower portion of the lower portion of the headgear 1200 to be adjusted.

Automatic adjusters can be positioned in any one, any combination or all of the locations 1200A, 1200B and 1200C, and/or elsewhere within the headgear. In some configurations, the provision of automatic adjusters is to allow the rear headgear portion to be adjusted to fit the user's head. Thus, such automatic adjusters can be in addition to the transformational locking arrangements between the rear headgear portion and the interface, which can be configured to adjust the relative position of the interface and the rear headgear portion, as well as apply an appropriate sealing or retention force to the interface.

Figure 34:
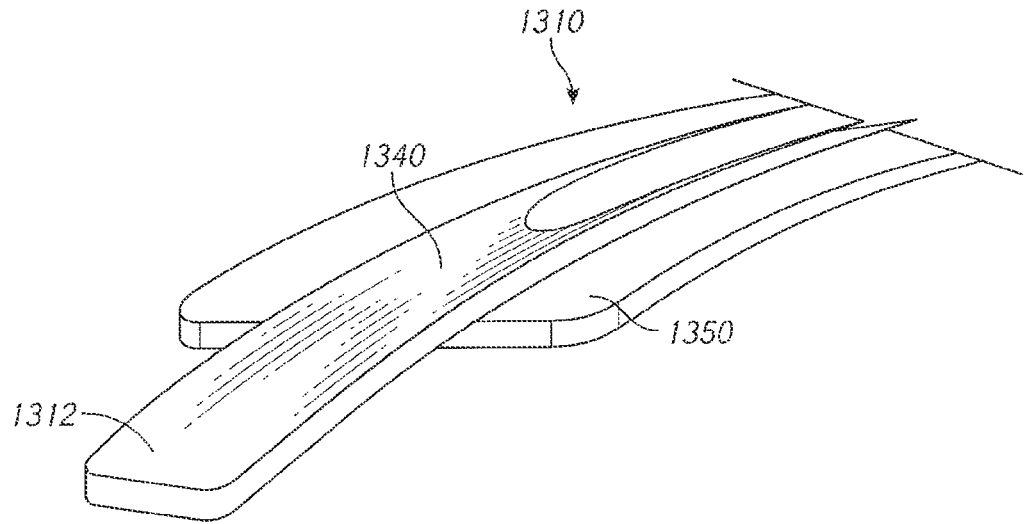
FIG. 34 is a perspective view of the second portion of the exemplary strap adjustment mechanism in FIG. 32.
Figure 40:
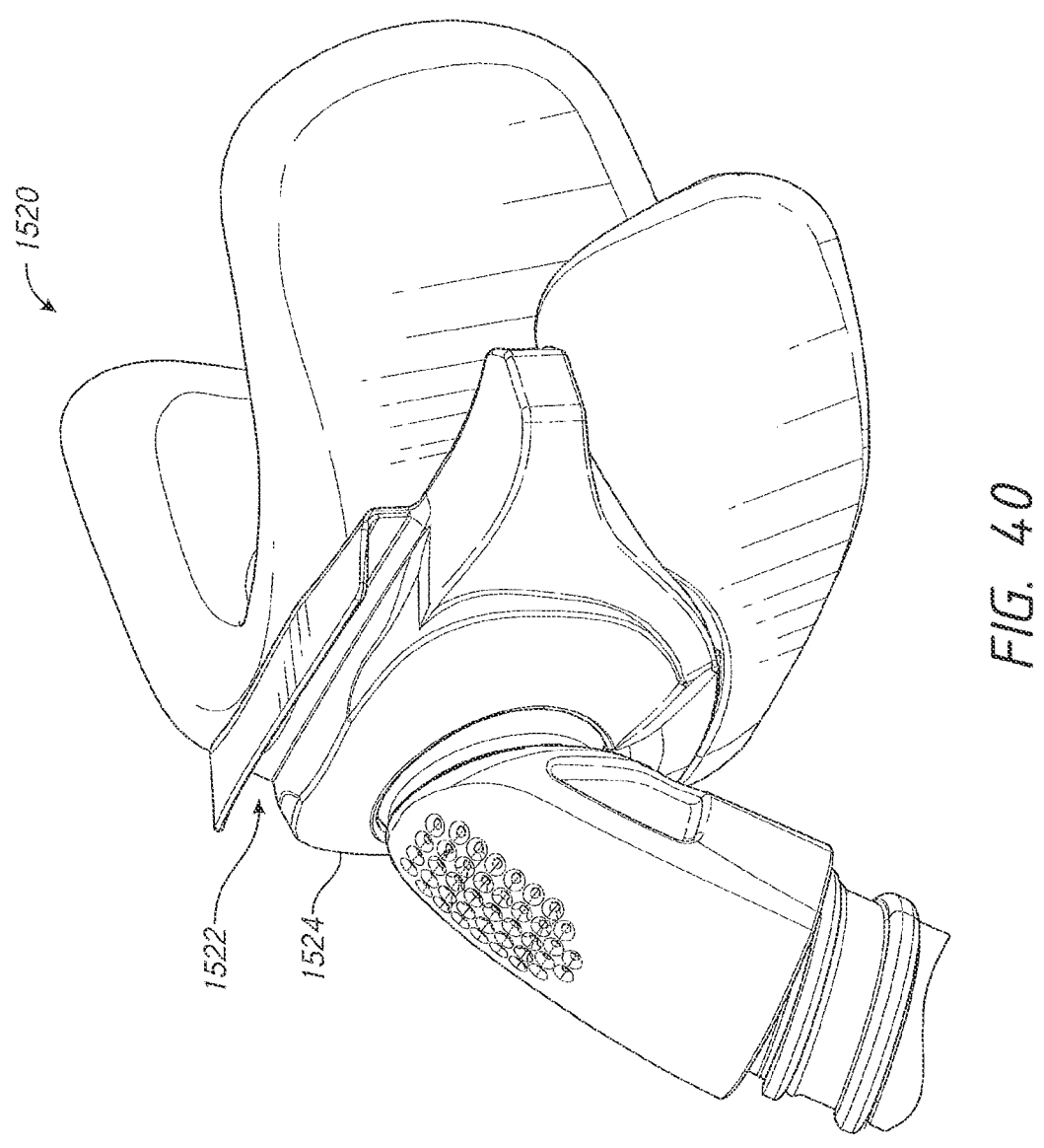
FIG. 40 is a perspective view of an exemplary interface assembly.
Figure 41:
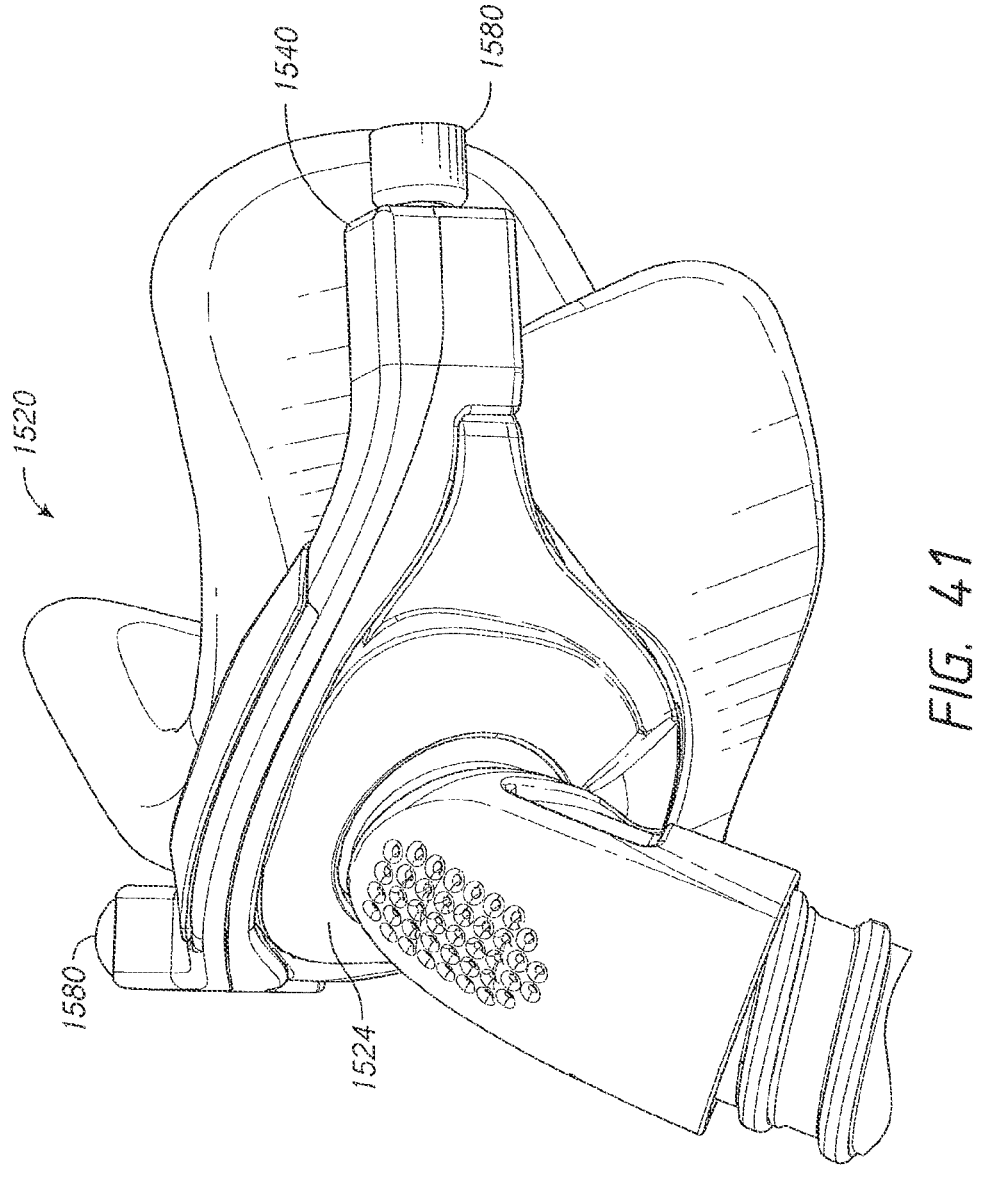
FIG. 41 is a left-side perspective view of an exemplary interface assembly attached to an interface coupling portion.
Figure 42:
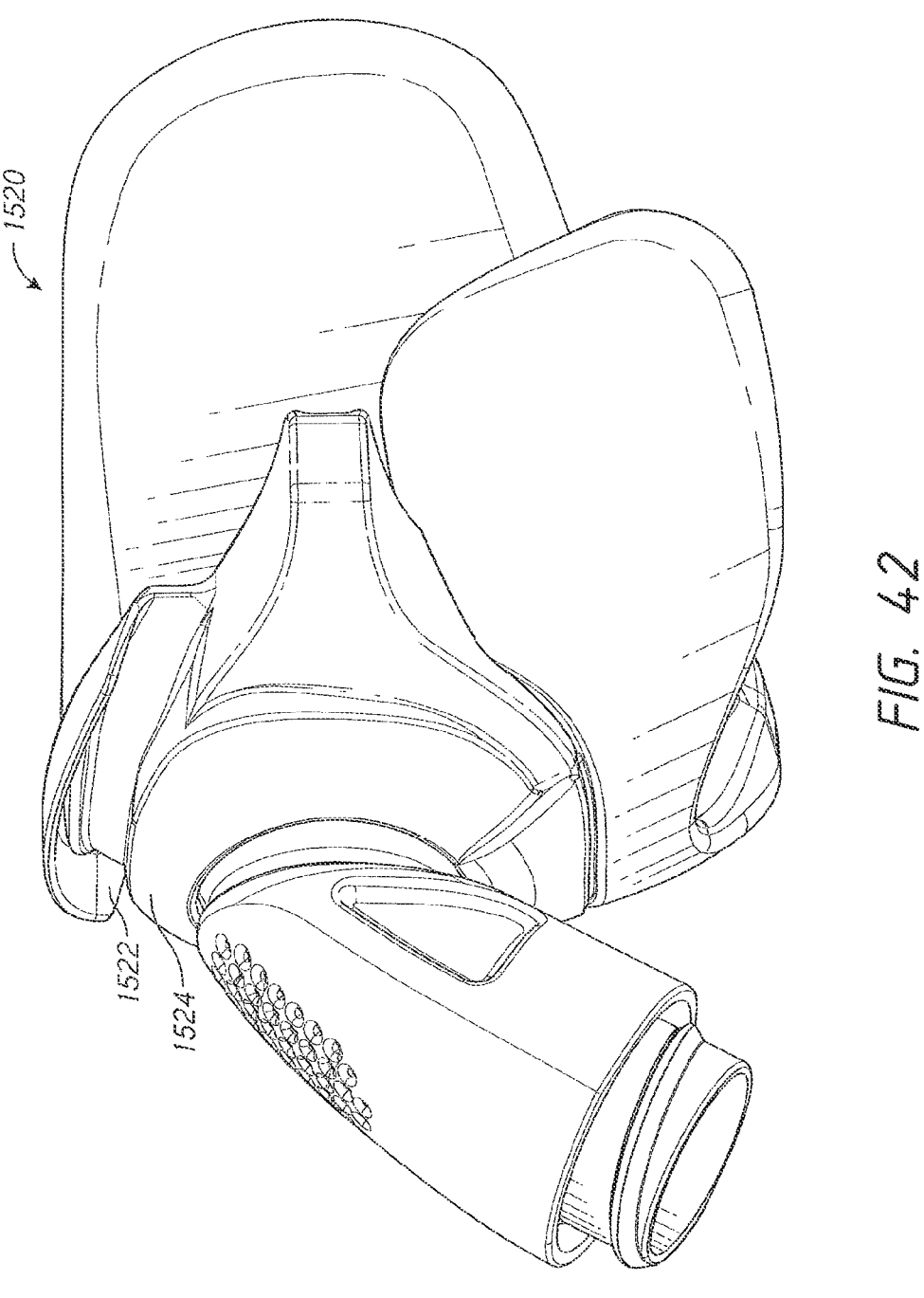
FIG. 42 is a side view of an exemplary interface assembly.
Figure 43:
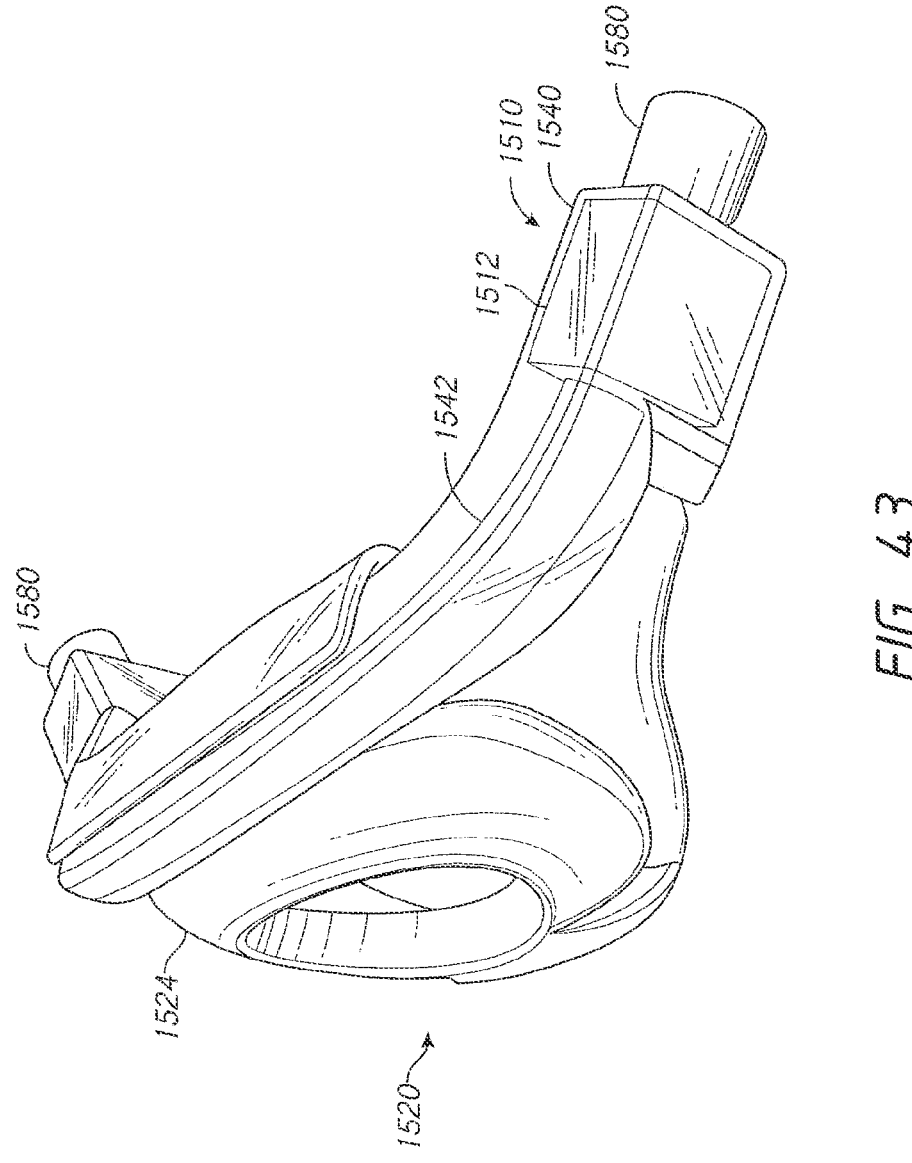
FIG. 43 is a perspective view of a frame element of an interface member attached to an interface coupling portion.
Figure 44:
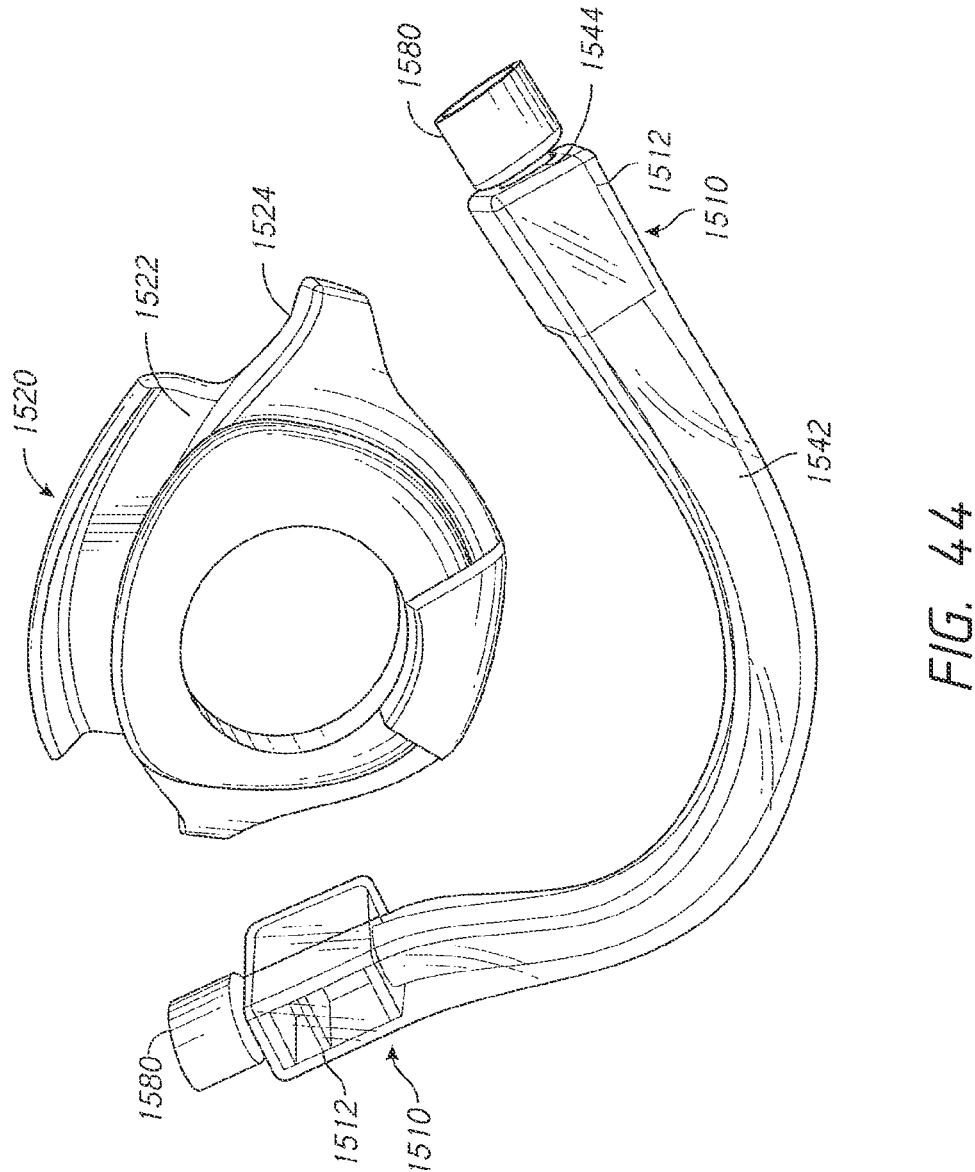
FIG. 44 is a front view of a frame element of an interface member and an interface coupling portion.
Figure 45:
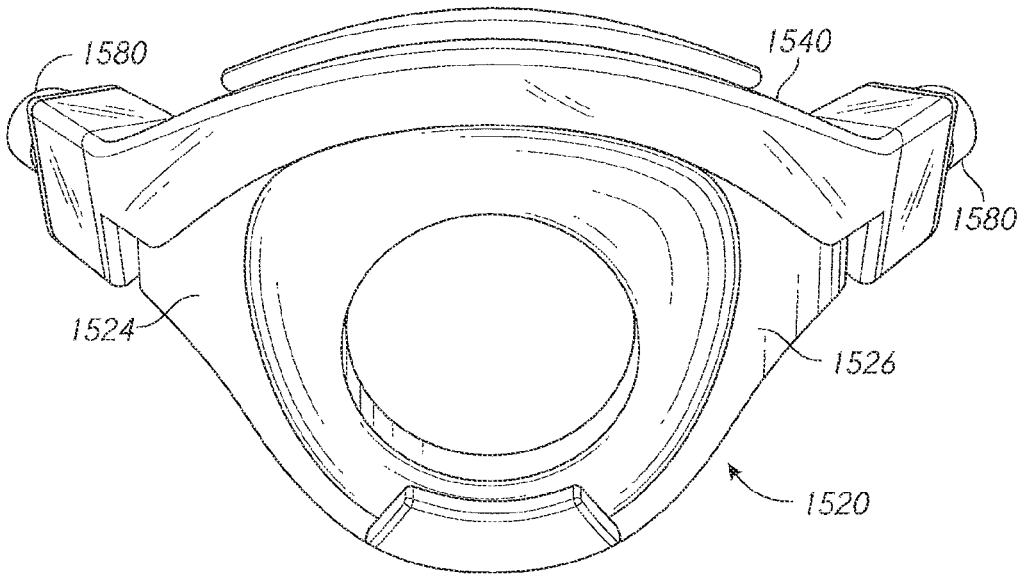
FIG. 45 is a front view of a frame element of an interface member attached to an interface coupling portion.
Figure 46:
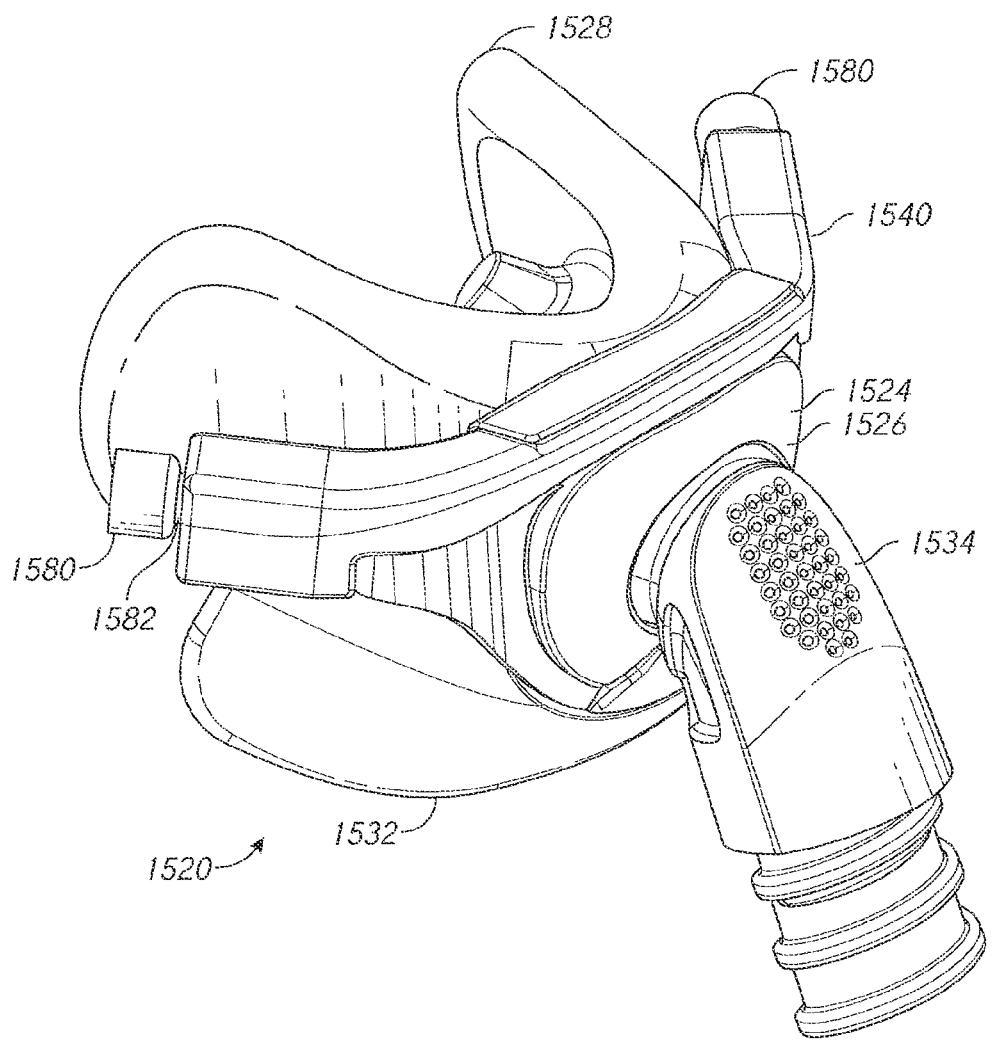
FIG. 46 is a right-side perspective view of an exemplary interface assembly attached to an interface coupling portion.
Figure 47:
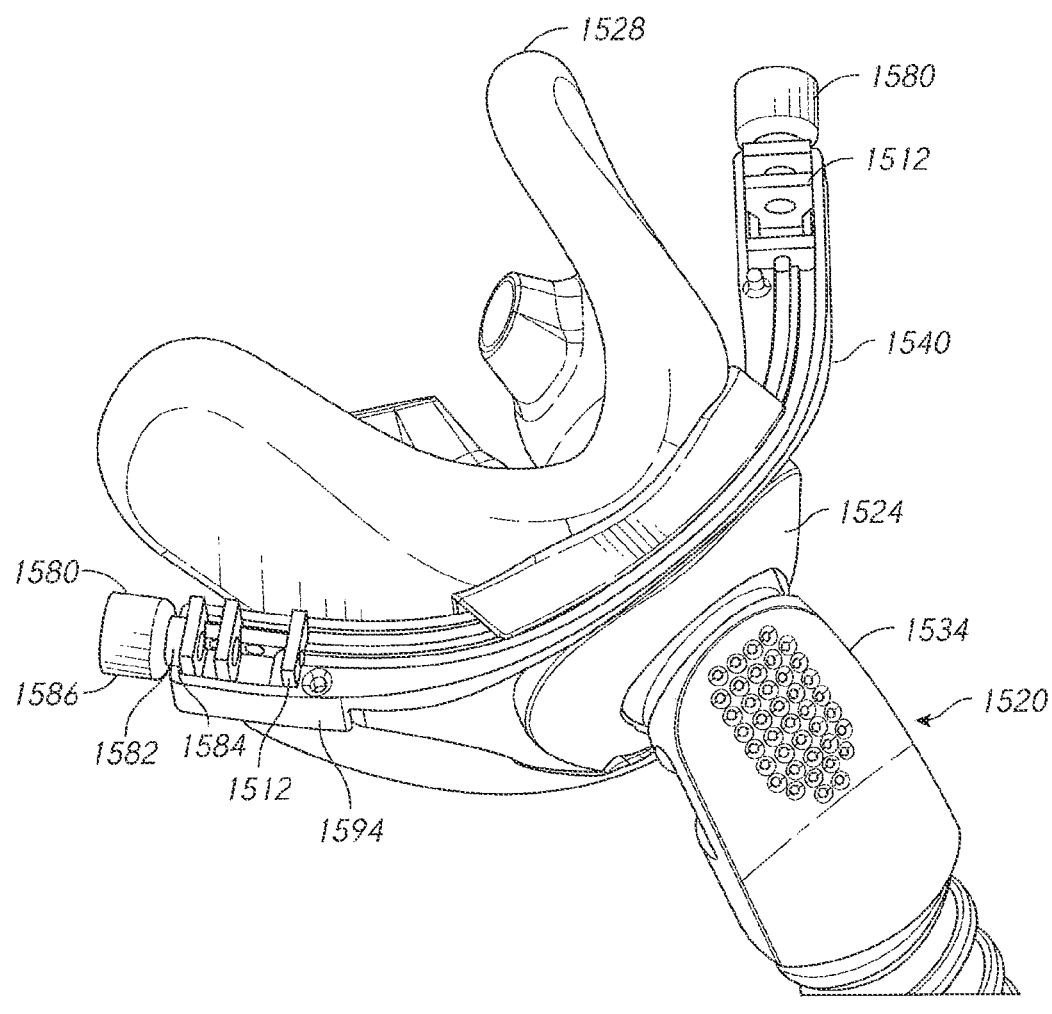
FIG. 47 is a top perspective view of an exemplary interface assembly attached to a second piece of an interface coupling portion.
Figure 48:
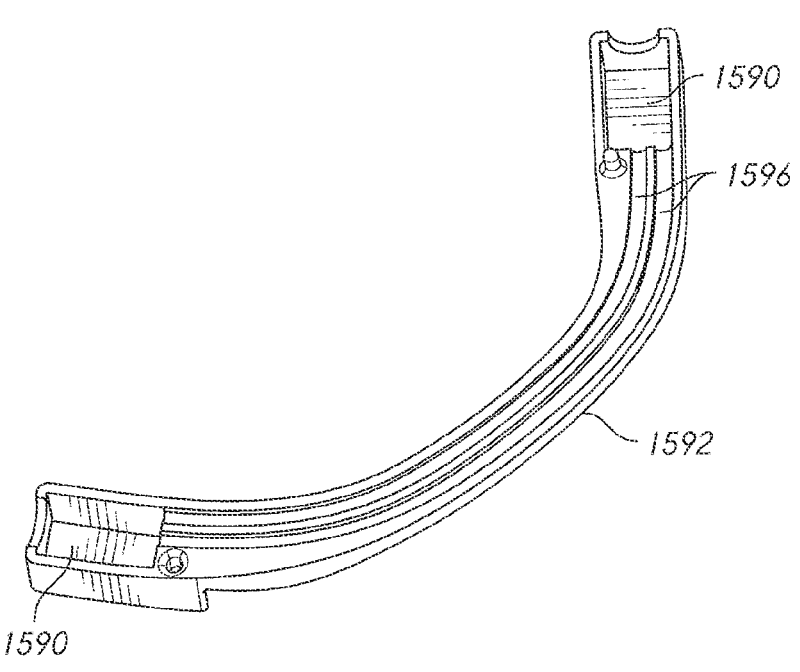
FIG. 48 is a top perspective view a first piece of an interface coupling portion.
Figure 49:
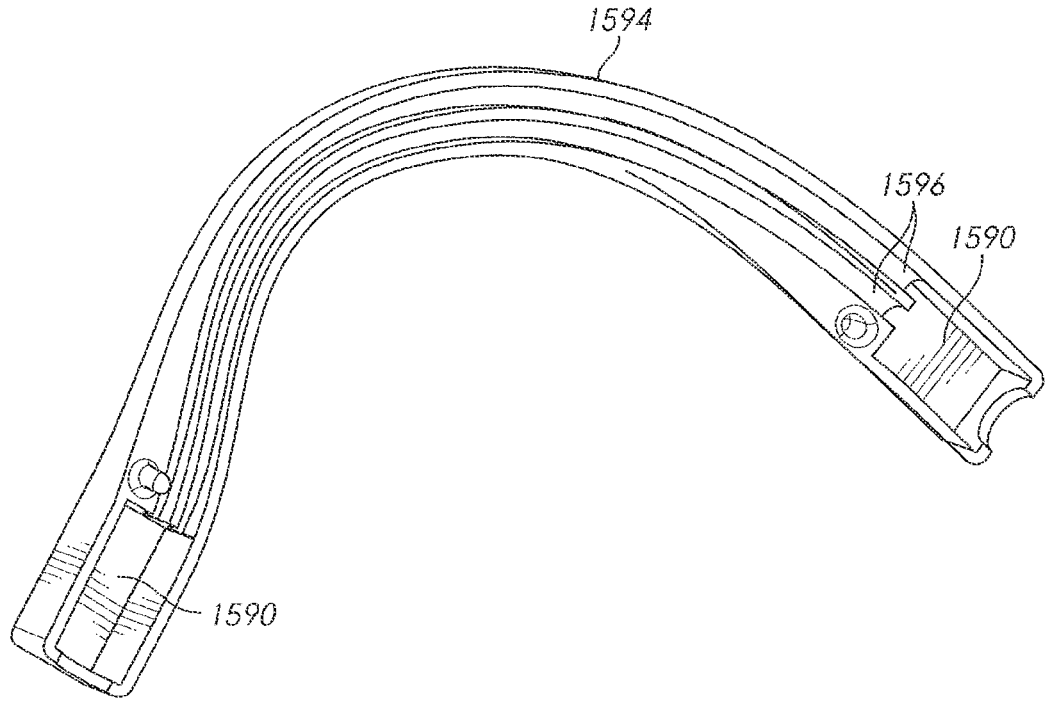
FIG. 49 is a top perspective view a second piece of an interface coupling portion.
Figure 50:
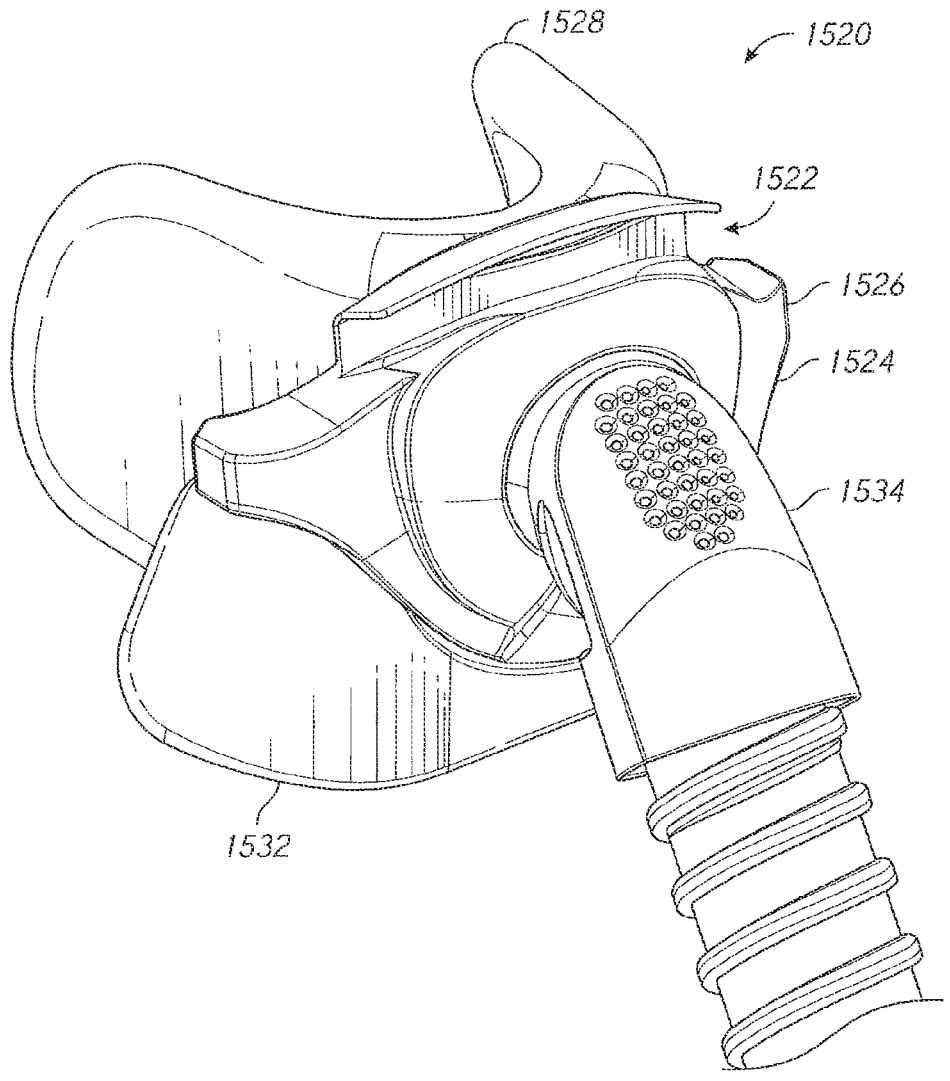
FIG. 50 is a right-side perspective view of an exemplary interface assembly.
Figure 51:
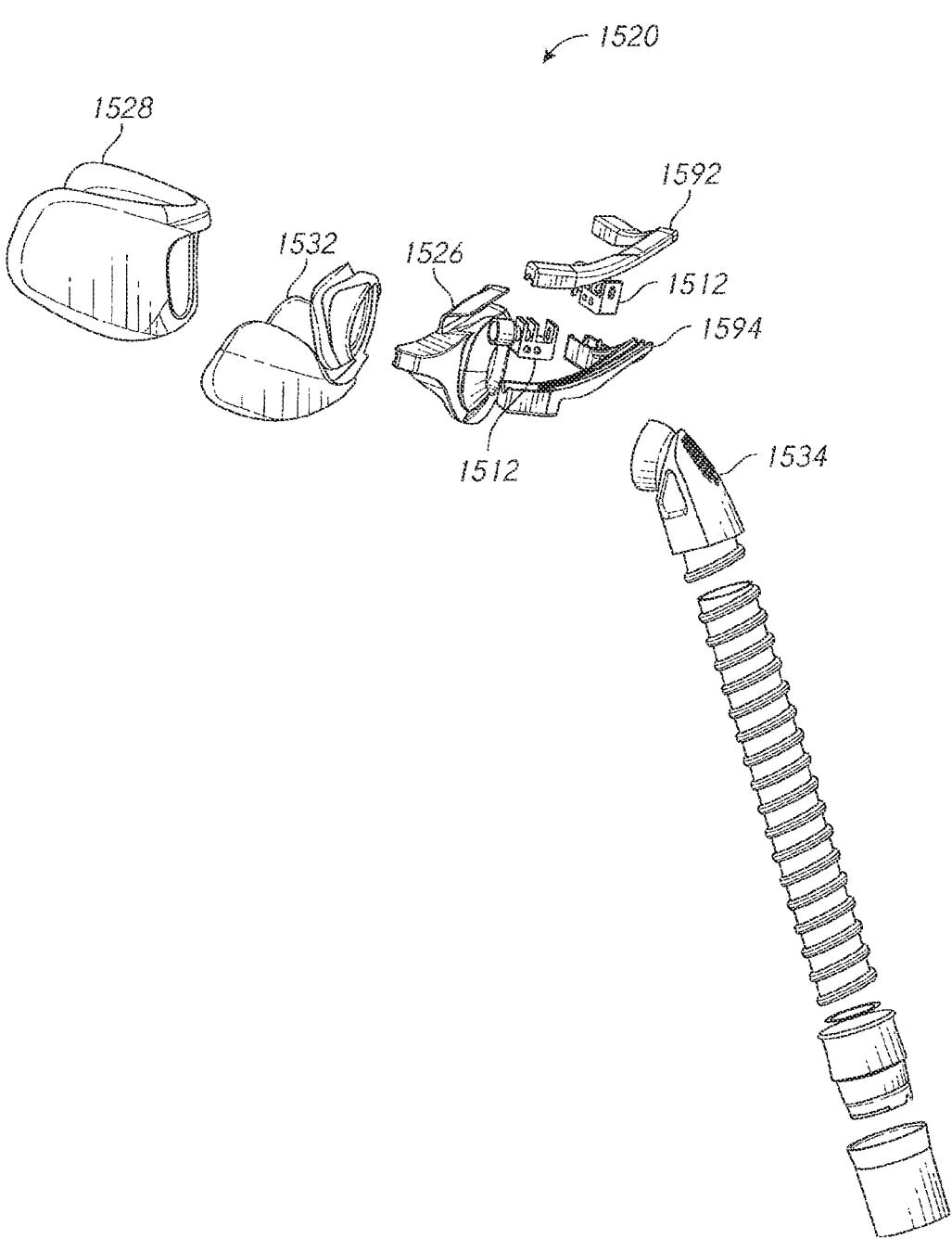
FIG. 51 is an exploded view of an exemplary interface assembly.
Figure 52:
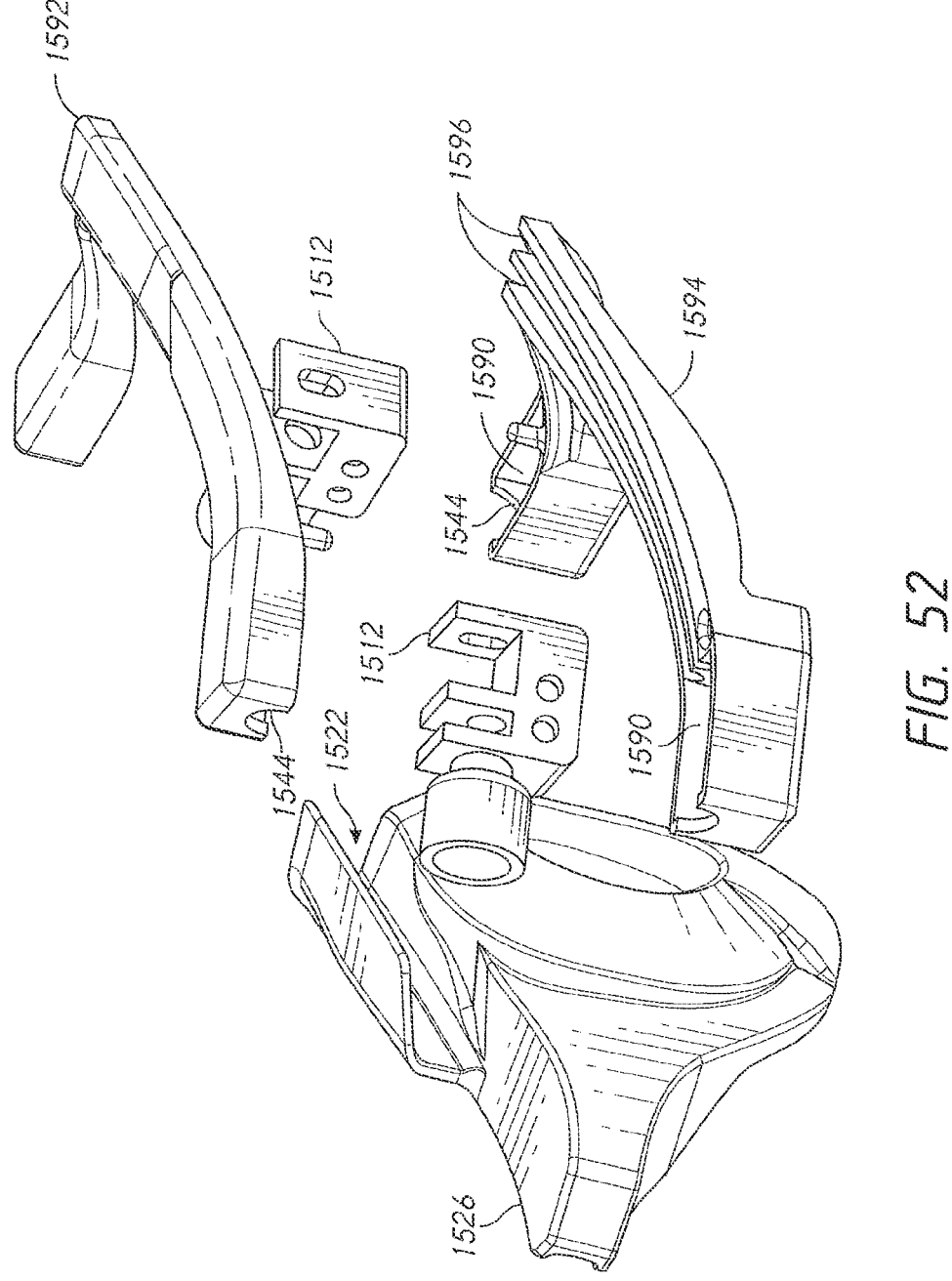
FIG. 52 is an exploded view of an exemplary interface coupling portion.
Figure 53:
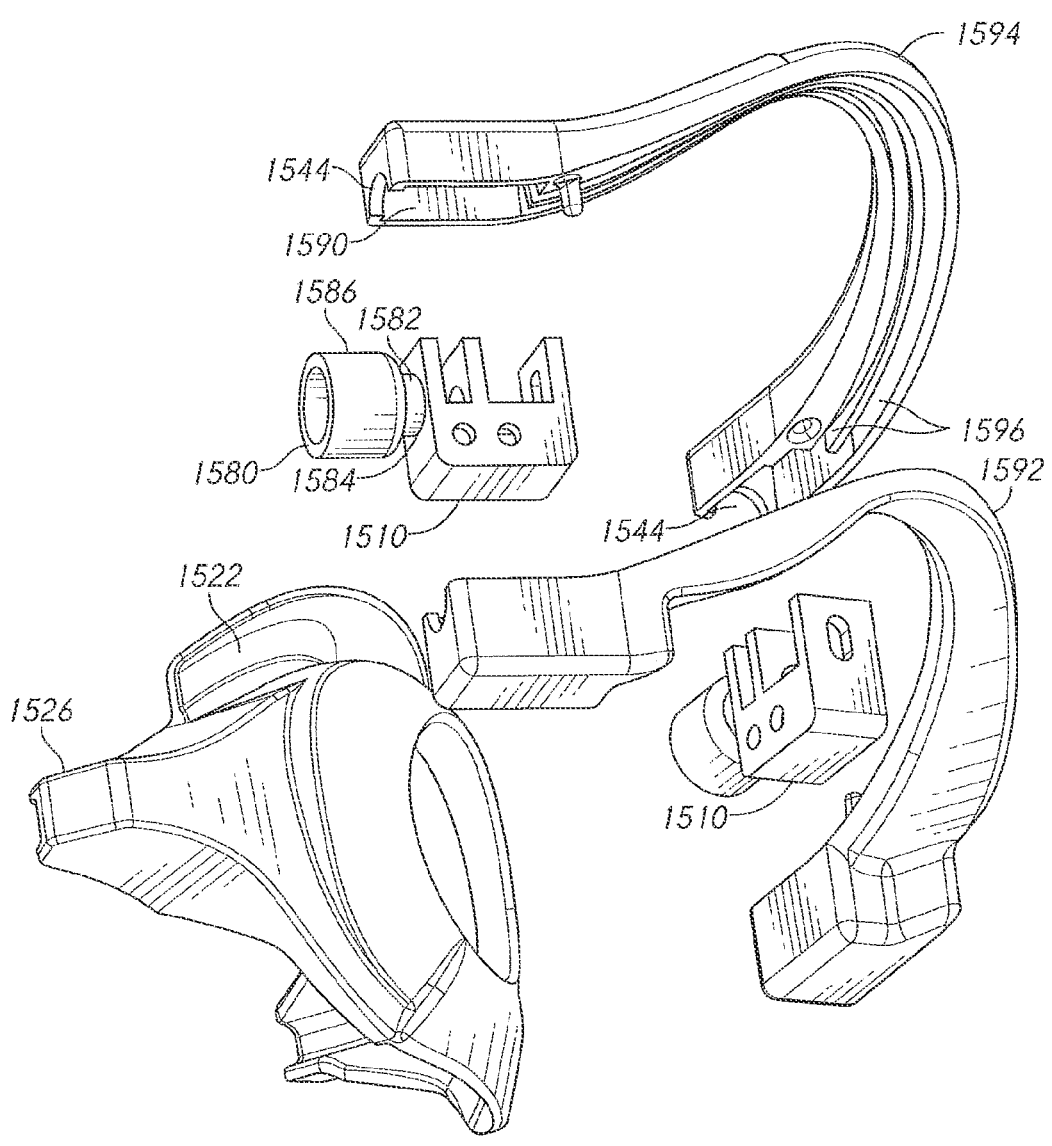
FIG. 53 is an inverted exploded view of an exemplary interface coupling portion.

With reference to FIGS. 32-34, a particular strap adjustment mechanism 1300 is shown. The adjustment mechanism 1300 of FIGS. 32-34 is substantially similar to the flat strap adjustment or directional locking mechanism shown and described in connection with FIGS. 40-42 in Applicant's PCT Application No. PCT/NZ2014/000074. However, in some configurations, the strap adjustment mechanism 1300 of FIGS. 32-34 incorporates an integrated padding or lining, as described above. In some configurations, the components of the strap adjustment mechanism 1300 are constructed by molding a moldable material onto a textile-based material.

FIGS. 32-34 illustrate the adjustable strap 1300 in assembled form and illustrates the portions of the adjustable strap separated and in plan view to illustrate the various components of the adjustment mechanism. The adjustment mechanism 1300 comprises a first portion 1310 that can be coupled to a second portion 1320 in multiple adjustment positions. In some configurations, the first portion 1310 and the second portion 1320 can be infinitely adjustable within the provided range of adjustment. The illustrated first and second portions 1310, 1320 are first and second portions of an adjustable top or crown strap; however, the adjustable strap can be provided in other locations as described in connection with FIGS. 30 and 31, for example. As described above, a biasing arrangement could be provided to bias the first and second portions 1310, 1320 relative to one another, such as toward a shortened position, for example.

Preferably, the adjustment mechanism 1300 comprises a directional lock 1330 that allows relative movement of the first portion 1310 and the second portion 1320 in a first direction (e.g., toward a shortened position) and provides a yield force that inhibits movement in a second direction. The yield force preferably is sufficient to prevent substantial movement in the second direction under normal or expected operating conditions, but may be overcome by an applied force to permit desired adjustment of the first portion 1310 and the second portion 1320.

The first portion 1310 of the adjustment mechanism 1300 can comprise a substantially flat strap 1312, which forms a male portion of the adjustment mechanism 1310. The second portion 1320 of the adjustment mechanism can comprise a receiver or a lock housing 1322, which forms a female portion of the adjustment mechanism. The lock housing 1322 can comprise a space 1324 that receives a lock member, such as a lock washer. The flat strap 1312 is movable within the receiver 1322 and passes through the space 1324 that receives the lock washer. The flat strap 1312 also passes through the lock washer. The lock washer is movable within the space 1324 of the lock housing 1322 between a release position and a lock position. In some configurations, the release position is defined by the lock washer being oriented substantially perpendicular to the length direction of the flat strap 1312 and the lock position is defined by the lock washer being tilted from the perpendicular orientation of the release position.

The position of the lock washer can be controlled by any suitable arrangement, such as being urged into the desired position by an end of the space 1324 of the lock housing 1322. For example, one end of the space 1324 of the lock housing 1322 can have a perpendicular surface and the other end can have a tilted surface. When the flat strap 1312 is moved in a direction toward the perpendicular surface, the lock washer is urged into the perpendicular orientation or release position and the flat strap 1312 is able to move relative to the lock housing 1322 with relatively low resistance. When the flat strap 1312 is moved in a direction toward the tilted surface, the lock washer is urged into the tilted orientation or lock position and relative movement between the flat strap 1312 and the lock housing 1322 is resisted by the yield force. The flat strap 1312 can comprise a gripping portion that facilitates movement of the lock washer. The gripping portion can be a higher friction material or material having a higher gripping force on the lock washer compared to the base material of the flat strap 1312.

In some configurations, each of the flat strap 1312 and the lock housing 1322 are constructed by molding a material onto the textile-based material of the first strap portion 1310 and the second strap portion 1320, respectively. In the illustrated configuration, a portion of the flat strap 1312 extends beyond an end of the textile-based material of the first strap portion 1310. In contrast, the textile-based material of the second strap portion 1320 extends beyond the lock housing 1322. Desirably, the portion of the flat strap 1312 that is received within the lock housing 1322 extends beyond the textile-based material of the first strap portion 1310 to avoid interference between the textile-based materials of the first strap portion 1310 and the second strap portion 1320 throughout an adjustment range of the adjustment mechanism. The portion of the second strap portion 1320 that extends beyond the lock housing 1322 can be configured such that the textile-based material of the first strap portion 1310 abuts or overlaps the textile-based material of the second strap portion 1320 in the largest position or most-separated position of the first portion 1310 and the second portion 1320.

In some configurations, the molded material extends along the textile-based material of the strap portions beyond the flat strap and/or lock housing. For example, the molded material can be provided as reinforcement for or as a stiffening member of the textile-based material of the strap portions. The additional molded material may be provided to increase the surface area between the molded material and the textile-based material to improve the connection therebetween and/or increase the holding force therebetween. In the illustrated arrangement, the additional molded material is in the form of strips or ribs that are separated from one another in a width direction of the strap portions and extend generally in the length direction of the strap portions.

In the illustrated configurations, the strap portions 1310, 1320 are desirably be relatively rigid in one direction (in a width direction to inhibit bending), but retain flexibility in another direction (in a thickness direction to allow the strap to bend and conform to the user's head). This can be achieved by the geometric design of the textile-based strap portion and/or the over-molded feature and/or through the use of different over-molded materials. In other configurations, such as other locations of the adjustment mechanism, other properties may be desired. Thus, other geometric shapes and/or materials can be selected to provide the strap portions with the desired properties.

In some configurations, the composite strap portions are constructed by an over-molding process involving molding a moldable material 1340 onto a textile or fabric material 1350. In some configurations, the moldable material 1340 can be a plastic material. The textile or fabric material 1350 preferably is selected to provide good adhesion of the moldable material.

The textile-based material can be placed into a mold. The mold can be closed and portions (e.g., edges) of the textile-based material can be captured between separable portions (e.g., halves) of the mold. The moldable material can then be injected into the mold and onto the textile-based material.

As disclosed in Applicant's patent application no. PCT/NZ2014/000074, many different types of directional locking mechanisms can be utilized in a headgear exhibiting balanced fit characteristics. In at least some configurations, a directional lock inhibits or prevents relative movement between two portions of the headgear in a first direction at least below a yield force of the directional lock. The directional lock also permits relative movement of the two portions of the headgear in a second direction opposite the first direction. Preferably, the movement in the second direction is permitted with no more than a relatively small amount of resistance.

Figure 35:
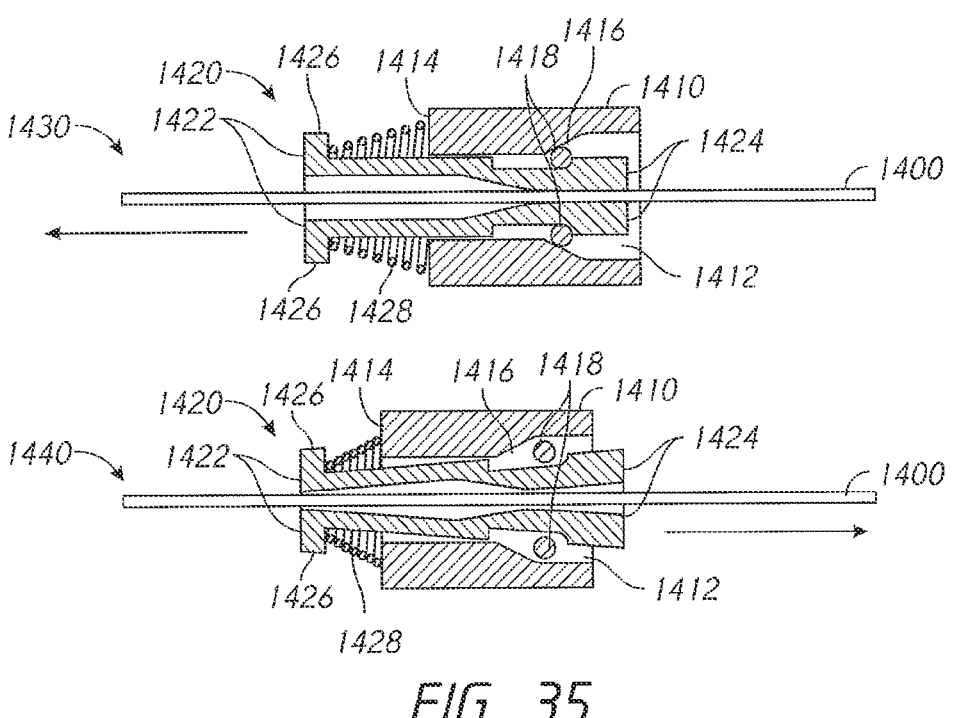
FIG. 35 is a sectional view of a directional lock in a lock position and release position.

With reference to FIG. 35, in some configurations, a first portion of the headgear comprises a core member 1400. The core member 1400 can be a wire, wire-like element or filament. A second portion of the headgear can comprise a housing 1410. The first portion and second portion of the headgear can be coupled to any suitable portions or components of the headgear that are movable relative to one another to vary or adjust a circumference of the headgear. The housing 1410 can be an element or receptacle that defines a space 1412 for receiving a lock arrangement 1420. The housing 1410 can be a separate component from the headgear or can be an integral component or portion of the headgear. The lock arrangement 1420 can engage the core member 1400 to inhibit or prevent movement of the core member 1400 relative to the housing 1410 in a first direction at least below a yield force of the directional lock. The lock arrangement 1420 can also disengage the core member 1400 to permit movement of the core member 1400 relative to the housing 1410 in a second direction opposite the first direction.

The lock arrangement 1420 can comprise two or more lock elements that are movable between a first or lock position 1430 and a second or release position 1440. The illustrated lock arrangement 1420 comprises a pair of lock elements in the form of lock jaws 1422. Each of the lock jaws 1422 is a generally semi-cylindrical member. The lock jaws 1422 cooperate to surround the core member 1400. An interior surface of each of the lock jaws 1422 facing the core member 1400 is concave. Each of the lock jaws 1422 comprises an engagement portion 1424 that contacts the core member 1400 in the lock position 1430 such that the lock jaws 1422 cooperate to engage the core member 1400. In the illustrated arrangement, the engagement portion 1424 is defined by an end portion of each of the lock jaws 1422.

An opposite end of each of the lock jaws 1422 extends through the housing 1410 and includes a radially-extending flange 1426. The directional lock can comprise a biasing arrangement that, in some configurations, provides a relatively light biasing force tending to move the lock arrangement toward the lock position or toward the left of the page in FIG. 35. The biasing arrangement can comprise a biasing element 1428, such as a spring, which acts against the flanges 1426 of the locking jaws 1422 and an end surface 1414 of the housing 1410. Preferably, the biasing arrangement provides a light biasing force that assists initial movement of the lock jaws 1422 toward the lock position 1430 when the core member 1400 is moved in a direction (to the left in FIG. 35) tending to increase a circumference of the headgear. The lock jaws 1422 can be moved toward the release position 1440 against the biasing force of the biasing arrangement when the core member is moved in a direction (to the right in FIG. 35) tending to decrease a circumference of the headgear.

As described above, the housing 1410 defines a space or passage for receiving the lock jaws 1422 and through which the core member 1400 can pass. The passage 1412 can define a chamfered, angled or tapered surface 1416 that facilitates movement of the lock jaws 1422 between the lock position 1430 and the release position 1440. One or more locking or roller elements 1418 can be positioned between each of the lock jaws 1422 and the housing 1410. Movement of the lock jaws 1422 along the longitudinal axis of the housing 1410 or passage 1412 in the direction toward the lock position 1430 causes engagement of the roller elements 1418 with the tapered surface 1416, which moves the roller elements 1418 and, thus, the lock jaws 1422 closer to one another such that the core member 1400 is clamped between the lock jaws 1422. Movement of the lock jaws 1422 along the horizontal axis in the direction toward the release position 1440 results in the roller elements 1418 being free to move away from the lock jaws 1422 in a radial direction thereby releasing the clamp force from the lock jaws 1422 and allowing the core member 1400 to move relatively free of substantial resistance. Such movement of the core member 1400 may result in axial movement of the lock jaws 1422 via frictional forces against the biasing force of the biasing arrangement.

The core member 1400, lock jaws 1422, tapered surface 1416 and/or roller elements 1418 can be configured such that the directional lock applies a clamping force to the core member 1400 that substantially inhibits or prevent movement of the core member 1400 relative to the housing 1410 when a force below a yield force acts on the core member 1400 attempting to elongate the headgear and allows movement of the core member 1400 attempting to elongate the headgear when a force above the yield force acts on the core member 1400. As described above, such an arrangement can allow a headgear incorporating one or more of the directional locks to resist normal or expected forces relating to therapy, while also permitting elongation of the headgear for fitment to or removal from the user. The directional lock can release the core member 1400 in response to movement of the core member 1400 attempting to retract the headgear to allow movement of the core member 1400 relative to the housing 1410 with relatively little resistance. Such an arrangement can allow headgear incorporating one or more of the directional locks to retract to fit the head size of the particular user. A retraction force tending to retract the headgear can be provided by any suitable method or mechanism, including manual retraction or automatic retraction caused by an elastic arrangement or elastic element(s) of the headgear.

Figure 36:
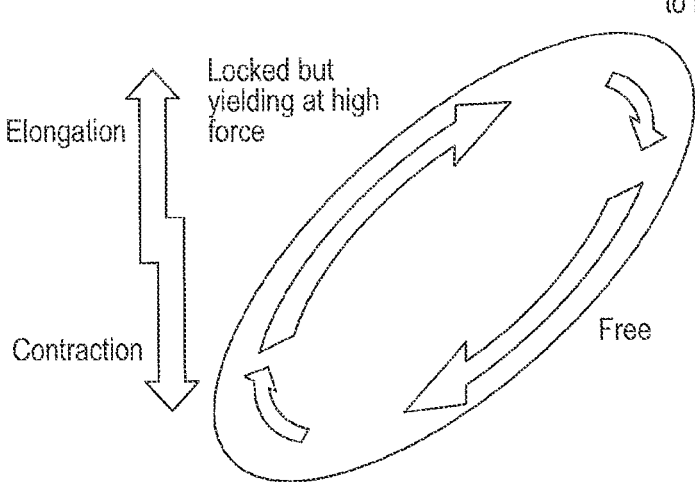
FIG. 36 illustrates an operation cycle for a headgear incorporating a directional lock.
Figure 37:
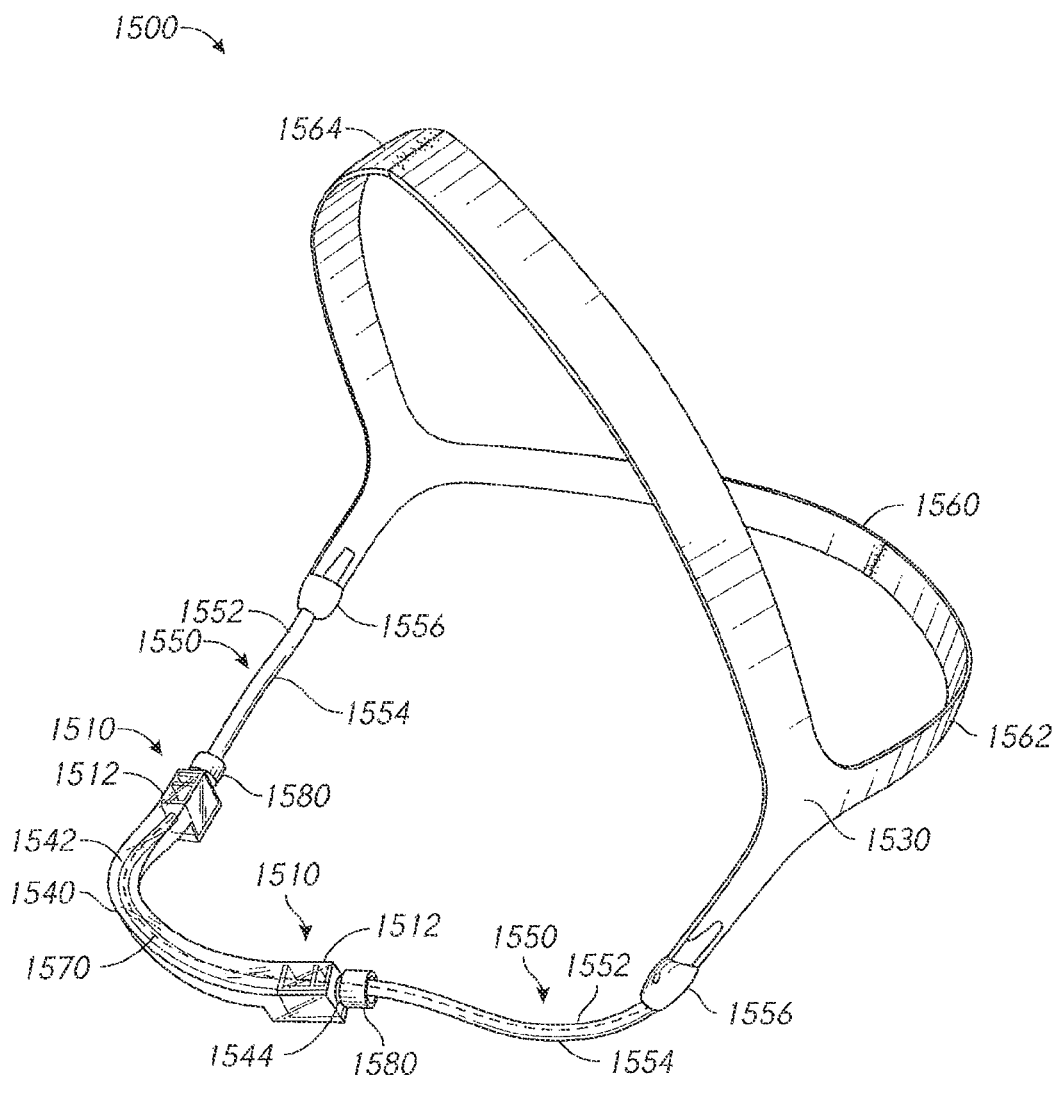
FIG. 37 is a perspective view of an exemplary headgear assembly incorporating one or more directional locks.
Figures 38, 39:
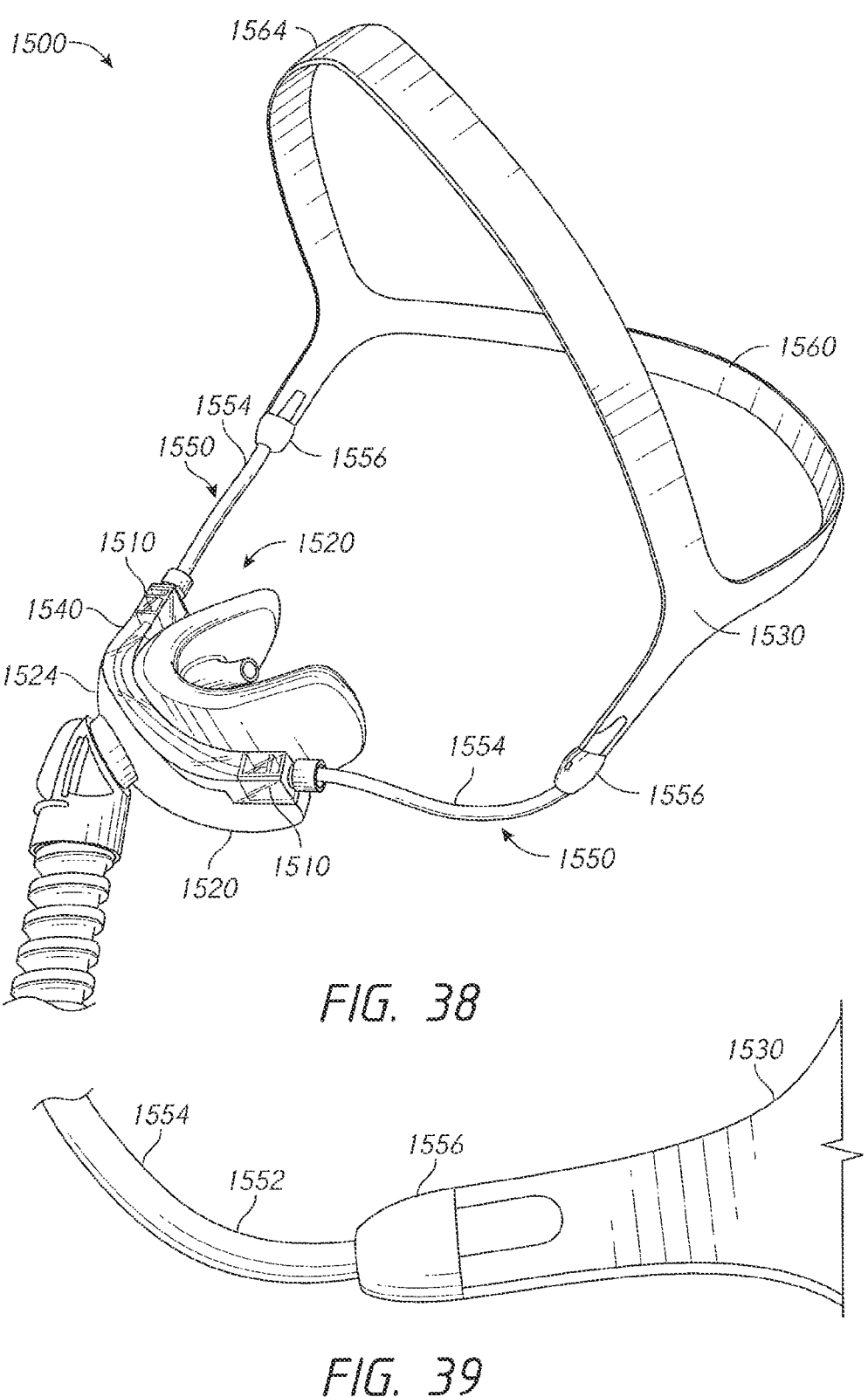
FIG. 38 is a perspective view of an exemplary headgear assembly incorporating one or more directional locks.
FIG. 39 is a side view of an attachment member attached to a headgear rear portion of the exemplary headgear assembly in FIG. 38.

FIG. 36 illustrates an operation cycle for a headgear incorporating a directional lock, such as the direction lock described above, any other directional lock described or incorporated by reference herein or any other suitable directional lock. In the operation cycle graphic, a component of an arrow in an upward direction represents elongation of the headgear (an increase in a circumference of the headgear) and a component of an arrow in a downward direction represents contraction of the headgear (a decrease in a circumference of the headgear). A component of an arrow to the right in FIG. 36 represents elongation movement of the headgear and a component of an arrow to the left represents retraction movement of the headgear.

FIG. 36 is described with reference to the structure of the directional lock described immediately above; however, the basic concepts highlighted by the description are equally applicable to many or all of the other directional locks described or incorporated herein. The upper, center arrow represents movement of the core member in a direction tending to elongate the headgear as a result of an application of force above the yield force of the directional lock. Thus, the core member is able to slip through the lock jaws, which are clamped against the core member by the interaction of the roller elements and the tapered surface of the passage of the housing. Such force may be applied in the application or removal of the headgear.

The next arrow in a clockwise direction represents a change in direction of the core member from elongation to retraction. Such a change in direction results in release of the clamping force on the core member.

The next arrow in the clockwise direction represents retraction movement of the core member. Thus, the core member movement can move the locking jaws such that the roller elements are no longer forced into the narrow portion of the tapered surface. As a result, relatively free retraction motion of the core member can occur. Such movement can allow the headgear to retract to fit the particular user or to retract to a minimum circumference when not in use.

The next arrow in the clockwise direction represents a change in direction of the core member from retraction to elongation. Such a change in direction results in the application of the clamping force to the core member. In each case of a change in direction, some movement of the core member may occur before the change in clamping force, or the change in the position of the direction lock, occurs or is fully reached. This cycle can be repeated each time the headgear is applied or removed from a user. In some cases, the cycle can occur when a user makes fine adjustments to the headgear.

FIGS. 37-53 illustrate an example of a headgear assembly 1500 incorporating one or more directional locks 1510. The illustrated headgear assembly 1500 is configured to be coupled to a portion of an interface 1520. In particular, the illustrated headgear assembly 1500 includes a headgear rear portion 1530, an interface coupling portion 1540 and a length or circumference adjusting portion 1550 that is interposed between the headgear rear portion 1530 to the interface coupling portion 1540. The headgear rear portion 1530 is configured in use to contact a rear portion of the user's head. The interface coupling portion 1540 is configured in use to be coupled to an interface 1520 such that the headgear assembly 1500 can support the interface 1520 in an appropriate position on the face of the user. The length or circumference adjusting portion 1550 is configured in use to permit a position of the interface coupling portion 1540 to be adjusted relative to the headgear rear portion 1530 such that the headgear assembly 1500 can be adjusted to the head size of a particular user. Thus, the length or circumference adjusting portion 1550 can permit a perimeter length or circumference of the headgear to be adjusted to allow the headgear assembly 1500 to fit the head size of a particular user.

Although illustrated and described as a headgear assembly 1500, in some configurations, the portions of the illustrated headgear assembly 1500 can be incorporated in any other suitable portion of an overall interface assembly. For example, the interface coupling portion 1540 can comprise a component or portion of an interface that is separate from and connectable to a headgear assembly 1500. The length or circumference adjusting portion 1550 can comprise a component or portion of an interface that is separate from and connectable to a headgear assembly 1500 or a component or portion of a headgear assembly 1500 that is separate from and connectable to an interface 1520. Advantageously, however, and as described further below, the illustrated headgear assembly 1500 can comprise a self-contained, automatic-fit headgear unit that exhibits balanced-fit characteristics and can be coupled to at least one and possible multiple types of interfaces. Thus, in at least some configurations, one type of the illustrated headgear assembly 1500 can be utilized with multiple types of interfaces. Accordingly, a seller can stock a lesser number of unique products while providing the same interface options. In addition, a user can utilize a single headgear assembly and interchange interfaces as desired, without requiring manual adjustment of the headgear assembly when changing from one interface to another.

In the illustrated arrangement, the headgear rear portion 1530 comprises at least one strap portion 1560 that contacts the head of the user. Preferably, the at least one strap portion 1560 contacts a rear portion or back of the head of the user such that the at least one strap portion 1560 can counteract forces induced in the headgear assembly 1500 by the pressurization of the interface during therapy. In some configurations, the strap portion 1560 extends generally or substantially in a lateral direction around the rear of the user's head and has an end one each side of the user's head. Each end can be coupled to another portion of the headgear assembly 1500, such as the circumference adjusting portion 1550, for example.

In some configurations, the at least one strap portion 1560 comprises a first strap portion and a second strap portion. The first strap portion can be a rear strap portion 1562 that extends around the back of the user's head and the second strap portion can be a top or upper strap portion 1564 that extends over the top of the user's head. The rear strap portion 1562 can be positioned to contact portions corresponding to one or both of the occipital or parietal bones of the user's head. The top strap portion 1564 can be positioned to contact portions corresponding to one or both of the parietal and frontal bones of the user's head. Thus, the top strap 1564 can be configured as either one of a crown strap or a forehead strap as such straps are sometimes characterized in the art. Other suitable arrangements can also be used.

Preferably, the headgear rear portion 1530 engages the user's head and provides a relatively stable platform for connection of the interface, such as utilizing the interface coupling portion 1540 and the circumference adjusting portion 1550. Thus, in at least some configurations, the headgear rear portion 1530 is substantially inelastic such that it holds its shape and effective length in response to applied forces within a range that is typical or expected for the intended application. In some configurations, the headgear rear portion 1530 can comprise a layer constructed from a relatively rigid material, such as a plastic material, coupled to one or more layers of a fabric material. Preferably, a fabric layer is provided at least on a user-contacting surface of the rigid material layer. In some configurations, a fabric layer is provided on each side of the rigid material layer. Furthermore, in some configurations, the rigid material layer can be formed between the material layers, such as by injection molding the rigid material into a space between two material layers within a mold. An example of such a headgear and a method of making such a headgear is disclosed in Applicant's U.S. Provisional Application No. 62/050,925, the entirety of which is incorporated by reference herein.

The circumference adjusting portion 1550 can comprise a pair of adjustment elements 1552 in which one adjustment element 1552 is positioned on each side of the headgear assembly 1500. In particular, each of the adjustment elements 1552 can couple one side of the headgear rear portion 1530 with one side of the interface coupling portion 1540. The adjustment elements 1552 can be coupled at or near a junction between the top strap 1564 and the rear strap 1562. In the illustrated arrangement, the adjustment elements 1552 are coupled to forward extensions of the headgear rear portion 1530 that extend in a forward direction from a junction between the top strap 1564 and the rear strap 1562. The adjustment elements 1552 are adjustable in length between a retracted length and an extended length. In some configurations, the adjustment elements 1552 cooperate to provide all or substantially all of the adjustment of a circumference of the headgear assembly 1500. Each of the adjustment elements 1552 can also include an elastic element or biasing arrangement that biases the adjustment element 1552 toward one of the retracted or extended lengths. Preferably, the adjustment elements 1552 are biased toward a retracted length, such that the headgear assembly 1500 is biased toward its smallest circumference. Such an arrangement permits the headgear assembly 1500 to be extended and then automatically retract to fit the particular user under the biasing force of the elastic element or other biasing arrangement of the adjustment element(s) 1552. In addition, preferably, the adjustment elements 1552 define a hard stop at a maximum extended length to limit extension of the headgear 1500 and define a maximum circumference of the headgear 1500.

In some configurations, the adjustment elements 1552 comprise a braided element 1554, which can extend or retract in length. The braided element 1554 can comprise one or more elastic elements in parallel with the braided element 1554. The elastic elements can be separate from the braided element 1554 or incorporated in the braided element 1554. In some configurations, the elastic elements are contained in internal spaces between filaments of the braided element 1554. An example of suitable braided elements is described in connection with FIGS. 46-54 of Applicant's patent application no. PCT/NZ2014/000074. However, other suitable constructions or arrangements can also be used. Alternatively, elastic element(s) or biasing element(s) can be located within the interface coupling portion and can interact with the core members to pull the core members into the interface coupling portion.

The interface coupling portion 1540 of the headgear assembly 1500 can extend between the pair of adjustment elements 1552 that comprise the circumference adjusting portion 1550. In some configurations, the interface coupling portion 1540 is coupled directly to the adjustment elements 1552. As described above, the interface coupling portion 1540 can facilitate connection of the headgear assembly 1500 to an interface 1520. However, the interface coupling portion 1540 can also accommodate at least a portion of one or more directional locks 1510. In the illustrated arrangement, a pair of directional locks 1510 is provided, with one directional lock 1510 associated with one of the pair of adjustment elements 1552. Portions (e.g., housings 1512) of the directional locks 1510 can be located at each end of the interface coupling portion 1540. In some configurations, a core member 1570 associated with each of the directional locks 1510 is coupled to the headgear rear portion 1530, extends along or through the adjustment element 1552, through the housing 1512 of the directional lock 1510 and into a collection space 1542 of the interface coupling portion 1540. The housing 1512 of the directional lock 1510 can comprise one or more members or elements (e.g., lock washers or lock jaws) that interact with the core member 1570 to selectively allow retraction of the headgear assembly 1500 or lock the headgear assembly 1500 in a particular circumference and inhibit or prevent extension of the headgear 1500 at least at forces below the yield force provided by of the directional lock(s) 1510. Additional particulars of the operation of the directional locks 1510 are described above and in Applicant's patent application no. PCT/NZ2014/000074.

In some configurations, one or both of the core member 1570 and the adjustment element 1552 are secured to the headgear rear portion 1530 by encapsulation of the core member 1570 and/or adjustment element 1552 within the headgear rear portion 1530. For example, the core member 1570 and/or adjustment element 1552 can be positioned within a mold and the rigid material portion of the headgear rear portion 1530 can be formed by injection molding such that it encapsulates the core member 1570 and/or adjustment element 1552. In the illustrated arrangement, an end portion of the adjustment element 1552 and an end portion of the core member 1570 are encapsulated within the rigid material portion of the headgear rear portion 1530. However, other suitable arrangements can also be used.

In some configurations, the adjustment element 1552 includes end cap portions 1556 that couple the braided element 1554 with the elastic element(s). The end cap portions 1556 can be applied to the ends of the adjustment element 1552 by an overmolding process. In particular, the braided element 1554 and elastic element(s) can be placed in a mold and the end cap portions 1556 can be created by injection molding over the end portions of the braided element 1554 and elastic element(s). In some configurations, the braided element 1554 and/or the clastic element(s) are held in a stretched state during the overmolding process. In some configurations, the adjustment element sub-assemblies are then coupled to the headgear rear portion 1530, such as by the above-described overmolding process. Thus, the end cap portion 1556 of the adjustment element 1552 can be encapsulated by the headgear rear portion 1530.

The end cap portion 1556 of each of the adjustment elements 1552 opposite the headgear rear portion 1530 can be coupled to the interface coupling portion 1540 by any suitable arrangement. In the illustrated configuration, the end cap portion 1556 of the adjustment element 1552 is coupled to a ferrule or socket 1580, which is, in turn, coupled to the interface coupling portion 1540. For example, the end cap portion 1556 can be press-fit or otherwise secured within the socket 1580. The socket 1580 can comprise a neck portion 1582 that spaces a retention portion 1584 from the main body 1586 of the socket 1580. The neck portion 1582 can extend through an opening 1544 in the interface coupling portion 1540 and the retention portion 1584 of the socket 1580 can prevent separation of the socket 1580 from the interface coupling portion 1540. In some configurations, the retention portion 1584 of the socket 1580 can be integrated with the housing 1512 of the directional lock 1510.

In some configurations, the interface coupling portion 1540 can be constructed from multiple pieces that cooperate to define the collection space. The multiple pieces can also cooperate to define a space 1590 for receiving the housing 1512 of each directional lock 1510. In the illustrated arrangement, the interface coupling portion 1540 comprises a first piece 1592 and a second piece 1594 that can be connected to define the collection space 1596 and a pair of spaces 1590 for receiving the housings 1512 of the directional locks 1510. The first and second pieces 1592, 1594 can be upper and lower pieces, respectively. In other arrangements, the first and second pieces 1592, 1594 could be forward and rearward pieces, for example. Provision of separate pieces facilitates assembly of the housings 1512 of the directional locks 1510, the core members 1570 of the directional locks 1510 and the sockets 1580 to the interface coupling portion 1540.

The collection space 1596 of the interface coupling portion 1540 is configured as an accumulator to receive end portions of the core members 1570 that, in the illustrated arrangement, are excess or inactive portions and do not form an operative portion of the core members 1570. That is, the portions of the core members 1570 between the mounting point at the headgear rear portion 1530 and the housing 1512 of the directional lock 1510 (or at the lock element(s) of the directional lock), are active and form a portion of the headgear circumference. Such portions of the core members 1570 are placed under tension when a force is applied tending to elongate the headgear. The lengths of the active core member portions and the inactive core member portions will vary along with variations in the adjusted or instantaneous circumference of the headgear assembly 1500. Thus, the collection space 1596 provides a location to accumulate and protect the inactive portions of the core members 1570.

Desirably, a length of the collection space 1596 is at least as great as a stretch distance (difference between the extended and retracted lengths) of one of the adjustment members 1552. In other words, the stretch distance of the adjustment members 1552 preferably is less than or equal to the length of the collection space 1596 so that ample space exists in the collection space 1596 for excess core member portion of sufficient length to allow movement of the adjustment members 1552 from a retracted position to an extended position with at least some excess core member 1570 length left within the collection space 1596 such that the core member 1570 is not pulled completely through the housing 1512 of the directional lock 1510. In some configurations, the collection space 1596 can comprise separate spaces or channels for each of the core members 1570.

A portion of the interface coupling portion 1540 can be configured for connection to an interface 1520 or a portion of an interface 1520. In some configurations, the interface coupling portion 1540 is able to be selectively coupled or removably coupled to an interface 1520. In the illustrated arrangement, a portion of the interface coupling portion 1540 that defines the collection space 1596 is configured to be received within a receiving channel 1522 of an interface member 1524. The receiving channel 1522 can be a semi-cylindrical space defined by the interface member 1524 and configured to receive the interface coupling portion 1540 in a snap-fit arrangement. The central portion of the interface coupling portion 1540 that defines the collection space 1542 can be generally columnar or cylindrical in outer shape. In the illustrated arrangement, the central portion of the interface coupling portion 1540 is curved along its length.

The interface member 1524 can be any portion of an interface 1520. For example, the interface member 1524 can be a relatively rigid portion of an interface 1520, such as a shell or frame element 1526. In the illustrated arrangement, the interface member 1524 is a frame element 1526, which can directly or indirectly support a mask seal 1528, cushion 1532 or other interface element. The frame element 1526 (or another portion of the interface) can support a conduit connector, such as an elbow 1534. In some configurations, the interface member 1524 can be configured to support several different types of mask seals 1528, cushions 1532 or other interface elements. In some configurations, the interface member 1524 can be integrated with or designed for use with a specific mask seal 1528, cushion 1532 or other interface element and different interface members 1524 can be integrated or associated with each type of mask seal 1528, cushion 1532 or interface element. In any event, in at least some configurations, the headgear assembly 1500 can be utilized with multiple types of mask seals 1528, cushions 1532 or other interface elements, including nasal cannula, nasal pillows, nasal masks or full face masks, for example.

Figure 54:
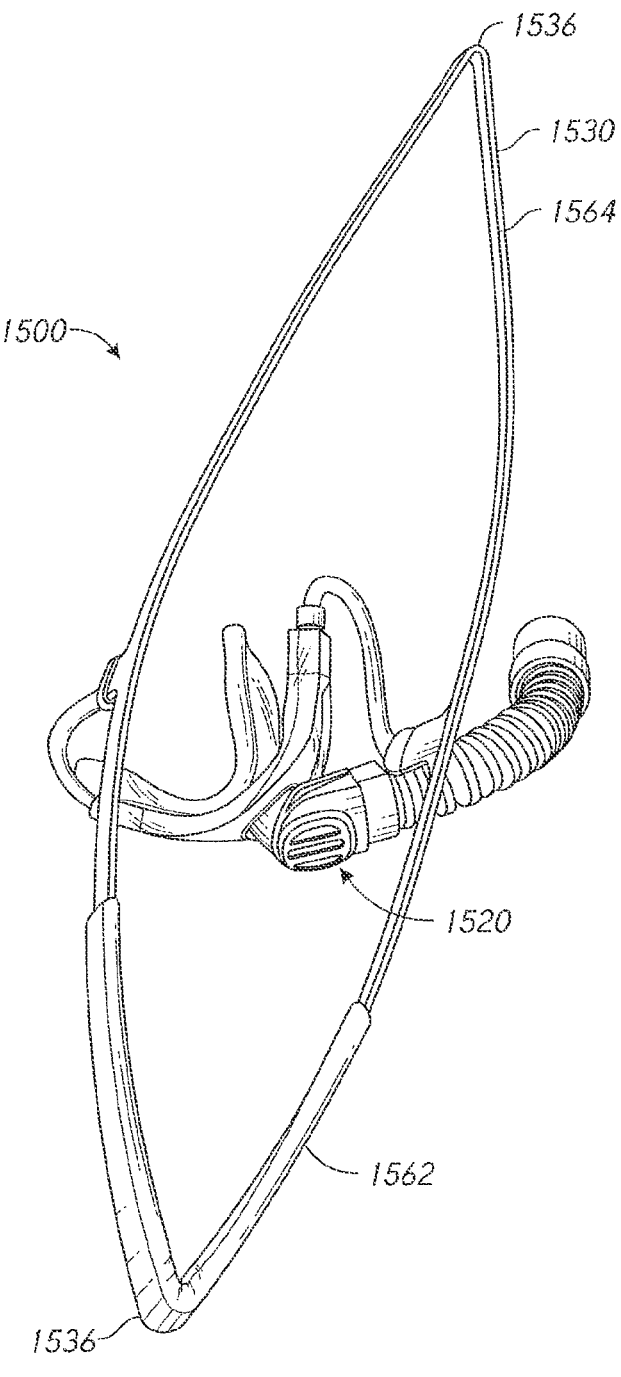
FIG. 54 is a top view of an exemplary collapsible headgear assembly.
Figure 55:
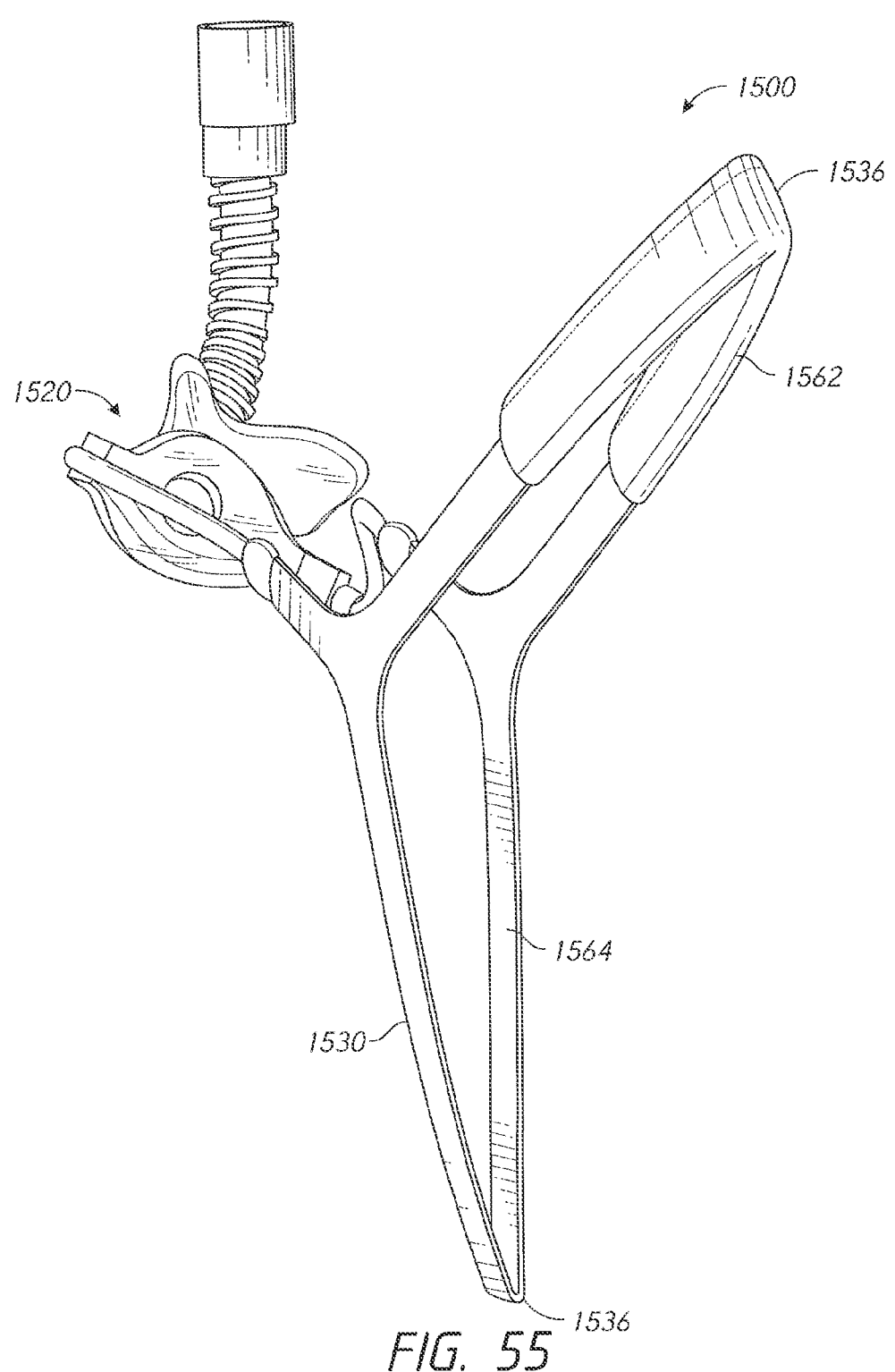
FIG. 55 a rear view of an exemplary collapsible headgear assembly.
Figure 56:
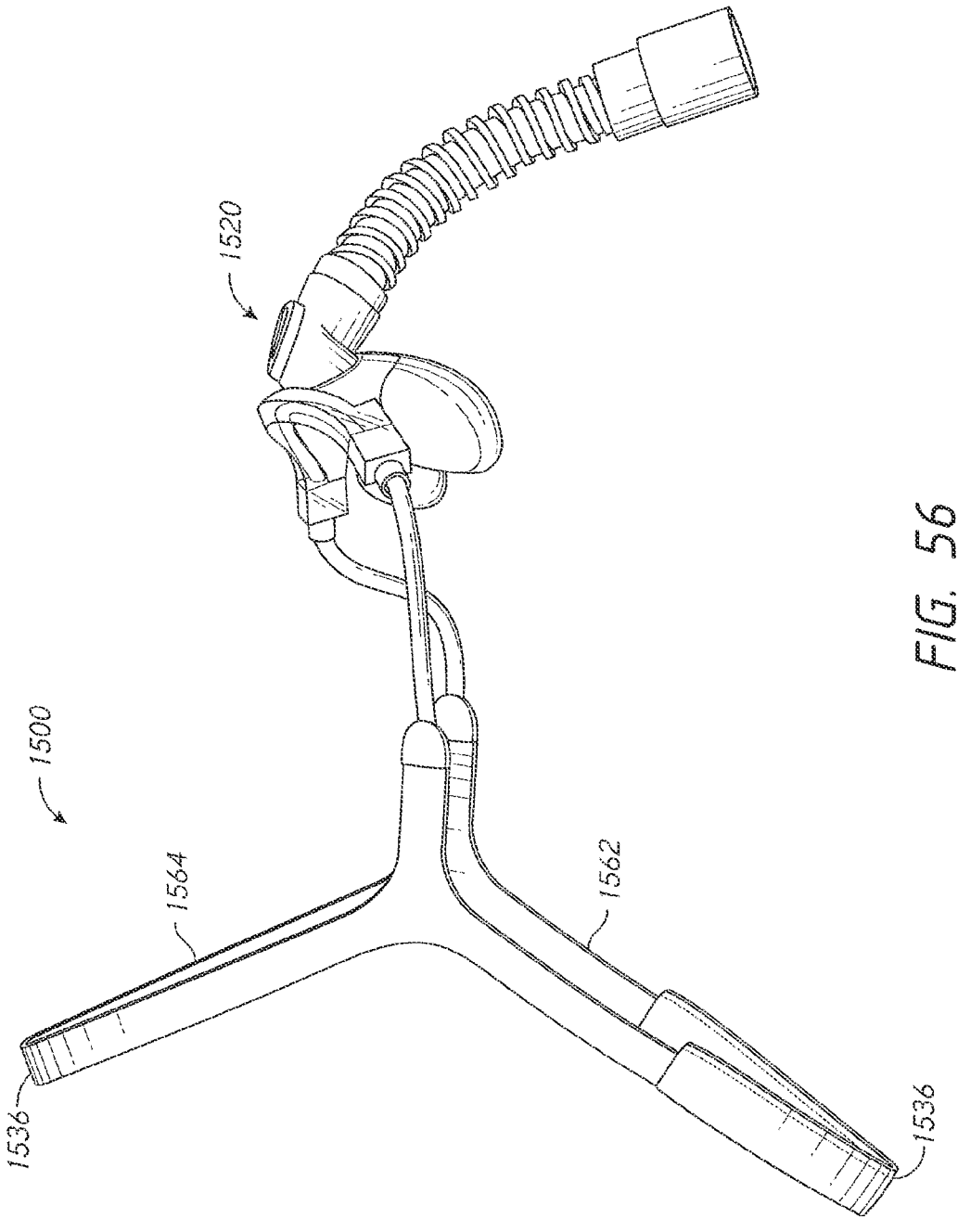
FIG. 56 a side view of an exemplary collapsible headgear assembly.

FIGS. 54-56 illustrate an interface assembly incorporating a headgear assembly 1500, which can be the same as or substantially to the headgear assembly 1500 described immediately above, or can be of another suitable arrangement. In the illustrated arrangement, the headgear rear portion 1530 is collapsible. In some configurations, the headgear rear portion 1530 can be collapsed or folded from an expanded configuration, in which the headgear rear portion 1530 assumes a three-dimensional form, to a collapsed configuration, in which the headgear rear portion 1530 can lay relatively flat. In the illustrated arrangement, a hinge, joint or fold 1536 is provided in one or both of the rear strap and the top strap. The hinge, joint or fold 1536 can comprise a section of the headgear rear portion 1530 that has less rigidity than other portions of the headgear rear portion 1530. The hinge, joint or fold 1536 can comprise a reduced thickness portion of the rigid headgear material, a separation between rigid headgear material portions such that the one or more fabric layers define the hinge, joint or fold 1536, or a coupling between separate portions of the headgear rear portion 1530, such as a sewn joint, for example. A separate hinge member could be utilized to join portions of the headgear rear portion.

Such an arrangement enables the headgear to be laid relatively flat, which can help with it being packed it the user is travelling with the mask. Having a designed fold point or line enables the headgear unit to have the shape sustaining behaviour, but also lets it be a compact unit if it has to be packed in a suitcase, etc. The fold line or hinge line 1536 could be constructed by any suitable process, such as with the use of stitching or injection molding both the left and right sides of the rigid material portion up to that point and then leaving an un-backed piece or pieces of fabric to act as the hinge.

Figures 57, 58, 59:
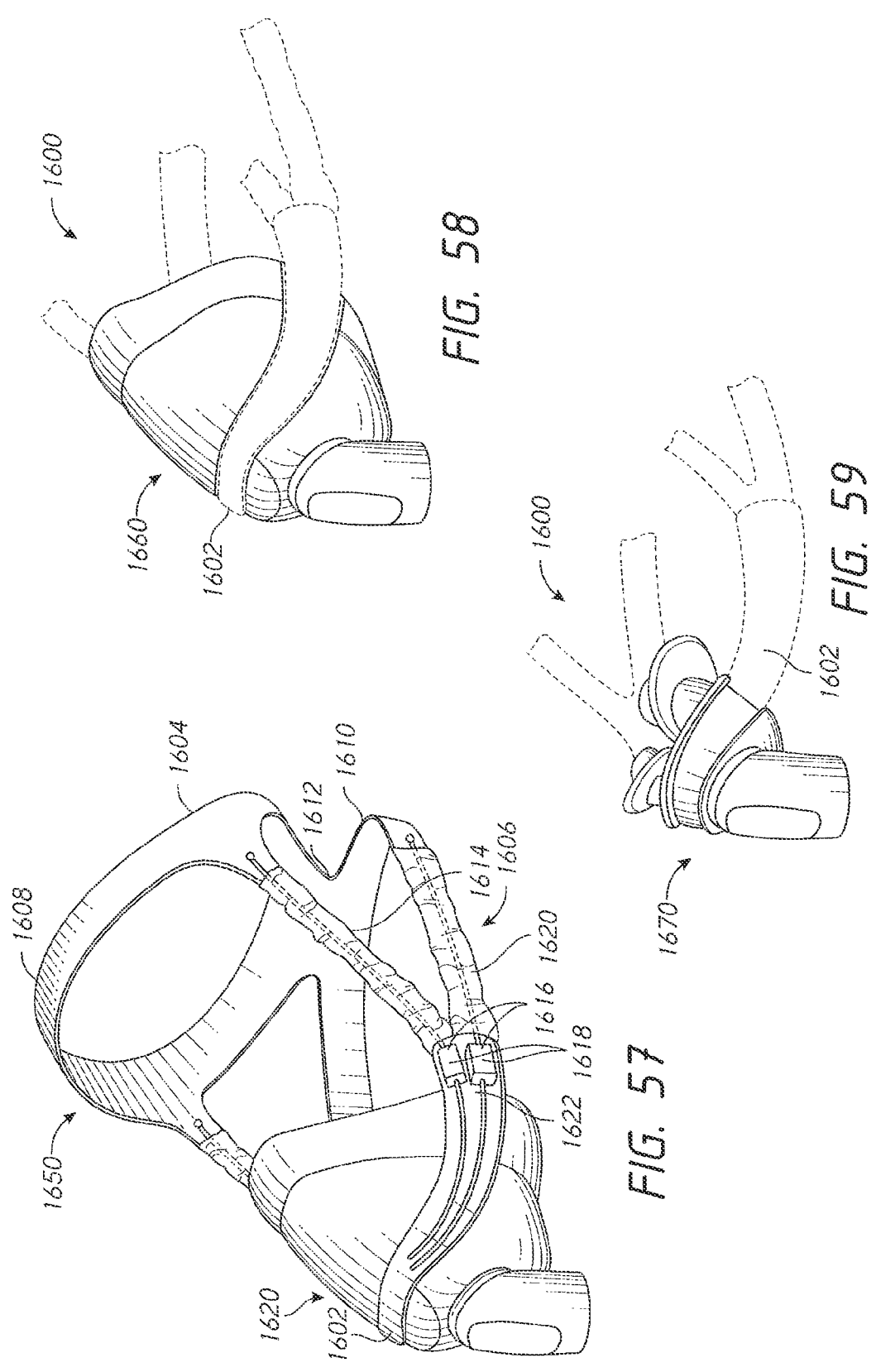
FIG. 57 illustrates an exemplary headgear assembly coupled to a full face mask type interface.
FIG. 58 illustrates the exemplary headgear assembly in FIG. 57 coupled to a nasal mask.
FIG. 59 illustrates the exemplary headgear assembly in FIG. 57 coupled to a nasal pillows/prongs mask.

FIGS. 57-59 illustrate another headgear assembly 1600 that, in at least some configurations, can be utilized with two or more interface types. For example, FIG. 57 illustrates the headgear assembly 1600 as forming a modular component of an interface assembly comprising a full face mask type interface 1650. The headgear assembly 1600 can comprise a portion 1602 that engages the interface 1650 or can otherwise be coupled to the interface 1610. In some configurations, the engagement or coupling portion 1602 of the headgear assembly 1600 can be engaged or coupled with at least one other type of interface. For example, FIG. 58 illustrates the headgear assembly 1600 of FIG. 57 (shown in dashed line) supporting a nasal mask 1660 and FIG. 59 illustrates the headgear assembly 1600 of FIG. 57 (shown in dashed line) supporting a nasal pillows/prongs mask 1670. Thus, with such a modular arrangement, a single headgear assembly can be utilized with multiple types of interfaces. Advantageously, the on-demand resistance feature of the headgear assembly as described herein allows the single headgear assembly to operate in a suitable manner with the different interface types. For example, the retention force provided by the headgear can automatically adjust to the force applied to the headgear by the particular interface that is used. The engagement or coupling portion 1602 can be of any suitable arrangement, such as the same as or similar to the arrangement disclosed in connection with FIGS. 37-53, for example.

The headgear assembly 1600 can be generally similar to the other headgear assemblies disclosed herein or in Applicant's Application No. PCT/NZ2014/000074. In particular, the illustrated headgear assembly 1600 includes a headgear rear portion 1604, an interface coupling portion 1602 and a length or circumference adjusting portion 1606 that is interposed between the headgear rear portion 1604 to the interface coupling portion 1602. The headgear rear portion 1604 is configured in use to contact a rear portion of the user's head. The interface coupling portion 1602 is configured in use to be coupled to an interface such that the headgear assembly 1600 can support the interface in an appropriate position on the face of the user. The length or circumference adjusting portion 1606 is configured in use to permit a position of the interface coupling portion 1602 to be adjusted relative to the headgear rear portion 1604 such that the headgear assembly 1600 can be adjusted to the head size of a particular user. Thus, the length or circumference adjusting portion 1606 can permit a perimeter length or circumference of the headgear to be adjusted to allow the headgear assembly 1600 to fit the head size of a particular user.

The headgear rear portion 1604 can be of any suitable arrangement, such as the same as or similar to any of those described herein or in Applicant's Application No. PCT/NZ2014/000074. Preferably, the headgear rear portion 1604 engages the user's head and provides a relatively stable platform for connection of the interface, such as utilizing the interface coupling portion 1602 and the circumference adjusting portion 1606. Thus, in at least some configurations, the headgear rear portion 1604 is substantially inelastic such that it holds its shape and effective length in response to applied forces within a range that is typical or expected for the intended application. The headgear rear portion 1604 can include a top strap portion 1608 that extends over the top of the user's head and a rear strap portion 1610 that extends around the back of the user's head. The top strap portion 1608 and rear strap portion 1610 can be separate or coupled in any suitable manner, such as by an intermediate connecting portion 1612.

The length or circumference adjusting portion 1606 can be of any suitable arrangement, such as the same as or similar to any of those described herein or in Applicant's Application No. PCT/NZ2014/000074. The circumference adjusting portion 1606 can comprise two pair of adjustment elements 1614 in which one pair of adjustment elements 1614 are positioned on each side of the headgear assembly 1600. Thus, the illustrated headgear arrangement 1600 can be generally described or categorized as a two retention plane headgear type. The headgear arrangement 1600 can be described as a two retention plane, forward converge headgear type or possibly a hybrid of a two retention plane, forward converge headgear type and a two retention plane, separated/angled headgear type.

Each pair of the adjustment elements 1614 can couple one side of the headgear rear portion 1604 with one side of the interface coupling portion 1602. The pair of adjustment elements 1614 one each side are coupled to the headgear rear portion 1604 at spaced locations. For example, one of the adjustment elements 1614 is coupled to the headgear rear portion 1604 at or near a portion of the top strap 1608 and the other of the adjustment elements 1614 is coupled the headgear rear portion 1604 at or near a portion of the rear strap 1610. In the illustrated arrangement, the upper adjustment elements 1614 are coupled to forward extensions of the headgear rear portion 1604 that extend in a forward direction from a portion of the top strap 1608 at or near a location above the user's ear. The lower adjustment elements 1614 are coupled to ends of the rear strap 1610 of the headgear rear portion 1604.

The adjustment elements 1614 are adjustable in length between a retracted length and an extended length. In some configurations, the adjustment elements 1614 cooperate to provide all or substantially all of the adjustment of a circumference of the headgear assembly 1600. Each of the adjustment elements 1614 can also include an elastic element or biasing arrangement that biases the adjustment element 1614 toward one of the retracted or extended lengths. Preferably, the adjustment elements 1614 are biased toward a retracted length, such that the headgear assembly 1600 is biased toward its smallest circumference. Such an arrangement permits the headgear assembly 1600 to be extended and then automatically retract to fit the particular user under the biasing force of the elastic element or other biasing arrangement of the adjustment element(s) 1614. In addition, preferably, the adjustment elements 1614 define a hard stop at a maximum extended length to limit extension of the headgear 1600 and define a maximum circumference of the headgear 1600.

In some configurations, each of the adjustment elements 1614 comprise a braided element, which can extend or retract in length. The braided element can comprise one or more elastic elements in parallel with the braided element. The elastic elements can be separate from the braided element or incorporated in the braided element. In some configurations, the elastic elements are contained in internal spaces between filaments of the braided element. An example of suitable braided elements is described in connection with FIGS. 46-54 of Applicant's patent application no. PCT/NZ2014/000074. However, other suitable constructions or arrangements can also be used. Alternatively, elastic element(s) or biasing element(s) can be located within the interface coupling portion and can interact with the core members to pull the core members into the interface coupling portion.

The interface coupling portion 1602 of the headgear assembly 1600 can extend between the pair of adjustment elements 1614 that comprise the circumference adjusting portion 1606. In some configurations, the interface coupling portion 1602 can be relatively rigid. In some configurations, the interface coupling portion 1602 is coupled directly to the adjustment elements 1614. As described above, the interface coupling portion 1602 can facilitate connection of the headgear assembly 1600 to an interface. However, the interface coupling portion 1602 can also accommodate at least a portion of one or more directional locks 1616. In the illustrated arrangement, two pair of directional locks 1616 is provided, with one directional lock 1616 associated with each one of the adjustment elements 1614. Portions (e.g., housings 1618) of the directional locks 1616 can be located at each end of the interface coupling portion 1602. In some configurations, a core member 1620 associated with each of the directional locks 1616 is coupled to the headgear rear portion 1604, extends along or through the adjustment element 1614, through the housing 1618 of the directional lock 1616 and into a collection space 1622. The collection space 1622 can be defined by a collection tube or conduit, which can be a separate member from or can be incorporated into the interface coupling portion 1602. The housing 1620 of the directional lock 1616 can comprise one or more members or elements (e.g., lock washers or lock jaws) that interact with the core member 1618 to selectively allow retraction of the headgear assembly 1600 or lock the headgear assembly 1600 in a particular circumference and inhibit or prevent extension of the headgear at least at forces below the yield force provided by of the directional lock(s). Additional particulars of the operation of the directional locks 1616 are described above and in Applicant's patent application no. PCT/NZ2014/000074.

In the illustrated arrangement, the directional locks 1616 on each side of the interface coupling portion 1602 are vertically stacked or positioned side-by-side. Although the directional locks 1616 are illustrated as separate units, in some configurations portions of the directional locks 1616 can be integrated. For example, a single housing could contain individual lock elements that interact with the separate core members of each adjustment element.

The interface coupling portion 1602 can be curved and the collection spaces 1622 (e.g., defined by collection tubes or channels) can be curved along with the interface coupling portion 1602. In the illustrated arrangement, a center portion of the interface coupling portion 1602 is located above end portions of the interface coupling portion 1602. Furthermore, when viewed from the front, side portions of interface coupling portion 1602 curve downwardly from the center portion. Thus, the interface coupling portion 1602 can complement or correspond to the shape of a body or shell portion of the full face mask interface 1650. The center portion of the interface coupling portion 1602 can be located above an elbow or other conduit connector of the mask 1650. Similarly, the interface coupling portion 1602 can be configured to complement or correspond to the shape of a body or shell portion of the nasal mask interface 1660. The center portion of the interface coupling portion 1602 can be located above an elbow or other conduit connector of the nasal mask 1660. The interface coupling portion 1602 can be configured to complement or correspond to the shape of a body of the nasal pillows/prongs mask 1670. The center portion of the interface coupling portion 1602 can be located above an elbow or other conduit connector of the nasal pillows/prongs mask 1670. In some configurations, the interface coupling portion 1602 can be located between the elbow or other conduit connector and the pillows/prongs of the nasal pillows/prongs mask 1670.

Figures 60, 61:
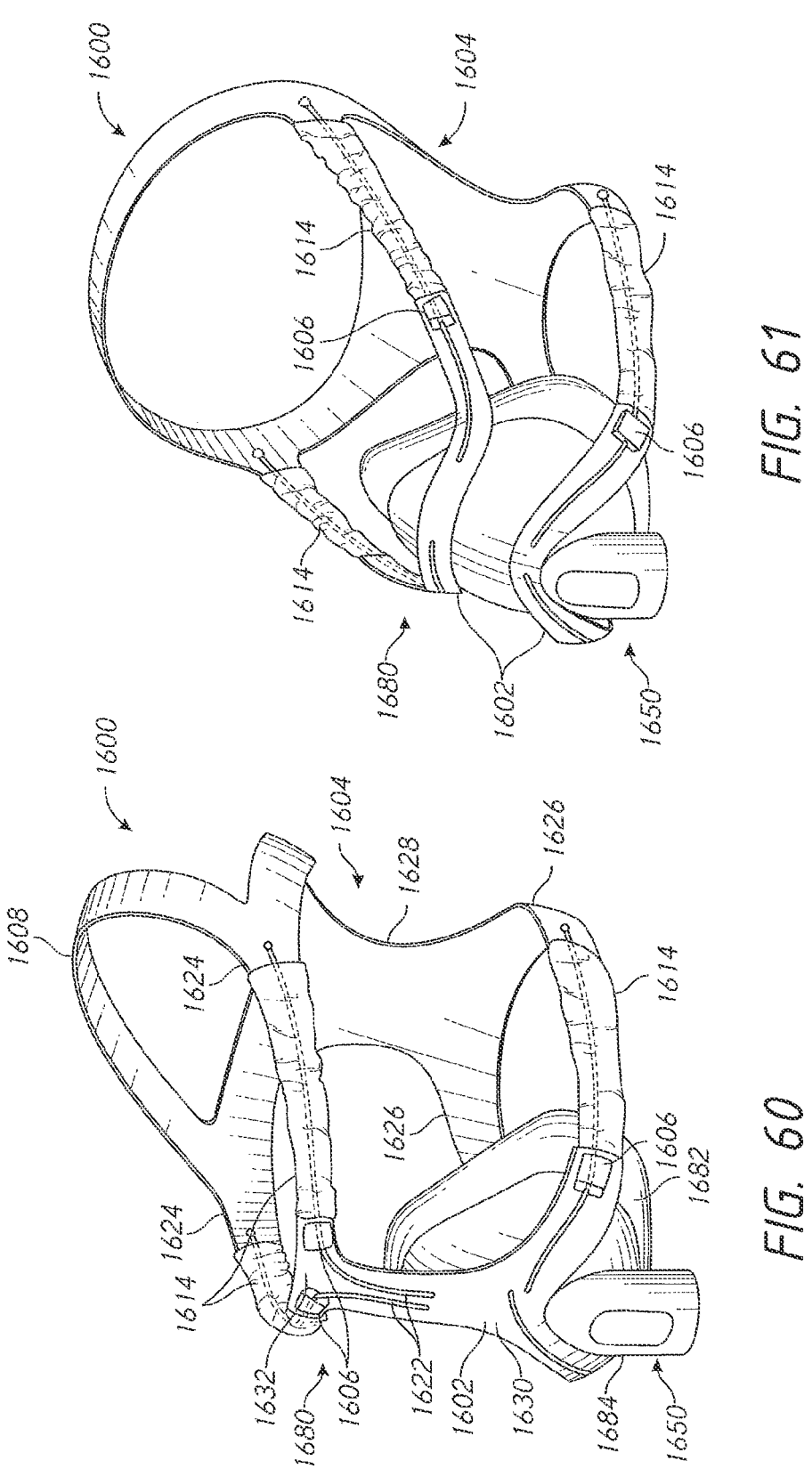
FIG. 60 illustrates an exemplary headgear and interface assembly with a T-piece.
FIG. 61 illustrates an exemplary headgear and interface assembly without a T-piece.

FIG. 60 illustrates an interface assembly 1680 that is similar in many respects to other interface assemblies disclosed herein, such as the interface assemblies of FIGS. 37-53 and FIGS. 57-59. The interface assembly 1680 of FIG. 60 comprises a headgear assembly 1600 and an interface in the form of a full face mask 1650 or nasal mask. The headgear assembly 1600 generally comprises a headgear rear portion 1604, a length or circumference adjusting portion 1606 and an interface coupling portion 1602. The headgear 1600 of FIG. 60 is described in the context of the differences relative to the interface assemblies of FIGS. 37-53 and FIGS. 57-59. Features or details not described can be the same as or similar to corresponding features or details of the interface assemblies of FIGS. 37-53, FIGS. 57-59, other interface assemblies disclosed herein or in Applicant's Application No. PCT/NZ2014/000074 or can be of any other suitable arrangement.

The headgear assembly 1600 of FIG. 60 can be described as or categorized as a two retention plane, parallel headgear type. The illustrated headgear rear portion 1604 comprises a top strap 1608, a pair of upper straps 1624 and a pair of lower straps 1626. The headgear rear portion 1604 comprises a vertically-elongated intermediate rear portion 1628 that extends between and couples the upper straps 1624 and the lower straps 1626. The illustrated interface coupling portion 1602 is in the form of a support frame 1630 for the shell portion 1682 of the full face mask or nasal mask. The shell portion 1682 and the elbow 1684 or other conduit connector (collectively referred to as the "elbow") can be secured, directly or indirectly, to the support frame 1630 by any suitable arrangement. For example, the shell portion 1682 and the elbow 1684 can be separately coupled to the support frame 1630 (directly or indirectly), the shell portion 1682 can be directly coupled to the frame 1630 and the elbow 1684 can be coupled to the shell portion 1682 or the elbow 1684 can be directly coupled to the frame 1630 and the shell portion 1682 can be coupled to the elbow 1684.

In the illustrated arrangement, the interface coupling portion or support frame defines a forehead rest or T-piece 1632. The upper pair of adjustment elements 1614 that comprise the circumference adjusting portion 1606 can be coupled to the T-piece 1632 such that the upper adjustment elements 1614 are positioned above the user's eyes and extend above the user's ears. The lower pair of adjustment elements 1614 that comprise the circumference adjusting portion 1606 can be coupled to a lower portion of the support frame 1630 (directly or through another member, such as the shell) such that the lower adjustment elements 1614 are positioned below the user's eyes and ears. The collection spaces 1622 (e.g., defined by collection tubes or channels) for the upper adjustment elements 1614 can curve and extend downwardly along the T-piece 1632 toward the elbow. The upper directional locks 1616 can be carried by the T-piece 1632. The lower directional locks 1616 can be carried (directly or indirectly) by a lower portion of the support frame 1630.

The micro-adjustment capability provided by the headgear assembly or interface assembly 1680 of FIG. 60 is particularly advantageous in a T-piece configuration because it allows for small adjustments of the fit around the bridge of the user's nose, which can be a particularly sensitive region, to be accomplished quickly and easily. Although each connection between the headgear rear portion 1604 and the interface coupling portion 1602 or interface is illustrated as an automatic adjustment arrangement, in some configurations a combination of automatic adjustment and manual adjustment arrangements could be used. For example, upper connections (e.g., to the T-piece 1632) could be manually adjustable (such as hook-and-loop fastened straps) and the lower connections could be automatically adjustable. With such an arrangement, the upper connections could be set and maintained in position throughout multiple fitting cycles with the lower connections providing all of the elongation necessary for donning and removal ("doffing") of the headgear assembly or interface assembly 1600. Such an arrangement could provide some of the advantages of automatic adjustment at a lower price point, for example. Other suitable combinations could also be used, such as lower manual adjustment and upper automatic adjustment or manual adjustment on one side and automatic adjustment on the opposite side.

FIG. 61 illustrates an interface assembly 1680 that is similar in many respects to other interface assemblies disclosed herein, such as the interface assemblies of FIGS. 37-53, FIGS. 57-59 and FIG. 60. The headgear 1600 of FIG. 61 is described in the context of the differences relative to the interface assemblies of FIGS. 37-53, FIGS. 57-59 and FIG. 60. Features or details not described can be the same as or similar to corresponding features or details of the interface assemblies of FIGS. 37-53, FIGS. 57-59, FIG. 60, other interface assemblies disclosed herein or in Applicant's Application No. PCT/NZ2014/000074 or can be of any other suitable arrangement.

The interface assembly 1680 of FIG. 61 comprises a headgear assembly 1600 and an interface in the form of a full face mask 1650 or nasal mask. The headgear assembly generally comprises a headgear rear portion 1604, a length or circumference adjusting portion 1606 and an interface coupling portion 1602. However, unlike the interface assembly of FIG. 60, the interface assembly 1680 of FIG. 61 does not include a forehead rest or T-piece 1632. As a result, each of the upper pair of adjustment elements 1614 connects to the interface coupling portion 1602 or interface at a lower position relative to the interface assembly 1680 of FIG. 60. For example, the upper adjustment elements 1614 can pass generally along the checks and below the eyes of the user.

The headgear assembly 1600 of FIG. 61 can be described as or characterized as a two retention plane, separated/angle headgear type. The upper and lower adjustment elements 1614 are spaced from one another on the mask 1650 to provide a retention force to the mask 1650 at spaced vertical locations, which can provide stability to the mask 1650. The headgear assembly 1600 can be coupled to the mask 1650 by separate interface coupling portions 1602, each of which can be substantially similar to the interface coupling portion 1602 described in connection with FIGS. 57-60. One of the interface coupling portions 1602 can be located on a lower portion (e.g., a lower half) of the mask 1650 and the other of the interface coupling portions 1602 can be located on an upper portion (e.g., an upper half) of the mask 1650. The lower interface coupling 1602 can pass above the elbow or other conduit connector. In some configurations, the upper and lower interface coupling portions 1602 could be coupled to one another or integrated with one another. For example, a bridge portion could extend between and connect the upper and lower interface coupling portions 1602. The bridge portion could be separate from or unitary with one or both of the interface coupling portions.

Figure 62:
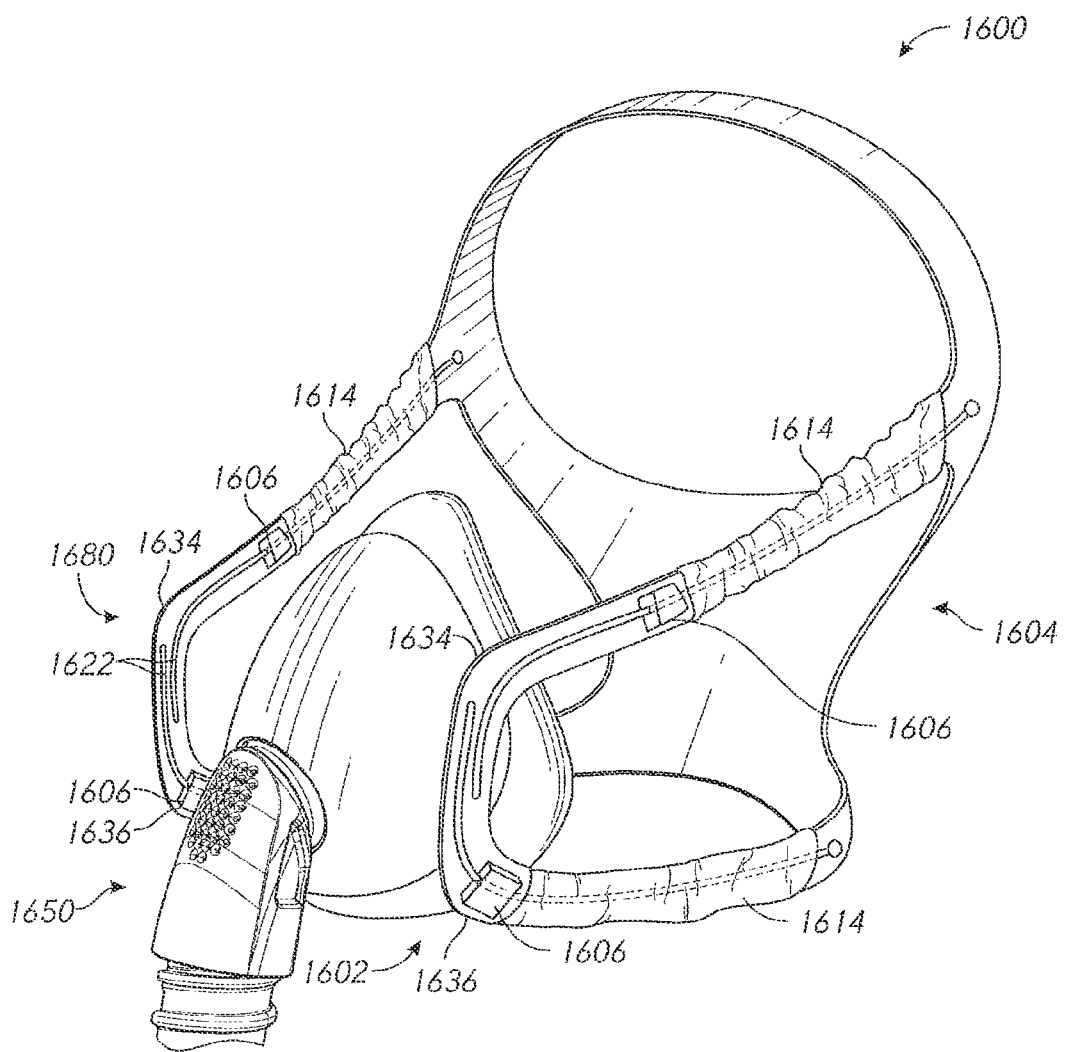
FIG. 62 illustrates an exemplary headgear and interface assembly with an interface coupling portion removably attached to an interface.

FIG. 62 illustrates an interface assembly 1680 that is similar in many respects to other interface assemblies disclosed herein, such as the interface assemblies of FIGS. 37-53, FIGS. 57-59, FIG. 60 and FIG. 61. The headgear 1600 of FIG. 62 is described in the context of the differences relative to the interface assemblies of FIGS. 37-53, FIGS. 57-59, FIG. 60 and FIG. 61. Features or details not described can be the same as or similar to corresponding features or details of the interface assemblies of FIGS. 37-53, FIGS. 57-59, FIG. 60, FIG. 61, other interface assemblies disclosed herein or in Applicant's Application No. PCT/ NZ2014/000074 or can be of any other suitable arrangement.

The interface assembly 1680 of FIG. 62 comprises a headgear assembly 1600 and an interface in the form of a full face mask 1650 or nasal mask, for example. The headgear assembly 1600 generally comprises a headgear rear portion 1604, a length or circumference adjusting portion 1606 and an interface coupling portion 1602. However, unlike the interface assembly 1680 of FIGS. 60 and 61, for example, the interface coupling portions 1602 of the interface assembly 1680 of FIG. 62 do not extend between adjustment elements on opposite sides of the interface assembly 1680 or headgear assembly 1600. Instead, the interface coupling portions 1602 couple the adjustment elements 1614 on the same side of the interface assembly 1680 or headgear assembly 1600. That is, each of the pair of interface coupling portions 1602 couple to one another the upper and lower adjustment elements 1614 of one side of the interface assembly 1680 or headgear assembly 1600.

In the illustrated arrangement, the interface coupling portions 1602 are generally U-shaped members having an upper end portion 1634 coupled to the upper adjustment element 1614 and a lower end portion 1636 coupled to the lower adjustment element 1614. A curved portion of the interface coupling portion 1602 extends between the upper and lower end portions 1634, 1636. The directional lock 1616 for the upper and lower adjustment elements 1614 can be carried by the respective upper and lower end portions 1634, 1636. The collection spaces 1622 (e.g., defined by collection tubes or channels) can curve along the central curved body portion of the interface coupling portion 1602 and, in some configurations, may overlap one another.

In the arrangement of FIG. 62, the headgear assembly 1600 itself may not define an entire closed perimeter. Rather, the interface 1650 may form a portion of the closed perimeter and, thus, a portion of the circumference or perimeter length of the interface assembly 1680. Advantageously, such an arrangement allows for the interface assembly 1680 to be optionally configured have the closed perimeter quickly and easily opened for donning or doffing of the interface assembly 1680. That is, one (or both) of the interface coupling portions 1602 can be removably attached to the interface 1650 (such as by one or more clips) such that one (or both) of the interface coupling portions 1602 can be disconnected and the closed perimeter can be opened. In some configurations, an automatic adjustment mechanism(s) may be provided on only one side of the interface assembly. Similarly, other interface assemblies or headgear assemblies disclosed herein or in Applicant's Application No. PCT/ NZ2014/000074 could be of a single-sided or asymmetric arrangement in which the automatic adjustment mechanism (s) may be provided on only one side.

Figures 63, 64, 65:
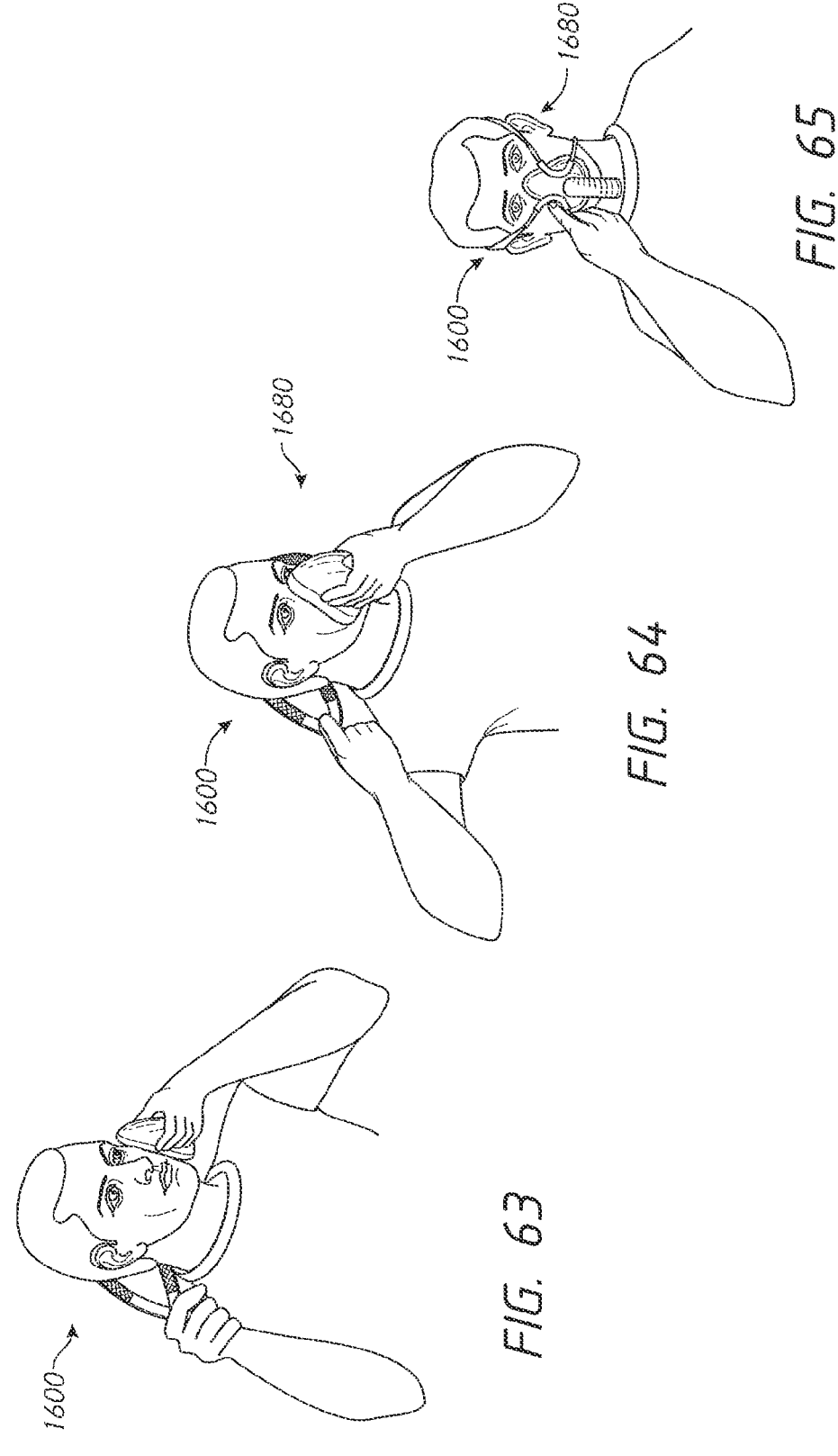
FIG. 63 illustrates a first position when donning the exemplary interface assembly of FIG. 62.
FIG. 64 illustrates a second position when donning the exemplary interface assembly of FIG. 62.
FIG. 65 illustrates a third position when donning the exemplary interface assembly of FIG. 62.

FIGS. 63-65 illustrate a series of discrete positions or steps of donning the interface assembly 1680 of FIG. 62. FIG. 63 illustrates a user placing the interface with interface coupling portion 1602 attached on one side of the head, looping the interface assembly 1600 around the back of the head and pulling the disconnected interface coupling portion 1602 toward the face. In FIG. 64, the interface is brought toward the appropriate position on the face and the disconnected interface coupling portion 1602 is brought toward the interface 1680. FIG. 65 illustrates the interface 1680 in place on the user's face and the user reconnecting the loose or disconnected interface coupling portion 1602 to close the perimeter loop. A portion or all of the movement between FIGS. 64 and 65 may require overcoming of the yield force of the directional locks, as described above. To remove or doff the interface assembly 1680, the procedure can be reversed.

Figures 66, 67:
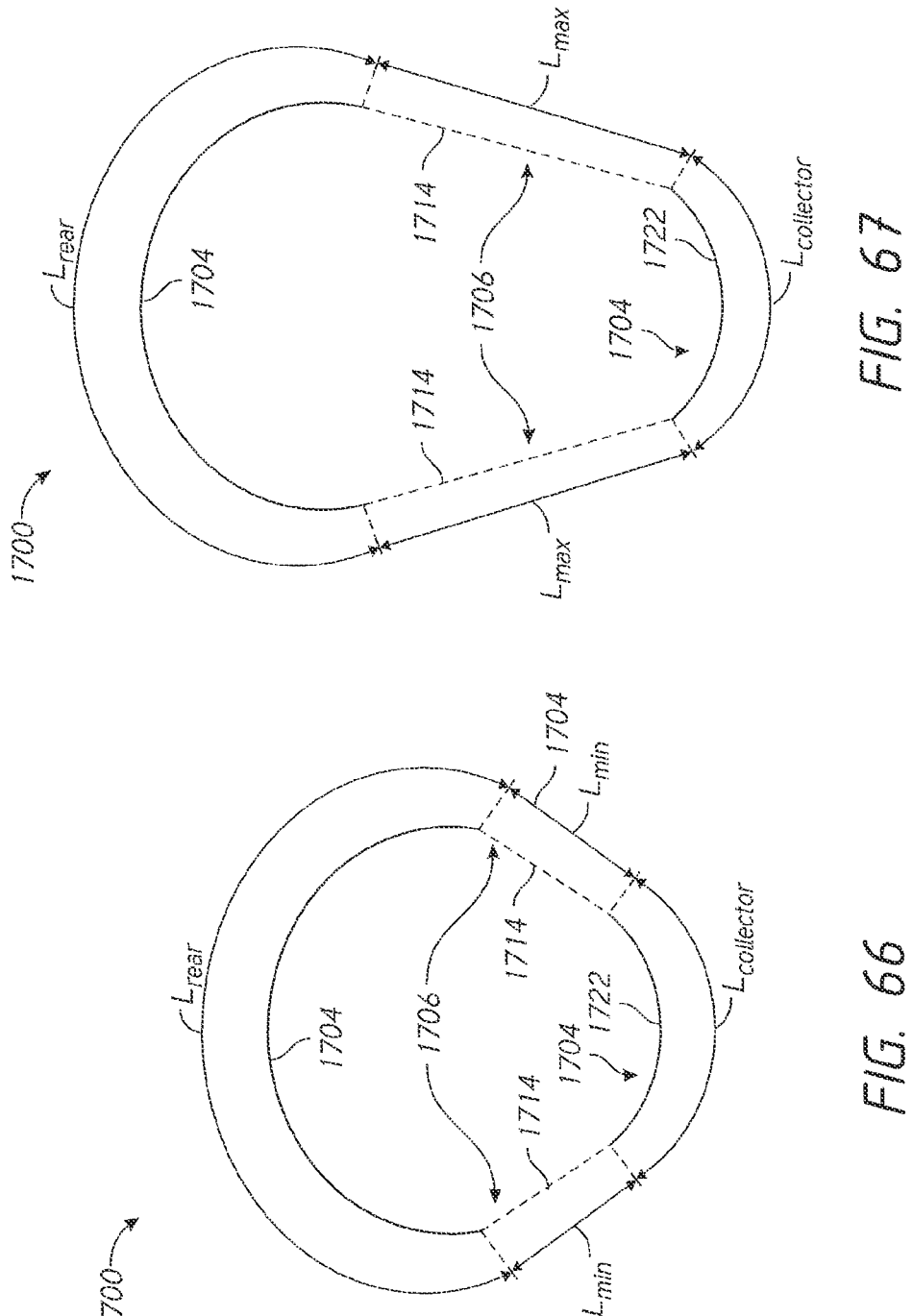
FIG. 66 illustrates a perimeter of an adjustable interface assembly or headgear assembly at a minimum length.
FIG. 67 illustrates a perimeter of an adjustable interface assembly or headgear assembly at a maximum length.

FIGS. 66 and 67 illustrate a perimeter of an automatically adjustable interface assembly or headgear assembly 1700 in a first position (e.g., a minimum perimeter length) and a second position (e.g., a maximum perimeter length), respectively. As described with respect to interface assemblies and headgear assemblies disclosed herein, the perimeter can comprise a length $L_{rear}$ defined by a headgear rear portion 1704. In some configurations, the length $L_{rear}$ can be zero. In other words, a fixed length headgear rear portion 1704 can be omitted and the rear section can be formed by a length adjusting portion or elastic component. In addition, one or more of the portions of the illustrated perimeter can be located in alternative locations or can be split into multiple portions.

The perimeter can also comprise a length $L_{elastic}$ defined by a circumference or length adjusting portion 1706, which in the illustrated arrangement is defined by a pair of elastic or adjustable elements 1714. However, in other configurations, the circumference or length adjusting portion 1706 could be defined by one elastic or adjustable element 1714 or more than two elastic or adjustable elements 1714, among other suitable arrangements. As described above, in some configurations the headgear rear portion 1704 defining the length $L_{rear}$ can be omitted and the length adjusting portion 1706 could extend the entire perimeter portion from one end of the interface coupling portion 1702 to the other end of the interface coupling portion 1702. In FIGS. 66 and 67, the $L_{elastic}$ lengths are labeled with the relative position indicators of minimum length $L_{min}$ and maximum length $L_{max}$, respectively.

The perimeter can further comprise a collector length $L_{collector}$, which can represent an individual or total available length of collection spaces 1722 that receive excess portions of the core elements of the directional lock arrangements. As described above, the collector spaces 1722 do not necessarily extend from one adjustable element 1714 to the other adjustable element 1714 and thereby define a physical section of the perimeter length. For example, in the interface assembly 1680 of FIG. 62, the collector spaces 1622 do not extend between opposite adjustable elements 1614. Thus, in a physical sense, the interface coupling portion(s) 1602, interface 1650 or other structures can define a portion of the perimeter length. However, in a conceptual sense, the clastic length(s) $L_{elastic}$ (minimum length $L_{min}$ and maximum length $L_{max}$) define a length adjustable portion of the perimeters of FIGS. 66 and 67, with the remaining portions (headgear rear portion length $L_{rear}$ and collector length $L_{collector}$) being of a fixed length.

In the illustrated arrangement, the perimeter length can comprise or be defined by the sum of the headgear rear portion length $L_{rear}$, the collector length $L_{collector}$ and the total elastic length $L_{elastic}$, which in the illustrated configuration is two times (2×) $L_{elastic}$ because two equal length adjustable elements 1714 are provided. The total elastic length $L_{elastic}$ at any point in time or for any particular position of the interface or headgear assembly 1700 is equal to or somewhere between the minimum length $L_{min}$ and maximum length $L_{max}$. As described herein, the length of each core member $L_{core}$ preferably is greater than or equal to the maximum length $L_{max}$ of each adjustable element and, therefore, the total core member length $L_{core}$ is preferably greater than or equal to the total maximum length $L_{max}$ such that the headgear assembly can be expanded to its maximum perimeter length without pulling the core member(s) completely through the directional locking element(s). In other words, it is preferable that a portion of the core member(s) is available for engagement by the directional locking element(s) when the headgear assembly is expanded to its maximum perimeter length.

In addition, it is preferable that the collector length $L_{collector}$ is sufficient to accommodate the total excess or unutilized portion(s) of the core members at the minimum and maximum perimeter lengths of the headgear assembly. Thus, in at least some configurations, the individual or total core length $L_{core}$ is less than or equal to the individual or total maximum length $L_{max}$ plus the individual or total collector length $L_{collector}$. In at least some configurations, the individual or total core length $L_{core}$ is less than or equal to the individual or total minimum length $L_{max}$ plus the individual or total collector length $L_{collector}$. In some configurations, the individual or total maximum length $L_{max}$ is less than or equal to the individual or total core length $L_{core}$, which is less than the individual or total maximum length $L_{max}$ plus the individual or total collector length $L_{collector}$. The length of the directional lock mechanism(s) is not specifically shown within the perimeter, but could be considered to form a portion of any of the length of the headgear rear portion $L_{rear}$, elastic length $L_{elastic}$ or collector length $L_{collector}$. In any event, the length of the directional lock mechanism(s) can be accounted for in determining the minimum length of the core $L_{core}$.

In at least some configurations, the individual or total core length $L_{core}$ can be greater than the sum of the individual or total elastic length $L_{elastic}$ and the collector length $L_{collector}$. In at least some configurations, the individual or total core length $L_{core}$ can be between the individual or total maximum length $L_{max}$ and the headgear rear portion length $L_{rear}$, or can be equal to either one of the individual or total maximum length $L_{max}$ and the headgear rear portion length $L_{rear}$.

The perimeters of FIGS. 66 and 67 can be representative of an actual perimeter of an interface assembly or a headgear assembly. That is, the perimeters of FIGS. 66 and 67 could represent the physical construction of a single retention plane interface or headgear assembly or a physical construction of one retention plane in a multi-retention plane interface or headgear assembly. However, as described, the perimeters of FIGS. 66 and 67 can be representative of other interface or headgear types in a conceptual sense. The illustrated perimeters could represent a single retention plane (e.g., upper or lower) of a multiple retention plane headgear type or could represent an average of two or more retention planes of a multiple retention plane headgear type, for example and without limitation.

FIGS. 68A to 68D show an embodiment of a directional lock comprising a housing 1810, a first and a second lock element (e.g., washer 1820, 1822) and a core member 1830. The housing comprises a first and a second chamber 1840, 1842 wherein the first and second chambers 1840, 1842 are configured to house the first and second lock washers 1820, 1822, respectively. In the illustrated arrangement, the first and second chambers 1840, 1842 are separated by an internal wall 1812 of the housing 1810. However, in other arrangements, the first and second chambers 1840, 1842 are not necessarily physically separate spaces, but can be portions of a chamber. The housing 1810 has two end walls 1814, which along with the internal wall 1812, have an elongate core opening 1860 for the core member 1830 pass through. The core openings 1860 are substantially aligned with each other. The core opening 1860 of the end wall 1814 shown on the right side of the figures is larger than the core opening of the internal wall 1812 and the end wall 1814 shown on the left of the figures. This allows for manipulation of the path of the core member 1830 through the housing 1810. The first and second chambers 1840, 1842 are each delimited by the internal wall 1812, one of the end walls 1814 and a pair of side walls 1816; wherein the side walls 1816 extend between the end walls 1814 of the housing 1810. The first and second chambers 1840, 1842 are configured to be open at one or both of a top and a bottom of the housing 1810.

Each of the first and second chambers 1840, 1842 has a pair of washer retainers 1850 that are aligned on opposing side walls 1816 of the housing 1810. Each pair of washer retainers 1850 is configured to pivotally retain one of the first or second lock washers 1820, 1822 within the respective first or second chamber 1840, 1842. The washer retainers comprise a circular bush 1852 and an elongate slot 1854, wherein circular bushes 1852 intersect with the bottom of the housing such that an entrance is formed. The entrance is configured to allow the first and/or second lock washers 1820, 1822 to be received into the washer retainers 1850. The slot 1854 extends radially from the circular bush 1852 towards the top of the housing 1810.

The first and second washers 1820, 1822 comprise a cylindrical shaft 1824 and an arm 1826 that extends from the shaft 1824. The cylindrical shaft 1824 is substantially the same width W, as the housing 1810 and the arm 1826 is narrower to fit within the first and second chambers 1840, 1842. In the illustrated arrangement, the arm 1826 comprises a first section 1872 and a second section 1874, wherein the first section 1872 extends radially or perpendicularly from the cylindrical shaft 1824 and the second section 1874 extends at an obtuse angle from the end of the first section 1872. The first section 1872 of the arm 1826 of the first washer 1820 is shorter than the first section 1872 of the arm 1826 of the second washer 1822. The angle between the first and second sections 1872, 1874 of the arm 1826 of the first washer 1820 is greater than the corresponding angle of the second washer 1822. The angles can be selected such that the second section 1874 of one or both of the first and second washers 1820, 1822 lies substantially flat against the corresponding wall (e.g., internal wall 1812 and end wall 1814, respectively) of the housing 1810 in one position of the washers 1820, 1822. The second section 1874 of the arm 1826 comprises a centrally located circular aperture 1876 configured to receive the core member 1830. The first and second chambers 1840, 1842 differ in size according to the size of the washer that is to be housed within it, i.e. the first chamber 1840 is smaller than the second chamber 1842 because the first washer 1820 is smaller than the second washer 1822.

The cylindrical shafts 1824 of the first and second lock washers 1820, 1822 have a diameter substantially the same as that of the circular bushes 1852 of the washer retainer 1850, and are configured to be received and retained by the circular bush 1852 in a snap-fit configuration. The snap-fit configuration is provided by the entrance of the circular bush 1852 being narrower than the diameter of the cylindrical shaft 1824. The slots 1854 of the washer retainers 1850 are configured to allow the entrance to be flexed open to increase the case with which the first and second lock washers 1820, 1822 can be pushed through the entrances and assembled to the housing 1810. Once assembled within the first and second chambers 1840, 1842 of the housing 1810, the first and second washers 1820, 1822 can pivot back and forward around a central axis that runs through the cylindrical shaft 1824.

Figure 68A:
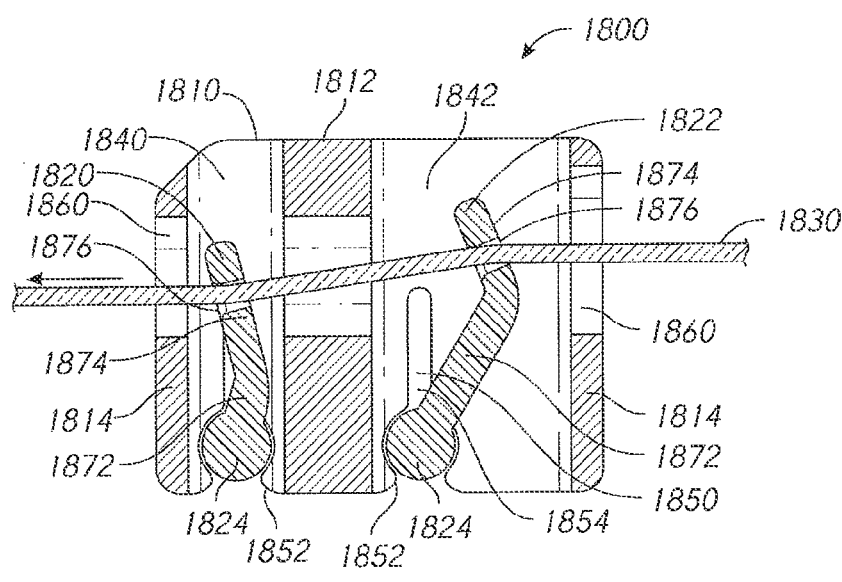
FIG. 68A is a cross-sectional view of a directional lock in a locked position.
Figure 68B:
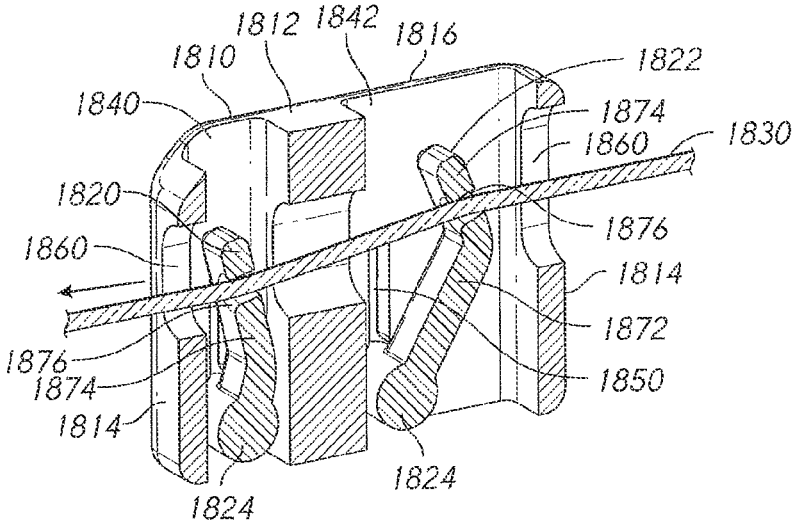
FIG. 68B is a perspective cross-sectional of the directional lock in FIG. 68A in the locked position.
Figure 68C:
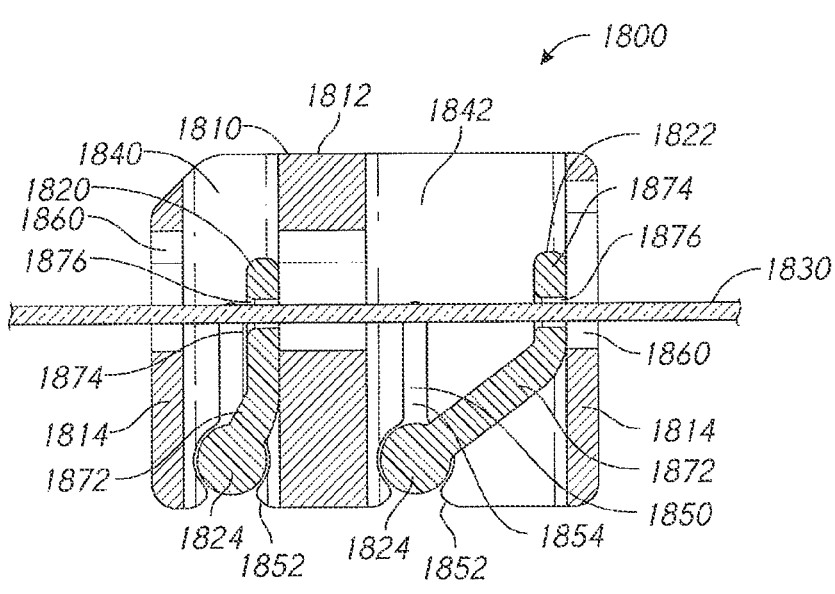
FIG. 68C is a cross-sectional view of the directional lock in FIG. 68A in the unlocked position.
Figure 68D:
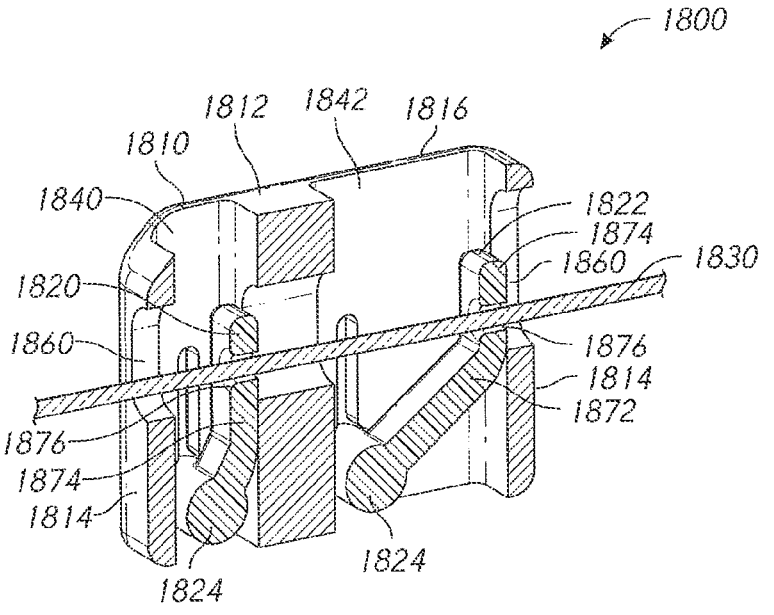
FIG. 68D is a perspective cross-sectional of the directional lock in FIG. 68A in the unlocked position.

The core member 1830 is configured to pass through the core openings 1860 of the housing 1810 and the apertures 1876 of the first and second washers 1820, 1822. Application of a tension force to the core member 1830 causes the first and second lock washers 1820, 1822 to pivot back and/or forward between a locked position and/or open position. FIGS. 68A and 68B show the directional lock in a locked configuration in which a force is applied to the core member 1830 in a direction towards the left side of the figure (as indicated by the arrow). The force applied to the core member 1830 in this configuration causes the first and second lock washers 1820, 1822 to pivot in an anti-clockwise direction, such that the path of the core member 1830 through the directional lock 1800 is non-linear or tortuous and movement of the core member 1830 is restricted. FIGS. 68C and 68D show the directional lock in an open configuration in which a force is applied to the core member 1830 in a direction towards the right side of the figure (as indicated by the arrow). In this configuration, the first and second lock washers 1820, 1822 are pivoted in a clockwise direction such that the circular apertures 1876 and core openings 1860 are aligned in a substantially straight line. This provides a smooth path for the core member 1830 to be pulled substantially freely through the directional lock 1800. Additional particulars of the operation of the directional locks 1800 are described above and in Applicant's patent application no. PCT/NZ2014/000074.

Figure 69A:
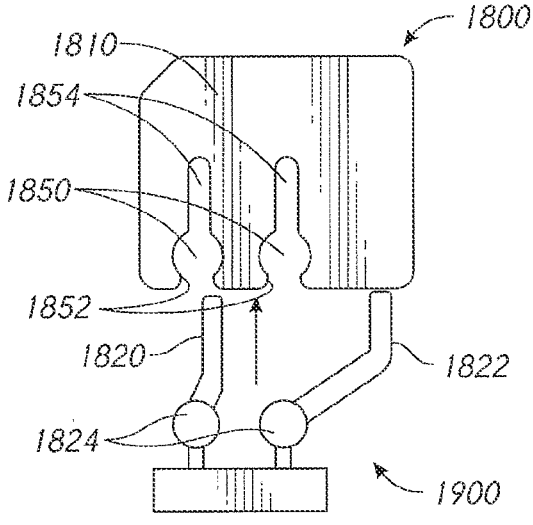
FIG. 69A is a view of a first assembly step for attaching lock washers to a housing of an exemplary directional lock.
Figure 69B:
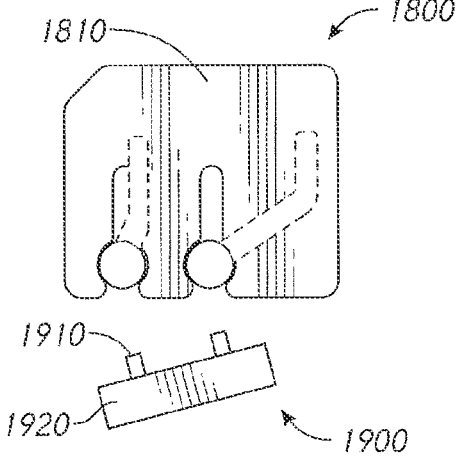
FIG. 69B is a view of a second assembly step for attaching lock washers to the housing of the exemplary directional lock of FIG. 69A.

FIGS. 69A-B show a non-limiting exemplary embodiment of a housing 1810 and first and second lock washer 1820, 1822. The first and second lock washers 1820, 1822 are configured to be moulded as a single component wherein they are connect by a runner and gate system 1900, as in known in the art. The runner and gate system is configured to be used as an assembly aid for the first and second lock washers 1820, 1822, wherein the runner and gate system 1900 can be gripped by a person or machine in order to align the first and second washers 1820, 1822 with the washer retainers 1850 of the housing 1810. A force (as shown by the arrow) can be applied to the lock washers 1820, 1822 through the gate and runner system 1900 to provide relative movement between the housing 1810 and the lock washers 1820, 1822. Such relative movement can be utilized to engage the first and second lock washers 1820, 1822 with the housing 1810 such that the cylindrical shafts 1824 of the lock washers 1820, 1822 are snap-fitted into the circular bush 1852 of the washer retainer 1850.

As shown in FIG. 69B, once the first and second lock washers 1820, 1822 are assembled within the housing 1810, the gate and runner system 1900 can be disconnected or broken away from the lock washers 1820, 1822. A force (shown by the arrow) can be applied to the gate and runner system 1900 in a direction that is substantially perpendicular to the direction in which the assembly force is applied (arrow in FIG. 69A) to detach the gate and runner system 1900 from the lock washers 1820, 1822. When the gate and runner system 1900 is detached, the lock washers 1820, 1822 remain assembled with the housing 1810. The gates 1910 of the gate and runner system 1900 can be designed to have a weak point that encourages them to break as close as possible to the cylindrical shaft 1824 of the lock washer 1820, 1822, such that the range of pivoting motion of the lock washer 1820, 1822 is not limited by excess gate material.

Figures 70A, 70B:
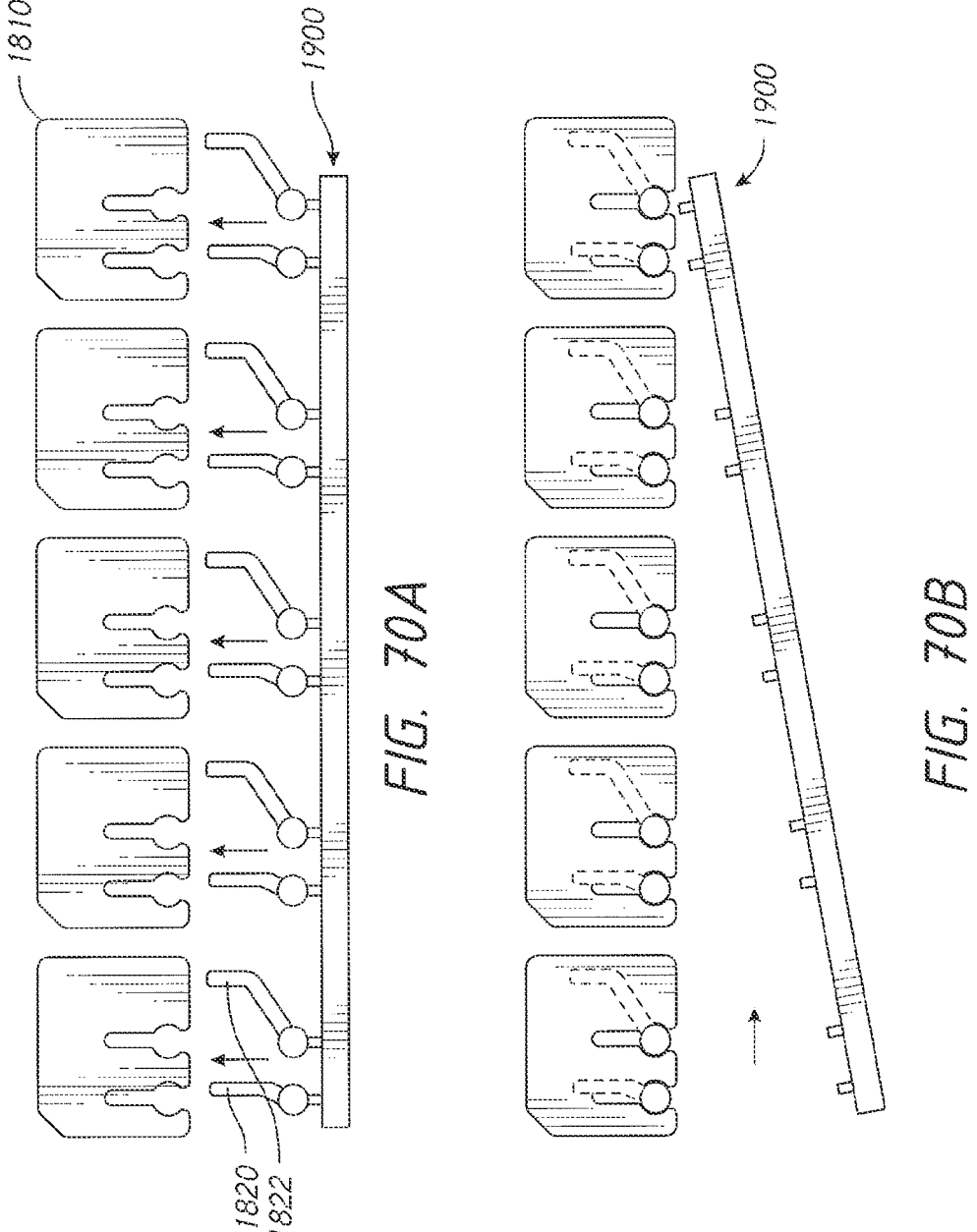
FIG. 70A is a view of a first assembly step for attaching lock washers to housings of a plurality of exemplary directional locks.
FIG. 70B is a view of a second assembly step for attaching lock washers to housings of the plurality of exemplary directional locks of FIG. 70A.

FIGS. 70A and 70B show an embodiment wherein multiple sets of first and second lock washers 1820, 1822 are moulded together on a single gate and runner system 1900. This configuration allows multiple directional locks 1820, 1822 to be assembled at once or sequentially, thus improving manufacturing efficiencies. To assemble the sets of lock washers 1820, 1822 to the housings 1810, the runner and gate system 1900 can be gripped by a person or machine in order to align the first and second washers 1820, 1822 with the washer retainers 1850 of each of the housings 1810. A force (as shown by the arrow) can be applied through the gate and runner system 1900 to engage the sets of first and second lock washers 1820, 1822 with the housings 1810 such that the cylindrical shafts 1824 of the lock washers 1820, 1822 are snap-fitted into the circular bushes 1852 of the washer retainers 1850.

Figure 71:
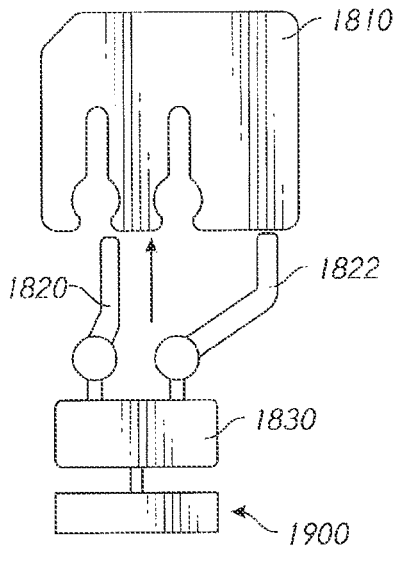
FIG. 71 is a view of an assembly step for attaching lock washers to a housing of an exemplary directional lock.

FIG. 71 shows a non-limiting exemplary configuration for assembling the first and second lock washers 1820, 1822 to the housing 1810 of a directional lock 1800. This configuration includes a grip portion or element, such as a grip tab 1930, that is used to align and apply an assembly force to the lock washers 1820, 1822. The grip tab 1930 is formed between the lock washers 1820, 1822 and the gate and runner system 1900 and can have a geometry specifically configured to be easily gripped by a person or a machine. In some configurations, the gate and runner system 1900 is configured to be removed from the grip tab 1930 during the moulding process. In a variation of this configuration (not shown) multiple pairs of first and second lock washers 1820, 1822 can be connected by a single grip tab 1930, which is then used to assemble the directional lock in a single action.

Figure 72:
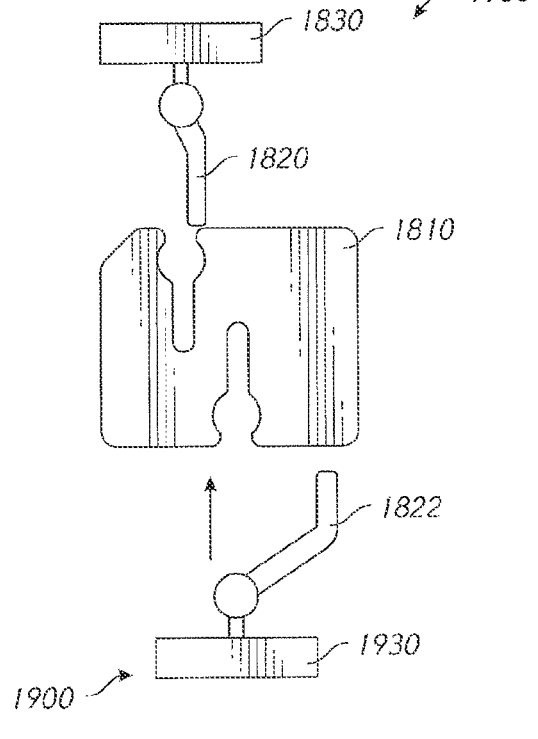
FIG. 72 is a view of an assembly step for attaching lock washers to a housing of an exemplary directional lock.

FIG. 72 shows a non-limiting exemplary embodiment of the direction lock. In this embodiment, the washer retainers 1850 are positioned in an opposing arrangement wherein the first washer retainer 1850 extends downwardly from the top of the housing and the second washer retainer 1850 extends upwardly from the bottom of the housing. The first and second lock washers 1820, 1822 are assembled to the housing 1810 in opposing directions. For example, a grip tab 1930 or the gate and runner system 1900 as described in relation to the embodiment of FIGS. 69a to 71 can be used to aid in the assembly of the lock washers 1820, 1822 to the housing 1810.

FIGS. 73-80 illustrate interfaces with headgear arrangements configured to allow the interface to be donned and doffed in the manner of a baseball cap. Preferably, the headgear arrangements do not include a strap that passes below the user's ear. Therefore, the interface with such as headgear arrangement can be fitted or donned by passing the interface over the user's head from above. The headgear arrangement could be positioned onto the rear of the user's head and then the interface arrangement rotated downward and the interface positioned on the user's face, or vice-versa. The headgear arrangements can include a portion forward of the user's ear, which can provide a mounting location for direction or indirect connection to the interface. In some configurations, the rear portion of the headgear arrangement is relatively rigid (e.g., to maintain an open shape when not on a user) and/or relatively inextensible.

Figure 73:
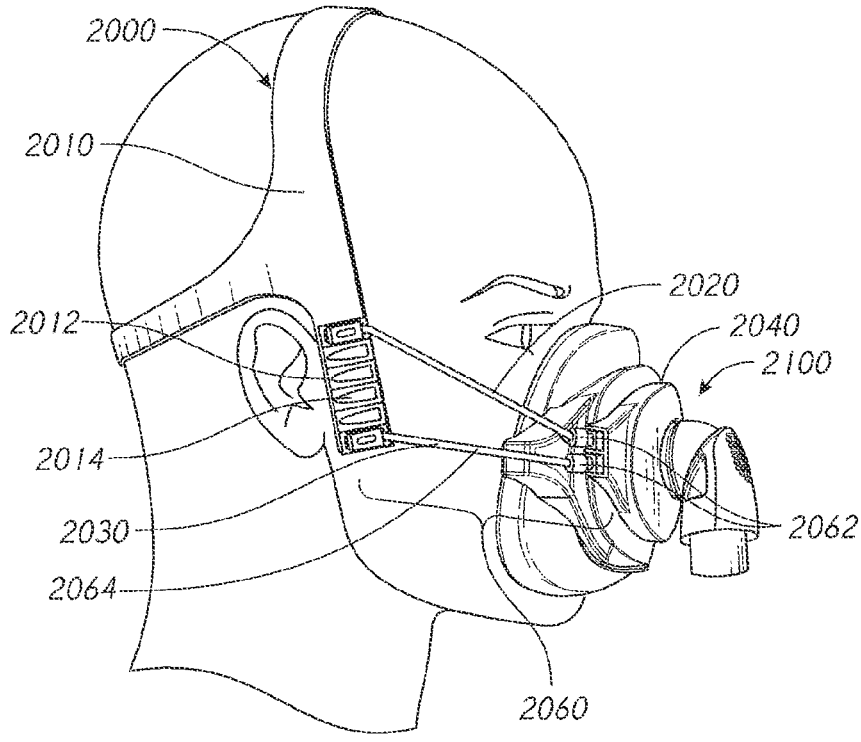
FIG. 73 is a side view of an exemplary full face mask without a forehead support.

FIG. 73 illustrates an alternate arrangement for a headgear system 2000 that is configured for use in combination with a full face mask 2100 that has no forehead support. However, the headgear system 2000 or portions thereof can also be used in combination with other types of interfaces, including interfaces having a forehead support, if desired. The full face mask 2100 is configured to seal around a user's nose and mouth, wherein it contacts the nasal bridge, checks and a lower lip or chin region. The headgear system 2000 comprises a headgear rear portion 2010, an upper retention plane 2020 and a lower retention plane 2030.

Preferably, the headgear rear portion 2010 engages the user's head and provides a relatively stable platform for connection of the interface, such as utilizing the interface coupling portion 2040 and the circumference adjusting portion (e.g., directional locking modules 2060). Thus, in at least some configurations, the headgear rear portion 2010 is substantially inelastic such that it holds its shape and effec- tive length in response to applied forces within a range that is typical or expected for the intended application. In some configurations, the headgear rear portion 2010 can comprise a layer constructed from a relatively rigid material, such as a plastic material, coupled to one or more layers of a fabric material. Preferably, a fabric layer is provided at least on a user-contacting surface of the rigid material layer. In some configurations, a fabric layer is provided on each side of the rigid material layer. Furthermore, in some configurations, the rigid material layer can be formed between the material layers, such as by injection molding the rigid material into a space between two material layers within a mold. An example of such a headgear and a method of making such a headgear is disclosed in Applicant's U.S. Provisional Appli- cation No. 62/050,925, the entirety of which is incorporated by reference herein.

The headgear rear portion 2010 comprises an arm 2012 that extends in front of the user's ear. The arm 2012 comprises a plurality of vertically spaced connectors 2014 configured to provide a series of locations at which one or more directional locking modules 2060 may be connected. Full face masks are generally larger and heavier than the direct nasal masks of previous embodiments. As a result of this, the full face masks may require more than one retention plane to provide the desirable or required level of stability to achieve a substantially airtight seal with a user's face.

The two retention planes 2020, 2030 converge towards a single point on the side of or possibly forward of the full face mask 2100, wherein they may or may not intersect. The retention planes 2020, 2030 can be vertically spaced from one another, such that they are spaced apart further at the point where they connect with the headgear than the point where they connect with the mask. This provides some degree of stability to the interface. For example, an upper retention plane 2020 can pass from the top of the ear through or above the underside of the nose of the user and a lower retention plane 2030 can pass from the bottom of the ear to near or below the mouth of the user.

Each of the two retention planes 2020, 2030 can be provided by two directional locking modules 2060, wherein one is located on each side of the headgear system 2000. The directional locking modules 2060 each comprise a direc- tional lock 2062 and an elastic portion 2064, which is connected to the directional lock 2062 at one end and one of the plurality of connectors 2014 at the other end. The angle of the retention planes 2020, 2030 can be adjusted by connecting the end of the elastic portion 2064 to a different connector 2014 on the headgear arm 2012. The illustrated full face mask 2100 does not include a forehead rest or "T-piece." However, in some configurations, a T-piece could be provided. If desired, additional headgear element(s) or strap(s) could couple a rear portion of the headgear to the T-piece of the mask.

Figure 74:
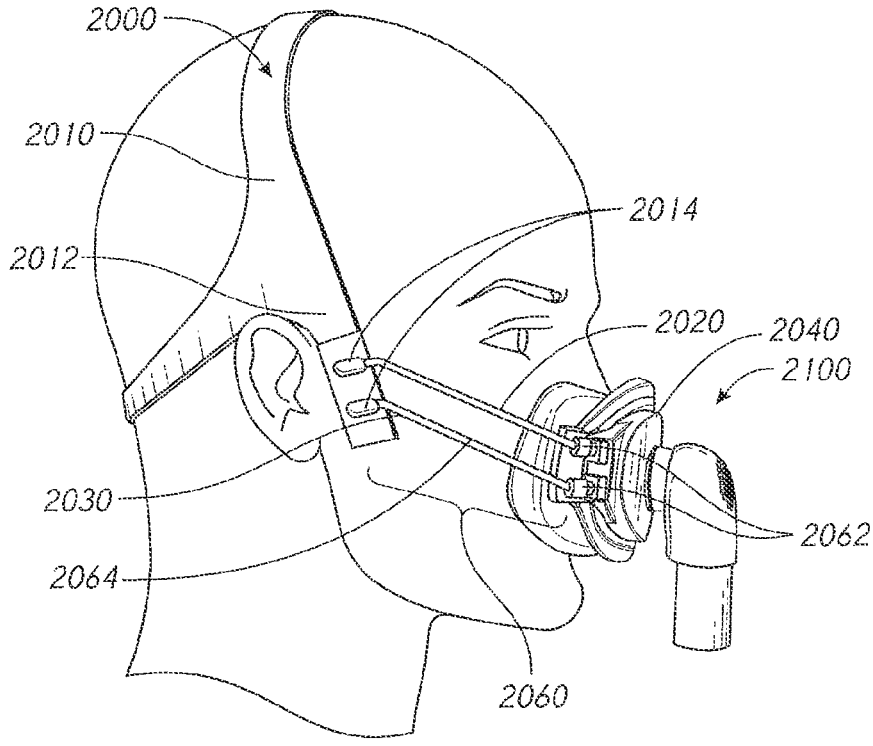
FIG. 74 is a side view of an another exemplary full face mask without a forehead support.

FIG. 74 illustrates a headgear system arrangement 2000 that comprises a headgear rear portion 2010 and two reten- tion planes 2020, 2030 that are configured to secure a full face mask 2100 to a user's face. In this arrangement the full face mask 2100 is configured to seal on the underside of a user's nose and around their mouth, such that the nasal bridge is not contacted by the mask 2100. The different sealing locations, relative to the previous embodiment, require or at least make it desirable that the angles of the retention planes 2020, 2030 differ in order to apply forces to the mask in an optimal or desirable direction. In FIG. 74, the two retention planes 2020, 2030 are shown to be vertically spaced and attached to an arm 2012 of the headgear rear portion 2010 such that there is an upper retention plane 2020 and a lower retention plane 2030 that are substantially parallel to each other. The upper retention plane 2020 is more horizontal than the upper retention plane 2020 of the previous embodiment and sits lower down on the user's face. The angle of the retention planes 2020, 2030 may be adjustable via a plurality of connectors 2014, such as those shown in the embodiment of FIG. 73.

Each of the retention planes 2020, 2030 is shown to comprise a directional lock module 2060, which further comprises an elastic portion 2064 and a directional lock 2062. In a variation of this arrangement, each directional lock module 2060 may comprise more than one directional lock 2062.

Figure 75:
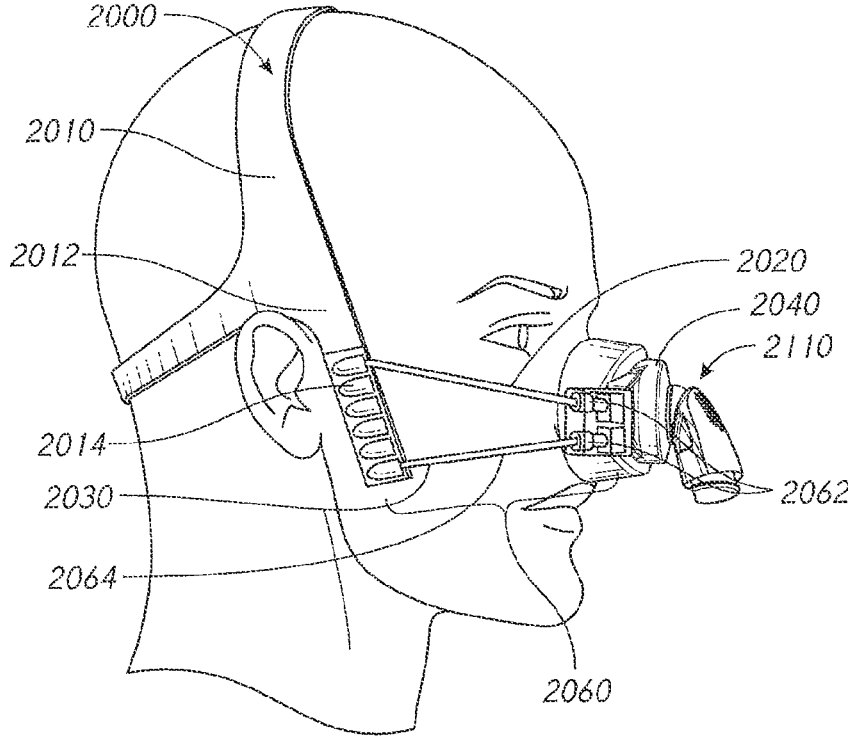
FIG. 75 is a side view of an exemplary nasal mask.

FIG. 75 shows the headgear system 2000 of FIG. 73 in combination with a nasal mask 2110. The nasal mask 2110 is configured to seal around the nose of a user, contacting the nasal bridge, cheeks and the upper lip. Two retention planes 2020, 2030 are desired or possibly required to provide appropriate stability to the mask 2110 when fitted to a user's face.

Figure 76:
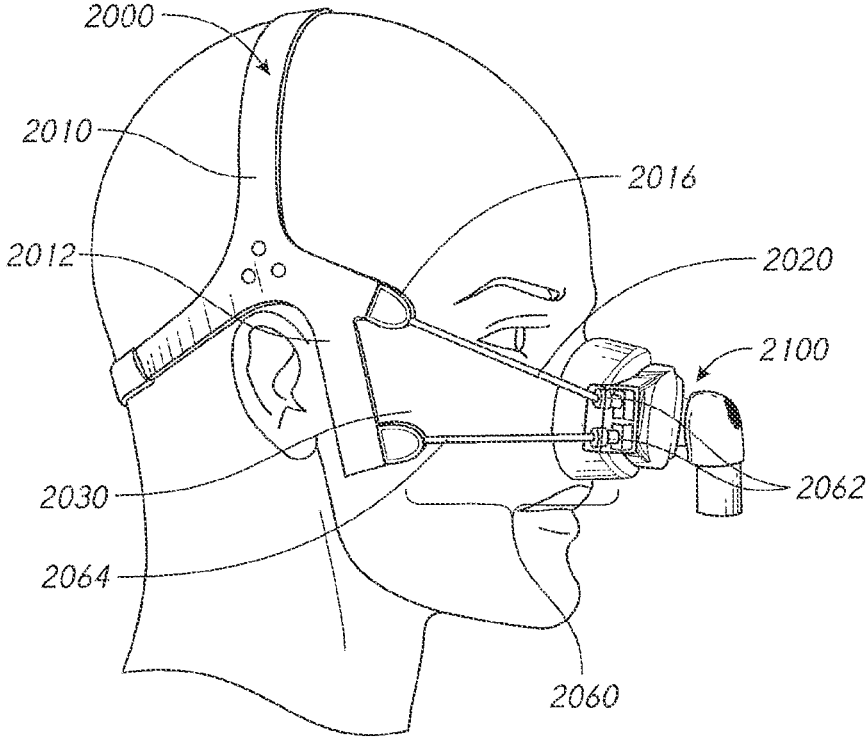
FIG. 76 is an exemplary headgear system having a headgear rear portion and two retention planes.

FIG. 76 illustrates a non-limiting exemplary embodiment of a headgear system 2000 that comprises a headgear rear portion 2010 and two retention planes 2020, 2030 config- ured to secure a nasal mask 2110 to a user's face. The headgear rear portion 2010 comprises a moulded plastic structure 2016, with an integrally formed fabric covering, having arms that extend downward in front of a user's ear. Upper and lower retention planes 2020, 2030 are provided by directional lock modules 2060 on each side of the headgear. The upper retention plane 2020 extends from the top of the arm 2012 to a location just above the tip of a user's nose. The lower retention plane 2030 extends from the bottom of the arm 2012 to a position that is approximately on the underside of the user's nose. In the illustrated arrangement, the directional lock modules 2060 comprise a braided elastic portion, core filament (not shown) and a directional lock, wherein the braided elastic portion and core filament are joined permanently to the arm 2012 of the headgear and the directional lock 2060 by an over-molded connection. The angle of the retention planes 2020, 2030 is fixed by the over-moulded connections 2016.

Figure 77:
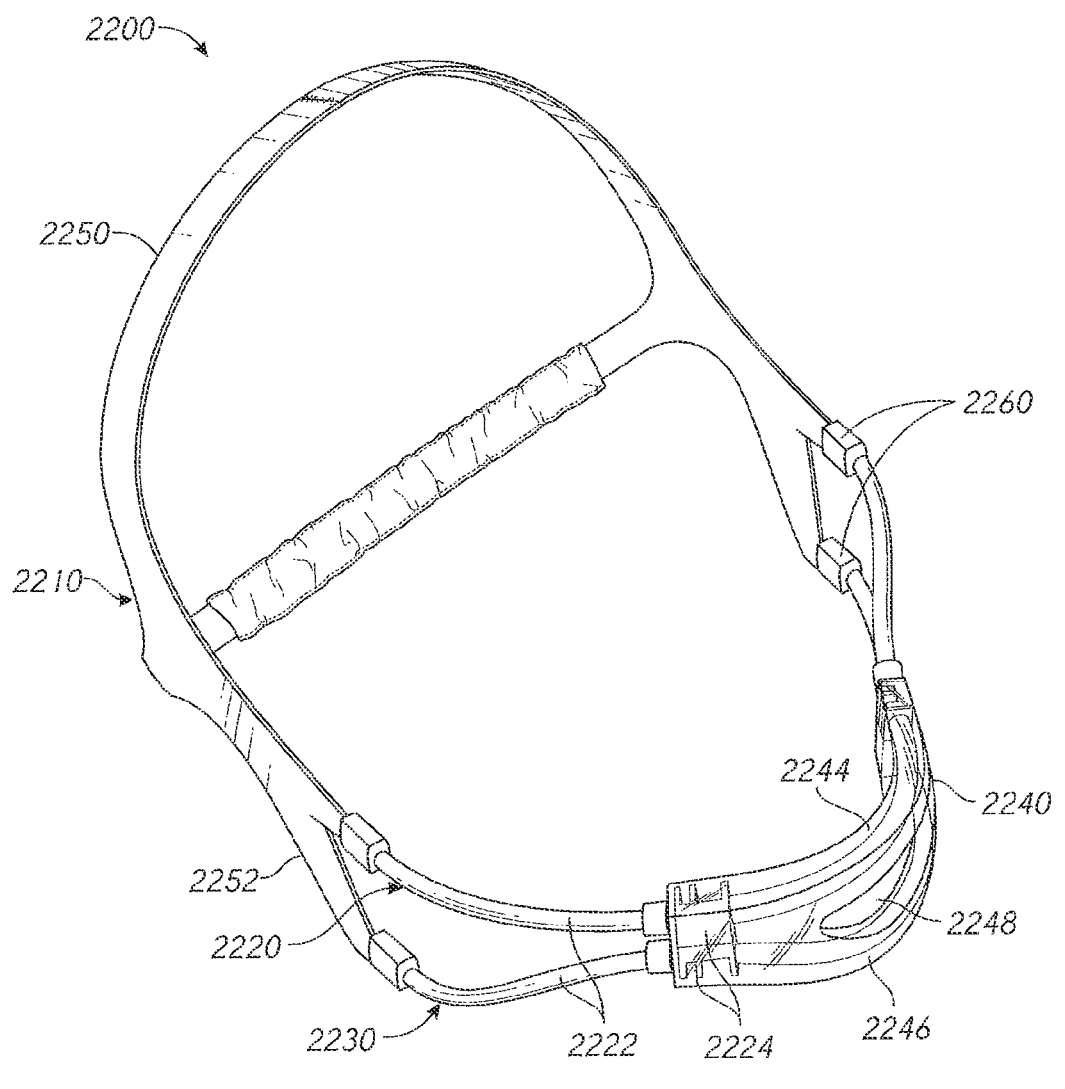
FIG. 77 is a front perspective view of an another exemplary headgear.
Figure 78:
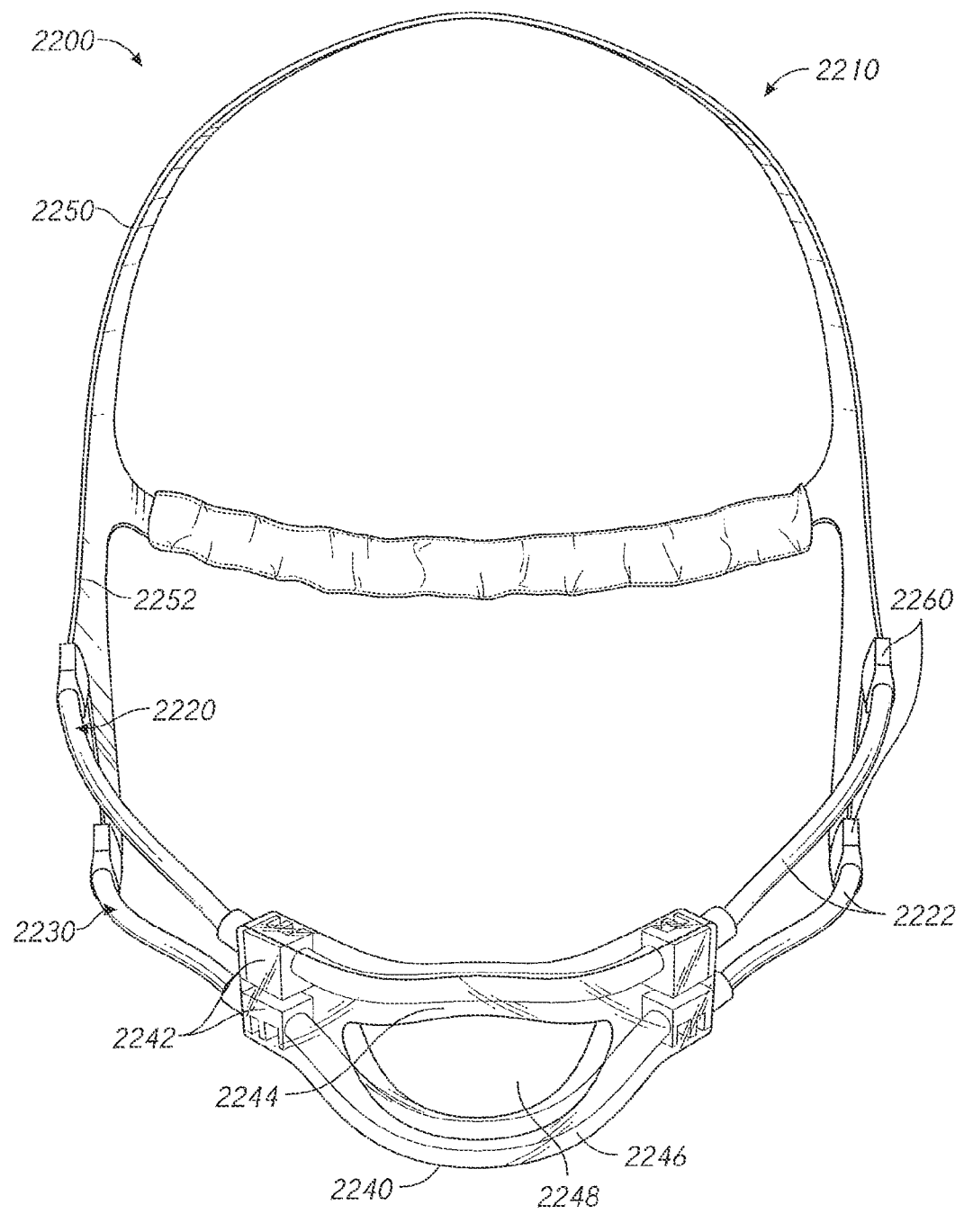
FIG. 78 is a front view of the exemplary headgear system in FIG. 77.
Figure 79:
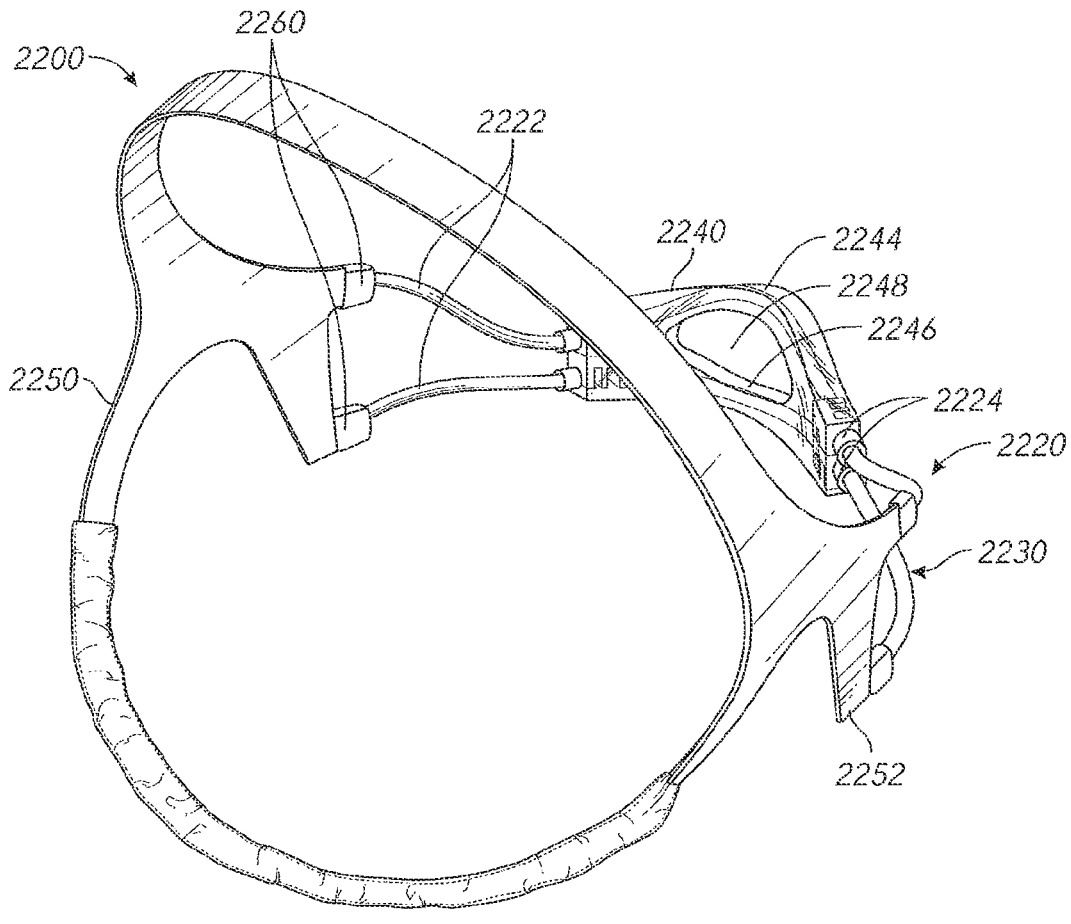
FIG. 79 is a rear perspective view of the exemplary headgear system in FIG. 77.

FIGS. 77 to 79 show views of a headgear system 2200 according to the presently disclosed subject matter. The headgear system 2200 is a closed loop and comprises a headgear 2210, two upper directional lock modules 2220, two lower directional lock modules 2230 and a housing 2240. The headgear rear portion 2250 comprises a bifurcated molded plastic structure with an integrally formed fabric cover, and a pair of arms 2252 configured to extend down- wardly in front of a user's ears, in use.

The upper and lower directional lock modules 2220, 2230 comprise an clastic portion 2222, a core filament (not shown) and a directional lock 2224. The core filament is configured to extend partially or throughout the length of the elastic portion 2222 and through the directional locks 2224. The directional locks 2224 are configured to interact with the core filament to allow the length of the directional lock module 2220, 2230 to automatically adjust. The core filament and elastic portions 2222 are permanently joined to the arms 2252 of the headgear 2210 by an over-molded connection 2260, wherein the upper directional lock modules 2220 are joined to an upper region of the arms 2252 and the lower directional lock modules 2230 are joined to a lower region of the arms 2252. The elastic portions 2222 are permanently joined to the directional lock 2220, 2230 by an over-molded connection 2260. The directional locks 2220, 2230 are contained within the housing 2240. The two upper directional lock modules 2220 form an upper retention plane, and the two lower directional lock modules 2230 form a lower retention plane that are substantially the same as those of FIG. 76.

The housing 2240 comprises substantially rigid body having four directional lock brackets 2242, an upper conduit 2244, a lower conduit 2246 and a central opening 2248 formed there between. Two directional lock brackets 2242 are positioned, one above the other, at each of the lateral ends of the housing 2240. The directional lock brackets 2242 are configured to retain the directional locks 2224. The upper conduit 2244 extends laterally between the two upper lock brackets 2242 and the lower conduit 2246 extends laterally between the lower lock brackets 2242. The upper and lower conduits 2244, 2246 are configured to house a free end of the core filaments. The central opening 2248 that is formed between the upper and lower conduits 2244, 2246 is configured to receive a nasal mask arrangement.

Figure 80:
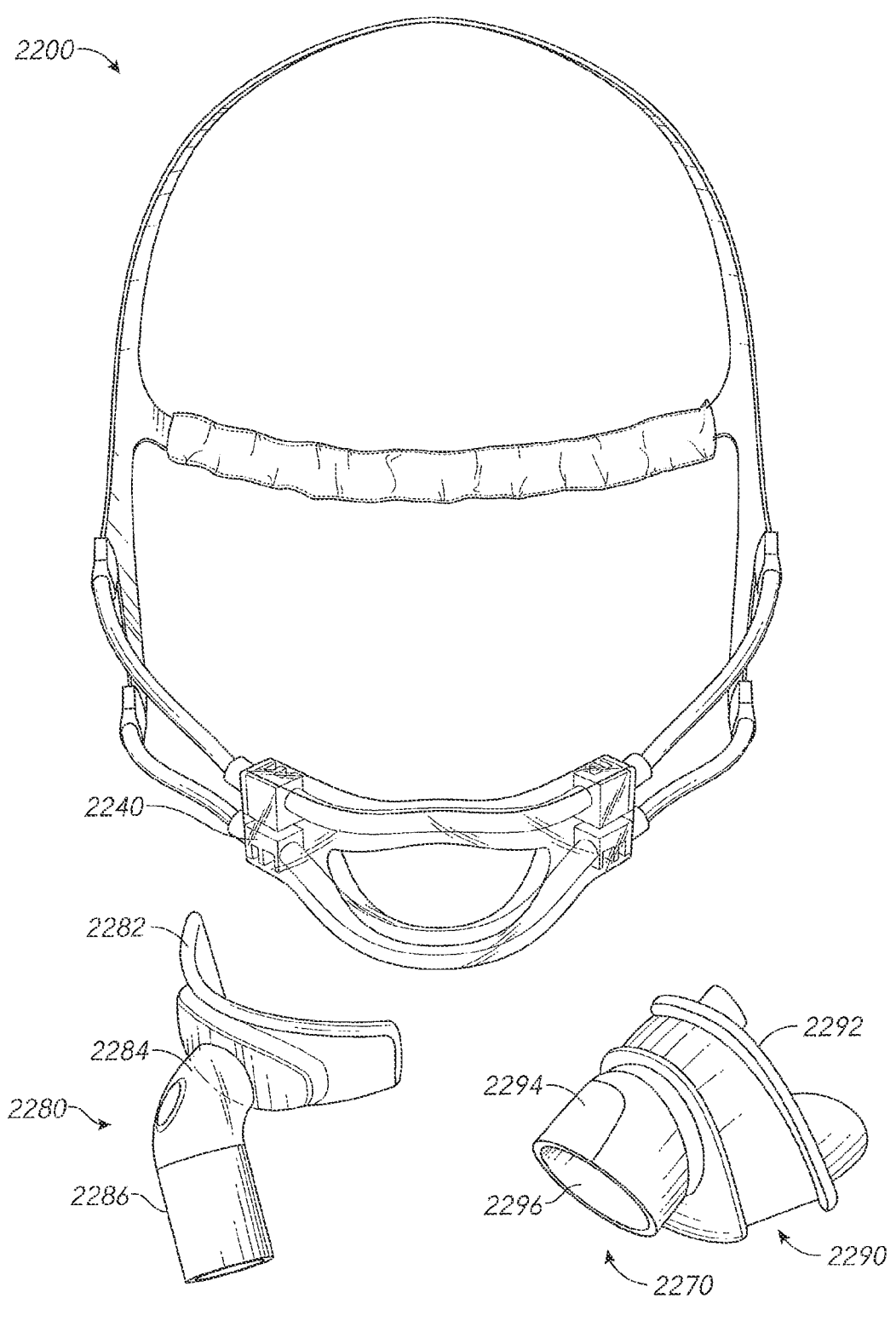
FIG. 80 is a front view of the exemplary headgear system in FIG. 77 with a mating nasal mask arrangement.

FIG. 80 shows the headgear system of FIG. 79 along with the nasal mask arrangement 2270 that is configured to assemble with it. The nasal mask arrangement 2270 comprises a frame assembly 2280 and a cushion module 2290. The frame assembly 2280 includes a frame 2282, elbow 2284 and a tube connector 2286. The frame 2282 and the elbow 2284 are configured to be joined together by a ball and socket connection, wherein the frame 2282 includes the socket 2410 and the elbow 2284 includes the ball 2400. The frame 2282 comprises a nylon component with geometry that provides a repeatably removable snap-fit connection with the housing 2240 of the headgear system 2200. In some configurations, the elbow is made of a different material to the frame 2282, such as polycarbonate, so that the two parts do not stick together when assembled. This can improve the freedom with which that elbow can move relative to the frame 2282 and may reduce hose drag. It is envisaged that other material combinations may also be used.

The tube connector 2286 connects to an end of the elbow 2284, which opposes the end that is connected to the frame 2282, in a snap fit configuration. The tube connector 2286 can swivel or rotate about the end of the elbow 2284. In some embodiments the tube connector 2286 can be made of a different material to the elbow 2284, such as nylon. Tube connector 2286 is configured to provide a means for connecting the nasal mask arrangement 2270 to a CPAP tube, which provides a pressurized air supply.

Figure 81:
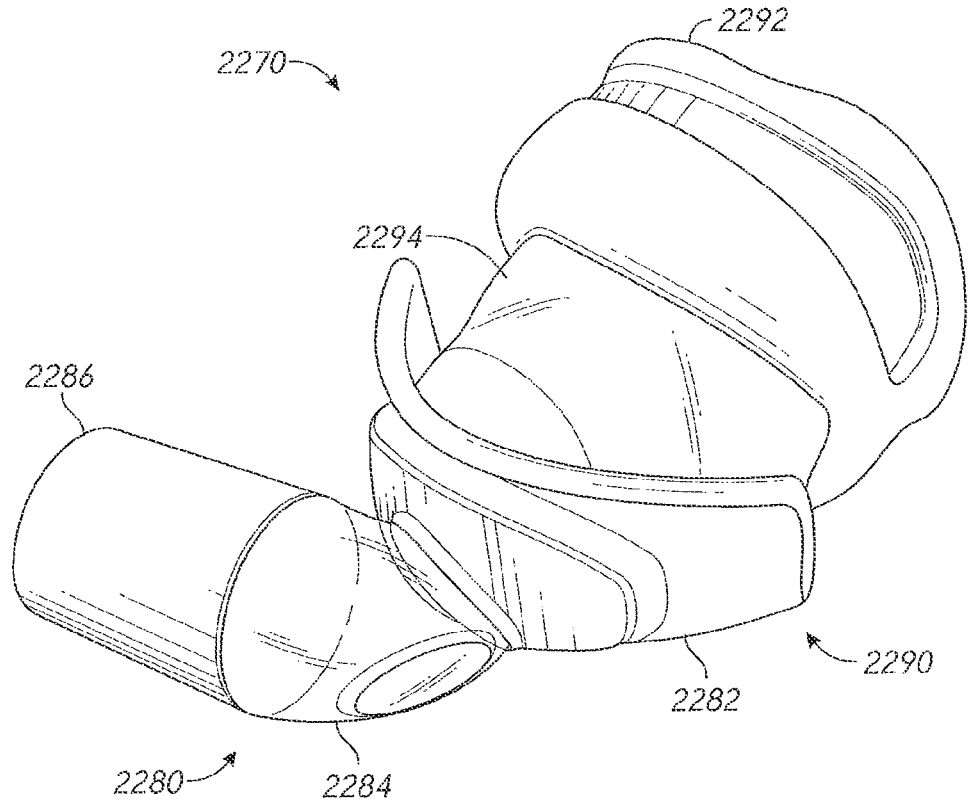
FIG. 81 is a front perspective view of an exemplary cushion module and frame assembly.

The cushion module 2290 comprises a sealing cushion 2292 that is integrally formed with a connector portion 2294, by means such as but not limited to over-molding. The sealing cushion 2292 comprises a compliant interface that is made from a flexibly resilient material such as, but not limited to, silicone or a thermoplastic elastomer. It is configured to form a substantially air tight breathing chamber that seals about the nose of a user. The connector portion 2294 is made of a substantially rigid material, such as but not limited to polycarbonate, and comprises a circular opening 2296 opposing the sealing cushion 2292. It is configured to provide a repeatably removable connection between the cushion module 2290 and the frame assembly 2280. The cushion module 2290 and frame assembly 2280 connect together such that an air path is formed through the tube connector 2286 and elbow 2284 and into the cushion module 2290, as shown in FIG. 81.

Figure 82:
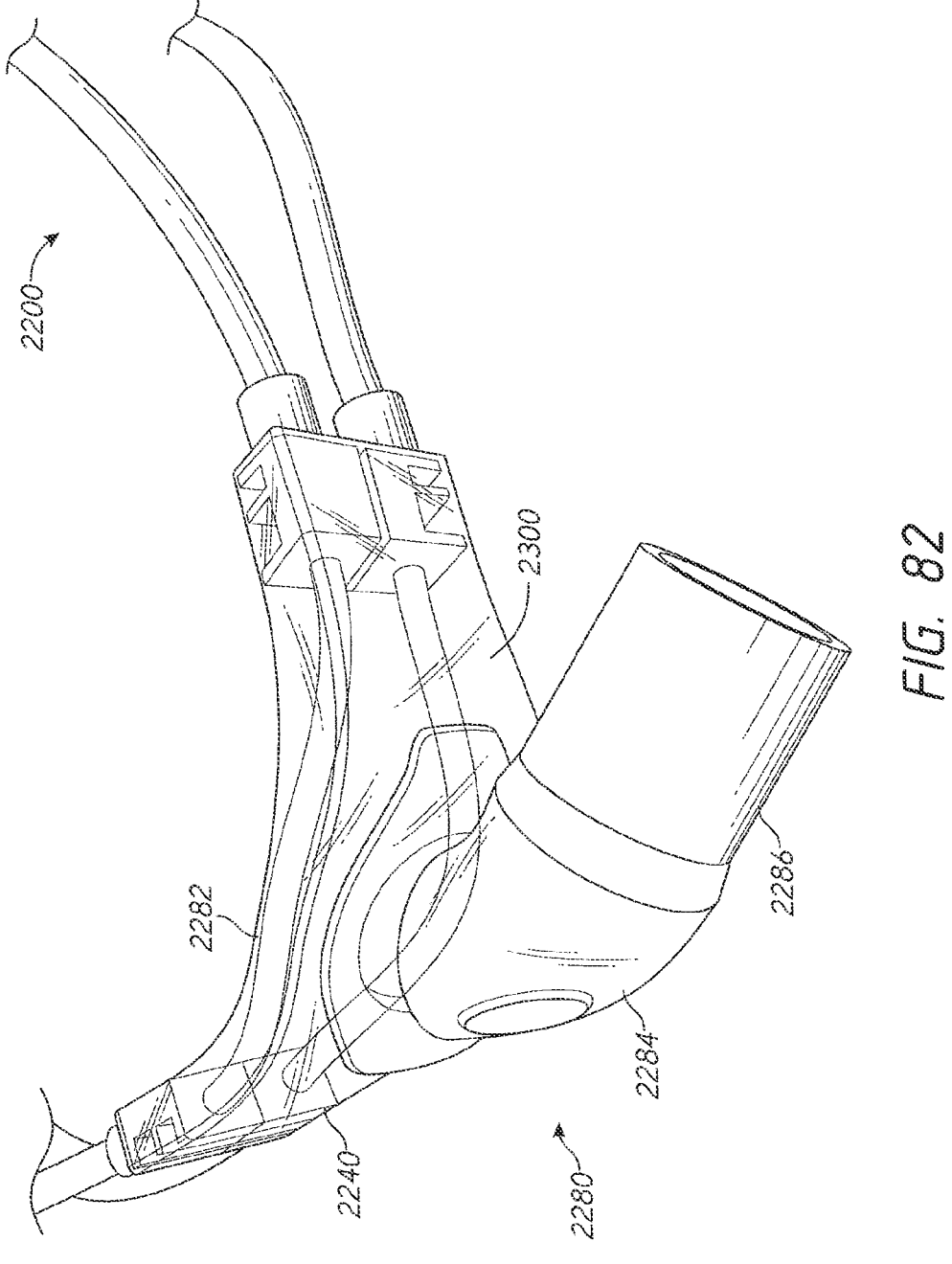
FIG. 82 is a front perspective view of the frame assembly connected to the housing of the headgear system.
Figure 83:
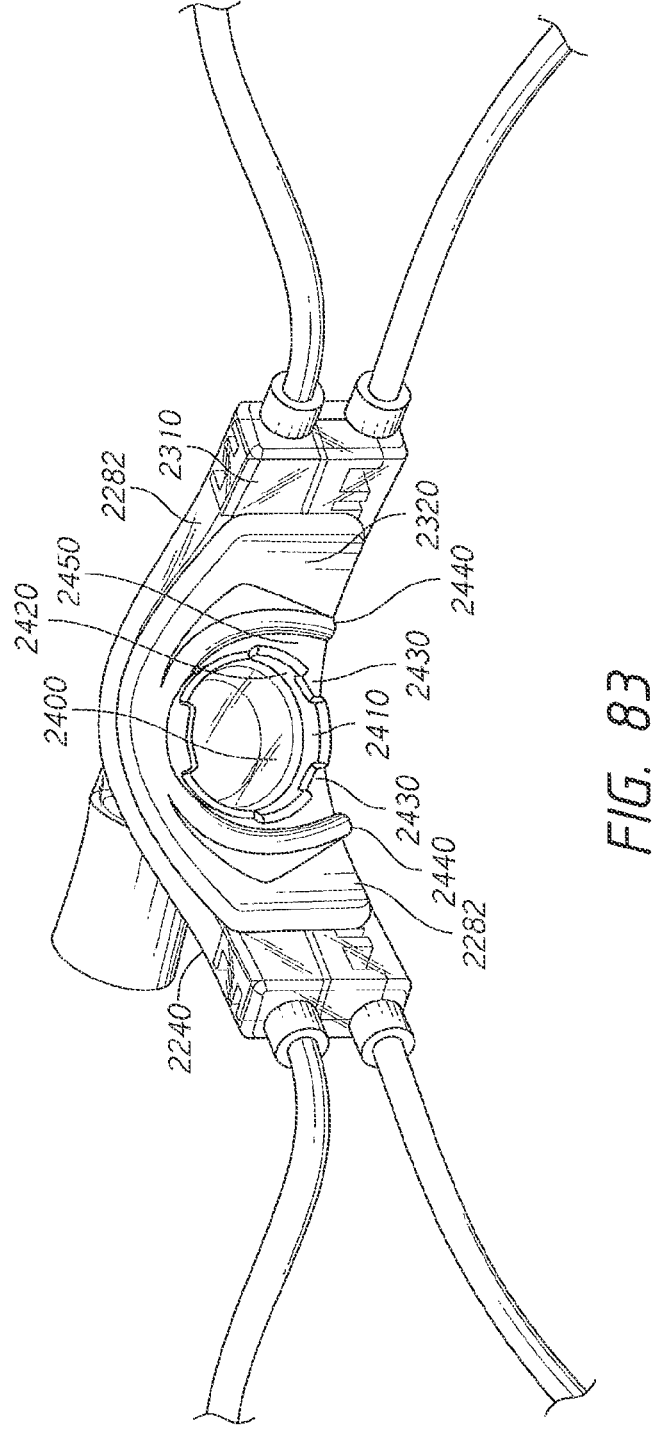
FIG. 83 is a rear view of the frame assembly connected to the housing of the headgear system.

FIGS. 82 and 83 show how the frame assembly 2280 connects to the housing 2240 of the headgear system 2200. The elbow 2284 and tube connector 2286 are configured to pass through the central opening of the housing 2240 in order to connect the frame 2282 to a rear surface 2310 of the housing 2240. A portion of the frame 2282 extends through the central opening 2248 of the housing 2240 and sits substantially flush with a front surface 2300 of the housing 2240.

Figure 84:
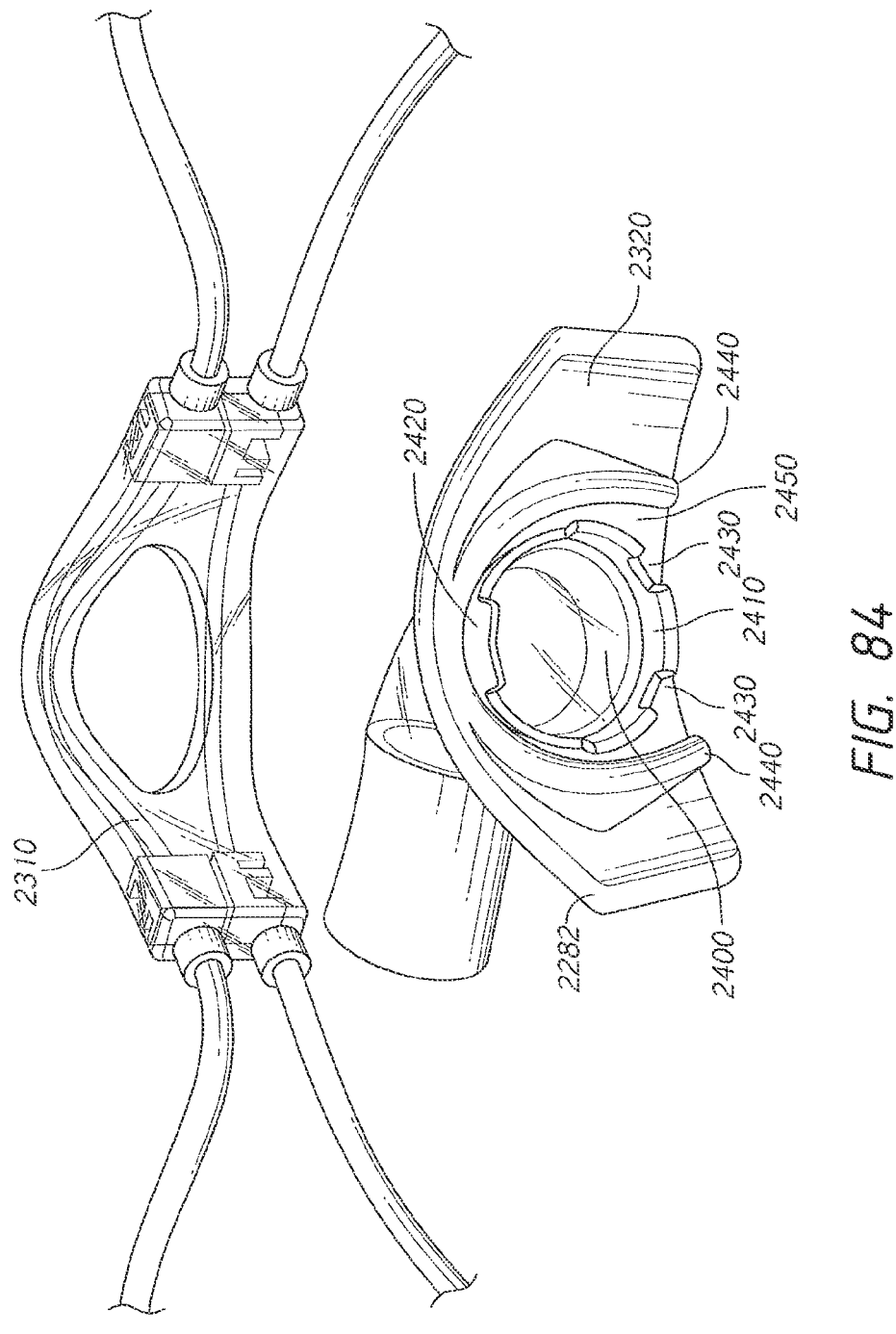
FIG. 84 is a rear view of the frame assembly removed from the housing of the headgear.

A rear surface 2320 of the frame 2282 is shown in FIGS. 83 and 84. It can be seen that the rear surface 2320 of the frame 2282 comprises a number of protrusions that form a circular inner cuff 2420 around the perimeter of the socket of the ball 2400 and socket 2410 connection. The inner cuff 2420 has a plurality of cut-outs 2430 that provide flexibility. A recessed channel 2450 extends around the periphery of the inner cuff 2420. The recessed channel 2450 retains the circular opening 2296 of the cushion module 2290 in a snap-fit configuration. There is one or more (e.g., a pair of) keying features 2440 located on the lower perimeter of the recessed channel 2450. The keying features 2440 are configured to interact with a corresponding feature on the connector portion 2294 of the cushion module 2290, such that rotation of the cushion module 2290 is prevented.

An advantage of the headgear adjustment systems disclosed in the previously described embodiments is that it provides a silent adjustment means. Hook and loop fastening systems (such as Velcro) are commonly used in the art to provide size adjustment to headgear systems for respiratory masks. When the tightness of the headgear system requires adjusting, the hook and loop fastener components must be separated from each other. The separation of hook and loop fastener components usually generates a ripping sound, which may be annoying to the mask user and in some circumstances may wake a bed partner of the user. The headgear system of the present disclosure is less likely to require the user to make a manual adjustment to achieve an improved size and fit and any adjustment that is required will not generate a noise, or at least not a significant level of noise, thus improving case of use and comfort for the user and their bed partner.

Figure 85:
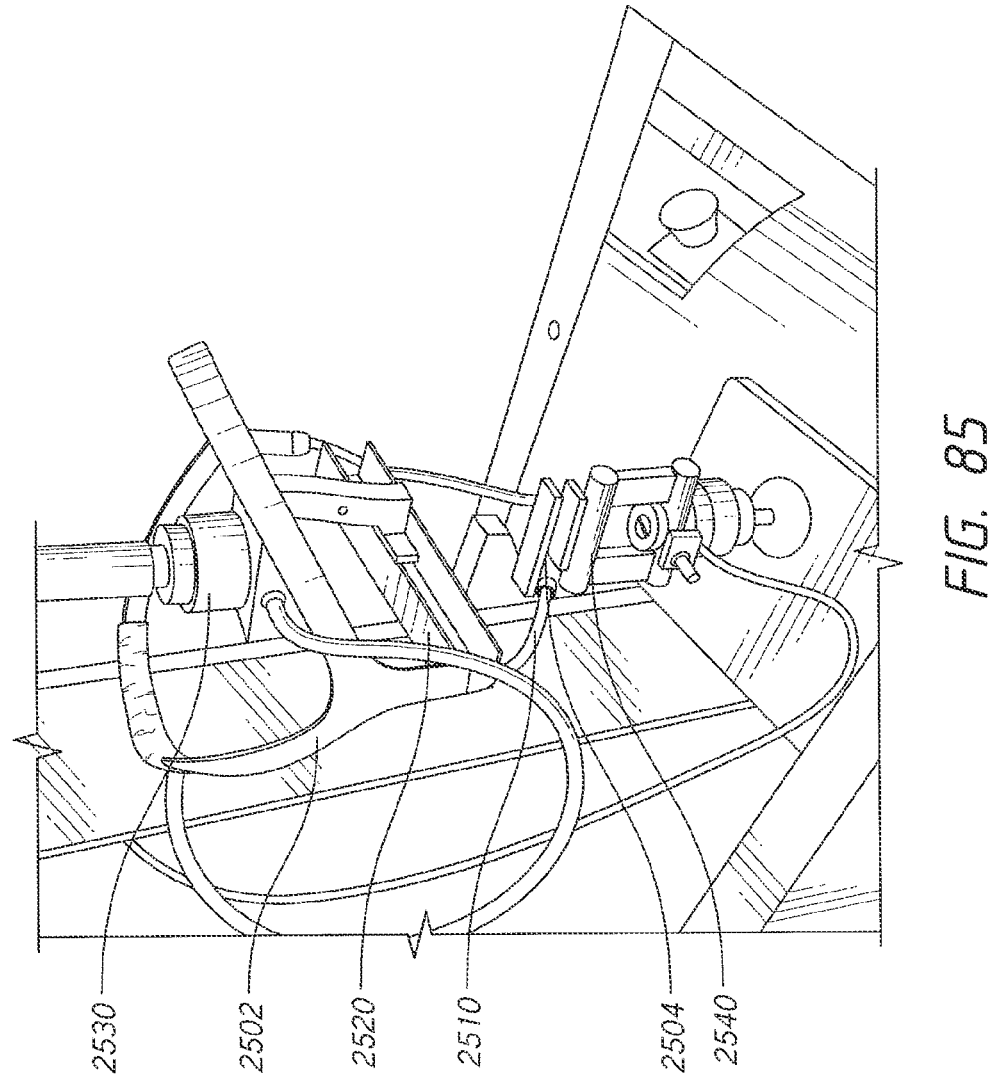
FIG. 85 illustrates a validation testing of the function of a headgear arrangement that includes at least one directional locking module.

Headgear Testing:

FIG. 85 shows a test set-up for validating the function of a headgear arrangement 2500 that includes at least one directional locking module 2510. The headgear arrangement 2500 being tested in FIG. 85 comprises a headgear 2502 and a mask frame 2504 that are connected together by a pair of lateral directional lock modules 2510. The frame 2504 is configured to receive a nasal pillows seal. The ends of the directional lock modules 2510 that are connected to the headgear 2500 are retained within a test jig 2520 that secures the headgear arrangement 2500 to a moving cross head 2530 of a universal testing machine. The mask frame 2504 is secured to a fixed cross head 2540 of the universal testing machine. The universal testing machine can run a test which simulates the donning and wearing of the mask in several phases. It is to be understood that this test set-up can be modified to test headgear arrangements that are configured to be used with different mask types, such as full-face and nasal masks.

The first phase of the test simulates the donning of the mask and headgear arrangement. The moving cross head is programmed to pull the headgear away from the frame, elongating the directional lock modules, until the headgear arrangement is near its maximum circumference. The second phase of the test simulates the fitting of the mask and headgear arrangement to a user's head. The universal testing machine is programmed to return the headgear back towards the mask frame to a distance wherein the circumference of the headgear arrangement is approximately half way between the maximum and minimum circumferences. This simulates the point at which the circumference of the headgear arrangement matches the circumference of the user's head. The third step of the test comprises extending the headgear arrangement back to its maximum circumference, which simulates the application of CPAP pressure and use of the mask system. The force profile is recorded during all three of the test phases.

During the first phase of the test it is expected that a force-extension plot should show an initial steep rise in the force as the lock, of the directional lock mechanism, engages during elongation of the headgear arrangement. If the plot does not show this there may be some slack in the headgear and the jig that needs to be taken up before the directional lock mechanism kicks in. Following this steep rise in force, a transition point will be reached at or near a predetermined yield force. Once the yield force has been reached the rate of increase of the force reduces and remains substantially constant until the maximum headgear circumference is reached.

The second phase of the test is expected to show the instant release of the directional lock mechanism, on the force-extension plot. An initial sharp drop in force indicates an instant release of the hold of the washer (or other appropriate locking mechanism), when the extension force is released from the headgear arrangement. The return force is driven by the elasticated component of the directional lock module. In this particular case; 4 strands of lycra in a braided sleeve. The return force can be controlled by selection of materials and manufacturing methods of the elasticated component. The return force should be below the expected blow-off force, which will change depending on the type mask (i.e. full-face, nasal or nasal pillows etc.).

The third phase simulates use, wherein the headgear has contracted to an imaginary user's head circumference. The application of CPAP pressure (blow off force) to the mask should result in the force-extension plot showing a steep increase in force, at substantially the same rate as the initial elongation force, before the yield force is reached. The application of the CPAP pressure should activate the washer (or other lock mechanism) and show a sharp rise in force against a short elongation. The balanced fit of the mask and headgear arrangement should fall somewhere along this force-extension curve, and will be dependent on the CPAP pressure that is applied. As the extension of the headgear arrangement continues towards the maximum circumference the yield force will be reached. This portion of the plot should follow or approximate the elongation of the headgear after the yield point during the first phase of the test. A close overlap indicates a repeatable yield force.

Figure 86:
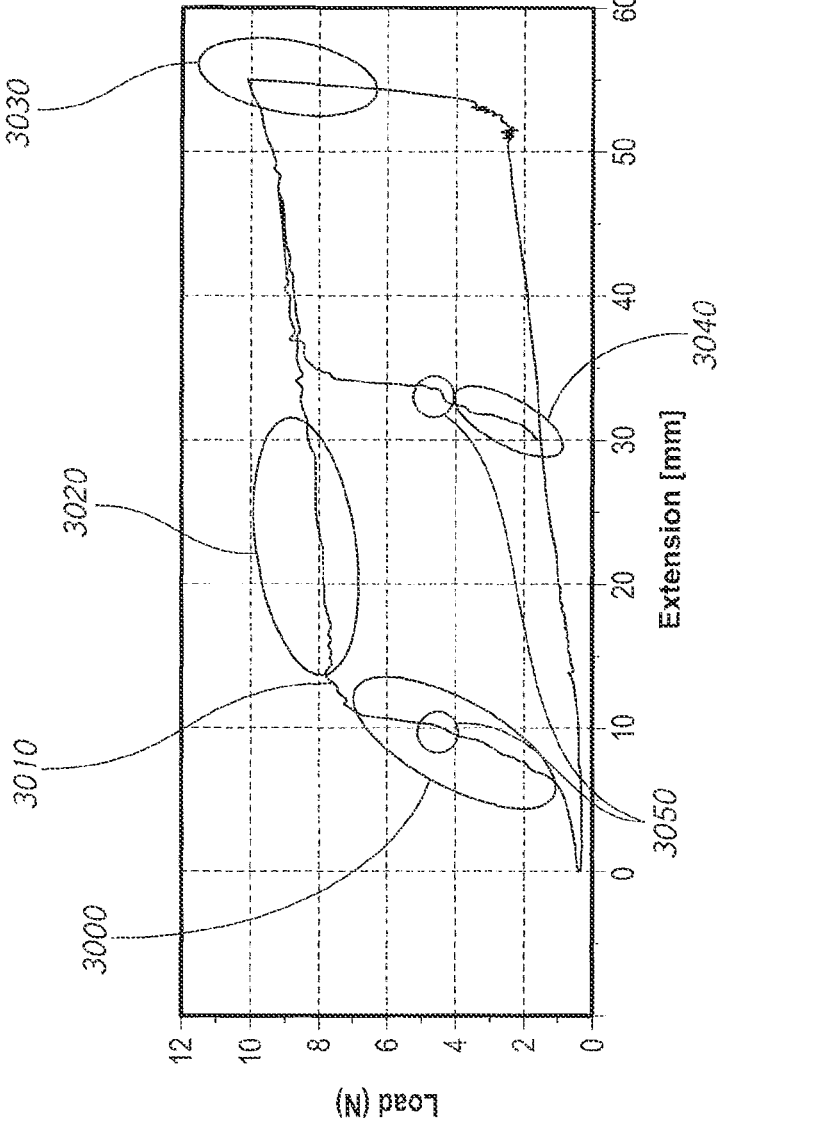
FIG. 86 is a graph illustrating a relationship between force versus extension of tested exemplary headgear arrangements.
Figure 87:
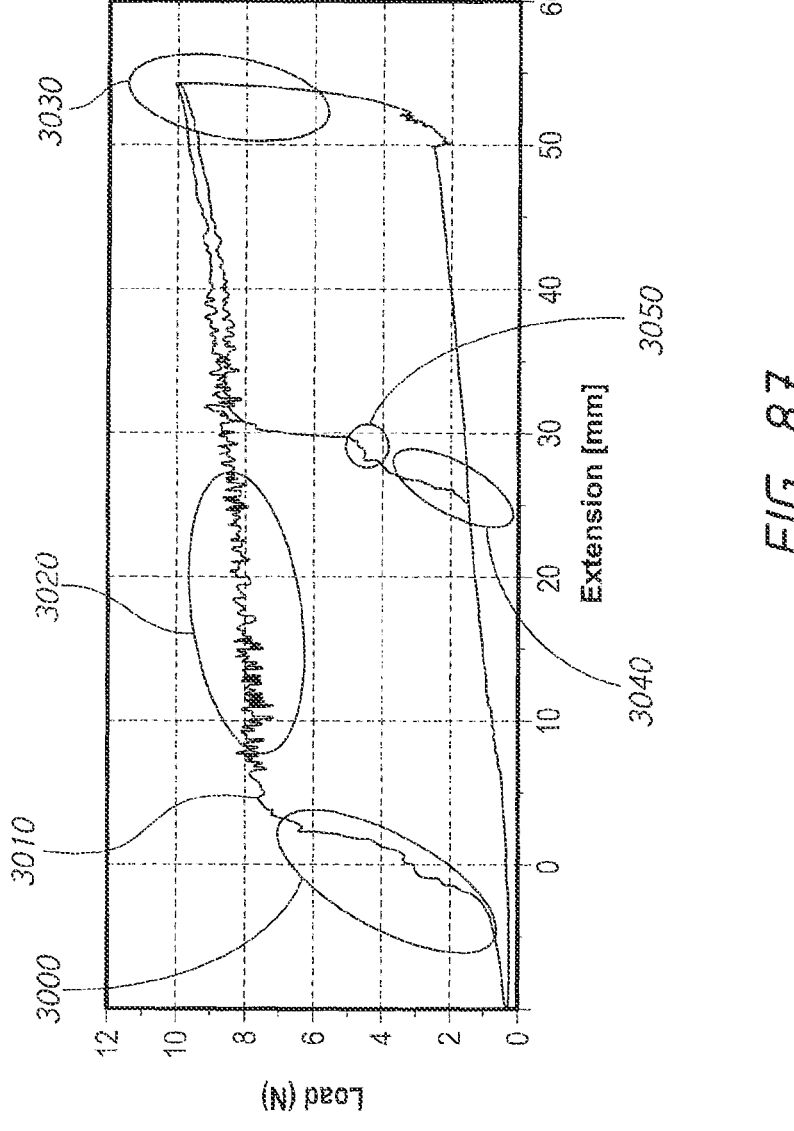
FIG. 87 is a force-extension graph illustrating force fluctuation during elongation after the transition.

FIGS. 86 and 87 show force-extension plots two headgear arrangement and mask samples (such as those shown in FIG. 85) obtained using the test set-up described above. The plots of both FIGS. 86 and 87 show that the headgear arrangement and mask samples that were tested meet the desired criteria as described above. Both plots show a steep increase in force during initial elongation 3000 followed by a lower rate of increase 3020 after the transition point 3010 has been reached. It can be seen in FIG. 87 that the force can fluctuate during elongation 3020 after the transition point 3010. This may be a result of imperfect tolerances between components of the directional lock module, or inaccuracies in how the sample is retained during the test. The two plots also show that both samples displayed a sharp drop 3030 in force indicating an instant release of the directional lock mechanism, and a low return force. A sharp increase 3040 in force was shown for both samples during the third phase of simulating use. The force-extension curve after the yield force also closely aligned with the initial elongation curve.

In both FIGS. 86 and 87, a hesitation/elongation 3050 can be seen approximately half way up the steep increases in force. This corresponds to the construction of the directional lock mechanism. In the samples that were tested the directional lock mechanisms included two washers, such the embodiments of FIGS. 68A to 68D. The hesitation is caused by the first washer having a lower yield force and allowing a small amount of elongation before the second washer is engaged and continues the steep slope.

FIGS. 88-102 illustrate several nasal cannula systems incorporating a headgear arrangement of the present disclosure, which can include at least one directional lock arrangement. The several nasal cannula systems are described below with emphasis on the differences between the several systems. Portions, components or features not specifically described can be the same as or similar to corresponding portions, components or features of other nasal cannula systems, or can be of another suitable arrangement. A number of example nasal cannula arrangements are disclosed in Applicant's PCT Application No. PCT/IB2015/054585 and PCT Publication No. WO2014/142681, the entireties of which are incorporated by reference herein. In addition, features of the several nasal cannula systems can be interchanged to create combinations in addition to those specifically illustrated. The same reference numbers are used to refer to the same or corresponding portions, features or components of the several nasal cannula systems.

In some configurations, the nasal cannula systems are configured for high flow therapy (HFT) and may be unsealed or may not create a substantial seal with the user's nares. However, in other arrangements, the nasal cannula systems could comprise sealing cannula. In addition, while well-suited for use with nasal cannula systems, the disclosed headgear arrangements could also be employed with systems utilizing other types of interfaces, such as nasal pillows, under-nose nasal masks, under-nose full face masks or traditional nasal or full-face masks, for example and without limitation. The headgear can be of any suitable configuration. For example, the headgear can be relatively rigid in at least one plane or can be soft. The headgear can be elastic (extensible or stretchable) or substantially inelastic (inextensible or non-stretchable).

Each of the nasal cannula systems preferably include at least one directional lock arrangement, which can be configured to provide different resistance to relative movement of portions of the system in different directions. For example, the directional lock arrangement(s) can be configured to allow movement tending to shorten an effective perimeter length or circumference of the system at a lesser resistance than movement tending to lengthen the effective perimeter length or circumference. In some configurations, the nasal cannula systems can also include a biasing arrangement, which can be configured to bias the system toward or to a minimum effective perimeter length or circumference. A resulting nasal cannula system can be applied onto the user's head and can automatically reduce in perimeter length or circumference to automatically adjust toward or to an appropriate size for the particular user. Such an automatically adjustable arrangement is useful in a nasal cannula application to maintain the position of the prongs in the user's nares. A similar, easily-adjustable arrangement (e.g., manually or otherwise adjustable) can also be useful in a nasal cannula application. In some cases, the nasal cannula does not require seal (and, thus, does not produce any or at least a substantial blow-off force), but there is still a moment arm that exists as a result of the weight of the nasal cannula and/or hose pull forces, possibly among other forces acting on the system. At least some of the configurations disclosed herein help to accommodate the nasal cannula in the operational position, such as by automatically or otherwise adjusting to a desired perimeter length or circumference and then resisting normal or expected forces acting on the nasal cannula. The directional lock arrangement(s) and biasing arrangement(s) can be the same as or similar to any of those disclosed herein, the same as or similar to any of those disclosed in Applicant's PCT Publication No. WO 2014/175752, published Oct. 30, 2014, entitled AUTOMATICALLY ADJUSTING HEADGEAR FOR PATIENT INTERFACE, the entirety of which is incorporated by reference herein, or can be of any other suitable arrangement.

Figure 88:
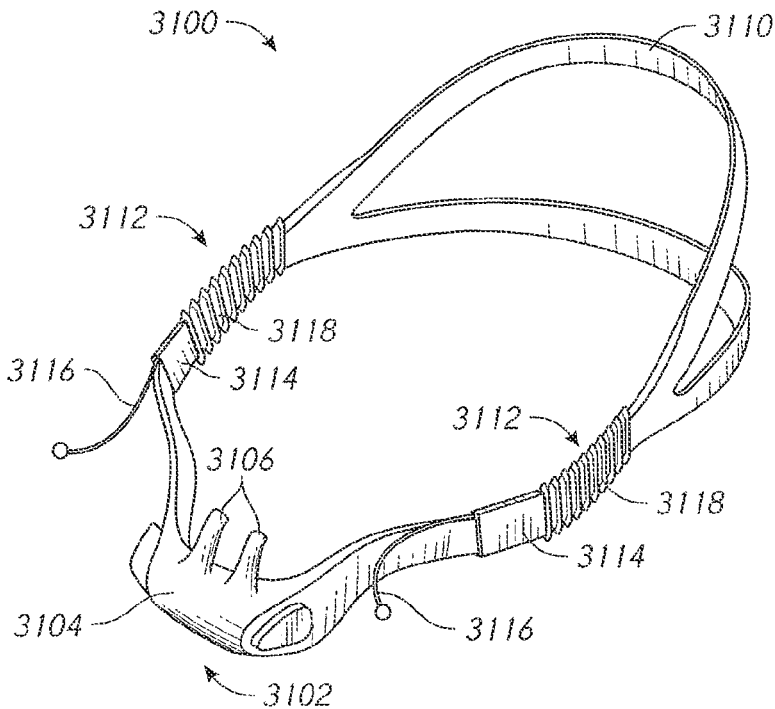
FIG. 88 is a perspective view of a respiratory cannula incorporating a headgear arrangement of the present disclosure, which can include at least one directional lock arrangement.

With reference to FIG. 88, a nasal cannula system 3100 comprises a cannula 3102 having a cannula body 3104 and at least one nozzle 3106, such as a pair of nozzles 3106. The cannula body 3104 can comprise an internal gas space that communicates with openings of the nozzles 3016. A suitable conduit can be connected to the cannula body 3104 to deliver a flow of breathing gases to the internal gas space and, ultimately, to the user. The nasal cannula system 3100 can also comprise a headgear 3110, which in the illustrated arrangement is a bifurcated headgear comprising a pair of straps (e.g., an upper strap and a lower strap). Opposing ends of the headgear 3110 connect directly or indirectly to opposing sides of the cannula body 3104. The illustrated headgear 3110 is a relatively rigid, non-stretch headgear, which can comprise an inner core and a cover. The cover can comprise one or more layers that partially or completely surround the inner core. In some configurations, the inner core is a plastic material and the cover comprises one or more fabric or textile materials.

In some configurations, at least one and preferably a pair of adjustment arrangements 3112 are positioned within the nasal cannula system 3100 to allow for adjustment of a perimeter length or circumference of the nasal cannula system 3100 (hereinafter, "circumference"). In the illustrated arrangement, a pair of adjustment arrangements 3112 are positioned between the nasal cannula 3102 and the headgear 3110. The adjustment arrangements 3112 can comprise a portion of or be integrated with one or both of the nasal cannula 3102 and the headgear 3110 or can be a separate component from one or both of the nasal cannula 3102 and the headgear 3110. The adjustment arrangements 3112 can each comprise a directional lock 3114, a core member or filament 3116 that moves relative to and is selectively engaged by the directional lock 3114, and a biasing element or arrangement 3118 (hereinafter, "biasing element"). In the illustrated arrangement, the biasing elements 3118 are configured to shorten a circumference of the nasal cannula system 3100. The directional locks 3114 are configured to provide greater resistance to lengthening of the circumference than to shortening of the circumference. Preferably, the directional locks 3114 are configured to substantially inhibit or prevent lengthening of the circumference of the nasal cannula system 3100 at least in response to normal or expected forces applied during therapy, such as forces caused by the flow of gases during therapy, the weight of the cannula system 3100 and/or hose pull forces. The directional locks 3114, the core members 3116 and the biasing elements 3118 can be located together or near one another to form a sub-assembly or can be dispersed throughout the nasal cannula assembly 3110.

In the illustrated system 3100 of FIG. 88, the core members 3116 are coupled to the headgear 3110 and the directional locks 3114 are coupled to the nasal cannula 3102. The biasing elements 3118 have one end coupled to the headgear 3110 and one end coupled to the nasal cannula 3102. The core members 3116 extend from each side of the headgear 3110 toward the front of the nasal cannula system 3100. The core members 3116 can be secured to the nasal cannula 3102, such as by a guide, for example. The adjustment arrangements 3112 are symmetrically positioned on each side of the nasal cannula system 3100. With such an arrangement, the adjustment of the circumference of the nasal cannula system 3100 can be symmetrical, such that a center line of the headgear 3110 remains aligned with the center line of the nasal cannula 3102. The pair of adjustment arrangements 3112 provide for a greater range of circumference adjustment in comparison to a single adjustment arrangement 3112. Such an arrangement can, in some configurations, allow for a single size nasal cannula system 3100 to cover a substantial portion or an entirety of an intended user population (e.g., an adult population). In addition, the adjustment arrangements 3112 positioned on the sides of the nasal cannula system 3100 keeps the adjustment arrangements 3112 away from the front and rear of the nasal cannula system 3100, which are the locations often grasped when applying (donning) or removing (doffing) the nasal cannula system 3100.

Figure 89A:
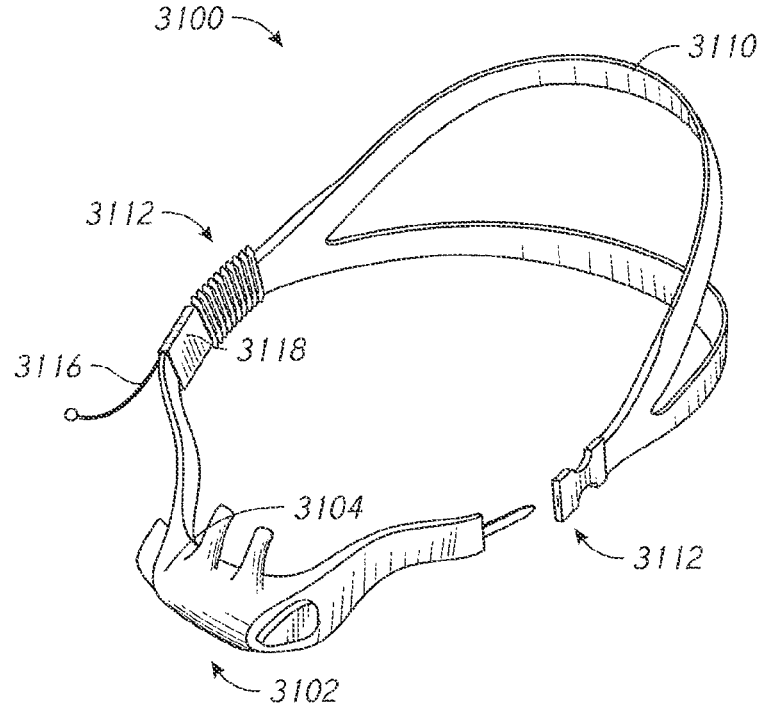
FIGS. 89a-89c are perspective views of additional respiratory cannulas incorporating headgear arrangements of the present disclosure, which headgear arrangements can include at least one directional lock arrangement and a headgear quick release arrangement.
Figure 89B:
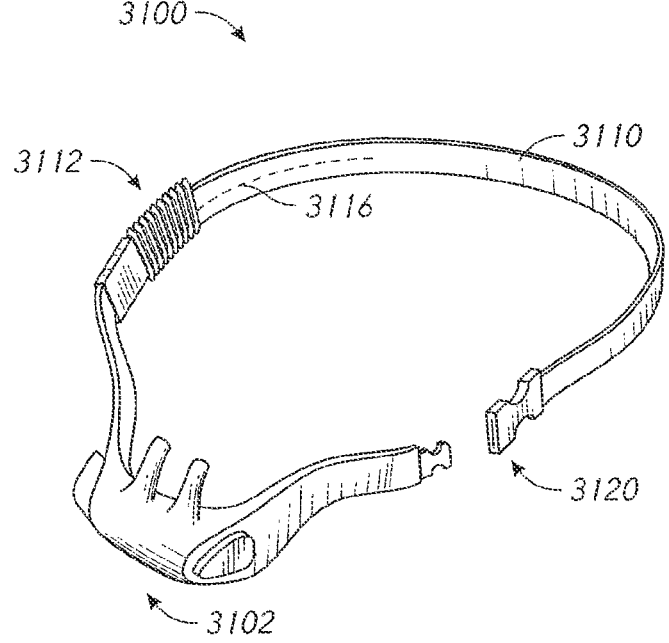
Figure 89C:
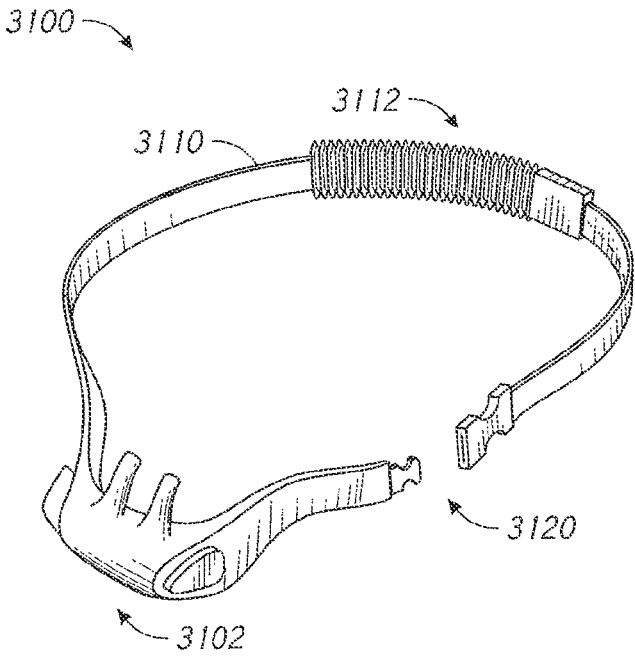

With reference to FIG. 89a, the illustrated nasal cannula system 3100 is similar to that of FIG. 88; however, the nasal cannula system 3100 of FIG. 89a includes an adjustment arrangement 3112 on one side of the nasal cannula system 3100 and a quick release arrangement 3120 on the opposite side of the nasal cannula system 3100. In the illustrated arrangement, the quick release arrangement 3120 is a buckle. However, other suitable arrangements (e.g., clip, latch, magnet, etc.) can also be used. The quick release arrangement 3120 can permit the nasal cannula system 3100 to be quickly and easily applied to or removed from the user. For example, in the context of an unresponsive patient, such as in a hospital environment, the quick release arrangement 3120 can permit a caregiver to quickly and easily break the closed loop of the nasal cannula system 3100 to facilitate removal of the system 3100 from the user. In addition, the single adjustment arrangement 3112 can result in a lower manufacturing cost compared to a similar system having two or more adjustment arrangements. FIG. 89b illustrates a similar system 3100 that incorporates a single strap headgear 3110 instead of the bifurcated headgear 3110 of the system 3100 of FIG. 89a. FIG. 89c illustrates a nasal cannula system 3100 having the adjustment arrangement 3112 integrated into a single strap headgear 3110. In the illustrated arrangement, the adjustment arrangement 3112 is positioned in a rearward portion of the headgear 3110; however, the adjustment arrangement 3112 could be positioned in other locations, as well.

Figure 90:
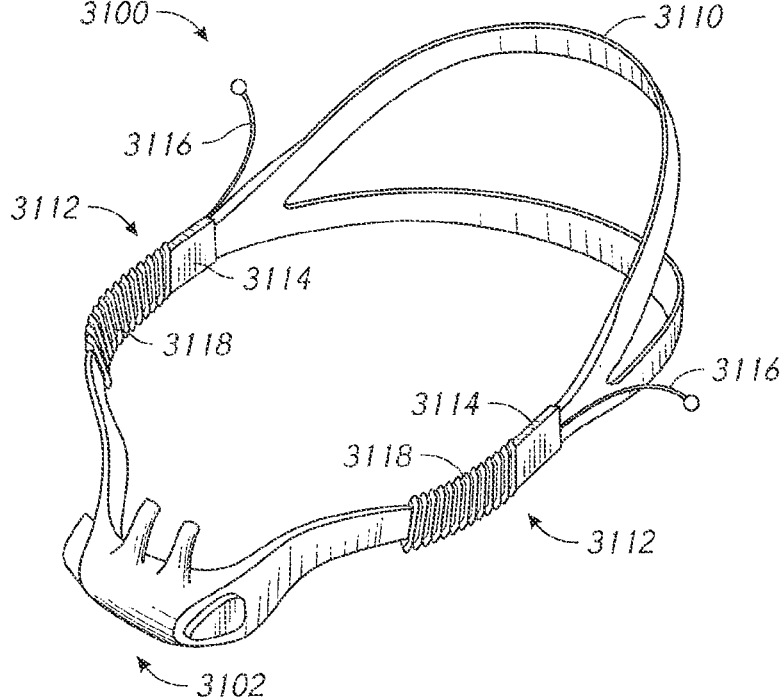
FIG. 90 is a perspective view of another respiratory cannula incorporating a headgear arrangement of the present disclosure, which can include at least one directional lock arrangement.

FIG. 90 illustrates a nasal cannula system 3100 that is similar to the system 3100 of FIG. 88 except, in the system 3100 of FIG. 90, the direction of the adjustment arrangements 3112 are reversed relative to the arrangements 3112 of FIG. 88. In particular, the core members 3116 are coupled to the nasal cannula 3102 and the directional locks 3114 are coupled to the headgear 3110. Although shown free of the headgear 3110, the excess portions of the core members 3116 can be secured to the headgear 3110 if desired, such as by a guide or accumulator. Locating the excess portions of the core members 3116 on the headgear 3110 can provide a greater accumulator length and, thus, can permit the system 3100 of FIG. 90 to have a greater adjustment range than other systems, such as the system 3100 of FIG. 88.

Figure 91:
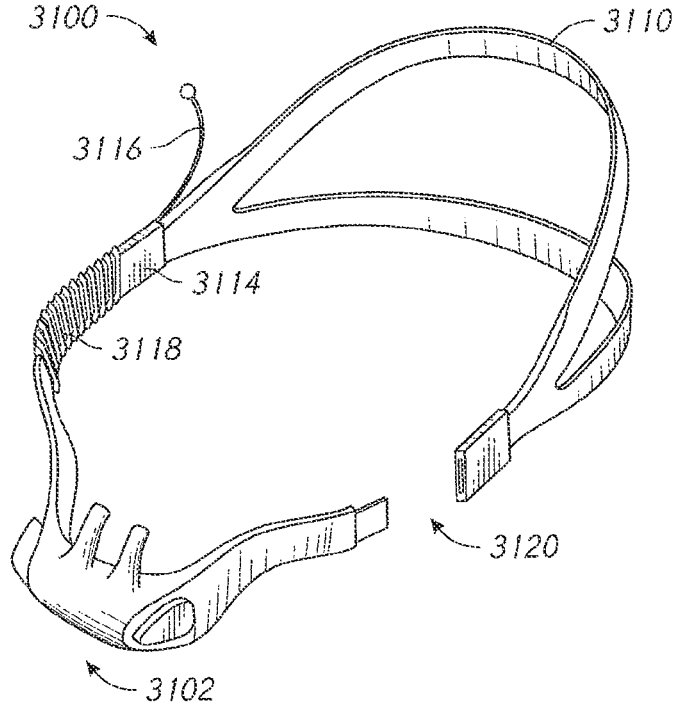
FIG. 91 is a perspective view of a respiratory cannula incorporating a headgear arrangement of the present disclosure, which can include at least one directional lock arrangement and a headgear quick release arrangement.

FIG. 91 illustrates a nasal cannula system 3100 that is similar to the system 3100 of FIG. 89*a* except, in the system 3100 of FIG. 91, the direction of the adjustment arrangement 3112 is reversed relative to the arrangement 3112 of FIG. 89*a*. In particular, the core member 3116 is coupled to the nasal cannula 3102 and the directional lock 3114 is coupled to the headgear 3110. Although shown free of the headgear 3110, the excess portion of the core member 3116 can be secured to the headgear 3110 if desired, such as by a guide or accumulator. Locating the excess portion of the core member 3116 on the headgear 3110 can provide a greater accumulator length and, thus, can permit the system 3100 of FIG. 91 to have a greater adjustment range than other systems, such as the system 3100 of FIG. 89*a*.

Figure 92:
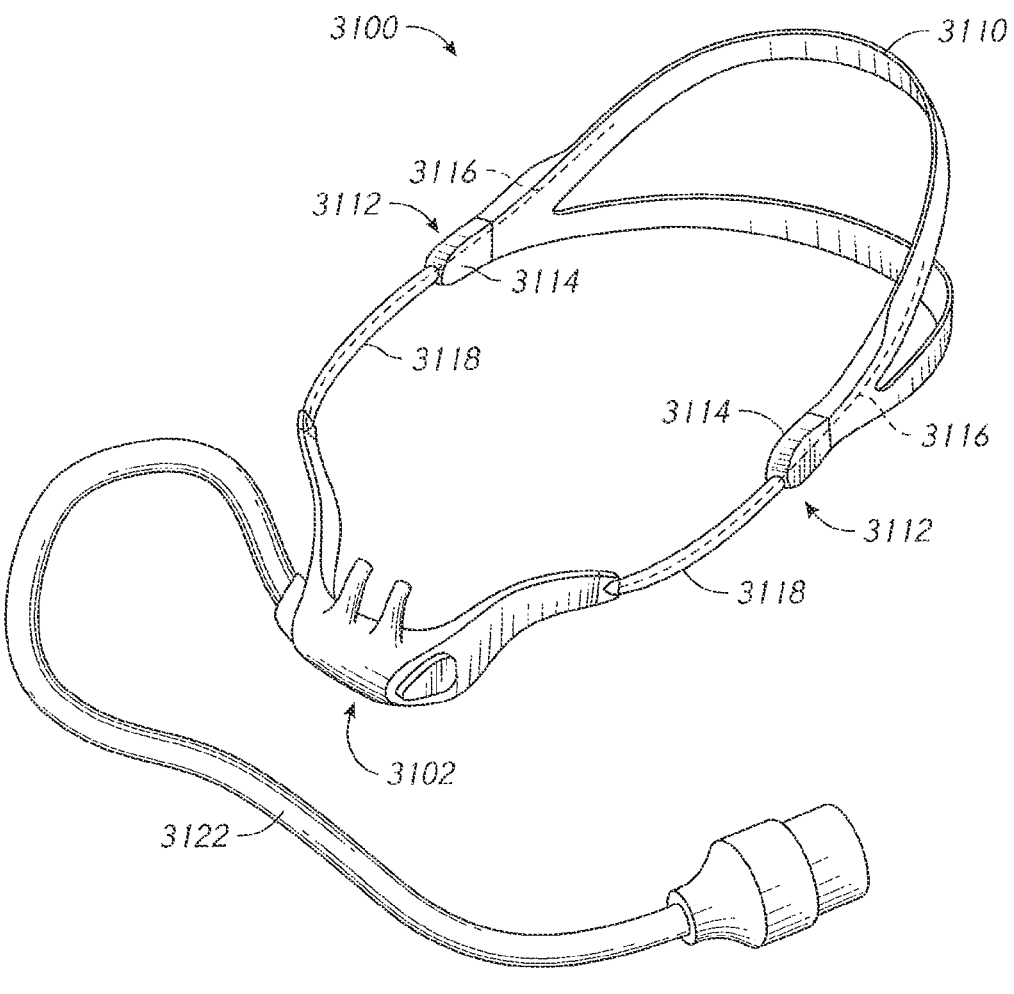
FIG. 92 is a perspective view of a respiratory cannula incorporating a headgear arrangement of the present disclosure, which can include at least one directional lock arrangement.

FIG. 92 illustrates a nasal cannula system 3100 that is similar to the system 3100 of FIG. 90 except, in the system 3100 of FIG. 92, the excess portions of the core members 3116 are contained within the nasal cannula system 3100. In particular, the core members 3116 are coupled to the nasal cannula 3102 and the directional locks 3114 are coupled to the headgear 3110. The core members 3116 extend through the biasing elements 3118, which in some configurations can be elastic tubular members. The biasing elements 3118 can be braided tubular elements that incorporate elastic elements that provide some or all of a biasing force of the biasing elements 3118. The excess portions of the core members 3116 are received within an interior of the headgear 3110, such as within a guide or accumulator. Locating the excess portions of the core members 3116 within the headgear 3110 can protect the excess portions of the core members 3116 to inhibit or prevent damage to the core members 3116, which could result in reduced performance. In some configurations, the headgear 3110 comprises an inner core and a cover, as described above. The headgear 3110 can define elongate interior spaces configured to receive the excess portions of the core members 3116 within the inner core, between the inner core and the cover, or elsewhere (e.g., a dedicated guide element). In FIG. 92, the breathing gases supply conduit 3122 is illustrated.

Figure 93:
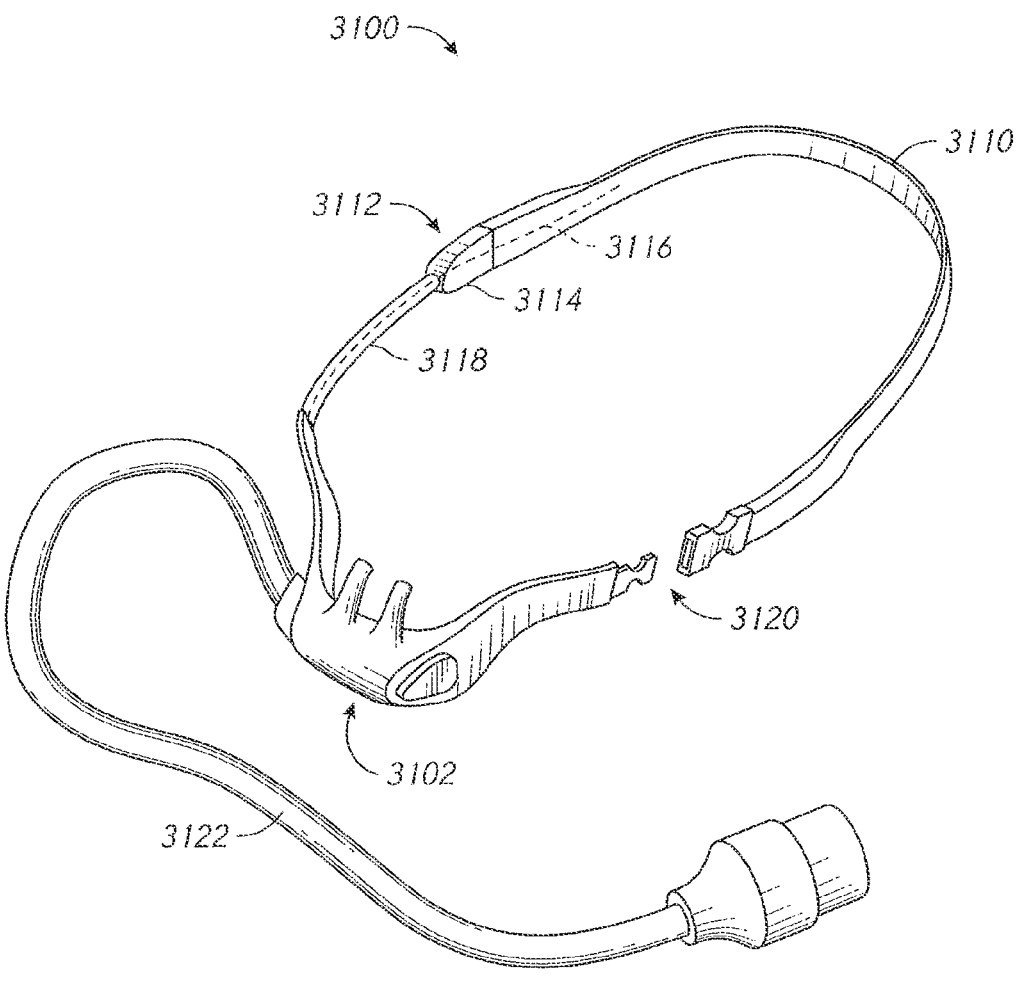
FIG. 93 is a perspective view of a respiratory cannula incorporating a headgear arrangement of the present disclosure, which can include at least one directional lock arrangement and a headgear quick release arrangement.

FIG. 93 illustrates a nasal cannula system 3100 that comprises a single adjustment arrangement 3112 in combination with a quick release arrangement 3120 similar to the systems 3100 of FIGS. 89*a*-89*c*. In the illustrated arrangement, the adjustment arrangement 3112 is located on one side of the system 3100 and the quick release arrangement 3120 is located on the opposite side of the system 3100. However, other locations for one or both of the adjustment arrangement 3112 and the quick release arrangement 3120 (e.g., a rearward location) can also be used. In addition, the nasal cannula system 3100 is configured such that the excess portion of the core member 3116 of the adjustment arrangement 3112 is contained within the headgear 3110 in a manner similar to the system 3100 of FIG. 92. That is, the headgear 3110 comprises an internal space configured to receive the excess portion of the core member 3116. In the illustrated system 3100, the headgear 3110 is a single strap arrangement; however, other types of headgear arrangements can also be used.

Figure 94:
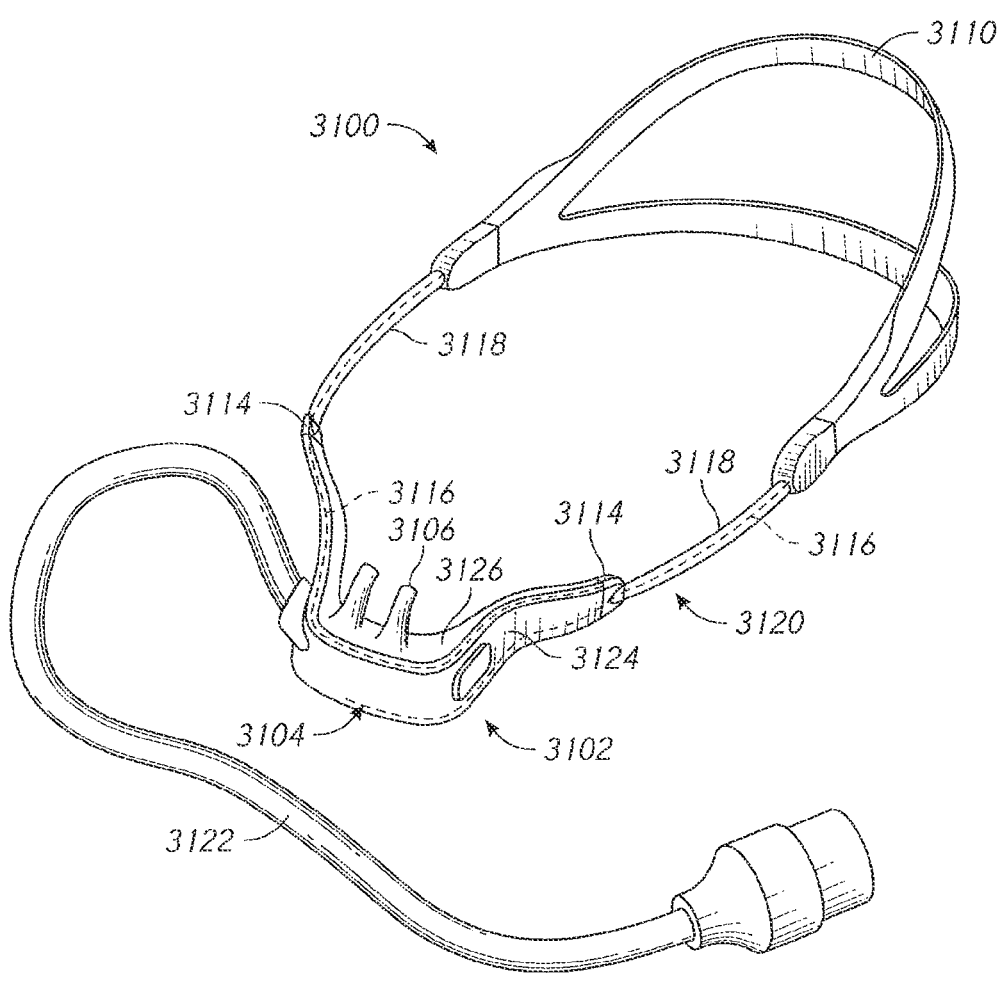
FIG. 94 is a perspective view of a respiratory cannula incorporating a headgear arrangement of the present disclosure, which can include at least one directional lock arrangement.

FIG. 94 illustrates a nasal cannula system 3100 similar to the system 3100 of FIG. 88; however, the system 3100 of FIG. 94 is configured such that the excess portions of the core members 3116 are internally contained. In particular, the nasal cannula 3102 can comprise internal spaces (e.g., conduits) configured to receive the excess portions of the core members 3116. The internal spaces can be defined by the cannula body 3104, by a guide member or by another suitable component or arrangement. In the illustrated arrangement, the cannula body 3104 comprises a rigid portion or frame 3124 that is coupled to the headgear 3110/adjustment arrangements 3112 and a softer, user-contacting portion 3126 supported by the frame 3124. The user-contacting portion 3126 can define or support the prongs 3106. The user-contacting portion 3126 can be permanently or removably coupled to the frame 3124. Such an arrangement provides for some amount of decoupling or independent movement between the frame 3124 and the user-contacting portion 3126. The internal spaces that receive the excess portions of the core members 3116 can be spaces molded into the frame 3124. In other configurations, the internal spaces can be defined between the frame 3124 and the user-contacting portion 3126. The biasing elements 3118 can be the same as or similar to those of FIG. 92 or can be of another suitable arrangement.

Figure 95:
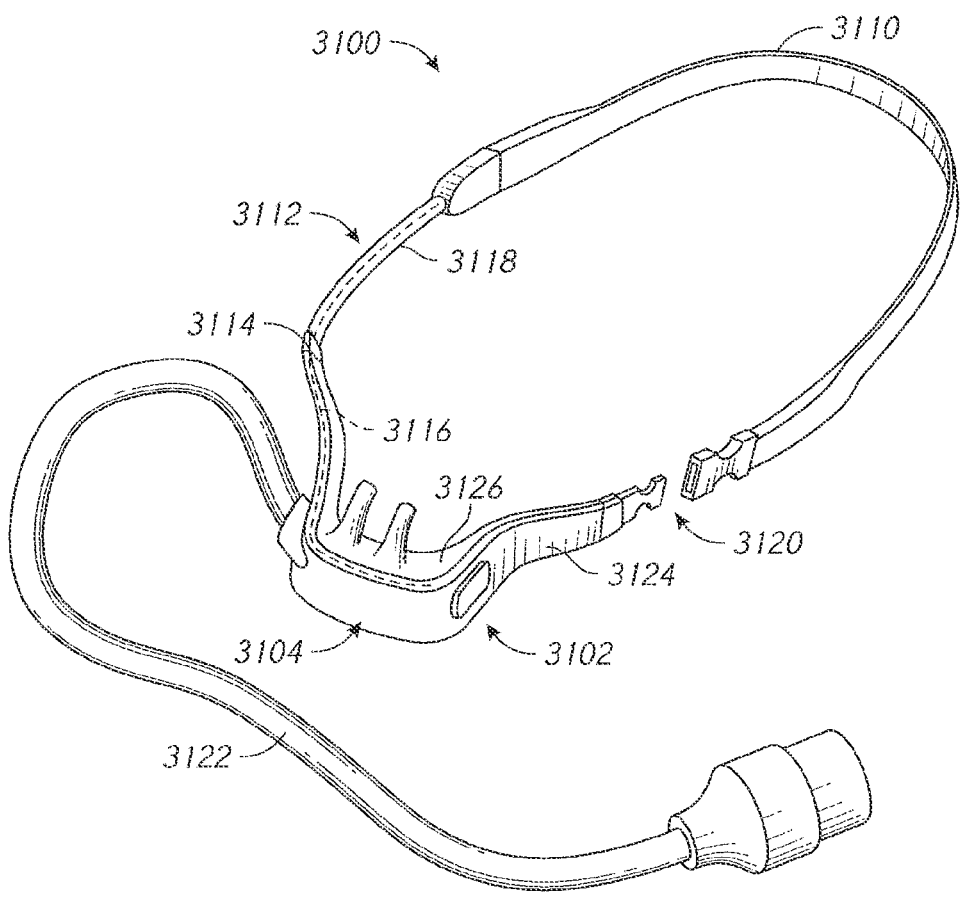
FIG. 95 is a perspective view of a respiratory cannula incorporating a headgear arrangement of the present disclosure, which can include at least one directional lock arrangement and a headgear quick release arrangement.

FIG. 95 illustrates a nasal cannula system 3100 that is similar to the system 3100 of FIG. 94. In particular, the system 3100 of FIG. 95 comprises a cannula body 3104 having a rigid portion or frame 3124 that is coupled to the headgear 3110/adjustment arrangement 3112 and a softer, user-contacting portion 3126 supported by the frame 3124. The nasal cannula 3102 can comprise an internal space configured to receive the excess portion of the core member 3116. However, similar to the system 3100 of FIG. 89*a*, the nasal cannula system 3100 of FIG. 95 includes a single adjustment arrangement 3112 and a quick release arrangement 3120. In the illustrated arrangement, the adjustment arrangement 3112 is located on one side of the nasal cannula system 3100 and the quick release arrangement 3120.

Figure 96:
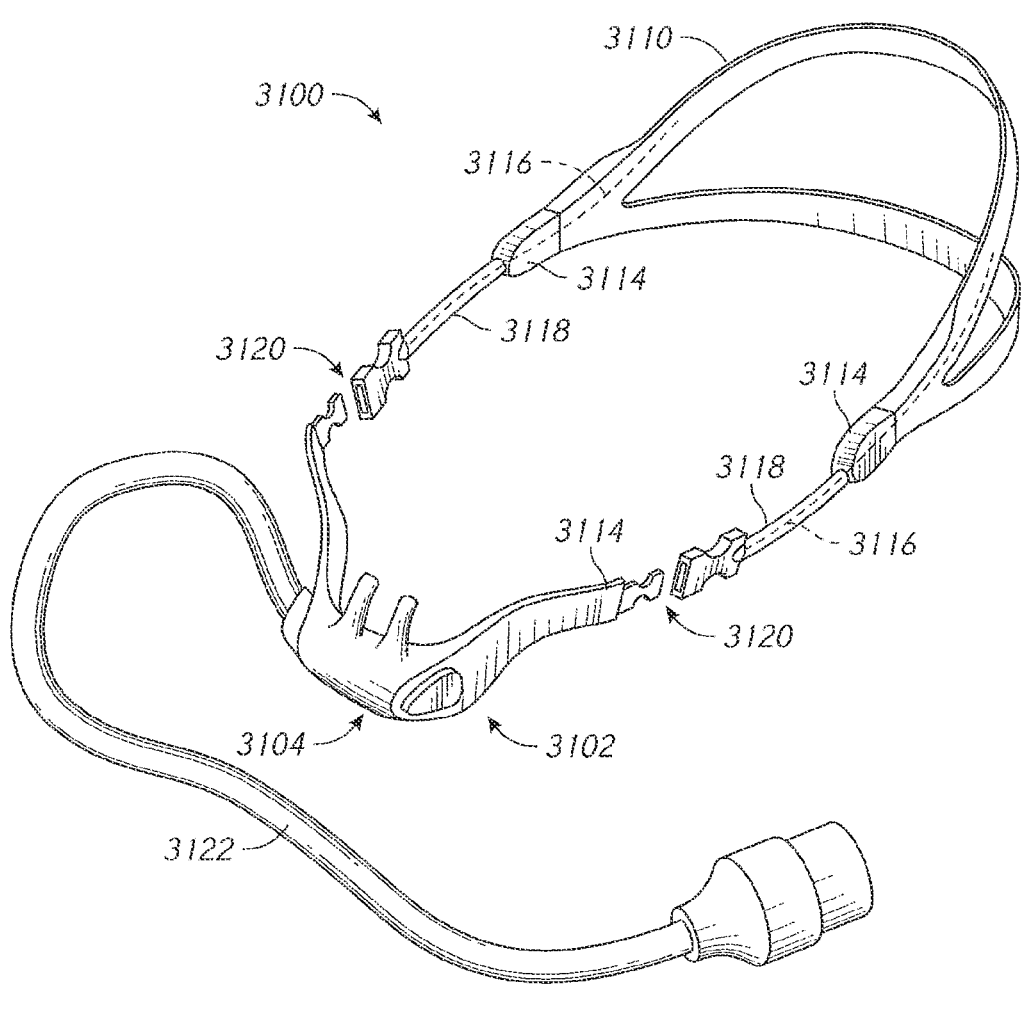
FIG. 96 is a perspective view of a respiratory cannula incorporating a headgear arrangement of the present disclosure, which can include a pair of directional lock arrangements and a pair of headgear quick release arrangements.

FIG. 96 illustrates a nasal cannula system 3100 that is similar to the system 3100 of FIG. 92 in that the excess portions of the core members 3116 are contained within the nasal cannula system 3100. In particular, the core members 3116 are coupled to the nasal cannula 3102 and the directional locks 3114 are coupled to the headgear 3110. The core members 3116 extend through the biasing elements 3118, which in some configurations can be elastic tubular members. In the illustrated arrangement, the excess portions of the core members 3116 are received within an interior of the headgear 3110, such as within a guide or accumulator. In some configurations, the headgear 3110 comprises an inner core and a cover, as described above. The headgear 3110 can define elongate interior spaces configured to receive the excess portions of the core members 3116 within the inner core, between the inner core and the cover, or elsewhere (e.g., a dedicated guide element). Unlike the system 3100 of FIG. 92, in the illustrated configuration of FIG. 96, the nasal cannula system 3100 also comprises one or more quick release arrangements 3120 between the headgear 3110/adjustment arrangements 3112 and the nasal cannula 3102. Preferably, a pair of quick release arrangements 3120 are provide, with one on each side of the nasal cannula system 3100.

Figure 97:
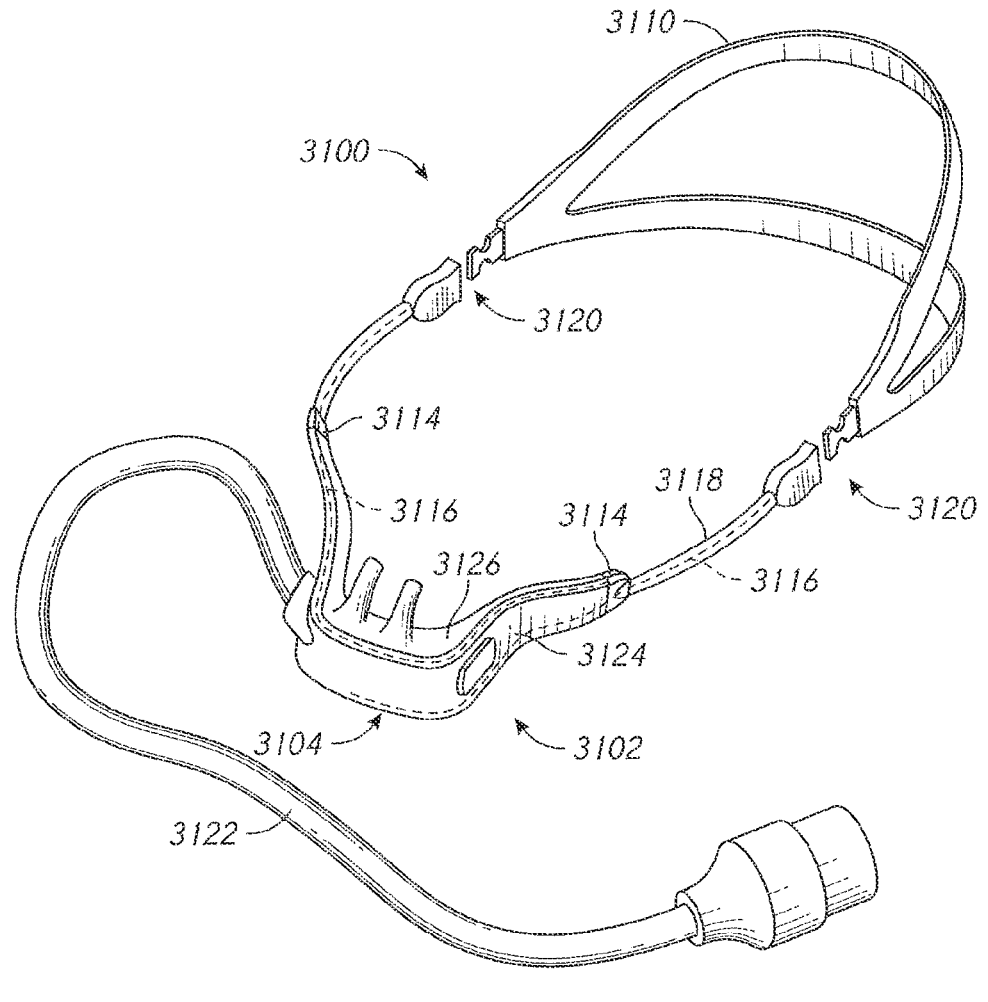
FIG. 97 is a perspective view of a respiratory cannula incorporating a headgear arrangement of the present disclosure, which can include a pair of directional lock arrangements and a pair of headgear quick release arrangements.

FIG. 97 illustrates a nasal cannula system 3100 that is similar to the system 3100 of FIG. 96 in that the system 3100 of FIG. 97 includes a pair of adjustment arrangements 3112 and a pair of quick release arrangements 3120. However, in the system of FIG. 97, the quick release arrangements 3120 are located between the headgear 3110 and the adjustment arrangements 3112. In addition, the directional locks 3114 are located at end portions of the cannula body 3104 of the nasal cannula 3102 or at forward ends of the biasing elements 3118. The excess portions of the core members 3116 are received within internal spaces of the cannula body 3104, which includes a frame 3124 and a user-contacting portion 3126 similar to the arrangements of FIGS. 94 and 95.

Figure 98:
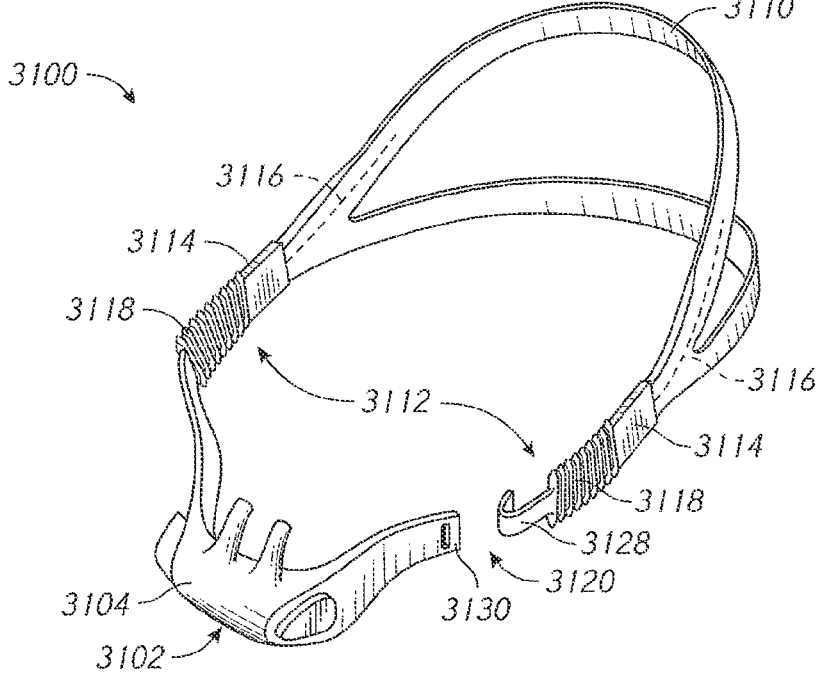
FIG. 98 is a perspective view of a respiratory cannula incorporating a headgear arrangement of the present disclosure, which can include a pair of directional lock arrangements and a headgear quick release arrangement.

FIG. 98 illustrates a nasal cannula system 3100 similar to the system 3100 of FIG. 92. For example, adjustment arrangements 3112 are provided on each side of the nasal cannula system 3100 and excess portions of the core members 3116 are received within the headgear 3110. However, the system 3100 of FIG. 98 includes a single quick release arrangement 3120. In the illustrated arrangement, the quick release arrangement 3120 is located on one side of the nasal cannula system 3100. In particular, the quick release arrangement 3120 is located between a forward end of one of the adjustment arrangements 3112 (e.g., at a forward end of the biasing element 3118) and the nasal cannula 3102. The illustrated quick release arrangement 3120 comprises a hook and post connection in which a hook 3128 is carried by the adjustment arrangement 3112 and a post 3130 is carried by the nasal cannula 3102. However, this arrangement could also be reversed. Other suitable quick release arrangements could also be used, including but not limited to any of those disclosed herein.

Figure 99:
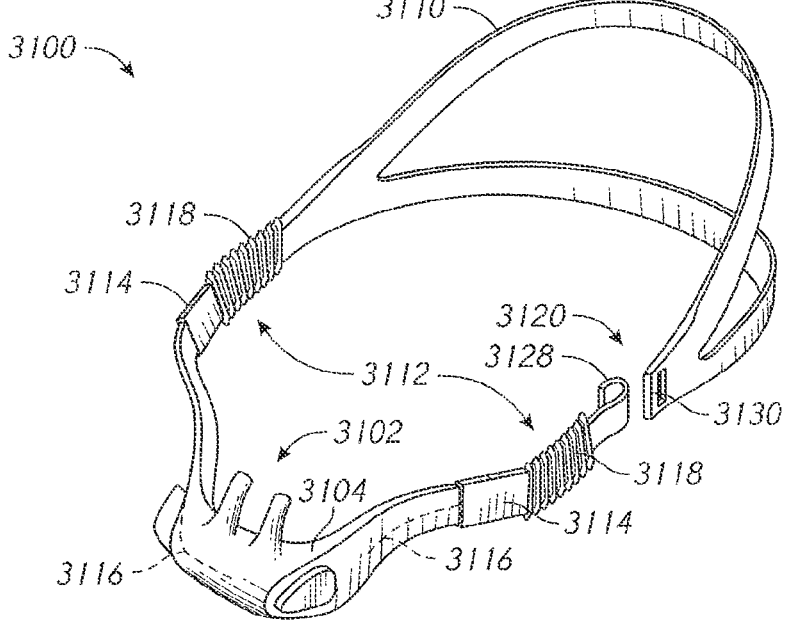
FIG. 99 is a perspective view of a respiratory cannula incorporating a headgear arrangement of the present disclosure, which can include a pair of directional lock arrangements and a headgear quick release arrangement.

FIG. 99 illustrates a nasal cannula system 3100 similar to the system 3100 of FIG. 98; however, in the system 3100 of FIG. 99, the direction of the adjustment arrangements 3112 are reversed. That is, the directional locks 3114 are located closer to the nasal cannula 3102 than the headgear 3110. In some configurations, the directional locks 3114 can be carried by the cannula body 3104 and the excess portions of the core members 3116 can be contained within the nasal cannula 3102. In addition, quick release arrangement 3120 is located between the adjustment arrangement 3112 and the headgear 3110. In particular, the hook 3128 is carried by the adjustment arrangement 3112 and the post 3130 is carried by the headgear 3110. However, this arrangement could be reversed and/or other suitable quick release arrangements could be used.

Figures 100, 101:
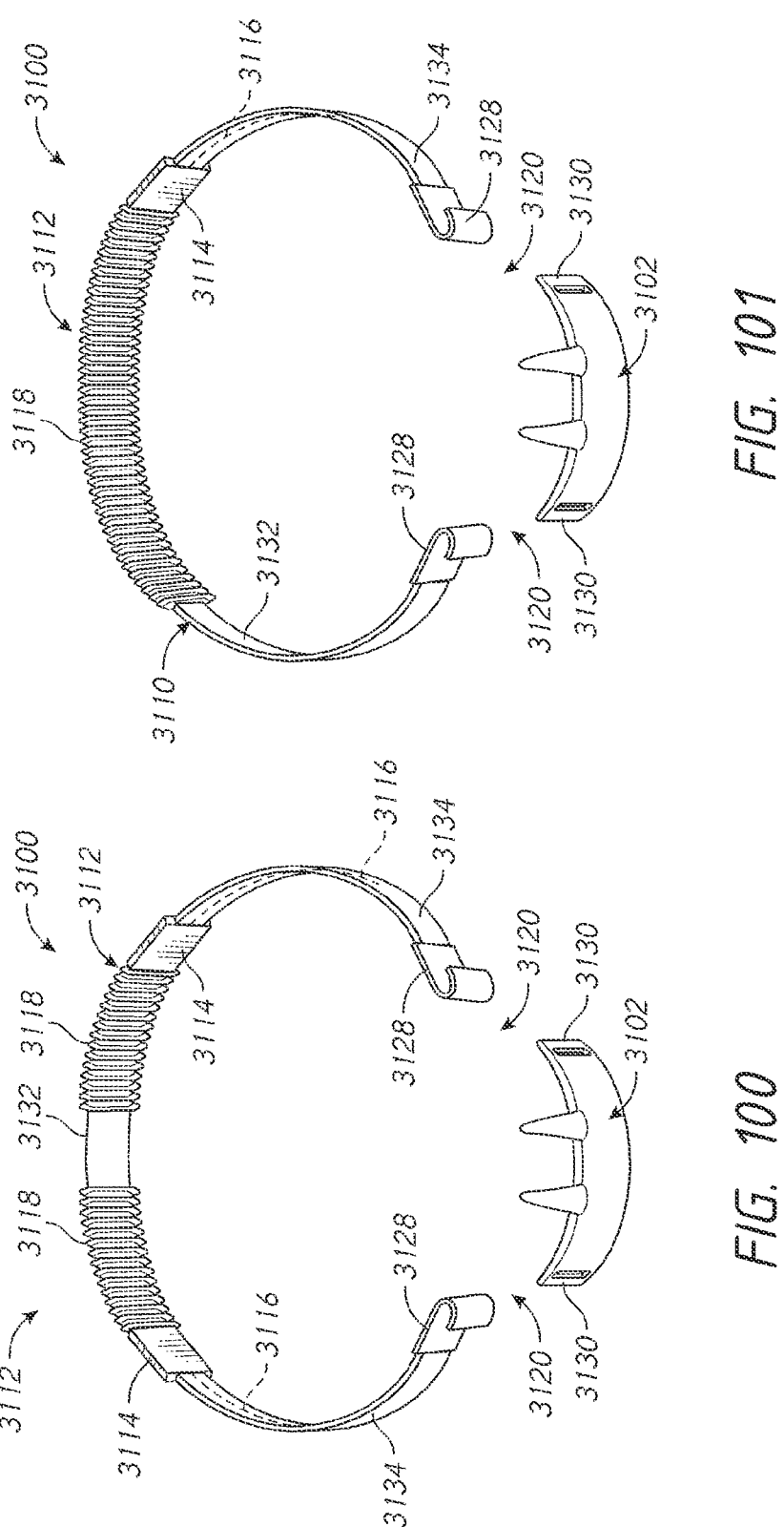
FIG. 100 is a perspective view of a respiratory cannula incorporating a headgear arrangement of the present disclosure, which can include a pair of directional lock arrangements and a pair of headgear quick release arrangements.
FIG. 101 is a perspective view of a respiratory cannula incorporating a headgear arrangement of the present disclosure, which can include at least one directional lock arrangement and a pair of headgear quick release arrangements.

FIG. 100 illustrates a nasal cannula system 3100 in which the adjustment arrangement(s) 3112 are integrated into the headgear 3110, which is a single strap headgear in the illustrated arrangement. In the illustrated system 3100, a pair of adjustment arrangements 3112 are provided. In addition, each end of the headgear 3110 is connected to the nasal cannula 3102 by a quick release arrangement 3120, such as a hook 3128 and post 3130 coupling arrangement. The adjustment arrangements 3112 are located toward a rear of the headgear 3110. Ends of the adjustment arrangements 3112 are coupled to one another, either directly or via a rear head strap portion 3132, which can be a non-stretch or inextensible strap in some configurations. One end of each core member 3116 can be coupled to the head strap portion 3132 and can extend forward through a respective one of a biasing element 3118, a directional lock 3114, and into an internal accumulator space of a front head strap portion 3134. The front head strap portions 3134 can be non-stretch or inextensible straps in some configurations.

FIG. 101 illustrates a nasal cannula system 3100 that is similar to the system 3100 of FIG. 100. However, the nasal cannula system 3100 of FIG. 101 includes a single adjustment arrangement 3112. The single adjustment arrangement is incorporated into the headgear 3110. The headgear 3110 is a single strap headgear arrangement having a first portion 3132 and a second portion 3134 coupled by the biasing element 3118. The core member 3116 is coupled to the first headgear portion 3132 and extends into an interior accumulation space of the second headgear portion 3134. The directional lock 3114 is coupled to the second headgear portion 3134 and selectively engages the core member 3116 to secure the headgear 3110 in a desired adjustment position of the circumference of the nasal cannula system 3100.

Figure 102:
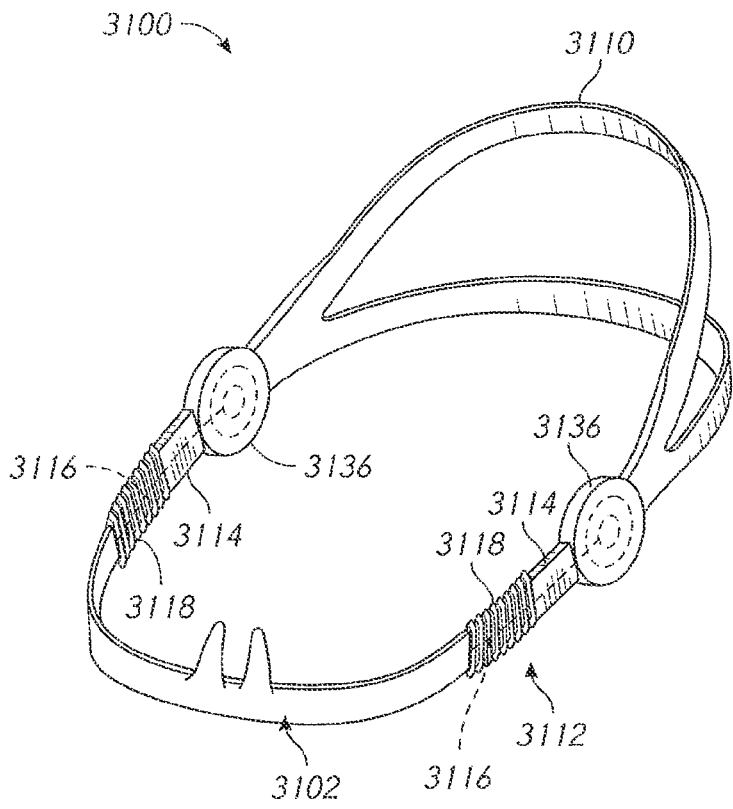
FIG. 102 is a perspective view of a respiratory cannula incorporating a headgear arrangement of the present disclosure, which can include a pair of directional lock arrangements.

FIG. 102 illustrates a nasal cannula system 3100 that is similar to the system 3100 of FIG. 90. In particular, the nasal cannula system 3100 comprises an adjustment arrangement 3112 on each side of the nasal cannula system 3100. In the illustrated arrangement, the excess portions of the core members 3116 are accumulated in disk-shaped accumulators 3136. Such an arrangement eliminates the need to provide for accumulation of the excess portions of the core members 3116 in the headgear 3110. In the illustrated arrangement, the adjustment arrangements include biasing elements 3118. However, in other configurations, the accumulators 3136 could be in the form of dial adjusters that take up or release the core members 3116. With such an arrangement, the circumference of the nasal cannula system 3100 can be adjusted by rotating the accumulators in one direction or the other to reduce or lengthen the circumference. In addition, although not specifically shown, the system 3100 of FIG. 102 can include one or more quick release arrangements 3120.

In at least some configurations, the core member ("filament") is circular in cross-sectional shape and the excess portion of the filament is received within an accumulator (e.g., tube or tubular pathway—hereinafter "tube") that is also circular in cross-sectional shape. In at least some configurations, the filament can be in the range of 0.6 mm to 0.8 mm in diameter. In at least some configurations, the diameter of the tube (the inner diameter) is approximately 0.1 mm greater than the filament diameter, when the filament is nylon and the tube is polyethylene (PE). Thus, in some configurations, the diameter of the tube is between about 10-20 percent greater, about 12-17 percent greater or about 12.5-16.67 percent greater than the diameter of the filament, including any sub-range or value within the above ranges.

In general, the smaller the tube diameter in relation to the filament diameter, the more friction will be applied to the filament by the tube. However, the bigger the diameter of the tube, the less guidance it will provide for the filament, which, in some cases, could negatively influence movement of the filament within the tube. As a result, the "return behavior" or shortening of the interface circumference or headgear length may feel rougher and/or less consistent. Furthermore, excessive movement of the filament within the tube could damage the internal walls of the tube. It has been determined that a nylon filament of 0.7 mm diameter sliding inside a PE tube of internal diameter of 0.8 mm increases the total force on the adjustment arrangement by about IN in the activation direction. It is possible that a similar excess force will be present in both the activation (lengthening) and return (shortening) directions. Excess force added as a result of movement of the filament within the tube preferably is reduced or minimized such that the return force provided by biasing element(s) can be kept low.

The ratio of the filament and tube diameters can be based, at least in part, on the curvature of the tube, the flexural modulus of both the tube and the filament, and the particular materials of the tube and filament. In addition, a factor of the tube design can include the external wall to internal wall ratio, where the higher that ratio is (external/internal), the higher the flexural modulus of the tube. Too high of a flexural modulus may reduce the flexibility of the tube. Reduced flexibility may cause the tube to kink if it is bent or curved in use. Different materials can also have different flexural moduli, as well as other properties that affect the forces resulting from the filament sliding within the tube. In some configurations, it is desirable that the tube has a higher Young's modulus relative to the filament because the tube acts as the guide to the filament. Therefore, it is desirable to reduce the possibility of the filament damaging the tube or creating excessive wear of the tube. In some configurations, it is preferable for the tube and the filament to be made of dissimilar materials to avoid cold welding through friction caused by sliding of the filament relative to the tube.

Figure 103:
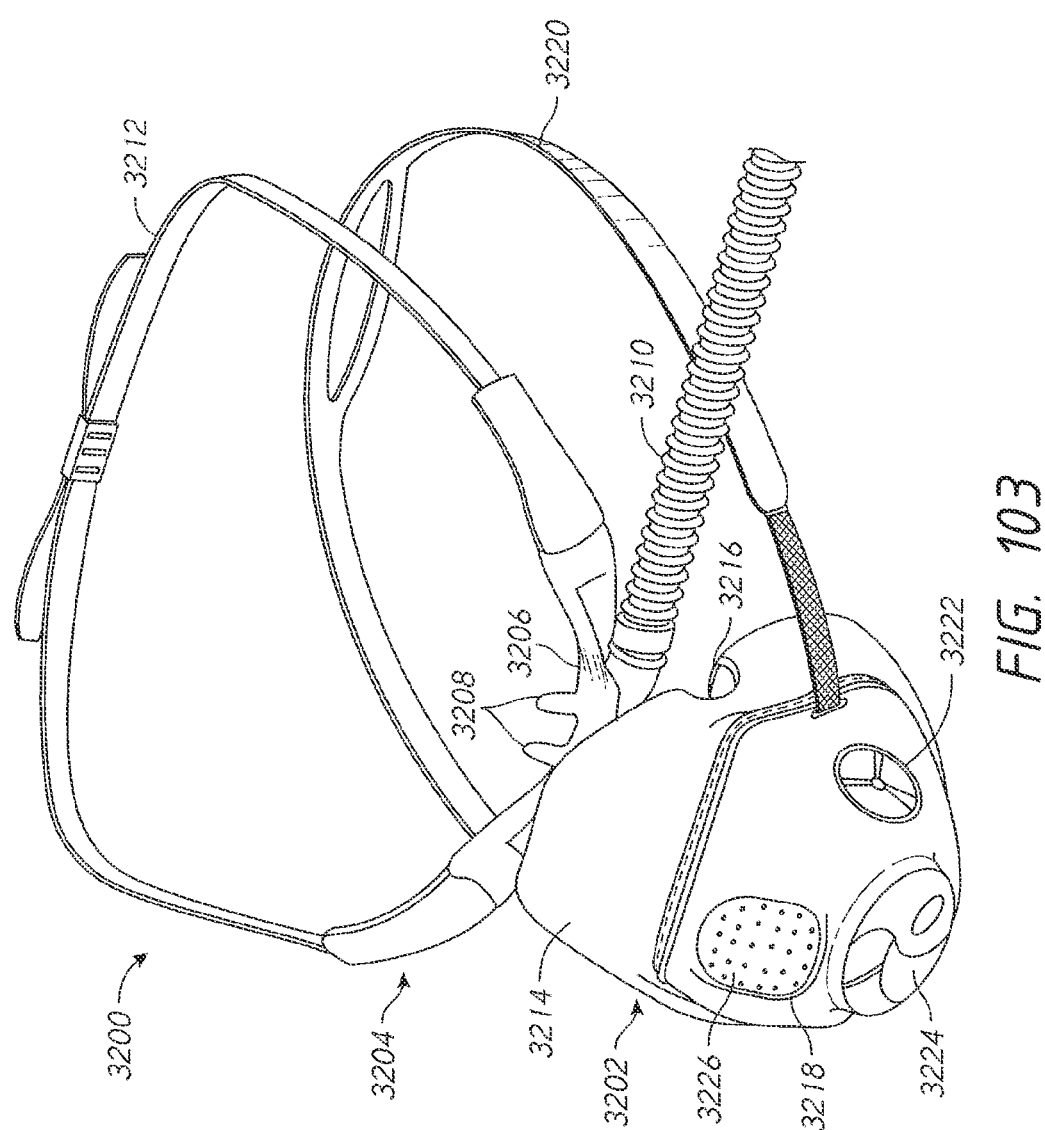
FIG. 103 is a perspective view of an increased or controlled expiratory pressure system comprising a respiratory mask for use in combination with a nasal high flow cannula. The respiratory mask can comprise one or more directional lock arrangements.
Figure 104:
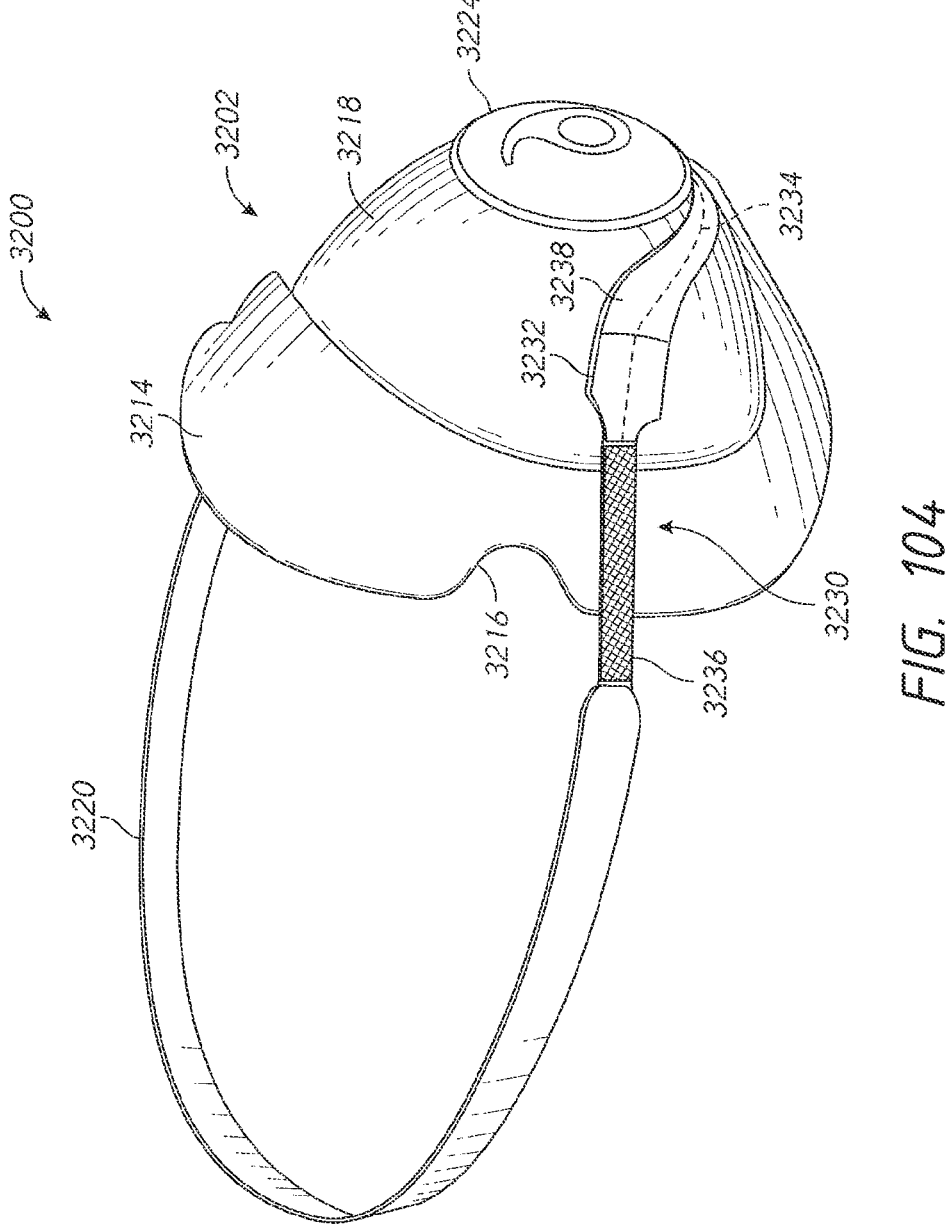
FIG. 104 is a perspective view of the respiratory mask of FIG. 103.

FIG. 103 illustrates a respiratory therapy system 3200 comprising a mask 3202 that covers a nasal cannula 3204 (e.g., nasal high flow cannula) to provide an increased or controlled expiratory pressure relative to the nasal cannula 3204 on its own. FIG. 104 illustrates the mask 3202 alone. Such a system is disclosed in Applicant's PCT Application No. PCT/IB2015/052257, entitled CANNULA PRESSURIZING MASK, the entirety of which is incorporated by reference herein. The mask 3202 and nasal cannula 3204 can be sold as a system or kit, in which the mask 3202 and nasal cannula 3204 are sold together or in a single package. In other configurations, the mask 3202 can be configured for use in combination with one or more particular models of nasal cannula 3204, but can be sold separately from such nasal cannula 3204.

The nasal cannula 3204 can be used to provide a flow of breathing gas to the user. Thus, the nasal cannula 3204 can be applied to the user separately from the mask 3202. The mask 3202 can be selectively applied to the user without removal of the nasal cannula 3204 and, preferably, without significant movement or other manipulation of the nasal cannula 3204. Similarly, the mask 3202 preferably can be removed from the user without removal of the nasal cannula 3204 and, preferably, without significant movement or other manipulation of the nasal cannula 3204.

The nasal cannula 3204 can be of any suitable configuration for the intended use, such as high-flow (HF) nasal therapy. The nasal cannula 3204 can have a body 3206 from which at least one nasal prong 3208 extends. In the illustrated arrangement, a pair of nasal prongs 3208 is provided. Preferably, when the nasal cannula 3204 is properly positioned on the user's head, the nasal prongs 3208 extend toward or into, but do not fully seal with, the user's nares. The nasal cannula 3204 includes a gases or breathing circuit that communicates with the nasal prongs 3208. In the illustrated arrangement, the gases circuit comprises at least one gases tube 3210 that supplies a flow of breathing gas to the nasal prongs 3208 and, thus, can be referred to as a supply tube. In the illustrated arrangement, a single supply tube 3210 is provided and extends to one side of the nasal cannula 3204. In other arrangements, the supply tube 3210 can extend in other directions and/or multiple supply tubes 3210 can be provided. For example, in some configurations, a supply tube 3210 can be provided on and extend to each side of the nasal cannula 3204. In use, the supply tube 3210 can be connected to a source of pressurized gas (e.g., a flow generator) and, optionally, a humidifier. The source of pressurized gas can be configured to supply supplemental oxygen to the user. Any suitable source of pressurized gas can be used.

The nasal cannula 3204 preferably also includes a retention or headgear arrangement that secures or retains the nasal cannula 3204 onto the user's head. In the illustrated cannula 3204, the headgear arrangement is in the form of a single strap 3212 that extends around the user's head from one side of the cannula body 3206 to the other side of the cannula body 3206. However, in other configurations, the headgear arrangement can more complex, such as including multiple straps or multiple strap portions. The headgear arrangement can include a rear portion that extends around the back of the user's head and/or an upper portion that extends over the top of the user's head. The headgear arrangement can include flexible or relatively rigid portions, elastic or relatively inelastic portions or any combination thereof. If desired, the headgear arrangement can comprise one or more adjustment arrangements as described herein.

The mask 3202 can comprise a sealing cushion 3214, one or more cannula cut-outs 3216, a mask frame 3218, a headgear arrangement or head strap 3220, a one-way valve 3222, a variable vent 3224 and a fixed bias flow vent 3226. Unlike non-invasive respiratory masks known in the art, the illustrated mask 3202 may not include an air supply conduit or connection port. Instead, a portion or most of the air flow to the user is supplied by the nasal cannula system 3204 with any deficit being supplied through the one-way valve(s) 3222. With such an arrangement, the mask 3202 can act as a pressure vessel that can increase the expiratory pressure within the airways of the user.

The mask 3202 can comprise a mask body, which can be made up of, in whole or in part, the mask frame 3218 and the sealing cushion 3214. The sealing cushion 3214 can be referred to herein as a "seal" or as a "cushion." The mask frame 3218 can be unitary with or can otherwise support the cushion 3214. The mask frame 3218 can be constructed from a material that is capable of at least substantially maintaining its shape in the absence of external forces applied to the mask frame 3218. In some configurations, the mask frame 3218 can be resilient. In other configurations, the mask frame 3218 can be relatively rigid or at least more rigid than the cushion 3214. For example, the mask frame 3218 can be constructed in whole or in part from polycarbonate, high-density polyethylene (HDPE) or another suitable material. The mask frame 3218 can be a one-piece structure or can be a multi-piece structure. For example, a first mask frame portion or element can support the cushion 3214 and a second mask frame portion or element can provide for connection of the headgear 3220. The first mask frame portion and the second mask frame portion can be permanently or, preferably, removably connected to one another.

The cushion 3214 can be configured to provide an interface between the user and the mask 3202 and can be made from a flexible material, such as silicone rubber, a thermoplastic elastomer or any other suitable seal material. The cushion 3214 can be secured to the mask frame 3218 by any suitable process or arrangement. For example, the cushion 3214 can be removably coupled to the mask frame 3218, such as by a flange-and-groove arrangement. In other configurations, the cushion 3214 can be attached to the mask frame 3218 by adhesives or during the forming process (e.g., overmolding or co-molding).

The cushion 3214 preferably includes one or more features configured to accommodate the nasal cannula 3204 when the mask 3202 is applied to a user while the nasal cannula 3204 is in use. For example, the cushion 3214 can include at least one cannula recess or cut-out 3216. In other configurations, the cushion 3214 can include other configurations to accommodate the nasal cannula 3204, such as regions of increased compliance or thin-walled regions that allow the cushion 3214 to stretch over the nasal cannula 3204. Such thin-walled regions may have a wall thickness that is significantly thinner than surrounding portions of the cushion 3214 and may be sized and/or shaped to generally correspond to the size and/or shape of the portion of the nasal cannula 3204 that passes underneath the cushion 3214. Examples of thin-walled regions are described in Applicant's PCT Publication No. WO2015/130179, published Sep. 3, 2015, entitled "RESPIRATORY MASK WITH NASOGASTRIC TUBE PATH," the entirety of which is incorporated by reference herein.

In the illustrated arrangement, the cushion 3214 includes a cannula cut-out 3216 on each side of the mask 3202. In particular, the illustrated cushion 3214 includes a cut-out 3216 on each lateral side of the mask 3202. The cut-outs 3216 can be configured to accommodate, complement or match the lateral geometry of a nasal cannula, in general, or a particular nasal cannula 3204. Such an arrangement enables a cannula to pass between the mask 3202 and a user's face, preferably with minimal or acceptable gaps between the cannula and mask 3202. Preferably, when properly positioned on the user in combination with the nasal cannula 3204, the mask 3202 can create a seal with the face of the user that is sufficient to allow for an increase in pressure within an interior space or breathing cavity of the mask 3202 and/or an increased expiratory pressure within the user's airways relative to the use of the nasal cannula 3204 without the mask 3202. Preferably, the mask 3202 also creates at least a substantial seal with the nasal cannula 3204. Preferably, the combination of the seal with the user's face and the nasal cannula 3204 is sufficient to allow for an increase in pressure within an interior space or breathing cavity of the mask 3202 and/or an increased expiratory pressure within the user's airways. In some configurations, the mask 3202 is capable of creating a seal with the user's face that is sufficient to allow for a therapeutically-significant increase in an increase in pressure within an interior space or breathing cavity of the mask 3202 and/or an increased expiratory pressure within the user's airways relative to the use of the nasal cannula 3204 without the mask 3202.

Preferably, the mask 3202 comprises at least one adjustment arrangement 3230, which can be the same as or similar to any of the adjustment arrangements disclosed herein, or can be of another suitable arrangement. With such an arrangement, the mask 3202 can be quickly and easily applied to a user over the nasal cannula 3204 to provide increased therapy pressure. In at least some configurations, the mask 3202 can automatically adjust toward or to an appropriate size for the particular user. Such an arrangement is beneficial for reducing the time that it takes a caregiver to apply the mask 3202 to initiate the increased therapy pressure by reducing the time needed to adjust the circumference of the mask 3202 and headgear 3220 to the particular user. Although not shown, the mask 3202 can include one or more quick release arrangements, such as any of those disclosed herein, to further facilitate the application or removal of the mask 3202 to a user.

In some configurations, the mask 3202 comprises a pair of adjustment arrangements 3230, with one adjustment arrangement 3230 positioned on each side of the mask 3202. The adjustment arrangements 3230 can each comprise a directional lock 3232, a core member or filament 3234 that moves relative to and is selectively engaged by the directional lock 3232, and a biasing element or arrangement 3236 that, in the illustrated arrangement, tends to shorten a circumference of the mask 3202 and headgear 3220. In the illustrated arrangement, one end of each of the core members 3234 is coupled to a respective end of the headgear 3220. The core members 3234 extend through the biasing elements 3236, the directional locks 3232 and into an accumulator 3238, which can be defined by any suitable structure. In the illustrated arrangement, the accumulator 3238 is a connector that clips onto the mask frame 3218 to connect the headgear 3220 to the mask frame 3218. In other configurations, a separate accumulator could be provided for each core member 3234. The excess portions of the core members 3234 could also be accommodated by other suitable structures, such as any of those disclosed herein. The illustrated direction of the adjustment arrangements 3230 could also be reversed. Furthermore, the number and/or location of the adjustment arrangements 3230 could be varied from that illustrated in FIGS. 103 and 104.

Figure 105:
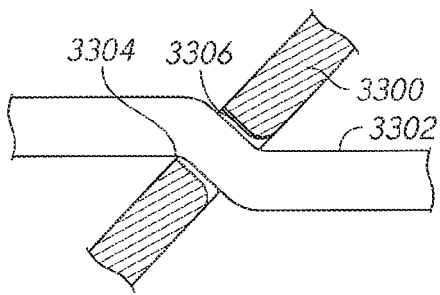
FIG. 105 is a side view of a lock member and core member of a directional lock arrangement.

FIG. 105 illustrates an example of a lock member, which in the illustrated arrangement is a lock washer 3300, in a locked position relative to a core member 3302. It has been discovered by the present inventors that a leading edge 3304 (relative to a direction of movement of the core member 3302 that tends to move the lock washer 3300 to the locked position) of the opening 3306 of the lock washer 3300 through which the core member 3302 passes can be an important design characteristic to achieve a desirable performance of the associated directional lock. Thus, the leading edge 3304 or a portion of the leading edge 3304 that engages the core member 3302 in a locked position of the lock washer 3300 can be referred to as the "working edge." In at least some configurations, it is desirable that at least a portion of the leading edge 3304 that engages the core member 3302 in the locked position (e.g., a lower portion or half) is relatively sharp. It is presently believed that the sharp leading edge 3304 provides a better grip on the core member 3302 than a more rounded edge. The sharpness of the leading edge 3304 can be defined as: $1/R$, wherein R is the radius of the leading edge 3304 or at least a portion of the leading edge 3304 that contacts or engages the core member 3302 in a locked position of the lock washer 3300.

Figure 106:
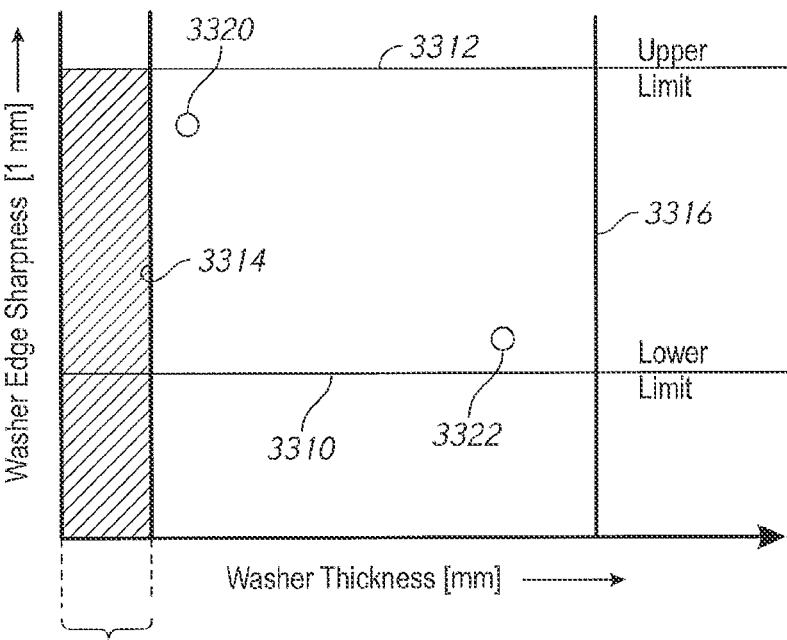
FIG. 106 is a graph of lock member edge sharpness versus lock member thickness illustrating a preferred operating envelope for the lock member.

FIG. 106 illustrates a graph of leading edge sharpness versus lock washer thickness. Performance and/or practical considerations can result in the creation of design limits on these variables with respect to a particular interface or application of use. Such design limits may be selected to achieve a desired level of performance, and values outside of the design limits may still be functional and suitable for use in at least some applications. Therefore, the design limits described herein are not considered limiting unless expressly indicated as such. Moreover, the design limits will likely vary between different interface or headgear types, or different applications of use.

The graph of FIG. 106 illustrates a target design envelope created by a lower limit 3310 and an upper limit 3312 of the leading edge sharpness and a lower limit 3314 and an upper limit 3316 of the lock washer thickness. As discussed above, if the leading edge sharpness of the lock washer 3300 (or other lock element) is too low, the associated directional lock may not provide a desired level of grip on the core member 3302 and the locking force of the directional lock may be lower than desirable. Thus, the lower limit 3310 of the lock washer sharpness may be determined by the desired lock force in view of the other relevant design characteristics, such as material selection, lock member angle, etc. The upper limit 3316 of the lock washer sharpness may be determined in view of practical considerations, such as manufacturability. That is, the upper limit 3316 of lock washer sharpness may be determined by the sharpness that can be produced by a given manufacturing process, which process may be selected on the basis of manufacturing cost.

The lower limit 3314 of lock washer thickness may be determined based on practical considerations, such as strength requirements or manufacturability. The upper limit 3316 of lock washer thickness can also be determined by practical considerations, such as space available for the lock washer 3300 and the associated directional lock. Thus, in at least some configurations, the lock washer thickness will not be substantially greater than necessary to provide adequate strength (or other physical characteristics) in order to allow the associated directional lock to be relatively small. In some configurations, the lower limit 3314 may be approximately 0.5 mm and the upper limit 3316 may be approximately 5 mm. However, these values can change depending on relevant design criteria, as described above.

FIG. 106 illustrates two points 3320, 3322 within the target design envelope that represent two different lock washers 3300 having a different thickness and leading edge sharpness relative to one another. Point 3320 represents a lock washer 3300 having relatively high leading edge sharpness and relatively low washer thickness. In other words, the lock washer 3300 represented by point 3320 is relatively thin. Such a lock washer 3300 represented by point 3320 can have a thickness of about 0.5 mm-1 mm (e.g., 0.8 mm). Point 3322 represents a lock washer 3300 having relatively low leading edge sharpness and relatively high washer thickness relative to the target design envelope and the washer 3300 represented by point 3320. Such a lock washer 3300 represented by point 3322 can have a thickness of about 2 mm-4 mm (e.g., 3 mm). The radius of the leading edge 3304 can be between 0.4 mm-0.6 mm (e.g., 0.5 mm).

Figure 107:
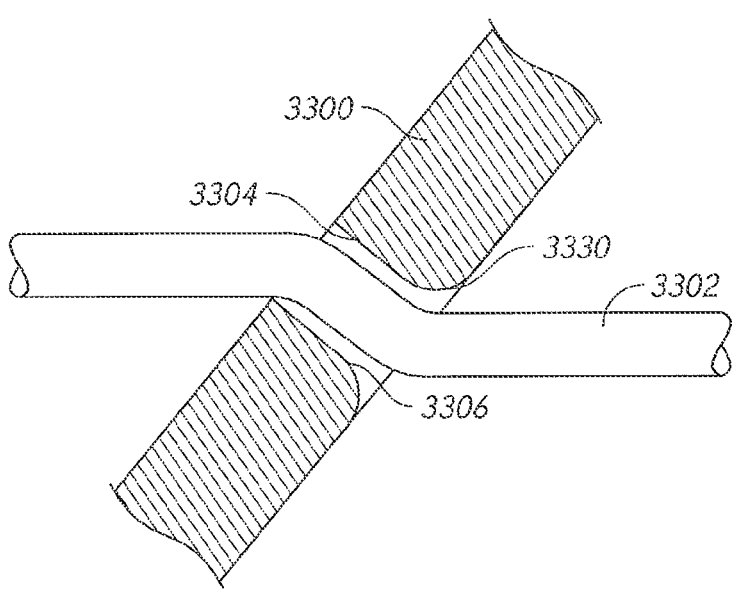
FIG. 107 is an enlarged view of a lock member in a locked position.
Figure 108:
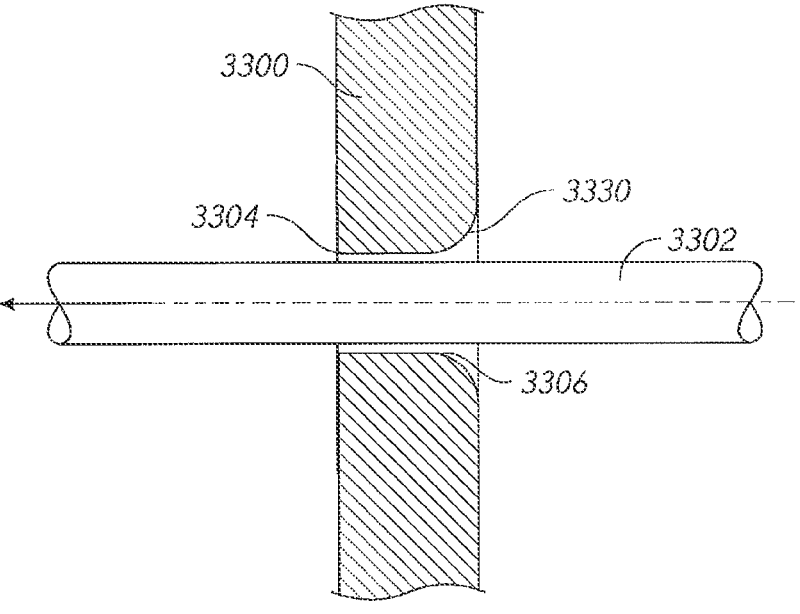
FIG. 108 is an enlarged view of the lock member of FIG. 107 in an unlocked position.

FIGS. 107 and 108 illustrate an embodiment of a lock member/lock washer 3300 and a core member 3302 in a locked position and a free or unlocked position, respectively. As illustrated, preferably, the leading edge 3304 of a portion of the lock washer 3300 that defines the opening 3306 and engages the core member 3302 is relatively sharp or has a relatively high sharpness, as described above. Preferably, the trailing edge 3330 of a portion of the lock washer 3300 that defines the opening 3306 for the core member 3302 has a lower sharpness than the leading edge 3304. In some configurations, the trailing edge 3330 is rounded or chamfered. Preferably, a diameter (or perimeter length) of the opening 3306 at the trailing edge 3330 is larger than a diameter (or perimeter length) of the opening 3306 at the leading edge 3304. Such an arrangement can provide a desirable locking force and can also allow the core member 3302 to move in a release direction (FIG. 108) at a reduced level of resistance compared to a constant diameter opening 3306. In addition, the arrangement of FIGS. 107 and 108 improves manufacturability by making it easier to pass the core member 3302 through the opening 3306 during assembly of the directional lock. That is, the core member 3302 can be inserted through the larger diameter (or perimeter length) trailing edge 3330, which can be easier and faster than attempting to insert the core member 3302 through the smaller diameter (or perimeter length) leading edge 3304.

FIGS. 109a-109c illustrate several core members 3300 having openings 3306 of different cross-sectional shapes between the leading edge 3304 and the trailing edge 3330. The opening 3306 of each of the core members 3300 of FIGS. 109a, 109b and 109c has a diameter (or perimeter length) at or near the leading edge 3304 that is less than the diameter (or perimeter length) at or near the trailing edge 3330. In FIG. 109a, the opening 3306 has a substantially constant diameter from the leading edge 3304 and extending toward the trailing edge 3330 through a substantial portion of a length of the opening 3306. However, the portion of the opening 3306 near the trailing edge 3330 is rounded or chamfered such that the diameter of the opening 3306 at the trailing edge 3330 is larger than the diameter of the opening 3306 at the leading edge 3304. The opening 3306 of FIG. 109a is substantially similar to the openings 3306 of FIGS. 107 and 108.

The opening 3306 of FIG. 109b is tapered along a portion or a substantial entirety of its length. In the illustrated arrangement, the opening 3306 tapers at a constant angle from a minimum diameter at the leading edge 3304 to a maximum diameter at the trailing edge 3330. However, in other configurations, the taper could be non-linear. The opening 3306 of FIG. 109c combines a linear or constant diameter portion and a tapered portion. The portion of the opening 3306 beginning at the leading edge 3304 and extending through a portion (e.g., one-third to two-thirds, or about one-half) of the thickness of the washer 3300 defines a constant diameter. The remaining portion of the opening 3306 defines an outwardly-tapered portion such that the diameter of the opening 3306 at the trailing edge 3330 is greater than the diameter of the opening 3306 at the leading edge 3304. The tapered portion can comprise a linear or non-linear taper.

Figures 111A, 111B:
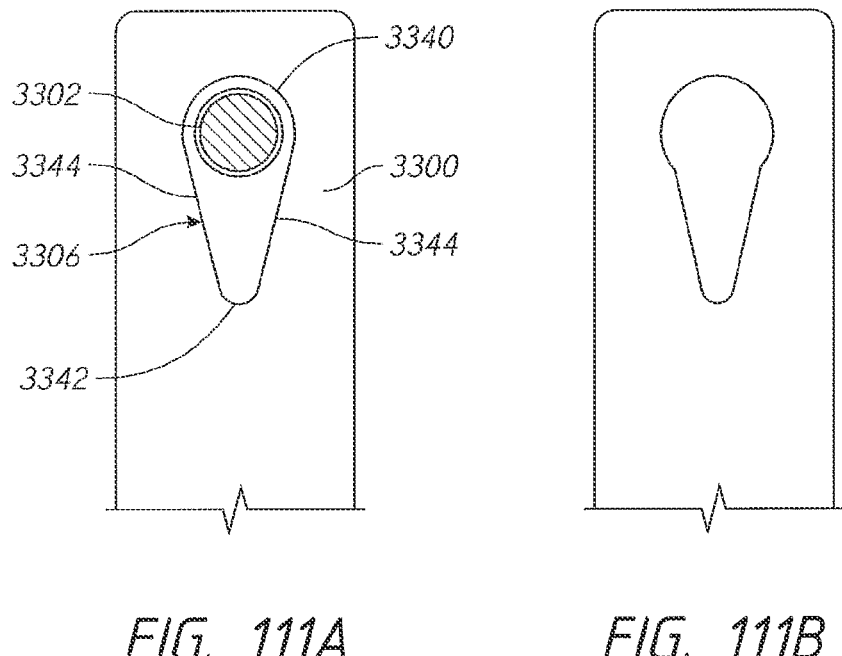

FIGS. 110, 111a and 111b illustrate lock members or lock washers 3300 having openings 3306 with non-circular profile shapes. For example, the lock washer 3300 of FIGS. 110 and 111a includes an opening 3306 that tapers from an upper portion 3340 to a lower portion 3342. In the illustrated arrangement, the opening 3306 has an upside-down teardrop or raindrop shape. The upper portion 3340 of the opening 3306 is generally semi-circular. The lower portion 3342 of the opening 3306 can also be semi-circular in shape and defines a diameter or width that is less than the diameter or width of the upper portion of the opening 3306. Sidewalls 3344 of the opening 3306 can taper or reduce in width from the upper portion 3340 toward the lower portion 3342. The diameter or width of the upper portion 3340 of the opening 3306 preferably is larger than the diameter or width of the core member 3302, and can be only slightly larger than the diameter or width of the core member 3302. With such an arrangement, each of the sidewalls 3344 can define a working edge of the opening 3306 that engages the core member 3302 in the locked position of the lock washer 3300. A width or lateral distance between the sidewalls 3344 or working edges that engage the core member 3302 can reduce the further the lock washer is rotated toward the locked position. Such an arrangement results in a progressively increasing locking force with increasing rotation of the lock washer 3300.

FIG. 111b illustrates an alternative non-circular or tapered profile shape of an opening 3306 of a lock washer 3300. The opening 3306 of the lock washer 3300 of FIG. 111b defines a keyhole shape, in which an upper portion 3340 is circular in shape and a lower portion 3342 tapers starting from a width that is less than the diameter of the circular upper portion 3340. The working edges of the opening 3306 can also be defined by the sidewalls 3344 in a manner similar to the opening 3306 of FIGS. 110 and 111a. Similarly, the opening 3306 of FIG. 111b can also result in a progressively increasing locking force, which may initially start or abruptly rise to a higher initial value than the opening 3306 of FIGS. 110 and 111a.

Figure 112:
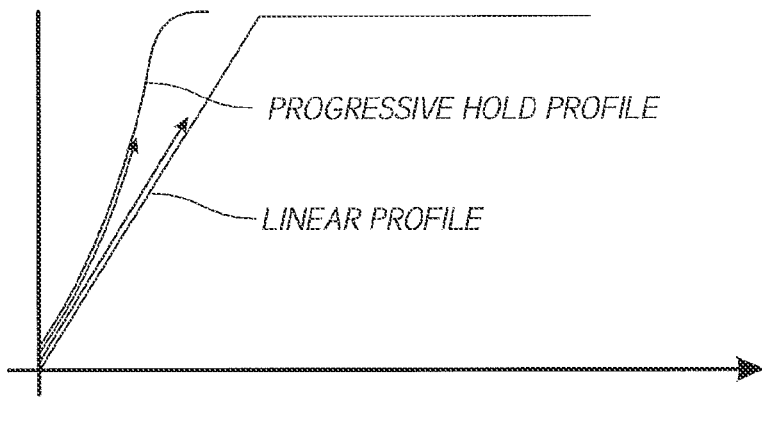

FIG. 112 illustrates a graph of locking or holding force versus core member displacement comparing a linear curve, which may be provided by a circular opening 3306, to a progressive curve, which may be provided by a non-circular (e.g., tapering) opening 3306. As illustrated, the non-circular or tapered openings, such as the openings 3306 of FIGS. 110, 111a and 111b, can rise to a desired locking or holding force at a lesser displacement of the core member 3302 compared to the linear curve of a circular opening 3306. Thus, a lock washer 3300 comprising a non-circular or tapered opening 3306 may reach a desired locking or holding force more quickly than a circular opening 3306.

Figure 113A:
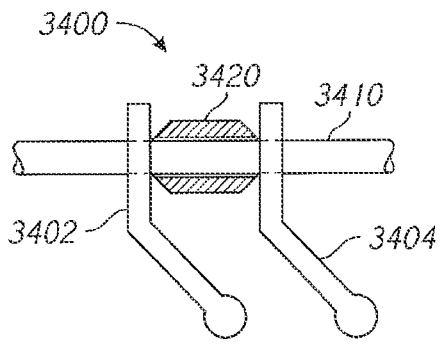
Figure 113B:
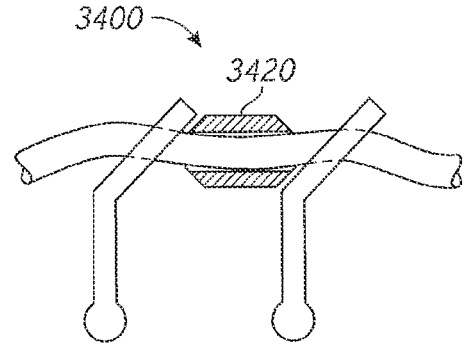

FIGS. 113a and 113b illustrate a directional lock 3400 having a first lock member or lock washer 3402 and a second lock member or lock washer 3404. The directional lock 3400 may be similar to the directional lock 1800 shown and described with respect to FIGS. 68A-68D. The first lock washer 3402 can be configured to move between a free position and a locked position, or throughout its available range of motion, with less displacement of the core member 3410 in comparison to the second lock washer 3404. The second lock washer 3404 can provide a greater holding or locking force than the first lock washer 3402, but has a greater range of motion between its free position and its locked position.

The directional lock 3400 of FIG. 113a includes a motion transfer arrangement to transfer motion from one of the first lock washer 3402 and the second lock washer 3404 to the other of the first lock washer 3402 and the second lock washer 3404. In the illustrated arrangement, the motion transfer arrangement comprises a motion transfer element 3420 positioned between the first lock washer 3402 and the second lock washer 3404. The illustrated motion transfer element 3420 is a tubular member carried on the core member 3410 and positioned between the first lock washer 3402 and the second lock washer 3404. The motion transfer element 3420 is configured to move the second lock washer 3404 along with movement of the first lock washer 3402 through at least a portion of the range of motion of one or both of the lock washers 3402, 3404. FIG. 113a illustrates the one or both of the lock washers 3402, 3404 in or relatively toward a free or unlocked position and FIG. 113b illustrates one or both of the lock washers 3402, 3404 in or relatively toward a locked position.

Thus, in at least some arrangements, the motion transfer element 3420 ensures that the second lock washer 3404 begins to move at substantially the same time as the first lock washer 3402, which may result in faster engagement of the second lock washer 3404 than without the motion transfer element 3420. As described above, because in at least some configurations, the range of motion of the second lock washer 3404 may be greater than the range of motion of the first lock washer 3402 (or vice-versa), the first lock washer 3402 and/or the second lock washer 3404 may be able to move relative to the motion transfer element 3420 such that the motion transfer element 3420 does not fix the lock washers 3402, 3404 to one another. In other words, in the illustrated arrangement, the motion transfer element 3420 pushes the second lock washer 3404 through a portion of its range of motion, but allows the second lock washer 3404 to move away from the motion transfer element 3420 and/or allows the motion transfer element 3420 to move away from the first lock washer 3402 such that the second lock washer 3404 can move through a longer range of motion than the first lock washer 3402.

Figure 114A:
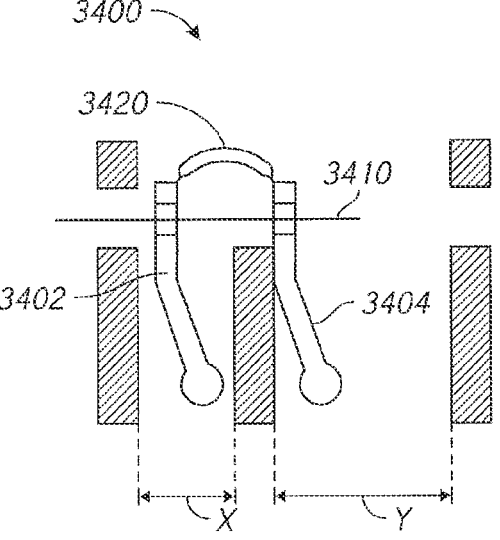
Figure 114B:
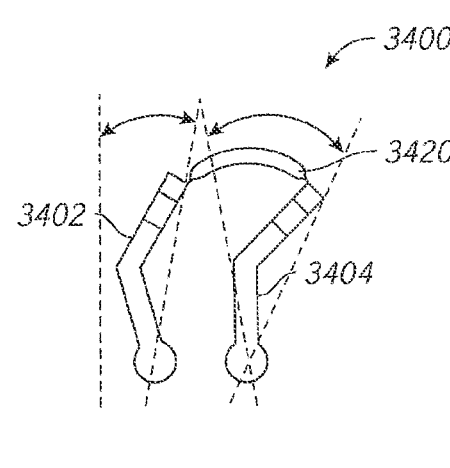

FIGS. 114a and 114b illustrate an arrangement similar to that of FIGS. 113a and 113b. However, in the arrangement of FIGS. 114a and 114b, the motion transfer element 3420 comprises a linking element. The linking motion transfer element 3420 couples the first lock washer 3402 and the second lock washer 3404. However, in at least some configurations, the linking motion transfer element 3420 is configured to allow the second lock washer 3404 to move away from the first lock washer 3402 (or vice-versa). The illustrated linking motion transfer element 3420 is a beam that defines a living hinge. The beam 3420 is deformable from a first position (FIG. 114a) having a first length to a second position (FIG. 114b) having a second length, which can be greater than the first length. The beam 3420 can have a curved shape in the first position, which can be a relaxed position of the beam 3420. The beam 3420 can flex or deform to a less-curved shape in the second position. Thus, the deformation of the beam 3420 from the curved shape to the less-curved shape can allow the second lock washer 3404 to move away from the first lock washer 3402.

Figure 115:
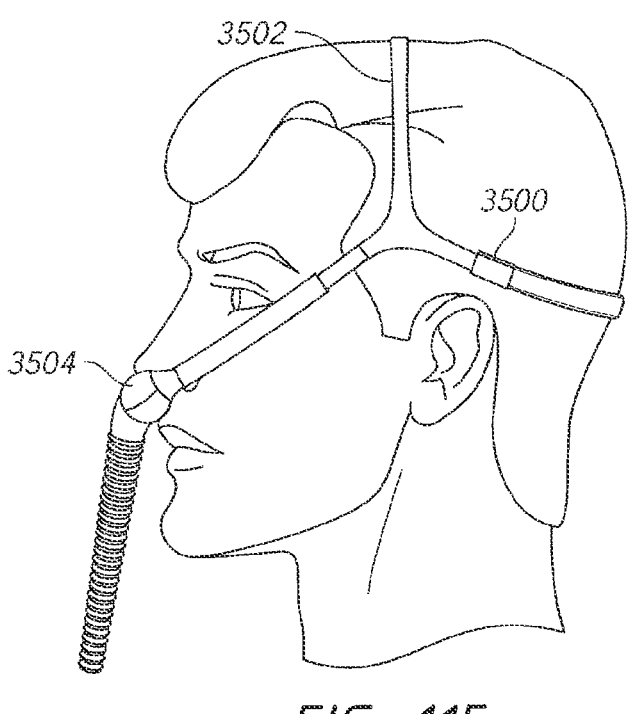
Figure 116:
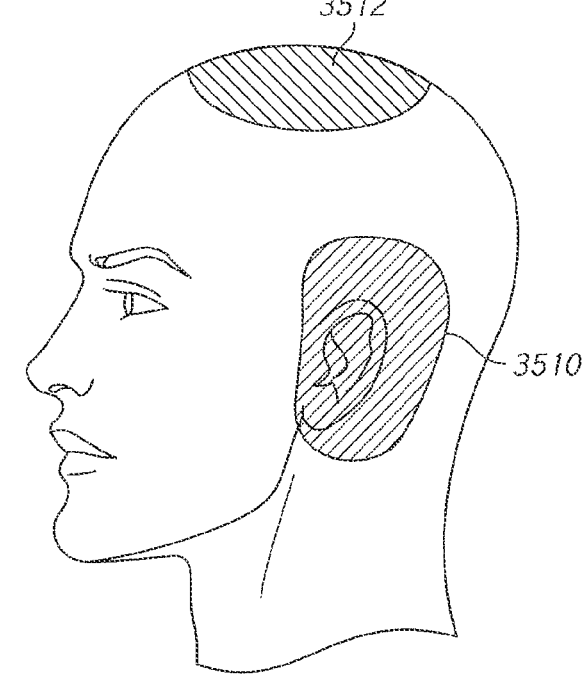
Figure 117:
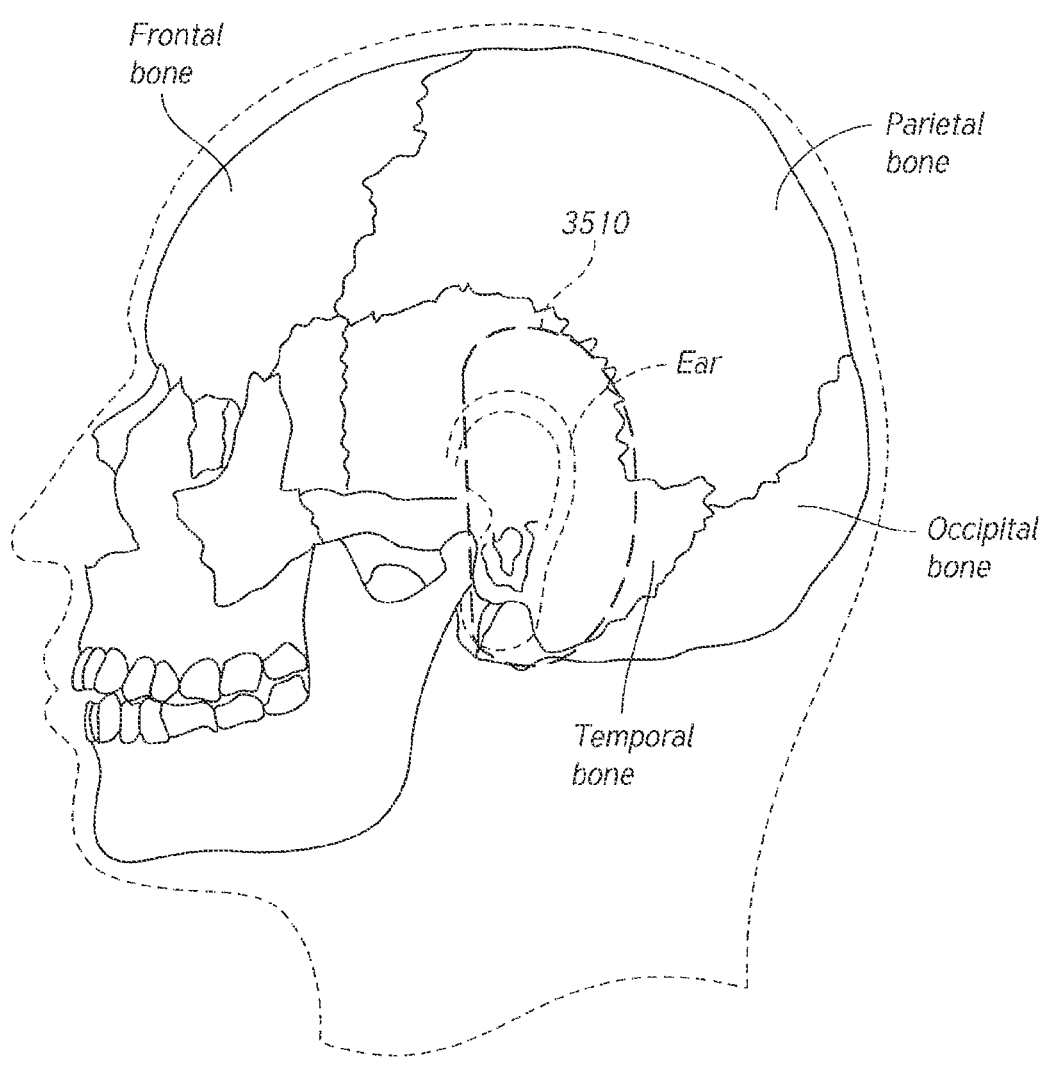

FIGS. 115-117 illustrate possible locations for placement of directional locks 3500 within a headgear 3502 of a patient interface 3504 relative to a user's head. The directional locks 3500 can be of any suitable arrangement, such as any of those disclosed herein. FIG. 115 illustrates the directional lock 3500 integrated within the headgear 3502, which is configured to position the directional lock 3500 aligned with an upper portion or slightly above the user's ear and/or aligned with a rearward portion or slightly behind the user's ear. In the illustrated arrangement, the excess portions of the core members can be accumulated in the rear strap of the headgear 3502; however, other suitable arrangements can also be used. The area in which the directional lock 3500 is positioned in FIG. 115 can be advantageous in that the user's ear projects from the user's head and creates a space that can accommodate the directional lock 3500. With the directional lock 3500 located as such, less pressure may be applied to the directional lock 3500 (such as from the user's pillow) when the user is lying on his or her side compared to other possible side locations for the directional lock 3500. In some cases, with such positioning of the directional lock 3500, there may be little to no significant pressure exerted on the directional lock 3500 when the user is lying on his or her side, which can provide a desirable level of comfort for the user. In addition, the reduced pressure or lack of any significant pressure on the directional lock 3500 can avoid crushing the directional lock 3500 to ensure operability or at least reduce the likelihood of malfunctioning due to crushing forces.

FIGS. 116 and 117 illustrate possible desirable zones relative to a user's head for placement of the directional lock 3500. For example, FIG. 116 illustrated that an area 3510 overlapping a portion of the ear and rearward and above the ear can provide a natural space for receiving the directional lock 3500 and inhibiting or preventing crushing or excessive pressure on the directional lock 3500 when the user is lying on his or her side. The portion of the area 3510 overlapping the ear preferably is the space behind or above the base of the ear. In addition, an area 3512 on top of the head can also provide a desirable location for placement of the directional lock 3500 to inhibit or prevent crushing or excessive pressure on the directional lock 3500 when the user is lying on his or her side or back.

FIG. 117 illustrates the area 3510 overlaid onto a user's head with the bones of the skull illustrated. The area 3510, as described above, can be overlapping a portion of the ear and rearward and above the ear. The area 3510 can be positioned on the temporal bone and can extend toward, to or somewhat beyond a boundary of the temporal bone and onto the parietal or occipital bones. However, in some configurations, the area 3510 does not extend significantly beyond the rearward or upper boundary of the temporal bone. The exact boundary of the area 3510 that would provide acceptable performance may vary between users; however, preferably, the area 3510 is configured to allow a large portion of the intended user population to comfortably utilize a patient interface 3504 and headgear 3502 having a directional lock 3500 positioned within the area 3510 when lying on his or her side. Although not specifically shown in FIG. 117, the area 3512 shown in FIG. 116 can be positioned on the top portions of the frontal and/or parietal bones. Preferably, the area 3512 is limited to substantially upward-facing portions of the frontal and/or parietal bones. The exact boundary of the area 3512 that would provide acceptable performance may vary between users; however, preferably, the area 3512 is configured to allow a large portion of the intended user population to comfortably utilize a patient interface 3504 and headgear 3502 having a directional lock 3500 positioned within the area 3512 when lying on his or her side or back.

Figure 118A:
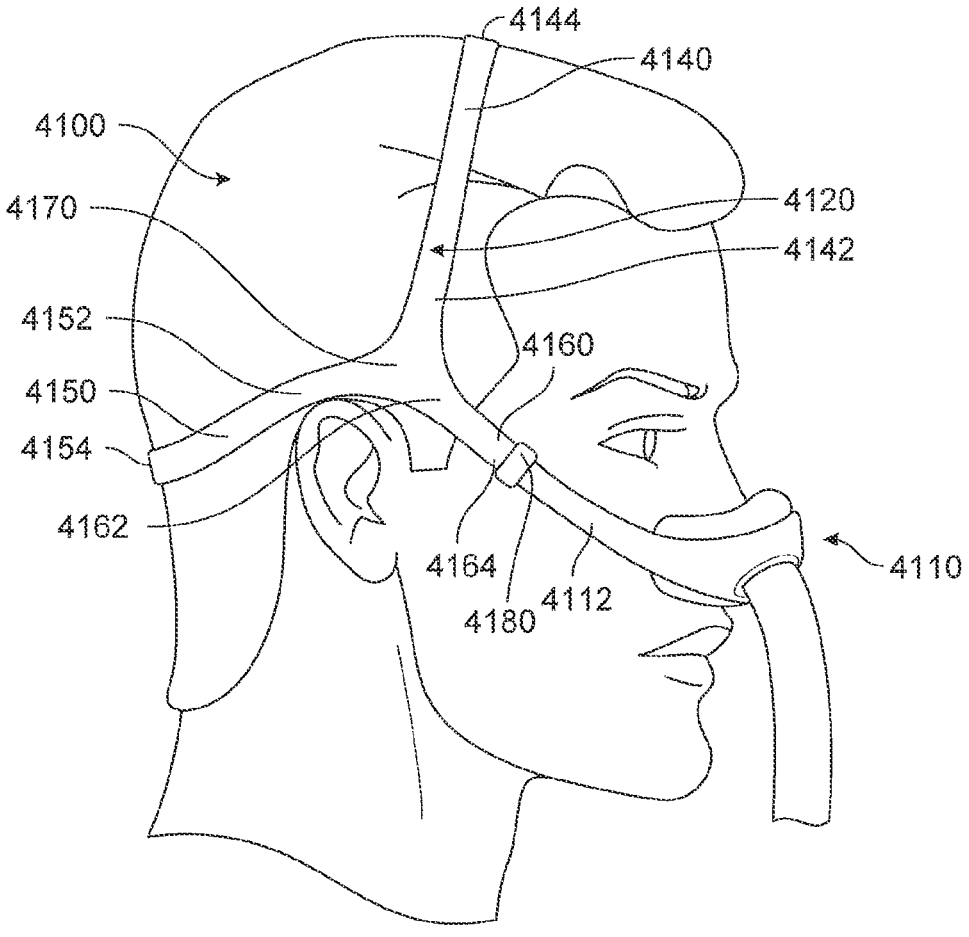
Figure 118B:
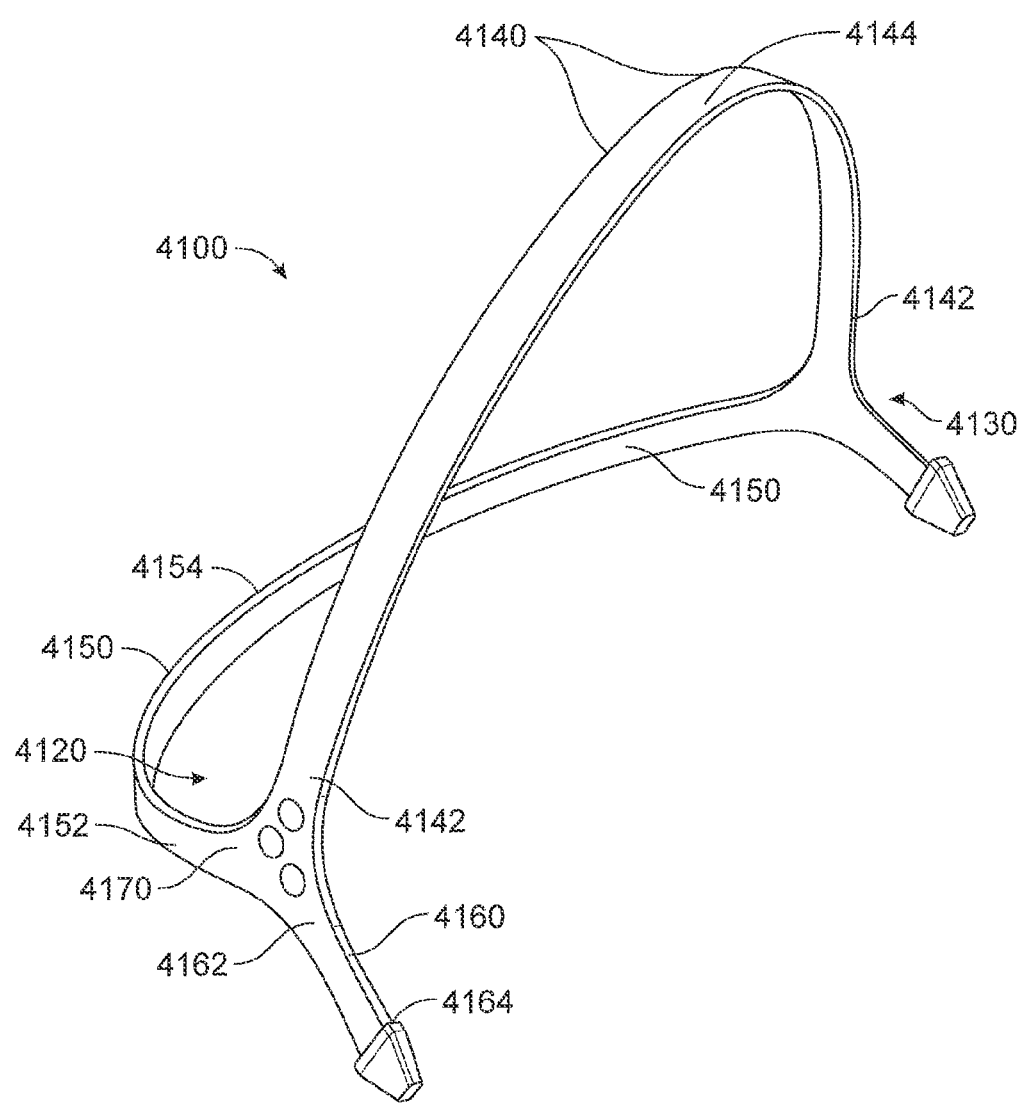

Headgear:

FIG. 118A shows a non-limiting exemplary embodiment of headgear 4100 of the present disclosure in use in combination with a breathing apparatus 4110. FIGS. 118A and 118B show that the headgear 4100 is configured to be substantially inelastic and three dimensional (3D) in structure. As used herein, a three dimensional structure is one that doesn't lie in a single plane, but is shaped to extend in multiple planes. In other words, the three dimensional structure is not flat. The illustrated headgear 4100 comprises a right side 4120 and a left side 4130. Both the right and left sides 4120, 4130 comprise a top strap 4140, a rear strap 4150, a front strap 4160, a yoke 4170, and a connector 4180. The top straps 4140 comprise an elongate member having a top strap lateral end 4142 and a top strap central end 4144. The top strap 4140 is configured to extend upwardly from the lateral end 4142 at a location generally above each ear of the user and over the parietal or frontal region of a user's head before terminating at the top strap central end 4144. The top strap central end 4144 is configured to be positioned at or near a central point or location on the top of the user's head. The top strap central ends 4144 of the right and left sides 4120, 4130 are configured to be joined together. Each top strap lateral end 4142 is configured to directly or indirectly adjoin a yoke 4170.

The rear straps 4150 comprise an elongate member having a rear strap lateral end 4152 and a rear strap central end 4154. The rear strap 4150 is configured to extend rearward from the lateral end 4152 from a location generally above each ear of the user and around the occipital region of the user's head before terminating at the rear strap central end 4154. The rear strap central end 4154 is configured to be positioned at or near a central point or location on the rear of the user's head. The rear strap central ends 4154 of the right and left sides 4120, 4130 are configured to be joined together. Each rear strap lateral end 4152 is configured to directly or indirectly adjoin a yoke 4170.

The front straps 4160 comprise elongate members that are configured to directly or indirectly adjoin the yokes 4170 at a front strap lateral end 4162 and extend forward across the user's temples towards their nose. In some configurations, the front straps 4160 are shorter than one or both of the top straps 4140 or the rear straps 4150 and terminate at a front strap forward end 4164. The front strap forward ends 4164 are configured to comprise, or at least attach to, a connector 4180. The connector 4180 comprises a push fit, snap fit or other suitable connector that is configured to provide a detachable connection to a mask frame 4112 of the breathing apparatus 4110. In some embodiments, the connector 4180 may be configured to connect to an adjustment mechanism, wherein the adjustment mechanism provides a means of automatically or manually adjusting the size of the headgear 4100.

In some configurations, each of the yokes 4170 comprises a relatively triangular section that is configured to provide a lateral junction between the corresponding top straps 4140, rear straps 4150 and front straps 4160. Each of the top, rear and front straps 4140, 4150, 4160 is adjoined directly or indirectly to the yoke 4170 in a continuous manner such that the right and left sides 4120, 4130 are formed as unitary pieces. The thickness and/or shape of the yoke 4170 can be defined to restrict rotational movement about a lateral axis or axis extending in a thickness direction of the yoke 4170 of the top, rear and front straps 4140, 4150, 4160 relative to each other. Such an arrangement can provide the breathing apparatus with greater stability on the user's face.

The right and left sides 4120, 4130 are formed as substantially two dimensional (2D) pieces, i.e., they are formed in a flat structure. When the top straps 4140 and the rear straps 4150 of the right and left sides 4120, 4130 are joined together, a 3D bifurcated structure is formed (as shown in FIG. 118B). The top straps 4140 and the rear straps 4150 may be joined together by any appropriate method known in the art, including but not limited to sewing, welding, over-moulding or a mechanical connection, which can be permanent or removable/disconnectable. In some configurations, the composition of the headgear 4100 is such that the 3D-bifurcated structure is maintained at all times, at least when the right and left sides 4120, 4130 are connected. This 3D structure may improve the ease with which a user interacts with and fits or dons the headgear 4100 and the associated breathing apparatus 4110. Because the headgear 4100 holds its shape, the straps are less likely to get tangled and it should be easier for a user to grasp and orient the headgear 4100. In some configurations, the headgear 4100 at least maintains partial or complete separation of the sides 4120, 4130. In some configurations, the headgear 4100 at least maintains partial or complete separation of the yokes 4170 and/or front straps 4160 of the opposite sides 4120, 4130.

A non-limiting exemplary embodiment of the composition of the headgear 4100 is shown in FIG. 119, which shows a cross-sectional view through any of the top strap 4140, the rear strap 4150 and/or the front strap 4160. In some configurations, the top, rear and front straps 4140, 4150, 4160 have a layered composition comprising a first portion or an inner casing 4200, a second portion or an outer casing 4210, a core 4220, and casing edges 4230. The inner casing 4200 and the outer casing 4210 comprise textile layers, wherein the inner casing is configured to contact the user's head and the outer casing 4210 is not and can be configured to face away from the user's head. The inner and outer casings 4200, 4210 may be made from the same or different textiles and can be configured to provide a soft and, in some embodiments, cushioned covering for the core 4220. However, in at least some preferred embodiments, the core 4220 forms the primary structure of the headgear 4100 and the casings 4200, 4210 are utilized to provide the headgear 4100 with a softer texture, improved moisture wicking properties and/or increased friction with the user's face relative to headgear constructed of the core 4220 without the casings 4200, 4210. Such an arrangement is in contrast to headgear arrangements constructed primarily of an elastic or flexible material that utilize localized rigidising structures.

In some configurations, the core 4220 comprises a relatively rectangular cross-section of a thermoform or thermoset plastic material that is configured to provide the headgear 4100 with the aforementioned 3D structure. The core 4220 provides the foundation for the overall structure of the headgear 4100. The plastic composition of the core 4220 offers the benefits of a resilient structure that is capable of maintaining a preformed shape while conforming somewhat to the individual cranial geometry of the user. The core 4220 has a width W and a depth D, wherein the width W is substantially greater than the depth D. The illustrated cross-sectional geometry in combination with the material selection allows the headgear 4100 to be flexible in a direction that is normal to the width W (the vertical direction in FIG. 119) and relatively inflexible in a direction that is normal to the depth D (the horizontal direction in FIG. 119). This flexibility in one direction allows the headgear 4100 to conform to a user's head while providing rigidity in a direction that stabilizes and minimizes dislodging of the breathing apparatus 4110 on a user's face.

In some configurations, the inner casing 4200 and the outer casing 4210 are configured to be permanently bonded to the core 4220 such that the core 4220 is completely encased and the headgear 4100 is formed from composite material. A casing edge 4230 can be formed where the inner and outer casings 4200, 4210 meet. The inner and outer casings 4200, 4210 are held together in close proximity by their bonds with the core 4220. In some configurations, the inner and outer casings 4200, 4210 are not directly connected to each other at the casing edge 4230. In the embodiment of FIG. 119, the casing edge 4230 is shown to be approximately at a midpoint of the depth D. In some embodiments, the casing edge 4230 may be skewed towards one or other of the inner and outer casings 4200, 4210. In other configurations, the casing edges 4230 can be coupled. In still other configurations, the casing edges 4230 can be separated from one another such that a portion of the core 4220 is left exposed.

The headgear 4100 can be configured to be substantially inelastic as a result of material selection, for example. One or more elements of the composite material may provide the headgear 4100 with substantially inelastic qualities. In the first non-limiting exemplary embodiment of this disclosure, the core 4220 is made from a substantially inelastic material, such as polypropylene or nylon, for example but without limitation. In embodiments where the headgear 4100 is expected to be subjected to low loading forces, the core 4220 may be made of other materials, such as, but not limited to, thermoplastic elastomers (TPE) or silicone. In some embodiments, the core 4220 may have a degree of elasticity and one or both of the inner casing 4200 and/or the outer casing 4210 can be substantially inelastic. The inclusion of a substantially inelastic material in the headgear 4100 is advantageous because the material reduces or eliminates the likelihood of the headgear being stretched or pulled too far over the user's head. If the headgear 4100 is pulled too far over the user's head, the breathing apparatus may not be effectively positioned to provide therapy and uncomfortable forces may be applied to the user's head, which can result in reduced compliance with therapy.

The right and left sides 4120, 4130 can be formed by injection moulding the core 4220 onto a textile material, such as one or both of the inner casing 4200 and/or the outer casing 4230. With such a method, the molten plastic material can be applied onto or put into contact with the textile material and allowed to cool to form an integral structure without the use of adhesives. In some configurations, the right and left sides 4120, 4130 can be formed by injection moulding the core 4220 into a sleeve formed by the inner casing 4200 and the outer casing 4210. The casing edges 4230 can be held together under compression within an injection moulding tool. Such a structure forms a sealed sleeve that allows the plastic material of the core 4220 to be injected into, and to thereby fill, the inside of the sleeve without creating significant flash at the casing edges 4230. In some configurations, the casing edges 4230 may not create a sealed sleeve. In such arrangements, flash can be removed in a post-forming operation as is done with other molded components.

In some embodiments, there may be a textile casing on only one side of the headgear or the inner and outer casings 4200, 4210 may be made from differing materials. This may provide the headgear 4100 with varied physical properties in different regions.

Mould Tool:

FIG. 120 shows a third angle orthographic view of one half of an injection moulding tool 4300 configured to form a strap 4400 (as shown in FIG. 121) that is similar to the front strap 4160 discussed above. A similar tool may be used to form any part of the headgear 4100. The strap 4400 comprises an elongate strap body 4410, a casing retainer 4420 and a connector 4430, wherein the casing retainer 4420 and the connector 4430 are located at one end of the strap body 4410. The strap body 4410 comprises an inner casing 4412, an outer casing 4414, a casing edge 4416 and a plurality of retention holes 4418. The inner and outer casings 4412, 4414 are made from a textile and, in the illustrated arrangement, are configured to substantially enclose and form a sleeve around an internal plastic core (not shown), thus forming the strap 4400 as a composite material structure.

The injection moulding tool 4300 is configured to have an opposing half that is substantially symmetrical about a parting surface 4310. Each half of the injection moulding tool 4300 comprises a sprue 4320, a gate 4325 and a mould cavity 4330. The sprue 4320 comprises a cylindrical recess, which forms the injection location for the tool 4300. The gate 4325 comprises a path through which the plastic material flows from the sprue 4320 into the mould cavity 4330. In some embodiments, the sprue 4320 and the gate 4325 may be provided on only one half of the injection moulding tool 4300. The mould cavity 4330 comprises a core cavity 4340, a casing clamp 4350, a casing slot 4360, and a connector cavity 4370 configured to form the composite material and geometry of the strap portion 4400.

The core cavity 4340 comprises a rectangular recess and, in some configurations, includes one or more retaining pins 4342. In the some embodiments, there are three retaining pins 4342, which comprise cylindrical posts that extend through a portion or the entire depth of the core cavity 4340. In some embodiments, there may be any suitable number of retaining pins 4342, which may have any appropriate cross-sectional geometry. The retaining pins 4342 are configured to form the retention holes 4418 in the strap 4400. The casing clamp 4350 comprises a relatively shallow recess that extends around three edges of the core cavity 4340 and is configured to form the casing edge 4416 of the strap 4400.

The casing clamp 4350 and the core cavity 4340 are terminated at one end by a casing slot 4360. The casing slot 4360 comprises a narrow rectangular slot that is deeper than the core cavity 4340. The casing slot 4360 is configured to have a width that is substantially the same as the combined width of the core cavity 4340 and the casing clamps 4350. The casing slot 4360 forms the casing retainer 4420. The connector cavity 4370 adjoins the casing slot 4360 on an opposite side from the core cavity and comprises a substantially trapezoidal recess. It is configured to be deeper than the core cavity 4340 and forms the connector 4430 of the strap 4400. In the illustrated arrangement, the gate 4325 connects to a central point on the short parallel wall of the connector cavity 4370.

Moulding Process:

A process of moulding the strap component 4400 using the injection moulding tool 4300 comprises the following steps: inserting textile layers that form the inner and outer casings 4410, 4420; closing the tool; injecting plastic; and opening the tool to release part. In some configurations, the steps are accomplished in this order; however, in other configurations the order may be changed and/or additional steps may be included. Such additional steps may be interposed within the above-identified steps.

With the two halves of the injection moulding tool 4300 separated (e.g., open), the pieces of textile that form the inner and outer casings 4412, 4414 are placed inside the mould cavity 4330, as shown in FIG. 122. The inner casing 4412 is placed inside one half of the injection moulding tool 4300 and the outer casing 4414 is placed inside the other half. The inner and outer casings 4412, 4414 can be cut to size such that they fit snugly within the mould cavity 4330. Alternatively, uncut pieces of inner and outer casings 4412, 4414 may be placed in the mould cavity 4330 and then cut by the injection moulding tool 4300 before or after the inner and outer casings 4412, 4414 are joined together.

The inner or outer casing 4412, 4414 can be aligned and secured within the mould cavity 4330 by one or more components of the injection mould tool 4300, including any one or combination of the retaining pins 4342, the casing clamp 4350 and the casing slot 4360. The alignment and securement of the inner and outer casings 4412, 4414 reduces the likelihood of the casings 4412, 4414 moving during injection of the plastic material. Movement of the casings 4412, 4414 during injection of the plastic may result in the strap 4400 being incorrectly formed. The retaining pins 4342 can be configured to at least partially pass through the retainer holes 4418 such that the inner or outer casing 4412, 4414 is properly aligned and held in place against the walls within the mould cavity 4330.

The casing clamp 4350 can be configured to apply a compressive force to one, two or three (or more) edges of the inner and outer casing 4412, 4414 when the injection moulding tool 4300 is shut and when both halves of the injection moulding tool 4300 are together. The recesses can have a depth that is less than the thickness of the textile that forms the inner and/or the outer casings 4412, 4414 such that the casing sits proud of the parting surface 4310, as shown in FIG. 122. When the injection moulding tool 4300 is shut, the depth of the casing clamp 4340 results in the inner and outer casings 4412, 4414 being compressed together, temporarily sealing the edges, and forming the casing edge 4416 and a hollow sleeve-like structure.

The casing slot 4360 can be configured to secure the end of the inner or outer casing 4412, 4414, which is not secured by the casing clamp 4350. The end of the casing 4412, 4414 can be folded at an angle of approximately 90°, such that it ends proximate the deepest part of the casing slot 4360, as shown in FIG. 123. The deep narrow geometry of the casing slot 4360 retains the ends of the inner and outer casings 4412, 4414 in a separated position such that, when the both halves of the injection moulding tool 4300 are in a shut position, there is an opening between the inner and outer casings at the end of the core cavity 4340. This opening between the inner and outer casings 4412, 4414 provides a path through which plastic can be injected into the core cavity to form the core of the strap 4400. Injection through the opening results in the plastic core being formed on the inside of the inner and outer casings 4412, 4414.

Once the inner and outer casings 4412, 4414 are aligned and secured within each half of the injection moulding tool 4300, the tool 4300 is shut such that the mould cavity 4330 becomes fully enclosed and the casing edge 4416 is secured and sealed by compression. Thermoset or thermoform plastic is then injected into the mould cavity 4330 via the sprue 4320 and the gate 4325. Once the plastic has set, the injection moulding tool 4300 can be opened and the strap 4400 can be removed.

In some embodiments, the inner and outer casings 4412, 4414 can be held against the walls of the mould cavity 4330 by other appropriate means, including, but not limited to, temporary adhesives or in mould design (IMD) techniques.

Integrally Moulded Features:

Traditionally, labels, connections, and adjustment features, such as, but not limited to, buckles or buttons, can be formed as separate components that are attached to, or assembled to, a headgear in a secondary process. In some embodiments, the headgear of the present disclosure can include integrally moulded labels and/or connection or adjustment features that are configured to connect the headgear to a breathing apparatus or to adjust the size and/or fit of the headgear. The integral moulding of such features is beneficial in eliminating assembly steps within the manufacturing process and, thus, reducing costs. The integral moulding may also be beneficial in improving the strength of the connection of these features and the headgear.

FIG. 124A shows another non-limiting exemplary embodiment of a headgear 700, wherein the headgear incorporates a button and hole size adjustment system 4710 within the top strap 4720. The size adjustment system 4710 can be similar to the 'snap fit' button and hole adjustment system, commonly used in baseball caps, but is moulded integrally as a part of the headgear 4700. The size adjustment system 4710 comprises an upper strap 4730 having a plurality of holes in it (not visible in FIG. 124A) and a lower strap 4740 having a plurality of buttons 4750 on its upper surface. With respect to features not specifically discussed, the headgear 4700 can be the same as or similar to other headgear disclosed herein, or can be of another suitable arrangement.

As shown in the enlarged cross-sectional view of FIG. 124B, the upper strap 4730 comprises an upper inner casing 4732, an upper outer casing 4734, an upper core 4736 and one or more holes 4738. The buttons 4750 are configured to pass through the holes 4738 in the upper strap 4730 and to secure the upper and lower straps 4730, 4740 together. The lower strap comprises a lower inner casing 4742, a lower outer casing 4744, a lower core 4746 and one or more buttons 4750. The lower outer casing 4744 comprises one or more openings through which the lower core extends to form the one or more buttons 4750. The buttons 4750 comprise a mushroom shaped geometry that includes a head 4752 and stalk 4754. The buttons can have a substantially circular or elliptical profile as shown in FIG. 124A.

FIGS. 125A and 125B show another non-limiting exemplary embodiment of a size adjustment system 4800 that is integrally moulded to a headgear structure. The size adjustment system 4800 comprises a 'snap fit' button 4810 and hole 4820 configuration. There are one or more buttons 4810 that are configured to be over-moulded directly onto a first strap 4830, such that the buttons are permanently bonded to the first strap. These buttons 4810 comprise a mushroom shaped geometry, which is configured to be received and retained within the one or more holes 4820. The holes 4820 comprise a plastic washer on one or both sides of the strap 4840 with a central opening that is configured to receive the buttons 4810. The holes 4820 are configured to be over-moulded through a second strap 4840, such that they are permanently bonded together.

In this embodiment, the first and second straps 4830, 4840 comprise an elongate member that is configured to be made from a single textile material, such as, but not limited to, Breath-o-prene™. This configuration provides greater flex-ibility than the previous embodiment and, depending on material selection, can provide a cushioning element. How-ever, in other configurations, the buttons 4810 and holes 4820 could be provided on a composite strap, such as the plastic/textile straps disclosed herein.

FIGS. 125C-E shows another non-limiting exemplary embodiment of a size adjustment system 9800 that is inte-grally moulded to a headgear structure. The size adjustment system 9800 comprises a 'snap fit' button 9810 and hole 9820 configuration. In contrast to FIGS. 125A and 125B, the hole 9820 is not a through hole and does not extend through the entire thickness of the strap 9840. The button 9810 is configured to be molded into or over-moulded directly onto the first strap 9830, such that the buttons are permanently bonded to the first strap 9830. The button 9810 may com-prise a single elongate button 9810 that extends along the length of the first strap 9830. In FIGS. 125C-E, the button 9810 and the hole 9820 have a trapezoidal cross-sectional shape. However, the button 9810 and the hole 9820 may have any suitable shape to provide a releasable interference or snap-fit connection. In operation, the button 9810 is inserted into the hole 9820 to releasably connect the first strap 9830 and the second strap 9840.

FIGS. 125F-I shows another non-limiting exemplary embodiment of a size adjustment system 9900 that is inte-grally moulded to a headgear structure. The size adjustment system 9900 comprises a 'snap fit' button 9910 and hole 9920 configuration. The button 9910 is configured to be molded into or over-moulded directly onto the first strap 9930, such that the buttons are permanently bonded to the first strap 9930. The button 9910 may comprise a single elongate button 9910 that extends along the length of the first strap 9930. Similar to the size adjustment system 9800 in FIGS. 125C-E, the hole 9920 is not a through hole and does not extend through the entire thickness of the second trap 9940. However, in contrast to the size adjustment system 9800, the button 9910 has an interlocking hexagonal shape along the length of the first strap 9930. The hexagonal button 9910 prevents translational movement between first strap 9930 and the second strap 9940.

This approach of moulding various plastic features to a textile base can be applied to breathing apparatus compo-nents other than headgear. For example, FIG. 126 shows that textile cushioning pads 4900 may be attached to a substan-tially rigid mask frame 4910 via over-moulded buttons 4920, wherein the over-moulded buttons 4920 are the same as or similar to the buttons 4750, 4810 described in the previous embodiments. In yet another embodiment, a similar con-figuration can be used to provide a connection between two breathing apparatus components, such as, but not limited to, a flexible headgear 5000 and a substantially rigid mask frame 5010, as shown in FIGS. 127A and 127B.

FIG. 128 shows a headgear component 5100 comprising a textile strap 5110, a grip 5120 and two buckles 5130. The headgear component 5100 is configured to form a substan-tially non-slip rear portion of a headgear assembly. The textile strap 5110 comprises an elongate body that can be made of any suitable textile, including, but not limited to, micro-fiber fabrics. The grip 5120 comprises a raised sili-cone, TPE or thermoplastic polyurethane (TPU) bead that substantially follows an outline of the textile strap 5110. The grip 5120 is configured to provide a non-slip surface that, in use, grips the user's head or hair, such that the headgear is stable and less likely to slip down and displace the respira-tory mask. In some embodiments, a grip bead, such as this may be applied to other regions of a headgear assembly.

The grip 5120 may be applied to the textile strap by a moulding process similar to the one described in relation to the previous embodiments. FIG. 129 shows a cross-section schematic view of a mould tool 5200 configured to form the headgear component 5100. The mould tool 5200 comprises a first tool half 5210 and second tool half 5220. The first tool half 5210 comprises a strap insert 5212 and a grip cavity 5214. The second tool half comprises a strap cavity 5222. The strap cavity 5222 is configured to receive the textile strap 5110. In some configurations, the textile strap 5110 is cut to fit exactly within the strap cavity 5222, such that it is easily aligned within the open mould tool 5200. The strap cavity is also configured to receive the strap insert 5212, which has corresponding geometry. The strap insert 5212 is configured to apply a compression force to the textile strap 5110 during moulding, such that the textile strap is held in place and will not move when the material of the grip 5120 is injected. When the mould tool 5200 is in a closed position and the textile strap 5110 is secured in place, the material of the grip 5120 can be injected into the grip cavity 5214, via a gate and runner system (not shown), which in some configurations can be the same as or similar to that of FIG. 120. The grip cavity 5214 is configured to form the geometry of the grip 5120 onto the textile strap 5110. Injection moulding the grip 5120 directly onto the textile strap 5110 forms a chemical and/or mechanical bond between them.

FIGS. 130 and 131 illustrate a strap 5300, which can be substantially similar to or the same as other straps disclosed herein, such as straps 4140, 4150, 4160, 4400, 4720, 4720, 4730, 4830, 4840. Similar to the arrangement illustrated in FIG. 119, the strap 5300 comprises an inner casing 5302, an outer casing 5304, a core 5306, and casing edges 5308. The inner casing 5302 and the outer casing 5304 comprise textile layers, wherein the inner casing 5302 is configured to face toward and/or contact the user's head and the outer casing 5304 is not. In the illustrated arrangement, the outer casing 5304 faces away from and/or doesn't contact the user's head.

However, in the illustrated arrangement, the strap 5300 comprises an interruption in the core 5306 along a length of the strap 5300. The interruption can form a flexible joint 5310 between two portions of the strap 5300. In some configurations, the flexible joint 5310 is formed in whole or in part by the inner casing 5302 and the outer casing 5304. Within the joint 5310, the casings 5302, 5304 can be secured to one another, such as with an adhesive, sewing, welding, or other suitable arrangements. In other configurations, the casings 5302, 5304 can be left separate within the joint 5310.

The core 5306 can be divided into two portions, each of which defines an end surface 5312 that face one another and are separated by a distance 5314. In some configurations, the distance 5314 is sufficient to allow the strap 5300 to fold to at least some extent at the location of the flexible joint 5310. In some configurations, the distance 5314 is sufficient to allow the strap 5300 to substantially fold in half at the joint 5310 such that the portions of the strap 5300 on each side of the joint 5310 are positioned one on top of the other. Such an arrangement can allow the strap 5300 to fold for storage or packaging. In some configurations, multiple straps 5300 of a headgear arrangement (e.g., top and rear straps) can include a flexible joint 5310 such that the entire headgear can collapse or fold in half for storage or packaging.

Preferably, however, the distance 5314 is not so great that the rigidity or the ability of the strap 5300 or associated headgear to accommodate external forces is compromised. In some configurations, the distance 5314 is no more than a small portion of an overall length of the strap 5300. In some configurations, the distance 5314 is equal to or less than 50 mm, 40 mm, 30 mm, 20 mm or 10 mm.

The joint 5310 can be located along the strap 5300 such that the flexible or foldable portion of the strap 5300 is located as desired within the overall form of the associated headgear. For example, the joint 5310 can be located within the strap 5300 such that the joint 5310 is located at or near a midline of the headgear in a lateral direction. Such an arrangement can allow the headgear to fold in half, as described above. In other configurations, the joint 5310 can be located elsewhere along the strap 5300 to provide flexibility in other locations.

FIGS. 132 and 133 illustrate another strap 5300 having a flexible joint 5310. The strap 5300 can be substantially similar to or the same as the strap 5300 of FIGS. 130 and 131. However, the strap 5300 of FIGS. 132 and 133 includes connecting structures that connect the portions of the core 5306 on opposing sides of the joint 5310. In the illustrated arrangement, the connecting structure comprises a bridge portion 5320 extending between and connecting the portions of the core 5306 on opposing sides of the joint 5310. Any suitable number of bridge portions 5320 can be provided. In the illustrated arrangement, a pair of spaced-apart bridge portions 5320 is provided. The bridge portions 5320 are spaced inwardly from lateral edges of the core 5306; however, in other configurations, the lateral edges of the bridge portions 5320 can be aligned with the lateral edges of the core 5306.

The bridge portions 5320 preferably are configured to retain the flexible nature of the joint 5310 in at least one direction (e.g., bending in the thickness direction). Thus, the bridge portions 5320 can be constructed to provide a living hinge. However, the bridge portions 5320 can provide additional rigidity or support to the joint 5310, at least relative to the casing(s) 5302, 5304 alone, in other directions. For example, the bridge portion(s) 5320 can resist bending in the width direction, can resist lengthwise extension or compression and can resist twisting about a lengthwise axis.

In some configurations, the bridge portion(s) 5320 are constructed from the same material as the core 5306. The bridge portion(s) 5320 can be coupled to or unitarily-formed with the portions of the core 5306. In the illustrated arrangement, the bridge portions 5320 are unitarily-formed with the portions of the core 5306 and have a thickness 5322 that is less than a thickness 5324 of the portions of the core 5306. In some configurations, the thickness 5322 of the bridge portion(s) 5320 is less than one-half or less than one-third of the thickness 5324 of the core 5306. Other proportions are also possible and the thicknesses 5322, 5324 of the bridge portion(s) 5320 and core 5306 can be selected to provide traits desirable for the intended use.

In the illustrated arrangement, the bridge portions 5320 are elongate, linear structures extending substantially along or parallel to a longitudinal axis of the strap 5300. However, the bridge portion(s) 5320 could be angled relative to the longitudinal axis of the strap 5300. In some configurations, the bridge portion(s) 5320 are non-linear in shape.

FIGS. 130-133 illustrate additional assemblies, tools and related methods for constructing the straps and associated headgear disclosed herein. In particular, the arrangements of FIGS. 130-133 are configured to assist in locating and/or maintaining the fabric casings in position within the mould prior to formation of the core. In other respects, the moulding tools of FIGS. 130-133 can be similar to or the same as the moulding tool 5400 disclosed herein. In addition to the arrangements disclosed herein, other suitable arrangements or methods for securing the fabric casings within the mould can also be used.

With reference to FIG. 130, a moulding tool 5400 is configured to form a strap and/or associated headgear, such as any of those disclosed herein. Preferably, one or more fabric casings are positioned within the moulding tool 5400 and then the core is formed adjacent to or between the fabric casings. The moulding tool 5400 is configured to secure the fabric casing(s) within the tool 5400 prior to formation of the core by utilizing an electrostatic force. Any suitable arrangement can be used to create an electrostatic charge within the fabric casing and/or the moulding tool 5400 suitable to attract the casing to the tool 5400. For example, the fabric casings and/or the moulding tool 5400 can be treated to create an electrostatic charge.

In some configurations, the moulding tool 5400 includes a first mould portion or half 5402 and a second mould portion or half 5404, each of which define a portion of a mould cavity 5406. The mould portions 5402, 5404 have mating surfaces that can be brought together and can be separated to close and open the mould cavity 5406. The illustrated moulding tool 5400 also comprises a static charging system 5410 comprising a charging generator 5412 and a charging applicator 5414. The charging generator 5412 is configured to create a static electrical charge, which can be applied to an object by the charging applicator 5414. The static charging system 5410 can be associated with the moulding tool 5400 or can be configured to apply a charge to the casings 5416 prior to the casings 5416 being positioned in the moulding tool 5400. If the static charging system 5410 is associated with the moulding tool 5400, the portions 5402, 5404 of the moulding tool 5400 can include an insulator 5418 to inhibit or prevent rapid dissipation of the charge applied thereto. Static charging systems suitable for industrial use can be employed, such as those manufactured by Simco-Ion of Hatfield, Pennsylvania, for example.

With reference to FIG. 131, air pressure systems can be utilized to retain the casings within a moulding tool 5400. For example, an air pressure system can be configured to create a pressure differential between sides of the casing thereby creating a force tending to retain casing against a surface of the moulding tool 5400. The illustrated air pressure system 5420 is a vacuum system comprising a vacuum source 5422 connected to one or more vacuum ports 5424 in the moulding tool 5400 by suitable conduits 5426. However, in other configurations, positive pressure could be used to press the casings against a surface of the moulding tool 5400 at least until the mould portions 5402, 5404 close, at which point the casings can be pinched between the mould portions 5402, 5404.

In some configurations, the vacuum source 5422 comprises a pump that moves air from the vacuum ports 5424 toward the vacuum source 5422 through the conduits 5426. When positioned in the mould portions 5402, 5404, the casings block the vacuum ports 5424 to prevent or substantially impede the passage of air into the vacuum ports 5424. As a result, a vacuum or relative low pressure condition is created in the vacuum ports 5424 thereby holding the casings in place within the moulding tool 5400. Any suitable number of vacuum ports 5424 can be provided. For example, while multiple ports 5424 are illustrated in each mould portion 5402, 5404, in some configurations a single vacuum port 5424 can be provided in each mould portion 5402, 5404 into which a casing is to be placed prior to the moulding process.

With reference to FIG. 132, the casings 5416 can be secured within the moulding tool 5400 by a component 5430. For example, the component 5430 can mechanically secure the casing 5416 within the moulding tool 5400. One or more components (e.g., a pair of components 5430) can be utilized in each mould portion 5402, 5404 into which a casing 5416 is to be placed prior to the moulding process to retain the casing 5416 in place within the mould portion 5402, 5404. For example, in the illustrated arrangement, a first component 5430a can be utilized to secure the casing 5416 within the mould portion 5402, 5404 at a first location (e.g., a first end) and a second component 5430b can be utilized to secure the casing 5416 within the mould portion 5402, 5404 at a second location (e.g., a second end) spaced from the first location.

The component 5430 can be received within a receiving portion or retaining portion, such as a receptacle or cavity 5432, of the mould portion 5402, 5404. The cavity 5432 or other receiving portion can be configured to receive the component 5430 and a portion of the casing 5416 such that a portion of the casing 5416 is positioned or pinched between the component 5430 and a surface of the mould portion 5402, 5404. With such an arrangement, the component 5430 and the cavity 5432 can cooperate to form a structure similar to the casing slot 4360 shown in FIG. 123 and can secure the casing 5416 within the mould portion 5402, 5404 in a manner similar to that shown and described with reference to FIG. 123. In an alternative arrangement, the component(s) 5430 can be secured to the casing 5416 prior to the casing 5416 being positioned within the mould portion 5402, 5404. The combination of the component(s) 5430 and the casing 5416 can be secured within the mould portion 5402, 5404 by positioning the component(s) 5430 within the cavity 5432 or other receiving portion.

The component 5430 can have a relatively tight fit within the associated cavity 5432 or other receiving portion, along with the portion of the casing 5416, such that frictional forces retain the component(s) 5430 and, thus, the casing 5416 in place within the mould portion 5402, 5404. In some configurations, the component 5430 can have a slight interference fit with the associated cavity 5432 in one or more directions. Other suitable arrangements for securing the component 5430 at a desired location within the mould portion 5402, 5404 with enough retention force to retain the casing 5416 in place during the moulding process can be used.

The component 5430 can be any structure suitable for securing the casing 5416 within the mould portion 5402, 5404. The component 5430 can form a portion of the resulting strap or associated headgear. For example, the component 5430 can comprise a portion or an entirety of a connector and/or casing retainer, which can be the same as or similar to the connector 4430 and/or casing retainer 4420 shown and described in connection with FIG. 121. In such arrangements, the component(s) 5430 can be configured to fuse with the injected plastic that forms the core of the strap or headgear. Alternatively, the component 5430 can be a sacrificial component, which does not form a part of the final strap or headgear. In such arrangements, the component 5430 can comprise a material or can be coated or otherwise treated with a material that does not fuse with the injected plastic. Accordingly, once the strap or headgear is formed, the component(s) 5430 can be discarded. In some configurations, the component 5430 can comprise a material that breaks down when the plastic is introduced into the moulding tool 5400 such that the injected plastic fills a space that was occupied by the component 5430. In such an arrangement, vents may be provided to permit venting of the broken down material of the component 5430.

With reference to FIG. 137, in some configurations the casings 5416 can be supported external of the cavities 5406 of the moulding tool 5400. In the illustrated arrangement, a bulk of material that forms the casings 5416 is supported for feeding into the mould portions 5402, 5404. The bulk of material can be, for example, a spool or roll 5440 of material that forms the casings 5416, which can be supported at one end of the moulding tool 5400. A loose or free end 5442 of the material or casing 5416 can be manually, automatically or otherwise passed through the space between the mould portions 5402, 5404 to the opposite end of the moulding tool 5400. Accordingly, a length of the material or casing 5416 is located adjacent to the moulding cavity 5406 of one or both of the moulding portions 5402, 5404. Once passed through the moulding tool 5400, the casings 5416 can be manually, automatically or otherwise positioned into the cavities 5406 of the mould portions 5402, 5404. For example, the operator can manually push the casings 5416 into the corners of the cavities 5406 or otherwise properly position the casings 5416 within the mould portions 5402, 5404. Once properly positioned, the plastic material can be injected onto the casing(s) 5416 within the moulding tool 5400. After the moulding process, excess material of the casing(s) 5416 can be trimmed.

In some configurations, the free ends 5442 of the casings 5416 can be secured relative to the mould portions 5402, 5404. For example, the free ends 5442 of the casings 5416 can be clipped or otherwise retained against or relative to the mould portions 5402, 5404 by clips or other suitable retention arrangements 5444 at locations outside of the cavities 5406 and away from the mating surfaces of the mould portions 5402, 5404. In other configurations, the free ends 5442 of the casings 5416 can be retained within the moulding tool 5400, such as within retention slots or utilizing retention holes in the casings 5416, for example. In some configurations, the rolls 5440 can provide some resistance to rotation to assist in keeping the casings 5416 relatively taut. If desired, tensioning rollers 5446 can be employed to assist in maintaining tension in the casings 5416.

FIGS. 138-157B illustrate several headgear configurations, which can be similar to other headgear disclosed herein and can by suitable for the same or similar applications. The headgear of FIGS. 138-157B can be connected to an interface by any suitable coupling arrangement, such as any of those disclosed herein. The headgear can be modified for used with other types of interfaces, such as those employing a forehead rest, for example. Accordingly, although the illustrated headgear has a single connection location on each side, other variations could include a pair of connection locations on each side. Other arrangements are also possible, such as a central, overhead strap, for example. In addition, features, components, materials or manufacturing methods of the headgear of FIGS. 138-157B can be interchanged with one another to create other headgear variations beyond those specifically disclosed. The illustrated headgears each comprise several straps, including a crown or top strap, a rear strap and a pair of front straps. Other variations can omit one or more of these straps and/or can include additional straps. Any of the straps can incorporate length or other adjustment mechanisms, as desired, including any of the adjustment mechanisms disclosed herein or other suitable arrangements.

FIGS. 138-140 illustrate a headgear 5500 have a first headgear portion or strap 5502 (a section of which is shown separately in FIG. 139B) and a second headgear portion or strap 5504 (a section of which is shown separately in FIG. 139A). The first strap 5502 can define a top strap or crown strap portion 5506 and the second strap 5504 can define a rear strap portion 5508. In the illustrated arrangement, the first strap 5502 and/or the second strap 5504 also define other portions of the headgear 5500. For example, the first strap 5502 also forms a portion of the rear strap portion 5508, such that the rear strap portion 5508 includes portions of both the first strap 5502 and the second strap 5504. In addition, the second strap 5504 defines front strap portions 5510 of the headgear 5500.

In some configurations, one or both of the first strap 5502 and the second strap 5504 have a composite structure. In the illustrated arrangement, each of the first strap 5502 and the second strap 5504 comprises a core 5512 and a cover layer 5514. The core 5512 can form a primarily structural element of the headgear 5500. In some configurations, the core 5512 can be constructed of a relatively rigid material, such as an injection-moulded or extruded plastic material. The cover layer 5514 can provide desirable characteristics for external surfaces of the headgear 5500. For example, the cover layer 5514 can be configured or selected to provide comfort for the user. In some configurations, the cover layer 5514 is a fabric or textile material. The cover layer 5514 surrounds a portion or an entirety of a periphery of the core 5512. An inelastic headgear can be desirable from a technical or performance standpoint because the headgear can retain an adjusted size (not stretch) in response to blow-off forces applied to the headgear by the mask. However, some elasticity may be desirable from a standpoint of user perception. In other words, a user may prefer a headgear that has some elasticity because the user perceives such a headgear as more comfortable. Thus, one or both of the core and cover layer in any of the headgear or portions thereof disclosed herein can be provided with some amount of elasticity or ability to stretch, such as in response to forces experienced during use and/or forces that could be manually applied by a user in evaluating the headgear or portions thereof. Furthermore, the cross-sectional dimensions (or other dimensions) of the headgear, straps or other headgear portions disclosed herein can be varied along a length of the headgear, strap or other portion. Such variations can be used to tune the performance of the headgear at particular locations or within particular sections. For example, regions around the user's ear may benefit from some additional structure, thus may be wider or thicker in order to provide the desired structure. In some configurations, it is preferable for the headgear to be wider at or around the user's ear, as increased thickness may lead to pressure points. Long strap lengths (e.g., along the top or rear of the user's head) typically need only be inelastic (or less elastic), but don't necessarily need to be rigid (e.g., could be flexible). Accordingly, these straps or strap portions may be thinner and/or narrower than other portions of the headgear. In other words, a width and/or thickness of a headgear, strap or strap portion can be tuned to customize stretch/elasticity and resistance to bending (i.e., rigidity). Additionally, the strap width may be increased towards the middle of the top or rear of the head. Such a configuration may be perceived as being more stable, yet allowing for narrow sections near, for example, the ears.

In the illustrated arrangement, the core 5512 of the first strap 5502 is plastic and the cover layer 5514 is a stretch fabric, as illustrated in FIG. 140A, which provides the first strap 5502 with a visually and/or physically lighter structure. The material of the cover layer 5514 can be formed into a tubular structure by joining opposing edges of the material, such as by sewing or otherwise, to form a seam 5516. The seam 5516 can be positioned on any desired surface portion of the first strap 5502, such as along either side (width direction) or either end (thickness direction). In the illustrated arrangement, the seam 5516 is positioned on the user-facing or inner surface of the first strap 5502.

The core 5512 of the illustrated second strap 5504 is plastic and the cover layer 5514 is a knitted material formed into a tubular structure, as shown in FIG. 140B. Because the cover layer 5514 of the second strap 5504 is knitted, the cover layer 5514 does not have a seam. In other configurations, the cover layers 5514 can be reversed between the first strap 5502 and the second strap 5504, the cover layers 5514 could be the same material on each of the first strap 5502 and the second strap 5504, or different materials could be used.

The cover layers 5514 of each of the first strap 5502 and the second strap 5504 can be formed separately from the cores 5512 and can be assembled onto the cores 5512, such as by sliding the cover layer 5514 onto the core 5512. In some configurations, the cover layers 5514 can be loosely received on the cores 5512. In other words, the cover layers 5514 may not be affixed to the cores 5512 such that some relative movement is permitted between the cover layer 5514 and the respective core 5512. Such an arrangement may provide increased comfort. However, if desired, the cover layers 5514 could be affixed to the cores 5512, such as by an adhesive, for example.

In some configurations, the first strap 5502 and the second strap 5504 are joined to one another along a portion or an entirety of the rear strap portion 5508. In the illustrated arrangement, the first strap 5502 and the second strap 5504 are joined along a substantial entirety of the rear strap portion 5508. The first strap 5502 and the second strap 5504 separate at a junction between the top strap portion 5506, the rear strap portion 5508 and the front strap portions 5510. The first strap 5502 and the second strap 5504 can be secured to one another by any suitable arrangement, such as by a sewn joint or adhesive joint between the cover layers 5514 of the first strap 5502 and the second strap 5504. In the illustrated arrangement, the first strap 5502 is located inwardly of the second strap 5504 in the rear strap portion 5508 such that the first strap 5502 is closer to the user than the second strap 5504 in use. Thus, the first strap 5502 can define a portion or an entirety of a user-contacting surface of the rear strap portion 5508. In the illustrated arrangement, because the first strap 5502 also defines the top strap portion 5506, the first strap 5502 defines a user-contacting surface of both the top strap portion 5506 and the rear strap portion 5508 of the headgear 5500. However, this arrangement could also be reversed such that the second strap 5504 is positioned inwardly of the first strap 5502 in the rear strap portion 5508. In such an arrangement, the first strap 5502 can form a portion of a user-contacting surface of the headgear 5500 (e.g., the top strap portion 5506) and the second strap 5504 can form a portion of a user-contacting surface of the headgear 5500 (e.g., the rear strap portion 5508).

In some configurations, the first strap 5502 and the second strap 5504 can have a different color from one another. For example, in the illustrated arrangement, the first strap 5502 is a lighter color and the second strap 5504 is a darker color; however, this arrangement could also be reversed. The different colors between the first strap 5502 and the second strap 5504 can assist a user in orienting the headgear 5500. For example, the lighter (or darker) color of the first strap 5502 can indicate the user-contacting surfaces of the headgear 5500 to the user in those constructions in which the first strap 5502 is positioned inwardly of the second strap 5504 in the rear strap portion 5508. If the second strap 5504 is positioned inwardly of the first strap 5502 in the rear strap portion 5508, the lighter and darker colors can allow the user to differentiate between the top strap portion 5506 and the rear strap portion 5508, or vice versa. Similarly, different materials or textures can be useful, alone or in combination with different colors, to assist a user in distinguishing between different surfaces (e.g., inward-facing and outward-facing) or different portions (e.g., top strap portion 5506 and rear strap portions 5508) of the headgear 5500.

The first strap 5502 and the second strap 5504 can have different dimensions from one another. In the illustrated arrangement, the first strap 5502 has a width 5520 that is different than the width 5522 of the second strap 5504. In particular, the width 5520 of the first strap 5502 is less than the width 5522 of the second strap 5504. In some configurations, the width 5522 of the second strap 5504 is between 1.5-2 times the width 5520 of the first strap 5502. However, other relative proportions can also be used. The arrangement could also be reversed such that the first strap 5502 is wider than the second strap 5504.

The first strap 5502 can define a thickness 5524 and the second strap 5504 can define a thickness 5526. In some configurations, the thickness 5524 and the thickness 5526 can be the same or substantially the same. However, in other configurations, the thickness 5524 and the thickness 5526 can be different from one another. The dimensions of headgear straps discussed herein (including, but not limited to straps 5502, 5504) can include or omit the cover layers 5514. That is, in at least some configurations, the core 5512 is responsible for a majority or substantial entirety of the structural performance (e.g., load carrying capability) of the headgear 5500. Therefore, in order to compare performance properties between various configurations disclosed herein, the width and height dimensions can be taken at the core 5512. However, in other configurations, the focus may be on comfort or fit, to which the cover layers 5514 may make substantial contributions. Or, in some configurations, the cover layers 5514 can be relatively thick and can make up a significant portion of the overall width or thickness of the strap 5502, 5504. Under these or similar circumstances, the width and height dimensions can include the cover layer 5514.

In the illustrated configuration, the width 5520 of the first strap 5502 is between 4 mm-8 mm. For the sake of comparison with other straps and headgear portions disclosed herein, or other headgear configurations generally, such a strap width can be categorized as very narrow. In the illustrated configuration, the width 5522 of the second strap 5504 is between 8 mm-12 mm. Such a strap width can be categorized as narrow. In the illustrated configuration, the thickness 5524 of the first strap 5502 and the thickness 5526 of the second strap 5504 are between 1 mm-2 mm. Such strap thicknesses can be categorized as thin. The overall construction of the headgear 5500, including the thicknesses 5524 and 5526, provides flexibility of the headgear 5500 that can be characterized as very high for the purpose of comparison to other headgear configurations disclosed herein, or other headgear configurations generally.

FIGS. 139C, 139D and 139E illustrate alternative arrangements for either one of the straps 5502, 5504. The arrangement of FIG. 139C illustrates a core 5512 having a relatively narrow channel or recess 5540 extending in a lengthwise direction and configured to receive the seam 5516 and/or edges of the cover layer 5514. As a result, the outer surface of the portion of the strap containing the seam 5516 can be relatively smooth or flat. In other words, the seam 5516 can be positioned within the recess 5540 and may not protrude outwardly or create a bump relative to adjacent or surrounding portions of the cover layer 5514 or strap. The recess 5540 can also function as an alignment feature for the cover layer 5514 relative to the core 5512. That is, the recess 5540 and seam 5516 can be aligned with one another to properly align the cover layer 5514 with the core 5512. In some configurations, such alignment can permit other features of the cover layer 5514 to also be properly aligned with the core 5512. The recess 5540 is illustrated on a width-defining surface (side) of the core 5512, but could be placed on thickness-defining surfaces (edge) or transitions therebetween in other configurations.

FIG. 139D illustrates a strap in which the core 5512 comprises one or more relatively large recesses 5542 or concave portions that accommodate the seam 5516 and limit or prevent the formation of a bump by the seam 5516. The illustrated core 5512 includes a recess 5542 defined on each side surface of the core 5512; however, the upper and/or lower edges could define concavities in addition or in the alternative. In the illustrated arrangement, the recesses 5542 occupy a relatively large portion of the side surfaces of the core 5512. In other words, the recesses 5542 extend along a substantial portion of a width of the core 5512. The recesses 5542 are illustrated as a gradual reduction in thickness of the core 5512 from the edges toward the center. However, in other configurations, the reduction in thickness can be more abrupt. The thicker upper and lower portions of the core 5512 provide for inelastic performance. The reduced thickness center can provide more flexibility for bending about an axis aligned with the width direction.

FIG. 139E illustrates a strap in which the seam 5516 is folded over or bent such that the seam 5516 contacts or is adjacent to the side surface (width direction) of the strap 5504. The headgear may be arranged such that the side of the strap 5504 having the seam 5516 is positioned away from the user. The seam 5516 may be positioned towards the middle of the strap 5504 and away from the rounded edges to position the seam 5516 away from areas of concentrated stress.

FIGS. 141-143 illustrate another configuration of a headgear 5600 having a first headgear portion or strap 5602 (a section of which is shown separately in FIG. 142A) and a second headgear portion or strap 5604 (a section of which is shown separately in FIG. 142B). The first strap 5602 can define a top strap or crown strap portion 5606 and the second strap 5604 can define a rear strap portion 5608. In the illustrated arrangement, the first strap 5602 and/or the second strap 5604 also define other portions of the headgear 5600. For example, the first strap 5602 and the second strap 5604 cooperate to define front strap portions 5610 of the headgear 5600. In the illustrated arrangement, the first strap 5602 is positioned above the second strap 5604 within the front strap portions 5610 such that a width of the front strap portions 5610 is equal to the combined widths of the first strap 5602 and the second strap 5604. The first strap 5602 and the second strap 5604 can be joined to one another within the front strap portions 5610 by any suitable arrangement, such as a by a sewn joint, adhesive joint or an over-moulded joint, for example.

The illustrated first strap 5602 and second strap 5604 comprise a composite structure having a core 5612 and a cover layer 5614. In some configurations, the core 5612 is constructed of a relatively rigid material, such as an injection-moulded plastic material. In some configurations, the cover layer 5614 is a fabric or textile material. The cover layer 5614 surrounds a portion or an entirety of a periphery of the core 5612.

In the illustrated arrangement, the core 5612 of the first strap 5602 is plastic and the cover layer 5614 is a ribbed textile material, as illustrated in FIG. 143A, which provides the first strap 5602 with tactile differentiation relative to the second strap 5604. The material of the cover layer 5614 can be formed into a tubular structure by joining opposing edges of the material, such as by sewing or otherwise, to form a seam 5616. The seam 5616 can be positioned on any desired surface portion of the first strap 5602, such as along either side (width direction) or either end (thickness direction). In the illustrated arrangement, the scam 5616 is positioned on the user-facing or inner surface of the first strap 5602.

The core 5612 of the illustrated second strap 5604 is plastic and the cover layer 5614 is a knitted material formed into a tubular structure, as shown in FIG. 143B. Because the cover layer 5614 of the second strap 5604 is knitted, the cover layer 5614 does not have a seam. In other configurations, the cover layers 5614 can be reversed between the first strap 5602 and the second strap 5604, the cover layers 5614 could be the same material on each of the first strap 5602 and the second strap 5604, or different materials could be used.

In the illustrated arrangement, the straps 5602, 5604 are formed by introducing molten plastic material into the cover layers 5614 and allowing the molten plastic material to cool to form the cores 5612 in accordance with any of the processes disclosed herein. As illustrated in FIG. 142A, the seam 5616 can be embedded in the core 5612. As a result, the seam 5616 is relatively flat or smooth relative to surrounding portions of the strap 5602. That is, the shape of the mold defines the overall shape of the strap 5602 and the seam 5616 does not protrude outwardly, unlike the seam 5516 of FIG. 139B. The seam 5616 may be visible. However, a patterned, textured, or soft/fluffy textile is used as the cover layer 5614, the seam 5616 may be obscured or may not be visible. Alternatively, the cover layers 5614 of each of the first strap 5602 and the second strap 5604 can be formed separately from the cores 5612 and can be assembled onto the cores 5612, such as by sliding the cover layer 5614 onto the core 5612. In some configurations, the cover layers 5614 may not be affixed to the cores 5612 such that some relative movement is permitted between the cover layer 5614 and the respective core 5612. However, if desired, the cover layers 5614 could be affixed to the cores 5612, such as by an adhesive, for example.

As described, the cover layers 5614 of the first strap 5602 and the second strap 5604 can have different textures to allow for differentiation of the straps 5602, 5604 from one another. In addition, the first strap 5602 and the second strap 5604 can have different colors to allow for differentiation between the straps 5602, 5604. If desired, inward-facing and outward-facing surfaces of the headgear 5600 can have different colors and/or textures to allow for differentiation between inward-facing and outward-facing surfaces.

In the illustrated arrangement, the first strap 5602 and the second strap 5604 have the same or substantially the same cross-sectional dimensions as one another. In the illustrated arrangement, the first strap 5602 has a width 5620 that is equal or substantially equal to the width 5622 of the second strap 5604. However, in other arrangements, the cross-sectional dimensions of the straps 5602, 5604 can be different from one another. The first strap 5602 can define a thickness 5624 and the second strap 5604 can define a thickness 5626. In some configurations, the thickness 5624 and the thickness 5626 can be the same or substantially the same. However, in other configurations, the thickness 5624 and the thickness 5626 can be different from one another.

In the illustrated configuration, the width 5620 of the first strap 5602 is between 4 mm-8 mm, or vary narrow. In the illustrated configuration, the width 5622 of the second strap 5604 is also between 4 mm-8 mm, or vary narrow. In the illustrated configuration, the thickness 5624 of the first strap 5602 and the thickness 5626 of the second strap 5604 are between 1 mm-2 mm. Such strap thicknesses can be categorized as thin. The overall construction of the headgear 5600, including the thicknesses 5624 and 5626, provides flexibility of the headgear 5600 that can be characterized as high for the purpose of comparison to other headgear configurations disclosed herein, or other headgear configurations generally.

FIGS. 144-146B illustrate another configuration of a headgear 5700 having a top strap or crown strap portion 5706, a rear strap portion 5708 and a pair of front strap portions 5710. The headgear 5700 can comprise a composite structure having a core 5712 and a cover, which comprises an inner cover layer 5714*a* and an outer cover layer 5714*b*. In some configurations, the core 5712 is constructed of a relatively rigid material, such as an injection-moulded plastic material. In some configurations, the cover layers 5714*a*, 5714*b* are constructed from a fabric or textile material. The cover layers 5714*a*, 5714*b* surround a portion or an entirety of a periphery of the core 5712. Edges of the cover layers 5714*a*, 5714*b* may or may not contact or be secured to one another. In the illustrated arrangement, the headgear 5700 is formed by introducing molten plastic material into the cover layers 5714*a*, 5714*b* and allowing the molten plastic material to cool to form the cores 5712 in accordance with any of the processes disclosed herein. Alternatively, the cover layers 5714*a*, 5714*b* can be formed separately from the cores 5712 and can be assembled onto the cores 5712 and secured, such as by adhesives, sewing, RF welding or another suitable process.

In the illustrated arrangement, the cover layer 5714*a* is a patterned polyester material, as illustrated in FIG. 146A, which provides the user-contacting or inward-facing (inner) surface with tactile and visual differentiation relative to the cover layer 5714*b* that defines the outward-facing (outer) surface, as illustrated in FIG. 146B. The patterned cover layer 5714*a* also indicates softness and comfort to the user, as well as hiding details resulting from the process used to create the headgear 5700, such as the edges of the core 5712. The illustrated cover layer 5714*b* is a polyurethane (imitation leather) material, which provides high slip to allow the headgear 5700 to slide along other objects (e.g., pillows) and a premium finish. As a result of such a construction, the cover layers 5714*a*, 5714*b* can have different textures to allow for differentiation of the inner and outer surfaces from one another. In addition, the layers 5714*a*, 5714*b* can have different colors to allow for differentiation between the inner and outer surfaces. In other configurations, the cover layers 5714*a*, 5714*b* can be reversed between the inner surface and the outer surface, the cover layers 5714*a*, 5714*b* could be the same material on each of the inner surface and the outer surface, or different materials from those shown could be used.

In the illustrated arrangement, the top strap portion 5706, the rear strap portion 5708 and the front strap portions 5710 have the same or substantially the same cross-sectional dimensions as one another. However, in other arrangements, the cross-sectional dimensions of the strap portions 5706, 5708, 5710 can be different from one another. In the illustrated arrangement, the strap portions 5706, 5708, 5710 each have a width 5720 that is the same or substantially the same. In addition, the strap portions 5706, 5708, 5710 can each define a thickness 5724 that is the same or substantially the same.

In the illustrated configuration, the width 5720 of each of the strap portions 5706, 5708, 5710 is between 12 mm-16 mm, or categorized as a medium width. In the illustrated configuration, the thickness 5724 of each of the strap portions 5706, 5708, 5710 is between 2 mm-3 mm. Such strap thicknesses can be categorized as medium. The overall construction of the headgear 5700, including the thicknesses 5724, provides flexibility of the headgear 5700 that can be characterized as medium for the purpose of comparison to other headgear configurations disclosed herein, or other headgear configurations generally.

FIGS. 147-149 illustrate another configuration of a headgear 5800 having a top strap or crown strap portion 5806, a rear strap portion 5808 and a pair of front strap portions 5810. The headgear 5800 can comprise a composite structure having a core 5812 and a cover, which comprises an inner cover layer 5814*a* and an outer cover layer 5814*b*. In some configurations, the core 5812 is constructed of a relatively rigid material, such as an injection-moulded plastic material. In some configurations, the cover layers 5814*a*, 5814*b* are constructed from a fabric or textile material. The cover layers 5814*a*, 5814*b* surround a portion or an entirety of a periphery of the core 5812. Edges of the cover layers 5814*a*, 5814*b* may or may not contact or be secured to one another. In the illustrated arrangement, the headgear 5800 is formed by introducing molten plastic material into the cover layers 5814*a*, 5814*b* and allowing the molten plastic material to cool to form the cores 5812 in accordance with any of the processes disclosed herein. Alternatively, the cover layers 5814*a*, 5814*b* can be formed separately from the cores 5812 and can be assembled onto the cores 5812 and secured, such as by adhesives, sewing, RF welding or another suitable process.

In the illustrated arrangement, the cover layer 5814*a* is a wool (e.g., Merino wool) material with a mesh knit, as illustrated in FIG. 149A, which provides the user-contacting or inward-facing (inner) surface with tactile and visual differentiation relative to the cover layer 5814*b* that defines the outward-facing (outer) surface, as illustrated in FIG. 149B. The patterned cover layer 5814*a* also conveys softness, comfort and performance to the user. The illustrated cover layer 5814*b* is a patterned polyester material, which conveys softness and comfort to the user, as well as hiding details resulting from the process used to create the headgear 5800, such as the edges of the core 5812. As a result of such a construction, the cover layers 5814*a*, 5814*b* can have different textures and/or colors to allow for differentiation of the inner and outer surfaces from one another. In other configurations, the cover layers 5814*a*, 5814*b* can be reversed between the inner surface and the outer surface, the cover layers 5814*a*, 5814*b* could be the same material on each of the inner surface and the outer surface, or different materials from those shown could be used.

In the illustrated arrangement, the top strap portion 5806, the rear strap portion 5808 and the front strap portions 5810 have the same or substantially the same cross-sectional dimensions as one another. However, in other arrangements, the cross-sectional dimensions of the strap portions 5806,

5808, 5810 can be different from one another. In the illustrated arrangement, the strap portions 5806, 5808, 5810 each have a width 5820 that is the same or substantially the same. In addition, the strap portions 5806, 5808, 5810 can each define a thickness 5824 that is the same or substantially the same.

In the illustrated configuration, the width 5820 of each of the strap portions 5806, 5808, 5810 is between 12 mm-16 mm, or categorized as a medium width. In the illustrated configuration, the thickness 5824 of each of the strap portions 5806, 5808, 5810 is between 2 mm-3 mm. Such strap thicknesses can be categorized as medium. The overall construction of the headgear 5800, including the thicknesses 5824, provides flexibility of the headgear 5800 that can be characterized as medium for the purpose of comparison to other headgear configurations disclosed herein, or other headgear configurations generally.

FIGS. 150-152 illustrate another configuration of a headgear 5900 having a top strap or crown strap portion 5906, a rear strap portion 5908 and a pair of front strap portions 5910. The headgear 5900 can comprise a composite structure having a core 5912 and a cover, which comprises an inner cover layer 5914*a* and an outer cover layer 5914*b*. In some configurations, the core 5912 is constructed of a relatively rigid material, such as an injection-moulded plastic material. In some configurations, the cover layers 5914*a*, 5914*b* are constructed from a fabric or textile material. The cover layers 5914*a*, 5914*b* surround a portion or an entirety of a periphery of the core 5912. Edges of the cover layers 5914*a*, 5914*b* may or may not contact or be secured to one another. In the illustrated arrangement, the headgear 5900 is formed by introducing molten plastic material into the cover layers 5914*a*, 5914*b* and allowing the molten plastic material to cool to form the cores 5912 in accordance with any of the processes disclosed herein. Alternatively, the cover layers 5914*a*, 5914*b* can be formed separately from the cores 5912 and can be assembled onto the cores 5912 and secured, such as by adhesives, sewing, RF welding or another suitable process.

In the illustrated arrangement, each of the cover layers 5914*a*, 5914*b* is a UBL (unbroken loop) material, as illustrated in FIGS. 149A and 149B, respectively. In such an arrangement, if desired, different colors can be used to provide the user-contacting or inward-facing (inner) surface with tactile and visual differentiation relative to the cover layer 5914*b* that defines the outward-facing (outer) surface. The UBL material conveys softness and comfort to the user. In addition, the UBL material can be connected to a hook portion of a hook and loop fastener. In other configurations, different materials from those shown could be used.

In the illustrated arrangement, the top strap portion 5906, the rear strap portion 5908 and the front strap portions 5910 have the same or substantially the same cross-sectional dimensions as one another. However, in other arrangements, the cross-sectional dimensions of the strap portions 5906, 5908, 5910 can be different from one another. In the illustrated arrangement, the strap portions 5906, 5908, 5910 each have a width 5920 that is the same or substantially the same. In addition, the strap portions 5906, 5908, 5910 can each define a thickness 5924 that is the same or substantially the same.

In the illustrated configuration, the width 5920 of each of the strap portions 5906, 5908, 5910 is between 12 mm-16 mm, or categorized as a medium width. In the illustrated configuration, the thickness 5924 of each of the strap portions 5906, 5908, 5910 is between 2 mm-3 mm. Such strap thicknesses can be categorized as medium. The overall construction of the headgear 5900, including the thicknesses 5924, provides flexibility of the headgear 5900 that can be characterized as medium for the purpose of comparison to other headgear configurations disclosed herein, or other headgear configurations generally.

FIGS. 153 and 154 illustrate another configuration of a headgear 6000 having a top strap or crown strap portion 6006, a rear strap portion 6008 and a pair of front strap portions 6010. The headgear 6000 can comprise a composite structure having a core 6012 and a cover, which comprises an inner cover layer 6014*a* and an outer cover layer 6014*b*. In some configurations, the core 6012 is constructed of a relatively rigid material, such as an injection-moulded plastic material. In some configurations, the cover layers 6014*a*, 6014*b* are constructed from a plastic sheet material. The cover layers 6014*a*, 6014*b* surround a portion or an entirety of a periphery of the core 6012. Edges of the cover layers 6014*a*, 6014*b* may or may not contact or be secured to one another. The headgear 6000 can be formed by any suitable process. In some configurations, the cover layers 6014*a*, 6014*b* are formed separately from the cores 6012 and can be assembled onto the cores 6012 and secured by RF welding. However, other securing processes or arrangements can also be used, such as adhesives, sewing, or other suitable methods.

In the illustrated arrangement, each of the cover layers 6014*a*, 6014*b* is a thin nylon sheet material. In such an arrangement, if desired, different colors can be used to provide the user-contacting or inward-facing (inner) surface with tactile and visual differentiation relative to the cover layer 6014*b* that defines the outward-facing (outer) surface. The nylon material provides high slip, is resistant to water and sweat and can be easily cleaned. In other configurations, different materials from those shown could be used.

In the illustrated arrangement, the top strap portion 6006, the rear strap portion 6008 and the front strap portions 6010 have the same or substantially the same cross-sectional dimensions as one another. However, in other arrangements, the cross-sectional dimensions of the strap portions 6006, 6008, 6010 can be different from one another. In the illustrated arrangement, the strap portions 6006, 6008, 6010 each have a width 6020 that is the same or substantially the same. In addition, the strap portions 6006, 6008, 6010 can each define a thickness 6024 that is the same or substantially the same.

In the illustrated configuration, the width 6020 of each of the strap portions 6006, 6008, 6010 is between 12 mm-16 mm, or categorized as a medium width. In the illustrated configuration, the thickness 6024 of each of the strap portions 6006, 6008, 6010 is between 2 mm-3 mm. Such strap thicknesses can be categorized as medium. The overall construction of the headgear 6000, including the thicknesses 6024, provides flexibility of the headgear 6000 that can be characterized as medium for the purpose of comparison to other headgear configurations disclosed herein, or other headgear configurations generally.

FIGS. 155-157 illustrate another configuration of a headgear 6100 having a top strap or crown strap portion 6106, a rear strap portion 6108 and a pair of front strap portions 6110. The headgear 6100 can comprise a composite structure having a core 6112 and a cover, which comprises an inner cover layer 6114*a* and an outer cover layer 6114*b*. In some configurations, the core 6112 is constructed of a relatively soft and flexible material, such as a foam or neoprene material. In the illustrated configuration, the cover layer 6114*a* is constructed from a soft fabric material, such as nylon. In the illustrated configuration, the cover layer

6114*b* is constructed from a soft fabric material, such as a UBL (unbroken loop) material so that the cover layer 6114*b* can cooperate with a hook portion of a hook and loop fastener. The cover layers 6114*a*, 6114*b* surround a portion or an entirety of a periphery of the core 6112. Edges of the cover layers 6114*a*, 6114*b* may or may not contact or be secured to one another. The headgear 6100 can be formed by any suitable process. In some configurations, a composite work piece (e.g., a sheet) of the core 6112, and the cover layers 6114*a*, 6114*b* are formed by any suitable arrangement or process, such as RF welding. However, other securing processes or arrangements can also be used, such as adhesives, or other suitable methods. The headgear 6100 can then be cut (e.g., die cut) from the composite work piece.

If desired, a first color can be used for the cover layer 6114*a* and a different color used for cover layer 6114*b* to provide the user-contacting or inward-facing (inner) surface with tactile and visual differentiation relative to the outward-facing (outer) surface. In other configurations, different materials from those shown could be used.

In the illustrated arrangement, the top strap portion 6106, the rear strap portion 6108 and the front strap portions 6110 have the same or substantially the same cross-sectional dimensions as one another. However, in other arrangements, the cross-sectional dimensions of the strap portions 6106, 6108, 6110 can be different from one another. In the illustrated arrangement, the strap portions 6106, 6108, 6110 each have a width 6120 that is the same or substantially the same. In addition, the strap portions 6106, 6108, 6110 can each define a thickness 6124 that is the same or substantially the same.

In the illustrated configuration, the width 6120 of each of the strap portions 6106, 6108, 6110 is between 16 mm-20 mm, or categorized as a wide. In the illustrated configuration, the thickness 6124 of each of the strap portions 6106, 6108, 6110 is between 3 mm-4 mm. Such strap thicknesses can be categorized as thick. The overall construction of the headgear 6100, including the thicknesses 6124, provides flexibility of the headgear 6100 that can be characterized as very high for the purpose of comparison to other headgear configurations disclosed herein, or other headgear configurations generally.

FIGS. 158-173 illustrate several strap configurations, which can form a portion or an entirety of a headgear, such as any of the headgear disclosed herein. For example, the illustrated strap configurations can form a portion or an entirety of a crown or top strap, a rear strap or a front strap of a headgear, such as those headgear disclosed herein. In other arrangements, the strap configurations could form a portion or an entirety of upper straps used to connect to a forehead rest of an interface. Features of other headgear arrangements disclosed herein can be applied to the strap configurations of FIGS. 158-173, such as color and/or tactile differentiation between the inner and outer (or other) surfaces of the strap, for example.

FIGS. 158 and 159 illustrate a strap 6200 comprising a core 6212 and a cover, which comprises a first cover layer 6214*a* and a second cover layer 6214*b*. In the illustrated arrangement, edges of the cover layers 6214*a*, 6214*b* are not connected to one another. Accordingly, edges of the core 6212 are exposed between the cover layers 6214*a*, 6214*b*. The core 6212 can be constructed of a relatively rigid material, such as a plastic. In some configurations, the core 6212 is formed by an injection molding process, which allows the edges of the core 6212 to be shaped (e.g., rounded). The cover layers 6214*a*, 6214*b* can be constructed of a relatively soft fabric or textile material. In the illustrated configuration, each of the cover layers 6214a, 6214b is constructed from a UBL (unbroken loop) material. The cover layers 6214a, 6214b can be secured to the cover 6212 by any suitable arrangement or method, such as RF welding, for example. Other suitable arrangements or methods could also be used, such as adhesives, for example.

As noted, the edges of the cover layers 6214a, 6214b are not connected to one another such that the edges of the core 6212 are exposed. The edges of the core 6212 are rounded to avoid sharp edges that could be uncomfortable or could be perceived as uncomfortable by a user. The rounded edges can include rounded corners or a rounding of the entire thickness of the core 6212. In some configurations, the edges of the cover layers 6214a, 6214b extend beyond or overhang from the core 6212, or at least the beyond the point that the edges of the core 6212 starts to round. Such an arrangement can disguise the rigid plastic core 6212 and provide an appearance that softens the hard edge of the core 6212.

The illustrated strap 6200 defines a width 6220 and a thickness 6224. A length of the strap 6200 can vary depending on the particular application. Accordingly, FIGS. 158-173 illustrate strap segments having a length of 80 mm. In the illustrated configuration, the width 6220 of the strap 6200 is 12 mm and the thickness 6224 of the strap 6200 is 2 mm. However, such dimensions are for the sake of example and comparison between the strap configurations of FIGS. 158-173 and other suitable strap dimensions can be used, such as those disclosed herein, for example.

FIGS. 160 and 161 illustrate a strap 6300 comprising a core 6312 and a cover, which comprises a first cover layer 6314a and a second cover layer 6314b. In the illustrated arrangement, edges of the cover layers 6314a, 6314b are not connected to one another. Accordingly, edges of the core 6312 are exposed between the cover layers 6314a, 6314b. The core 6312 can be constructed of a relatively rigid material, such as a plastic. In some configurations, the core 6312 is formed by an injection molding process, which allows the edges of the core 6312 to be shaped (e.g., rounded). The cover layers 6314a, 6314b can be constructed of a relatively soft fabric or textile material. In the illustrated configuration, each of the cover layers 6314a, 6314b is constructed from a UBL (unbroken loop) material. The cover layers 6314a, 6314b can be secured to the core 6312 by any suitable arrangement or method, such as RF welding, for example. Other suitable arrangements or methods could also be used, such as adhesives, for example.

In some configurations, the core 6312 can include a recess or cut-out along a portion of the core 6312. The illustrated core 6312 includes a cut-out 6330 of a central portion of the core 6312 in a width direction that extends through the entire thickness of the core 6312. The cut-out 6330 can be sized and shaped as desired, such as dependent on the overall shape of the strap 6300 or associate headgear. Such an arrangement may help disguise the rigidity of the strap 6300 by creating compressibility in the width direction. Because the edges of the cover layers 6314a, 6314b are not connected to one another, the edges of the core 6312 are exposed. The edges of the core 6312 are rounded to avoid sharp edges that could be uncomfortable or could be perceived as uncomfortable by a user. The rounded edges can include rounded corners or a rounding of the entire thickness of the core 6312. In some configurations, the edges of the cover layers 6314a, 6314b extend beyond or overhang from the core 6312, or at least the beyond the point that the edges of the core 6312 starts to round. Such an arrangement can disguise the rigid plastic core 6312 and provide an appearance that softens the hard edge of the core 6312.

The illustrated strap 6300 defines a width 6320 and a thickness 6324. In the illustrated configuration, the width 6320 of the strap 6300 is 12 mm and the thickness 6324 of the strap 6300 is 2 mm. However, such dimensions are for the sake of example and comparison between the strap configurations of FIGS. 158-173 and other suitable strap dimensions can be used, such as those disclosed herein, for example.

FIGS. 152 and 153 illustrate a strap 6400 comprising a core 6412 and a cover 6414, which comprises a first cover portion 6414a and a second cover portion 6414b. In the illustrated arrangement, the first cover portion 6414a is wrapped around the core 6412 such that the first cover portion 6414a surrounds at least one side and two edges of the core 6412. Accordingly, opposing edges of the first cover portion 6414a are located on a side of the core 6412 opposite the side that is covered by the first cover portion 6414a. The edges of the first cover portion 6414a can be spaced apart or can meet. Accordingly, edges of the core 6412 are covered by the first cover portion 6414a. The second cover portion 6414b is positioned on the side of the core 6412 on which the edges of the first cover portion 6414a are located and cover the edges of the first cover portion 6414a. The second cover portion 6414b can cover a portion or an entirety of the associated side of the core 6412.

The core 6412 can be constructed of a relatively rigid material, such as a plastic. In some configurations, the core 6412 is formed by an injection molding process, which allows the edges of the core 6412 to be shaped (e.g., rounded). The cover portions 6414a, 6414b can be constructed of a relatively soft fabric or textile material. In the illustrated configuration, each of the cover portions 6414a, 6414b is constructed from a UBL (unbroken loop) material. The cover portions 6414a, 6414b can be secured to the core 6412 by any suitable arrangement or method, such as RF welding, for example. Other suitable arrangements or methods could also be used, such as adhesives, for example.

The edges of the core 6412 can be rounded to avoid sharp edges that could be uncomfortable or could be perceived as uncomfortable by a user. The rounded edges can include rounded corners or a rounding of the entire thickness of the core 6412. The wrapping of the core 6412 by the first cover portion 6414a can disguise the rigid plastic core 6412 and provide an appearance that softens the hard edge of the core 6412. The second cover portion 6414b can provide additional comfort or perceived comfort if used as the inner surface and can enable wrapping of curved headgear geometry.

The illustrated strap 6400 defines a width 6420 and a thickness 6424. In the illustrated configuration, the width 6420 of the strap 6400 is 12 mm and the thickness 6424 of the strap 6400 is 2.5 mm. However, such dimensions are for the sake of example and comparison between the strap configurations of FIGS. 158-173 and other suitable strap dimensions can be used, such as those disclosed herein, for example.

FIGS. 162 and 163 illustrate a strap 6500 that is similar to the strap 6400 of FIGS. 162 and 163. The strap 6500 of FIGS. 164 and 165 comprises a core 6512 and a cover 6514, which comprises a first cover portion 6514a and a second cover portion 6514b. In the illustrated arrangement, the first cover portion 6514a is wrapped around the core 6512 such that the first cover portion 6514a surrounds at least one side and two edges of the core 6512. Accordingly, opposing edges of the first cover portion 6514a are located on a side of the core 6512 opposite the side that is covered by the first cover portion 6514a. However, the first cover portion 6514a is not tightly wrapped on the core 6512 such that an air gap 6532 is provided adjacent one or both edges of the core 6512 between the core 6512 and the first cover portion 6514*a*. The edges of the first cover portion 6514*a* can be spaced apart or can meet. Accordingly, edges of the core 6512 are covered by the first cover portion 6514*a*, but with intervening air gaps 6532 on one or both edges. The second cover portion 6514*b* is positioned on the side of the core 6512 on which the edges of the first cover portion 6514*a* are located and cover the edges of the first cover portion 6514*a*. The second cover portion 6514*b* can cover a portion or an entirety of the associated side of the core 6512.

The core 6512 can be constructed of a relatively rigid material, such as a plastic. In some configurations, the core 6512 is formed by an injection molding process, which allows the edges of the core 6512 to be shaped (e.g., rounded). The cover portions 6514*a*, 6514*b* can be constructed of a relatively soft fabric or textile material. In the illustrated configuration, each of the cover portions 6514*a*, 6514*b* is constructed from a UBL (unbroken loop) material. The cover portions 6514*a*, 6514*b* can be secured to the core 6512 by any suitable arrangement or method, such as RF welding, for example. Other suitable arrangements or methods could also be used, such as adhesives, for example.

The edges of the core 6512 can be rounded to avoid sharp edges that could be uncomfortable or could be perceived as uncomfortable by a user. The rounded edges can include rounded corners or a rounding of the entire thickness of the core 6512. The wrapping of the core 6512 by the first cover portion 6514*a* and provision of the air gap(s) 6532 can disguise the rigid plastic core 6512 and provide an appearance that softens the hard edge of the core 6512. The second cover portion 6514*b* can provide additional comfort or perceived comfort if used as the inner surface and can enable wrapping of curved headgear geometry.

The illustrated strap 6500 defines a width 6520 and a thickness 6524. In the illustrated configuration, the width 6520 of the strap 6500 is 12 mm and the thickness 6524 of the strap 6500 is 2.5 mm. However, such dimensions are for the sake of example and comparison between the strap configurations of FIGS. 158-173 and other suitable strap dimensions can be used, such as those disclosed herein, for example.

FIGS. 166 and 167 illustrate a strap 6600 comprising a core 6612 and a cover, which comprises a first cover layer 6614*a* and a second cover layer 6614*b*. As used herein, the term "layer" can refer to a construction having a single material or multiple materials (e.g., a composite material), unless otherwise indicated. In the illustrated arrangement, edges of the cover layers 6614*a*, 6614*b* are not connected to one another. Accordingly, edges of the core 6612 are exposed between the cover layers 6614*a*, 6614*b*. The core 6612 can be constructed of a relatively rigid material, such as a plastic. In some configurations, the core 6612 is formed by an injection molding process, which allows the edges of the core 6612 to be shaped (e.g., rounded). The cover layers 6614*a*, 6614*b* can be constructed of a composite of multiple materials, such as relatively soft fabric or textile materials. In the illustrated configuration, each of the cover layers 6614*a*, 6614*b* is constructed from a UBL (unbroken loop) material with a spacer fabric material on top. That is, in some configurations, the UBL material is closer to the core 6612 and the spacer fabric is further away from the core 6612. The cover layers 6614*a*, 6614*b* can be secured to the core 6612 by any suitable arrangement or method, such as RF welding, for example. Other suitable arrangements or methods could also be used, such as adhesives, for example.

Because the edges of the cover layers 6614*a*, 6614*b* are not connected to one another, the edges of the core 6612 are exposed. The edges of the core 6612 are rounded to avoid sharp edges that could be uncomfortable or could be perceived as uncomfortable by a user. The rounded edges can include rounded corners or a rounding of the entire thickness of the core 6612. In some configurations, the edges of the cover layers 6614*a*, 6614*b* extend beyond or overhang from the core 6612, or at least the beyond the point that the edges of the core 6612 starts to round. Such an arrangement can disguise the rigid plastic core 6612 and provide an appearance that softens the hard edge of the core 6612. In addition, the spacer fabric provides additional compressibility in the thickness direction (the vertical direction in the illustrated orientation) to further disguise rigidity and provide cushioning for sensitive areas (e.g., a user's checks).

The illustrated strap 6600 defines a width 6620 and a thickness 6624. In the illustrated configuration, the width 6620 of the strap 6600 is 12 mm and the thickness 6624 of the strap 6600 is 8 mm. However, such dimensions are for the sake of example and comparison between the strap configurations of FIGS. 158-173 and other suitable strap dimensions can be used, such as those disclosed herein, for example.

FIGS. 168 and 167 illustrate a strap 6700 comprising a core 6712 and a cover, which comprises a first cover layer 6714*a* and a second cover layer 6714*b*. In the illustrated arrangement, edges of the cover layers 6714*a*, 6714*b* are not connected to one another. Accordingly, edges of the core 6712 are exposed between the cover layers 6714*a*, 6714*b*. The core 6712 can be constructed of a relatively rigid material, such as a plastic. In some configurations, the core 6712 is formed by an injection molding process, which allows the edges of the core 6712 to be shaped (e.g., rounded). The cover layers 6714*a*, 6714*b* can be constructed of a composite of multiple materials, such as relatively soft fabric or textile and foam or similar cushioning materials. In the illustrated configuration, each of the cover layers 6714*a*, 6714*b* is constructed from a UBL (unbroken loop) material with a breath-o-prene material on top. That is, in some configurations, the UBL material is closer to the core 6712 and the breath-o-prene material is further away from the core 6712. The cover layers 6714*a*, 6714*b* can be secured to the core 6712 by any suitable arrangement or method, such as RF welding, for example. Other suitable arrangements or methods could also be used, such as adhesives, for example.

Because the edges of the cover layers 6714*a*, 6714*b* are not connected to one another, the edges of the core 6712 are exposed. The edges of the core 6712 are rounded to avoid sharp edges that could be uncomfortable or could be perceived as uncomfortable by a user. The rounded edges can include rounded corners or a rounding of the entire thickness of the core 6712. In some configurations, the edges of the cover layers 6714*a*, 6714*b* extend beyond or overhang from the core 6712, or at least the beyond the point that the edges of the core 6712 starts to round. Such an arrangement can disguise the rigid plastic core 6712 and provide an appearance that softens the hard edge of the core 6712. In addition, the breath-o-prene material provides additional compressibility in the thickness direction (the vertical direction in the illustrated orientation) to further disguise rigidity and provide cushioning for sensitive areas (e.g., a user's checks).

The illustrated strap 6700 defines a width 6720 and a thickness 6724. In the illustrated configuration, the width 6720 of the strap 6700 is 12 mm and the thickness 6724 of the strap 6700 is 8 mm. However, such dimensions are for the sake of example and comparison between the strap configurations of FIGS. 158-173 and other suitable strap dimensions can be used, such as those disclosed herein, for example.

FIGS. 170 and 171 illustrate a strap 6800 comprising a core 6812 and a cover, which comprises a first cover layer 6814*a* and a second cover layer 6814*b*. In the illustrated arrangement, edges of the cover layers 6814*a*, 6814*b* are not connected to one another. Accordingly, edges of the core 6812 are exposed between the cover layers 6814*a*, 6814*b*. The core 6812 can be constructed of a relatively rigid material, such as a plastic. In some configurations, the core 6812 is formed by an injection molding process. The cover layers 6814*a*, 6814*b* can be constructed of a relatively soft fabric or textile material. In the illustrated configuration, each of the cover layers 6814*a*, 6814*b* is constructed from a UBL (unbroken loop) material. The cover layers 6814*a*, 6814*b* can be secured to the core 6812 by any suitable arrangement or method. In the illustrated arrangement, the molten material of the core 6812 is injected between the cover layers 6814*a*, 6814*b*, such as by a method disclosed herein. However, other suitable arrangements or methods could also be used, such as adhesives or RF welding, for example.

Because the edges of the cover layers 6814*a*, 6814*b* are not connected to one another, the edges of the core 6812 are exposed. The edges of the core 6812 can be square or sharp, but in other configurations could be rounded to avoid sharp edges that could be uncomfortable or could be perceived as uncomfortable by a user. In some configurations, the edges of the cover layers 6814*a*, 6814*b* extend beyond or overhang from the core 6812. Such an arrangement can disguise the rigid plastic core 6812 and provide an appearance that softens the hard edge of the core 6812.

The illustrated strap 6800 defines a width 6820 and a thickness 6824. In the illustrated configuration, the width 6820 of the strap 6800 is 10 mm and the thickness 6824 of the strap 6800 is 2 mm. However, such dimensions are for the sake of example and comparison between the strap configurations of FIGS. 158-173 and other suitable strap dimensions can be used, such as those disclosed herein, for example.

FIGS. 172 and 173 illustrate a strap 6900 comprising a core 6912 and a cover 6914, which is wrapped around the core 6912. In the illustrated arrangement, edges of the cover layer 6914 are embedded within the core 6912. The core 6912 can be constructed of a relatively rigid material, such as a plastic. In some configurations, the core 6912 is formed by an injection molding process. The cover layer 6914 can be constructed of a relatively soft fabric or textile material. In the illustrated configuration, the cover layer 6914 is constructed from a UBL (unbroken loop) material. The cover layer 6914 can be secured to the core 6912 by any suitable arrangement or method. In the illustrated arrangement, the cover layer 6914 is constructed as a tubular structure, such as by sewing of opposing edges of a flat piece of material. The molten material of the core 6912 is injected into a center of the tubular cover layer 6914, such as by a method disclosed herein. However, other suitable arrangements or methods could also be used, such as adhesives or RF welding, for example.

The edges of the core 6912 can be rounded to avoid sharp edges that could be uncomfortable or could be perceived as uncomfortable by a user. In addition, the cover layer 6914 preferably is wrapped around the edges of the core 6912. Such an arrangement can disguise the rigid plastic core 6912 and provide an appearance that softens the hard edge of the core 6912.

The illustrated strap 6900 defines a width 6920 and a thickness 6924. In the illustrated configuration, the width 6920 of the strap 6900 is 10 mm and the thickness 6924 of the strap 6900 is 2 mm. However, such dimensions are for the sake of example and comparison between the strap configurations of FIGS. 158-173 and other suitable strap dimensions can be used, such as those disclosed herein, for example.

FIGS. 174 and 175A illustrated a headgear 5500 that is similar to the headgear 5500 of FIGS. 138 and 139. Accordingly, the same reference numbers are used to indicate the same or similar features. In addition, any details not discussed in connection with FIGS. 174 and 175A can be the same as or similar to the corresponding features or components of FIGS. 138 and 139, or can be of another suitable arrangement. The headgear 5500 has a first headgear portion or strap 5502 and a second headgear portion or strap 5504. The first strap 5502 defines a top strap or crown strap portion 5506 and the second strap 5504 defines a rear strap portion 5508. In the illustrated arrangement, the first strap 5502 also forms a portion of the rear strap portion 5508, such that the rear strap portion 5508 includes portions of both the first strap 5502 and the second strap 5504. In addition, the second strap 5504 defines front strap portions 5510 of the headgear 5500.

In the illustrated arrangement, each of the first strap 5502 and the second strap 5504 comprises a core 5512 and a cover layer 5514. In some configurations, the core 5512 can be constructed of a relatively rigid material, such as an injection-moulded plastic material. In some configurations, the cover layer 5514 is a fabric or textile material. The cover layer 5514 surrounds a portion or an entirety of a periphery of the core 5512. In the illustrated arrangement, the core 5512 of the first strap 5502 is plastic and the cover layer 5514 is a soft, quilted fabric material. The material of the cover layer 5514 can be formed into a tubular structure by joining opposing edges of the material, such as by sewing or otherwise, to form a seam 5516. The seam 5516 can be positioned on any desired surface portion of the first strap 5502, such as along either side (width direction) or either end (thickness direction). In the illustrated arrangement, the seam 5516 is positioned on the user-facing or inner surface of the first strap 5502.

The core 5512 of the illustrated second strap 5504 is plastic and the cover layer 5514 is a relatively durable and slippery material formed into a tubular structure. The material of the cover layer 5514 can be formed into a tubular structure by joining opposing edges of the material, such as by sewing or otherwise, to form a seam 5516. The cover layers 5514 of each of the first strap 5502 and the second strap 5504 can be formed separately from the cores 5512 and can be assembled onto the cores 5512, such as by sliding the cover layer 5514 onto the core 5512. In some configurations, the cover layers 5514 can be loosely received on the cores 5512. In other words, the cover layers 5514 may not be affixed to the cores 5512 such that some relative movement is permitted between the cover layer 5514 and the respective core 5512. In some configurations, air gaps 5532 can be provided between edges of the cores 5512 and edges of the cover layers 5514. Such an arrangement may provide increased comfort. However, if desired, the cover layers 5514 could be tightly affixed to the cores 5512, such as by molding within the cover layers 5514, as described herein, or by adhesives, for example.

In the illustrated arrangement, the first strap 5502 and the second strap 5504 are joined along a substantial entirety of the rear strap portion 5508. The first strap 5502 and the second strap 5504 separate at a junction between the top strap portion 5506, the rear strap portion 5508 and the front strap portions 5510. The first strap 5502 and the second strap 5504 can be secured to one another by any suitable arrangement, such as by a sewn joint or adhesive joint between the cover layers 5514 of the first strap 5502 and the second strap 5504. RF welding or Ultrasonic welding could also be used. If desired, the straps 5502, 5504 could be secured to one another during a molding process in which the molten material of the cores 5512 is introduced into the cover layers 5514.

In the illustrated arrangement, the first strap 5502 is located inwardly of the second strap 5504 in the rear strap portion 5508 such that the first strap 5502 is closer to the user than the second strap 5504 in use. Thus, the first strap 5502 can define a portion or an entirety of a user-contacting surface of the rear strap portion 5508. In the illustrated arrangement, because the first strap 5502 also defines the top strap portion 5506, the first strap 5502 defines a user-contacting surface of both the top strap portion 5506 and the rear strap portion 5508 of the headgear 5500. The quilted material of the first strap 5502 can provide and/or convey softness and comfort to the user. The material of the second strap can provide durability and good pillow slide properties.

FIGS. 175B and 175C illustrate an alternative arrangement of the straps 5502, 5504 of the headgear 5500 of FIG. 174. Both designs of FIGS. 175B and 175C provide for a reduced thickness stack up in contrast with the arrangement of FIG. 175A, in which the rear portion 5508 has the combined thickness of both straps 5502, 5504. With reference to FIG. 175B, a recess 5550 is provided in a lengthwise direction along the strap 5504. The recess 5550 is configured to receive a portion or an entirety of the strap 5502. In the illustrated arrangement, at least a substantial entirety of the strap 5502 is accommodated within the recess 5550 such that the inner surfaces of the straps 5502, 5504 are substantially aligned to provide comfort to the user. In at least some embodiments, the strap 5504 is a higher load bearing strap than strap 5502 such that the strap 5504 holds the associated mask in scaling engagement with the user's face. In at least some embodiments, the strap 5502 is a lower load bearing strap compared to strap 5504. The top strap 5506 (defined by strap 5502 alone in the illustrated arrangement) typically maintains a vertical force vector, which keeps the headgear assembly 5500 above the cars. The force required to achieve this may be a lower force that the mask blow-off force. Thus, the top strap 5506 can be smaller and/or lighter than the strap 5504. The recess 5550 can extend upwardly at its ends to allow the strap 5502 to transition from the rear strap portion 5508 to the top strap portion 5506 of the headgear 5500. The illustrated strap 5504 includes upper and lower ends or edges that are relatively thick, which allows the strap 5504 to accommodate a relatively high tensile force. That is, the middle region can define the recess 5550 without compromising inelastic performance of strap 5504. The strap 5502 may be narrow as shown in FIG. 175B throughout its entire length or a substantial entirety of its length, as discussed above. In other embodiments, the strap 5502 may vary in width along its length. For example, the strap 5502 may be the same width as strap 5504 in the top strap portion 5506 and transition to a reduced width where positioned within the recess 5550 of strap 5504. If desired, various suitable attachment mechanisms could be employed (e.g., adhesive, overmoulding, stitching, etc.) to secure the straps 5502, 5504 to one another. In some configurations, a baseball cap-style snap fits (e.g., a plurality of protrusions on one of strap 5502 or 5504 and corresponding snap-in receptacles on the other strap 5502 or 5504). The cover layers 5514 could include access openings for each, several or an entirety of the protrusions or receptacles, or other interlocking features. The illustrated arrangement could also be reversed and strap 5504 could be received within strap 5502 such that the recess 5550 is on the non-patient contacting side of the headgear 5500. FIG. 175C illustrates an arrangement similar to that of FIG. 175B; however, in the arrangement of FIG. 175C the straps 5502, 5504 are interlocked with one another. In particular, the recess 5550 has an opening 5552 that is narrower than the internal portion of the recess 5550 such that the strap 5502 cannot pass through the opening 5552. The illustrated recess 5550 has a trapezoid cross-sectional shape and the strap 5502 has a corresponding shape. The strap 5502 does not necessarily have to fill the entire recess 5550. The strap 5502 could be shaped to limit contact surface with the strap 5504 to case assembly. However other shapes that have a narrow opening could also be used or other suitable interlocking arrangements, as well. The illustrated shapes work together to form a mechanical interlock, which in at least some configurations does not require any other attachment mechanisms. However, if desired, suitable attachment mechanisms, such as those described above, could be employed.

FIGS. 176-196 illustrate several headgear configurations 5600 similar to the headgear 5600 of FIGS. 141-143. Accordingly, the same reference numbers are used to indicate the same or similar features. In addition, any details not discussed in connection with FIGS. 176-193 can be the same as or similar to the corresponding features or components of FIGS. 141-143, or can be of another suitable arrangement. Each headgear 5600 has a first headgear portion or strap 5602 and a second headgear portion or strap 5604. The first strap 5602 defines a top strap or crown strap portion 5606 and the second strap 5604 defines a rear strap portion 5608.

The first strap 5602 and the second strap 5604 cooperate to define front strap portions 5610 in each headgear 5600. The first strap 5602 is positioned above the second strap 5604 within the front strap portions 5610 such that a width of the front strap portions 5610 is equal to the combined widths of the first strap 5602 and the second strap 5604. The first strap 5602 and the second strap 5604 are joined to one another within the front strap portions 5610 by a coupling arrangement, coupler or connector 5650. In the illustrated arrangements, the coupling arrangement 5650 also joins the first strap 5602 and the second strap 5604 to a front strap connector or extension strap 5652, which can be coupled to an interface by any suitable arrangement. The extension strap 5652 can be of any suitable arrangement, such as any of the strap arrangements disclosed herein or otherwise known. In some configurations, the coupling arrangement 5650 is over-moulded onto the first strap 5602 and the second strap 5604 to join the straps 5602, 5604. The coupling arrangement 5650 can also be over-moulded onto the extension strap 5652. In some configurations, the coupling arrangement 5650 is not over-moulded onto the extension strap 5652 and the extension strap 5652 is coupled to the coupling arrangement 5650 by another suitable, coupling arrangement, such as a snap-fit connection, for example. The coupling arrangement 5650 can surround the first and second straps 5602, 5604 (and, in some configurations, the extension strap 5652) such that a portion of the coupling arrangement 5650 is positioned on opposing sides (e.g., inner and outer and/or upper and lower) of the straps 5602, 5604. In some configurations, the coupling arrangement 5650 could be otherwise assembled to the straps 5602, 5604, 5652, such as a clamshell or snap-together arrangement, for example.

In the illustrated arrangements, the first strap 5602 and second strap 5604 comprise a composite structure having a core 5612 and a cover layer 5614. In some configurations, the core 5612 is constructed of a relatively rigid material, such as an injection-moulded plastic material. In some configurations, the cover layer 5614 is a fabric or textile material. The cover layer 5614 surrounds a portion or an entirety of a periphery of the core 5612. Any suitable materials or combinations of materials can be used, such as those disclosed herein.

In the illustrated arrangements, the straps 5602, 5604 are formed by introducing molten plastic material into the cover layers 5614 and allowing the molten plastic material to cool to form the cores 5612 in accordance with any of the processes disclosed herein. The cover layers 5614 can be separate layers, a knitted tubular structure or can be a sewn tube having a seam, which can be embedded in the core 5612. Alternatively, the cover layers 5614 of each of the first strap 5602 and the second strap 5604 can be formed separately from the cores 5612 and can be secured to the cores 5612, such as by adhesives or other suitable arrangements.

As disclosed herein, the cover layers 5614 of the first strap 5602 and the second strap 5604 can have different textures to allow for differentiation of the straps 5602, 5604 from one another. In addition or in the alternative, the first strap 5602 and the second strap 5604 can have different colors to allow for differentiation between the straps 5602, 5604. If desired, inward-facing and outward-facing surfaces of the headgear 5600 can have different colors and/or textures to allow for differentiation between inward-facing and outward-facing surfaces.

The headgear arrangements of FIGS. 176-193 differ in the coupling arrangement 5650 that couples the first strap 5602 and the second strap 5604 to one another and, if desired, to the extension strap 5652. The different coupling arrangements 5650 of FIGS. 176-193 are described in turn. The coupling arrangement 5650 of FIGS. 176-178 is generally triangular in shape when viewed from the side with rounded corners. The coupling arrangement 5650 increases in size in a width direction of the straps 5602, 5604 from a rearward position toward a forward position relative to the orientation of the headgear 5600, or in a direction from the straps 5602, 5604 toward the extension strap 5652.

The coupling arrangement 5650 includes a relatively thick perimeter portion 5654 and a relatively thinner interior portion 5656, which can define a recessed portion of the coupling arrangement 5650. The coupling arrangement 5650 can have the same configuration or appearance on the opposite surface (the inner surface), or it can have a relatively planar surface facing the user. In the illustrated arrangement, a portion 5658 of the coupling arrangement 5650 extends between the first strap 5602 and the second strap 5604 to assist in joining the straps 5602, 5604 to one another.

FIGS. 179-181 illustrate a coupling arrangement 5650 having a band portion 5660 at each end, which completely encircles the straps. The rear band portion 5660 can encircle only the straps 5602, 5604. The front band portion 5660 can encircle the straps 5602, 5604, as well as the extension strap 5652, or can encircle just the extension strap 5652. A bridge portion 5662 can extend between the band portions 5660. The bridge portion 5662 can encircle only one of the straps 5602, 5604. In the illustrated arrangement, the bridge portion 5662 surrounds the second strap 5604 or lower strap;

however, in other configurations, the bridge portion 5662 can surround the first strap 5602 or upper strap. A portion 5658 of the bridge portion 5662 and/or the band portions 5660 can be positioned between the straps 5602, 5604. That is, the portion 5658 between the straps 5602, 5604 can extend between the straps 5602, 5604 along some or all of the portions of the straps 5602, 5604 within the coupling arrangement 5650.

Figure 184:
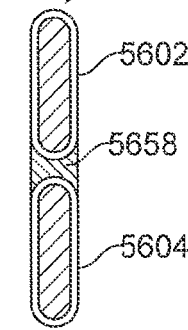

The coupling arrangement 5650 of FIGS. 182-184 omits material along one or both sides of the first strap 5602 and the second strap 5604 such that the sides of the straps 5602, 5604 are left exposed. The coupling arrangement 5650 includes the portion 5658 between the straps 5602, 5604, which can extend along a portion or an entirety of the coupling arrangement 5650. In some configurations, the coupling arrangement 5650 comprises a front band 5660 that surrounds the straps 5602, 5604 and, in some configurations, the extension strap 5652. The band 5660 could be configured to otherwise connect to the extension strap 5652. In some configurations, the coupling arrangement 5650 comprises a web or gusset 5664 at a rearward end. The gusset 5664 can be generally triangular in shape and can reinforce a rearward end of the connection between the straps 5602, 5604 to inhibit or prevent the straps 5602, 5604 from separating. The gusset 5664 can also hold the straps 5602, 5604 at a desired angle to properly position the top strap 5606 and the rear strap 5608.

The coupling arrangement 5650 of FIGS. 185-197 is similar to the coupling arrangement 5650 of FIGS. 182-184. However, the coupling arrangement 5650 of FIGS. 185-187 extends onto or covers a portion of one or both of the inner side and outer side surfaces of the straps 5602, 5604. The coupling arrangement 5650 includes a front band 5660, a rear gusset 5664 and bridge portion 5662 that extends between the front band 5660 and the rear gusset 5664. The bridge portion 5662 includes the portion 5658 positioned between the straps 5602, 5604 as well as portions that extend along a portion of the side surfaces of the one or both of the straps 5602, 5604 in a width direction. From a side view, the coupling arrangement 5650 can taper from each end toward the center.

The coupling arrangement 5650 of FIGS. 188-190 includes only the portion 5658 that is positioned between the straps 5602, 5604. In the illustrated arrangement, the portion 5658 does not extend completely through the front straps 5610 in a thickness direction of the straps 5602, 5604 such that the portion 5658 includes a pair of distinct portions on each of the inner and outer sides of the front straps 5610. However, in other arrangements, the portion 5658 could extend completely through the front strap 5610 in a thickness direction of the straps 5602, 5604. The portion 5658 can extend along an entirety of, or could be intermittent along, the coupling arrangement 5650.

The coupling arrangement 5650 of FIGS. 191-193 is similar to the coupling arrangement 5650 of FIGS. 179-181 except the bridge portion 5662 is centrally-located relative to the combination of the straps 5602, 5604, similar to the bridge portion 5662 of FIGS. 185-184. The coupling arrangement 5650 of FIGS. 191-193 includes a front band portion 5660, a rear band portion 5660 and the bridge portion 5662 extending between the band portions 5660. The bridge portion 5662 can be a relatively thin member that comprises the portion 5658 between the straps 5602, 5604, as well as portions that extend along one or both of the inner and outer sides of one or both of the straps 5602, 5604 in a width direction of the straps 5602, 5604.

FIGS. 194-221 illustrate variations of strap portions suitable for use in headgear, portions of headgear or headgear. The arrangements disclosed in FIGS. 194-221 can be constructed by introducing a molten plastic material into a void or space defined by a layer or layers of one or more materials in accordance with any of the processes or methods disclosed herein. The arrangements disclosed in FIGS. 194-221 could be constructed by other suitable processes or methods, as well. The arrangements generally comprise a relatively rigid or semi-rigid core 7012 and an outer layer or layers 7014. The core 7012 can be constructed from a plastic material, any other materials disclosed herein or any other suitable material. The outer layer or layers 7014 can be constructed from a fabric or textile material, any other materials disclosed herein or any other suitable material. The cover layers 7014 can comprise knitted, woven or braided materials and can be elastic or inelastic.

FIG. 194 illustrates a strap 7000 having a core 7012 and an outer layer 7014. The outer layer 7014 is secured to the long sides of the core 7012 and is spaced from the short sides or edges of the core 7012 to create voids or air gaps 7032 on each lateral edge 7050 of the strap 7000. With such an arrangement, the lateral edges 7050 of the outer layer 7014 can compress toward the plastic core 7012 to provide some ability of the lateral edges 7050 to deform or provide some cushioning in a width and/or thickness direction of the strap 7000. The cushioning provided by the voids 7032 can improve comfort by reducing or eliminating contact between a hard edge of the core 7012 and the user's head and, in particular, the ears. In a width direction of the strap 7000, the voids 7032 could each have a dimension of, for example, 3 mm and the core 7012 could have a dimension of, for example, 3 mm for a total of 9 mm of width. As a result, each of the voids 7032 and the core 7012 could occupy about one-third of the width dimension of the strap 7000. Such an arrangement provides relatively high flexibility due to the relatively small dimensions of the core 7012, which may be desirable to some users from a perception standpoint, as described above. The user can manually apply a force to the strap 7000 and detect some stretch. However, in use, headgear incorporating the strap 7000 can perform substantially as an inelastic headgear due to friction between the user's head and the strap 7000. Alternatively, the voids 7032 could each have a dimension of, for example, 2 mm and the core 7012 could have a dimension of, for example, 5 mm in a width direction of the strap 7000 for a total of 9 mm of width. Such an arrangement (e.g., a medium width core 7012) can provide good flexibility and less elasticity than a strap 7000 having a smaller core 7012. Other suitable relative dimensions could also be used depending on the desired amounts of flexibility and cushioning or compressibility provided by the voids 7032. Such arrangements, including the dimensions or proportions described, can also be applied to other straps or headgear disclosed herein, such as those shown in FIGS. 138 and 174, for example. For example, in the headgear 5500 of FIG. 138, the strap 5502 could have 3 mm voids and a 3 mm core 5512 and the strap 5504 could have 2 mm voids and a 5 mm core 5512. This can provide the top strap 5506 with greater elasticity than the rear strap 5508.

FIGS. 195 and 196 illustrate straps 7000 similar to the strap 7000 of FIG. 194 including a core 7012, an outer layer 7014 and voids 7032 at the lateral edges 7050 thereof. However, the straps 7000 of FIGS. 195 and 196 each include a conduit 7052 extending in a lengthwise direction along the strap 7000 within an interior of the cover layer 7014. FIG. 195 illustrates a relatively large conduit 7052 relative to a cross-sectional size of the strap 7000 and that is partially recessed into the generally rectangular core 7012. FIG. 196 illustrates a relatively small conduit 7052 positioned within one of the voids 7032 and a rounded core 7012. In other configurations, additional conduits 7032 could be provided in one or both of the voids 7032. The conduits 7052 can be utilized as an air supply, for use in an adjustment mechanism (e.g., containing a locking filament), electrical wiring or any other purpose.

FIGS. 197-199 illustrate straps 7000 similar to the straps 7000 of FIGS. 195 and 196 except the straps 7000 of FIGS. 197-199 omit voids 7032. The strap 7000 of FIG. 197 includes a conduit 7052 encased within a center of the rectangular core 7012. In other configurations, the conduit 7052 could be off-center and/or additional conduits 7052 could be included. FIG. 198 illustrates a strap 7000 having a pair of conduits 7052 encased within a generally rectangular core 7012. The outer casing comprises a pair of outer layers 7014, the edges of which may or may not be secured to one another. FIG. 199 illustrates a strap 7000 having a pair of conduits 7052 defined by a core 7012 that has an elliptical cross-sectional shape. In some configurations, the core 7012 can be constructed from a somewhat flexible material (e.g., TPE) so that the conduits 7052 are compressible and provide cushioning.

FIGS. 200-203 illustrate straps 7000 that include at least one air gap 7032. The air gap 7032 of the straps 7000 of FIGS. 200-203 may be larger than the voids 7032 of FIGS. 194-196 and/or may be located (or capable of being located) on more than one side or edge of the core 7012. For example, FIG. 200 illustrates a strap 7000 having an air gap 7032 that, under at least some circumstances, is positioned on one side and both lateral edges of the core 7012. The outer layer 7014 can be attached to the side of the core 7012 opposite the air gap 7032. In some configurations, the air gap 7032 can be located on the inner or user-contacting side of the strap 7000. FIGS. 201*a* and 201*b* illustrate how the strap 7000 can permit decoupled movement of the core 7012 and outer layer 7014. Thus, the core 7012 can move without corresponding movement of the outer layer 7014 on the user's skin. FIG. 202 illustrates a similar strap 7000 except a portion of core 7012 is externally exposed. For example, the non-user side of the core 7012 can be exposed and the outer layer 7014 does not completely encircle the core 7012, but only partially surrounds the core 7012. FIG. 203 illustrates a strap 7000 in which the lateral edges of the outer layer 7014 are not exposed, but are overlapped by a portion of the core 7012. The core 7012 can define pockets or recesses configured to receive the lateral edges of the outer layer 7014. The overall arrangement of the core 7012 and outer layer 7014 can provide the strap 7000 with an elliptical cross-sectional shape.

FIGS. 204-207 illustrate straps 7000 having one or more reinforcement members 7060 within the outer layer 7014. In particular, the illustrated embodiments include one or more reinforcement members 7060 at least partially contained within or surrounded by the core 7012. The reinforcement members 7060 can be fibers or strands of reinforcement materials, such as inelastic thread or carbon fiber, a preformed structural component (e.g., plastic or metal) or a malleable element (e.g., metal wire) that can be deformed and retain the strap 7000 in the deformed state to permit customization of the shape of the strap 7000. The reinforcement members 7060 can modify the properties of the strap 7000 by provided additional or localized rigidity or inelasticity. Thus, the reinforcement members 7060 can extend along a portion or an entirety of the strap 7000 or associated headgear. FIGS. 204 and 88 illustrate a strap 7000 having multiple, elongate reinforcement members 7060 having a generally rectangular cross-sectional shape encapsulated within the core 7012. FIG. 204 illustrates the cover layer 7014 and reinforcement members 7060 prior to the formation of the core 7012. FIG. 206 illustrates a strap 7000 having reinforcement members 7060 that extend partially, a substantial entirely or entirely through the thickness of the core 7012. Such reinforcement members 7060 can assist in maintaining the cover layers 7014 or opposing sides of a tubular cover member separated from one another prior to the formation of the core 7012. In such an arrangement, the members 7060 could be made from the same material of the core 7012 and, thus, may not provide reinforcement to the core 7012, but may simply be cover retention members 7060. FIG. 207 illustrates a strap 7000 having a reinforcement member 7060 having a generally I-shaped cross-section similar to an I-beam. The reinforcement member 7060 has two thickened portions or flanges separated by a thin portion or web.

FIGS. 208 and 209 illustrate straps 7000 having a plastic core 7012, an outer layer or layers 7014 and an additional cushioning layer 7062 within the outer layer 7014. In the illustrated arrangements, the cushioning layer 7062 is positioned partially or completely around the core 7012. In FIG. 208, the cushioning layer 7062 is completely enclosed by the outer layer 7014. In FIG. 209, the outer layer 7014 only partially surrounds the cushioning layer 7062 such that a portion of the cushioning layer 7062 is externally exposed. The cushioning layer 7062 can be constructed from any suitable material, such as a soft TPE, foamed plastic or other plastic material that provides a desired amount of cushioning. In some configurations, the cushioning layer 7062 has a hardness of 0-40 on the shore hardness 00 scale. The cushioning layer 7062 can be co-molded with the core 7012, or can be otherwise formed. The illustrated arrangements provide the structure of a semi-rigid headgear with the comfort of a cushioning layer 7062 around it. The cushioning layer 7062 can be deformable so that is can conform to a certain extent to the user, such as above the cars, which can improve comfort. The protrusion of the cushioning layer 7062, as illustrated in FIG. 209, can act as an alignment indicator or provide a region that grips the user's head in use. The outer layer 7014 and the cushioning layer 7062 can be different colors to facilitate recognition of the alignment indicator.

FIGS. 210 and 211 illustrate a headgear having multiple straps, some or all of which can be straps 7000 having a core 7012 and an outer layer 7012, possibly among other features disclosed herein. The headgear of FIGS. 210 and 211 comprises a coupling arrangement 7070 that can secure multiple straps 7000 together and/or in a desired position relative to one another. The coupling arrangement 7070 can be similar to the coupling arrangements of 5650 of FIGS. 176-193. The illustrated coupling arrangement 7070 is in the form of an over-moulded joint between multiple straps 7000. FIG. 211 illustrates a cross-sectional view of a connection between the coupling arrangement 7070 and one of the straps 7000. A portion of the coupling arrangement 7070 covers a portion of each side of the outer layer 7014 of the strap 7000 and can be adhered or attached to the cover 7014 via the over-moulding process. In the illustrated arrangement, the coupling arrangement 7070 is separate from the core 7012 (although it could be adhered or attached via the over-molding process); however, in other arrangements, the coupling arrangement 7070 could be formed at the same time as the core 7012. The coupling arrangement 7070 can be rigid or flexible (e.g., TPE). The coupling arrangement 7070 can be substantially flat or shaped, such as shaped to correspond to facial geometry and/or to orient the straps 7000 in three dimensions. Such an arrangement can provide a tidy appearance and prevent fraying or rough edges.

FIGS. 212-218 illustrate straps 7000 that either have no seam in the cover layer(s) 7014 or encapsulate the lateral edges of the outer layer(s) 7014 in the core 7012. Such an arrangement avoids external fabric edges that require finishing in a post processing step. The straps 7000 can include a core 7012, one or more outer layers 7014 and, in some configurations, one or more voids 7032. The core 7012 can have any suitable cross-sectional shape and, if desired, can have a three dimensional curvature. The outer layer 7012 can be any suitable material, such as natural or synthetic fibers, and can be elastic or inelastic.

FIGS. 212-214 illustrate straps 7000 having a single piece outer layer 7014. FIG. 212 illustrates a strap 7000 having a seamless, tubular outer layer 7014. The illustrated strap 7000 includes voids 7032 at each lateral edge of the strap 7000 between the core 7012 and the outer layer 7014, which could be omitted. FIG. 213 illustrates a strap 7000 in which the lateral edges of the outer layer 7014 are encapsulated within the core 7012. The illustrated arrangement includes voids 7032, which could be omitted. FIG. 214 illustrates a strap 7000 having an outer layer 7014 with a seam 7016. The seam 7016 can be a sewn, welded, bonded or other type of seam created by another joining method. The lateral edges of the outer layer 7014 can be encapsulated in the core 7012. The seam 7016 is positioned on a side of the strap 7000, which could be the outer side, but could be otherwise positioned, as well.

FIGS. 215 and 216 illustrate straps 7000 having multi-piece outer layers 7014. The illustrated straps 7000 have two-piece outer layers 7014. FIG. 215 illustrates a two-piece outer layer 7014 having two seams 7016 positioned on one side of the strap 7000 (e.g., an outer side of the strap 7000). The illustrated arrangement includes voids 7032, which could be omitted, if desired. FIGS. 216*a* and 216*b* illustrate a strap 7000 having a two-piece outer layer 7014 in which one or both of the pieces are preformed that are configured to align and temporarily interlock together before the core 7012 is formed. One of the pieces surrounds, overlaps and retains the other piece. When the core material is injected, one piece is pushed toward the other piece and both are bonded to the core 7012. The edges of both pieces are turned inwardly and are encapsulated in the core 7012. FIG. 216*a* illustrates the two pieces of the outer layer 7014 prior to the formation of the core 7012 and FIG. 99*b* illustrates the strap 7000 after formation of the core 7012.

FIGS. 217 and 218 illustrate straps 7000 having multi-piece outer layers 7014 comprising more than two pieces. In FIG. 218, the outer layer 7014 comprises four pieces, which one on each side and one on each end. The pieces are joined by seams 7016, with the edges of the pieces encapsulated in the core 7012. The illustrated strap 7000 includes voids 7032, which could be omitted. FIG. 219 illustrates a strap 7000 having an outer layer 7014 with three pieces. Two of the pieces are on one side, with one piece on the other side and both ends. The pieces are joined at seams 7016, with the edges of the pieces encapsulated in the core 7012. The illustrated strap 7000 includes voids 7032, which could be omitted.

FIGS. 219-221 illustrate straps 7000 having shaped or textured fabric outer layers 7014. FIG. 219 illustrates a strap 7000 having a core 7012 and a ribbed cover layer 7014. FIG. 220 illustrates a strap 7000 having core 7012 and a quilted cover layer 7014. FIG. 221 illustrates a strap 7000 having a shaped core 7012 that provides shaping or texture to the outer layer 7014. For example, the core material can be injected into a space defined by or between one or more outer layers 7014 within a mold having a three dimensional textured surface, which results in the outer layer 7014 being pushed into the texture of the mold and the final strap 7000 having a textured surface. In some configurations, the core 7012 is a relatively soft material, such as TPE. Such arrangements provide visual indication that the strap 7000 is soft and/or cushioned.

FIGS. 222-224 illustrate a headgear configuration 5600 similar to the headgear 5600 of FIGS. 141-143 and FIGS. 176-193. Accordingly, the same reference numbers are used to indicate corresponding or similar features. The straps 5602, 5604 can be constructed in a manner similar to that described with reference to FIG. 194 to include voids, air gaps or air pockets 5632 on each lateral edge of the strap 5602, 5604. In the illustrated arrangement, in a width direction, each of the voids 5632 and the core 5612 could each make up about one-third of the overall width of the strap 5602. In some configurations, the voids 5632 could each have a dimension of, for example, 3 mm and the core 5612 could have a dimension of, for example, 3 mm for a total of 9 mm of width. Such an arrangement provides relatively high flexibility due to the relatively small dimensions of the core 5612, which may be desirable to some users from a perception standpoint, as described above. The user can manually apply a force to the strap 5602 and detect some stretch. However, in use, headgear incorporating the strap 5602 can perform substantially as an inelastic headgear due to friction between the user's head and the strap 5602. In the strap 5604, each of the voids 5632 can make up about one-sixth of the overall width of the strap 5604 and the core 5612 can make up the other two-thirds of the width. The voids 5632 could each have a dimension of, for example, 1.5 mm and the core 5612 could have a dimension of, for example, 6 mm in a width direction of the strap 5604 for a total of 9 mm of width. Such an arrangement can provide good flexibility and less elasticity than a strap having a smaller core 5612. Other suitable relative dimensions could also be used depending on the desired amounts of flexibility and cushioning or compressibility provided by the voids 5632. In the illustrated arrangements, the cover layers 5614 wrap at least partially around the core 5612 to create folds 5334 between the portion of the strap 5602, 5604 having the core 5612 and the portions having the air pockets 5632. These folds can appear as stripes extending lengthwise along the straps 5602, 5604 to provide a nice aesthetic look to the strap 5602, 5604 and associated headgear 5600.

FIGS. 225-227 illustrate a headgear configuration 5600 similar to the headgear 5600 of FIGS. 141-143 and FIGS. 176-193. Accordingly, the same reference numbers are used to indicate corresponding or similar features. However, the straps 5602, 5604 can neck down or have a reduced thickness in at least the portions that are connected by the connector 5650 such that the combined thickness of the connected portion of the straps 5602, 5604 are less than twice the thickness of the strap 5602, 5604 outside of the connected portion. In some configurations, the thicknesses of the individual straps 5602, 5604 in the connected portion is about one-half of the thicknesses outside the connected portion such that the connected portion has a thickness approximately equal to the thickness of each strap 5602, 5604 outside of the connected portions. In other arrangements, the top strap 5602 can be narrower than the rear strap 5604 and the rear strap 5604 narrows at the connection 5650 to the top strap 5602. In such an arrangement, the rear strap 5604 can narrow by an amount that is approximately the width of the top strap 5602. Other combinations of variable or tapering thicknesses between the connection portion and portions outside of the connection portion can also be employed. Similarly, the straps 5602, 5604 could be overlapped in a thickness direction and the thicknesses of the individual straps 5602, 5604 could be reduced in the connected portion compared to portions outside of the connected portion.

FIGS. 228-231 illustrate a headgear configuration 5600 similar to the headgear 5600 of FIGS. 141-143 and FIGS. 176-193. Accordingly, the same reference numbers are used to indicate corresponding or similar features. In some configurations, the straps 5602, 5604 can be reduced in the portion connected by the connector 5650 compared to portions outside of the connected portion. As described above, in at least some configurations, the combined width of the straps 5602, 5604 in the connected portion is substantially equal to the thickness of one or both of the straps 5602, 5604 outside of the connected portion.

FIG. 230 illustrates several arrangements of connecting the straps 5602, 5604. For example, the straps 5602, 5604 can each be substantially L-shaped in cross-section. The L-shape can be defined by both the core 5612 and the cover layer 5614 or by just the cover layer 5614, for example. The cover layer 5614 can be formed into the L-shape by the mold tool by a process as described herein or by a post-molding step, for example. The cover layer 5614 can have a loose fabric portion or edge that can be shaped during the molding process or afterwards. The L-shaped cover layers 5614 of the straps 5602, 5604 could be reversed so that the fit together and the connector 5650 can be overmolded onto or between the straps 5602, 5604. Alternatively, the straps 5602, 5604 could include a convex edge and a concave edge that complement one another. The connector 5650 can be overmolded onto or between the straps 5602, 5604. As described above, the cross-sectional shape can be defined by the core 5612 and cover 5614 or by the cover 5614 alone. In some configurations, the straps 5602, 5604 both have concave edges that cooperate to define a relatively large space therebetween. The connector 5650 can be overmolded onto or between the straps 5602, 5604, such as within the space defined by the concave edges. As described above, the cross-sectional shape can be defined by the core 5612 and cover 5614 or by the cover 5614 alone. At least the second or rear strap 5604 can include air gaps on one or both lateral ends, as disclosed herein and shown in FIG. 231.

FIGS. 232A-235 illustrate an intra-moulded bifurcated headgear configuration 5600 similar to the headgear 5600 of FIGS. 141-143 and FIGS. 176-193. Accordingly, the same reference numbers are used to indicate corresponding or similar features. As shown in FIGS. 233-235, the arrangements generally comprise a front strap 5610 connected to bifurcated straps 5602, 5604. Providing bifurcated straps 5602, 5604 stabilizes the headgear 5600 on the user's head. The front strap 5610 can be connected to an attachment clip 5680 for attaching to a mask. The bifurcated straps 5602, 5604 of the headgear 5600 are positioned around the cars of the user for improved comfort.

As illustrated in FIGS. 232A-C, the straps 5602, 5604, 5610 have a cover layer 5614. The cover layer 5614 can be a fabric casing constructed from natural or synthetic fabric or textile material, any other materials disclosed herein or any other suitable material. The cover layer 5614 can comprise knitted, woven or braided materials and can be elastic. Preferably, the cover layer 5614 has a texture that is soft to the touch and in appearance. The cover layer 5614 may be circular, tubular and hollow in cross-section. As illustrated in FIGS. 232B-C, the cover layer 5614 may be formed by joining first and second cover layers 5614A, 5614B. Alternatively, the cover layer 5614 may be formed or knitted into an integrally woven fabric tube. That is, the cover layer 5614 may be woven and preformed into a woven fabric tube that includes the front strap and the bifurcated straps 5602, 5604.

As illustrated in FIGS. 232A-235, portions of the front strap 5610 and/or the bifurcated straps 5602, 5604 may be filled with a relatively rigid or semi-rigid intra-moulded core 5612. In other words, core material may be injected into the hollow cover layer 5614 to allow specific portions of the headgear 5600 to be relatively rigid or semi-rigid while allowing other portions of the headgear to be elastic. As shown in FIG. 232A, only the front strap 5610 and the junction 5603 of the bifurcated straps 5602, 5604 may be filled with the intra-moulded core 5612. As such, the front strap 5610 and the junction 5603 may be substantially rigid or inelastic while the portion of the bifurcated straps 5602, 5604 beyond the junction 5603 remains elastic. Similarly, in FIG. 233, only the front straps 5610 include the intra-moulded core 5612. As such, the semi-rigid front region stabilizes the mask on the user's face while the elastic portions allow the headgear to be easily fitted onto the user. Further, the elastic portions allow the rear of the headgear to fit a range of head sizes. In FIG. 233, the front straps 5610 and portions of the bifurcated straps 5602, 5604 may be filled with the intra-moulded core 5612. Accordingly, the front straps 5610 and the bifurcated region of the bifurcated straps 5602, 5604 are rigid while the rear portions of the bifurcated straps 5602, 5604 are elastic. In FIG. 236, the front straps 5610 and the bifurcated straps 5602, 5604 may be filled with the intra-moulded core 5612 to form a headgear 5600 that is substantially rigid throughout.

The intra-moulded core 5612 may be a plastic material or any other suitable material. Further, the intra-moulded core 5612 may be fused and permanently bonded with the cover layer 5614 to produce a substantially rigid or inelastic structure. As illustrated in FIG. 232A, the attachment clips 5680 may be integrally formed and molded with the intra-moulded core 5612.

FIGS. 236A-B show a mould tool 5200 configured to form the intra-moulded bifurcated headgear configuration 5600. The mould tool 5200 comprises a first tool half 5210 and second tool half 5220. The first and second tool halves 5210, 5220 are joined together to form a strap cavity 5222. The strap cavity 5222 is configured to receive the fabric casing 5110. In some configurations, the fabric casing 5110 may be cut or preformed to fit exactly within the fabric casing 5110, such that the fabric casing 5110 is easily aligned within the strap cavity 5222. When the mould tool 5200 is in a closed position and the fabric casing 5110 is secured in place, the core material can be injected into the fabric casing 5110, via a gate and runner system (not shown), which in some configurations can be the same as or similar to that of FIG. 237. Accordingly, the headgear 5600 may be easily molded in a single manufacturing process.

FIG. 236C shows a cross-section schematic view of a mould tool 5200 configured to secure the fabric casing 5110 in place within the mould tool 5200 during forming process. The mould tool 5200 comprises a first tool half 5210 and second tool half 5220. The first and second tool halves 5210, 5220 are joined together to form a fabric casing cavity 5222, a mould insert cavity 5224 and a gate 5325. An insert 5326 is inserted into an open end of the fabric casing 5110 and the mould insert 5326 and the fabric casing 5110 are both positioned within the mould insert cavity 5224 and the fabric casing cavity 5222, respectively. When using a fabric casing 5110 to form the straps of a headgear, the fabric casing 5110 must be held open in order to allow the plastic core to be injected within the fabric casing 5110. Accordingly, the mould insert 5326 prevents the open end of the fabric casing 5110 from closing. The mould insert 5326 comprises a pre-made component that fits inside the open end of the fabric casing 5110 and pushes the opening of the fabric casing 5110 outwards towards the walls of the fabric casing cavity 5222 in the first and second tool halves 5210, 5220. The mould insert 5326 has a central opening 5328 that is aligned with the gate 5325 through which a direct flow path is provided for core material to be injected into the fabric casing 5110. The mould insert 5326 may be made of plastic or metal. If made of plastic, the mould insert 5326 may be made of the same plastic as that of the core so that a chemical bond can be formed between the mould insert 5326 and the core material during the intra-moulding process. Further, the insert 5326 may be formed in a shape that can have additional function as a connector between headgear components, adjustment mechanisms or between the headgear and mask (e.g., attachment clips 5680).

FIGS. 236D-G illustrate a mould tool arrangement 5200 configured to retain the fabric casing 5110 in a fixed position so that it does not move under the injection forces of the core material. FIG. 236D shows a cross-sectional schematic view of a mould tool 5200 configured to retain the fabric casing 5110. The mould tool 5200 comprises a first tool half 5210 and second tool half 5220. The first and second tool halves 5210, 5220 are joined together to form a mould tool cavity 5224. The surface of first and second tool halves 5210, 5220 include a plurality of retention spikes 5327 that protrude from the surface of first and second tool halves 5210, 5220 and extend in a direction towards the fabric casing 5110. As shown in FIG. 236E, the retention spikes 5327 may be spaced equidistant apart and across the surfaces of the tool halves 5210, 5220 that are perpendicular to the opening/closing directions of the first and second tool halves 5210, 5220. As shown in FIGS. 236F and 236G, the retention spikes 5327 are configured to prevent movement between the fabric casing 5110 and the walls of the mould tool cavity 5224. The spikes 5327 can have a sharp tip that penetrates the surface of the fabric casing. The retaining spikes 5327 may have a height such that the retention spikes 5327 are either submerged in the fabric casing 5110 such that they do not pierce through the entire thickness of the fabric casing 5110 (see FIG. 236F) or pierce through the entire thickness of the fabric casing 5110 (FIG. 236G). Accordingly, prior to the plastic core being injected, retaining spikes 5327 may secure and hold open the fabric casing 5110 within the mould tool cavity 5224.

In contrast to fabric casings constructed from bonded layers, woven fabric tubes have a tendency to remain open outside of forces being applied to the woven fabric tube. As such, the moulding tool may not need separate structures to hold an open end of the woven fabric tube open in order for core material to have a path into the woven fabric tube. FIGS. 237A and 237B show a mould tool 5200 configured to form a fabric casing comprising of a woven fabric tube 5110. The mould tool 5200 comprises a first tool half 5210 and second tool half 5220. The woven fabric tube 5110 may be positioned within the mould tool cavity 5224 and the first and second tool halves 5210, 5220 are joined together. As illustrated in FIG. 237B, the end of the woven fabric tube remains open despite the closing of the tool cavity. Accordingly, the core material has a path into the woven fabric tube 5110.

FIG. 238 illustrates an alternative construction of an intra-moulded strap 5604 comprising a core 5612 and a cover layer, which comprises a first cover layer 5614A and a second cover layer 5614B and rails 5618. The cover layers 5614A, 5614B can be constructed from a composite of multiple materials, such as relatively soft fabric or textile and foam or similar cushioning materials. The first and second cover layers 5614A, 5614B and the rails 5618 define a cavity for receiving an intra-moulded core 5612 that comprises a relatively rigid material, such as a plastic. In the illustrated arrangement, edges of the cover layers 5614A, 5614B are covered by the rails 5618. The rails 5618 may be formed from a soft silicone or plastic material to provide the strap with a soft and rounded edge and finish. The soft and rounded edge of the rails 5618 improves comfort and reduces irritation caused by the strap when rubbed against the skin. Further, the soft and compliant texture of the rails 5618 provides the perception that the strap 5604 is soft or has a soft construction despite the actual rigidity of the strap 5604 created by the intra-moulded core 5612. That is, the rails 5618 may partially mask or conceal the rigid construction of the strap 5604, which may affect user perception. Moreover, the soft silicone rails 5618 may reduce wear and improve the usable life of the strap 5604.

FIG. 239A-C illustrates an alternative construction of an intra-moulded tubular strap head strap 5602 comprising an airpocket core 5632, a cover layer 5614 and intra-moulded rails 5618. The cover layer 5614 covers the intra-moulded rails 5618 and defines the airpocket core 5632. The cover layer 5614 may be constructed from a fabric that is airtight such that the airpocket core 5632 is sealed and remains inflated.

The intra-moulded rails 5618 combined with the airpocket core 5632 provide a head strap 5602 that is rigid in structure but also lightweight. Further, the airpocket core 5632 of the head strap 5602 provides cushioning and padding to improve user comfort. Further, the cover layer 5614 may be arranged such that the air pocket core 5632 is formed closer to one side of the strap 5604 than the other. Accordingly, as shown in FIG. 237C, the air pocket core 5632 may extend in a direction towards the user's face and prevent the harder and more rigid intra-moulded rails 5618 from contacting the user's skin.

FIG. 240A illustrates an alternative construction of an intra-moulded tubular strap 5602 comprising a cover layer 5614 surrounding a structured core 5642 having internal structure. The cover layer 5614 may be constructed from a composite of multiple materials, such as relatively soft fabric or textile and foam or similar cushioning materials. The core 5642 may be formed by injection molding a semi-rigid plastic into the cavity within the hollow center within the cover layer 5614. The core 5642 may be substantially rectangular in cross-section. The core 5642 has a pattern of apertures 5644 that extend through the thickness of the core 5642. The apertures 5644 allow the strap 5602 to be flexible along the length of the strap 5602 while retaining stiffness in other directions. That is, the strap 5602 may be stretched or compressed in a direction parallel to the length-wise direction of the strap 5602 while still being rigid in other directions. As such, the apertures 5644 may partially mask or conceal the rigid construction of the strap 5602, which may affect user perception. Moreover, the apertures 5644 provide for a lighter weight and breathable strap that may improve user comfort. The apertures 5644 may be positioned at specific areas of the strap 5602 where elasticity is desired. Alternatively, the apertures 5644 may be positioned throughout the entire length of the strap 5602.

FIG. 240B illustrates the construction of the strap 5602 by using a mould tool 5200. Initially, the semi-rigid plastic is injected into the hollow center of the cover layer 5614. Then, the apertures 5644 within the core 5642 are then formed by compressing layers of the fabric cover layer 5614 together, by a mould tool shut-off, such that the molten plastic of the core 5642 cannot flow between the layers of the fabric cover layer 5614 in the regions where an aperture 5644 is to be formed, as shown in FIG. 240B.

FIG. 241A illustrates an alternative construction for an intra-moulded tubular head strap 5602 having a complex 3D shape with continuously variable geometry and cross-section along its length. In other words, the head strap 5602 may have varying width, thickness, edge radii, surface curvature (concave/convex) along its length, as shown along cross-sectional line A-A in FIG. 241B and cross-sectional line B-B in FIG. 241C. The varying curvature along the length of the head strap 5602 provides customised performance and structure to specific regions of the headgear. For example, the curved surface 5646 of the head strap 5602 along cross-sectional line A-A in FIG. 241B may be shaped to conform to the head geometry closer to the mask and the face of the user (e.g., check bones). In contrast, the head strap 5602 along cross-sectional line B-B in FIG. 241C may be shaped to have minimal size/volume such that the head strap 5602 may fit closely above, behind, under and/or around the user's ear.

The cover layer 5614 may be knitted or woven and the core 5642 may be formed by injection molding a semi-rigid plastic into the cavity within the hollow center within the woven cover layer 5614. It should be noted that the complex 3D shape of the strap 5602 cannot be achieved by sliding a knitted strap over a continuous curvature plastic core because the knitted strap has to be large enough to pass over the largest cross-section of the core, thus the knitted strap will be over sized and bulky in some regions. Further, injection moulding allows branding or orientation indicators to be moulded into the continuous curvature head strap 5602 in a single manufacturing process.

FIGS. 242A-G and 243A-C illustrate straps 7602, 7702 having permanently formed features 7652, 7752 such as branding logos (FIG. 242A-C), indicators (FIG. 242E), grip bumps (FIGS. 242F-G and 243B-C), etc. FIGS. 242A-G illustrate a strap 7602 with features 7652 permanently and integrally formed into the strap by intra-moulding. FIGS. 243A-C illustrate a strap 7702 with features 7752 permanently and integrally formed onto the strap by over-moulding. Accordingly, the features 7652, 7752 are integral with the strap 7652, 7752 and cannot be removed such that the features are always visible and identifiable (i.e., logos, branding, indicators). Further, the features 7652, 7752 may be positioned anywhere on the strap 7602, 7702 to vary the texture of the strap 7602, 7702 to increase tactile grip (i.e., grips) which improves handling of the headgear.

FIGS. 242A-G illustrates an intra-moulded strap 7602 with the features 7652 embossed on the strap 7602. Similar to intra-moulded straps previously described, the strap 7602 may comprise a semi-rigid plastic core 7612 that is covered by a fabric skin 7614. The features 7652 may be embossed during the intra-moulding process such that the features 7652 may be integrally applied to the headgear without a separate manufacturing step or process (i.e., reduces manufacturing steps and cost).

As illustrated in FIGS. 242A, the features 7652 may be embossed into the strap 7602 in a thickness direction of the strap 7602. In other words, the features 7652 may be recessed into the strap 7602 to form a depression 7616 in both the core 7612 and the fabric skin 7614. Alternatively, the features 7652 may extend or protrude above and beyond the fabric skin 7614 to form a protrusion 7618, as shown in FIGS. 242E-G. That is, the features 7652 may be formed on a thicker region of the core 7612 that is still covered by the fabric skin 7614.

In some configurations, openings 7618 may be formed through the fabric skin 7614 such that the core 7612 is exposed, as shown in FIGS. 242B and 242E. The openings 7618 may be formed by any variety of techniques, such as but not limited to, laser-cutting. The exposed portions of the core 7612 may protrude through the openings 7618 of the fabric skin 7614 (FIGS. 242C and 242E), be flush with the fabric skin 7614 (FIG. 125D), or be recessed below the fabric skin 7614 (FIGS. 242B and 242C).

FIGS. 243A-C illustrate a strap 7702 having features 7752 overmoulded onto the strap 7702. The strap 7702 comprises a single layer of fabric such as, but not limited to, Breath-o-prene™. The logo 7752 can be a flexible plastic such as a TPE or a silicone, to provide a soft touch that does not interfere with the functionality of the strap. The features 7702 may be overmoulded onto the strap 7702 and positioned anywhere along the length of the strap 7702.

FIGS. 244A-253 illustrate various moulded headgear configurations, which can be similar to other headgear disclosed herein and can by suitable for the same or similar applications. The headgear of FIGS. 244A-253 can be connected to an interface by any suitable coupling arrangement, such as any of those disclosed herein. The headgear can be modified for use with other types of interfaces, such as those employing a forehead rest, for example. Similarly, the headgear can be connected to an interface at single or multiple connections at various locations, for example, by using side, central or overhead straps. In addition, features, components, materials or manufacturing methods of the headgear of FIGS. 244A-253 can be interchanged with one another to create other headgear variations beyond those specifically disclosed. The illustrated headgears each comprise several straps, including a crown or top strap, a rear strap and at least one front strap. Other variations can omit one or more of these straps and/or can include additional straps. Any of the straps can incorporate length or other adjustment mechanisms, as desired, including any of the strap adjustment mechanisms disclosed herein or other suitable arrangements.

FIGS. 242A-B illustrate a headgear configuration 10100 having a single back strap 10120 (i.e., without a crown strap). The back strap 10120 may include a rear portion 10122 and a frontal portion 10124. When donned by the user, the frontal portion 10124 of the single rear strap 10120 is positioned across the user's checks just below the eyes and rearward towards the user's ears. As illustrated in FIG. 242A, the frontal portion 10124 is connected with the rear portion 10122 above and slightly forward of the user's ear. The rear portion 122 extends above the user's ears before extending downward towards the lower rear portion (i.e., occipital bone) of user's head. The rear and frontal portions 10122, 10124 may have different constructions. In other words, the rear portion 10122 may be more rigid than the frontal portion 10124. Accordingly, the frontal portion 10124 stretches to provide a retention force to the mask 10102 and allows the headgear 10100 to stretch such that the headgear may be donned on the user's face. The headgear configuration 10100 having the single back strap 10120 provides a headgear arrangement that is low in cost, easily manufactured and easily fitted to a user.

FIG. 242B illustrates a cross-sectional view of the rear portion 10122 along a line A-A in FIG. 242A. The rear portion 10122 includes a core 10130 that is covered by a cover layer 10132. The core 10130 may be a plastic material or any other suitable material, as previously disclosed herein. Similarly, the cover layer 10132 may be constructed from a composite of multiple materials, such as relatively soft fabric or textile and foam or similar cushioning materials. Also, as shown in FIG. 242B, the strap 10120 can be constructed in a manner similar to that described with reference to FIG. 194 to include voids, air gaps or air pockets 10134 on each lateral edge of the strap 10120. The air pockets 10134 provide flexibility and cushioning or compressibility. The frontal portion 10124 may be constructed from elastic knitted, woven or braided materials. In some configurations, the frontal portion 10124 may also include an intra-moulded core. In an alternative configuration (not shown), the same core material may be used in both the rear and front portions 10122, 10124 to provide a headgear arrangement having substantially the same modulus of elasticity throughout.

FIGS. 245A-C illustrates a headgear configuration 10200 having a lower strap 10220 connected to a crown strap 10230 by an arched connector 10240. The lower strap 10220 may be similar in construction as the single rear strap 10120 in FIGS. 244A-B. Therefore, duplicative discussion is omitted. The crown strap 10230 may be constructed from relatively soft fabric, textile, foam or similar cushioning materials, as previously disclosed herein. The arched connector 10240 may be constructed from plastic that is overmolded onto both the lower strap 10220 and the crown strap 10230. The arched connector 10240 is positioned above the user's ear and has a curved shape that is contoured similar to the curvature of the lower strap 10220. Overmolding the arched connector 10240 allows the lower strap 10220 and the crown strap 10230 to be easily joined. Further, the arched connector 10240 provides a relatively low profile connector that is substantially the same width and thickness as the lower strap 10220.

FIG. 246 illustrates a headgear configuration 10300 having a rear strap 10320, a crown strap 10330, and a front strap 10340. The front strap 10340 may have a different construction than the rear and crown straps 10320, 10330. In other words, the front strap 10340 may be substantially more rigid than the rear and crown straps 10320, 10330. The front strap 10340 may have a core formed from a relatively rigid material while the rear and crown straps 10320, 10330 have a core formed from a more flexible core material. In some configurations, the rear and crown straps 10320, 10330 are not filled with a core material. The rear and crown straps 10320, 10330 have a cover layer formed from elastic knitted, woven or braided materials. The rear and crown straps 10320, 10330 are flexible in construction such that the rear and crown straps 10320, 10330 may stretch to fit a wide range of head sizes as well as providing a retention force for the mask 10310. Further, the rear and crown straps 10320, 10330 relocate the retention force portions of the headgear away from the sensitive parts of the head (i.e., the face).

FIGS. 247A-D illustrates a bifurcating headgear configuration 10400 having a variable knit intra-mould. The bifurcating headgear configuration 10400 is similar in construction as the headgear configuration 10100 with the single rear strap 10120 in FIGS. 244A-B. However, the rear portion of the bifurcating headgear configuration 10400 is bifurcated into a lower rear portion 10422 and an upper rear portion 10424. The headgear 10400 may have an outer cover 10430 that is formed entirely from an elastic woven material, as previously described herein. The outer cover 10430 may span between the lower and upper rear portions 10422, 10424. FIG. 247B illustrates a cross-section of the headgear 10400 along a line A-A in FIG. 247A. FIG. 247C illustrates a cross-section of the headgear 10400 along a line B-B in FIG. 247A. As illustrated, the outer covering 10430 is tightly knitted or woven over the lower and upper rear portions 10422, 10424 while the portion of the outer covering 10430 between the lower and upper rear portions 10422, 10424 does not include core material. Accordingly, the portion of the outer covering 10430 between the lower and upper rear portions 10422, 10424 stretches to control movement and provide a retention force on the mask 10402. As shown in FIG. 247D, the headgear 10400 may be constructed as a single piece within a mould tool 10450. In other words, the headgear 10400 may be easily molded in a single manufacturing process.

FIGS. 248A-C illustrate a construction of a headgear configuration 10500 having a fully integrated bifurcated rear strap 10520 and crown strap 10530. As shown in FIG. 248B, two layers of outer cover 10540 may be joined together by sewing, adhesives, or any bonding techniques. The outer cover 10540 may be the same material or different materials. As shown in FIG. 248C, a core material 10550 may be positioned between the outer covers 10540. Voids, air gaps or air pockets 10534 on each lateral edge of the straps. The air pockets 10534 provide flexibility and cushioning or compressibility. Further, the seams 10536 may be positioned within the air pockets 10534 to provide a seamless aesthetic appearance.

FIGS. 249A-C illustrate an alternate configuration having a headgear 10600 with the core material 10640 exposed and formed on the outside surface of the outer cover 10630. The exposed core material 10640 allows the straps of the headgear 10600 to be easily moulded and formed into complex shapes. Further, the exposed core material 10640 allows the headgear 10600 to be easily cleaned. Even further, the plastic core material 10640 provides low friction such that the headgear 10600 easily slides against other objects, such as a pillow. In FIG. 249B, the core material 10640 is recessed into the outer cover 10630 such that the core material 10640 is substantially flush with the outer cover 10630. In contrast, FIG. 249C illustrates the core material 10640 positioned over the outer cover 10630 without being recessed into the outer cover 10630.

FIG. 250 illustrates a headgear 8000 for use in combination with a full-face mask 8100. The full-face mask 8100 has a mask frame 8110 with a T-piece 8112. The headgear 8000 is not limited to use with only a full-face mask breathing apparatus 8100 and may be used in combination with a nasal mask with a T-piece. The headgear 8000 has a bifurcated top strap 8010 and rear strap 8020. The top strap 8010 and rear strap 8020 are connected near an upper connection point 8030 that is located at the sides of the user's forehead. A fabric strap 8040 extends from the upper connection point 8030 and loops through an opening 8114 of the T-piece 8112 of the mask frame 8110. The end of the fabric strap 8040 may include a hook pads or patches that can be secured to complementary loop surfaces on the fabric strap 8040. The fabric strap 8040 allows the user to adjust the tightness between the top portion of the headgear 8000 and the T-piece 8112. The fabric strap 8040 may be attached to the T-piece 8112 by any variety of releasable mechanical fastening arrangements, such as, but not limited to, clips, push or snap connectors, etc. A lower connection point 8050 is positioned below the upper connection point 8030 and located forward of the user's ear and approximately in line with the user's mouth. The lower connection point 8050 may be connected to the mask frame 8110 by one or more adjustment mechanisms 8120. The adjustment mechanisms 8120 may include one of a variety of adjustment mechanism configurations, such as but not limited to, a one-way friction mechanism or any other appropriate locking mechanism.

FIG. 251 illustrates a headgear 8000 in use in combination with a nasal mask 8200. The nasal mask 8200 has a mask frame 8210. Similar to FIG. 250, the headgear 8000 has a bifurcated top strap 8010 and rear strap 8020. The headgear 8000 is not limited to use with only a nasal mask and may be used in combination with a full-face mask with or without a T-piece or a respiratory mask having an under-nose sealing region. The headgear 8000 has an upper strap 8032 that is connected to the top strap 8010 and the rear strap 8012. The headgear 8000 is located on the side portion of the user's forehead that extends across the check between the user's ear and eye. The upper strap 8032 can be connected directly to the mask frame 8210. Alternatively, there may be an adjustment mechanism positioned between the upper strap 8032 and the mask frame 8210. A lower strap 8052 is connected to the rear strap at a position behind the user's ear and extends substantially downward to a position below the user's ear and forward towards the mask frame 8210. In other words, the lower strap 8052 is connected to the rear strap 8012 and extends downward around the user's ear and extends across the user's check. The lower strap 8052 is connected to the mask frame 8210 by one or more adjustment mechanisms 8120. The adjustment mechanisms 8120 may include one of a variety of adjustment mechanism configurations, such as but not limited to, a one-way friction mechanism or any other appropriate locking mechanism.

FIG. 252 illustrates a headgear 8000 in use in combination with a nasal pillows (direct nasal) mask 8300. Similar to FIGS. 250 and 251, the headgear 8000 has a bifurcated top strap 8010 and rear strap 8020. The headgear 8000 has a front strap 8034 that is connected to the top strap 8010 and the rear strap 8012. The front strap 8034 extends between the ear and eye of the user and towards the bottom of the nose. The front strap 8034 also extends across the front of the mask 8300 to form a portion of the frame 8310. In alternative embodiments the front strap 8034 may terminate before the mask 8300 and connect to a separate mask frame 8310. Further, in some configurations, an adjustment mechanism (not shown) may be positioned between the front strap 8034 and mask frame 8310.

FIG. 253 illustrates a headgear 8000 in use in combination with a nasal mask 8200. The nasal mask 8200 has a mask frame 8210. The headgear 8000 is not limited to use with only a nasal mask breathing apparatus 8200 and may be used in combination with a nasal mask without a T-piece or a respiratory mask having an under-nose sealing region. The headgear 8000 has a bifurcated top strap 8010 and rear strap 8020. The top strap 8010 and rear strap 8020 are connected near an upper connection point 8030 that is located at the sides of the user's forehead and in line with the user's eye. The upper connection point 8030 is connected to the mask frame 8210 by an adjustment mechanism 8120. The adjustment mechanisms 8120 may include one of a variety of adjustment mechanism configurations, such as but not limited to, a one-way friction mechanism or any other appropriate locking mechanism. The adjustment mechanism 8120 extends towards the mask frame 8210 across the user's cheeks just below the eyes. A lower connection point 8050 is connected to the headgear 8000 below the upper connection point 8030 and is positioned approximately in line with the bottom of the user's nose. The lower connection point 8050 is also connected to the mask frame 8210 by an adjustment mechanism 8120, which extends towards the mask frame 8210 across the user's cheeks just below the eyes.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A patient interface assembly comprising:
   an interface;
   a headgear assembly comprising:
   a rear headgear portion; and
   an interface coupling portion removably attachable to the interface; and
   a length or circumference adjusting portion interposed between the rear headgear portion and the interface coupling portion, the length or circumference adjusting portion comprising a pair of adjustment elements, the pair of adjustment elements being positioned with one adjusting element on each lateral side of the headgear assembly, each one of the pair of adjustment elements being coupled at one end to the rear headgear portion and at another end to the interface coupling portion;
   wherein, a pair of directional locks are associated with each one of the pair of adjustment elements,
   wherein the interface coupling portion connects at least two of the adjustment elements that are positioned on each side of the headgear assembly, and
   wherein the length or circumference adjusting portion exhibits an elastic force tending to contract a headgear length or a circumference length and wherein the length or circumference adjusting portion also exhibits a non-elastic lock force tending to inhibit elongation of the headgear length or the circumference length.

2. The patient interface assembly of claim 1, wherein each pair of directional locks comprise one or more lock elements; the one or more lock elements interacting with a core member:

to automatically adjust in response to movement of the core member;

to selectively allow retraction of the headgear assembly; and to lock the headgear assembly in a particular circumference to inhibit or prevent extension of the headgear assembly.

3. The patient interface assembly of claim 1, wherein the interface coupling portion comprises at a least a portion of each pair of directional locks.

4. The patient interface assembly of claim 1, wherein the adjustment elements comprise an elastic element and/or a braided element.

5. The patient interface assembly of claim 1, wherein the interface coupling portion comprises two coupling portions, and wherein each of the two coupling portions removably attach to the interface at separate positions on the interface.

6. The patient interface assembly of claim 1, wherein the interface is a nasal mask, a nasal pillows/prongs mask or a full face mask.

7. The patient interface assembly of claim 1, wherein the rear headgear portion comprises a top strap portion and a rear strap portion.

8. The patient interface assembly of claim 7, wherein the top strap portion and rear strap portion are coupled by an intermediate connecting portion.

9. The patient interface assembly of claim 1, wherein the interface coupling portion is relatively rigid.

10. The patient interface assembly of claim 2, wherein the core member associated with each of the directional locks, extends through each of the pair of adjustment elements and a housing of each of the directional locks, and into a collection space.

11. The patient interface assembly of claim 10, wherein the collection space is a collection tube or conduit, which is incorporated into the interface coupling portion.

12. The patient interface assembly of claim 1, wherein the interface coupling portion is curved.

13. The patient interface assembly of claim 11, wherein the collection space is curved along with the interface coupling portion.

14. The patient interface assembly of claim 5, wherein a bridge portion extends between and connects the interface coupling portion.

15. The patient interface assembly of claim 7, wherein one of each pair of adjustment elements on each side of the headgear assembly is coupled to the rear headgear portion at or near a portion of the top strap portion and another of each pair of the adjustment elements on each side of the headgear assembly is coupled to the rear headgear portion at or near a portion of the rear strap portion.

16. The patient interface assembly of claim 1, wherein each of the directional locks is configured to provide a first resistance force in response to a force applied in a direction to elongate the headgear length or the circumference length and a second resistance force in response to a force applied in a direction tending to contract the headgear length or the circumference length, wherein the first resistance force is different than the second resistance force.

17. The patient interface assembly of claim 16, wherein the second resistance force is less than the first resistance force.

18. The patient interface assembly of claim 10, wherein the collection space is located outside of the housing.

19. The patient interface assembly of claim 1, wherein each of the directional locks is configured to selectively allow retraction of the headgear assembly or to lock the headgear assembly in a particular circumference and inhibit or prevent extension of the headgear assembly without manual interaction by a user.

20. The patient interface assembly of claim 3, wherein the interface coupling portion is configured to be removably attachable to the interface by a snap-fit arrangement located at a central portion of the interface coupling portion.

21. A patient interface assembly comprising:

an interface;

a headgear assembly comprising:

a rear headgear portion; and an interface coupling portion removably attachable to the interface; and a length or circumference adjusting portion interposed between the rear headgear portion and the interface coupling portion, the length or circumference adjusting portion comprising a pair of adjustment elements on each side of the headgear assembly, the pair of adjustment elements being coupled at one end to the rear headgear portion and at another end to the interface coupling portion;

the interface coupling portion extending between at least two of the adjustment elements, and the length or circumference adjusting portion exhibiting an elastic force tending to contract a headgear length or a circumference length and a non-elastic lock force tending to inhibit elongation of the headgear length or the circumference length, and a pair of directional locks being associated with each one of the pair of adjustment elements, each of the directional locks being configured to provide a first resistance force in response to a force applied in a direction to elongate the headgear length or the circumference length and a second resistance force in response to a force applied in a direction tending to contract the headgear length or the circumference length, wherein the first resistance force is different from the second resistance force.

22. A patient interface assembly comprising:

an interface;

a headgear assembly comprising:

a rear headgear portion; and an interface coupling portion removably attachable to the interface; and a length or circumference adjusting portion interposed between the rear headgear portion and the interface coupling portion, the length or circumference adjusting portion comprising a pair of adjustment elements on each side of the headgear assembly, the pair of adjustment elements being coupled at one end to the rear headgear portion and at another end to the interface coupling portion;

the interface coupling portion extending between at least two of the adjustment elements, and the length or circumference adjusting portion exhibiting an elastic force tending to contract a headgear length or a circumference length and a non-elastic lock force tending to inhibit elongation of the headgear length or the circumference length and a pair of directional locks being associated with each one of the pair of adjustment elements, each of the directional locks being configured to selectively allow retraction of the headgear assembly or to lock the headgear assembly in a particular circumference and inhibit or prevent extension of the headgear assembly without manual interaction by a user.

\* \* \* \* \*